United States Patent
Aida et al.

(10) Patent No.: US 9,776,962 B2
(45) Date of Patent: Oct. 3, 2017

(54) AROMATIC COMPOUNDS WITH GPR40 AGONISTIC ACTIVITY

(71) Applicant: TAKEDA PHARMACEUTICAL COMPANY LIMITED, Osaka-shi, Osaka (JP)

(72) Inventors: Jumpei Aida, Fujisawa (JP); Yayoi Yoshitomi, Fujisawa (JP); Yuko Hitomi, Fujisawa (JP); Naoyoshi Noguchi, Fujisawa (JP); Yasuhiro Hirata, Fujisawa (JP); Hideki Furukawa, Fujisawa (JP); Akito Shibuya, Fujisawa (JP); Koji Watanabe, Fujisawa (JP); Yasufumi Miyamoto, Fujisawa (JP); Tomohiro Okawa, Fujisawa (JP); Nobuyuki Takakura, Fujisawa (JP); Seiji Miwatashi, Tokyo (JP)

(73) Assignee: TAKEDA PHARMACEUTICAL COMPANY LIMITED, Osaka (JP)

(*) Notice: Subject to any disclaimer, the term of this patent is extended or adjusted under 35 U.S.C. 154(b) by 0 days.

(21) Appl. No.: 14/898,633

(22) PCT Filed: Aug. 8, 2014

(86) PCT No.: PCT/JP2014/070972
§ 371 (c)(1),
(2) Date: Dec. 15, 2015

(87) PCT Pub. No.: WO2015/020184
PCT Pub. Date: Feb. 12, 2015

(65) Prior Publication Data
US 2016/0115128 A1    Apr. 28, 2016

(30) Foreign Application Priority Data
Aug. 9, 2013    (JP) ................. 2013-167065

(51) Int. Cl.
| | | |
|---|---|---|
| C07D 211/34 | (2006.01) |
| C07D 211/22 | (2006.01) |
| C07D 213/30 | (2006.01) |
| C07D 401/10 | (2006.01) |
| C07D 401/12 | (2006.01) |
| C07D 401/14 | (2006.01) |
| C07D 405/12 | (2006.01) |
| C07D 405/14 | (2006.01) |
| C07D 409/12 | (2006.01) |
| C07D 413/10 | (2006.01) |
| C07D 413/14 | (2006.01) |

(52) U.S. Cl.
CPC .......... *C07D 211/34* (2013.01); *C07D 211/22* (2013.01); *C07D 213/30* (2013.01); *C07D 401/10* (2013.01); *C07D 401/12* (2013.01); *C07D 401/14* (2013.01); *C07D 405/12* (2013.01); *C07D 405/14* (2013.01); *C07D 409/12* (2013.01); *C07D 413/10* (2013.01); *C07D 413/14* (2013.01)

(58) Field of Classification Search
CPC .. C07D 211/34; C07D 211/22; C07D 213/30; C07D 401/10; C07D 401/12; C07D 401/14; C07D 405/12; C07D 405/14; C07D 409/12; C07D 413/10; C07D 413/14
See application file for complete search history.

(56) References Cited

U.S. PATENT DOCUMENTS 7,968,552 B2 *   6/2011   Negoro ................ C07D 271/06
                                                    514/256

FOREIGN PATENT DOCUMENTS

WO    WO 2007/123225    * 11/2007

* cited by examiner

*Primary Examiner* — Sahar Javanmard
(74) *Attorney, Agent, or Firm* — Nath, Goldberg & Meyer; Joshua B. Goldberg; Scott H. Blackman

(57) ABSTRACT

Provided is a novel aromatic ring compound having a GPR40 agonist activity and a GLP-1 secretagogue action. A compound represented by the formula:

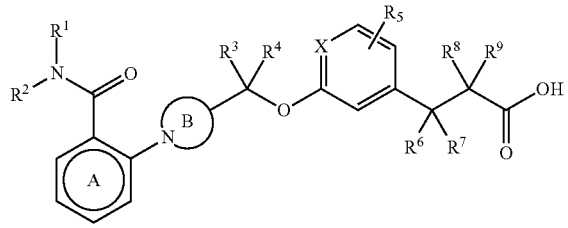

wherein each symbol is as described in the DESCRIPTION, or a salt thereof has a GPR40 agonist activity and a GLP-1 secretagogue action, is useful for the prophylaxis or treatment of cancer, obesity, diabetes, hypertension, hyperlipidemia, cardiac failure, diabetic complications, metabolic syndrome, sarcopenia and the like, and affords superior efficacy.

16 Claims, No Drawings

AROMATIC COMPOUNDS WITH GPR40 AGONISTIC ACTIVITY

This is a National Phase Application filed under 35 U.S.C. 371 as a national stage of PCT/JP2014/070972, filed Aug. 8, 2014, an application claiming the benefit of Japanese Application No. 2013-167065, filed Aug. 9, 2013, the content of each of which is hereby incorporated by reference in its entirety.

TECHNICAL FIELD

The present invention relates to a novel aromatic ring compound having a GPR40 agonist activity and GLP-1 secretagogue action.

The Sequence Listing submitted in text format (.txt) filed on Dec. 15, 2015, named "JPOXMLDOC01.txt", (created on Dec. 2, 2015, 2 KB), is incorporated herein by reference.

BACKGROUND OF THE INVENTION

Patent document 1 describes the following compound.

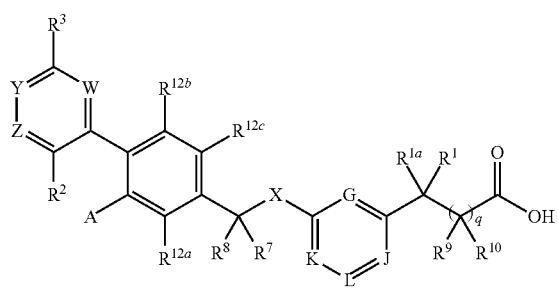

wherein each symbol is as described in patent document 1.

Patent document 2 describes the following compound.

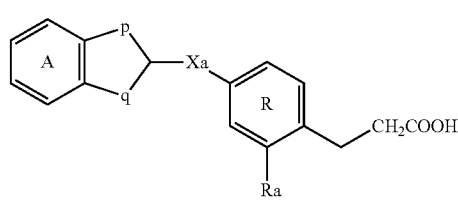

wherein each symbol is as described in patent document 2.

Patent document 3 describes the following compound.

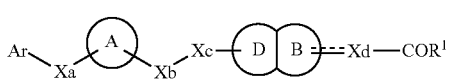

wherein each symbol is as described in patent document 3.

Patent document 4 describes the following compound.

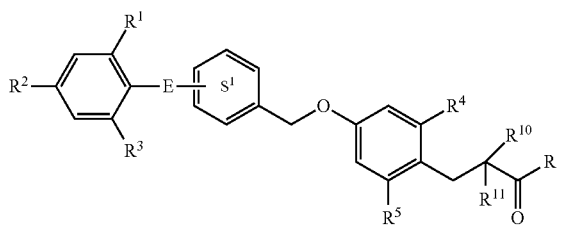

wherein each symbol is as described in patent document 4.

Patent document 5 describes the following compound.

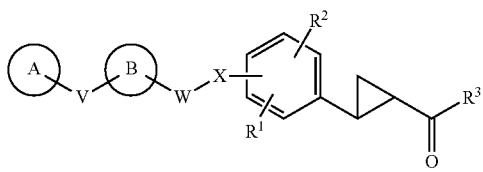

wherein each symbol is as described in patent document 5.

Patent document 6 describes the following compound.

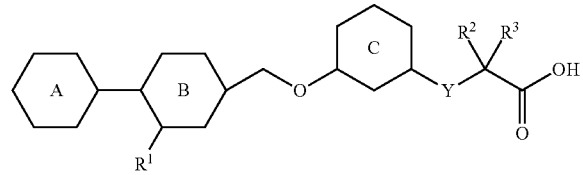

wherein each symbol is as described in patent document 6.

However, no documents specifically disclose the compound of the present application.

DOCUMENT LIST

Patent Documents

[patent document 1] WO 2009/048527
[patent document 2] US2009-0012093
[patent document 3] US2006-0258722
[patent document 4] US2007-0149608
[patent document 5] US2010-0144806
[patent document 6] WO 2013/122029

SUMMARY OF THE INVENTION

Problems to be Solved by the Invention

The present invention aims to provide a novel aromatic ring compound having a GPR40 agonist activity and GLP-1 secretagogue action, and useful as an agent for the prophylaxis or treatment of diabetes and the like.

Means of Solving the Problems

The present inventors have conducted various intensive studies and found that the compound represented by the following formula (I) unexpectedly has a superior GPR40 agonist activity and GLP-1 secretagogue action, and provides a safe and useful medicament to be an agent for the prophylaxis or treatment of mammalian GPR40 receptor-related pathology or disease. Based on these findings, they have completed the present invention.

That is, the present invention relates to

[1] a compound represented by the formula (I):

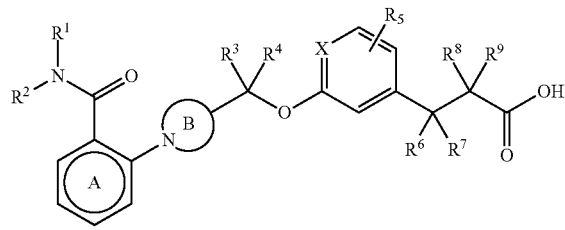

wherein
ring A is a further optionally substituted aromatic ring;
ring B is a further optionally substituted 4-6-membered nitrogen-containing saturated ring;
X is —N═ or —CH═;
$R^1$ and $R^2$ are each independently a hydrogen atom or a substituent;
$R^1$ and $R^2$ are optionally bonded to each other to form, together with the adjacent nitrogen atom, an optionally substituted 3- to 10-membered ring;
$R^3$ and $R^4$ are each independently a hydrogen atom, a halogen atom or a $C_{1-6}$ alkyl group;
$R^5$, $R^7$, $R^8$ and $R^9$ are each independently a hydrogen atom, a halogen atom, a $C_{1-6}$ alkyl group or a $C_{1-6}$ alkoxy group;
$R^6$ is a halogen atom, an optionally substituted $C_{1-6}$ alkyl group, an optionally substituted $C_{1-6}$ alkoxy group or an optionally substituted $C_{3-10}$ cycloalkyl group; and
$R^6$ and $R^7$ are optionally bonded to each other to form, together with the adjacent carbon atom, an optionally substituted 3- to 10-membered ring,
or a salt thereof (hereinafter sometimes to be referred to as compound (I));

[2] the compound of the above-mentioned [1], wherein ring A is a benzene ring optionally further substituted by 1 or 2 substituents selected from
(1) a $C_{1-6}$ alkylsulfonyl group;
(2) a carbamoyl group;
(3) a hydroxy group;
(4) a $C_{1-6}$ alkoxy group optionally substituted by 1 to 3 halogen atoms;
(5) a $C_{1-6}$ alkylthio group;
(6) a cyano group;
(7) a halogen atom; and
(8) a $C_{1-6}$ alkyl group,
or a salt thereof;

[3] the compound of the above-mentioned [1] or [2], wherein ring B is
(1) an azetidine ring, (2) a pyrrolidine ring or (3) a piperidine ring optionally further substituted by 1 or 2 substituents selected from a halogen atom and a $C_{1-6}$ alkyl group,
or a salt thereof;

[4] the compound of any of the above-mentioned [1]-[3], wherein X is —N═, or a salt thereof;

[5] the compound of any of the above-mentioned [1]-[4], wherein $R^1$ and $R^2$ are each independently
(i) a $C_{1-8}$ alkyl group optionally substituted by 1 or 2 substituents selected from
(1) cyano, (2) hydroxy, (3) a $C_{3-10}$ cycloalkyl group optionally substituted by 1 to 3 substituents selected from a halogen atom and a $C_{1-6}$ alkyl group, (4) a $C_{1-6}$ alkoxy group optionally substituted by 1 to 3 halogen atoms, (5) a $C_{6-14}$ aryl group optionally substituted by 1 to 3 halogen atoms, (6) an aromatic heterocyclic group, (7) a nonaromatic heterocyclic group, (8) a $C_{1-6}$ alkylsulfonyl group, (9) a mono- or di-$C_{1-6}$ alkyl-amino group optionally substituted by 1 to 3 halogen atoms and (10) a halogen atom, or
(ii) an aromatic heterocyclic group optionally substituted by 1 or 2 substituents selected from
(1) cyano, (2) a halogen atom, (3) a $C_{1-6}$ alkyl group optionally substituted by 1 to 3 halogen atoms, (4) a $C_{3-10}$ cycloalkyl group, (5) a $C_{1-6}$ alkoxy group, (6) a nitrogen-containing heterocyclyl-carbonyl group and (7) a mono- or di-$C_{1-6}$ alkyl-carbamoyl group, or a salt thereof;

[6] the compound of any of the above-mentioned [1]-[5], wherein $R^3$, $R^4$, $R^5$, $R^7$, $R^8$ and $R^9$ are hydrogen atoms, or a salt thereof;

[7] the compound of any of the above-mentioned [1]-[6], wherein $R^6$ is a $C_{3-10}$ cycloalkyl group, or a salt thereof;

[8] the compound of the above-mentioned [1], wherein ring A is a benzene ring optionally further substituted by 1 or 2 substituents selected from
(1) a $C_{1-6}$ alkylsulfonyl group;
(2) a carbamoyl group;
(3) a hydroxy group;
(4) an $C_{1-6}$ alkoxy group optionally substituted by 1 to 3 halogen atoms;
(5) a $C_{1-6}$ alkylthio group;
(6) a cyano group;
(7) a halogen atom; and
(8) a $C_{1-6}$ alkyl group,
ring B is (1) an azetidine ring, (2) a pyrrolidine ring or (3) a piperidine ring optionally further substituted by 1 or 2 substituents selected from a halogen atom and a $C_{1-6}$ alkyl group,
X is —N═,
$R^1$ and $R^2$ are each independently
(i) a $C_{1-8}$ alkyl group optionally substituted by 1 or 2 substituents selected from
(1) cyano, (2) hydroxy, (3) a $C_{3-10}$ cycloalkyl group optionally substituted by 1 to 3 substituents selected from a halogen atom and a $C_{1-6}$ alkyl group, (4) a $C_{1-5}$ alkoxy group optionally substituted by 1 to 3 halogen atoms, (5) a $C_{6-14}$ aryl group optionally substituted by 1 to 3 halogen atoms, (6) an aromatic heterocyclic group, (7) a nonaromatic heterocyclic group, (8) a $C_{1-6}$ alkylsulfonyl group, (9) a mono- or di-$C_{1-6}$ alkyl-amino group optionally substituted by 1 to 3 halogen atoms and (10) a halogen atom, or
(ii) an aromatic heterocyclic group optionally substituted by 1 or 2 substituents selected from
(1) cyano, (2) a halogen atom, (3) a $C_{1-6}$ alkyl group optionally substituted by 1 to 3 halogen atoms, (4) a $C_{3-10}$ cycloalkyl group, (5) a $C_{1-6}$ alkoxy group, (6) a nitrogen-containing heterocyclyl-carbonyl group and (7) a mono- or di-$C_{1-6}$ alkyl-carbamoyl group,
$R^3$, $R^4$, $R^5$, $R^7$, $R^8$ and $R^9$ are hydrogen atoms, and
$R^6$ is a $C_{3-10}$ cycloalkyl group,
or a salt thereof;

[9] (3S)-3-cyclopropyl-3-(2-((1-(2-((2,2-dimethylpropyl)(6-methylpyridin-2-yl)carbamoyl)-5-methoxyphenyl)piperidin-4-yl)methoxy)pyridin-4-yl)propanoic acid or a salt thereof;

[10] (3S)-3-cyclopropyl-3-(2-((1-(2-((2,2-dimethylpropyl) (4,6-dimethylpyrimidin-2-yl)carbamoyl)-5-methoxyphenyl) piperidin-4-yl)methoxy)pyridin-4-yl)propanoic acid or a salt thereof;

[11] (3S)-3-cyclopropyl-3-(2-((1-(2-((2,2-dimethylpropyl)(pyridin-2-yl)carbamoyl)-5-methoxyphenyl)piperidin-4-yl)methoxy)pyridin-4-yl)propanoic acid or a salt thereof;

[12] a medicament comprising the compound of [1] or a salt thereof;

[13] the medicament of [12] above, which is a GPR40 receptor function regulator;

[14] the medicament of [12] above, which is a prophylactic or therapeutic agent for diabetes;

[15] a method of preventing or treating diabetes in a mammal, comprising administering an effective amount of the compound of the above-mentioned [1] or a salt thereof to the mammal;

[16] a method of regulating GPR40 receptor function in a mammal, comprising administering an effective amount of the compound of the above-mentioned [1] or a salt thereof to the mammal;

[17] use of the compound of the above-mentioned [1] or a salt thereof for the production of an agent for the prophylaxis or treatment of diabetes;

[18] the compound of the above-mentioned [1] or a salt thereof for use for the prophylaxis or treatment of diabetes; and the like.

Effect of the Invention

Since compound (I) has a superior GPR40 agonist activity and GLP-1 secretagogue action, is superior in the property as a pharmaceutical product such as stability and the like, and particularly shows high solubility, low toxicity, good kinetics such as sustainability in blood and the like, it can provide a safe and useful agent for the prophylaxis or treatment of mammalian GPR40 receptor-related pathology or disease.

DETAILED DESCRIPTION OF THE INVENTION

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ arylcarbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),

(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacridinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di- (optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di- (optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., alkylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane, and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane, and cyclooctane.

In the present specification, examples of the "$C_{3-10}$ cycloalkene" include cyclopropene, cyclobutene, cyclopentene, cyclohexene, cycloheptene, and cyclooctene.

In the present specification, examples of the "heterocycle" include aromatic heterocycle and non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi- or tricyclic) aromatic heterocycles such as benzothiophene, benzofuran, benzimidazole, benzoxazole, benzoisoxazole, benzothiazole, benzoisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiine, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic the formula (preferably 2- or tricyclic) non-aromatic heterocycles such as dihydrobenzofuran, dihydrobenzoimidazole, dihydrobenzooxazole, dihydrobenzothiazole, dihydrobenzoisothiazole, dihydronaphto[2,3-b]thiophene, tetrahydroisoquinoline, tetrahydroquinoline, 4H-quinolizine, indoline, isoindoline, tetrahydrothieno[2,3-c]pyridine, tetrahydrobenzoazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring constituting atom.

In the present specification, examples of the "aromatic ring" (including "aromatic ring" in the "optionally further substituted aromatic ring") include a $C_{6-14}$ aromatic hydrocarbon ring, and aromatic heterocycle.

In the present specification, the "aromatic ring" of the "optionally further substituted aromatic ring" optionally has 1 to 5, preferably 1 to 3, substituents at substitutable position(s). When the number of the substituents is not less than 2, the respective substituents may be the same or different.

In the present specification, examples of the "optionally substituted $C_{1-6}$ alkyl group" include the "optionally substituted hydrocarbon group" wherein the hydrocarbon group is a "$C_{1-6}$ alkyl group".

In the present specification, examples of the "optionally substituted $C_{3-10}$ cycloalkyl group" include the "optionally substituted hydrocarbon group" wherein the hydrocarbon group is a "$C_{3-10}$ cycloalkyl group".

In the present specification, the "$C_{1-6}$ alkoxy group" of the "optionally substituted $C_{1-6}$ alkoxy group" optionally has 1 to 5, preferably 1 to 3, substituents, at substitutable position(s). When the number of the substituents is not less than 2, the respective substituents may be the same or different.

In the present specification, examples of the "4-6-membered nitrogen-containing saturated ring" (including the "4-6-membered nitrogen-containing saturated ring" of the "optionally further substituted 4-6-membered nitrogen-containing saturated ring") include the above-mentioned "nitrogen-containing heterocycle" which is 4- to 6-membered and saturated.

In the present specification, the "4-6-membered nitrogen-containing saturated ring" of the "optionally further substituted 4- to 6-membered nitrogen-containing saturated ring" preferably optionally has 1 to 5, preferably 1 to 3 substituents at substitutable position(s). When the number of the substituents is not less than 2, the respective substituents may be the same or different.

In the present specification, examples of the "3- to 10-membered ring" (including the "3- to 10-membered ring" of the "optionally substituted 3- to 10-membered ring") include the above-mentioned "hydrocarbon ring" and "heterocycle" which are 3- to 10-membered.

In the present specification, the "3- to 10-membered ring" of the "optionally substituted 3- to 10-membered ring" optionally has 1 to 5, preferably 1 to 3, substituents, at substitutable position(s). When the number of the substituents is not less than 2, the respective substituents may be the same or different.

The definition of each symbol in the formula (I) is described in detail in the following.

Ring A is an optionally further substituted 6-membered aromatic ring.

Preferred as the "aromatic ring" of the "optionally further substituted aromatic ring" for ring A is a $C_{6-14}$ aromatic hydrocarbon ring (e.g., benzene ring) or an aromatic heterocycle (e.g., pyridine ring), more preferably a benzene ring or a pyridine ring, particularly preferably a benzene ring.

The "aromatic ring" is optionally further substituted by 1-4 (preferably 1-3, more preferably 1 or 2) substituents other than a $R^1R^2N—C(=O)—$ group and $—O—CR^3R^4-$ring B-group, at substitutable position(s).

Such substituent is preferably
(1) a $C_{1-6}$ alkylsulfonyl group (e.g., methylsulfonyl) optionally substituted by 1 to 3 halogen atoms;
(2) a carbamoyl group optionally mono- or di-substituted by a $C_{1-6}$ alkyl group optionally substituted by 1 to 3 halogen atoms;
(3) a hydroxy group;
(4) a $C_{1-6}$ alkoxy group (e.g., methoxy, ethoxy) optionally substituted by 1 to 3 substituents selected from
   (a) a halogen atom (e.g., a fluorine atom),
   (b) a carboxy group,
   (c) a $C_{1-6}$ alkoxy group,
   (d) a $C_{1-6}$ alkoxy-carbonyl group optionally substituted by 1 to 3 $C_{6-14}$ aryl groups,
   (e) an amino group optionally mono- or di-substituted by a substituent selected from a $C_{1-6}$ alkyl group and a $C_{1-6}$ alkoxy-carbonyl group, and
   (f) a $C_{3-10}$ cycloalkyl group;
(5) a $C_{1-6}$ alkylthio group (e.g., methylthio) optionally substituted by 1 to 3 substituents selected from
   (a) a halogen atom, and
   (b) a $C_{1-6}$ alkoxy-carbonyl group;
(6) a cyano group;
(7) a halogen atom (e.g., a fluorine atom, a chlorine atom, a bromine atom); or
(8) a $C_{1-6}$ alkyl group (e.g., methyl, ethyl) optionally substituted by 1 to 3 substituents selected from
   (a) a halogen atom,
   (b) a carboxy group,
   (c) a hydroxy group,
   (d) a $C_{1-6}$ alkoxy-carbonyl group, (e) a $C_{1-6}$ alkoxy group, and (f) an amino group optionally mono- or di-substituted by a $C_{1-6}$ alkyl group, more preferably, (1) a $C_{1-6}$ alkylsulfonyl group (e.g., methylsulfonyl);
(2) a carbamoyl group;
(3) a hydroxy group;
(4) a $C_{1-6}$ alkoxy group (e.g., methoxy) optionally substituted by 1 to 3 halogen atoms (e.g., a fluorine atom);
(5) a $C_{1-6}$ alkylthio group (e.g., methylthio);
(6) a cyano group;
(7) a halogen atom (e.g., a fluorine atom, a chlorine atom, a bromine atom); or
(8) a $C_{1-6}$ alkyl group (e.g., methyl, ethyl).

Ring A is preferably an optionally further substituted benzene ring or an optionally further substituted pyridine ring, more preferably, a benzene ring or a pyridine ring, each of which is optionally further substituted by 1-4 (preferably 1-3, more preferably 1 or 2) substituents selected from (1) a $C_{1-6}$ alkylsulfonyl group (e.g., methylsulfonyl);
(2) a carbamoyl group;
(3) a hydroxy group;
(4) a $C_{1-6}$ alkoxy group (e.g., methoxy) optionally substituted by 1 to 3 halogen atoms (e.g., a fluorine atom);
(5) a $C_{1-6}$ alkylthio group (e.g., methylthio);
(6) a cyano group;
(7) a halogen atom (e.g., a fluorine atom, a chlorine atom, a bromine atom); and
(8) a $C_{1-6}$ alkyl group (e.g., methyl, ethyl), more preferably a benzene ring optionally further substituted by 1-4 (preferably 1-3, more preferably 1 or 2) substituents selected from (1) a $C_{1-6}$ alkylsulfonyl group (e.g., methylsulfonyl);
(2) a carbamoyl group;
(3) a hydroxy group;
(4) a $C_{1-6}$ alkoxy group (e.g., methoxy) optionally substituted by 1 to 3 halogen atoms (e.g., a fluorine atom);
(5) a $C_{1-6}$ alkylthio group (e.g., methylthio);
(6) a cyano group;
(7) a halogen atom (e.g., a fluorine atom, a chlorine atom, a bromine atom); and
(8) a $C_{1-6}$ alkyl group (e.g., methyl, ethyl), or a pyridine ring optionally further substituted by 1-4 (preferably 1-3, more preferably 1 or 2) substituents selected from (1) a $C_{1-6}$ alkoxy group (e.g., methoxy);
(2) a halogen atom (e.g., a chlorine atom); and
(3) a $C_{1-6}$ alkyl group (e.g., ethyl).

Ring A is particularly preferably a benzene ring optionally further substituted by 1-4 (preferably 1-3, more preferably 1 or 2) substituents selected from (1) a $C_{1-6}$ alkylsulfonyl group (e.g., methylsulfonyl);
(2) a carbamoyl group;
(3) a hydroxy group;
(4) a $C_{1-6}$ alkoxy group (e.g., methoxy) optionally substituted by 1 to 3 halogen atoms (e.g., fluorine atom);
(5) a $C_{1-6}$ alkylthio group (e.g., methylthio);
(6) a cyano group;
(7) a halogen atom (e.g., fluorine atom, chlorine atom, bromine atom); and
(8) a $C_{1-6}$ alkyl group (e.g., methyl, ethyl).

Ring B is a further optionally substituted 4- to 6-membered nitrogen-containing saturated ring.

The "4- to 6-membered nitrogen-containing saturated ring" of the "optionally further substituted 4- to 6-membered nitrogen-containing saturated ring" for ring B is preferably monocyclic and, for example, an azetidine ring, a pyrrolidine ring, and a piperidine ring can be mentioned.

The "4- to 6-membered nitrogen-containing saturated ring" is optionally further substituted by 1-4 (preferably 1-3, more preferably 1 or 2) substituents other than a $R^1R^2N\text{—}C(=O)\text{—}$ ring A-group and a $\text{—}O\text{—}CR^3R^4\text{—}$ group, at substitutable position(s).

Such substituent is preferably a halogen atom (e.g., a fluorine atom) or a $C_{1-6}$ alkyl group (e.g., methyl).

Ring B is preferably an optionally further substituted azetidine ring, an optionally further substituted pyrrolidine ring or an optionally further substituted piperidine ring, more preferably an azetidine ring, a pyrrolidine ring or a piperidine ring, each of which is optionally further substituted by 1-4 (preferably 1-3, more preferably 1 or 2) substituents selected from a halogen atom (e.g., a fluorine atom) and a $C_{1-6}$ alkyl group (e.g., methyl), further preferably (1) an azetidine ring, (2) a pyrrolidine ring or (3) a piperidine ring optionally further substituted by 1-4 (preferably 1-3, more preferably 1 or 2) substituents selected from a halogen atom (e.g., a fluorine atom) and a $C_{1-6}$ alkyl group (e.g., methyl).

Ring B is particularly preferably a piperidine ring.

X is $\text{—}N=$ or $\text{—}CH=$.

X is preferably $\text{—}N=$.

$R^1$ and $R^2$ are each independently a hydrogen atom or a substituent.

The "substituent" for $R^1$ or $R^2$ is preferably an optionally substituted $C_{1-8}$ alkyl group (e.g., methyl, ethyl, propyl, isopropyl, butyl, isobutyl, 1-methylpropyl, isopentyl, neopentyl, 1,1-dimethylpropyl, 1,2-dimethylpropyl, 1-ethylpropyl, 2-methylbutyl, hexyl, neohexyl, 1,2,2-trimethylpropyl, 2,2-dimethylbutyl, 1-ethyl-1-methylbutyl), an optionally substituted $C_{3-10}$ cycloalkyl group (e.g., cyclopropyl, cyclobutyl, cyclopentyl, cyclohexyl), an optionally substituted $C_{6-14}$ aryl group (e.g., phenyl), an optionally substituted aromatic heterocyclic group (e.g., pyrazolyl, oxazolyl, pyridyl, pyrimidinyl, pyrazinyl, pyridazinyl), an optionally substituted nonaromatic heterocyclic group (e.g., piperidinyl, tetrahydrofuranyl, dihydropyridinyl, tetrahydropyranyl, tetrahydrothiopyranyl, dihydroindenyl), an optionally substituted $C_{1-6}$ alkylsulfonyl group (e.g., neopentylsulfonyl) or an optionally substituted $C_{1-6}$ alkyl-carbonylamino group (e.g., tert-butylcarbonylamino).

The "$C_{1-8}$ alkyl group" of the "optionally substituted $C_{1-8}$ alkyl group" is optionally substituted by 1-5 (preferably 1-3, more preferably 1 or 2) substituents, at substitutable position(s).

The substituent is preferably (1) cyano, (2) hydroxy, (3) a $C_{3-10}$ cycloalkyl group (e.g., cyclopropyl, cyclobutyl, cyclohexyl, cycloheptyl, bicyclo[2.2.1]heptyl) optionally substituted by 1 to 3 substituents selected from a halogen atom (e.g., a fluorine atom) and a $C_{1-6}$ alkyl group (e.g., methyl), (4) a $C_{1-6}$ alkoxy group (e.g., methoxy, ethoxy, isopropoxy) optionally substituted by 1 to 3 halogen atoms (a fluorine atom), (5) a $C_{6-14}$ aryl group (e.g., phenyl) optionally substituted by 1 to 3 halogen atoms (e.g., a fluorine atom, a chlorine atom), (6) an aromatic heterocyclic group (e.g., pyridyl, pyrimidinyl), (7) a nonaromatic heterocyclic group (e.g., piperidinyl, tetrahydropyranyl), (8) a $C_{1-6}$ alkylsulfonyl group (e.g., methylsulfonyl), (9) a mono- or di-$C_{1-6}$ alkyl-amino group (e.g., ethylamino) optionally substituted by 1 to 3 halogen atoms (e.g., a fluorine atom) or (10) a halogen atom (e.g., a fluorine atom).

The "$C_{3-10}$ cycloalkyl group" of the "optionally substituted $C_{3-10}$ cycloalkyl group" is optionally substituted by 1-5 (preferably 1-3, more preferably 1 or 2) substituents, at substitutable position(s).

Examples of such substituent include the above-mentioned "substituent". When the number of the substituents is not less than 2, the respective substituents may be the same or different. The substituent is preferably a halogen atom (e.g., fluorine atom).

The "$C_{6-14}$ aryl group" of the "optionally substituted $C_{6-14}$ aryl group" is optionally substituted by 1-5 (preferably 1-3, more preferably 1 or 2) substituents, at substitutable position(s).

The substituent is preferably (1) cyano, (2) a halogen atom (e.g., a fluorine atom, a chlorine atom) or (3) a $C_{1-6}$ alkyl group (e.g., methyl).

The "aromatic heterocyclic group" of the "optionally substituted aromatic heterocyclic group" is optionally substituted by 1-5 (preferably 1-3, more preferably 1 or 2) substituents, at substitutable position(s).

The substituent is preferably (1) cyano, (2) a halogen atom (e.g., a fluorine atom, a chlorine atom), (3) a $C_{1-6}$ alkyl group (e.g., methyl) optionally substituted by 1 to 3 halogen atoms (e.g., a fluorine atom), (4) a $C_{3-10}$ cycloalkyl group (e.g., cyclopropyl), (5) a $C_{1-6}$ alkoxy group (e.g., methoxy), (6) a nitrogen-containing heterocyclyl-carbonyl group (e.g., pyrrolidinylcarbonyl) or (7) a mono- or di-$C_{1-6}$ alkyl-carbamoyl group (e.g., neopentylcarbamoyl).

The "nonaromatic heterocyclic group" of the "optionally substituted nonaromatic heterocyclic group" is optionally substituted by 1-5 (preferably 1-3, more preferably 1 or 2) substituents, at substitutable position(s).

The substituent is preferably (1) a $C_{1-6}$ alkyl group (e.g., ethyl) optionally substituted by 1 to 3 halogen atoms (e.g., a fluorine atom), (2) a $C_{7-16}$ aralkyl group (e.g., benzyl) or (3) oxo.

$R^1$ and $R^2$ are preferably and each independently
(A) a hydrogen atom,
(B) a $C_{1-8}$ alkyl group (e.g., methyl, ethyl, propyl, isopropyl, butyl, isobutyl, 1-methylpropyl, isopentyl, neopentyl, 1,1-dimethylpropyl, 1,2-dimethylpropyl, 1-ethylpropyl, 2-methylbutyl, hexyl, neohexyl, 1,2,2-trimethylpropyl, 2,2-dimethylbutyl, 1-ethyl-1-methylbutyl) optionally substituted by 1-5 (preferably 1-3, more preferably 1 or 2) substituents selected from (1) cyano, (2) hydroxy, (3) a $C_{3-10}$ cycloalkyl group (e.g., cyclopropyl, cyclobutyl, cyclohexyl, cycloheptyl, bicyclo[2.2.1]heptyl) optionally substituted by 1 to 3 substituents selected from a halogen atom (e.g., a fluorine atom) and a $C_{1-6}$ alkyl group (e.g., methyl), (4) a $C_{1-6}$ alkoxy group (e.g., methoxy, ethoxy, isopropoxy) optionally substituted by 1 to 3 halogen atoms (a fluorine atom), (5) a $C_{6-14}$ aryl group (e.g., phenyl) optionally substituted by 1 to 3 halogen atoms (e.g., a fluorine atom, a chlorine atom), (6) an aromatic heterocyclic group (e.g., pyridyl, pyrimidinyl), (7) a nonaromatic heterocyclic group (e.g., piperidinyl, tetrahydropyranyl), (8) a $C_{1-6}$ alkylsulfonyl group (e.g., methylsulfonyl), (9) a mono- or di-$C_{1-6}$ alkyl-amino group (e.g., ethylamino) optionally substituted by 1 to 3 halogen atoms (e.g., a fluorine atom) and (10) a halogen atom (e.g., a fluorine atom),
(C) a $C_{3-10}$ cycloalkyl group (e.g., cyclopropyl, cyclobutyl, cyclopentyl, cyclohexyl) optionally substituted by 1-5 (preferably 1-3, more preferably 1 or 2) halogen atoms (e.g., a fluorine atom),
(D) a $C_{6-14}$ aryl group (e.g., phenyl) optionally substituted by 1-5 (preferably 1-3, more preferably 1 or 2) substituents selected from (1) cyano, (2) a halogen atom (e.g., a fluorine atom, a chlorine atom) and (3) a $C_{1-6}$ alkyl group (e.g., methyl), (E) an aromatic heterocyclic group (e.g., pyrazolyl, oxazolyl, pyridyl, pyrimidinyl, pyrazinyl, pyridazinyl) optionally substituted by 1-5 (preferably 1-3, more preferably 1 or 2) substituents selected from (1) cyano, (2) a halogen atom (e.g., a fluorine atom, a chlorine atom), (3) a $C_{1-6}$ alkyl group (e.g., methyl) optionally substituted by 1 to 3 halogen atoms (e.g., a fluorine atom), (4) a $C_{3-10}$ cycloalkyl group (e.g., cyclopropyl), (5) a $C_{1-6}$ alkoxy group (e.g., methoxy), (6) a nitrogen-containing heterocyclyl-carbonyl group (e.g., pyrrolidinylcarbonyl) and (7) a mono- or di-$C_{1-6}$ alkyl-carbamoyl group (e.g., neopentylcarbamoyl),
(F) a nonaromatic heterocyclic group (e.g., piperidinyl, tetrahydrofuranyl, dihydropyridinyl, tetrahydropyranyl, tetrahydrothiopyranyl, dihydroindenyl) optionally substituted by 1-5 (preferably 1-3, more preferably 1 or 2) substituents selected from (1) a $C_{1-6}$ alkyl group (e.g., ethyl) optionally substituted by 1 to 3 halogen atoms (e.g., a fluorine atom), (2) a $C_{7-16}$ aralkyl group (e.g., benzyl) and (3) oxo,
(G) a $C_{1-6}$ alkylsulfonyl group (e.g., neopentylsulfonyl) or
(H) a $C_{1-6}$ alkyl-carbonylamino group (e.g., tert-butylcarbonylamino).

$R^1$ and $R^2$ are more preferably
(i) a $C_{1-8}$ alkyl group (e.g., methyl, ethyl, propyl, isopropyl, butyl, isobutyl, 1-methylpropyl, isopentyl, neopentyl, 1,1-dimethylpropyl, 1,2-dimethylpropyl, 1-ethylpropyl, 2-methylbutyl, hexyl, neohexyl, 1,2,2-trimethylpropyl, 2,2-dimethylbutyl, 1-ethyl-1-methylbutyl) optionally substituted by 1-5 (preferably 1-3, more preferably 1 or 2) substituents selected from (1) cyano, (2) hydroxy, (3) a $C_{3-10}$ cycloalkyl group (e.g., cyclopropyl, cyclobutyl, cyclohexyl, cycloheptyl, bicyclo[2.2.1]heptyl) optionally substituted by 1 to 3 substituents selected from a halogen atom (e.g., a fluorine atom) and a $C_{1-6}$ alkyl group (e.g., methyl), (4) a $C_{1-6}$ alkoxy group (e.g., methoxy, ethoxy, isopropoxy) optionally substituted by 1 to 3 halogen atoms (a fluorine atom), (5) a $C_{6-14}$ aryl group (e.g., phenyl) optionally substituted by 1 to 3 halogen atoms (e.g., a fluorine atom, a chlorine atom), (6) an aromatic heterocyclic group (e.g., pyridyl, pyrimidinyl), (7) a nonaromatic heterocyclic group (e.g., piperidinyl, tetrahydropyranyl), (8) a $C_{1-6}$ alkylsulfonyl group (e.g., methylsulfonyl), (9) a mono- or di-$C_{1-6}$ alkyl-amino group (e.g., ethylamino) optionally substituted by 1 to 3 halogen atoms (e.g., a fluorine atom) and (10) a halogen atom (e.g., a fluorine atom), or
(ii) an aromatic heterocyclic group (e.g., pyrazolyl, oxazolyl, pyridyl, pyrimidinyl, pyrazinyl, pyridazinyl) optionally substituted by 1-5 (preferably 1-3, more preferably 1 or 2) substituents selected from (1) cyano, (2) a halogen atom (e.g., a fluorine atom, a chlorine atom), (3) a $C_{1-6}$ alkyl group (e.g., methyl) optionally substituted by 1 to 3 halogen atoms (e.g., a fluorine atom), (4) a $C_{3-10}$ cycloalkyl group (e.g., cyclopropyl), (5) a $C_{1-6}$ alkoxy group (e.g., methoxy), (6) a nitrogen-containing heterocyclyl-carbonyl group (e.g., pyrrolidinylcarbonyl) and (7) a mono- or di-$C_{1-6}$ alkyl-carbamoyl group (e.g., neopentylcarbamoyl).

$R^1$ and $R^2$ are particularly preferably
(i) a $C_{1-8}$ alkyl group (e.g., methyl, ethyl, propyl, isopropyl, butyl, isobutyl, 1-methylpropyl, isopentyl, neopentyl, 1,1-dimethylpropyl, 1,2-dimethylpropyl, 1-ethylpropyl, 2-methylbutyl, hexyl, neohexyl, 1,2,2-trimethylpropyl, 2,2-dimethylbutyl, 1-ethyl-1-methylbutyl) optionally substituted by 1-5 (preferably 1-3, more preferably 1 or 2) substituents selected from
(1) cyano, (2) hydroxy, (3) a $C_{3-10}$ cycloalkyl group (e.g., cyclopropyl, cyclobutyl, cyclohexyl, cycloheptyl, bicyclo[2.2.1]heptyl) optionally substituted by 1 to 3 substituents selected from a halogen atom (e.g., fluorine atom) and a $C_{1-6}$ alkyl group (e.g., methyl), (4) a $C_{1-6}$ alkoxy group (e.g., methoxy, ethoxy, isopropoxy) optionally substituted by 1 to 3 halogen atoms (fluorine atom), (5) a $C_{6-14}$ aryl group (e.g., phenyl) optionally substituted 1 to 3 halogen atoms (e.g., fluorine atom, chlorine atom), (6) a 5- or 6-membered monocyclic aromatic heterocyclic group (e.g., pyridyl, pyrimidinyl), (7) a 3- to 8-membered monocyclic nonaromatic heterocyclic group (e.g., piperidinyl, tetrahydropyranyl), (8) a $C_{1-6}$ alkylsulfonyl group (e.g., methylsulfonyl), (9) a mono- or di-$C_{1-6}$ alkyl-amino group (e.g., ethylamino) optionally substituted by 1 to 3 halogen atoms (e.g., fluorine atom) and (10) a halogen atom (e.g., fluorine atom), or (ii) a 5- or 6-membered monocyclic aromatic heterocyclic group (e.g., pyrazolyl, oxazolyl, pyridyl, pyrimidinyl, pyrazinyl, pyridazinyl) optionally substituted by 1-5 (preferably 1-3, more preferably 1 or 2) substituents selected from (1) cyano, (2) a halogen atom (e.g., fluorine atom, chlorine atom), (3) a $C_{1-6}$ alkyl group (e.g., methyl) optionally substituted by 1 to 3 halogen atoms (e.g., fluorine atom), (4) a $C_{3-10}$ cycloalkyl group (e.g., cyclopropyl), (5) a $C_{1-6}$ alkoxy group (e.g., methoxy), (6) a nitrogen-containing heterocyclyl-carbonyl group (e.g., pyrrolidinylcarbonyl) and (7) a mono- or di-$C_{1-6}$ alkyl-carbamoyl group (e.g., neopentylcarbamoyl).

$R^1$ and $R^2$ are optionally bonded to each other to form an optionally substituted 3- to 10-membered ring together with the adjacent nitrogen atom.

Examples of the "3- to 10-membered ring" of the "optionally substituted 3- to 10-membered ring" which $R^1$ and $R^2$ form include a 3- to 10-membered monocyclic non-aromatic heterocycle (e.g., a pyrrolidine ring, a piperidine ring, a piperazine ring, a morpholine ring), and a 3- to 10-membered fused bicyclic non-aromatic heterocycle (e.g., a dihydroindole ring, a dihydrobenzoxazine ring).

The "3- to 10-membered ring" is optionally substituted by 1-5 (preferably 1-3, more preferably 1 or 2) substituents, at substitutable position(s).

The substituent is preferably (1) cyano, (2) a halogen atom (e.g., a fluorine atom), (3) a $C_{1-6}$ alkyl group (e.g., methyl, propyl, isobutyl, tert-butyl) optionally substituted by 1 to 3 substituents selected from a halogen atom (e.g., a fluorine atom) and a $C_{6-14}$ aryl group (e.g., phenyl), (4) a $C_{1-6}$ alkoxy group (e.g., methoxy) or (5) a $C_{6-14}$ aryl group (e.g., phenyl).

The optionally substituted 3- to 10-membered ring formed by $R^1$ and $R^2$, which are bonded to each other, together with the adjacent nitrogen atom, is preferably (A) a 3- to 10-membered monocyclic non-aromatic heterocycle (e.g., pyrrolidine ring, piperidine ring, piperazine ring, morpholine ring) optionally substituted by 1-5 (preferably 1-3, more preferably 1 or 2) substituents selected from (1) cyano, (2) a halogen atom (e.g., a fluorine atom), (3) a $C_{1-6}$ alkyl group (e.g., methyl, propyl, isobutyl, tert-butyl) optionally substituted by 1 to 3 substituents selected from a halogen atom (e.g., a fluorine atom) and a $C_{6-14}$ aryl group (e.g., phenyl), (4) a $C_{1-6}$ alkoxy group (e.g., methoxy) and (5) a $C_{6-14}$ aryl group (e.g., phenyl) or (B) a 3- to 10-membered fused bicyclic non-aromatic heterocycle (e.g., a dihydroindole ring, a dihydrobenzoxazine ring).

$R^3$ and $R^4$ are each independently a hydrogen atom, a halogen atom or a $C_{1-6}$ alkyl group.

$R^3$ and $R^4$ are preferably each independently a hydrogen atom or a $C_{1-6}$ alkyl group (e.g., methyl), more preferably, each independently a hydrogen atom or methyl.

$R^3$ and $R^4$ are particularly preferably hydrogen atoms.

$R^5$, $R^7$, $R^8$ and $R^9$ are each independently a hydrogen atom, a halogen atom, a $C_{1-6}$ alkyl group or a $C_{1-6}$ alkoxy group.

$R^5$ is preferably a hydrogen atom or a halogen atom (e.g., a fluorine atom), more preferably a hydrogen atom or a fluorine atom.

$R^5$ is further preferably a hydrogen atom.

$R^7$ is preferably a hydrogen atom or a $C_{1-6}$ alkyl group (e.g., methyl), more preferably a hydrogen atom or methyl.

$R^7$ is further preferably a hydrogen atom.

$R^8$ and $R^9$ are preferably hydrogen atoms.

In one embodiment of the present invention, $R^3$, $R^4$, $R^5$, $R^7$, $R^8$ and $R^9$ are preferably hydrogen atoms.

$R^6$ is a halogen atom, an optionally substituted $C_{1-6}$ alkyl group, an optionally substituted $C_{1-6}$ alkoxy group or an optionally substituted $C_{3-10}$ cycloalkyl group.

The "$C_{1-6}$ alkyl group", "$C_{1-6}$ alkoxy group" and "$C_{3-10}$ cycloalkyl group" are optionally substituted by 1-5 (preferably 1-3, more preferably 1 or 2) substituents, at substitutable position(s).

The substituent is preferably a $C_{1-6}$ alkoxy group (e.g., methoxy).

$R^6$ is preferably a $C_{1-6}$ alkyl group (e.g., methyl) optionally substituted by a $C_{1-6}$ alkoxy group (e.g., methoxy), a $C_{1-6}$ alkoxy group (e.g., methoxy, ethoxy) or a $C_{3-10}$ cycloalkyl group (e.g., cyclopropyl). $R^6$ is more preferably a $C_{3-10}$ cycloalkyl group (e.g., cyclopropyl).

$R^6$ and $R^7$ are optionally bonded to each other to form, together with the adjacent nitrogen atom, an optionally substituted 3- to 10-membered ring.

Here, as the "3- to 10-membered ring", a 3- to 10-membered monocyclic non-aromatic heterocycle (e.g., an oxetane ring) is preferable.

The "3- to 10-membered ring" is optionally substituted by 1-5 (preferably 1-3, more preferably 1 or 2) substituents, at substitutable position(s).

The optionally substituted 3- to 10-membered ring, which is formed by $R^6$ and $R^7$ bonded to each other together with the adjacent carbon atom is preferably a 3- to 10-membered monocyclic non-aromatic heterocycle (e.g., an oxetane ring).

Preferable examples of compound (I) include the following compounds.

[Compound I-1]

Compound (I) wherein ring A is an optionally further substituted benzene ring or an optionally further substituted pyridine ring;

Ring B is an optionally further substituted azetidine ring, an optionally further substituted pyrrolidine ring or an optionally further substituted piperidine ring;

$R^1$ and $R^2$ are each independently a hydrogen atom, an optionally substituted $C_{1-6}$ alkyl group (e.g., methyl, ethyl, propyl, isopropyl, butyl, isobutyl, 1-methylpropyl, isopentyl, neopentyl, 1,1-dimethylpropyl, 1,2-dimethylpropyl, 1-ethylpropyl, 2-methylbutyl, hexyl, neohexyl, 1,2,2-trimethylpropyl, 2,2-dimethylbutyl, 1-ethyl-1-methylbutyl), an optionally substituted $C_{3-10}$ cycloalkyl group (e.g., cyclopropyl, cyclobutyl, cyclopentyl, cyclohexyl), an optionally substituted $C_{6-14}$ aryl group (e.g., phenyl), an optionally substituted aromatic heterocyclic group (e.g., pyrazolyl, oxazolyl, pyridyl, pyrimidinyl, pyrazinyl, pyridazinyl), an optionally substituted nonaromatic heterocyclic group (e.g., piperidinyl, tetrahydrofuranyl, dihydropyridinyl, tetrahydropyranyl, tetrahydrothiopyranyl, dihydroindenyl), an optionally substituted $C_{1-6}$ alkylsulfonyl group (e.g., neopentylsulfonyl) or an optionally substituted $C_{1-6}$ alkyl-carbonylamino group (e.g., tert-butylcarbonylamino);

or, $R^1$ and $R^2$ are bonded to each other to form an optionally substituted 3- to 10-membered monocyclic non-aromatic heterocycle (e.g., a pyrrolidine ring, a piperidine ring, a piperazine ring, a morpholine ring) or an optionally substituted 3- to 10-membered fused bicyclic non-aromatic heterocycle (e.g., a dihydroindole ring, a dihydrobenzoxazine ring) together with the adjacent nitrogen atom;

$R^3$ and $R^4$ are each independently a hydrogen atom or a $C_{1-6}$ alkyl group (e.g., methyl);

$R^5$ is a hydrogen atom or a halogen atom (e.g., a fluorine atom);

$R^6$ is an optionally substituted $C_{1-6}$ alkyl group (e.g., methyl), an optionally substituted $C_{1-6}$ alkoxy group (e.g., methoxy, ethoxy) or an optionally substituted $C_{3-10}$ cycloalkyl group (e.g., cyclopropyl);

$R^7$ is a hydrogen atom or a $C_{1-6}$ alkyl group (e.g., methyl);

or, $R^6$ and $R^7$ are bonded to each other to form an optionally substituted 3- to 10-membered monocyclic non-aromatic heterocycle (e.g., an oxetane ring) together with the adjacent carbon atom; and $R^8$ and $R^9$ is a hydrogen atom.

[Compound I-2]

Compound (I) wherein ring A is a benzene ring or a pyridine ring each optionally further substituted by 1-4 (preferably 1-3, more preferably 1 or 2) substituents selected from (1) a $C_{1-6}$ alkylsulfonyl group (e.g., methylsulfonyl);
(2) a carbamoyl group;
(3) a hydroxy group;
(4) a $C_{1-6}$ alkoxy group (e.g., methoxy) optionally substituted by 1 to 3 halogen atoms (e.g., a fluorine atom);
(5) a $C_{1-6}$ alkylthio group (e.g., methylthio);
(6) a cyano group;
(7) a halogen atom (e.g., a fluorine atom, a chlorine atom, a bromine atom); and
(8) a $C_{1-6}$ alkyl group (e.g., methyl, ethyl);

ring B is an azetidine ring, a pyrrolidine ring or a piperidine ring each optionally further substituted by 1-4 (preferably 1-3, more preferably 1 or 2) substituents selected from a halogen atom (e.g., a fluorine atom) and a $C_{1-6}$ alkyl group (e.g., methyl);

$R^1$ and $R^2$ are each independently a hydrogen atom, an optionally substituted $C_{1-8}$ alkyl group (e.g., methyl, ethyl, propyl, isopropyl, butyl, isobutyl, 1-methylpropyl, isopentyl, neopentyl, 1,1-dimethylpropyl, 1,2-dimethylpropyl, 1-ethylpropyl, 2-methylbutyl, hexyl, neohexyl, 1,2,2-trimethylpropyl, 2,2-dimethylbutyl, 1-ethyl-1-methylbutyl), an optionally substituted $C_{3-10}$ cycloalkyl group (e.g., cyclopropyl, cyclobutyl, cyclopentyl, cyclohexyl), an optionally substituted $C_{6-14}$ aryl group (e.g., phenyl), an optionally substituted aromatic heterocyclic group (e.g., pyrazolyl, oxazolyl, pyridyl, pyrimidinyl, pyrazinyl, pyridazinyl), an optionally substituted nonaromatic heterocyclic group (e.g., piperidinyl, tetrahydrofuranyl, dihydropyridinyl, tetrahydropyranyl, tetrahydrothiopyranyl, dihydroindenyl), a $C_{1-6}$ alkylsulfonyl group (e.g., neopentylsulfonyl) or a $C_{1-6}$ alkylcarbonylamino group (e.g., tert-butylcarbonylamino);

or, $R^1$ and $R^2$ are bonded to each other to form an optionally substituted 3- to 10-membered monocyclic non-aromatic heterocycle (e.g., a pyrrolidine ring, a piperidine ring, a piperazine ring, a morpholine ring), or a 3- to 10-membered fused bicyclic non-aromatic heterocycle (e.g., a dihydroindole ring, a dihydrobenzoxazine ring), together with the adjacent nitrogen atom;

$R^3$ and $R^4$ are each independently a hydrogen atom or a $C_{1-6}$ alkyl group (e.g., methyl);

$R^5$ is a hydrogen atom or a halogen atom (e.g., a fluorine atom);

$R^6$ is an optionally substituted $C_{1-6}$ alkyl group (e.g., methyl), an optionally substituted $C_{1-6}$ alkoxy group (e.g., methoxy, ethoxy) or an optionally substituted $C_{3-10}$ cycloalkyl group (e.g., cyclopropyl);

$R^7$ is a hydrogen atom or a $C_{1-6}$ alkyl group (e.g., methyl);

or, $R^6$ and $R^7$ are bonded to each other to form an optionally substituted 3- to 10-membered monocyclic non-aromatic heterocycle (e.g., an oxetane ring) together with the adjacent carbon atom; and $R^8$ and $R^9$ are hydrogen atoms.

[Compound I-3]

Compound (I) wherein ring A is a benzene ring optionally further substituted by 1-4 (preferably 1-3, more preferably 1 or 2) substituents selected from (1) a $C_{1-6}$ alkylsulfonyl group (e.g., methylsulfonyl);
(2) a carbamoyl group;
(3) a hydroxy group;
(4) a $C_{1-6}$ alkoxy group (e.g., methoxy) optionally substituted by 1 to 3 halogen atoms (e.g., a fluorine atom);
(5) a $C_{1-6}$ alkylthio group (e.g., methylthio);
(6) a cyano group;
(7) a halogen atom (e.g., a fluorine atom, a chlorine atom, a bromine atom); and
(8) a $C_{1-6}$ alkyl group (e.g., methyl, ethyl), or a pyridine ring optionally further substituted by 1-4 (preferably 1-3, more preferably 1 or 2) substituents selected from (1) a $C_{1-6}$ alkoxy group (e.g., methoxy);
(2) a halogen atom (e.g., a chlorine atom); and
(3) a $C_{1-6}$ alkyl group (e.g., ethyl);

ring B is (1) an azetidine ring, (2) a pyrrolidine ring or (3) a piperidine ring optionally further substituted by 1-4 (preferably 1-3, more preferably 1 or 2) substituents selected from a halogen atom (e.g., a fluorine atom) and a $C_{1-6}$ alkyl group (e.g., methyl);

$R^1$ and $R^2$ are each independently (A) a hydrogen atom,
(B) a $C_{1-8}$ alkyl group (e.g., methyl, ethyl, propyl, isopropyl, butyl, isobutyl, 1-methylpropyl, isopentyl, neopentyl, 1,1-dimethylpropyl, 1,2-dimethylpropyl, 1-ethylpropyl, 2-methylbutyl, hexyl, neohexyl, 1,2,2-trimethylpropyl, 2,2-dimethylbutyl, 1-ethyl-1-methylbutyl) optionally substituted by 1-5 (preferably 1-3, more preferably 1 or 2) substituents selected from (1) cyano, (2) hydroxy, (3) a $C_{3-10}$ cycloalkyl group (e.g., cyclopropyl, cyclobutyl, cyclohexyl, cycloheptyl, bicyclo[2.2.1]heptyl) optionally substituted by 1 to 3 substituents selected from a halogen atom (e.g., a fluorine atom) and a $C_{1-6}$ alkyl group (e.g., methyl), (4) a $C_{1-6}$ alkoxy group (e.g., methoxy, ethoxy, isopropoxy) optionally substituted by 1 to 3 halogen atoms (a fluorine atom), (5) a $C_{6-14}$ aryl group (e.g., phenyl) optionally substituted by 1 to 3 halogen atoms (e.g., a fluorine atom, a chlorine atom), (6) an aromatic heterocyclic group (e.g., pyridyl, pyrimidinyl), (7) a nonaromatic heterocyclic group (e.g., piperidinyl, tetrahydropyranyl), (8) a $C_{1-6}$ alkylsulfonyl group (e.g., methylsulfonyl), (9) a mono- or di-$C_{1-6}$ alkyl-amino group (e.g., ethylamino) optionally substituted by 1 to 3 halogen atoms (e.g., a fluorine atom) and (10) a halogen atom (e.g., a fluorine atom), (C) a $C_{3-10}$ cycloalkyl group (e.g., cyclopropyl, cyclobutyl, cyclopentyl, cyclohexyl) optionally substituted by 1-5 (preferably 1-3, more preferably 1 or 2) halogen atoms (e.g., a fluorine atom), (D) a $C_{6-14}$ aryl group (e.g., phenyl) optionally substituted by 1-5 (preferably 1-3, more preferably 1 or 2) substituents selected from (1) cyano, (2) a halogen atom (e.g., a fluorine atom, a chlorine atom) and (3) a $C_{1-6}$ alkyl group (e.g., methyl), (E) an aromatic heterocyclic group (e.g., pyrazolyl, oxazolyl, pyridyl, pyrimidinyl, pyrazinyl, pyridazinyl) optionally substituted by 1-5 (preferably 1-3, more preferably 1 or 2) substituents selected from (1) cyano, (2) a halogen atom (e.g., a fluorine atom, a chlorine atom), (3) a $C_{1-6}$ alkyl group (e.g., methyl) optionally substituted by 1 to 3 halogen atoms (e.g., a fluorine atom), (4) a $C_{3-10}$ cycloalkyl group (e.g., cyclopropyl), (5) a $C_{1-6}$ alkoxy group (e.g., methoxy), (6) a nitrogen-containing heterocyclyl-carbonyl group (e.g., pyrrolidinylcarbonyl) and (7) a mono- or di-$C_{1-6}$ alkyl-carbamoyl group (e.g., neopentylcarbamoyl),
(F) a nonaromatic heterocyclic group (e.g., piperidinyl, tetrahydrofuranyl, dihydropyridinyl, tetrahydropyranyl, tetrahydrothiopyranyl, dihydroindenyl) optionally substituted by 1-5 (preferably 1-3, more preferably 1 or 2) substituents selected from (1) a $C_{1-6}$ alkyl group (e.g., ethyl) optionally substituted by 1 to 3 halogen atoms (e.g., a fluorine atom), (2) a $C_{7-16}$ aralkyl group (e.g., benzyl) and (3) oxo,
(G) a $C_{1-6}$ alkylsulfonyl group (e.g., neopentylsulfonyl) or
(H) a $C_{1-6}$ alkyl-carbonylamino group (e.g., tert-butylcarbonylamino);

or, $R^1$ and $R^2$ are bonded to each other to form (A) a 3- to 10-membered monocyclic non-aromatic heterocycle (e.g., pyrrolidine ring, piperidine ring, piperazine ring, morpholine ring) optionally substituted by 1-5 (preferably 1-3, more preferably 1 or 2) substituents selected from (1) cyano, (2) a halogen atom (e.g., a fluorine atom), (3) a $C_{1-6}$ alkyl group (e.g., methyl, propyl, isobutyl, tert-butyl) optionally substituted by 1 to 3 substituents selected from a halogen atom (e.g., a fluorine atom) and a $C_{6-14}$ aryl group (e.g., phenyl), (4) a $C_{1-6}$ alkoxy group (e.g., methoxy) and (5) a $C_{6-14}$ aryl group (e.g., phenyl) or (B) a 3- to 10-membered fused bicyclic non-aromatic heterocycle (e.g., a dihydroindole ring, a dihydrobenzoxazine ring), together with the adjacent nitrogen atom;

$R^3$ and $R^4$ are each independently a hydrogen atom or methyl;

$R^5$ is a hydrogen atom or a fluorine atom;

$R^6$ is a $C_{1-6}$ alkyl group (e.g., methyl) optionally substituted by a $C_{1-6}$ alkoxy group (e.g., methoxy), a $C_{1-6}$ alkoxy group (e.g., methoxy, ethoxy) or a $C_{1-10}$ cycloalkyl group (e.g., cyclopropyl);

$R^7$ is a hydrogen atom or methyl;

or, $R^6$ and $R^7$ are bonded to each other to form a 3- to 10-membered monocyclic non-aromatic heterocycle (e.g., an oxetane ring) together with the adjacent carbon atom; and $R^8$ and $R^9$ are hydrogen atoms.

[Compound I-4]

Compound (I) wherein ring A is a benzene ring optionally further substituted by 1-4 (preferably 1-3, more preferably 1 or 2) substituents selected from
(1) a $C_{1-6}$ alkylsulfonyl group (e.g., methylsulfonyl);
(2) a carbamoyl group;
(3) a hydroxy group;
(4) a $C_{1-6}$ alkoxy group (e.g., methoxy) optionally substituted by 1 to 3 halogen atoms (e.g., a fluorine atom);
(5) a $C_{1-6}$ alkylthio group (e.g., methylthio);
(6) a cyano group;
(7) a halogen atom (e.g., a fluorine atom, a chlorine atom, a bromine atom); and
(8) a $C_{1-6}$ alkyl group (e.g., methyl, ethyl), or a pyridine ring optionally further substituted by 1-4 (preferably 1-3, more preferably 1 or 2) substituents selected from
(1) a $C_{1-6}$ alkoxy group (e.g., methoxy);
(2) a halogen atom (e.g., a chlorine atom); and
(3) a $C_{1-6}$ alkyl group (e.g., ethyl);

ring B is (1) an azetidine ring, (2) a pyrrolidine ring or (3) a piperidine ring optionally further substituted by 1-4 (preferably 1-3, more preferably 1 or 2) substituents selected from a halogen atom (e.g., a fluorine atom) and a $C_{1-6}$ alkyl group (e.g., methyl);

$R^1$ and $R^2$ are each independently
(i) a $C_{1-8}$ alkyl group (e.g., methyl, ethyl, propyl, isopropyl, butyl, isobutyl, 1-methylpropyl, isopentyl, neopentyl, 1,1-dimethylpropyl, 1,2-dimethylpropyl, 1-ethylpropyl, 2-methylbutyl, hexyl, neohexyl, 1,2,2-trimethylpropyl, 2,2-dimethylbutyl, 1-ethyl-1-methylbutyl) optionally substituted by 1-5 (preferably 1-3, more preferably 1 or 2) substituents selected from (1) cyano, (2) hydroxy, (3) a $C_{3-10}$ cycloalkyl group (e.g., cyclopropyl, cyclobutyl, cyclohexyl, cycloheptyl, bicyclo[2.2.1]heptyl) optionally substituted by 1 to 3 substituents selected from a halogen atom (e.g., a fluorine atom) and a $C_{1-6}$ alkyl group (e.g., methyl), (4) a $C_{1-6}$ alkoxy group (e.g., methoxy, ethoxy, isopropoxy) optionally substituted by 1 to 3 halogen atoms (a fluorine atom), (5) a $C_{6-14}$ aryl group (e.g., phenyl) optionally substituted by 1 to 3 halogen atoms (e.g., a fluorine atom, a chlorine atom), (6) an aromatic heterocyclic group (e.g., pyridyl, pyrimidinyl), (7) a nonaromatic heterocyclic group (e.g., piperidinyl, tetrahydropyranyl), (8) a $C_{1-6}$ alkylsulfonyl group (e.g., methylsulfonyl), (9) a mono- or di-$C_{1-6}$ alkyl-amino group (e.g., ethylamino) optionally substituted by 1 to 3 halogen atoms (e.g., a fluorine atom) and (10) a halogen atom (e.g., a fluorine atom), or
(ii) an aromatic heterocyclic group (e.g., pyrazolyl, oxazolyl, pyridyl, pyrimidinyl, pyrazinyl, pyridazinyl) optionally substituted by 1-5 (preferably 1-3, more preferably 1 or 2) substituents selected from (1) cyano, (2) a halogen atom (e.g., a fluorine atom, a chlorine atom), (3) a $C_{1-6}$ alkyl group (e.g., methyl) optionally substituted by 1 to 3 halogen atoms (e.g., a fluorine atom), (4) a $C_{3-10}$ cycloalkyl group (e.g., cyclopropyl), (5) a $C_{1-6}$ alkoxy group (e.g., methoxy), (6) a nitrogen-containing heterocyclyl-carbonyl group (e.g., pyrrolidinylcarbonyl) and (7) a mono- or di-$C_{1-6}$ alkyl-carbamoyl group (e.g., neopentylcarbamoyl);

$R^3$ and $R^4$ are each independently a hydrogen atom or methyl;

$R^5$ is a hydrogen atom or a fluorine atom;

$R^6$ is a $C_{3-10}$ cycloalkyl group (e.g., cyclopropyl);

$R^7$ is a hydrogen atom or methyl; and $R^8$ and $R^9$ are hydrogen atoms.

[Compound I-5]

Compound (I) wherein ring A is a benzene ring optionally further substituted by 1-4 (preferably 1-3, more preferably 1 or 2) substituents selected from
(1) a $C_{1-6}$ alkylsulfonyl group (e.g., methylsulfonyl);
(2) a carbamoyl group;
(3) a hydroxy group;
(4) a $C_{1-6}$ alkoxy group (e.g., methoxy) optionally substituted by 1 to 3 halogen atoms (e.g., a fluorine atom);
(5) a $C_{1-6}$ alkylthio group (e.g., methylthio);
(6) a cyano group;
(7) a halogen atom (e.g., a fluorine atom, a chlorine atom, a bromine atom); and
(8) a $C_{1-6}$ alkyl group (e.g., methyl, ethyl);

ring B is (1) an azetidine ring, (2) a pyrrolidine ring or (3) a piperidine ring optionally further substituted by 1-4 (preferably 1-3, more preferably 1 or 2) substituents selected from a halogen atom (e.g., a fluorine atom) and a $C_{1-6}$ alkyl group (e.g., methyl);

X is —N=;

$R^1$ and $R^2$ are each independently
(i) a $C_{1-8}$ alkyl group (e.g., methyl, ethyl, propyl, isopropyl, butyl, isobutyl, 1-methylpropyl, isopentyl, neopentyl, 1,1-dimethylpropyl, 1,2-dimethylpropyl, 1-ethylpropyl, 2-methylbutyl, hexyl, neohexyl, 1,2,2-trimethylpropyl, 2,2-dimethylbutyl, 1-ethyl-1-methylbutyl) optionally substituted by 1-5 (preferably 1-3, more preferably 1 or 2) substituents selected from (1) cyano, (2) hydroxy, (3) a $C_{3-10}$ cycloalkyl group (e.g., cyclopropyl, cyclobutyl, cyclohexyl, cycloheptyl, bicyclo[2.2.1]heptyl) optionally substituted by 1 to 3 substituents selected from a halogen atom (e.g., a fluorine atom) and a $C_{1-6}$ alkyl group (e.g., methyl), (4) a $C_{1-6}$ alkoxy group (e.g., methoxy, ethoxy, isopropoxy) optionally substituted by 1 to 3 halogen atoms (a fluorine atom), (5) a $C_{6-14}$ aryl group (e.g., phenyl) optionally substituted by 1 to 3 halogen atoms (e.g., a fluorine atom, a chlorine atom), (6) an aromatic heterocyclic group (e.g., pyridyl, pyrimidinyl), (7) a nonaromatic heterocyclic group (e.g., piperidinyl, tetrahydropyranyl), (8) a $C_{1-6}$ alkylsulfonyl group (e.g., methylsulfonyl), (9) a mono- or di-$C_{1-6}$ alkyl-amino group (e.g., ethylamino) optionally substituted by 1 to 3 halogen atoms (e.g., a fluorine atom) and (10) a halogen atom (e.g., a fluorine atom) or (ii) an aromatic heterocyclic group (e.g., pyrazolyl, oxazolyl, pyridyl, pyrimidinyl, pyrazinyl, pyridazinyl) optionally substituted by 1-5 (preferably 1-3, more preferably 1 or 2) substituents selected from (1) cyano, (2) a halogen atom (e.g., a fluorine atom, a chlorine atom), (3) a $C_{1-6}$ alkyl group (e.g., methyl) optionally substituted by 1 to 3 halogen atoms (e.g., a fluorine atom), (4) a $C_{3-10}$ cycloalkyl group (e.g., cyclopropyl), (5) a $C_{1-6}$ alkoxy group (e.g., methoxy), (6) a nitrogen-containing heterocyclyl-carbonyl group (e.g., pyrrolidinylcarbonyl) and (7) a mono- or di-$C_{1-6}$ alkyl-carbamoyl group (e.g., neopentylcarbamoyl);

$R^3$ and $R^4$ are hydrogen atoms;
$R^5$ is a hydrogen atom;
$R^6$ is a $C_{3-10}$ cycloalkyl group (e.g., cyclopropyl);
$R^7$ is a hydrogen atom; and
$R^8$ and $R^9$ are hydrogen atoms.

[Compound I-6]
Compound (I) wherein ring A is a benzene ring optionally further substituted by 1-4 (preferably 1-3, more preferably 1 or 2) substituents selected from
(1) a $C_{1-6}$ alkylsulfonyl group (e.g., methylsulfonyl);
(2) a carbamoyl group;
(3) a hydroxy group;
(4) a $C_{1-6}$ alkoxy group (e.g., methoxy) optionally substituted by 1 to 3 halogen atoms (e.g., fluorine atom);
(5) a $C_{1-6}$ alkylthio group (e.g., methylthio);
(6) a cyano group;
(7) a halogen atom (e.g., fluorine atom, chlorine atom, bromine atom); and
(8) a $C_{1-6}$ alkyl group (e.g., methyl, ethyl);
ring B is (1) an azetidine ring, (2) a pyrrolidine ring or (3) a piperidine ring optionally further substituted by 1-4 (preferably 1-3, more preferably 1 or 2) substituents selected from a halogen atom (e.g., fluorine atom) and a $C_{1-6}$ alkyl group (e.g., methyl);
X is —N=;
$R^1$ and $R^2$ are each independently
(i) a $C_{1-8}$ alkyl group (e.g., methyl, ethyl, propyl, isopropyl, butyl, isobutyl, 1-methylpropyl, isopentyl, neopentyl, 1,1-dimethylpropyl, 1,2-dimethylpropyl, 1-ethylpropyl, 2-methylbutyl, hexyl, neohexyl, 1,2,2-trimethylpropyl, 2,2-dimethylbutyl, 1-ethyl-1-methylbutyl) optionally substituted by 1-5 (preferably 1-3, more preferably 1 or 2) substituents selected from
(1) cyano, (2) hydroxy, (3) a $C_{3-10}$ cycloalkyl group (e.g., cyclopropyl, cyclobutyl, cyclohexyl, cycloheptyl, bicyclo[2.2.1]heptyl) optionally substituted by 1 to 3 substituents selected from a halogen atom (e.g., fluorine atom) and a $C_{1-6}$ alkyl group (e.g., methyl), (4) a $C_{1-6}$ alkoxy group (e.g., methoxy, ethoxy, isopropoxy) optionally substituted by 1 to 3 halogen atoms (fluorine atom), (5) a $C_{6-14}$ aryl group (e.g., phenyl) optionally substituted by 1 to 3 halogen atoms (e.g., fluorine atom, chlorine atom), (6) a 5- or 6-membered monocyclic aromatic heterocyclic group (e.g., pyridyl, pyrimidinyl), (7) a 3- to 8-membered monocyclic nonaromatic heterocyclic group (e.g., piperidinyl, tetrahydropyranyl), (8) a $C_{1-6}$ alkylsulfonyl group (e.g., methylsulfonyl), (9) a mono- or di-$C_{1-6}$ alkyl-amino group (e.g., ethylamino) optionally substituted by 1 to 3 halogen atoms (e.g., fluorine atom) and (10) a halogen atom (e.g., fluorine atom), or (ii) a 5- or 6-membered monocyclic aromatic heterocyclic group (e.g., pyrazolyl, oxazolyl, pyridyl, pyrimidinyl, pyrazinyl, pyridazinyl) optionally substituted by 1-5 (preferably 1-3, more preferably 1 or 2) substituents selected from (1) cyano, (2) a halogen atom (e.g., fluorine atom, chlorine atom), (3) a $C_{1-6}$ alkyl group (e.g., methyl) optionally substituted by 1 to 3 halogen atoms (e.g., fluorine atom), (4) a $C_{3-10}$ cycloalkyl group (e.g., cyclopropyl), (5) a $C_{1-6}$ alkoxy group (e.g., methoxy), (6) a nitrogen-containing heterocyclyl-carbonyl group (e.g., pyrrolidinylcarbonyl) and (7) a mono- or di-$C_{1-6}$ alkyl-carbamoyl group (e.g., neopentylcarbamoyl);

$R^3$ and $R^4$ are hydrogen atoms;
$R^5$ is a hydrogen atom;
$R^6$ is a $C_{3-10}$ cycloalkyl group (e.g., cyclopropyl);
$R^7$ is a hydrogen atom; and
$R^8$ and $R^9$ are hydrogen atoms.

[Compound I-7]
The aforementioned [compound 1-6] wherein ring B is a piperidine ring.

Specific examples of compound (I) include the compounds of Examples 1-287. Of these,
(3S)-3-cyclopropyl-3-(2-((1-(2-((2,2-dimethylpropyl)(6-methylpyridin-2-yl)carbamoyl)-5-methoxyphenyl)piperidin-4-yl)methoxy)pyridin-4-yl)propanoic acid or a salt thereof (Example 245);
(3S)-3-cyclopropyl-3-(2-((1-(2-((2,2-dimethylpropyl)(4,6-dimethylpyrimidin-2-yl)carbamoyl)-5-methoxyphenyl)piperidin-4-yl)methoxy)pyridin-4-yl)propanoic acid or a salt thereof (Example 246); and
(3S)-3-cyclopropyl-3-(2-((1-(2-((2,2-dimethylpropyl)(pyridin-2-yl)carbamoyl)-5-methoxyphenyl)piperidin-4-yl)methoxy)pyridin-4-yl)propanoic acid or a salt thereof (Example 247)
are preferable.

Examples of salts of compounds represented by the formula (I) include metal salt, ammonium salt, salt with organic base, salt with inorganic acid, salt with organic acid, salt with basic or acidic amino acid and the like.

Preferable examples of the metal salt include alkali metal salts such as sodium salt, potassium salt and the like; alkaline earth metal salts such as calcium salt, magnesium salt, barium salt and the like; aluminum salt and the like.

Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

Preferable examples of the salt with inorganic acid include salt with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like, and preferable examples of the salt with acidic amino acid include salts with aspartic acid, glutamic acid and the like.

Among the above-mentioned salts, a pharmaceutically acceptable salt is preferable.

Compound (I) may be a prodrug.

A prodrug of compound (I) means a compound which is converted to compound (I) with a reaction due to an enzyme, an gastric acid, etc. under the physiological condition in the living body, that is, a compound which is converted to compound (I) by oxidation, reduction, hydrolysis, etc. due to an enzyme; a compound which is converted to compound (I) by hydrolysis etc. due to gastric acid, etc.

Examples of the prodrug of compound (I) include a compound obtained by subjecting amino in compound (I) to an acylation, alkylation or phosphorylation (e.g., a compound obtained by subjecting amino in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting hydroxy in compound (I) to an acylation, alkylation, phosphorylation or boration (e.g., a compound obtained by subjecting hydroxy in compound (I) to an acetylation, palmitoylation, propanoylation, pivaloylation, succinylation, fumarylation, alanylation or dimethylaminomethylcarbonylation); a compound obtained by subjecting carboxy in compound (I) to an esterification or amidation (e.g., a compound obtained by subjecting carboxy in compound (I) to a $C_{1-6}$ alkyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methyl amidation etc.) and the like. Among these, compound (I) wherein carboxy is esterified by $C_{1-6}$ alkyl such as methyl, ethyl, tert-butyl and the like is preferably used. These compounds can be produced from compound (I) according to a method known per se.

A prodrug for compound (I) may also be one which is converted to compound (I) under a physiological condition, such as those described in IYAKUHIN no KAIHATSU, Development of Pharmaceuticals, Vol. 7, Design of Molecules, p. 163-198, Published by HIROKAWA SHOTEN, 1990.

In the present specification, a prodrug may be in the form of a salt. Examples of the salt include those exemplified as the salt of the compound represented by the aforementioned formula (I).

The production method of compound (I) is explained below.

The starting materials and reagents used and the compounds obtained in each step of the following production methods may form each salt. Examples of such salt include those similar to the salts of the aforementioned compound (I) and the like.

When the compound obtained in each step is a free compound, it can be converted to a desired salt by a method known per se. Conversely, when the compound obtained in each step is a salt, it can be converted to a free form or other desired kind of salt by a method known per se.

The compound obtained in each step can also be used for the next reaction in the form of the reaction mixture or after obtaining as a crude product. Alternatively, the compound obtained in each step can be isolated and/or purified from the reaction mixture by a separation means such as concentration, crystallization, recrystallization, distillation, solvent extraction, fractionation, chromatography and the like according to conventional methods.

When the starting materials and reagent compounds in each step are commercially available, such commercially available products can be directly used.

In the reaction of each step, the reaction time may vary depending on the reagent and the solvent to be used. Unless particularly described, it is generally 1 min-48 hr, preferably 10 min-8 hr.

In the reaction of each step, the reaction temperature may vary depending on the reagent and solvent to be used. Unless particularly described, it is generally −78° C.-300° C., preferably −78° C.-150° C.

In the reaction of each step, the pressure may vary depending on the reagent and solvent to be used. Unless particularly described, it is generally 1 atm-20 atm, preferably 1 atm-3 atm.

In the reaction of each step, for example, Microwave synthesis apparatus such as Initiator manufactured by Biotage and the like may be used. The reaction temperature may vary depending on the reagent and solvent to be used. Unless particularly described, it is generally room temperature—300° C., preferably 50° C.-250° C. While the reaction time varies depending on the reagent and solvent to be used, unless particularly described, it is generally 1 min-48 hr, preferably 1 min-8 hr.

In the reaction of each step, unless particularly described, a reagent is used in 0.5 equivalents-20 equivalents, preferably 0.8 equivalents-5 equivalents, relative to the substrate. When a reagent is used as a catalyst, the reagent is used in 0.001 equivalent-1 equivalent, preferably 0.01 equivalent-0.2 equivalent, relative to the substrate. When a reagent also acts as a reaction solvent, the reagent is used in a solvent amount.

In the reaction of each step, unless particularly described, the reaction is performed without solvent, or by dissolving or suspending in a suitable solvent. Specific examples of the solvent include the solvents described in the Examples and the following.

alcohols: methanol, ethanol, tert-butyl alcohol, 2-methoxyethanol and the like;

ethers: diethyl ether, diphenyl ether, tetrahydrofuran, 1,2-dimethoxyethane and the like;

aromatic hydrocarbons: chlorobenzene, toluene, xylene and the like;

saturated hydrocarbons: cyclohexane, hexane and the like;

amides: N,N-dimethylformamide, N-methylpyrrolidone and the like;

halogenated hydrocarbons: dichloromethane, carbon tetrachloride and the like;

nitriles: acetonitrile and the like;

sulfoxides: dimethyl sulfoxide and the like;

aromatic organic bases: pyridine and the like;

acid anhydrides: acetic anhydride and the like;

organic acids: formic acid, acetic acid, trifluoroacetic acid and the like;

inorganic acids: hydrochloric acid, sulfuric acid and the like;

esters: ethyl acetate and the like;

ketones: acetone, methyl ethyl ketone and the like;

water.

Two or more kinds of the above-mentioned solvents may be mixed at an appropriate ratio and used.

When a base is used in the reaction of each step, for example, the bases shown below or the bases described in the Examples are used.

inorganic bases: sodium hydroxide, magnesium hydroxide and the like;

basic salts: sodium carbonate, calcium carbonate, sodium hydrogen carbonate and the like;

organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;

metal alkoxides: sodium ethoxide, potassium tert-butoxide and the like;

alkali metal hydrides: sodium hydride and the like;

metal amides: sodium amide, lithium diisopropylamide, lithium hexamethyldisilazide and the like;

organic lithiums: n-butyllithium and the like.

When an acid or an acidic catalyst is used in the reaction of each step, for example, the acids and acidic catalysts shown below or the acids and acidic catalysts described in the Examples are used.

inorganic acids: hydrochloric acid, sulfuric acid, nitric acid, hydrobromic acid, phosphoric acid and the like;

organic acids: acetic acid, trifluoroacetic acid, citric acid, p-toluenesulfonic acid, 10-camphorsulfonic acid and the like;

Lewis acid: boron trifluoride diethyl ether complex, zinc iodide, anhydrous aluminum chloride, anhydrous zinc chloride, anhydrous iron chloride and the like.

The reaction of each step is, unless otherwise specified, performed by a method known per se, for example, the methods described in the Fifth Series of Experimental Chemistry, vol. 13-vol. 19 (The Chemical Society of Japan ed.); Experimental Chemistry, vol. 14-vol. 15 (The Chemical Society of Japan ed.); Fine Organic Chemistry, rev. 2nd edition (L. F. Tietze, Th. Eicher, NANKODO); rev. Organic Name Reaction (Hideo Togo, Kodansha); ORGANIC SYNTHESES Collective Volume I-VII (John Wiley & Sons Inc); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (Kiyoshi Tomioka, supervisor of translation, KAGAKUDOJIN); Comprehensive Organic Transformations (VCH Publishers Inc.) 1989 and the like, or the methods described in the Examples.

When reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney-nickel; Raney cobalt; hydrogen; formic acid and the like. When carbon-carbon double bond or triple bond is reduced, a method using a catalyst such as palladium-carbon, Lindlar catalyst and the like is available.

When oxidation reaction is performed in each step, examples of the oxidant to be used include peracids such as m-chloroperbenzoic acid (MCPBA), hydrogen peroxide, t-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents having manganese such as manganese dioxide, potassium permanganate and the like; leads such as lead tetraacetate and the like; reagents having chrome such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetraoxide; selenium dioxide; 2,3-dichloro-5,6-dicyano-1,4-benzoquinone (DDQ) and the like.

When radical cyclization reaction is performed in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is performed in each step, examples of the Wittig reagent to be used include alkylidenephosphoranes and the like. Alkylidenephosphoranes can be prepared by a method known per se, for example, by reacting a phosphonium salt and a strong base.

When Horner-Emmons reaction is performed in each step, examples of the reagent to be used include phosphonoacetic acid esters such as methyl dimethylphosphonoacetate, ethyl diethylphosphonoacetate and the like; bases such as alkali metal hydrides, organic lithiums and the like.

When Friedel-Crafts reaction is performed in each step, examples of the reagent to be used include Lewis acid, acid chloride or alkylating agent (e.g., alkyl halides, alcohol, olefins and the like). Alternatively, organic acid or inorganic acid can also be used instead of the Lewis acid, and acid anhydrides such as acetic anhydride and the like can also be used instead of acid chloride.

When aromatic nucleophilic substitution reaction is performed in each step, the reagent includes nucleophilic agent (e.g., amines, imidazole and the like) and base (e.g., basic salts, organic bases and the like).

When nucleophilic addition reaction by carbanion, nucleophilic 1,4-addition reaction by carbanion (Michael addition reaction), or nucleophilic substitution reaction by carbanion is performed in each step, examples of the base to be used for developing carbanion include organic lithium, metal alkoxide, inorganic base, organic base and the like.

When Grignard reaction is performed in each step, examples of the Grignard reagent include arylmagnesium halides such as phenyl magnesium bromide and the like; and alkylmagnesium halides such as methyl magnesium bromide and the like. The Grignard reagent can be prepared by a method known per se, for example, by reacting alkyl halide or aryl halide with metal magnesium using ether or tetrahydrofuran as a solvent.

When Knoevenagel condensation reaction is performed in each step, the reagent includes an active methylene compound (e.g., malonic acid, diethyl malonate, malononitrile and the like) located between two electron-withdrawing groups and a base (e.g., organic bases, metal alkoxides, inorganic bases).

When Vilsmeier-Haack reaction is performed in each step, the reagent includes phosphoryl chloride and amide derivative (e.g., N,N-dimethylformamide and the like).

When azidation reaction of alcohol, alkyl halide, sulfonic acid ester is performed in each step, examples of the azidation agent to be used include diphenylphosphoryl azide (DPPA), trimethylsilylazide, sodium azide and the like. For example, when alcohols is azidated, a method using diphenylphosphoryl azide and 1,8-diazabicyclo[5,4,0]undec-7-ene (DBU), a method using trimethylsilylazide and Lewis acid and the like are used.

When reductive amination reaction is performed in each step, examples of the reducing agent to be used include sodium triacetoxyborohydride, sodium cyanoborohydride, hydrogen, formic acid and the like. When the substrate is an amine compound, the carbonyl compound to be used is para-formaldehyde, aldehydes such as acetaldehyde and the like, or ketones such as cyclohexanone and the like. When the substrate is a carbonyl compound, the amine to be used is primary amine such as ammonia, methylamine and the like; secondary amine such as dimethylamine and the like, or the like.

When Mitsunobu reaction is performed in each step, examples of the reagent include azodicarboxylates (e.g., diethyl azodicarboxylate (DEAD), diisopropyl azodicarboxylate (DIAD) and the like) and triphenylphosphine.

When esterification reaction, amidation reaction, or ureation reaction is performed in each step, examples of the reagent to be used include halogenated acyl forms such as acid chloride, acid bromide and the like; activated carboxylic acids such as acid anhydride, active ester form, sulfuric acid ester form and the like. As an activator of carboxylic acid, carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; or combination thereof and the like can be mentioned. When a carbodiimide condensing agent is used, additives such as 1-hydroxybenzotriazole (HOBt), N-hydroxysuccinimide (HOSu), dimethylaminopyridine (DMAP) and the like may be further added to the reaction.

When coupling reaction is performed in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, palladium (II) acetate and the like; nickel compounds such as tetrakis (triphenylphosphine)nickel (0) and the like; rhodium compounds such as tris(triphenylphosphine)rhodium(III) chloride and the like; cobalt compound; copper compounds such as copper oxide, copper(I) iodide and the like; platinum compound and the like. A base may be further added to the reaction, and examples of such base include inorganic bases, basic salts and the like.

When thiocarbonylation reaction is performed in each step, representative example of the thiocarbonylating agent is diphosphorus pentasulfide. Besides diphosphorus pentasulfide, a reagent having a 1,3,2,4-dithiadiphosphetane-2,4-disulfide structure such as 2,4-bis(4-methoxyphenyl-1,3,2,4-dithiadiphosphetane-2,4-disulfide (Lowesson's reagent) and the like may also be used.

When Wohl-Ziegler reaction is performed in each step, examples of the halogenating agent to be used include N-succinimide, N-bromosuccinimide (NBS), N-chlorosuccinimide (NCS), bromine, sulfuryl chloride and the like. The reaction can be accelerated by adding heat, light, a radical initiator such as benzoyl peroxide, azobisisobutyronitrile and the like to the reaction.

When halogenation reaction of the hydroxy group is performed in each step, examples of the halogenating agent to be used include acid halide of hydrohalic acid and inorganic acid, specifically, hydrochloric acid, thionyl chloride, phosphorus oxychloride and the like for chlorination, and 48% hydrobromic acid and the like for bromination. In addition, a method of obtaining a halogenated alkyl form from alcohol by reacting triphenylphosphine with carbon tetrachloride or carbon tetrabromide and the like may also be used. Alternatively, a method of synthesizing a halogenated alkyl form by two-step reactions including converting alcohol to sulfonic acid ester and reacting same with lithium bromide, lithium chloride or sodium iodide may also be used.

When Arbuzov reaction is performed in each step, examples of the reagent to be used include alkyl halides such as ethyl bromoacetate and the like; phosphites such as triethylphosphite, tri(isopropyl)phosphite and the like.

When sulfonation reaction is performed in each step, examples of the sulfonating agent to be used include methanesulfonyl chloride, p-toluenesulfonyl chloride, methanesulfonic anhydride, p-toluenesulfonic anhydride and the like.

When hydrolysis reaction is performed in each step, examples of the reagent include acid or base. When acid hydrolysis of t-butyl ester is performed, formic acid, triethylsilane and the like may be added to reductively trap by-produced t-butyl cation.

When dehydrating reaction is performed in each step, examples of the dehydrating agent to be used include sulfuric acid, phosphorus pentaoxide, phosphorus oxychloride, N,N'-dicyclohexylcarbodiimide, alumina, polyphosphoric acid and the like.

In the present specification, the protecting group includes protecting group of hydroxyl group of alcohol and the like and phenolic hydroxyl group, protecting group of carbonyl group of aldehyde, protecting group of carbonyl group of ketone, protecting group of carboxyl group, thiol-protecting group, protecting group of amino group, protecting group of aromatic hetero ring such as imidazole, pyrrole, indole and the like, and the like.

Here, ring A, ring B, $R^1$, $R^2$, $R^3$, $R^4$, $R^5$, $R^6$, $R^7$, $R^8$, $R^9$ and X in the formulas in the following reaction schemes are as defined above.

In any step of the production methods shown below, substituent on ring A can be converted to a desired functional group by combining chemical reactions known per se in each production method. The substituent on ring A is not limited as long as it does not influence the reaction. Examples of the chemical reaction include oxidation reaction, reduction reaction, alkylation reaction, acylation reaction, ureation reaction, hydrolysis reaction, amination reaction, esterification reaction, coupling reaction, condensation reaction, deprotection reaction and the like. These reactions are performed according to a method known per se. Examples of such method include the methods described in ORGANIC FUNCTIONAL GROUP PREPARATIONS, 2nd edition, Academic Press (Academic Press Inc.), 1989, or Comprehensive Organic Transformations: A Guide to Functional Group Preparations, 2nd edition, Wiley-VCH, 1999 and the like, and the like.

Compound (I) can be produced from compound (IV) by the method shown in reaction scheme 1.

[reaction scheme 1]

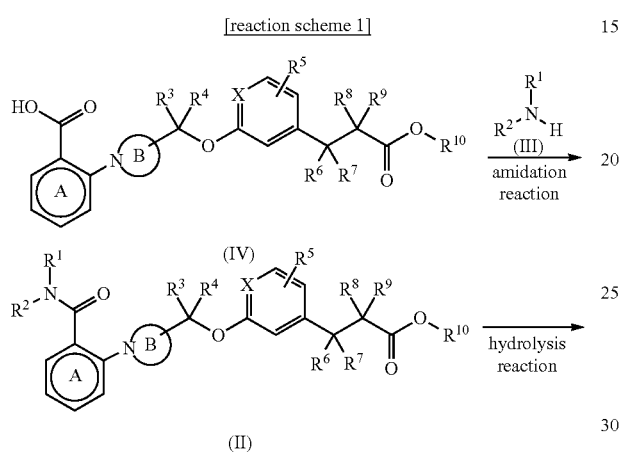

-continued

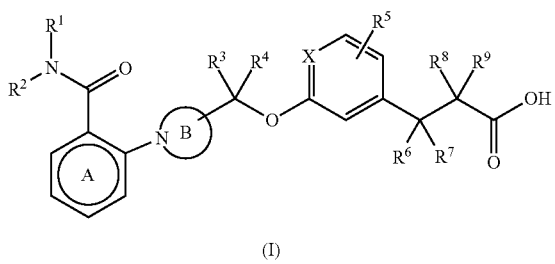

wherein $R^{10}$ is an optionally substituted $C_{1-6}$ alkyl group or an optionally substituted $C_{7-16}$ aralkyl group, and other symbols are as defined above.

In the present specification, the "optionally substituted $C_{7-16}$ aralkyl group" is an "optionally substituted hydrocarbon group" wherein the hydrocarbon group is a "$C_{7-16}$ aralkyl group".

Compound (II) can be produced from compound (IV) by the method shown in reaction scheme 2.

[reaction scheme 2]

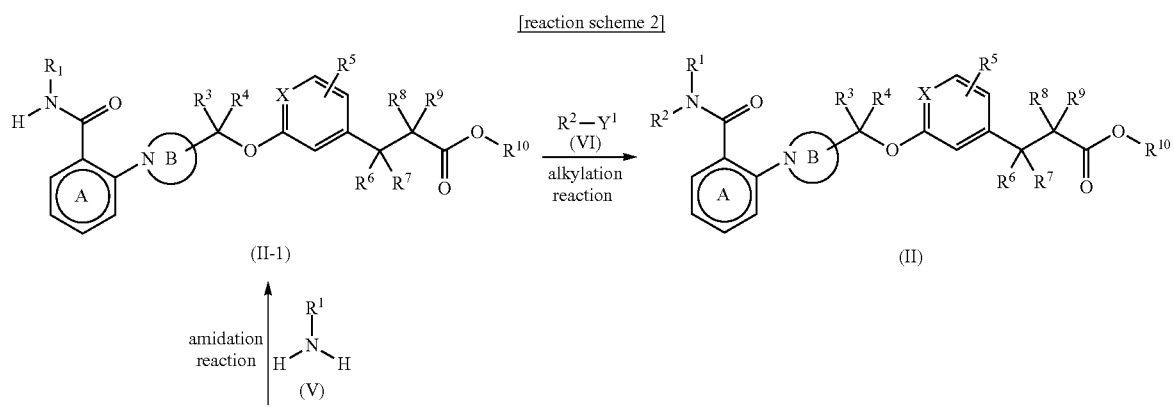

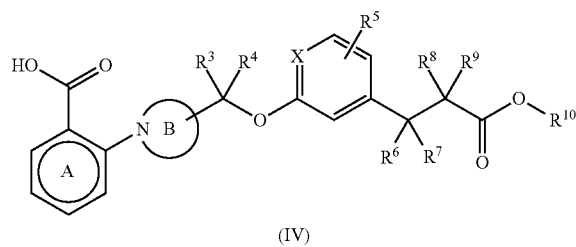

wherein $Y^1$ is a leaving group (e.g., a halogen atom or —$OSO_2Me$, —$OSO_2$(4-tolyl), —$OSO_2CF_3$ and the like), and other symbols are as defined above.

Compound (V) and compound (VI) can be produced by a method known per se.

Compound (II) can be produced by, for example, an alkylation reaction of compound (II-1) with compound (VI). This reaction is performed in the presence of a base in an inert solvent. Examples of the base include alkali metal hydride, inorganic base, basic salt, alkali metal alkoxide, organic base, organic lithium, metal amide and the like.

Compound (II) can be produced from compound (XI) by the method shown in reaction scheme 3.

[reaction scheme 3]

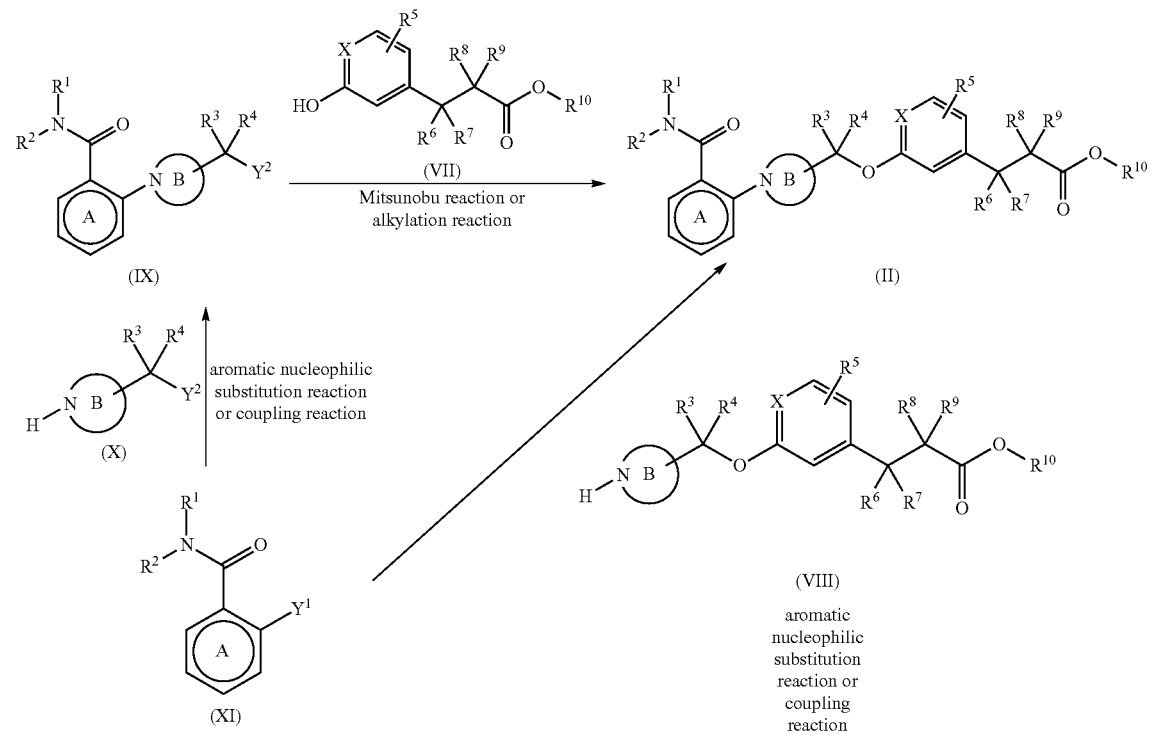

wherein $Y^2$ is an optionally protected hydroxyl group or a leaving group (e.g., a halogen atom or —$OSO_2Me$, —$OSO_2$(4-tolyl), —$OSO_2CF_3$ and the like), and other symbols are as defined above. In the present specification, the optionally protected hydroxyl group is, for example, a hydroxyl group optionally protected by the below-mentioned hydroxy-protecting group.

Compound (X) and compound (XII) can be produced by a method known per se.

Compound (II) wherein $Y^2$ is a leaving group can be produced by, for example, an alkylation reaction of compound (IX) with compound (VII). Alkylation reaction can be performed according to the method shown in reaction scheme 2, or according thereto.

Compound (IV) can be produced from compound (XIV) by the method shown in reaction scheme 4.

[reaction scheme 4]

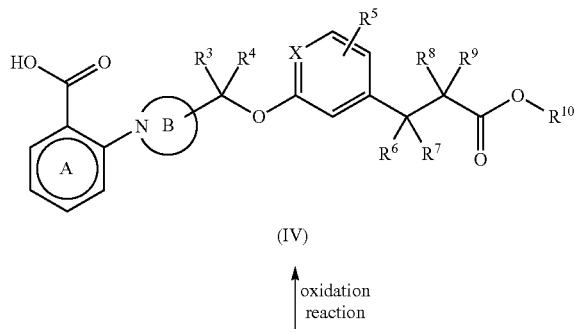

↑ oxidation reaction

-continued
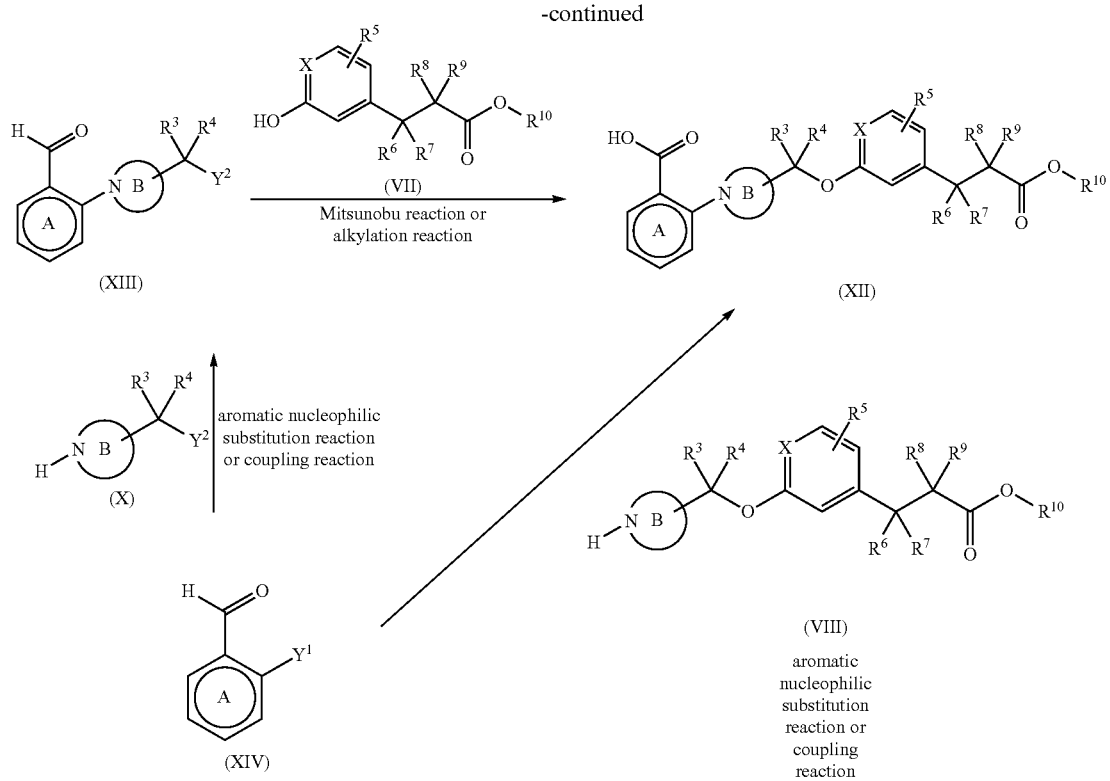
wherein the symbols are as defined above.
Alkylation reaction can be performed according to the method shown in reaction scheme 2, or according thereto.
Compound (XIV) can be produced by a method known per se.
Compound (IV) can be produced from compound (XVII) by the method shown in reaction scheme 5.
[reaction scheme 5]
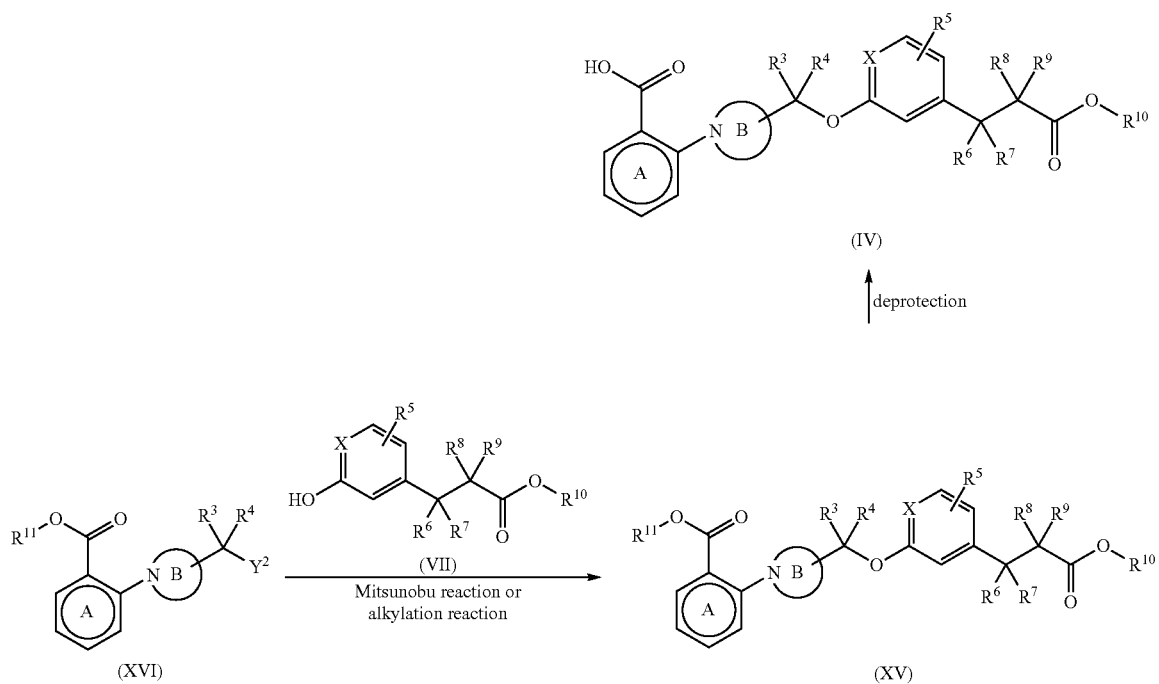

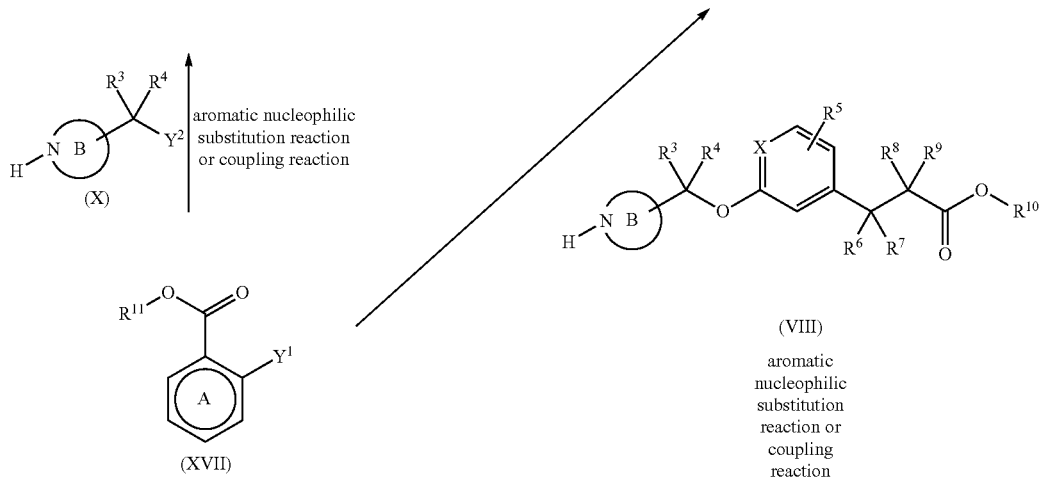

wherein $R^{11}$ is an optionally substituted $C_{1-6}$ alkyl group or an optionally substituted $C_{7-16}$ aralkyl group, and other symbols are as defined above.

Alkylation reaction can be performed according to the method shown in reaction scheme 2, or according thereto.

Compound (XVII) can be produced by a method known per se.

Compound (IX) can be produced from compound (XIII) or compound (XVI) by the method shown in reaction scheme 6.

[reaction scheme 6]

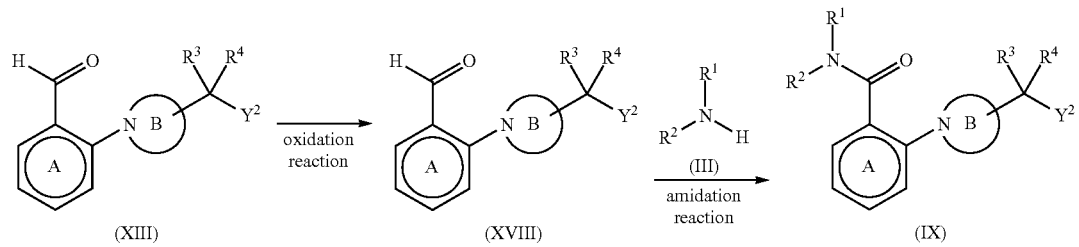

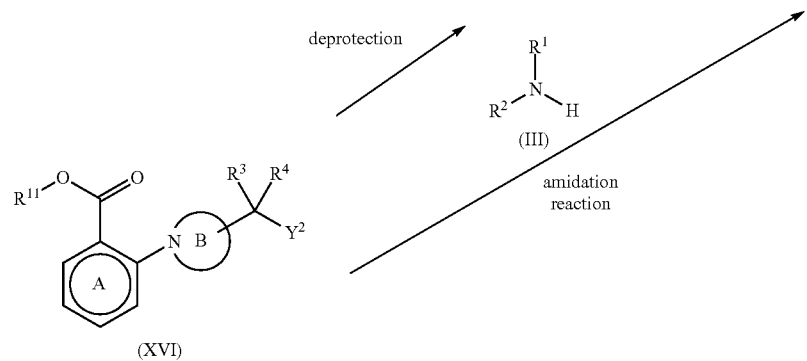

wherein the symbols are as defined above.

Compound (IX-1) and compound (IX-2) can be produced from compound (IX-6) or compound (IX-8) by the method shown in reaction scheme 7. Compound (IX-1) is compound (IX) wherein $Y^2$ is a hydroxyl group.

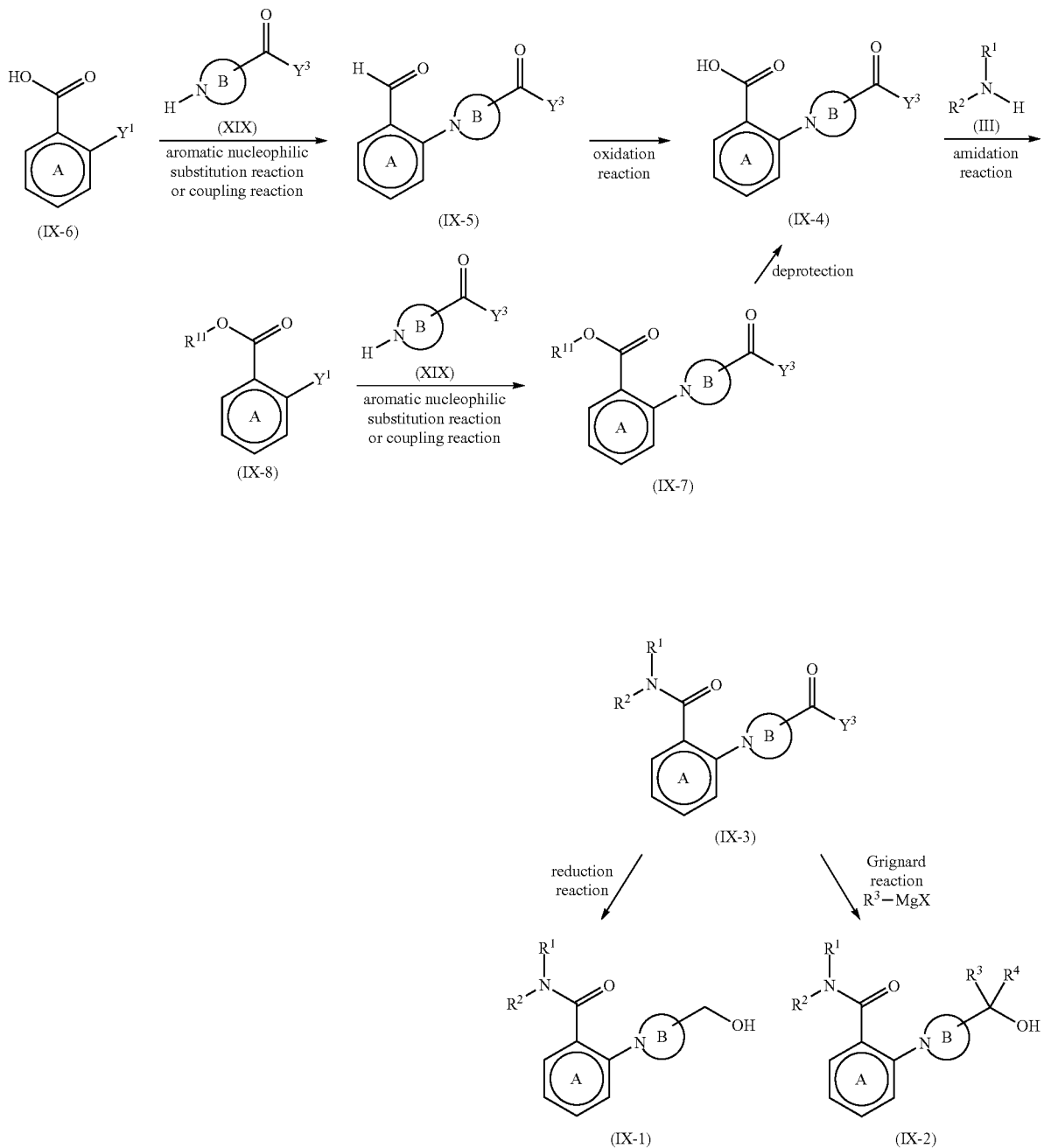

[reaction scheme 7]

wherein $Y^3$ is hydrogen, an optionally substituted $C_{1-6}$ alkyl group, an optionally substituted $C_{1-6}$ alkoxy group or a hydroxyl group, and other symbols are as defined above.

Compound (IX-1) can also be produced by the reaction of compound (IX-2) with an alkyllithium reagent and the like. Examples of the alkyllithium reagent include methyllithium and the like.

Compound (IX-6), compound (IX-8) and compound (XIX) can be produced by a method known per se.

Compound (VII), compound (VIII) and compound (XX) can be produced by the method shown in reaction scheme 8 or a method analogous thereto or the method exemplified in WO 2009/048527 or a method analogous thereto.

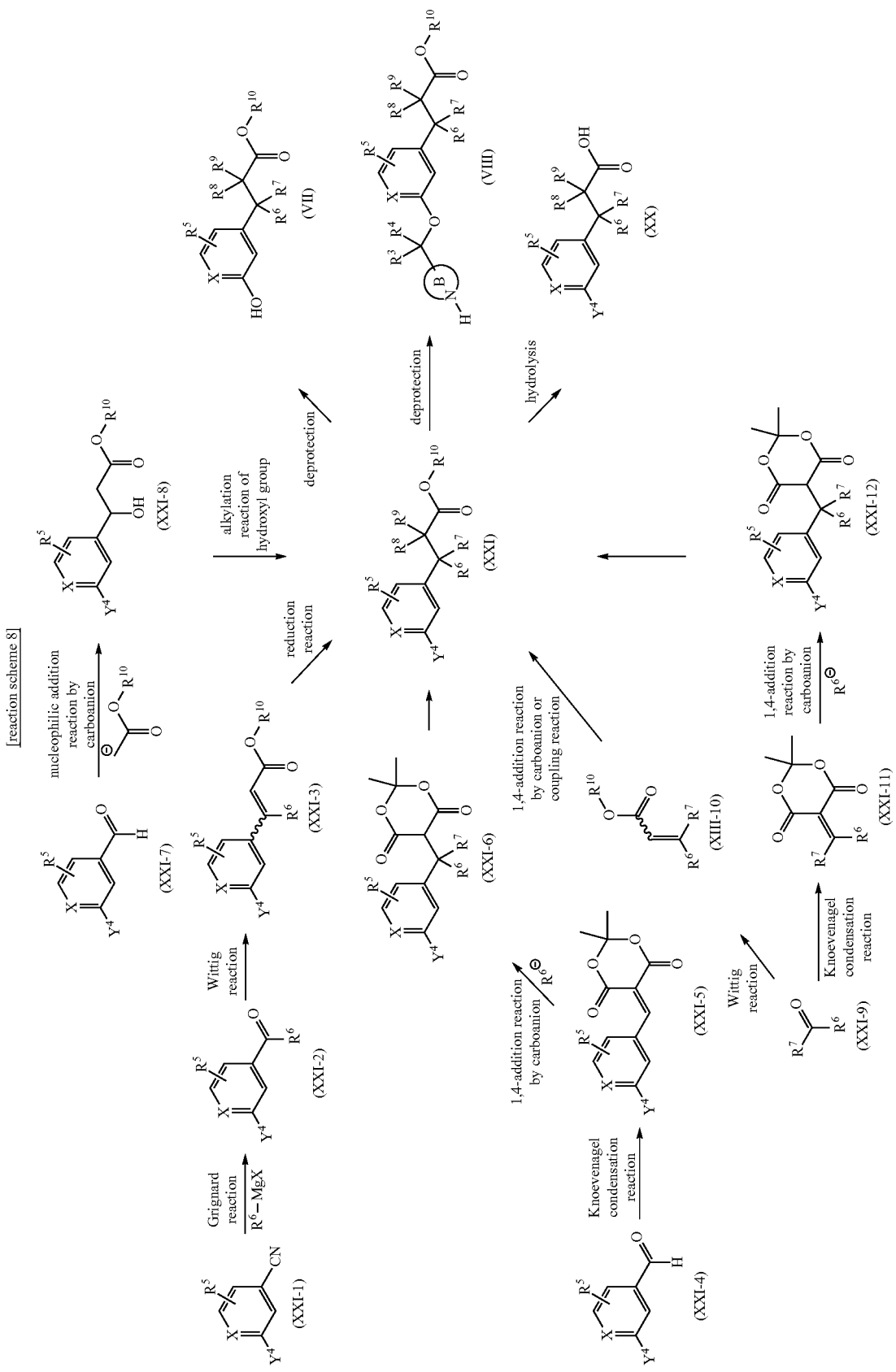

wherein Y⁴ is a halogen atom (e.g., fluorine, chlorine, bromine, iodine), an optionally substituted $C_{1-6}$ alkyl group, an optionally substituted $C_{1-6}$ alkoxy group, or an optionally protected hydroxyl group, and other symbols are as defined above.

Compound (XXI) can be produced by, for example, converting the meldrum's acid moiety of compound (XXI-6) and compound (XXI-12) to an ester. This reaction is performed by reacting methanol or ethanol in an inert solvent such as DMF and the like.

Compound (XXI) can be produced by, for example, alkylation of the hydroxyl group of compound (XXI-8). This reaction is performed by reacting alkyl halide in an inert solvent such as toluene and the like in the presence of silver oxide and the like.

Compound (XXI-1), compound (XXI-4), compound (XXI-7) and compound (XXI-9) can be produced by a method known per se.

Compound (III), compound (III-1) and compound (III-2) can be produced from compound (V) by the method shown in reaction scheme 9.

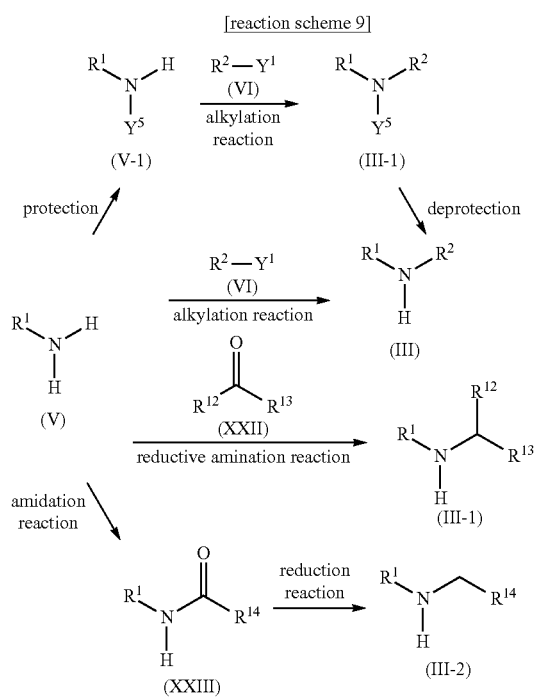

wherein Y⁵ is a protecting group, $R^{12}$, $R^{13}$ and $R^{14}$ are each a hydrogen atom, an optionally substituted $C_{1-6}$ alkyl group, an optionally substituted $C_{7-16}$ aralkyl group or an optionally substituted $C_{6-14}$ aryl group.

Alkylation reaction can be performed according to the method shown in reaction scheme 2, or according thereto.

Compound (XXII) can be produced by a method known per se.

Compound (III-3) can be produced from compound (III-5) by the method shown in reaction scheme 10, for example, the method described in Organic Letters, 2010, 22 (vol. 12), pages 5254-5257, or according thereto. Compound (III-3) is compound (III) wherein R² is an optionally further substituted 2-pyridyl group.

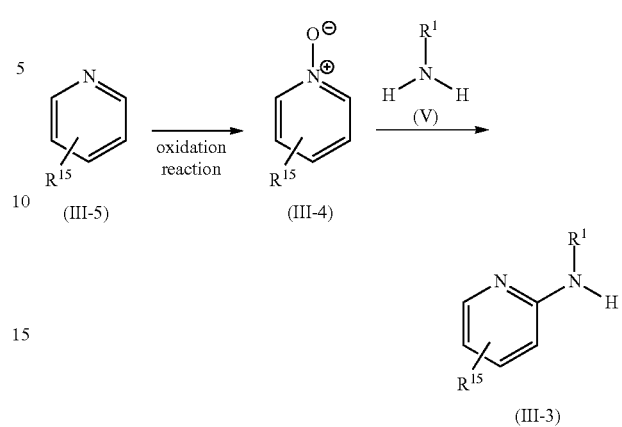

wherein $R^{15}$ is a substituent, and other symbols are as defined above.

Compound (III-3) can be produced by the reaction of compound (III-4) with compound (V). The reaction is performed in the presence of phosphate represented by bromotris(pyrrolidino)phosphonium hexafluorophosphate (Py-Brop) and a base. Examples of the base include alkali metal hydride, inorganic base, basic salt, alkali metal alkoxide, organic base, organic lithium, metal amide and the like.

Compound (III-5) can be produced by a method known per se.

Compound (XIX-1) can be produced from compound (XIX-2) by the method shown in reaction scheme 11, or according thereto. Compound (XIX-1) is compound (XIX) wherein ring B is an optionally further substituted piperidine ring.

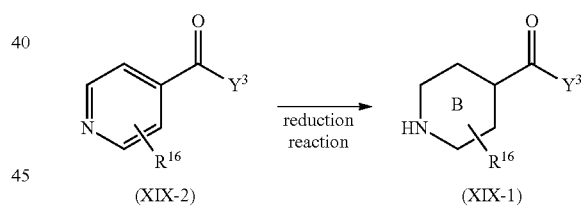

wherein $R^{16}$ is a substituent, and other symbols are as defined above.

Compound (XIX-2) can be produced by a method known per se.

Compound (XXIV) can be produced from compound (XXIV-3) by the method shown in reaction scheme 12, or the method described in J. Org. Chem., 2010, vol. 75, pages 929-932 or a method analogous thereto.

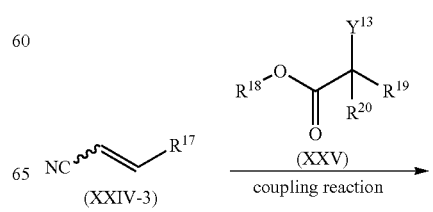

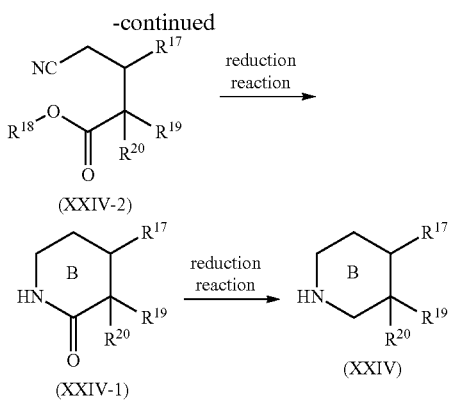

wherein $R^{18}$ is an optionally substituted $C_{1-6}$ alkyl group or an optionally substituted $C_{7-16}$ aralkyl group, $R^{17}$, $R^{19}$ and $R^{20}$ are each a halogen atom (e.g., fluorine, chlorine, bromine, iodine), an optionally substituted alkyl group, an optionally substituted alkoxy group, or an optionally protected hydroxyl group, and other symbols are as defined above.

Compound (XXIV-2) can be produced by a method using a coupling reaction of compound (XXIV-3) and compound (XXV), or a method analogous thereto. The coupling reaction can be performed by, for example, according to a method including reacting compound (XXIV-3) with compound (XXV) generally in the presence of a base and a catalyst (e.g., palladium catalyst, copper catalyst, nickel catalyst and the like) and an appropriate ligand (e.g., tetramethylethylenediamine (TMEDA)).

Compound (XXIV-3) and compound (XXV) can be produced by a method known per se.

In each of the aforementioned reactions, when the starting compound has an amino group, a carboxy group, a hydroxy group, a carbonyl group or a mercapto group as a substituent, a protecting group generally used in the peptide chemistry and the like may be introduced into these groups, and the object compound can be obtained by eliminating the protecting group as necessary after the reaction.

Examples of the amino-protecting group include a formyl group; a $C_{1-6}$ alkyl-carbonyl group, a $C_{1-6}$ alkoxy-carbonyl group, a benzoyl group, a $C_{7-13}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, an N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxyl-protecting group include a $C_{1-6}$ alkyl group, a $C_{7-11}$ aralkyl group (e.g., benzyl), a phenyl group, a trityl, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl), and the like. These groups are optionally substituted by 1 to 3 substituents selected from a halogen atom, a $C_{1-6}$ alkyl group, a $C_{1-6}$ alkoxy group and a nitro group.

Examples of the carbonyl-protecting group include a cyclic acetal (e.g., 1,3-dioxane), a non-cyclic acetal (e.g., a di-$C_{1-6}$ alkylacetal) and the like.

Examples of the mercapto-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$ alkylaminocarbonyl group (e.g., methylaminocarbonyl, ethylaminocarbonyl) and the like. These groups are optionally substituted by 1 to 3 substituents selected from a halogen atom, a $C_{1-6}$ alkyl group, a $C_{1-6}$ alkoxy group and a nitro group.

The above-mentioned protecting groups can be removed by a method known per se, for example, the method described in Protective Groups in Organic Synthesis, John Wiley and Sons (1980) and the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method and the like can be mentioned.

In compound (I) obtained by each of the above-mentioned production methods, a functional group in a molecule can also be converted to a desired functional group by a combination of chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

Compound (I) obtained by each of the above-mentioned production methods can be isolated and purified by a known means such as concentration, concentration under reduced pressure, solvent extraction, crystallization, recrystallization, phase transfer, chromatography and the like. In addition, the starting compounds used for each of the above-mentioned production methods can be isolated and purified by a known means similar to the aforementioned methods. These starting compounds may be used in the form of a reaction mixture without isolation, as a starting material for the next step.

When compound (I) contains an isomer such as an optical isomer, a stereoisomer, a regioisomer or a rotamer, any one of them and a mixture thereof are also encompassed in compound (I). For example, when compound (I) contains an optical isomer, an optical isomer resolved from racemate is also encompassed in compound (I). Each of these isomers can be obtained as a single product by a synthesis means, separation means (e.g., concentration, solvent extraction, column chromatography, recrystallization etc.), optical resolution means (e.g., fractional recrystallization method, chiral column method, diastereomer method etc.) and the like, which are known per se.

Compound (I) may be a crystal, and the crystal form may be single or a mixture of crystal forms, both of which are encompassed in compound (I). The crystal can be produced by a crystallization method known per se.

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

In the present specification, the melting point means that measured using, for example, a micromelting point apparatus (Yanako, MP-500D or Buchi, B-545), a DSC (differential scanning calorimetry) device (SEIKO, EXSTAR6000) or the like.

In general, the melting points vary depending on the measurement apparatuses, the measurement conditions and the like. The crystal in the present specification may show different values from the melting point described in the present specification, as long as they are within each of a general error range.

The crystal of the present invention is superior in physicochemical properties (e.g., melting point, solubility, stability) and biological properties (e.g., pharmacokinetics (absorption, distribution, metabolism, excretion), efficacy expression), and thus it is extremely useful as a medicament.

Compound (I) may be a solvate (e.g., hydrate etc.), or a non-solvate (e.g., non-hydrate etc.), and both are encompassed in compound (I).

A compound labeled with an isotope (e.g., $^3$H, $^{13}$C, $^{14}$C, $^{18}$F, $^{35}$S, $^{125}$I etc.) and the like is also encompassed in compound (I).

Compound (I) also encompasses a deuterium conversion form wherein $^1$H is converted to $^2$H(D).

Compound (I) labeled or substituted with an isotope can be used as, for example, a tracer (PET tracer) used for Positron Emission Tomography (PET), and is useful in the fields of medical diagnosis and the like.

Compound (I) and a prodrug thereof (hereinafter, these are collectively abbreviated as the compound of the present invention) have a GPR40 receptor function modulating action, particularly, a GPR40 agonist activity. GPR40 agonist activates GPR40 expressed in pancreatic β cells to promote insulin secretion, and activates GPR40 expressed in the intestine to promote glucagon-like peptide-1 (glucagon-like peptide-1; GLP-1) secretion. That is, the compound of the present invention has a hypoglycemic action, an insulin secretagogue action, a GLP-1 secretagogue action and a pancreatic β cell protecting action. The GLP-1 secretagogue action of the compound of the present invention can be measured using, for example, an ELISA kit containing a GLP-1 antibody. Moreover, the compound of the present invention may have a glucose-dependent insulinotropic polypeptide (GIP) secretagogue action, a food ingestion suppressive action and a glucagon secretion suppressive action.

The compound of the present invention shows low toxicity (e.g., acute toxicity, chronic toxicity, genetic toxicity, reproductive toxicity, cardiotoxicity, carcinogenicity, cytotoxicity) and can be safely administered a mammal (e.g., mouse, rat, hamster, rabbit, cat, dog, bovine, sheep, monkey, human) directly or as a pharmaceutical composition by mixing same with a pharmacologically acceptable carrier and the like.

The compound of the present invention is useful as modulators of physiological function in which GPR40 receptor is involved or as agents for the prophylaxis or treatment of pathology or disease in which GPR40 receptor is involved.

To be specific, the compound of the present invention is useful as an agent for the prophylaxis or treatment of diabetes (e.g., type 1 diabetes, type 2 diabetes, gestational diabetes, obese diabetes), an insulin secretagogue, a pancreatic β cell protector, a GLP-1 secretion promoter, a GIP secretion promoter, an agent for the prophylaxis or treatment of impaired glucose tolerance (IGT) and an agent for preventing progression of impaired glucose tolerance to diabetes.

Particularly, the compound of the present invention is useful as blood glucose level-dependent insulin secretagogues based on the GPR40 agonist activity thereof. That is different from sulfonylureas, the compound of the present invention is useful as insulin secretagogues that do not cause hypoglycemia.

Furthermore, the compound of the present invention can be used as an agent for the prophylaxis or treatment of obesity, hyperlipidemia (e.g., hypertriglyceridemia, hypercholesterolemia, high LDL-cholesterolemia, hypo HDL-cholesterolemia, postprandial hyperlipidemia), hypertension, cardiac failure, diabetic complications [e.g., neuropathy, nephropathy, diabetic retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (according to the diagnostic criteria for Japanese people as reported in 2005 by the Japan Society for the Study of Obesity and the like, the metabolic syndrome refers to males having an abdominal circumference of 85 cm or above and females having an abdominal circumference of 90 cm or above and satisfying two items out of three items of: systolic blood pressure of not less than 130 or diastolic blood pressure of not less than 85 mmHg, neutral triglyceride not less than 150 mg/dl or HDLc less than 40 mg/dl, and fasting blood sugar level (venous plasma glucose concentration) not less than 110 mg/dl) and the like.

For diagnostic criteria of diabetes, Japan Diabetes Society reported diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) and WHO reported diagnostic criteria of diabetes.

According to these reports, diabetes is a condition showing a fasting blood glucose level (glucose concentration of intravenous plasma) of not less than 126 mg/dl, or a 75 g oral glucose tolerance test 2 h level (glucose concentration of intravenous plasma) of not less than 200 mg/dl.

According to the above-mentioned reports by ADA and WHO, impaired glucose tolerance is a condition showing a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a fasting blood glucose level (glucose concentration of intravenous plasma) of not less than 110 mg/dl and less than 126 mg/dl is called IFG (Impaired Fasting Glycemia).

The compound of the present invention can also be used as an agent for the prophylaxis or treatment of diabetes, borderline type, impaired glucose tolerance, IFG (Impaired Fasting Glucose) and IFG (Impaired Fasting Glycemia), as determined according to the above-mentioned diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention is also useful as a therapeutic agent for diabetes with sulfonylurea secondary failure and affords a superior insulin secretion effect and a hypoglycemic effect for diabetic patients for whom sulfonylurea compounds and fast-acting insulin secretagogues fail to provide an insulin secretion effect, and therefore, fail to provide a sufficient hypoglycemic effect.

As the sulfonylurea compound here, a compound having a sulfonylurea skeleton or a derivative thereof (e.g., tolbutamide, glibenclamide, gliclazide, chlorpropamide, tolazamide, acetohexamide, glyclopyramide, glimepiride, glipizide, glybuzole and the like) can be mentioned.

As the fast-acting insulin secretagogue, a compound that promotes insulin secretion from pancreatic B cell in the same manner as a sulfonylurea compound, though it does not have a sulfonylurea skeleton, such as glinide compounds (e.g., repaglinide, senaglinide, nateglinide, mitiglinide or a calcium salt hydrate thereof etc.), and the like, can be mentioned.

The compound of the present invention can also be used as an agent for the prophylaxis or treatment of, for example, cognitive impairment, osteoporosis, cachexia (e.g., cancerous cachexia, tuberculous cachexia, diabetic cachexia, hemopathic cachexia, endocrinopathic cachexia, infectious cachexia or cachexia induced by acquired immunodeficiency syndrome), fatty liver, polycystic ovary syndrome, renal disease (e.g., diabetic nephropathy, glomerulonephritis, glomerulosclerosis, nephrotic syndrome, hypertensive nephrosclerosis, end-stage renal disorder), muscular dystrophy, myocardial infarction, angina pectoris, cerebrovascular disorder (e.g., cerebral infarction, cerebral apoplexy), insulin resistance syndrome, syndrome X, hyperinsulinemia, perception disorder in hyperinsulinemia, tumor (e.g., leukemia, breast cancer, prostate cancer, skin cancer), irritable bowel syndrome, acute or chronic diarrhea, inflammatory disease (e.g., arteriosclerosis (e.g., atherosclerosis), rheumatoid arthritis, spondylitis deformans, osteoarthritis, lumbago, gout, postoperative or post-traumatic inflammation, swelling, neuralgia, pharyngolaryngitis, bladder inflammation, hepatitis (including nonalcoholic steatohepatitis), pneumonia, pancreatitis, inflammatory colitis, ulcerative colitis, chronic obstructive pulmonary diseases (COPD)), visceral fat syndrome, foot ulcer, sepsis, psoriasis and the like.

In addition, the compound of the present invention can also be used for the improvement of the symptoms of abdominal pain, nausea, vomiting, uncomfortable feeling in the upper abdomen and the like, which are associated with peptic ulcer, acute or chronic gastritis, biliary dyskinesia, cholecystitis and the like, and the like.

Since the compound of the present invention has a pancreatic β cell protection action, it can be used for the prognosis improvement in pancreatic islet transplantation.

The compound of the present invention can also be used for decreasing the visceral fat, suppressing visceral fat accumulation, improving sugar metabolism, improving lipid metabolism, insulin sensitizing, suppressing oxidized LDL production, improving lipoprotein metabolism, improving coronary metabolism, preventing or treating cardiovascular complication, preventing or treating heart failure complication, decreasing blood remnant, preventing or treating anovulation, preventing or treating hirsutism, preventing or treating hyperandrogenism and the like.

The compound of the present invention can also be used for the secondary prevention and the suppression of progression of the above-mentioned various diseases (e.g., cardiovascular event such as myocardial infarction and the like).

A medicament containing the compound of the present invention can be safely administered solely to a mammal or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal tablet and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD

[Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The content of the compound of the present invention in a pharmaceutical preparation is about 0.01 to about 100% by weight relative to the whole preparation. While the dose of the compound of the present invention varies depending on the administration subject, administration route, diseases, condition and the like, for example, the compound of the present invention (as an active ingredient) can be orally administered to a patient with diabetes (body weight about 60 kg) in about 0.01 to about 30 mg/kg body weight per day, preferably about 0.1 to about 20 mg/kg body weight per day, more preferably about 1 to about 20 mg/kg body weight per day, which may be given at once or in several portions (e.g., 1-3 portions) a day.

As the above-mentioned pharmacologically acceptable carrier, various organic or inorganic carrier substances conventionally used as a preparation material can be mentioned. For example, excipient, lubricant, binder and disintegrant for solid preparations; solvent, solubilizing agents, suspending agent, isotonic agent, buffer and soothing agent for liquid preparations and the like can be mentioned. Where necessary, conventional additives such as preservatives, antioxidants, colorants, sweetening agents, adsorbing agents, wetting agents and the like can be used.

As the excipient, for example, lactose, sucrose, D-mannitol, starch, corn starch, crystalline cellulose, light anhydrous silicic acid and the like can be mentioned.

As the lubricant, for example, magnesium stearate, calcium stearate, talc, colloidal silica and the like can be mentioned.

As the binder, for example, crystalline cellulose, sucrose, D-mannitol, dextrin, hydroxypropylcellulose, hydroxypropylmethylcellulose, polyvinylpyrrolidone, starch, saccharose, gelatin, methylcellulose, carboxymethylcellulose sodium and the like can be mentioned.

As the disintegrant, for example, starch, carboxymethylcellulose, carboxymethylcellulose calcium, carboxymethylstarch sodium, L-hydroxypropylcellulose and the like can be mentioned.

As the solvent, for example, water for injection, alcohol, propylene glycol, macrogol, sesame oil, corn oil, olive oil and the like can be mentioned.

As the solubilizing agents, for example, polyethylene glycol, propylene glycol, D-mannitol, benzyl benzoate, ethanol, trisaminomethane, cholesterol, triethanolamine, sodium carbonate, sodium citrate and the like can be mentioned.

As the suspending agent, for example, surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like, and the like can be mentioned.

As the isotonic agent, for example, glucose, D-sorbitol, sodium chloride, glycerin, D-mannitol and the like can be mentioned.

As the buffer, for example, buffers such as phosphates, acetates, carbonates, citrates and the like, and the like can be mentioned.

As the soothing agent, for example, benzyl alcohol and the like can be mentioned.

As the preservative, for example, p-hydroxybenzoates, chlorobutanol, benzyl alcohol, phenethyl alcohol, dehydroacetic acid, sorbic acid and the like can be mentioned.

As the antioxidant, for example, sulfites, ascorbic acid, α-tocopherol and the like can be mentioned.

As the colorant, for example, water-soluble edible tar pigments (e.g., food colors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment and the like), natural pigments (e.g., β-carotene, chlorophil, ferric oxide red etc.) and the like can be mentioned.

As the sweetening agent, for example, saccharin sodium, dipotassium glycyrrhizinate, aspartame, stevia and the like can be mentioned.

Moreover, the compound of the present invention can be used in combination with drugs other than the compound of the present invention.

As the drugs that can be used in combination with the compound of the present invention (hereinafter sometimes to be abbreviated as a concomitant drug), for example, therapeutic agents for diabetes, therapeutic agents for diabetic complications, therapeutic agents for hyperlipidemia, antihypertensive agents, antiobesity agents, diuretics, chemotherapeutic agents, immunotherapeutic agents, antiinflammatory agents, antithrombotic agents, therapeutic agents for osteoporosis, vitamins, antidementia agents, erectile dysfunction improving drugs, therapeutic agents for pollakiuria or urinary incontinence, therapeutic agents for dysuria and the like can be mentioned. Specifically, the following agents can be mentioned.

Examples of therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, the compound described in WO 2007/013694, WO 2007/018314, WO 2008/093639 and WO 2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl-peptidase IV inhibitors (e.g., Alogliptin or a salt thereof (preferably benzoate), Vildagliptin, Sitagliptin, Saxagliptin, BI1356, GRC8200, MP-513, PF-00734200, PHX1149, SK-0403, ALS2-0426, TA-6666, TS-021, KRP-104, Trelagliptin or a salt thereof (preferably, succinate)), β3 agonist (e.g., N-5984), GPR40 agonist (e.g., Fasiglifam or a hydrate thereof (preferably, 0.5 hydrate), the compound described in WO 2004/041266, WO 2004/106276, WO 2005/063729, WO 2005/063725, WO 2005/087710, WO 2005/095338, WO 2007/013689 and WO 2008/001931), GLP-1 receptor agonists (e.g., GLP-1, GLP-1MR agent, Liraglutide, Exenatide, AVE-0010, BIM-51077, Aib(8,35)hGLP-1(7,37) NH$_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, Canagliflozin, Empagliflozin, Ipragliflozin, Tofogliflozin, PF-04971729, TS-071), SGLT1 inhibitor, 11β-hydroxysteroid dehydrogenase inhibitors (e.g., BVT-3498, INCB-13739), adiponectin or agonist thereof, IKK inhibitors (e.g., AS-2868), leptin resistance improving drugs, somatostatin receptor agonists, glucokinase activators (e.g., Piragliatin, AZD1656, AZD6370, TTP-355, the compound described in WO 2006/112549, WO 2007/028135, WO 2008/047821, WO 2008/050821, WO 2008/136428 and WO 2008/156757), GIP (Glucose-dependent insulinotropic peptide), GPR119 agonists (e.g., PSN821, MBX-2982, APD597), FGF21, FGF analogue and the like.

Examples of the therapeutic agents for diabetic complications include aldose reductase inhibitors (e.g., Tolrestat, Epalrestat, Zopolrestat, Fidarestat, CT-112, ranirestat (AS-3201), Lidorestat), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole), compound described in WO 2004/039365), PKC inhibitors (e.g., ruboxistaurin mesylate), AGE inhibitors (e.g., ALT-946, N-phenacylthiazolium bromide (ALT-766), EXO-226, Pyridorin, Pyridoxamine), GABA receptor agonists (e.g., gabapentin, Pregabalin), serotonin.noradrenaline reuptake inhibitors (e.g., duloxetine), sodium channel inhibitors (e.g., Lacosamide), active oxygen scavengers (e.g., thioctic acid), cerebral vasodilators (e.g., tiapuride, mexiletine), somatostatin receptor agonists (BIM23190), apoptosis signal regulating kinase-1 (ASK-1) inhibitors and the like.

Examples of the therapeutic agent for hyperlipidemia include HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterol (e.g., soysterol, gamma oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like.

Examples of the antihypertensive agent include angiotensin converting enzyme inhibitors (e.g., captopril, enalapril, delapril and the like), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil and the like), calcium antagonists (e.g., manidipine, nifedipine, amlodipine, efonidipine, nicardipine, cilnidipine and the like), β blockers (e.g., metoprolol, atenolol, propranolol, carvedilol, pindolol and the like), clonidine and the like.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor modulator, GABA modulator (e.g., topiramate), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetylCoA carboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754, remogliflozin), NFK inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN821, MBX-2982, APD597), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine or swine; human GLP-1 preparations genetically synthesized using *Escherichia coli* or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine or swine; human FGF21 preparations genetically synthesized using *Escherichia coli* or yeast; fragments or derivatives of FGF21), anorexigenic agents (e.g., P-57) and the like.

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide and the like.

Examples of the chemotherapeutic agents include alkylating agents (e.g., cyclophosphamide, ifosfamide), metabolic antagonists (e.g., methotrexate, 5-fluorouracil), antitumor antibiotics (e.g., mitomycin, adriamycin), plant-derived antitumor agents (e.g., vincristine, vindesine, Taxol), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivatives, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.

Examples of the antiinflammatory agents include non-steroidal antiinflammatory agents such as aspirin, acetaminophen, indomethacin and the like.

Examples of the antithrombotic agents include heparin (e.g., heparin sodium, heparin calcium, enoxaparin sodium, dalteparin sodium), warfarins (e.g., warfarin potassium), anti-thrombin drugs (e.g., argatroban, dabigatran)), FXa inhibitors (e.g., rivaroxaban, apixaban, edoxaban, YM150, the compounds described in WO02/06234, WO 2004/048363, WO 2005/030740, WO 2005/058823 and WO 2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the therapeutic agents for osteoporosis include alfacalcidol, calcitriol, elcatonin, calcitonin salmon, estriol, ipriflavone, pamidronate disodium, alendronate sodium hydrate, incadronate disodium, risedronate disodium and the like.

Examples of the vitamins include vitamin $B_1$, vitamin $B_{12}$ and the like.

Examples of the antidementia drugs include tacrine, donepezil, rivastigmine, galanthamine and the like.

Examples of the erectile dysfunction improving drug include apomorphine, sildenafil citrate and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M and the like, can be used in combination with the compound of the present invention.

Furthermore, glycosylation inhibitors (e.g., ALT-711), nerve regeneration promoting drugs (e.g., Y-128, VX853, prosaptide), antidepressants (e.g., desipramine, amitriptyline, imipramine), antiepileptics (e.g., lamotrigine, Trileptal, Keppra, Zonegran, Pregabalin, Harkoseride, carbamazepine), antiarrhythmic agents (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin, gabapentin MR agent), $\alpha_2$ receptor agonists (e.g., clonidine), local analgesics (e.g., capsaicin), antianxiety drugs (e.g., benzothiazepines), phosphodiesterase inhibitors (e.g., sildenafil), dopamine receptor agonists (e.g., apomorphine), midazolam, Ketoconazole and the like can also be used in combination with the compound of the present invention.

The concomitant drug is preferably an insulin preparation, am insulin sensitizer (preferably pioglitazone or its hydrochloride), an α-glucosidase inhibitor (preferably voglibose), a biguanide (preferably metformin or hydrochloride thereof), a sulfonylurea (preferably glibenclamide, glimepiride), mitiglinide or calcium salt hydrate thereof, nateglinide, a dipeptidyl peptidase IV inhibitor (preferably alogliptin or benzoate thereof, trelagliptin or succinate thereof), SGLT2 inhibitor, GLP-1 receptor agonist and the like. For enhancing the food ingestion suppressive action, a combined use with a dipeptidyl peptidase IV inhibitor (preferably, alogliptin or a salt thereof) is more preferable. Two or more kinds of the above-mentioned concomitant drugs may be used in combination at an appropriate ratio.

When the compound of the present invention is used in combination with a concomitant drug, the amounts thereof can be increased or decreased within the safe range in consideration of the counter effect thereof. Particularly, the doses of insulin sensitizer, dipeptidyl peptidase IV inhibitor, α-glucosidase inhibitor, biguanide, insulin secretagogue, SGLT2 inhibitor and GLP-1 receptor agonist can be reduced from the general doses. Therefore, the counter effects that will be caused by these agents can be prevented safely. In addition, the doses of therapeutic agents for diabetic complications, therapeutic agents for hyperlipidemia, and antihypertensive agents can be reduced and, as a result, the counter effects that will be caused by these agents can be prevented effectively.

By combining the compound of the present invention with a concomitant drug, superior effects such as
(1) decreased dose of the compound of the present invention or a concomitant drug as compared to single administration of the compound of the present invention or a concomitant drug,
(2) possible setting of a long treatment period by selecting a concomitant drug having different action and mechanism from those of the compound of the present invention,
(3) possible designing of a sustained treatment effect by selecting a concomitant drug having different action and mechanism from those of the compound of the present invention,
(4) a synergistic effect afforded by a combined use of the compound of the present invention and a concomitant drug, and the like can be achieved.

When the compound of the present invention and a concomitant drug are used in combination, the administration time of the compound of the present invention and the concomitant drug is not restricted, and the compound of the present invention and the concomitant drug may be administered simultaneously, or may be administered at staggered times, to an administration subject. The dosage of the concomitant drug may be determined according to the dose clinically used, and can be appropriately selected depending on an administration subject, administration route, disease, combination and the like.

As the administration mode of the compound of the present invention and the concomitant drug, the following methods can be mentioned: (1) The compound of the present invention and the concomitant drug are simultaneously formulated to give a single preparation which is administered. (2) The compound of the present invention and the concomitant drug are separately formulated to give two kinds of preparations which are administered simultaneously by the same administration route. (3) The compound of the present invention and the concomitant drug are separately formulated to give two kinds of preparations which are administered by the same administration route at staggered times. (4) The compound of the present invention and the concomitant drug are separately formulated to give two kinds of preparations which are administered simultaneously by the different administration routes. (5) The compound of the present invention and the concomitant drug are separately formulated to give two kinds of preparations which are administered by the different administration routes at staggered times (e.g., the compound of the present invention and the concomitant drug are administered in this order, or in the reverse order), and the like.

EXAMPLES

The present invention is explained in detail in the following by referring to Examples, Experimental Examples and Formulation Examples. However, the examples do not limit the present invention and the present invention can be modified within the scope of the present invention.

The "room temperature" in the following Examples is generally about 10° C. to about 35° C. The ratio for a mixed solvent is, unless otherwise specified, a volume mixing ratio and % means wt % unless otherwise specified.

In silica gel column chromatography, the indication of NH means use of aminopropylsilane-bonded silica gel. In HPLC (high performance liquid chromatography), the indication of C18 means use of octadecyl-bonded silica gel. The ratio of elution solvents is, unless otherwise specified, a volume mixing ratio. In the mobile phase, the description of "water/acetonitrile (0.1% TFA-containing system)" and the like means that water and acetonitrile containing 0.1% by volume of TFA were mixed at an appropriate ratio and used. Description of the columns used for SFC (supercritical fluid chromatography) is provided. The ratios of elution solvents are volume mixing ratios, unless otherwise specified. In the mobile phase, the description of "carbon dioxide/methanol/diethylamine" and the like means that carbon dioxide, methanol and diethylamine were mixed at an appropriate ratio and used.

In the following Examples, the following abbreviations are used.
THF: tetrahydrofuran
DMF: dimethylformamide
DME: 1,2-dimethoxyethane
DMSO: dimethyl sulfoxide
$^1$H NMR proton nuclear magnetic resonance (spectrum) was measured by Fourier-transform type NMR. The chemical shift of $^1$H NMR spectrum is described in δ unit (ppm) using TMS (tetramethylsilane) as an internal standard substance and taking the peak of internal standard substance as 0 ppm, and the coupling constant is described in hertz (Hz). For the analysis, ACD/SpecManager (trade name) and the like were used. Peaks with very mild protons such as carboxy group, hydroxyl group, amino group and the like are not described in some cases.

Other abbreviations used in the specification mean the following.
s: singlet
d: doublet
t: triplet
q: quartet
quin: quintet
m: multiplet
br: broad
J: coupling constant
Hz: Hertz
CDCl$_3$: deuterated chloroform
DMSO-d$_6$: dimethyl sulfoxide-d$_6$
CD$_3$OD: deuterated methanol
$^1$H-NMR: proton nuclear magnetic resonance
TFA: trifluoroacetic acid
MS (mass spectrum) was measured by LC/MS (liquid chromatography mass spectrometer). As the ionization method, ESI (ElectroSpray Ionization) method, or APCI (Atmospheric Pressure Chemical Ionization) method was used. As the ionization mode, both or either one of the positive mode (ESI+) and negative mode (ESI−) were/was used and either data are described. The data indicates those found. Generally, molecular ion peak is observed; however, a peak derived from isotope is sometimes observed (e.g., compound having a bromine atom). Moreover, when the compound has a tert-butoxycarbonyl group (-Boc), a peak after elimination of a tert-butoxycarbonyl group or tert-butyl group may be observed as a fragment ion. When the compound has a hydroxyl group (—OH), a peak after elimination of H$_2$O may be observed as a fragment ion. In the case of a salt, a molecular ion peak or fragment ion peak of free form is generally observed.

Example 1

3-cyclopropyl-3-(3-((1-(5-methoxy-2-(methyl(2-methylpropyl)carbamoyl)phenyl)piperidin-4-yl)methoxy)phenyl)propanoic acid Step 1) 2-fluoro-4-methoxy-N-methyl-N-(2-methylpropyl)benzamide To a solution of 2-fluoro-4-methoxybenzoic acid (3.0 g) in THF (50 mL) was added oxalyl chloride (1.7 mL) at room temperature, one drop of DMF was added and the mixture was stirred for 10 min. The reaction mixture was concentrated and the residue was dissolved in THF (5 mL), and added to a solution of N,2-dimethylpropan-1-amine (1.69 g) and triethylamine (4.9 mL) in THF (50 mL). The mixture was stirred for 30 min. To the reaction mixture was added water, and the mixture was extracted with ethyl acetate. The extract was washed with water and saturated brine, and dried over anhydrous magnesium sulfate. The solvent was evaporated under reduced pressure to give a crude product (4.26 g) of the title compound as a colorless oil. This compound was used for the next step without further purification.
MS (ESI+): [M+H]$^+$ 240.3.

Step 2) 2-(4-(hydroxymethyl)piperidin-1-yl)-4-methoxy-N-methyl-N-(2-methylpropyl)benzamide A mixture of 2-fluoro-4-methoxy-N-methyl-N-(2-methylpropyl)benzamide (4.26 g), piperidin-4-ylmethanol (1.37 g), cesium carbonate (7.7 g), tetrabutylammonium iodide (438 mg) and DMF (100 mL) was stirred at 110° C. for 3 days. To the reaction mixture was added water at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (400 mg) as a pale-yellow oil.
MS (ESI+): [M+H]$^+$ 335.4.

Step 3) methyl 3-cyclopropyl-3-(3-((1-(5-methoxy-2-(methyl(2-methylpropyl)carbamoyl)phenyl)piperidin-4-yl)methoxy)phenyl)propanoate To a solution of 2-(4-(hydroxymethyl)piperidin-1-yl)-4-methoxy-N-methyl-N-(2-methylpropyl)benzamide (180 mg) and triethylamine (113 μL) in THF (5 mL) was added methanesulfonyl chloride (50 μL), and the mixture was stirred at room temperature for 30 min. To the reaction mixture was added water at room temperature, and the mixture was extracted with ethyl acetate. The extract was washed with water and saturated brine, and dried over anhydrous magnesium sulfate. The solvent was evaporated under reduced pressure to give a residue. To a solution of methyl 3-cyclopropyl-3-(3-hydroxyphenyl)propanoate (119 mg) in DMF (5 mL) was added sodium hydride (oily)(22 mg), and the mixture was stirred at room temperature for 10 min. To the mixture was added the obtained residue, and the mixture was stirred at 100° C. for 1 hr. To the reaction mixture was added water at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (158 mg) as a pale-yellow oil.

MS (ESI+): [M+H]$^+$ 537.7.

Step 4) 3-cyclopropyl-3-(3-((1-(5-methoxy-2-(methyl(2-methylpropyl)carbamoyl)phenyl)piperidin-4-yl)methoxy)phenyl)propanoic acid To a solution of methyl 3-cyclopropyl-3-(3-((1-(5-methoxy-2-(methyl(2-methylpropyl)carbamoyl)-phenyl)piperidin-4-yl)methoxy)phenyl)propanoate (150 mg) in THF (2 mL) and methanol (2 mL) was added 1N aqueous sodium hydroxide solution (1 mL), and the mixture was stirred at room temperature for 15 hr. To the reaction mixture was added 1N hydrochloric acid (1 mL), and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (92 mg) as a white amorphous powder.

MS (ESI+): [M+H]$^+$ 523.3.

Example 2

3-cyclopropyl-3-(3-((1-(2-((2,2-dimethylpropyl)carbamoyl)-5-methoxyphenyl)piperidin-4-yl)methoxy)phenyl)propanoic acid Step 1) benzyl 2-fluoro-4-methoxybenzoate Under a nitrogen atmosphere, to a solution of 2-fluoro-4-methoxybenzoic acid (15.1 g) in DMF (356 mL) were added potassium carbonate (18.4 g) and benzyl bromide (11.6 mL) at room temperature, and the mixture was stirred for 8 hr. Ice water was poured into the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (22.7 g) as a colorless oil.

MS (ESI+): [M+H]$^+$ 260.9.

Step 2) benzyl 2-(4-(hydroxymethyl)piperidin-1-yl)-4-methoxybenzoate

By a method similar to that in Example 1, step 2, the title compound (4.26 g) was obtained as a pale-yellow oil from piperidin-4-ylmethanol (6.17 g) and benzyl 2-fluoro-4-methoxybenzoate (20.9 g).

MS (ESI+): [M+H]$^+$ 356.3.

Step 3) benzyl 2-(4-((3-(1-cyclopropyl-3-methoxy-3-oxopropyl)phenoxy)methyl)piperidin-1-yl)-4-methoxybenzoate (1) and benzyl 2-(4-((3-(1-cyclopropyl-3-ethoxy-3-oxopropyl)phenoxy)methyl)piperidin-1-yl)-4-methoxybenzoate (2)

By a method similar to that in Example 1, step 3, the title compound (1) (4.32 g) was obtained as a colorless oil and the title compound (2) (0.75 g) was obtained as a colorless oil from benzyl 2-(4-(hydroxymethyl)piperidin-1-yl)-4-methoxybenzoate (4.26 g) and methyl 3-cyclopropyl-3-(3-hydroxyphenyl)propanoate (3.14 g).

MS (ESI+): [M+H]$^+$ 572.3. (1), 558.3. (2)

Step 4) 2-(4-((3-(1-cyclopropyl-3-ethoxy-3-oxopropyl)phenoxy)methyl)piperidin-1-yl)-4-methoxybenzoic acid Benzyl 2-(4-((3-(1-cyclopropyl-3-ethoxy-3-oxopropyl)phenoxy)methyl)piperidin-1-yl)-4-methoxybenzoate (751 mg) was dissolved in a mixed solution of ethanol (17.5 mL) and THF (8.76 mL), and reaction was performed in H-Cube provided with a 10% palladium/carbon (70 mm) cartridge at a flow rate of 1 mL/min at room temperature for 2 hr. The solvent was evaporated under reduced pressure, and the residue was purified by silica gel column chromatography (ethyl acetate/hexane) to give the title compound (492 mg) as a colorless oil.

MS (ESI+): [M+H]$^+$ 482.5.

Step 5) ethyl 3-cyclopropyl-3-(3-((1-(2-((2,2-dimethylpropyl)carbamoyl)-5-methoxyphenyl)piperidin-4-yl)methoxy)phenyl)propanoate To a solution of 2-(4-((3-(1-cyclopropyl-3-ethoxy-3-oxopropyl)phenoxy)methyl)piperidin-1-yl)-4-methoxybenzoic acid (62.4 mg) in DMF (1.30 mL) were added 2,2-dimethylpropanamine (30.5 µl), 2-(7-aza-1H-benzotriazol-1-yl)-1,1,3,3-tetramethyluronium hexafluorophosphate (HATU) (76.9 mg) and N-ethyldiisopropylamine (33.9 µl) at room temperature, and the mixture was stirred for 20 hr. Ice water was poured into the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (59.4 mg) as a colorless oil.

MS (ESI+): [M+H]$^+$ 551.7.

Step 6) 3-cyclopropyl-3-(3-((1-(2-((2,2-dimethylpropyl)carbamoyl)-5-methoxyphenyl)piperidin-4-yl)methoxy)phenyl)propanoic acid By a method similar to that in Example 1, step 4, the title compound (46.6 mg) was obtained as a white amorphous powder from ethyl 3-cyclopropyl-3-(3-((1-(2-((2,2-dimethylpropyl)carbamoyl)-5-methoxyphenyl)piperidin-4-yl)methoxy)phenyl)propanoate (59.4 mg).
MS (ESI+): [M+H]+ 523.4.

Example 3

3-cyclopropyl-3-(3-((1-(5-methoxy-2-(morpholin-4-ylcarbonyl)phenyl)piperidin-4-yl)methoxy)phenyl)propanoic acid By a method similar to that in Example 2, step 5 and Example 1, step 4, the title compound (46.0 mg) was obtained as a white amorphous powder from 2-(4-((3-(1-cyclopropyl-3-ethoxy-3-oxopropyl)phenoxy)methyl)piperidin-1-yl)-4-methoxybenzoic acid (62.4 mg) and morpholine (22.5 μl).
MS (ESI+): [M+H]+ 523.3.

Example 4

3-cyclopropyl-3-(3-((1-(2-(2,3-dihydro-1H-indol-1-ylcarbonyl)-5-methoxyphenyl)piperidin-4-yl)methoxy)phenyl)propanoic acid By a method similar to that in Example 2, step 5 and Example 1, step 4, the title compound (43.8 mg) was obtained as a colorless oil from 2-(4-((3-(1-cyclopropyl-3-ethoxy-3-oxopropyl)phenoxy)methyl)piperidin-1-yl)-4-methoxybenzoic acid (50.4 mg) and indoline (23.4 μl).
MS (ESI+): [M+H]+ 555.3.

Example 5

3-cyclopropyl-3-(3-((1-(2-((cis-2,6-dimethylmorpholin-4-yl)carbonyl)-5-methoxyphenyl)piperidin-4-yl)methoxy)phenyl)propanoic acid By a method similar to that in Example 2, step 5 and Example 1, step 4, the title compound (43.4 mg) was obtained as a pale-yellow amorphous powder from 2-(4-((3-(1-cyclopropyl-3-ethoxy-3-oxopropyl)phenoxy)methyl)piperidin-1-yl)-4-methoxybenzoic acid (55.4 mg) and cis-2,6-dimethylmorpholine (28.5 μl).
MS (ESI+): [M+H]+ 551.3.

Example 6

3-(3-((1-(2-((2-cyanoethyl)(phenyl)carbamoyl)-5-methoxyphenyl)piperidin-4-yl)methoxy)phenyl)-3-cyclopropylpropanoic acid By a method similar to that in Example 2, step 5 and Example 1, step 4, the title compound (38 mg) was obtained as a white amorphous powder from 3-anilinopropanenitrile (34.4 mg).
MS (ESI+): [M+H]+ 582.3.

Example 7

3-cyclopropyl-3-(3-((1-(2-((4-fluorophenyl)(methyl)carbamoyl)-5-methoxyphenyl)piperidin-4-yl)methoxy)phenyl)propanoic acid In the same manner as in Example 2, step 5 and Example 1, step 4, the title compound (68 mg) was obtained as a white amorphous powder from 4-fluoro-N-methylaniline (29.4 mg).
MS (ESI+): [M+H]+ 561.3.

Example 8

3-cyclopropyl-3-(3-((1-(2-((3-fluorophenyl)(methyl)carbamoyl)-5-methoxyphenyl)piperidin-4-yl)methoxy)phenyl)propanoic acid In the same manner as in Example 2, step 5 and Example 1, step 4, the title compound (86 mg) was obtained as a white amorphous powder from 3-fluoro-N-methylaniline (71 mg).
MS (ESI+): [M+H]+ 561.3.

Example 9

3-cyclopropyl-3-(3-((1-(2-((2-fluorophenyl)(methyl)carbamoyl)-5-methoxyphenyl)piperidin-4-yl)methoxy)phenyl)propanoic acid In the same manner as in Example 2, step 5 and Example 1, step 4, the title compound (44 mg) was obtained as a white amorphous powder from 2-fluoro-N-methylaniline (53.5 mg).
MS (ESI+): [M+H]+ 561.3.

Example 10

3-(3-((1-(2-((4-chlorophenyl)(methyl)carbamoyl)-5-methoxyphenyl)piperidin-4-yl)methoxy)phenyl)-3-cyclopropylpropanoic acid In the same manner as in Example 2, step 5 and Example 1, step 4, the title compound (36 mg) was obtained as a white amorphous powder from 4-chloro-N-methylaniline (60.6 mg).
MS (ESI+): [M+H]+ 577.2.

Example 11

3-cyclopropyl-3-(3-((1-(2-(ethyl(pyridin-2-yl)carbamoyl)-5-methoxyphenyl)piperidin-4-yl)methoxy)phenyl)propanoic acid In the same manner as in Example 2, step 5 and Example 1, step 4, the title compound (10 mg) was obtained as a white amorphous powder from N-ethylpyridin-2-amine (52.3 mg).
MS (ESI+): [M+H]+ 558.3.

Example 12

3-(3-((1-(2-((2-chlorophenyl)(methyl)carbamoyl)-5-methoxyphenyl)piperidin-4-yl)methoxy)phenyl)-3-cyclopropylpropanoic acid In the same manner as in Example 1, step 1 and Example 1, step 4, the title compound (13.6 mg) was obtained as a pale-yellow oil from 2-(4-((3-(1-cyclopropyl-3-methoxy-3-oxopropyl)phenoxy)methyl)piperidin-1-yl)-4-methoxybenzoic acid (100 mg) and 2-chloro-N-methylaniline (53 μL).
MS (ESI+): [M+H]+ 577.2.

Example 13

3-cyclopropyl-3-(3-((1-(5-methoxy-2-(methyl(pyridin-4-yl)carbamoyl)phenyl)piperidin-4-yl)methoxy)phenyl)propanoic acid In the same manner as in Example 2, step 5 and Example 1, step 4, the title compound (72.9 mg) was obtained as a pale-yellow amorphous powder from 2-(4-((3-(1-cyclopropyl-3-methoxy-3-oxopropyl)phenoxy)methyl)piperidin-1-yl)-4-methoxybenzoic acid (100 mg) and N-methylpyridin-4-amine (46.3 mg).

MS (ESI+): [M+H]+ 544.2.

Example 14

3-cyclopropyl-3-(3-((1-(5-methoxy-2-((4-(2,2,3,3,3-pentafluoropropyl)piperazin-1-yl)carbonyl)phenyl) piperidin-4-yl)methoxy)phenyl)propanoic acid Step 1) tert-butyl 4-(2,2,3,3,3-pentafluoropropyl) piperazine-1-carboxylate A mixture of tert-butyl piperazine-1-carboxylate (1.48 g), 2,2,3,3,3-pentafluoropropyl trifluoromethanesulfonate (3.36 g), triethylamine (2.22 mL) and acetonitrile (5 mL) was stirred at 70° C. for 18 hr. The solvent was evaporated under reduced pressure, and the residue was purified by silica gel column chromatography (ethyl acetate/hexane) to give the title compound (2.45 g) as a colorless oil.

$^1$H NMR (300 MHz, CDCl$_3$) δ 1.46 (9H, s), 2.55-2.64 (4H, m), 2.92-3.06 (2H, m), 3.40-3.47 (4H, m).

Step 2) 1-(2,2,3,3,3-pentafluoropropyl)piperazine di-hydrochloride

To a solution of tert-butyl 4-(2,2,3,3,3-pentafluoropropyl) piperazine-1-carboxylate (2.45 g) in ethyl acetate (15 mL) and methanol (15 mL) was added 4N hydrogen chloride ethyl acetate solution (20 mL), and the mixture was stirred at room temperature for 18 hr. The reaction mixture was diluted with hexane, and the resultant precipitate was collected by filtration, washed with ethyl acetate, and dried under reduced pressure to give the title compound (2.00 g) as a colorless solid.

$^1$H NMR (300 MHz, DMSO-d$_6$) δ 2.77-2.91 (4H, m), 2.97-3.11 (4H, m), 3.34 (2H, td, J=16.3, 1.1 Hz), 7.21-9.58 (3H, m).

Step 3) 3-cyclopropyl-3-(3-((1-(5-methoxy-2-(4-(2,2,3,3,3-pentafluoropropyl)piperazine-1-carbonyl) phenyl)piperidin-4-yl)methoxy)phenyl)propanoic acid In the same manner as in Example 2, step 5 and Example 1, step 4, the title compound (74 mg) was obtained as a colorless amorphous powder from 1-(2,2,3,3,3-pentafluoropropyl)piperazine di-hydrochloride (125 mg) and 2-(4-((3-(1-cyclopropyl-3-methoxy-3-oxopropyl)phenoxy)methyl) piperidin-1-yl)-4-methoxybenzoic acid (100 mg).

MS (ESI+): [M+H]+ 654.3.

Example 15

3-(3-((1-(2-((4-tert-butylpiperazin-1-yl)carbonyl)-5-methoxyphenyl)piperidin-4-yl)methoxy)phenyl)-3-cyclopropylpropanoic acid In the same manner as in Example 2, step 5 and Example 1, step 4, the title compound (55 mg) was obtained as a colorless amorphous powder from 1-tert-butylpiperazine (61 mg) and 2-(4-((3-(1-cyclopropyl-3-methoxy-3-oxopropyl) phenoxy)methyl)piperidin-1-yl)-4-methoxybenzoic acid (100 mg).

MS (ESI+): [M+H]+ 578.3.

Example 16

3-cyclopropyl-3-(3-((1-(5-methoxy-2-((4-methylpiperazin-1-yl)carbonyl)phenyl)piperidin-4-yl)methoxy) phenyl)propanoic acid In the same manner as in Example 2, step 5 and Example 1, step 4, the title compound (42 mg) was obtained as a colorless amorphous powder from 1-methylpiperazine (43 mg) and 2-(4-((3-(1-cyclopropyl-3-methoxy-3-oxopropyl) phenoxy)methyl)piperidin-1-yl)-4-methoxybenzoic acid (100 mg).

MS (ESI+): [M+H]+ 536.3.

Example 17

3-cyclopropyl-3-(3-((1-(5-methoxy-2-(methyl(pyridin-3-yl)carbamoyl)phenyl)piperidin-4-yl)methoxy) phenyl)propanoic acid In the same manner as in Example 2, step 5 and Example 1, step 4, the title compound (12.3 mg) was obtained as a pale-yellow oil from 2-(4-((3-(1-cyclopropyl-3-methoxy-3-oxopropyl)phenoxy)methyl)piperidin-1-yl)-4-methoxybenzoic acid (100 mg) and N-methylpyridin-3-amine (44 μL).

MS (ESI+): [M+H]+ 544.2.

Example 18

3-(3-((1-(2-((3-chlorophenyl)(methyl)carbamoyl)-5-methoxyphenyl)piperidin-4-yl)methoxy)phenyl)-3-cyclopropylpropanoic acid In the same manner as in Example 2, step 5 and Example 1, step 4, the title compound (27.6 mg) was obtained as a colorless oil from 2-(4-((3-(1-cyclopropyl-3-methoxy-3-oxopropyl)phenoxy)methyl)piperidin-1-yl)-4-methoxybenzoic acid (100 mg) and 3-chloro-N-methylaniline (52 μL).

MS (ESI+): [M+H]+ 577.2.

Example 19

3-cyclopropyl-3-(3-((1-(2-((2-fluorobenzyl)(methyl) carbamoyl)-5-methoxyphenyl)piperidin-4-yl) methoxy)phenyl)propanoic acid By a method similar to that in Example 2, step 5 and Example 1, step 4, the title compound (112 mg) was obtained as a red amorphous powder from 2-(4-((3-(1-cyclopropyl-3-ethoxy-3-oxopropyl)phenoxy)methyl)piperidin-1-yl)-4-methoxybenzoic acid (109.3 mg) and 2-fluoro-N-methylbenzylamine (60.3 μl).

MS (ESI+): [M+H]+ 575.3.

Example 20

3-cyclopropyl-3-(3-((1-(2-((3-fluorobenzyl)(methyl) carbamoyl)-5-methoxyphenyl)piperidin-4-yl) methoxy)phenyl)propanoic acid By a method similar to that in Example 2, step 5 and Example 1, step 4, the title compound (92 mg) was obtained as a red amorphous powder from 2-(4-((3-(1-cyclopropyl- 3-ethoxy-3-oxopropyl)phenoxy)methyl)piperidin-1-yl)-4-methoxybenzoic acid (109.3 mg) and 3-fluoro-N-methyl-benzylamine (61.5 μl).

MS (ESI+): [M+H]+ 575.3.

Example 21

3-cyclopropyl-3-(3-((1-(2-((4-fluorobenzyl)(methyl) carbamoyl)-5-methoxyphenyl)piperidin-4-yl) methoxy)phenyl)propanoic acid Step 1) 2-(4-((3-(1-cyclopropyl-3-methoxy-3-oxo-propyl)phenoxy)methyl)piperidin-1-yl)-4-methoxy-benzoic acid By a method similar to that in Example 2, step 4, the title compound (3.74 g) was obtained as a colorless oil from benzyl 2-(4-((3-(1-cyclopropyl-3-methoxy-3-oxopropyl) phenoxy)methyl)piperidin-1-yl)-4-methoxybenzoate (5.29 g).

MS (ESI+): [M+H]+ 468.4.

Step 2) 3-cyclopropyl-3-(3-((1-(2-((4-fluorobenzyl) (methyl)carbamoyl)-5-methoxyphenyl)piperidin-4-yl)methoxy)phenyl)propanoic acid By a method similar to that in Example 2, step 5 and Example 1, step 4, the title compound (94 mg) was obtained as a white amorphous powder from 2-(4-((3-(1-cyclopropyl-3-methoxy-3-oxopropyl)phenoxy)methyl)piperidin-1-yl)-4-methoxybenzoic acid (102.1 mg) and 4-fluoro-N-methyl-benzylamine (57.9 μl).

MS (ESI+): [M+H]+ 575.3.

Example 22

3-cyclopropyl-3-(3-((1-(5-methoxy-2-(methyl(pyridin-2-ylmethyl)carbamoyl)phenyl)piperidin-4-yl) methoxy)phenyl)propanoic acid By a method similar to that in Example 2, step 5 and Example 1, step 4, the title compound (45.3 mg) was obtained as a pale-yellow amorphous powder from 2-(4-((3-(1-cyclopropyl-3-ethoxy-3-oxopropyl)phenoxy)methyl)piperidin-1-yl)-4-methoxybenzoic acid (105.3 mg) and methyl (pyridin-2-ylmethyl)amine (53.7 μl).

MS (ESI+): [M+H]+ 558.3.

Example 23

3-cyclopropyl-3-(3-((1-(5-methoxy-2-(methyl(pyridin-3-ylmethyl)carbamoyl)phenyl)piperidin-4-yl) methoxy)phenyl)propanoic acid By a method similar to that in Example 2, step 5 and Example 1, step 4, the title compound (74.2 mg) was obtained as a white powder from 2-(4-((3-(1-cyclopropyl-3-ethoxy-3-oxopropyl)phenoxy)methyl)piperidin-1-yl)-4-methoxybenzoic acid (112.0 mg) and N-methyl(pyridin-3-yl)methanamine (56.8 μl).

MS (ESI+): [M+H]+ 558.3.

Example 24

3-(3-((1-(2-((3-chlorobenzyl)(methyl)carbamoyl)-5-methoxyphenyl)piperidin-4-yl)methoxy)phenyl)-3-cyclopropylpropanoic acid By a method similar to that in Example 2, step 5 and Example 1, step 4, the title compound (109 mg) was obtained as a white amorphous powder from 2-(4-((3-(1-cyclopropyl-3-ethoxy-3-oxopropyl)phenoxy)methyl)piperidin-1-yl)-4-methoxybenzoic acid (116.3 mg) and 3-chloro-N-methyl-benzenemethanamine (70.1 μl).

MS (ESI+): [M+H]+ 591.2.

Example 25

3-cyclopropyl-3-(3-((1-(5-methoxy-2-(methyl(6-methylpyridin-2-yl)carbamoyl)phenyl)piperidin-4-yl)methoxy)phenyl)propanoic acid Step 1) ethyl 3-cyclopropyl-3-(3-((1-(5-methoxy-2-((6-methylpyridin-2-yl)carbamoyl)phenyl)piperidin-4-yl)methoxy)phenyl)propanoate In the same manner as in Example 2, step 5, the title compound (82.5 mg) was obtained as a white solid from 2-(4-((3-(1-cyclopropyl-3-ethoxy-3-oxopropyl)phenoxy) methyl)piperidin-1-yl)-4-methoxybenzoic acid (100 mg) and 6-methylpyridin-2-amine (112 mg).

$^1$H NMR (400 MHz, DMSO-$d_6$) δ 0.07-0.17 (1H, m), 0.18-0.27 (1H, m), 0.28-0.38 (1H, m), 0.44-0.57 (1H, m), 0.97-1.05 (1H, m), 1.07 (3H, t, J=7.1 Hz), 1.79-2.04 (4H, m), 2.19-2.29 (1H, m), 2.39 (3H, s), 2.64-2.80 (4H, m), 2.87-2.99 (2H, m), 3.16 (2H, d, J=11.8 Hz), 3.85 (3H, s), 3.90-4.01 (3H, m), 6.79 (1H, d, J=8.4 Hz), 6.81-6.88 (2H, m), 6.92 (1H, dd, J=8.9, 2.4 Hz), 6.94-7.00 (2H, m), 7.20 (1H, t, J=7.7 Hz), 7.69 (1H, t, J=7.8 Hz), 8.07 (2H, t, J=7.9 Hz), 13.14 (1H, s).

Step 2) ethyl 3-cyclopropyl-3-(3-((1-(5-methoxy-2-(methyl(6-methylpyridin-2-yl)carbamoyl)phenyl) piperidin-4-yl)methoxy)phenyl)propanoate Under a nitrogen atmosphere, to a solution of ethyl 3-cyclopropyl-3-(3-((1-(5-methoxy-2-((6-methylpyridin-2-yl)carbamoyl)phenyl)piperidin-4-yl)methoxy)phenyl)propanoate (82.5 mg) and iodomethane (45.0 μL) in DMF (1.5 mL) was added 60% sodium hydride (oily) (17.3 mg) at 0° C., and the mixture was stirred at room temperature for 3 hr. The reaction mixture was added to water at 0° C., and the mixture was extracted with ethyl acetate. The extract was washed with water, saturated aqueous sodium hydrogen carbonate solution and saturated brine, and dried over anhydrous magnesium sulfate. The solvent was evaporated under reduced pressure, and the residue was purified by silica gel column chromatography (ethyl acetate/hexane) to give the title compound (77.5 mg) as a colorless oil.

$^1$H NMR (400 MHz, DMSO-$d_6$) δ 0.06-0.17 (1H, m), 0.18-0.26 (1H, m), 0.27-0.37 (1H, m), 0.43-0.56 (1H, m), 0.98-1.08 (1H, m), 1.08 (3H, t, J=7.0 Hz), 1.70 (3H, d, J=9.7 Hz), 2.24 (1H, q, J=8.0 Hz), 2.38 (3H, s), 2.46-2.62 (5H, m), 2.62-2.80 (3H, m), 3.41 (3H, s), 3.74 (3H, s), 3.81 (2H, d, J=5.8 Hz), 3.90-4.00 (2H, m), 6.28 (1H, brs), 6.60 (2H, dd, J=8.4, 2.0 Hz), 6.76 (1H, d, J=7.5 Hz), 6.80-6.86 (2H, m), 6.90 (1H, d, J=7.5 Hz), 7.18 (1H, t, J=8.0 Hz), 7.28 (1H, d, J=8.4 Hz), 7.37 (1H, t, J=7.4 Hz).

Step 3) 3-cyclopropyl-3-(3-((1-(5-methoxy-2-(methyl(6-methylpyridin-2-yl)carbamoyl)phenyl) piperidin-4-yl)methoxy)phenyl)propanoic acid In the same manner as in Example 1, step 4, the title compound (70.0 mg) was obtained as a white amorphous powder from ethyl 3-cyclopropyl-3-(3-((1-(5-methoxy-2-

(methyl(6-methylpyridin-2-yl)carbamoyl)phenyl)piperidin-4-yl)methoxy)phenyl)propanoate (77.5 mg).
MS (ESI+): [M+H]⁺ 558.3

Example 26

3-cyclopropyl-3-(3-((1-(5-methoxy-2-(methyl(4-methylpyridin-2-yl)carbamoyl)phenyl)piperidin-4-yl)methoxy)phenyl)propanoic acid Step 1) ethyl 3-cyclopropyl-3-(3-((1-(5-methoxy-2-((4-methylpyridin-2-yl)carbamoyl)phenyl)piperidin-4-yl)methoxy)phenyl)propanoate In the same manner as in Example 2, step 5, the title compound (74.5 mg) was obtained as a white solid from 2-(4-((3-(1-cyclopropyl-3-ethoxy-3-oxopropyl)phenoxy)methyl)piperidin-1-yl)-4-methoxybenzoic acid (100 mg) and 4-methylpyridin-2-amine (112 mg).
¹H NMR (400 MHz, DMSO-d₅) δ 0.08-0.17 (1H, m), 0.18-0.27 (1H, m), 0.28-0.40 (1H, m), 0.45-0.58 (1H, m), 1.00-1.06 (1H, m), 1.08 (3H, t, J=7.1 Hz), 1.73-1.98 (5H, m), 2.19-2.29 (1H, m), 2.34 (3H, s), 2.72 (2H, t, J=8.0 Hz), 2.86-2.98 (2H, m), 3.16 (2H, d, J=11.8 Hz), 3.85 (3H, s), 3.91 (2H, d, J=5.8 Hz), 3.94-4.01 (2H, m), 6.73-6.87 (3H, m), 6.89-7.00 (3H, m), 7.20 (1H, t, J=7.8 Hz), 8.06 (1H, d, J=8.8 Hz), 8.15 (1H, s), 8.20 (1H, d, J=5.0 Hz), 12.86 (1H, s).

Step 2) ethyl 3-cyclopropyl-3-(3-((1-(5-methoxy-2-(methyl(4-methylpyridin-2-yl)carbamoyl)phenyl)piperidin-4-yl)methoxy)phenyl)propanoate In the same manner as in Example 25, step 2, the title compound (69.7 mg) was obtained as a colorless oil from ethyl 3-cyclopropyl-3-(3-((1-(5-methoxy-2-((4-methylpyridin-2-yl)carbamoyl)phenyl)piperidin-4-yl)methoxy)phenyl)propanoate (74.5 mg).
¹H NMR (400 MHz, DMSO-d₆) δ 0.04-0.17 (1H, m), 0.17-0.26 (1H, m), 0.27-0.38 (1H, m), 0.43-0.56 (1H, m), 0.97-1.06 (1H, m), 1.08 (3H, t, J=7.1 Hz), 1.72 (3H, brs), 2.08 (3H, s), 2.20-2.30 (1H, m), 2.45-2.63 (5H, m), 2.64-2.80 (3H, m), 3.39 (3H, s), 3.74 (3H, s), 3.80 (2H, d, J=6.0 Hz), 3.90-4.02 (2H, m), 6.30 (1H, brs), 6.60 (1H, dd, J=8.5, 2.1 Hz), 6.66-6.79 (2H, m), 6.79-6.86 (2H, m), 6.90 (1H, d, J=4.6 Hz), 7.18 (1H, t, J=8.0 Hz), 7.26 (1H, d, J=8.4 Hz), 8.19 (1H, d, J=5.1 Hz).

Step 3) 3-cyclopropyl-3-(3-((1-(5-methoxy-2-(methyl(4-methylpyridin-2-yl)carbamoyl)phenyl)piperidin-4-yl)methoxy)phenyl)propanoic acid In the same manner as in Example 1, step 4, the title compound (61.9 mg) was obtained as a white amorphous powder from ethyl 3-cyclopropyl-3-(3-((1-(5-methoxy-2-(methyl(4-methylpyridin-2-yl)carbamoyl)phenyl)piperidin-4-yl)methoxy)phenyl)propanoate (69.7 mg).
MS (ESI+): [M+H]⁺ 558.3.

Example 27

3-(3-((1-(2-((3-cyanophenyl)(methyl)carbamoyl)-5-methoxyphenyl)piperidin-4-yl)methoxy)phenyl)-3-cyclopropylpropanoic acid Step 1) ethyl 3-(3-((1-(2-((3-cyanophenyl)carbamoyl)-5-methoxyphenyl)piperidin-4-yl)methoxy)phenyl)-3-cyclopropylpropanoate In the same manner as in Example 2, step 5, the title compound (102 mg) was obtained as a white amorphous powder from 2-(4-((3-(1-cyclopropyl-3-ethoxy-3-oxopropyl)phenoxy)methyl)piperidin-1-yl)-4-methoxybenzoic acid (100 mg) and 3-aminobenzonitrile (123 mg).
¹H NMR (400 MHz, DMSO-d₆) δ 0.12 (1H, dt, J=9.2, 4.7 Hz), 0.17-0.26 (1H, m), 0.27-0.38 (1H, m), 0.45-0.56 (1H, m), 0.96-1.06 (1H, m), 1.07 (3H, t, J=7.1 Hz), 1.47-1.62 (2H, m), 1.83-1.97 (3H, m), 2.18-2.29 (1H, m), 2.63-2.78 (2H, m), 2.85 (2H, t, J=10.9 Hz), 3.21 (2H, d, J=11.3 Hz), 3.84 (3H, s), 3.88 (2H, d, J=5.3 Hz), 3.92-3.99 (2H, m), 6.76 (1H, d, J=9.3 Hz), 6.80-6.90 (4H, m), 7.18 (1H, t, J=7.8 Hz), 7.50-7.62 (2H, m), 7.86 (1H, d, J=8.5 Hz), 7.91 (1H, d, J=8.0 Hz), 8.37 (1H, s), 11.91 (1H, s).

Step 2) ethyl 3-(3-((1-(2-((3-cyanophenyl)(methyl)carbamoyl)-5-methoxyphenyl)piperidin-4-yl)methoxy)phenyl)-3-cyclopropylpropanoate In the same manner as in Example 25, step 2, a crude product of the title compound was obtained as a colorless oil from ethyl 3-(3-((1-(2-((3-cyanophenyl)carbamoyl)-5-methoxyphenyl)piperidin-4-yl)methoxy)phenyl)-3-cyclopropylpropanoate (102 mg). This compound was used for the next step without further purification.

Step 3) 3-(3-((1-(2-((3-cyanophenyl)(methyl)carbamoyl)-5-methoxyphenyl)piperidin-4-yl)methoxy)phenyl)-3-cyclopropylpropanoic acid In the same manner as in Example 1, step 4, the title compound (85.5 mg) was obtained as a white amorphous powder from a crude product of ethyl 3-(3-((1-(2-((3-cyanophenyl)(methyl)carbamoyl)-5-methoxyphenyl)piperidin-4-yl)methoxy)phenyl)-3-cyclopropylpropanoate (entire amount).
MS (ESI+): [M+H]⁺ 568.3.

Example 28

3-cyclopropyl-3-(3-((1-(2-((2,2-dimethylpropyl)(2-methylpropyl)carbamoyl)-5-methoxyphenyl)piperidin-4-yl)methoxy)phenyl)propanoic acid By a method similar to that in Example 2, step 5 and Example 1, step 4, the title compound (77.0 mg) was obtained as a white amorphous powder from 2-(4-((3-(1-cyclopropyl-3-ethoxy-3-oxopropyl)phenoxy)methyl)piperidin-1-yl)-4-methoxybenzoic acid (104.2 mg) and 2,2-dimethyl-N-(2-methylpropyl)propan-1-amine (62.0 mg).
MS (ESI+): [M+H]⁺ 579.3.

Example 29

3-cyclopropyl-3-(3-((1-(2-((2,2-dimethylmorpholin-4-yl)carbonyl)-5-methoxyphenyl)piperidin-4-yl)methoxy)phenyl)propanoic acid By a method similar to that in Example 2, step 5 and Example 1, step 4, the title compound (71.0 mg) was obtained as a white amorphous powder from 2-(4-((3-(1-cyclopropyl-3-ethoxy-3-oxopropyl)phenoxy)methyl)piperidin-1-yl)-4-methoxybenzoic acid (104.2 mg) and 2,2-dimethylmorpholine (49.8 mg).
MS (ESI+): [M+H]⁺ 551.3.

Example 30

3-(3-((1-(2-((2-tert-butylpyrrolidin-1-yl)carbonyl)-5-methoxyphenyl)piperidin-4-yl)methoxy)phenyl)-3-cyclopropylpropanoic acid By a method similar to that in Example 2, step 5 and Example 1, step 4, the title compound (108 mg) was obtained as a white amorphous powder from 2-(4-((3-(1-cyclopropyl-3-ethoxy-3-oxopropyl)phenoxy)methyl)piperidin-1-yl)-4-methoxybenzoic acid (104.2 mg) and 2-(tert-butyl)pyrrolidine (55.1 mg).

MS (ESI+): [M+H]$^+$ 563.3.

Example 31

3-cyclopropyl-3-(3-((1-(5-methoxy-2-(((3R)-3-(2-methylpropyl)morpholin-4-yl)carbonyl)phenyl)piperidin-4-yl)methoxy)phenyl)propanoic acid By a method similar to that in Example 2, step 5 and Example 1, step 4, the title compound (103 mg) was obtained as a white amorphous powder from 2-(4-((3-(1-cyclopropyl-3-ethoxy-3-oxopropyl)phenoxy)methyl)piperidin-1-yl)-4-methoxybenzoic acid (106.1 mg) and (R)-3-(2-methylpropyl)morpholine hydrochloride (79 mg).

MS (ESI+): [M+H]$^+$ 579.3.

Example 32

3-cyclopropyl-3-(3-((1-(2-((2,2-dimethylpropyl)(6-methylpyridin-2-yl)carbamoyl)-5-methoxyphenyl)piperidin-4-yl)methoxy)phenyl)propanoic acid Step 1)
N-(2,2-dimethylpropyl)-6-methylpyridin-2-amine Under a nitrogen atmosphere, 2,2-dimethylpropanoyl chloride (8.53 mL) was added to a solution of 6-methylpyridin-2-amine (5.00 g) in DMA (25 mL) at room temperature, and the mixture was stirred at room temperature for 48 hr. Saturated aqueous sodium hydrogen carbonate solution was added to the reaction mixture, and the mixture was extracted with ethyl acetate. The extract was washed with water and saturated brine, dried over anhydrous magnesium sulfate, and the solvent was evaporated under reduced pressure. Under a nitrogen atmosphere, the obtained residue was added to a suspension of lithium aluminum hydride (8.78 g) in THF (100 mL) at 0° C., and the mixture was heated under reflux for 1 hr. Water and aqueous sodium hydroxide solution were added to the reaction mixture, and the resultant white precipitate was filtered off. The solvent in the filtrate was evaporated under reduced pressure to give the title compound (7.24 g) as a colorless oil.

1H NMR (400 MHz, DMSO-d6) δ 0.90 (9H, s), 2.22 (3H, s), 3.07 (2H, d, J=6.1 Hz), 6.15 (1H, t, J=5.7 Hz), 6.27 (1H, d, J=7.2 Hz), 6.32 (1H, d, J=8.4 Hz), 7.20 (1H, t, J=7.7 Hz).

Step 2) ethyl 3-cyclopropyl-3-(3-((1-(2-((2,2-dimethylpropyl)(6-methylpyridin-2-yl)carbamoyl)-5-methoxyphenyl)piperidin-4-yl)methoxy)phenyl)propanoate Under a nitrogen atmosphere, to a solution of 2-(4-((3-(1-cyclopropyl-3-ethoxy-3-oxopropyl)phenoxy)methyl)piperidin-1-yl)-4-methoxybenzoic acid (112.7 mg) in THF (2.34 mL) was added 1-chloro-N,N-2-trimethylpropylamine (37.2 μl) at 0° C. After stirring at room temperature for 30 min, N-(2,2-dimethylpropyl)-6-methylpyridin-2-amine (83 mg) and triethylamine (42.4 μl) were added at 0° C., and the mixture was stirred at room temperature for 20 hr. The reaction mixture was poured into water at room temperature, and the mixture was extracted with ethyl acetate. The extract was washed with saturated brine, and dried over anhydrous sodium sulfate. The solvent was evaporated under reduced pressure, and the residue was purified by silica gel column chromatography (NH, ethyl acetate/hexane) to give the title compound (54.3 mg) as a colorless oil.

MS (ESI+): [M+H]$^+$ 642.6.

Step 3) 3-cyclopropyl-3-(3-((1-(2-((2,2-dimethylpropyl)(6-methylpyridin-2-yl)carbamoyl)-5-methoxyphenyl)piperidin-4-yl)methoxy)phenyl)propanoic acid By a method similar to that in Example 1, step 4, the title compound (27.5 mg) was obtained as a white solid from ethyl 3-cyclopropyl-3-(3-((1-(2-((2,2-dimethylpropyl)(6-methylpyridin-2-yl)carbamoyl)-5-methoxyphenyl)piperidin-4-yl)methoxy)phenyl)propanoate (54.3 mg).

MS (ESI+): [M+H]$^+$ 614.4.

Example 33

3-cyclopropyl-3-(3-((1-(2-((2,2-dimethylpropyl)(4-methylpyridin-2-yl)carbamoyl)-5-methoxyphenyl)piperidin-4-yl)methoxy)phenyl)propanoic acid By a method similar to that in Example 32, step 2 and Example 1, step 4, the title compound (118 mg) was obtained as a white amorphous powder from 2-(4-((3-(1-cyclopropyl-3-ethoxy-3-oxopropyl)phenoxy)methyl)piperidin-1-yl)-4-methoxybenzoic acid (110.0 mg) and N-(2,2-dimethylpropyl)-4-methylpyridin-2-amine (81 mg).

MS (ESI+): [M+H]$^+$ 614.4.

Example 34

3-cyclopropyl-3-(3-((1-(2-((2,2-dimethylpropyl)(pyridin-2-yl)carbamoyl)-5-methoxyphenyl)piperidin-4-yl)methoxy)phenyl)propanoic acid By a method similar to that in Example 32, step 2 and Example 1, step 4, the title compound (129 mg) was obtained as a white amorphous powder from 2-(4-((3-(1-cyclopropyl-3-ethoxy-3-oxopropyl)phenoxy)methyl)piperidin-1-yl)-4-methoxybenzoic acid (114.4 mg) and N-(2,2-dimethylpropyl)pyridin-2-amine (78 mg).

MS (ESI+): [M+H]$^+$ 600.3.

Example 35

3-cyclopropyl-3-(3-((1-(5-methoxy-2-((2-methoxy-2-methylpropyl)(pyridin-2-yl)carbamoyl)phenyl)piperidin-4-yl)methoxy)phenyl)propanoic acid Step 1) ethyl 2-(pyridin-2-ylamino)acetate Under a nitrogen atmosphere, 40% glyoxal aqueous solution (10.7 mL) and ethanol (80 mL) were added to a mixture of 2-aminopyridine (8.00 g) and 70% aqueous perchloric acid solution (19.0 mL) at room temperature, and the mixture was heated under reflux for 16 hr. The reaction mixture was neutralized with saturated aqueous sodium hydrogen carbonate solution, and extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (9.01 g) as a colorless oil.

$^1$H NMR (400 MHz, CDCl$_3$) δ 1.29 (3H, t, J=7.1 Hz), 4.14 (2H, d, J=5.5 Hz), 4.24 (2H, q, J=7.1 Hz), 4.89 (1H, brs), 6.46 (1H, d, J=8.3 Hz), 6.61 (1H, dd, J=6.8, 5.4 Hz), 7.36-7.49 (1H, m), 8.10 (1H, d, J=4.9 Hz).

Step 2) 2-methyl-1-(pyridin-2-ylamino)propan-2-ol

Under a nitrogen atmosphere, 1.0 M methylmagnesium bromide (44.4 mL) was added to a solution of ethyl 2-(pyridin-2-ylamino)acetate (2.0 g) in THF (30 mL) at 0° C., and the mixture was stirred at 0° C. for 20 min. Saturated aqueous ammonium chloride solution was added to the reaction mixture, and the mixture was extracted with ethyl acetate. The extract was washed with water and saturated brine, and dried over anhydrous magnesium sulfate. The solvent was evaporated under reduced pressure, the residue was purified by silica gel column chromatography (ethyl acetate/hexane), and the obtained pale-orange solid was washed with diisopropyl ether to give the title compound (508 mg) as a white solid.

$^1$H NMR (400 MHz, CDCl$_3$) δ 1.26 (6H, s), 3.36 (2H, d, J=6.0 Hz), 4.74 (1H, brs), 4.91 (1H, brs), 6.46 (1H, d, J=8.4 Hz), 6.57 (1H, dd, J=6.6, 5.6 Hz), 7.39 (1H, td, J=7.8, 1.9 Hz), 8.02 (1H, d, J=5.1 Hz).

Step 3) N-(2-methoxy-2-methylpropyl)pyridin-2-amine

Under a nitrogen atmosphere, to a solution of 2-methyl-1-(pyridin-2-ylamino)propan-2-ol (250 mg) in DMF (5 mL) was added 60% sodium hydride (oily) (66.2 mg) at 0° C., and the mixture was stirred for 5 min. Iodomethane (188 µL) was added to the reaction mixture at 0° C., and the mixture was stirred for 30 min. Water was added to the reaction mixture at 0° C., and the mixture was extracted with ethyl acetate. The extract was washed with water and saturated brine, and dried over anhydrous magnesium sulfate. The solvent was evaporated under reduced pressure, and the residue was purified by silica gel column chromatography (NH, ethyl acetate/hexane) to give the title compound (150 mg) as a colorless oil.

$^1$H NMR (300 MHz, CDCl$_3$) δ 1.24 (6H, s), 3.23 (3H, s), 3.33 (2H, d, J=5.4 Hz), 4.72 (1H, brs), 6.40 (1H, dt, J=8.4, 0.8 Hz), 6.53 (1H, ddd, J=7.1, 5.1, 0.8 Hz), 7.38 (1H, ddd, J=8.5, 6.9, 1.9 Hz), 7.97-8.15 (1H, m).

Step 4) ethyl 3-cyclopropyl-3-(3-((1-(5-methoxy-2-((2-methoxy-2-methylpropyl)(pyridin-2-yl)carbamoyl)phenyl)piperidin-4-yl)methoxy)phenyl)propanoate In the same manner as in Example 32, step 2, the title compound (85.0 mg) was obtained as a colorless oil from ethyl 3-cyclopropyl-3-(3-((1-(5-ethyl-2-(pyridin-2-yl(2,2,2-trifluoroethyl)carbamoyl)phenyl)piperidin-4-yl)methoxy)phenyl)propanoate (100 mg) and N-(2-methoxy-2-methylpropyl)pyridin-2-amine (55.1 mg).

$^1$H NMR (400 MHz, CDCl$_3$) δ 0.11-0.21 (1H, m), 0.24-0.35 (1H, m), 0.38-0.49 (1H, m), 0.52-0.64 (1H, m), 0.97-1.08 (1H, m), 1.12-1.23 (9H, m), 1.71-1.91 (3H, m), 2.27-2.79 (4H, m), 2.29-2.39 (1H, m), 2.73 (3H, tt, J=14.6, 7.4 Hz), 2.83 (3H, s), 3.40 (1H, brs), 3.75 (3H, s), 3.83 (2H, d, J=6.0 Hz), 3.98-4.12 (2H, m), 4.22-4.63 (2H, m), 6.20 (1H, s), 6.47 (1H, dd, J=8.4, 2.3 Hz), 6.57 (1H, brs), 6.73-6.92 (4H, m), 7.21 (2H, t, J=7.8 Hz), 7.24-7.32 (1H, m), 8.35 (1H, dd, J=4.8, 1.2 Hz).

Step 5) 3-cyclopropyl-3-(3-((1-(5-methoxy-2-((2-methoxy-2-methylpropyl)(pyridin-2-yl)carbamoyl)phenyl)piperidin-4-yl)methoxy)phenyl)propanoic acid In the same manner as in Example 1, step 4, the title compound (77.9 mg) was obtained as a white amorphous powder from ethyl 3-cyclopropyl-3-(3-((1-(5-methoxy-2-((2-methoxy-2-methylpropyl)(pyridin-2-yl)carbamoyl)phenyl)piperidin-4-yl)methoxy)phenyl)propanoate (85.0 mg).

MS (ESI+): [M+H]$^+$ 616.3.

Example 36

3-cyclopropyl-3-(3-((1-(2-((cyclopropylmethyl)(4-methylpyridin-2-yl)carbamoyl)-5-methoxyphenyl)piperidin-4-yl)methoxy)phenyl)propanoic acid Step 1) N-(cyclopropylmethyl)-4-methylpyridin-2-amine To a solution (20 mL) of 4-methylpyridin-2-amine (2.89 g) and cyclopropanecarbaldehyde (1 mL) in acetic acid was added sodium triacetoxyborohydride (7.09 g) at 0° C., and the mixture was stirred at room temperature for 3 hr. Aqueous sodium hydroxide solution (8 N) was added to the reaction mixture, and the mixture was vigorously stirred and extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (1.11 g) as a pale-yellow oil. MS (ESI+): [M+H]$^+$ 163.0.

Step 2) 3-cyclopropyl-3-(3-((1-(2-((cyclopropylmethyl)(4-methylpyridin-2-yl)carbamoyl)-5-methoxyphenyl)piperidin-4-yl)methoxy)phenyl)propanoic acid In the same manner as in Example 32, step 2 and Example 1, step 4, the title compound (133 mg) was obtained as a white amorphous powder from 2-(4-((3-(1-cyclopropyl-3-ethoxy-3-oxopropyl)phenoxy)methyl)piperidin-1-yl)-4-methoxybenzoic acid (150 mg) and N-(cyclopropylmethyl)-4-methylpyridin-2-amine (101 mg).

MS (ESI+): [M+H]$^+$ 598.3.

Example 37

3-(3-((1-(2-((4-cyano-4-methylpiperidin-1-yl)carbonyl)-5-methoxyphenyl)piperidin-4-yl)methoxy)phenyl)-3-cyclopropylpropanoic acid Step 1) 4-methylpiperidine-4-carbonitrile hydrochloride A solution (1 M, 2.85 mL) of lithium hexamethyldisilazane in THF was added to a solution (5 mL) of tert-butyl 4-cyanopiperidine-1-carboxylate (300 mg) in THF at −78° C., and the mixture was stirred at −78° C. for 20 min. Iodomethane (5 mL) was added dropwise to the reaction mixture at −78° C. The mixture was allowed to gradually warm from −78° C. to room temperature, and stirred for 21 hr. Water was added to the reaction mixture, and the mixture was extracted with ethyl acetate. The extract was washed with saturated brine, and dried over anhydrous magnesium sulfate. A solution (4 N, 5 mL) of hydrochloric acid in ethyl acetate was added to the residue, and the mixture was stirred at room temperature for 1.5 hr. The solvent of the reaction mixture was evaporated under reduced pressure to give a crude product of the title compound (195 mg) as an orange solid. This compound was used for the next step without further purification.

Step 2) 3-(3-((1-(2-((4-cyano-4-methylpiperidin-1-yl)carbonyl)-5-methoxyphenyl)piperidin-4-yl)methoxy)phenyl)-3-cyclopropylpropanoic acid In the same manner as in Example 32, step 2 and Example 1, step 4, the title compound (153 mg) was obtained as a yellow amorphous powder from 2-(4-((3-(1-cyclopropyl-3-ethoxy-3-oxopropyl)phenoxy)methyl)piperidin-1-yl)-4-methoxybenzoic acid (150 mg) and 4-methylpiperidine-4-carbonitrile hydrochloride (100 mg).
MS (ESI+): [M+H]$^+$ 560.3.

Example 38

3-(3-((1-(2-((4-cyano-4-(2-methylpropyl)piperidin-1-yl)carbonyl)-5-methoxyphenyl)piperidin-4-yl)methoxy)phenyl)-3-cyclopropylpropanoic acid Step 1) 4-(2-methylpropyl)piperidine-4-carbonitrile hydrochloride In the same manner as in Example 37, step 1, the title compound (153 mg) was obtained as a pale-yellow solid from tert-butyl 4-cyanopiperidine-1-carboxylate (300 mg) and 1-bromo-2-methylpropane (156 μL). This compound was used for the next step without further purification.

Step 2) 3-(3-((1-(2-((4-cyano-4-(2-methylpropyl)piperidin-1-yl)carbonyl)-5-methoxyphenyl)piperidin-4-yl)methoxy)phenyl)-3-cyclopropylpropanoic acid In the same manner as in Example 32, step 2 and Example 1, step 4, the title compound (134 mg) was obtained as a white amorphous powder from 2-(4-((3-(1-cyclopropyl-3-ethoxy-3-oxopropyl)phenoxy)methyl)piperidin-1-yl)-4-methoxybenzoic acid (150 mg) and 4-(2-methylpropyl)piperidine-4-carbonitrile hydrochloride (126 mg).
MS (ESI+): [M+H]$^+$ 602.3.

Example 39

3-cyclopropyl-3-(3-((1-(2-((2-fluoro-2-methylpropyl)(pyridin-2-yl)carbamoyl)-5-methoxyphenyl)piperidin-4-yl)methoxy)phenyl)propanoic acid Step 1) N-(2-fluoro-2-methylpropyl)pyridin-2-amine To a solution of 2-methyl-1-(pyridin-2-ylamino)propan-2-ol (390 mg) obtained in Example 35, step 2, in toluene (4 mL) was added N,N-diethylaminosulfur trifluoride (0.78 mL) at room temperature, and the mixture was stirred for 1.5 hr. The reaction mixture was added dropwise to an ice-cooled mixture of saturated aqueous sodium hydrogen carbonate solution and ethyl acetate, and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (160 mg) as a colorless oil.
$^1$H NMR (300 MHz, CDCl$_3$) δ 1.42 (6H, d, J=21.6 Hz), 3.56 (2H, dd, J=21.2, 5.9 Hz), 4.67 (1H, brs), 6.40-6.46 (1H, m), 6.56 (1H, ddd, J=7.1, 5.1, 0.8 Hz), 7.39 (1H, ddd, J=8.6, 7.0, 1.9 Hz), 8.03-8.11 (1H, m).

Step 2) 3-cyclopropyl-3-(3-((1-(2-((2-fluoro-2-methylpropyl)(pyridin-2-yl)carbamoyl)-5-methoxyphenyl)piperidin-4-yl)methoxy)phenyl)propanoic acid In the same manner as in Example 32, step 2 and Example 1, step 4, the title compound (189 mg) was obtained as a colorless amorphous powder from N-(2-fluoro-2-methylpropyl)pyridin-2-amine (140 mg) and 2-(4-((3-(1-cyclopropyl-3-ethoxy-3-oxopropyl)phenoxy)methyl)piperidin-1-yl)-4-methoxybenzoic acid (200 mg).
MS (ESI+): [M+H]$^+$ 604.4.

Example 40

3-cyclopropyl-3-(3-((1-(2-((cyclopropylmethyl)(pyridin-2-yl)carbamoyl)-5-methoxyphenyl)piperidin-4-yl)methoxy)phenyl)propanoic acid Step 1) N-(cyclopropylmethyl)pyridin-2-amine In the same manner as in Example 36, step 1, the title compound (1.46 g) was obtained as a colorless liquid from cyclopropanecarbaldehyde (1.21 mL) and 2-aminopyridine (3.03 g).
$^1$H NMR (400 MHz, DMSO-d$_6$) δ 0.11-0.27 (2H, m), 0.33-0.53 (2H, m), 0.91-1.11 (1H, m), 3.09 (2H, t, J=6.1 Hz), 6.26-6.59 (3H, m), 7.32 (1H, ddd, J=8.5, 6.9, 2.0 Hz), 7.83-8.00 (1H, m).

Step 2) ethyl 3-cyclopropyl-3-(3-((1-(2-((cyclopropylmethyl)(pyridin-2-yl)carbamoyl)-5-methoxyphenyl)piperidin-4-yl)methoxy)phenyl)propanoate In the same manner as in Example 32, step 2, the title compound (116 mg) was obtained as a colorless oil from 2-(4-((3-(1-cyclopropyl-3-ethoxy-3-oxopropyl)phenoxy)methyl)piperidin-1-yl)-4-methoxybenzoic acid (100 mg) and N-(cyclopropylmethyl)pyridin-2-amine (77 mg).
$^1$H NMR (400 MHz, CDCl$_3$) δ 0.08-0.23 (3H, m), 0.24-0.32 (1H, m), 0.37 (2H, d, J=8.0 Hz), 0.40-0.48 (1H, m), 0.53-0.64 (1H, m), 0.94-1.09 (1H, m), 1.10-1.21 (1H, m), 1.18 (4H, t, J=7.1 Hz), 1.43-1.61 (2H, m), 1.67-1.89 (3H, m), 2.29-2.39 (1H, m), 2.56 (2H, brs), 2.64-2.83 (3H, m), 3.78 (3H, s), 3.81 (2H, d, J=6.3 Hz), 3.99-4.11 (4H, m), 6.21 (1H, s), 6.53 (1H, dd, J=8.4, 2.3 Hz), 6.67 (1H, brs), 6.73-6.76 (1H, m), 6.78 (1H, s), 6.82 (1H, d, J=7.7 Hz), 6.88-6.95 (1H, m), 7.21 (1H, t, J=7.8 Hz), 7.24-7.34 (1H, m), 7.42 (1H, d, J=8.4 Hz), 8.32-8.44 (1H, m).

Step 3) 3-cyclopropyl-3-(3-((1-(2-((cyclopropylmethyl)(pyridin-2-yl)carbamoyl)-5-methoxyphenyl)piperidin-4-yl)methoxy)phenyl)propanoic acid In the same manner as in Example 1, step 4, the title compound (94.6 mg) was obtained as a white amorphous powder from ethyl 3-cyclopropyl-3-(3-((1-(2-((cyclopropylmethyl)(pyridin-2-yl)carbamoyl)-5-methoxyphenyl)piperidin-4-yl)methoxy)phenyl)propanoate (116 mg).

MS (ESI+): [M+H]$^+$ 584.3.

Example 41

3-cyclopropyl-3-(3-((1-(5-methoxy-2-((2-methylpropyl)(6-methylpyridin-2-yl)carbamoyl)phenyl)piperidin-4-yl)methoxy)phenyl)propanoic acid By a method similar to that in Example 32, step 2 and Example 1, step 4, the title compound (98 mg) was obtained as a white amorphous powder from 2-(4-((3-(1-cyclopropyl-3-ethoxy-3-oxopropyl)phenoxy)methyl)piperidin-1-yl)-4-methoxybenzoic acid (111.8 mg) and 6-methyl-N-(2-methylpropyl)pyridin-2-amine (76 mg).

MS (ESI+): [M+H]$^+$ 600.3.

Example 42

3-cyclopropyl-3-(3-((1-(5-methoxy-2-((2-methylpropyl)(4-methylpyridin-2-yl)carbamoyl)phenyl)piperidin-4-yl)methoxy)phenyl)propanoic acid Step 1) ethyl 3-cyclopropyl-3-(3-((1-(5-methoxy-2-((2-methylpropyl)(4-methylpyridin-2-yl)carbamoyl)phenyl)piperidin-4-yl)methoxy)phenyl)propanoate In the same manner as in Example 32, step 2, the title compound (86 mg) was obtained as a colorless oil from 2-(4-((3-(1-cyclopropyl-3-ethoxy-3-oxopropyl)phenoxy)methyl)piperidin-1-yl)-4-methoxybenzoic acid (120 mg) and 4-methyl-N-(2-methylpropyl)pyridin-2-amine (82.0 mg).

MS (ESI+): [M+H]$^+$ 628.5.

Step 2) 3-cyclopropyl-3-(3-((1-(5-methoxy-2-((2-methylpropyl)(4-methylpyridin-2-yl)carbamoyl)phenyl)piperidin-4-yl)methoxy)phenyl)propanoic acid In the same manner as in Example 1, step 4, the title compound (41.0 mg) was obtained as a grayish white solid from ethyl 3-cyclopropyl-3-(3-((1-(5-methoxy-2-((2-methylpropyl)(4-methylpyridin-2-yl)carbamoyl)phenyl)piperidin-4-yl)methoxy)phenyl)propanoate (86 mg).

MS (ESI+): [M+H]$^+$ 600.3.

Example 43

3-(3-((1-(2-((2-cyano-2-methylpropyl)(pyridin-2-yl)carbamoyl)-5-methoxyphenyl)piperidin-4-yl)methoxy)phenyl)-3-cyclopropylpropanoic acid Step 1) methyl 3-(1,3-dioxoisoindolin-2-yl)-2,2-dimethylpropanoate Under a nitrogen atmosphere, a 2.2 M solution of diethyl azodicarboxylate in toluene (12.4 mL) was added to a solution of phthalimide (4.01 g), methyl 3-hydroxy-2,2-dimethylpropanoate (3.00 g) and triphenylphosphine (7.14 g) in THF (30 mL) at room temperature, and the mixture was stirred at room temperature for 16 hr. The solvent was evaporated under reduced pressure, and the residue was purified by silica gel column chromatography (ethyl acetate/hexane) to give the title compound (5.3 g) as a white solid.

$^1$H NMR (400 MHz, CDCl$_3$) δ 1.25 (6H, s), 3.73 (3H, s), 3.85 (2H, s), 7.72 (2H, dd, J=5.3, 3.1 Hz), 7.84 (2H, dd, J=5.4, 3.0 Hz).

Step 2) methyl 3-amino-2,2-dimethylpropanoate

Under a nitrogen atmosphere, hydrazine monohydrate (4.92 mL) was added to a solution of methyl 3-(1,3-dioxoisoindolin-2-yl)-2,2-dimethylpropanoate (5.3 g) in methanol (100 mL) at room temperature, and the mixture was stirred at 60° C. for 1 hr. The reaction mixture was diluted with diethyl ether, and the resultant white precipitate was removed by filtration. The solvent was evaporated under reduced pressure to give a crude product of the title compound (2.42 g) as a pale-yellow oil.

$^1$H NMR (400 MHz, DMSO-d) δ 1.06 (6H, s), 1.35 (2H, brs), 2.59 (2H, s), 3.58 (3H, s).

Step 3) methyl 2,2-dimethyl-3-(pyridin-2-ylamino)propanoate

In the same manner as in Example 135, step 1, the title compound (744 mg) was obtained as a pale-yellow oil from methyl 3-amino-2,2-dimethylpropanoate (1.00 g) and pyridine N-oxide (1.81 g).

$^1$H NMR (400 MHz, CDCl$_3$) δ 1.26 (6H, s), 3.49 (2H, d, J=6.4 Hz), 3.68 (3H, s), 4.78 (1H, brs), 6.39 (1H, d, J=8.4 Hz), 6.53 (1H, dd, J=6.6, 5.6 Hz), 7.32-7.44 (1H, m), 8.05 (1H, d, J=4.8 Hz).

Step 4) 2,2-dimethyl-3-(pyridin-2-ylamino)propanamide

A 28% solution of sodium methoxide in methanol (3.62 mL) was added to a solution of methyl 2,2-dimethyl-3-(pyridin-2-ylamino)propanoate (744 mg) and formamide (1.42 mL) in DMF (10 mL) at room temperature, and the mixture was stirred at 70° C. for 30 min. Water was added to the reaction mixture, and the mixture was extracted with ethyl acetate. The extract was washed with water and saturated brine, and dried over anhydrous magnesium sulfate. The solvent was evaporated under reduced pressure to give a crude product of the title compound as a pale-yellow oil. This compound was used for the next step without further purification.

Step 5) 2,2-dimethyl-3-(pyridin-2-ylamino)propanenitrile

Trifluoroacetic anhydride (1.51 mL) was added to a solution of 2,2-dimethyl-3-(pyridin-2-ylamino)propanamide (entire amount) in pyridine (10 mL) at room temperature, and the mixture was stirred at room temperature for 5 min. Water was added to the reaction mixture, and the mixture was extracted with ethyl acetate. The extract was washed with water and saturated brine, dried over anhydrous magnesium sulfate and the solvent was evaporated under reduced pressure. To a solution of the obtained residue in methanol (10 mL) was added potassium carbonate (1.48 g) at room temperature, and the mixture was stirred at 60° C. for 5 min. Water was added to the reaction mixture, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (203 mg) as a yellow oil.

¹H NMR (400 MHz, CDCl₃) δ 1.40 (6H, s), 3.62 (2H, d, J=6.8 Hz), 4.64 (1H, brs), 6.46 (1H, d, J=8.3 Hz), 6.60 (1H, dd, J=6.7, 5.5 Hz), 7.32-7.48 (1H, m), 8.07 (1H, d, J=4.1 Hz).

Step 6) ethyl 3-(3-((1-(2-((2-cyano-2-methylpropyl) (pyridin-2-yl)carbamoyl)-5-methoxyphenyl)piperidin-4-yl)methoxy)phenyl)-3-cyclopropylpropanoate In the same manner as in Example 32, step 2, the title compound (108 mg) was obtained as a white amorphous powder from 2-(4-((3-(1-cyclopropyl-3-ethoxy-3-oxopropyl)phenoxy)methyl)piperidin-1-yl)-4-methoxybenzoic acid (100 mg) and 2,2-dimethyl-3-(pyridin-2-ylamino)propanenitrile (91.0 mg).

¹H NMR (400 MHz, CDCl₃) δ 0.12-0.21 (1H, m), 0.23-0.32 (1H, m), 0.38-0.49 (1H, m), 0.53-0.64 (1H, m), 0.96-1.10 (1H, m), 1.19 (3H, t, J=7.2 Hz), 1.39 (6H, brs), 1.38-1.68 (2H, m), 1.69-1.92 (3H, m), 2.30-2.39 (1H, m), 2.35-2.71 (3H, m), 2.67-2.80 (2H, m), 3.14-3.42 (1H, m), 3.78 (3H, s), 3.82 (2H, d, J=6.3 Hz), 4.00-4.12 (2H, m), 4.33-4.86 (2H, m), 6.20 (1H, d, J=2.1 Hz), 6.54 (2H, dd, J=8.4, 2.3 Hz), 6.70-6.88 (3H, m), 6.90-7.01 (1H, m), 7.18-7.25 (2H, m), 7.37 (1H, d, J=8.4 Hz), 8.40 (1H, d, J=3.6 Hz).

Step 7) 3-(3-((1-(2-((2-cyano-2-methylpropyl)(pyridin-2-yl)carbamoyl)-5-methoxyphenyl)piperidin-4-yl)methoxy)phenyl)-3-cyclopropylpropanoic acid In the same manner as in Example 1, step 4, the title compound (98.0 mg) was obtained as a white amorphous powder from ethyl 3-(3-((1-(2-((2-cyano-2-methylpropyl) (pyridin-2-yl)carbamoyl)-5-methoxyphenyl)piperidin-4-yl)methoxy)phenyl)-3-cyclopropylpropanoate (108 mg).

MS (ESI+): [M+H]⁺ 611.2.

Example 44

3-cyclopropyl-3-(3-((1-(5-methoxy-2-((2-methylpropyl)(6-oxo-1,6-dihydropyridin-2-yl)carbamoyl)phenyl)piperidin-4-yl)methoxy)phenyl)propanoic acid Step 1) ethyl 3-cyclopropyl-3-(3-((1-(5-methoxy-2-((2-methylpropyl)(6-methoxypyridin-2-yl)carbamoyl)phenyl)piperidin-4-yl)methoxy)phenyl)propanoate In the same manner as in Example 32, step 2, the title compound (153 mg) was obtained as a colorless oil from 2-(4-(((4-(1-cyclopropyl-3-ethoxy-3-oxopropyl)pyridin-2-yl)oxy)methyl)piperidin-1-yl)-4-methoxybenzoic acid (150 mg) and 6-methoxy-N-(2-methylpropyl)pyridin-2-amine (140 mg).

¹H NMR (400 MHz, CDCl₃) δ 0.09-0.21 (1H, m), 0.23-0.35 (1H, m), 0.38-0.49 (1H, m), 0.52-0.64 (1H, m), 0.89 (6H, d, J=5.5 Hz), 0.98-1.07 (1H, m), 1.18 (3H, t, J=7.1 Hz), 1.22-1.52 (2H, m), 1.69-1.99 (4H, m), 2.27-2.40 (1H, m), 2.42-2.84 (5H, m), 3.20-3.46 (1H, m), 3.74-3.85 (2H, m), 3.78 (3H, s), 3.80 (3H, s), 3.98-4.12 (4H, m), 6.25 (1H, brs), 6.35 (1H, d, J=8.2 Hz), 6.51 (1H, d, J=8.7 Hz), 6.74 (1H, d, J=8.0 Hz), 6.77 (1H, s), 6.82 (1H, d, J=7.5 Hz), 7.15-7.24 (2H, m), 7.34 (1H, d, J=8.3 Hz).

Step 2) ethyl 3-cyclopropyl-3-(3-((1-(5-methoxy-2-((2-methylpropyl)(6-oxo-1,6-dihydropyridin-2-yl) carbamoyl)phenyl)piperidin-4-yl)methoxy)phenyl) propanoate Under a nitrogen atmosphere, a mixture of ethyl 3-cyclopropyl-3-(3-((1-(5-methoxy-2-((2-methylpropyl)(6-methoxypyridin-2-yl)carbamoyl)phenyl)piperidin-4-yl) methoxy)phenyl)propanoate (153 mg), pyridinium chloride (274 mg) and DMF (0.2 mL) was stirred at 130° C. for 16 hr. 1N Hydrochloric acid was added to the reaction solution at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (32.0 g) as a yellow oil.

¹H NMR (400 MHz, CDCl₃) δ 0.10-0.21 (1H, m), 0.22-0.32 (1H, m), 0.37-0.48 (1H, m), 0.53-0.63 (1H, m), 0.88-1.08 (7H, m), 1.18 (3H, t, J=7.1 Hz), 1.50-1.69 (2H, m), 1.93 (4H, dd, J=13.4, 6.5 Hz), 2.34 (1H, q, J=7.9 Hz), 2.49-3.01 (4H, m), 3.17-3.81 (4H, m), 3.77 (3H, s), 3.81 (2H, d, J=5.4 Hz), 4.00-4.11 (2H, m), 5.80 (1H, d, J=7.2 Hz), 6.25 (1H, d, J=9.0 Hz), 6.48-6.58 (2H, m), 6.71 (1H, d, J=8.0 Hz), 6.77 (1H, s), 6.82 (1H, d, J=7.5 Hz), 7.09 (1H, d, J=8.3 Hz), 7.14-7.24 (2H, m), 10.51 (1H, br. s).

Step 3) 3-cyclopropyl-3-(3-((1-(5-methoxy-2-((2-methylpropyl)(6-oxo-1,6-dihydropyridin-2-yl)carbamoyl)phenyl)piperidin-4-yl)methoxy)phenyl)propanoic acid In the same manner as in Example 1, step 4, the title compound (7.70 mg) was obtained as a white solid from ethyl 3-cyclopropyl-3-(3-((1-(5-methoxy-2-((2-methylpropyl)(6-oxo-1,6-dihydropyridin-2-yl)carbamoyl)phenyl)piperidin-4-yl)methoxy)phenyl)propanoate (32.0 mg).

MS (ESI+): [M+H]⁺ 602.2.

Example 45

3-cyclopropyl-3-(3-((1-(2-((2,2-dimethylpropyl) (pyrimidin-2-yl)carbamoyl)-5-ethylphenyl)piperidin-4-yl)methoxy)phenyl)propanoic acid Step 1) 4-bromo-2-(4-(hydroxymethyl)piperidin-1-yl)benzaldehyde In the same manner as in Example 1, step 2, the title compound (8.33 g) was obtained as a yellow oil from 4-bromo-2-fluorobenzaldehyde (10 g).

¹H NMR (400 MHz, DMSO-d₆) δ 1.29-1.43 (2H, m), 1.45-1.60 (1H, m), 1.77 (2H, d, J=12.9 Hz), 2.87 (2H, t, J=11.0 Hz), 3.20-3.45 (4H, m), 7.28 (1H, d, J=8.3 Hz), 7.33 (1H, d, J=1.5 Hz), 7.58 (1H, d, J=8.2 Hz), 10.06 (1H, s).

Step 2) 4-bromo-2-(4-(((tert-butyldiphenylsilyl)oxy) methyl)piperidin-1-yl)benzaldehyde To a solution of 4-bromo-2-(4-(hydroxymethyl)piperidin-1-yl)benzaldehyde (8.33 g) and imidazole (5.71 g) in DMF (50 mL) was added tert-butyldiphenylchlorosilane (8.72 mL), and the mixture was stirred at room temperature for 1 hr. Water was added to the reaction mixture, and the mixture was extracted with ethyl acetate. The extract was washed with water and saturated brine, and dried over anhydrous magnesium sulfate. The solvent was evaporated under reduced pressure to give a crude product of the title compound as a yellow gummy substance. This compound was used for the next step without further purification.

Step 3) 4-bromo-2-(4-(((tert-butyldiphenylsilyl)oxy)methyl)piperidin-1-yl)benzoic acid In the same manner as in Example 262, step 2, the title compound (13.1 g) was obtained as a white solid from a crude product of 4-bromo-2-(4-(((tert-butyldiphenylsilyl)oxy)methyl)piperidin-1-yl)benzaldehyde (entire amount).
$^1$H NMR (300 MHz, DMSO-$d_6$) δ 1.03 (9H, s), 1.36-1.56 (2H, m), 1.74-1.95 (3H, m), 2.97-3.19 (4H, m), 3.61 (2H, d, J=5.5 Hz), 7.40-7.51 (6H, m), 7.56 (1H, dd, J=8.5, 1.6 Hz), 7.60-7.68 (4H, m), 7.84-7.93 (2H, m).

Step 4) benzyl 4-bromo-2-(4-(((tert-butyldiphenylsilyl)oxy)methyl)piperidin-1-yl)benzoate Under a nitrogen atmosphere, to a solution of 4-bromo-2-(4-(((tert-butyldiphenylsilyl)oxy)methyl)piperidin-1-yl)benzoic acid (13.0 g) and DMF (180 μL) in THF (130 mL) was added oxalyl chloride (3.10 mL) at 0° C., and the mixture was stirred at 0° C. for 20 min. To the reaction solution was added benzylalcohol (4.88 mL) at 0° C., and the mixture was stirred at 0° C. for 15 min. Saturated aqueous sodium hydrogen carbonate solution was added to the reaction mixture, and the mixture was extracted with ethyl acetate. The extract was washed with water and saturated brine, and dried over anhydrous magnesium sulfate. The solvent was evaporated under reduced pressure, and the residue was purified by silica gel column chromatography (NH, ethyl acetate/hexane) to give the title compound (14.9 g) as a colorless oil.
$^1$H NMR (400 MHz, DMSO-$d_6$) δ 1.01 (9H, s), 1.55-1.70 (3H, m), 2.68 (2H, t, J=11.4 Hz), 3.19 (2H, d, J=11.9 Hz), 3.26-3.31 (2H, m), 3.46 (2H, d, J=5.6 Hz), 5.28 (2H, s), 7.14 (1H, dd, J=8.3, 1.3 Hz), 7.18 (1H, s), 7.24-7.37 (3H, m), 7.40-7.56 (9H, m), 7.58-7.70 (4H, m).

Step 5) benzyl 2-(4-(hydroxymethyl)piperidin-1-yl)-4-vinylbenzoate

Under a nitrogen atmosphere, a mixture of benzyl 4-bromo-2-(4-(((tert-butyldiphenylsilyl)oxy)methyl)piperidin-1-yl)benzoate (14.7 g), vinyltrimethylsilane (9.95 mL), palladium acetate (256 mg), tris(2-methylphenyl)phosphine (1.04 g) and triethylamine (9.55 mL) was stirred in a DMF (50 mL) solvent at 130° C. for 1 hr. To the reaction mixture was added water, and the mixture was extracted with ethyl acetate. The extract was washed with water and saturated brine, dried over anhydrous magnesium sulfate and the solvent was evaporated under reduced pressure. The obtained residue was dissolved in THF (50 mL), 1 M tetrabutylammonium fluoride THF solution (45.7 mL) was added, and the mixture was stirred at 70° C. for 30 min. To the reaction mixture was added water, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (3.1 g) as a yellow oil.
$^1$H NMR (400 MHz, DMSO-$d_6$) δ 1.09-1.25 (2H, m), 1.35-1.51 (1H, m), 1.64 (2H, d, J=11.3 Hz), 2.67 (2H, t, J=11.1 Hz), 3.17-3.27 (4H, m), 4.43 (1H, t, J=5.2 Hz), 5.29 (2H, s), 5.35 (1H, d, J=10.9 Hz), 5.91 (1H, d, J=17.7 Hz), 6.73 (1H, dd, J=17.6, 11.0 Hz), 7.06-7.14 (2H, m), 7.30-7.42 (3H, m), 7.43-7.51 (2H, m), 7.57 (1H, d, J=7.9 Hz).

Step 6) benzyl 2-(4-((3-(1-cyclopropyl-3-ethoxy-3-oxopropyl)phenoxy)methyl)piperidin-1-yl)-4-vinylbenzoate Under a nitrogen atmosphere, to a solution of benzyl 2-(4-(hydroxymethyl)piperidin-1-yl)-4-vinylbenzoate (3.1 g) and ethyl 3-cyclopropyl-3-(3-hydroxyphenyl)propanoate (2.50 g) in toluene (15 mL) was added a 0.7 M solution (20 mL) of 2-(tributylphosphoranylidene)acetonitrile in toluene at room temperature, and the mixture was stirred at 100° C. for 30 min. The solvent was evaporated under reduced pressure, and the residue was purified by silica gel column chromatography (ethyl acetate/hexane) to give the title compound (3.39 g) as a yellow oil.
$^1$H NMR (300 MHz, DMSO-$d_6$) δ 0.07-0.17 (1H, m), 0.18-0.27 (1H, m), 0.28-0.40 (1H, m), 0.43-0.59 (1H, m), 0.97-1.07 (1H, m), 1.08 (3H, t, J=7.1 Hz), 1.25-1.43 (2H, m), 1.68-1.84 (3H, m), 2.17-2.31 (1H, m), 2.65-2.81 (4H, m), 3.21-3.29 (2H, m), 3.79 (2H, d, J=6.0 Hz), 3.92-4.01 (2H, m), 5.30 (2H, s), 5.36 (1H, d, J=11.7 Hz), 5.92 (1H, d, J=17.0 Hz), 6.66-6.79 (2H, m), 6.80-6.85 (2H, m), 7.08-7.15 (2H, m), 7.16-7.22 (1H, m), 7.31-7.42 (3H, m), 7.45-7.50 (2H, m), 7.60 (1H, d, J=7.9 Hz).

Step 7) 2-(4-((3-(1-cyclopropyl-3-ethoxy-3-oxopropyl)phenoxy)methyl)piperidin-1-yl)-4-ethylbenzoic acid In the same manner as in Example 2, step 4, the title compound (2.76 g) was obtained as a colorless oil from benzyl 2-(4-((3-(1-cyclopropyl-3-ethoxy-3-oxopropyl)phenoxy)methyl)piperidin-1-yl)-4-vinylbenzoate (3.39 g).
$^1$H NMR (300 MHz, DMSO-$d_6$) δ 0.08-0.17 (1H, m), 0.18-0.27 (1H, m), 0.28-0.38 (1H, m), 0.44-0.57 (1H, m), 0.97-1.07 (1H, m), 1.09 (3H, t, J=7.1 Hz), 1.21 (3H, t, J=7.6 Hz), 1.42-1.64 (2H, m), 1.95-2.13 (3H, m), 2.18-2.31 (1H, m), 2.62-2.79 (4H, m), 3.11 (4H, brs), 3.90-4.01 (4H, m), 6.75-6.89 (3H, m), 7.20 (1H, t, J=7.8 Hz), 7.28 (1H, d, J=8.1 Hz), 7.60 (1H, s), 7.96 (1H, d, J=8.0 Hz).

Step 8) N-(2,2-dimethylpropyl)pyrimidin-2-amine

Under a nitrogen atmosphere, to a solution of 2-chloropyrimidine (3.00 g) and 2,2-dimethylpropan-1-amine (4.62 mL) in DMF (30 mL) was added diisopropylethylamine (13.7 mL) at room temperature, and the mixture was stirred at 130° C. for 2 hr. To the reaction mixture was added water, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (1.91 g) as a white solid.
$^1$H NMR (400 MHz, DMSO-$d_6$) δ 0.88 (9H, s), 3.16 (2H, d, J=6.3 Hz), 6.50 (1H, t, J=4.8 Hz), 7.01 (1H, brs), 8.22 (2H, d, J=4.6 Hz).

Step 9) ethyl 3-cyclopropyl-3-(3-((1-(2-((2,2-dimethylpropyl)(pyrimidin-2-yl)carbamoyl)-5-ethylphenyl)piperidin-4-yl)methoxy)phenyl)propanoate In the same manner as in Example 32, step 2, the title compound (20.3 mg) was obtained as a colorless oil from 2-(4-((3-(1-cyclopropyl-3-ethoxy-3-oxopropyl)phenoxy)methyl)piperidin-1-yl)-4-ethylbenzoic acid (100 mg) and N-(2,2-dimethylpropyl)pyrimidin-2-amine (86 mg).

$^1$H NMR (400 MHz, CDCl$_3$) δ 0.11-0.21 (1H, m), 0.23-0.33 (1H, m), 0.38-0.48 (1H, m), 0.52-0.63 (1H, m), 0.87 (9H, s), 0.98-1.09 (1H, m), 1.15-1.22 (6H, m), 1.46-1.61 (2H, m), 1.67-1.88 (3H, m), 2.30-2.40 (1H, m), 2.40-2.65 (4H, m), 2.56 (2H, q, J=7.6 Hz), 2.66-2.80 (2H, m), 3.82 (2H, d, J=5.9 Hz), 4.01-4.11 (2H, m), 4.29 (2H, s), 6.44 (1H, s), 6.72-6.90 (5H, m), 7.22 (1H, t, J=7.8 Hz), 7.40 (1H, d, J=7.8 Hz), 8.30 (2H, d, J=4.8 Hz).

Step 10) 3-cyclopropyl-3-(3-((1-(2-((2,2-dimethylpropyl)(pyrimidin-2-yl)carbamoyl)-5-ethylphenyl)piperidin-4-yl)methoxy)phenyl)propanoic acid In the same manner as in Example 1, step 4, the title compound (9.2 mg) was obtained as a white amorphous powder from ethyl 3-cyclopropyl-3-(3-((1-(2-((2,2-dimethylpropyl)(pyrimidin-2-yl)carbamoyl)-5-ethylphenyl)piperidin-4-yl)methoxy)phenyl)propanoate (20.3 mg).
MS (ESI+): [M+H]$^+$ 599.4.

Example 46

3-cyclopropyl-3-(3-((1-(5-ethyl-2-(pyridin-2-yl(2,2,2-trifluoroethyl)carbamoyl)phenyl)piperidin-4-yl)methoxy)phenyl)propanoic acid Step 1) N-(2,2,2-trifluoroethyl)pyridin-2-amine In the same manner as in Example 32, step 1, the title compound (1.25 g) was obtained as white crystals from 2-aminopyridine (1.0 g).
$^1$H NMR (300 MHz, DMSO-d$_6$) δ 4.14 (2H, qd, J=9.9, 6.7 Hz), 6.56-6.65 (2H, m), 7.08 (1H, t, J=6.3 Hz), 7.40-7.47 (1H, m), 7.98-8.04 (1H, m).

Step 2) ethyl 3-cyclopropyl-3-(3-((1-(5-ethyl-2-(pyridin-2-yl(2,2,2-trifluoroethyl)carbamoyl)phenyl)piperidin-4-yl)methoxy)phenyl)propanoate In the same manner as in Example 32, step 2, the title compound (97.8 mg) was obtained as a colorless oil from 2-(4-((3-(1-cyclopropyl-3-ethoxy-3-oxopropyl)phenoxy)methyl)piperidin-1-yl)-4-ethylbenzoic acid (100 mg) and N-(2,2,2-trifluoroethyl)pyridin-2-amine (92.0 mg).
$^1$H NMR (400 MHz, DMSO-d$_6$) δ 0.08-0.17 (1H, m), 0.17-0.26 (1H, m), 0.28-0.37 (1H, m), 0.45-0.55 (1H, m), 1.00-1.09 (1H, m), 1.09 (3H, t, J=7.2 Hz), 1.14 (3H, t, J=7.4 Hz), 1.61-1.84 (3H, m), 2.18-2.30 (1H, m), 2.42-2.62 (8H, m), 2.61-2.82 (2H, m), 3.83 (2H, d, J=6.1 Hz), 3.91-4.01 (2H, m), 4.97 (2H, brs), 6.65 (1H, s), 6.71 (1H, brs), 6.75-6.91 (4H, m), 7.04-7.13 (1H, m), 7.19 (1H, t, J=7.8 Hz), 7.23 (1H, d, J=7.8 Hz), 7.47 (1H, t, J=7.3 Hz), 8.39 (1H, d, J=3.8 Hz).

Step 3) 3-cyclopropyl-3-(3-((1-(5-ethyl-2-(pyridin-2-yl(2,2,2-trifluoroethyl)carbamoyl)phenyl)piperidin-4-yl)methoxy)phenyl)propanoic acid In the same manner as in Example 1, step 4, the title compound (82.9 mg) was obtained as a white amorphous powder from ethyl 3-cyclopropyl-3-(3-((1-(5-ethyl-2-(pyridin-2-yl(2,2,2-trifluoroethyl)carbamoyl)phenyl)piperidin-4-yl)methoxy)phenyl)propanoate (97.8 mg).
MS (ESI+): [M+H]$^+$ 610.3.

Example 47

3-cyclopropyl-3-(3-((1-(2-((2,2-dimethylpropyl)(4-methylpyridin-2-yl)carbamoyl)-5-ethylphenyl)piperidin-4-yl)methoxy)phenyl)propanoic acid By a method similar to that in Example 32, step 2 and Example 1, step 4, the title compound (100 mg) was obtained as a white amorphous powder from 2-(4-((3-(1-cyclopropyl-3-ethoxy-3-oxopropyl)phenoxy)methyl)piperidin-1-yl)-4-ethylbenzoic acid (108.7 mg) and 4-methyl-N-(2,2-dimethylpropyl)pyridin-2-amine (81 mg).
MS (ESI+): [M+H]$^+$ 612.4.

Example 48

3-(3-((1-(2-((3-chlorophenyl)(2,2-dimethylpropyl)carbamoyl)-5-ethylphenyl)piperidin-4-yl)methoxy)phenyl)-3-cyclopropylpropanoic acid Step 1) 3-chloro-N-(2,2-dimethylpropyl)aniline In the same manner as in Example 32, step 1, the title compound (1.38 g) was obtained as a pale-yellow oil from 3-chloroaniline (4.00 g).
$^1$H NMR (300 MHz, CDCl$_3$) δ 0.98 (9H, s), 2.87 (2H, d, J=5.9 Hz), 3.71 (1H, brs), 6.47 (1H, ddd, J=8.2, 2.3, 0.8 Hz), 6.55-6.65 (2H, m), 7.04 (1H, t, J=8.0 Hz).

Step 2) 3-(3-((1-(2-((3-chlorophenyl)(2,2-dimethylpropyl)carbamoyl)-5-ethylphenyl)piperidin-4-yl)methoxy)phenyl)-3-cyclopropylpropanoic acid In the same manner as in Example 32, step 2 and Example 1, step 4, the title compound (101 mg) was obtained as a colorless amorphous powder from 3-chloro-N-(2,2-dimethylpropyl)aniline (103 mg) and 2-(4-((3-(1-cyclopropyl-3-ethoxy-3-oxopropyl)phenoxy)methyl)piperidin-1-yl)-4-ethylbenzoic acid (100 mg).
MS (ESI+): [M+H]$^+$ 631.3.

Example 49

3-cyclopropyl-3-(3-((1-(5-ethyl-2-((2,2,3,3,3-pentafluoropropyl)(tetrahydro-2H-pyran-4-yl)carbamoyl)phenyl)piperidin-4-yl)methoxy)phenyl)propanoic acid Step 1) N-(2,2,3,3,3-pentafluoropropyl)tetrahydro-2H-pyran-4-amine In the same manner as in Example 14, step 1, the title compound (1.43 g) was obtained as a colorless oil from tetrahydro-2H-pyran-4-amine (800 mg).
$^1$H NMR (300 MHz, CDCl$_3$) δ 1.14 (1H, brs), 1.32-1.48 (2H, m), 1.78-1.89 (2H, m), 2.72-2.85 (1H, m), 3.25 (2H, t, J=15.4 Hz), 3.40 (2H, td, J=11.5, 2.3 Hz), 3.98 (2H, dt, J=11.6, 3.7 Hz).

Step 2) 3-cyclopropyl-3-(3-((1-(5-ethyl-2-((2,2,3,3,3-pentafluoropropyl)(tetrahydro-2H-pyran-4-yl)carbamoyl)phenyl)piperidin-4-yl)methoxy)phenyl)propanoic acid In the same manner as in Example 32, step 2 and Example 1, step 4, the title compound (140 mg) was obtained as colorless amorphous powder from N-(2,2,3,3,3-pentafluoropropyl)tetrahydro-2H-pyran-4-amine (122 mg) and 2-(4-((3-(1-cyclopropyl-3-ethoxy-3-oxopropyl)phenoxy)methyl)piperidin-1-yl)-4-ethylbenzoic acid (100 mg).

MS (ESI+): [M+H]$^+$ 667.4.

Example 50

3-cyclopropyl-3-(3-((1-(5-ethyl-2-((2,2,3,3,3-pentafluoropropyl)(tetrahydrofuran-3-yl)carbamoyl)phenyl)piperidin-4-yl)methoxy)phenyl)propanoic acid Step 1) N-(2,2,3,3,3-pentafluoropropyl)tetrahydrofuran-3-amine In the same manner as in Example 14, step 1, the title compound (1.16 g) was obtained as a colorless oil from tetrahydrofuran-3-amine (730 mg).

$^1$H NMR (300 MHz, CDCl$_3$) δ 1.23-1.39 (1H, m), 1.67-1.81 (1H, m), 2.05-2.19 (1H, m), 3.22 (2H, t, J=15.2 Hz), 3.45-3.55 (1H, m), 3.56-3.64 (1H, m), 3.73-3.86 (2H, m), 3.88-4.00 (1H, m).

Step 2) 3-cyclopropyl-3-(3-((1-(5-ethyl-2-((2,2,3,3,3-pentafluoropropyl)(tetrahydrofuran-3-yl)carbamoyl)phenyl)piperidin-4-yl)methoxy)phenyl)propanoic acid In the same manner as in Example 32, step 2 and Example 1, step 4, the title compound (91 mg) was obtained as a colorless amorphous powder from N-(2,2,3,3,3-pentafluoropropyl)tetrahydrofuran-3-amine (114 mg) and 2-(4-((3-(1-cyclopropyl-3-ethoxy-3-oxopropyl)phenoxy)methyl)piperidin-1-yl)-4-ethylbenzoic acid (100 mg).

MS (ESI+): [M+H]$^+$ 653.4.

Example 51

3-cyclopropyl-3-(3-((1-(5-ethyl-2-((2,2,3,3,3-pentafluoropropyl)(pyridin-2-yl)carbamoyl)phenyl)piperidin-4-yl)methoxy)phenyl)propanoic acid Step 1)
N-(2,2,3,3,3-pentafluoropropyl)pyridin-2-amine In the same manner as in Example 32, step 1, the title compound (530 mg) was obtained as a colorless solid from pyridin-2-amine (300 mg).

$^1$H NMR (300 MHz, CDCl$_3$) δ 4.09-4.27 (2H, m), 4.52 (1H, brs), 6.49 (1H, dt, J=8.3, 0.8 Hz), 6.67 (1H, ddd, J=7.2, 5.1, 0.8 Hz), 7.40-7.50 (1H, m), 8.12 (1H, ddd, J=5.0, 1.8, 0.8 Hz).

Step 2) 3-cyclopropyl-3-(3-((1-(5-ethyl-2-((2,2,3,3,3-pentafluoropropyl)(pyridin-2-yl)carbamoyl)phenyl)piperidin-4-yl)methoxy)phenyl)propanoic acid In the same manner as in Example 32, step 2 and Example 1, step 4, the title compound (150 mg) was obtained as a colorless amorphous powder from N-(2,2,3,3,3-pentafluoropropyl)pyridin-2-amine (130 mg) and 2-(4-((3-(1-cyclopropyl-3-ethoxy-3-oxopropyl)phenoxy)methyl)piperidin-1-yl)-4-ethylbenzoic acid (110 mg).

MS (ESI+): [M+H]$^+$ 660.3.

Example 52

3-cyclopropyl-3-(3-((1-(5-ethyl-2-(methyl(1-methyl-1H-pyrazol-4-yl)carbamoyl)phenyl)piperidin-4-yl)methoxy)phenyl)propanoic acid Step 1) ethyl 3-(3-((1-(2-((1H-pyrazol-4-yl)carbamoyl)-5-ethylphenyl)piperidin-4-yl)methoxy)phenyl)-3-cyclopropylpropanoate In the same manner as in Example 2, step 5, the title compound (81.7 mg) was obtained as a white amorphous powder from 2-(4-((3-(1-cyclopropyl-3-ethoxy-3-oxopropyl)phenoxy)methyl)piperidin-1-yl)-4-ethylbenzoic acid (100 mg) and 1H-pyrazol-4-amine (87 mg).

$^1$H NMR (400 MHz, DMSO-d$_6$) δ 0.07-0.18 (1H, m), 0.18-0.26 (1H, m), 0.29-0.38 (1H, m), 0.44-0.56 (1H, m), 1.00-1.08 (1H, m), 1.08 (3H, t, J=7.2 Hz), 1.21 (3H, t, J=7.5 Hz), 1.52-1.70 (2H, m), 1.84-1.98 (3H, m), 2.17-2.30 (1H, m), 2.61-2.79 (4H, m), 2.87 (2H, t, J=11.3 Hz), 3.15 (2H, d, J=11.3 Hz), 3.88-4.01 (4H, m), 6.77-6.86 (2H, m), 6.88 (1H, s), 7.09 (1H, d, J=7.9 Hz), 7.14-7.25 (2H, m), 7.73 (1H, brs), 7.86 (1H, d, J=8.0 Hz), 8.06 (1H, brs), 12.03 (1H, s), 12.65 (1H, brs).

Step 2) ethyl 3-cyclopropyl-3-(3-((1-(5-ethyl-2-(methyl(1-methyl-1H-pyrazol-4-yl)carbamoyl)phenyl)piperidin-4-yl)methoxy)phenyl)propanoate In the same manner as in Example 25, step 2, the title compound (73.2 mg) was obtained as a colorless oil from ethyl 3-(3-((1-(2-((1H-pyrazol-4-yl)carbamoyl)-5-ethylphenyl)piperidin-4-yl)methoxy)phenyl)-3-cyclopropylpropanoate (81.7 mg).

MS (ESI+): [M+H]$^+$ 573.5.

Step 3) 3-cyclopropyl-3-(3-((1-(5-ethyl-2-(methyl(1-methyl-1H-pyrazol-4-yl)carbamoyl)phenyl)piperidin-4-yl)methoxy)phenyl)propanoic acid In the same manner as in Example 1, step 4, the title compound (59.3 mg) was obtained as a white amorphous powder from ethyl 3-cyclopropyl-3-(3-((1-(5-ethyl-2-(methyl(1-methyl-1H-pyrazol-4-yl)carbamoyl)phenyl)piperidin-4-yl)methoxy)phenyl)propanoate (73.2 mg).

MS (ESI+): [M+H]$^+$ 545.3.

Example 53

3-cyclopropyl-3-(3-((1-(2-(((2,2-dimethylpropyl)sulfonyl)carbamoyl)-5-ethylphenyl)piperidin-4-yl)methoxy)phenyl)propanoic acid Step 1) ethyl 3-cyclopropyl-3-(3-((1-(2-(((2,2-dimethylpropyl)sulfonyl)carbamoyl)-5-ethylphenyl)piperidin-4-yl)methoxy)phenyl)propanoate To a solution (3 mL) of 2-(4-((3-(1-cyclopropyl-3-ethoxy-3-oxopropyl)phenoxy)methyl)piperidin-1-yl)-4-ethylbenzoic acid (176 mg) in acetonitrile were added 2,2-dimethylpropane-1-sulfonamide (83 mg), triethylamine (153 μL), 2-methyl-6-nitrobenzoic anhydride (190 mg) and dimethylaminopyridine (67.2 mg), and the mixture was stirred at room temperature for 17.5 hr. To the reaction mixture was added water, and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (173 mg) as a colorless oil.

MS (ESI+): [M+H]$^+$ 613.3.

Step 2) 3-cyclopropyl-3-(3-((1-(2-(((2,2-dimethylpropyl)sulfonyl)carbamoyl)-5-ethylphenyl)piperidin-4-yl)methoxy)phenyl)propanoic acid In the same manner as in Example 1, step 4, the title compound (170 mg) was obtained as a pale-yellow amorphous powder from ethyl 3-cyclopropyl-3-(3-((1-(2-(((2,2-dimethylpropyl)sulfonyl)carbamoyl)-5-ethylphenyl)piperidin-4-yl)methoxy)phenyl)propanoate (173 mg).

MS (ESI+): [M+H]$^+$ 585.3.

Example 54

3-cyclopropyl-3-(3-((1-(5-ethyl-2-((2,2,3,3,3-pentafluoropropyl)(propan-2-yl)carbamoyl)phenyl)piperidin-4-yl)methoxy)phenyl)propanoic acid Step 1) N-benzyl-2,2,3,3,3-pentafluoro-N-(propan-2-yl)propan-1-amine In the same manner as in Example 14, step 1, the title compound (2.10 g) was obtained as a colorless oil from N-benzylpropan-2-amine (2.00 g).

$^1$H NMR (300 MHz, CDCl$_3$) δ 1.00 (6H, d, J=6.6 Hz), 2.93 (1H, dt, J=13.3, 6.6 Hz), 3.07 (2H, td, J=15.4, 1.1 Hz), 3.77 (2H, s), 7.19-7.38 (5H, m).

Step 2) 2,2,3,3,3-pentafluoro-N-(propan-2-yl)propan-1-amine hydrochloride

Under a hydrogen atmosphere, a solution of N-benzyl-2,2,3,3,3-pentafluoro-N-(propan-2-yl)propan-1-amine (2.10 g) and 20% palladium hydroxide (containing water (50%), 315 mg) in methanol (20 mL) was stirred at room temperature for 18 hr. The reaction mixture was filtered through celite, 4N hydrogen chloride ethyl acetate solution (3.73 mL) was added to the obtained filtrate, and the solvent was evaporated under reduced pressure. The residue was suspended in ethyl acetate and hexane, and the resultant precipitate was collected by filtration, washed with ethyl acetate, and dried under reduced pressure to give the title compound (1.33 g) as a colorless solid.

$^1$H NMR (300 MHz, DMSO-d$_6$) δ 1.32 (6H, d, J=6.5 Hz), 3.58-4.19 (3H, m), 9.92 (2H, brs).

Step 3) 3-cyclopropyl-3-(3-((1-(5-ethyl-2-((2,2,3,3,3-pentafluoropropyl)(propan-2-yl)carbamoyl)phenyl)piperidin-4-yl)methoxy)phenyl)propanoic acid In the same manner as in Example 32, step 2 and Example 1, step 4, the title compound (97 mg) was obtained as a colorless amorphous powder from 2,2,3,3,3-pentafluoro-N-(propan-2-yl)propan-1-amine hydrochloride (100 mg) and 2-(4-((3-(1-cyclopropyl-3-ethoxy-3-oxopropyl)phenoxy)methyl)piperidin-1-yl)-4-ethylbenzoic acid (105 mg).

MS (ESI+): [M+H]$^+$ 625.3.

Example 55

3-cyclopropyl-3-(3-((1-(2-((2,2-dimethylpropyl)(6-methylpyridin-2-yl)carbamoyl)-5-ethylphenyl)piperidin-4-yl)methoxy)phenyl)propanoic acid By a method similar to that in Example 32, step 2 and Example 1, step 4, the title compound (68.1 mg) was obtained as a white amorphous powder from 2-(4-((3-(1-cyclopropyl-3-ethoxy-3-oxopropyl)phenoxy)methyl)piperidin-1-yl)-4-ethylbenzoic acid (113.4 mg) and N-(2,2-dimethylpropyl)-6-methylpyridin-2-amine (84 mg).

MS (ESI+): [M+H]$^+$ 612.3.

Example 56

3-cyclopropyl-3-(3-((1-(2-((2,2-dimethylpropyl)(pyridin-2-yl)carbamoyl)-5-ethylphenyl)piperidin-4-yl)methoxy)phenyl)propanoic acid By a method similar to that in Example 32, step 2 and Example 1, step 4, the title compound (105 mg) was obtained as a white amorphous powder from 2-(4-((3-(1-cyclopropyl-3-ethoxy-3-oxopropyl)phenoxy)methyl)piperidin-1-yl)-4-ethylbenzoic acid (116.3 mg) and N-(2,2-dimethylpropyl)pyridin-2-amine (80 mg).

MS (ESI+): [M+H]$^+$ 598.4.

Example 57

3-cyclopropyl-3-(3-((1-(5-ethyl-2-(methyl(1,3-oxazol-2-yl)carbamoyl)phenyl)piperidin-4-yl)methoxy)phenyl)propanoic acid Step 1) ethyl 3-cyclopropyl-3-(3-((1-(5-ethyl-2-(1,3-oxazol-2-ylcarbamoyl)phenyl)piperidin-4-yl)methoxy)phenyl)propanoate In the same manner as in Example 2, step 5, the title compound (27.7 mg) was obtained as a colorless oil from 2-(4-((3-(1-cyclopropyl-3-ethoxy-3-oxopropyl)phenoxy)methyl)piperidin-1-yl)-4-ethylbenzoic acid (100 mg) and 1,3-oxazol-2-amine (88 mg).

$^1$H NMR (400 MHz, CDCl$_3$) δ 0.12-0.22 (1H, m), 0.23-0.33 (1H, m), 0.38-0.49 (1H, m), 0.54-0.64 (1H, m), 0.96-1.10 (1H, m), 1.18 (3H, t, J=7.2 Hz), 1.25-1.32 (3H, m), 1.71-1.89 (2H, m), 1.97-2.14 (3H, m), 2.31-2.40 (1H, m), 2.66-2.82 (4H, m), 2.95 (2H, t, J=11.0 Hz), 3.24 (2H, d, J=11.8 Hz), 3.93 (2H, d, J=5.9 Hz), 4.01-4.12 (2H, m), 6.72-6.89 (3H, m), 7.04 (1H, s), 7.14-7.19 (2H, m), 7.20-7.25 (1H, m), 7.46 (1H, s), 8.27 (1H, d, J=8.5 Hz), 14.34 (1H, s).

Step 2) ethyl 3-cyclopropyl-3-(3-((1-(5-ethyl-2-(methyl(1,3-oxazol-2-yl)carbamoyl)phenyl)piperidin-4-yl)methoxy)phenyl)propanoate In the same manner as in Example 25, step 2, the title compound (14.8 mg) was obtained as a colorless oil from ethyl 3-cyclopropyl-3-(3-((1-(5-ethyl-2-(1,3-oxazol-2-ylcarbamoyl)phenyl)piperidin-4-yl)methoxy)phenyl)propanoate (27.7 mg).

$^1$H NMR (400 MHz, CDCl$_3$) δ 0.10-0.21 (1H, m), 0.23-0.32 (1H, m), 0.38-0.49 (1H, m), 0.52-0.63 (1H, m), 0.96-1.09 (1H, m), 1.18 (3H, t, J=7.2 Hz), 1.23 (3H, t, J=7.6 Hz), 1.30 (2H, d, J=18.2 Hz), 1.73-1.89 (3H, m), 2.29-2.40 (1H, m), 2.63 (4H, q, J=7.5 Hz), 2.69-2.81 (2H, m), 2.86-3.10 (2H, m), 3.57 (3H, s), 3.81 (2H, d, J=6.0 Hz), 3.97-4.14 (2H, m), 6.68 (1H, s), 6.73-6.80 (2H, m), 6.82 (1H, d, J=7.7 Hz), 6.88 (1H, s), 6.92 (1H, d, J=7.8 Hz), 7.17 (1H, s), 7.21 (1H, t, J=7.8 Hz), 7.42 (1H, d, J=7.8 Hz).

Step 3) 3-cyclopropyl-3-(3-((1-(5-ethyl-2-(methyl(1,3-oxazol-2-yl)carbamoyl)phenyl)piperidin-4-yl)methoxy)phenyl)propanoic acid In the same manner as in Example 1, step 4, the title compound (59.3 mg) was obtained as a white amorphous powder from ethyl 3-cyclopropyl-3-(3-((1-(5-ethyl-2-(methyl(1,3-oxazol-2-yl)carbamoyl)phenyl)piperidin-4-yl)methoxy)phenyl)propanoate (14.8 mg).
MS (ESI+): [M+H]$^+$ 532.3.

Example 58

3-cyclopropyl-3-(3-((1-(2-(((2,2-dimethylpropyl)sulfonyl)(methyl)carbamoyl)-5-ethylphenyl)piperidin-4-yl)methoxy)phenyl)propanoic acid In the same manner as in Example 25, step 2 and Example 1, step 4, the title compound (68.3 mg) was obtained as a pale-yellow oil from ethyl 3-cyclopropyl-3-(3-((1-(2-(((2,2-dimethylpropyl)sulfonyl)carbamoyl)-5-ethylphenyl)piperidin-4-yl)methoxy)phenyl)propanoate (175 mg) obtained in Example 53, step 1.
MS (ESI+): [M+H]$^+$ 599.3.

Example 59

3-(3-((1-(6-chloro-3-((2,2-dimethylpropyl)(pyridin-2-yl)carbamoyl)pyridin-2-yl)piperidin-4-yl)methoxy)phenyl)-3-cyclopropylpropanoic acid Step 1) tert-butyl 4-((3-(1-cyclopropyl-3-ethoxy-3-oxopropyl)phenoxy)methyl)piperidine-1-carboxylate To a solution of ethyl 3-cyclopropyl-3-(3-hydroxyphenyl)propanoate (543 mg) in toluene (23.2 mL) were added tert-butyl 4-(hydroxymethyl)piperidine-1-carboxylate (499 mg) and cyanomethylenetri-n-butylphosphorane (1823 µl) at room temperature, and the mixture was stirred at 100° C. for 1 hr. The reaction mixture was cooled to room temperature, the solvent was evaporated under reduced pressure, and the residue was purified by silica gel column chromatography (ethyl acetate/hexane) to give the title compound (811 mg) as a pale-yellow oil.
MS (ESI+). found: 376.3.

Step 2) ethyl 3-cyclopropyl-3-(3-(piperidin-4-ylmethoxy)phenyl)propanoate hydrochloride To a solution of tert-butyl 4-((3-(1-cyclopropyl-3-ethoxy-3-oxopropyl)phenoxy)methyl)piperidine-1-carboxylate (811 mg) in ethyl acetate (0.2 mL) was added 4N hydrochloric acid-ethyl acetate solution (4.7 mL) at room temperature, and the mixture was stirred for 4 hr. The solvent was evaporated under reduced pressure to give the title compound (691 mg) as a pale-white solid.
MS (ESI+): [M+H]$^+$ 332.3.

Step 3) N-(2,2-dimethylpropyl)pyridin-2-amine

In the same manner as in Example 32, step 1, the title compound (3.13 g) was obtained as a white solid from pyridin-2-amine (5.00 g).
MS (ESI+): [M+H]$^+$ 165.1.

Step 4) benzyl 2,6-dichloronicotinate

To a solution (50 mL) of 2,6-dichloronicotinic acid (5.00 g) in DMF were added (bromomethyl)benzene (4 mL) and potassium carbonate (5.04 g) at room temperature, and the mixture was stirred for 3.5 hr. Water was added to the reaction mixture, and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (7.14 g) as a yellow oil.
MS (ESI+): [M+H]$^+$ 282.0.

Step 5) benzyl 6-chloro-2-(4-((3-(1-cyclopropyl-3-ethoxy-3-oxopropyl)phenoxy)methyl)piperidin-1-yl)nicotinate To a solution (20 mL) of benzyl 2,6-dichloronicotinate (1.00 g) in THF were added ethyl 3-cyclopropyl-3-(3-(piperidin-4-ylmethoxy)phenyl)propanoate (1.41 g) and triethylamine (988 µL) at room temperature, and the mixture was stirred at 80° C. for 8 hr. To the reaction mixture was added water, and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (1.56 g) as a colorless oil.
MS (ESI+): [M+H]$^+$ 577.2.

Step 6) 6-chloro-2-(4-((3-(1-cyclopropyl-3-ethoxy-3-oxopropyl)phenoxy)methyl)piperidin-1-yl)nicotinic acid Under a hydrogen atmosphere, to a solution (30 mL) of benzyl 6-chloro-2-(4-((3-(1-cyclopropyl-3-ethoxy-3-oxopropyl)phenoxy)methyl)piperidin-1-yl)nicotinate (1.56 g) in THF was added 10% palladium carbon (100 mg), and the mixture was stirred at room temperature for 3 hr. The reaction mixture was filtered through celite, and the solvent in the filtrate was evaporated under reduced pressure to give a crude product of the title compound (1.37 g) as a pale-yellow oil. This compound was used for the next step without further purification.
MS (ESI+): [M+H]$^+$ 487.2.

Step 7) ethyl 3-(3-((1-(6-chloro-3-((2,2-dimethylpropyl)(pyridin-2-yl)carbamoyl)pyridin-2-yl)piperidin-4-yl)methoxy)phenyl)-3-cyclopropylpropanoate In the same manner as in Example 32, step 2, the title compound was obtained as a pale-yellow oil (152 mg) from 6-chloro-2-(4-((3-(1-cyclopropyl-3-ethoxy-3-oxopropyl)phenoxy)methyl)piperidin-1-yl)nicotinic acid (150 mg) and N-(2,2-dimethylpropyl)pyridin-2-amine (152 mg).
MS (ESI+): [M+H]$^+$ 633.3.

Step 8) 3-(3-((1-(6-chloro-3-((2,2-dimethylpropyl)(pyridin-2-yl)carbamoyl)pyridin-2-yl)piperidin-4-yl)methoxy)phenyl)-3-cyclopropylpropanoic acid In the same manner as in Example 1, step 4, the title compound (149 mg) was obtained as a white amorphous powder from ethyl 3-(3-((1-(6-chloro-3-((2,2-dimethylpropyl)(pyridin-2-yl)carbamoyl)pyridin-2-yl)piperidin-4-yl)
methoxy)phenyl)-3-cyclopropylpropanoate (152 mg).

MS (ESI+): [M+H]$^+$ 605.3.

Example 60

3-cyclopropyl-3-(3-((1-(3-((2,2-dimethylpropyl)
(pyridin-2-yl)carbamoyl)-6-ethylpyridin-2-yl)piperi-
din-4-yl)methoxy)phenyl)propanoic acid Step 1) ethyl 3-cyclopropyl-3-(3-((1-(3-((2,2-dim-
ethylpropyl)(pyridin-2-yl)carbamoyl)-6-vinylpyri-
din-2-yl)piperidin-4-yl)methoxy)phenyl)propanoate Under a nitrogen atmosphere, to a solution (2 mL) of ethyl 3-(3-((1-(6-chloro-3-((2,2-dimethylpropyl)(pyridin-2-yl) carbamoyl)pyridin-2-yl)piperidin-4-yl)methoxy)phenyl)-3-cyclopropylpropanoate obtained in Example 59, step 7, in DME were added tetrakistriphenylphosphinepalladium (38.1 mg), aqueous sodium carbonate solution (2 M, 495 µL) and 4,4,5,5-tetramethyl-2-vinyl-1,3,2-dioxaborolane (153 mg), and the mixture was stirred at 80° C. for 7.5 hr. Tetrakistriphenylphosphinepalladium (38.1 mg) was added, and the mixture was further stirred at 80° C. for 16 hr. To the reaction mixture was added water, and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (181 mg) as a pale-yellow oil.

MS (ESI+): [M+H]$^+$ 625.4.

Step 2) ethyl 3-cyclopropyl-3-(3-((1-(3-((2,2-dim-
ethylpropyl)(pyridin-2-yl)carbamoyl)-6-ethylpyri-
din-2-yl)piperidin-4-yl)methoxy)phenyl)propanoate Under a hydrogen atmosphere (1 atmosphere), to a solution (4 mL) of ethyl 3-cyclopropyl-3-(3-((1-(3-((2,2-dimeth-ylpropyl)(pyridin-2-yl)carbamoyl)-6-vinylpyridin-2-yl)pip-eridin-4-yl)methoxy)phenyl)propanoate (181 mg) in ethyl acetate was added 10% palladium carbon (20 mg), and the mixture was stirred at room temperature for 20 min. The reaction mixture was filtered through celite, the solvent in the filtrate was evaporated under reduced pressure, and the residue was purified by silica gel column chromatography (ethyl acetate/hexane) to give the title compound (173 mg) as a pale-yellow oil.

MS (ESI+): [M+H]$^+$ 627.4.

Step 3) 3-cyclopropyl-3-(3-((1-(3-((2,2-dimethyl-
propyl)(pyridin-2-yl)carbamoyl)-6-ethylpyridin-2-yl)
piperidin-4-yl)methoxy)phenyl)propanoic acid In the same manner as in Example 1, step 4, the title compound (163 mg) was obtained as a white amorphous powder from ethyl 3-cyclopropyl-3-(3-((1-(3-((2,2-dimeth-ylpropyl)(pyridin-2-yl)carbamoyl)-6-ethylpyridin-2-yl)pip-eridin-4-yl)methoxy)phenyl)propanoate (173 mg).

MS (ESI+): [M+H]$^+$ 599.4.

Example 61

3-cyclopropyl-3-(3-((1-(2-((2-(2,2-dimethylpro-
panoyl)hydrazino)carbonyl)-5-methoxyphenyl)pip-
eridin-4-yl)methoxy)phenyl)propanoic acid Step 1) methyl 2-(4-(hydroxymethyl)piperidin-1-
yl)-4-methoxybenzoate In the same manner as in Example 1, step 1, the title compound was obtained as a pale-yellow oil (3.77 g) from methyl 2-fluoro-4-methoxybenzoate.

MS (ESI+): [M+H]$^+$ 280.2.

Step 2) methyl 4-methoxy-2-(4-((methoxymethoxy)
methyl)piperidin-1-yl)benzoate

A solution of chloromethyl methyl ether (0.84 mL), methyl 2-(4-(hydroxymethyl)piperidin-1-yl)-4-methoxy-benzoate (1.03 g) and diisopropylamine (2.58 mL) in THF (10 mL) was stirred at room temperature overnight. The reaction mixture was added to water, and the mixture was extracted with ethyl acetate. The extract was washed with water and saturated brine, and dried over anhydrous magnesium sulfate. The solvent was evaporated under reduced pressure to give a crude product of the title compound as a colorless oil. This compound was used for the next step without further purification.

MS (ESI+): [M+H]$^+$ 324.1.

Step 3) 4-methoxy-2-(4-((methoxymethoxy)methyl)
piperidin-1-yl)benzohydrazide

A solution of methyl 4-methoxy-2-(4-((methoxymethoxy) methyl)piperidin-1-yl)benzoate (entire amount) and hydrazine monohydrate (1.84 g) in ethanol (9.2 mL) was stirred overnight under heated reflux. The reaction mixture was concentrated under reduced pressure, the residue was added to water, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane and methanol/ethyl acetate) to give the title compound (1.04 g) as a white solid.

MS (ESI+): [M+H]$^+$ 324.1.

Step 4) N'-(2,2-dimethylpropanoyl)-4-methoxy-2-
(4-((methoxymethoxy)methyl)piperidin-1-yl)benzo-
hydrazide To a solution of 4-methoxy-2-(4-((methoxymethoxy) methyl)piperidin-1-yl)benzohydrazide (400 mg) and triethylamine (0.517 mL) in THF (4 mL) was added 2,2-dimeth-ylpropanoyl chloride (0.305 mL) at 0° C., and the mixture was stirred for 30 min. The reaction mixture was added to water, and the mixture was extracted with ethyl acetate. The extract was washed with water and saturated brine, and dried over anhydrous magnesium sulfate. The solvent was evaporated under reduced pressure to give a crude product (499.5 mg) of the title compound as a white solid. This compound was used for the next step without further purification.

MS (ESI+): [M+H]$^+$ 408.2.

Step 5) 1-(2-(5-tert-butyl-1,3,4-oxadiazol-2-yl)-5-
methoxyphenyl)-4-((methoxymethoxy)methyl)pip-
eridine A solution of N'-(2,2-dimethylpropanoyl)-4-methoxy-2-(4-((methoxymethoxy)methyl)piperidin-1-yl)benzohydrazide (250 mg) obtained in step 4 and 3,3,3-triethyl-1-(methoxycarbonyl)diazathian-3-ium-1-ide 2,2-dioxide (292 mg) in THF (4 mL) was stirred at 60° C. for 2 hr. The reaction mixture was evaporated under reduced pressure, and the residue was purified by silica gel column chromatography (ethyl acetate/hexane) to give the title compound (119.6 mg) as a pale-yellow oil.

MS (ESI+): [M+H]$^+$ 390.2.

Step 6) ethyl 3-cyclopropyl-3-(3-((1-(2-((2-(2,2-dimethylpropanoyl)hydrazino)carbonyl)-5-methoxyphenyl)piperidin-4-yl)methoxy)phenyl)propanoate Concentrated hydrochloric acid (0.256 mL) was added to a solution of 1-(2-(5-tert-butyl-1,3,4-oxadiazol-2-yl)-5-methoxyphenyl)-4-((methoxymethoxy)methyl)piperidine (119.6 mg) in methanol (2 mL) at room temperature, and the mixture was stirred at 60° C. for 1 hr. The reaction mixture was neutralized with saturated aqueous sodium hydrogen carbonate solution, and extracted with ethyl acetate. The extract was washed with water and saturated brine, and dried over anhydrous magnesium sulfate. To a solution of the residue in toluene (2 mL) were added (tributylphosphoranylidene)acetonitrile (0.161 mL) and ethyl 3-cyclopropyl-3-(3-hydroxyphenyl)propanoate (94 mg), and the mixture was stirred at 100° C. for 2 hr under a nitrogen atmosphere. The reaction mixture was concentrated under reduced pressure, and the residue was purified by silica gel column chromatography (ethyl acetate/hexane) to give the title compound (20.9 mg) as a colorless oil.

MS (ESI+): [M+H]$^+$ 580.4.

Step 7) 3-cyclopropyl-3-(3-((1-(2-((2-(2,2-dimethylpropanoyl)hydrazino)carbonyl)-5-methoxyphenyl)piperidin-4-yl)methoxy)phenyl)propanoic acid In the same manner as in Example 1, step 4, the title compound (18.9 mg) was obtained as a white amorphous powder from ethyl 3-cyclopropyl-3-(3-((1-(2-((2-(2,2-dimethylpropanoyl)hydrazino)carbonyl)-5-methoxyphenyl)piperidin-4-yl)methoxy)phenyl)propanoate (20.9 mg).

MS (ESI+): [M+H]$^+$ 552.3.

Example 62

3-cyclopropyl-3-(3-((1-(5-methoxy-2-((2-methylpropyl)(pyridin-2-yl)carbamoyl)phenyl)piperidin-4-yl)methoxy)phenyl)propanoic acid Step 1) methyl 3-cyclopropyl-3-(3-((1-(5-methoxy-2-(pyridin-2-ylcarbamoyl)phenyl)piperidin-4-yl)methoxy)phenyl)propanoate In the same manner as in Example 2, step 5, the title compound (520 mg) was obtained as white crystals from 2-aminopyridine (403 mg).

MS (ESI+): [M+H]$^+$ 544.5.

Step 2) 3-cyclopropyl-3-(3-((1-(2-((2-methylpropyl)(pyridin-2-yl)carbamoyl)-5-methoxyphenyl)piperidin-4-yl)methoxy)phenyl)propanoic acid In the same manner as in Example 25, step 2 and Example 1, step 4, the title compound (50 mg) was obtained as a white amorphous powder from methyl 3-cyclopropyl-3-(3-((1-(5-methoxy-2-(pyridin-2-ylcarbamoyl)phenyl)piperidin-4-yl)methoxy)phenyl)propanoate (170 mg).

MS (ESI+): [M+H]$^+$ 586.4.

Example 63

3-(3-((1-(2-((cycloheptylmethyl)carbamoyl)-5-methoxyphenyl)piperidin-4-yl)methoxy)phenyl)-3-cyclopropylpropanoic acid To a solution of 2-(4-((3-(1-cyclopropyl-3-methoxy-3-oxopropyl)phenoxy)methyl)piperidin-1-yl)-4-methoxybenzoic acid (37.4 mg) in DMF (500 uL) were added cycloheptylmethanamine (20.36 mg), N-ethyldiisopropylamine (27.9 ul) and O-(7-azabenzotriazol-1-yl)-N,N,N',N'-tetramethyluronium hexafluorophosphate (60.8 mg), and the mixture was stirred at room temperature overnight. To the reaction solution were added aqueous sodium hydrogen carbonate solution (1 mL) and ethyl acetate (3 mL), and the mixture was stirred. The organic layer was extracted, and the solvent was evaporated by Multi-sample solvent extraction system with solvent recovery (Soltrapper, The Institute of Creative Chemistry Co., Ltd.). The residue was purified by HPLC (column: YMC Triart C18, mobile phase: acetonitrile/10 mM aqueous ammonium hydrogen carbonate solution), and the solvent was evaporated by Multi-sample solvent extraction system with solvent recovery. To the residue were added methanol (500 μL), tetrahydrofuran (500 μL) and 2 M aqueous sodium hydroxide solution (500 μL), and the mixture was stirred at 60° C. overnight. The solvent was evaporated by Multi-sample solvent extraction system with solvent recovery. The residue was purified by HPLC (column: YMC Triart C18, mobile phase: acetonitrile/10 mM aqueous ammonium hydrogen carbonate solution), and the solvent was evaporated by Multi-sample solvent extraction system with solvent recovery to give the title compound (21.3 mg).

Examples 64-108

The compounds shown in the following Tables were produced by a method similar to that in Example 63.

TABLE 1-1

| Ex. | compound name | MS (ESI+) | M.W. |
|---|---|---|---|
| 63 | 3-(3-((1-(2-((cycloheptylmethyl)-carbamoyl)-5-methoxyphenyl)piperidin-4-yl)methoxy)phenyl)-3-cyclopropylpropanoic acid | 563.3 | 562.7 |
| 64 | 3-(3-((1-(2-((2-cyclohexylethyl)-carbamoyl)-5-methoxyphenyl)piperidin-4-yl)methoxy)phenyl)-3-cyclopropylpropanoic acid | 563.3 | 562.7 |
| 65 | 3-(3-((1-(2-(((1R)-1-cyclohexylethyl)-carbamoyl)-5-methoxyphenyl)piperidin-4-yl)methoxy)phenyl)-3-cyclopropylpropanoic acid | 563.3 | 562.7 |
| 66 | 3-(3-((1-(2-(((1S,4R)-bicyclo[2.2.1]hept-2-ylmethyl)carbamoyl)-5-methoxyphenyl)-piperidin-4-yl)methoxy)phenyl)-3-cyclopropylpropanoic acid | 561.3 | 560.7 |
| 67 | 3-cyclopropyl-3-(3-((1-(2-(2,3-dihydro-1H-inden-5-ylcarbamoyl)-5-methoxyphenyl)-piperidin-4-yl)methoxy)phenyl)propanoic acid | 569.3 | 568.7 |
| 68 | 3-cyclopropyl-3-(3-((1-(2-(bis(2-methylpropyl)carbamoyl)-5-methoxyphenyl)-piperidin-4-yl)methoxy)phenyl)propanoic acid | 565.4 | 564.8 |

TABLE 1-1-continued

| Ex. | compound name | MS (ESI+) | M.W. |
|---|---|---|---|
| 69 | 3-cyclopropyl-3-(3-((1-(2-((cyclopropyl-(phenyl)methyl)carbamoyl)-5-methoxyphenyl)piperidin-4-yl)methoxy)phenyl)propanoic acid | 583.4 | 582.7 |

TABLE 1-2

| Ex. | compound name | MS (ESI+) | M.W. |
|---|---|---|---|
| 70 | 3-(3-((1-(2-((cyclohexylmethyl)carbamoyl)-5-methoxyphenyl)piperidin-4-yl)methoxy)-phenyl)-3-cyclopropylpropanoic acid | 549.3 | 548.7 |
| 71 | 3-cyclopropyl-3-(3-((1-(5-methoxy-2-((2-phenylpropyl)carbamoyl)phenyl)piperidin-4-yl)methoxy)phenyl)propanoic acid | 571.4 | 570.7 |
| 72 | 3-cyclopropyl-3-(3-((1-(2-(hexyl(methyl)-carbamoyl)-5-methoxyphenyl)piperidin-4-yl)methoxy)phenyl)propanoic acid | 551.4 | 550.7 |
| 73 | 3-cyclopropyl-3-(3-((1-(2-((3,3-dimethylbutyl)carbamoyl)-5-methoxyphenyl)piperidin-4-yl)methoxy)phenyl)propanoic acid | 537.3 | 536.7 |
| 74 | 3-cyclopropyl-3-(3-((1-(2-(2,3-dihydro-1H-inden-1-ylcarbamoyl)-5-methoxyphenyl)piperidin-4-yl)methoxy)phenyl)propanoic acid | 569.3 | 568.7 |
| 75 | 3-cyclopropyl-3-(3-((1-(5-methoxy-2-(methyl(3-phenylpropyl)-carbamoyl)phenyl)piperidin-4-yl)methoxy)phenyl)propanoic acid | 585.3 | 584.7 |
| 76 | 3-cyclopropyl-3-(3-((1-(5-methoxy-2-(((1R)-1-phenylethyl)carbamoyl)-phenyl)piperidin-4-yl)methoxy)phenyl)propanoic acid | 557.3 | 556.7 |

TABLE 1-3

| Ex. | compound name | MS (ESI+) | M.W. |
|---|---|---|---|
| 77 | 3-(3-((1-(2-(benzyl(methyl)carbamoyl)-5-methoxyphenyl)piperidin-4-yl)methoxy)-phenyl)-3-cyclopropylpropanoic acid | 557.3 | 556.7 |
| 78 | 3-cyclopropyl-3-(3-((1-(5-methoxy-2-(((2S)-2-methylbutyl)carbamoyl)-phenyl)piperidin-4-yl)methoxy)phenyl)propanoic acid | 523.3 | 552.7 |
| 79 | 3-(3-((1-(2-(benzylcarbamoyl)-5-methoxyphenyl)piperidin-4-yl)methoxy)-phenyl)-3-cyclopropylpropanoic acid | 543.3 | 542.7 |
| 80 | 3-cyclopropyl-3-(3-((1-(5-methoxy-2-(methyl(2-phenylethyl)carbamoyl)-phenyl)piperidin-4-yl)methoxy)phenyl)propanoic acid | 571.4 | 570.7 |
| 81 | 3-cyclopropyl-3-(3-((1-(5-methoxy-2-(pentan-3-ylcarbamoyl)phenyl)piperidin-4-yl)methoxy)phenyl)propanoic acid | 523.3 | 522.7 |
| 82 | 3-(3-((1-(2-(cyclohexyl(methyl)carbamoyl)-5-methoxyphenyl)piperidin-4-yl)methoxy)phenyl)-3-cyclopropylpropanoic acid | 549.3 | 548.7 |
| 83 | 3-(3-((1-(2-(cyclopentyl(ethyl)carbamoyl)-5-methoxyphenyl)piperidin-4-yl)methoxy)-phenyl)-3-cyclopropylpropanoic acid | 549.3 | 548.7 |

TABLE 1-4

| Ex. | compound name | MS (ESI+) | M.W. |
|---|---|---|---|
| 84 | 3-cyclopropyl-3-(3-((1-(5-methoxy-2-(phenylcarbamoyl)phenyl)piperidin-4-yl)methoxy)phenyl)propanoic acid | 529.2 | 528.6 |
| 85 | 3-cyclopropyl-3-(3-((1-(5-methoxy-2-((3-methylbutan-2-yl)carbamoyl)-phenyl)piperidin-4-yl)methoxy)phenyl)propanoic acid | 523.3 | 522.7 |
| 86 | 3-cyclopropyl-3-(3-((1-(5-methoxy-2-((2-methylphenyl)carbamoyl)phenyl)piperidin-4-yl)methoxy)phenyl)propanoic acid | 543.3 | 542.7 |
| 87 | 3-cyclopropyl-3-(3-((1-(5-methoxy-2-(methyl(phenyl)carbamoyl)phenyl)piperidin-4-yl)methoxy)phenyl)propanoic acid | 543.3 | 542.7 |
| 88 | 3-(3-((1-(2-((cyclobutylmethyl)carbamoyl)-5-methoxyphenyl)piperidin-4-yl)methoxy)-phenyl)-3-cyclopropylpropanoic acid | 521.3 | 520.7 |
| 89 | 3-cyclopropyl-3-(3-((1-(2-((2-fluorophenyl)carbamoyl)-5-methoxyphenyl) piperidin-4-yl)methoxy)phenyl)propanoic acid | 547.2 | 546.6 |
| 90 | 3-(3-((1-(2-(butyl(methyl)carbamoyl)-5-methoxyphenyl)piperidin-4-yl)methoxy)-phenyl)-3-cyclopropylpropanoic acid | 523.3 | 522.7 |

TABLE 1-5

| Ex. | compound name | MS (ESI+) | M.W. |
|---|---|---|---|
| 91 | 3-cyclopropyl-3-(3-((1-(2-(((2S)-1-hydroxy-4-methylpentan-2-yl)carbamoyl)-5-methoxyphenyl)piperidin-4-yl)methoxy)phenyl)propanoic acid | 553.3 | 552.7 |
| 92 | 3-cyclopropyl-3-(3-((1-(2-(ethyl(2,2,2-trifluoroethyl)carbamoyl)-5-methoxyphenyl)piperidin-4-yl)methoxy)phenyl)propanoic acid | 563.3 | 562.6 |
| 93 | 3-cyclopropyl-3-(3-((1-(5-methoxy-2-((1-methoxybutan-2-yl)carbamoyl)-phenyl)piperidin-4-yl)methoxy)phenyl)propanoic acid | 539.3 | 538.7 |
| 94 | 3-cyclopropyl-3-(3-((1-(2-(ethyl(pyridin-4-ylmethyl)carbamoyl)-5-methoxyphenyl)piperidin-4-yl)methoxy)phenyl)propanoic acid | 572.4 | 571.7 |
| 95 | 3-cyclopropyl-3-(3-((1-(5-methoxy-2-(piperidin-1-ylcarbonyl)phenyl)piperidin-4-yl)methoxy)phenyl)propanoic acid | 521.3 | 520.7 |
| 96 | 3-cyclopropyl-3-(3-((1-(2-(diethylcarbamoyl)-5-methoxyphenyl)-piperidin-4-yl)methoxy)phenyl)propanoic acid | 509.3 | 508.7 |
| 97 | 3-cyclopropyl-3-(3-((1-(5-methoxy-2-(tetrahydro-2H-thiopyran-4-ylcarbamoyl)phenyl)piperidin-4-yl)methoxy)phenyl)propanoic acid | 553.3 | 552.7 |

TABLE 1-6

| Ex. | compound name | MS (ESI+) | M.W. |
|---|---|---|---|
| 98 | 3-cyclopropyl-3-(3-((1-(2-(((2S)-1-hydroxy-3-methylbutan-2-yl)carbamoyl)-5-methoxyphenyl)piperidin-4-yl)methoxy)phenyl)propanoic acid | 539.3 | 538.7 |
| 99 | 3-cyclopropyl-3-(3-((1-(2-((3-hydroxy-2,2-dimethylpropyl)carbamoyl)-5-methoxyphenyl)piperidin-4-yl)methoxy)phenyl)propanoic acid | 539.3 | 538.7 |

TABLE 1-6-continued

| Ex. | compound name | MS (ESI+) | M.W. |
|---|---|---|---|
| 100 | 3-cyclopropyl-3-(3-((1-(5-methoxy-2-((pyridin-4-ylmethyl)carbamoyl)-phenyl)piperidin-4-yl)methoxy)phenyl)propanoic acid | 544.2 | 543.7 |
| 101 | 3-cyclopropyl-3-(3-((1-(5-methoxy-2-(pyrimidin-5-ylcarbamoyl)phenyl)piperidin-4-yl)methoxy)phenyl)propanoic acid | 531.2 | 530.6 |
| 102 | 3-cyclopropyl-3-(3-((1-(5-methoxy-2-(methyl(pyridin-2-yl)carbamoyl)phenyl)piperidin-4-yl)methoxy)phenyl)propanoic acid | 544.2 | 543.7 |
| 103 | 3-(3-((1-(2-((2-cyanoethyl)-(methyl)carbamoyl)-5-methoxyphenyl)-piperidin-4-yl)methoxy)phenyl)-3-cyclopropylpropanoic acid | 520.3 | 519.6 |
| 104 | 3-cyclopropyl-3-(3-((1-(2-((2,2-dimethylpropyl)(methyl)carbamoyl)-5-methoxyphenyl)piperidin-4-yl)methoxy)phenyl)propanoic acid | 537.3 | 536.7 |

TABLE 1-7

| Ex. | compound name | MS (ESI+) | M.W. |
|---|---|---|---|
| 105 | 3-cyclopropyl-3-(3-((1-(5-methoxy-2-((4-methoxypiperidin-1-yl)carbonyl)phenyl)piperidin-4-yl)methoxy) phenyl)propanoic acid | 551.3 | 550.7 |
| 106 | 3-cyclopropyl-3-(3-((1-(5-methoxy-2-((pyrimidin-2-ylmethyl)carbamoyl)phenyl)piperidin-4-yl)methoxy)phenyl)propanoic acid | 545.2 | 544.6 |
| 107 | 3-cyclopropyl-3-(3-((1-(5-methoxy-2-((2-(piperidin-1-yl)ethyl)carbamoyl)-phenyl)piperidin-4-yl)methoxy)phenyl)propanoic acid | 564.3 | 563.7 |
| 108 | 3-cyclopropyl-3-(3-((1-(5-methoxy-2-(methyl(2-(methylsulfonyl)ethyl)-carbamoyl)phenyl)piperidin-4-yl)methoxy)phenyl)propanoic acid | 573.3 | 572.7 |

Example 109

3-cyclopropyl-3-(2-((1-(2-((2,2-dimethylpropyl)(6-methylpyridin-2-yl)carbamoyl)-5-ethylphenyl)piperidin-4-yl)methoxy)pyridin-4-yl)propanoic acid Step 1) 4-bromo-N-(2,2-dimethylpropyl)-2-fluoro-N-(6-methylpyridin-2-yl)benzamide By a method similar to that in Example 1, step 1, the title compound (464 mg) was obtained as a white solid from 4-bromo-2-fluorobenzoic acid (593 mg) and N-(2,2-dimethylpropyl)-6-methylpyridin-2-amine (241.2 mg).
MS (ESI+). found: 379.1, 381.2.

Step 2) N-(2,2-dimethylpropyl)-4-ethyl-2-fluoro-N-(6-methylpyridin-2-yl)benzamide Under a nitrogen atmosphere, to a solution of 4-bromo-N-(2,2-dimethylpropyl)-2-fluoro-N-(6-methylpyridin-2-yl)benzamide (459.5 mg) in DMF (8 mL) were added potassium carbonate (419 mg), diethyl zinc (1817 µl) and [1,1'-bis(diphenylphosphino)ferrocene]dichloropalladium(II) (22.0 mg) at room temperature, and the mixture was stirred at 80° C. for 1.5 hr. The reaction mixture was cooled to 0° C., ice water was added, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (379 mg) as a white solid.
MS (ESI+): [M+H]$^+$ 329.3.

Step 3) N-(2,2-dimethylpropyl)-4-ethyl-2-(4-(hydroxymethyl)piperidin-1-yl)-N-(6-methylpyridin-2-yl)benzamide By a method similar to that in Example 1, step 2, the title compound (107 mg) was obtained as a colorless oil from 4-ethyl-2-fluoro-N-(6-methylpyridin-2-yl)-N-(2,2-dimethylpropyl)benzamide (375.6 mg).
MS (ESI+): [M+H]$^+$ 424.3.

Step 4) 3-cyclopropyl-3-(2-((1-(2-((2,2-dimethylpropyl)(6-methylpyridin-2-yl)carbamoyl)-5-ethylphenyl)piperidin-4-yl)methoxy)pyridin-4-yl)propanoic acid By a method similar to that in Example 45, step 6 and Example 1, step 4, the title compound (93 mg) was obtained as a white amorphous powder from N-(2,2-dimethylpropyl)-4-ethyl-2-(4-(hydroxymethyl)piperidin-1-yl)-N-(6-methylpyridin-2-yl)benzamide (106.4 mg) and ethyl 3-cyclopropyl-3-(2-hydroxypyridin-4-yl)propanoate (65.0 mg).
MS (ESI+): [M+H]$^+$ 613.4.

Example 110

3-cyclopropyl-3-(2-((1-(2-((2,2-dimethylpropyl)(6-methylpyridin-2-yl)carbamoyl)-5-methoxyphenyl)piperidin-4-yl)methoxy)pyridin-4-yl)propanoic acid Step 1) N-(2,2-dimethylpropyl)-2-fluoro-4-methoxy-N-(6-methylpyridin-2-yl)-benzamide By a method similar to that in Example 1, step 1, the title compound (1.65 g) was obtained as a white solid from 2-fluoro-4-methoxybenzoic acid (2.16 g) and N-(2,2-dimethylpropyl)-6-methylpyridin-2-amine (1.13 g).
MS (ESI+): [M+H]$^+$ 331.3.

Step 2) N-(2,2-dimethylpropyl)-2-(4-(hydroxymethyl)piperidin-1-yl)-4-methoxy-N-(6-methylpyridin-2-yl)benzamide By a method similar to that in Example 1, step 2, the title compound (1.08 g) was obtained as a white powder from N-(2,2-dimethylpropyl)-2-fluoro-4-methoxy-N-(6-methylpyridin-2-yl)benzamide (1.65 g).
MS (ESI+): [M+H]$^+$ 426.4.

Step 3) 3-cyclopropyl-3-(2-((1-(2-((2,2-dimethylpropyl)(6-methylpyridin-2-yl)carbamoyl)-5-methoxyphenyl)piperidin-4-yl)methoxy)pyridin-4-yl)propanoic acid By a method similar to that in Example 45, step 6 and Example 1, step 4, the title compound (167 mg) was obtained as a pale-yellow amorphous powder from N-(2,2-dimethylpropyl)-2-(4-(hydroxymethyl)piperidin-1-yl)-4- methoxy-N-(6-methylpyridin-2-yl)benzamide (212.3 mg) and ethyl 3-cyclopropyl-3-(2-hydroxypyridin-4-yl)propanoate (129 mg).

MS (ESI+): [M+H]$^+$ 615.3.

Example 111

3-cyclopropyl-3-(2-((1-(2-((2,2-dimethylpropyl) (pyridin-2-yl)carbamoyl)-5-methoxyphenyl)piperidin-4-yl)methoxy)pyridin-4-yl)propanoic acid Step 1) benzyl 2-(4-(((4-(1-cyclopropyl-3-ethoxy-3-oxopropyl)pyridin-2-yl)oxy)methyl)piperidin-1-yl)-4-methoxybenzoate By a method similar to that in Example 45, step 6, the title compound (153 mg) was obtained as a colorless oil from benzyl 2-(4-(hydroxymethyl)piperidin-1-yl)-4-methoxybenzoate (164.1 mg) and ethyl 3-cyclopropyl-3-(2-hydroxypyridin-4-yl)propanoate (119 mg).

MS (ESI+): [M+H]$^+$ 573.5.

Step 2) 2-(4-(((4-(1-cyclopropyl-3-ethoxy-3-oxopropyl)pyridin-2-yl)oxy)methyl)piperidin-1-yl)-4-methoxybenzoic acid By a method similar to that in Example 2, step 4, the title compound (845 mg) was obtained as a colorless oil from benzyl 2-(4-(((4-(1-cyclopropyl-3-ethoxy-3-oxopropyl)pyridin-2-yl)oxy)methyl)piperidin-1-yl)-4-methoxybenzoate (1.06 g).

MS (ESI+): [M+H]$^+$ 483.4.

Step 3) 3-cyclopropyl-3-(2-((1-(2-((2,2-dimethylpropyl)(pyridin-2-yl)carbamoyl)-5-methoxyphenyl) piperidin-4-yl)methoxy)pyridin-4-yl)propanoic acid By a method similar to that in Example 32, step 2 and Example 1, step 4, the title compound (95 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (109.4 mg) and N-(2,2-dimethylpropyl)pyridin-2-amine (74.5 mg).

MS (ESI+): [M+H]$^+$ 601.3.

Example 112

3-cyclopropyl-3-(2-((1-(2-((2,2-dimethylpropyl)(4-methylpyridin-2-yl)carbamoyl)-5-methoxyphenyl) piperidin-4-yl)methoxy)pyridin-4-yl)propanoic acid By a method similar to that in Example 32, step 2 and Example 1, step 4, the title compound (100 mg) was obtained as a white amorphous powder from 2-(4-(((4-(1-cyclopropyl-3-ethoxy-3-oxopropyl)pyridin-2-yl)oxy) methyl)piperidin-1-yl)-4-methoxybenzoic acid (101.0 mg) and N-(2,2-dimethylpropyl)-4-methylpyridin-2-amine (74.6 mg).

MS (ESI+): [M+H]$^+$ 615.3.

Example 113

3-cyclopropyl-3-(2-((1-(5-methoxy-2-((2-methylpropyl)(pyridin-2-yl)carbamoyl)phenyl)piperidin-4-yl) methoxy)pyridin-4-yl)propanoic acid By a method similar to that in Example 32, step 2 and Example 1, step 4, the title compound (99 mg) was obtained as a pale-yellow amorphous powder from 2-(4-(((4-(1-cyclopropyl-3-ethoxy-3-oxopropyl)pyridin-2-yl)oxy)methyl) piperidin-1-yl)-4-methoxybenzoic acid (101.0 mg) and N-(2-methylpropyl)pyridin-2-amine (62.9 mg).

MS (ESI+): [M+H]$^+$ 587.3.

Example 114

3-cyclopropyl-3-(2-((1-(5-methoxy-2-(((1-methylcyclopropyl)methyl)(pyridin-2-yl)carbamoyl)phenyl) piperidin-4-yl)methoxy)pyridin-4-yl)propanoic acid Step 1) N-((1-methylcyclopropyl)methyl)pyridin-2-amine In the same manner as in Example 32, step 1, the title compound (2.88 g) was obtained as a colorless solid from pyridin-2-amine (4.20 g) and 1-methylcyclopropanecarboxylic acid (4.11 g).

$^1$H NMR (300 MHz, CDCl$_3$) δ 0.31-0.39 (2H, m), 0.43-0.50 (2H, m), 1.16 (3H, s), 3.12 (2H, d, J=5.5 Hz), 4.54 (1H, brs), 6.36 (1H, dt, J=8.4, 0.8 Hz), 6.54 (1H, ddd, J=7.1, 5.1, 0.9 Hz), 7.40 (1H, ddd, J=8.5, 7.0, 1.9 Hz), 8.02-8.10 (1H, m).

Step 2) 3-cyclopropyl-3-(2-((1-(5-methoxy-2-(((1-methylcyclopropyl)methyl)(pyridin-2-yl)carbamoyl) phenyl)piperidin-4-yl)methoxy)pyridin-4-yl)propanoic acid In the same manner as in Example 32, step 2 and Example 1, step 4, the title compound (59 mg) was obtained as a colorless amorphous powder from N-((1-methylcyclopropyl)methyl)pyridin-2-amine (101 mg) and 2-(4-(((4-(1-cyclopropyl-3-ethoxy-3-oxopropyl)pyridin-2-yl)oxy)methyl) piperidin-1-yl)-4-methoxybenzoic acid (100 mg).

MS (ESI+): [M+H]$^+$ 599.3.

Example 115

3-cyclopropyl-3-(2-((1-(5-methoxy-2-((2-methylpropyl)(5-methylpyridin-2-yl)carbamoyl)phenyl)piperidin-4-yl)methoxy)pyridin-4-yl)propanoic acid Step 1) 5-methyl-N-(2-methylpropyl)pyridin-2-amine In the same manner as in Example 32, step 1, the title compound (386 mg) was obtained as a pale-yellow solid from 2-methylpyridin-2-amine (500 mg).

MS (ESI+): [M+H]$^+$ 165.1.

Step 2) 3-cyclopropyl-3-(2-((1-(5-methoxy-2-((2-methylpropyl)(5-methylpyridin-2-yl)carbamoyl) phenyl)piperidin-4-yl)methoxy)pyridin-4-yl)propanoic acid In the same manner as in Example 32, step 2 and Example 1, step 4, the title compound (171 mg) was obtained as a white amorphous powder from 2-(4-(((4-(1-cyclopropyl-3-ethoxy-3-oxopropyl)pyridin-2-yl)oxy)methyl)piperidin-1- yl)-4-methoxybenzoic acid (167 mg) and 5-methyl-N-(2-methylpropyl)pyridin-2-amine (114 mg).
MS (ESI+): [M+H]+ 601.3.

Example 116

3-cyclopropyl-3-(2-((1-(5-methoxy-2-(pyridin-2-yl (2,2,2-trifluoroethyl)carbamoyl)phenyl)piperidin-4-yl)methoxy)pyridin-4-yl)propanoic acid Step 1) ethyl 3-cyclopropyl-3-(2-((1-(5-methoxy-2-(pyridin-2-yl(2,2,2-trifluoroethyl)carbamoyl)phenyl)piperidin-4-yl)methoxy)pyridin-4-yl)propanoate In the same manner as in Example 32, step 2, the title compound (111 mg) was obtained as a colorless oil from 2-(4-(((4-(1-cyclopropyl-3-ethoxy-3-oxopropyl)pyridin-2-yl)oxy)methyl)piperidin-1-yl)-4-methoxybenzoic acid (100 mg) and N-(2,2,2-trifluoroethyl)pyridin-2-amine (91.0 mg).
MS (ESI+): [M+H]+ 641.2.

Step 2) 3-cyclopropyl-3-(2-((1-(5-methoxy-2-(pyridin-2-yl(2,2,2-trifluoroethyl)carbamoyl)phenyl)piperidin-4-yl)methoxy)pyridin-4-yl)propanoic acid In the same manner as in Example 1, step 4, the title compound (96.4 mg) was obtained as a white amorphous powder from ethyl 3-cyclopropyl-3-(2-((1-(5-methoxy-2-(pyridin-2-yl(2,2,2-trifluoroethyl)carbamoyl)phenyl)piperidin-4-yl)methoxy)pyridin-4-yl)propanoate (111 mg).
MS (ESI+): [M+H]+ 613.2.

Example 117

3-cyclopropyl-3-(2-((1-(2-((cyclopropylmethyl)(pyridin-2-yl)carbamoyl)-5-methoxyphenyl)piperidin-4-yl)methoxy)pyridin-4-yl)propanoic acid Step 1) ethyl 3-cyclopropyl-3-(2-((1-(2-((cyclopropylmethyl)(pyridin-2-yl)carbamoyl)-5-methoxyphenyl)piperidin-4-yl)methoxy)pyridin-4-yl)propanoate In the same manner as in Example 32, step 2, the title compound (120 mg) was obtained as a colorless oil from 2-(4-(((4-(1-cyclopropyl-3-ethoxy-3-oxopropyl)pyridin-2-yl)oxy)methyl)piperidin-1-yl)-4-methoxybenzoic acid (100 mg) and N-(cyclopropylmethyl)pyridin-2-amine (77.0 mg).
$^1$H NMR (400 MHz, CDCl$_3$) δ 0.07-0.24 (3H, m), 0.24-0.33 (1H, m), 0.36 (2H, d, J=8.2 Hz), 0.42-0.51 (1H, m), 0.55-0.65 (1H, m), 0.98 (1H, tt, J=12.8, 4.8 Hz), 1.09-1.22 (1H, m), 1.19 (3H, t, J=7.1 Hz), 1.55 (4H, s), 1.67-1.91 (3H, m), 2.25-2.36 (1H, m), 2.56 (2H, brs), 2.64-2.80 (2H, m), 3.77 (3H, s), 4.00-4.11 (4H, m), 4.14 (3H, d, J=6.7 Hz), 6.21 (1H, s), 6.52 (1H, dd, J=8.4, 2.1 Hz), 6.62 (1H, s), 6.66 (1H, brs), 6.76 (1H, d, J=5.3 Hz), 6.86-6.93 (1H, m), 7.42 (1H, d, J=8.4 Hz), 8.06 (1H, d, J=5.3 Hz), 8.36 (1H, d, J=3.4 Hz).

Step 2) 3-cyclopropyl-3-(2-((1-(2-((cyclopropylmethyl)(pyridin-2-yl)carbamoyl)-5-methoxyphenyl)piperidin-4-yl)methoxy)pyridin-4-yl)propanoic acid In the same manner as in Example 1, step 4, the title compound (106 mg) was obtained as a white amorphous powder from ethyl 3-cyclopropyl-3-(2-((1-(2-((cyclopropylmethyl)(pyridin-2-yl)carbamoyl)-5-methoxyphenyl)piperidin-4-yl)methoxy)pyridin-4-yl)propanoate (120 mg).
MS (ESI+): [M+H]+ 585.3.

Example 118

3-(2-((1-(2-((cyclobutylmethyl)(pyridin-2-yl)carbamoyl)-5-methoxyphenyl)piperidin-4-yl)methoxy)pyridin-4-yl)-3-cyclopropylpropanoic acid Step 1) N-(cyclobutylmethyl)pyridin-2-amine In the same manner as in Example 32, step 1, the title compound (1.82 g) was obtained as a white solid from 2-aminopyridine (1.50 g) and cyclobutanecarboxylic chloride (2.73 mL).
$^1$H NMR (400 MHz, DMSO-d$_6$) δ 1.60-1.74 (2H, m), 1.77-1.89 (2H, m), 1.94-2.06 (2H, m), 2.48-2.58 (1H, m), 3.18-3.27 (2H, m), 6.27-6.50 (3H, m), 7.20-7.38 (1H, m), 7.92 (1H, d, J=4.3 Hz).

Step 2) ethyl 3-(2-((1-(2-((cyclobutylmethyl)(pyridin-2-yl)carbamoyl)-5-methoxyphenyl)piperidin-4-yl)methoxy)pyridin-4-yl)-3-cyclopropylpropanoate In the same manner as in Example 32, step 2, the title compound (106 mg) was obtained as a colorless oil from 2-(4-(((4-(1-cyclopropyl-3-ethoxy-3-oxopropyl)pyridin-2-yl)oxy)methyl)piperidin-1-yl)-4-methoxybenzoic acid (100 mg) and N-(cyclobutylmethyl)pyridin-2-amine (84.0 mg).
$^1$H NMR (400 MHz, CDCl$_3$) δ 0.06-0.24 (1H, m), 0.25-0.36 (1H, m), 0.37-0.53 (1H, m), 0.55-0.68 (1H, m), 0.90-1.07 (1H, m), 1.19 (3H, t, J=7.1 Hz), 1.45-1.96 (13H, m), 2.23-2.35 (1H, m), 2.47-2.73 (4H, m), 2.65-2.82 (2H, m), 3.76 (3H, s), 4.02-4.13 (2H, m), 4.16 (2H, d, J=6.5 Hz), 4.23 (2H, d, J=6.8 Hz), 6.20 (1H, brs), 6.50 (1H, dd, J=8.5, 2.2 Hz), 6.62 (2H, s), 6.76 (1H, d, J=5.3 Hz), 6.83-6.93 (1H, m), 7.35 (1H, d, J=8.4 Hz), 8.07 (1H, d, J=5.4 Hz), 8.36 (1H, d, J=4.5 Hz).

Step 3) 3-(2-((1-(2-((cyclobutylmethyl)(pyridin-2-yl)carbamoyl)-5-methoxyphenyl)piperidin-4-yl)methoxy)pyridin-4-yl)-3-cyclopropylpropanoic acid In the same manner as in Example 1, step 4, the title compound (94.1 mg) was obtained as a white amorphous powder from ethyl 3-(2-((1-(2-((cyclobutylmethyl)(pyridin-2-yl)carbamoyl)-5-methoxyphenyl)piperidin-4-yl)methoxy)pyridin-4-yl)-3-cyclopropylpropanoate (106 mg).
MS (ESI+): [M+H]+ 599.3.

Example 119

3-cyclopropyl-3-(2-((1-(2-((2-hydroxy-2-methylpropyl)(pyridin-2-yl)carbamoyl)-5-methoxyphenyl)piperidin-4-yl)methoxy)pyridin-4-yl)propanoic acid Step 1) ethyl 3-cyclopropyl-3-(2-((1-(2-((2-hydroxy-2-methylpropyl)(pyridin-2-yl)carbamoyl)-5-methoxyphenyl)piperidin-4-yl)methoxy)pyridin-4-yl)propanoate In the same manner as in Example 32, step 2, the title compound (262 mg) was obtained as a colorless oil from 2-(4-(((4-(1-cyclopropyl-3-ethoxy-3-oxopropyl)pyridin-2-yl)oxy)methyl)piperidin-1-yl)-4-methoxybenzoic acid (200 mg) and 2-methyl-1-(pyridin-2-ylamino)propan-2-ol (172 mg) obtained in Example 35, step 2.

$^1$H NMR (400 MHz, DMSO-d$_6$) δ 0.12-0.21 (1H, m), 0.22-0.30 (1H, m), 0.30-0.40 (1H, m), 0.43-0.58 (1H, m), 1.01 (6H, brs), 1.05-1.14 (1H, m), 1.07 (3H, t, J=7.3 Hz), 1.59-1.86 (3H, m), 2.17-2.29 (1H, m), 2.35-2.68 (6H, m), 2.75 (2H, d, J=7.5 Hz), 3.69 (3H, s), 3.89-4.01 (2H, m), 4.02-4.40 (2H, m), 4.12 (2H, d, J=6.7 Hz), 4.60 (1H, s), 6.24 (1H, s), 6.48-6.59 (1H, m), 6.72 (2H, s), 6.91 (1H, d, J=5.3 Hz), 6.96-7.04 (1H, m), 7.16 (1H, d, J=8.4 Hz), 7.41 (1H, t, J=7.5 Hz), 7.90 (1H, d, J=5.0 Hz), 8.04 (1H, d, J=5.4 Hz), 8.32 (1H, d, J=3.5 Hz).

Step 2) 3-cyclopropyl-3-(2-((1-(2-((2-hydroxy-2-methylpropyl)(pyridin-2-yl)carbamoyl)-5-methoxyphenyl)piperidin-4-yl)methoxy)pyridin-4-yl)propanoic acid In the same manner as in Example 1, step 4, the title compound (13.7 mg) was obtained as a white amorphous powder from ethyl 3-cyclopropyl-3-(2-((1-(2-((2-hydroxy-2-methylpropyl)(pyridin-2-yl)carbamoyl)-5-methoxyphenyl)piperidin-4-yl)methoxy)pyridin-4-yl)propanoate (31 mg).

MS (ESI+): [M+H]$^+$ 603.3.

Example 120

3-cyclopropyl-3-(2-((1-(2-((2-fluoro-2-methylpropyl)(pyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (151 mg) was obtained as a colorless amorphous powder from N-(2-fluoro-2-methylpropyl)pyridin-2-amine (105 mg) obtained in Example 39, step 1 and 2-(4-(((4-(1-cyclopropyl-3-ethoxy-3-oxopropyl)pyridin-2-yl)oxy)methyl)piperidin-1-yl)-4-methoxybenzoic acid (150 mg).

MS (ESI+): [M+H]$^+$ 605.3.

Example 121

3-cyclopropyl-3-(2-((1-(5-methoxy-2-((3-methylbutan-2-yl)(pyridin-2-yl)carbamoyl)phenyl)piperidin-4-yl)methoxy)pyridin-4-yl)propanoic acid Step 1) N-(3-methylbutan-2-yl)pyridin-2-amine A solution of pyridin-2-amine (2.00 g) and 3-methylbutan-2-one (3.66 g) in acetic acid (10 mL) was stirred at 70° C. for 10 min, sodium triacetoxyborohydride (6.76 g) was added, and the mixture was further stirred for 2 hr. The solvent was evaporated under reduced pressure, saturated aqueous sodium hydrogen carbonate solution was added to the residue, and the mixture was extracted with ethyl acetate. The extract was washed with saturated brine, dried over anhydrous magnesium sulfate, and the solvent was evaporated under reduced pressure. The obtained residue was dissolved in methanol (15 mL), sodium borohydride (0.804 g) was added, and the mixture was stirred at 70° C. for 1 hr. To the reaction mixture was added saturated aqueous ammonium chloride solution at room temperature, and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (180 mg) as a colorless solid.

$^1$H NMR (300 MHz, CDCl$_3$) δ 0.88-1.01 (6H, m), 1.13 (3H, d, J=6.5 Hz), 1.69-1.91 (1H, m), 3.53-3.69 (1H, m), 4.23-4.53 (1H, m), 6.34 (1H, d, J=8.5 Hz), 6.51 (1H, ddd, J=7.1, 5.1, 0.9 Hz), 7.38 (1H, ddd, J=8.6, 7.0, 1.9 Hz), 7.99-8.10 (1H, m).

Step 2) 3-cyclopropyl-3-(2-((1-(5-methoxy-2-((3-methylbutan-2-yl)(pyridin-2-yl)carbamoyl)phenyl)piperidin-4-yl)methoxy)pyridin-4-yl)propanoic acid In the same manner as in Example 32, step 2 and Example 1, step 4, the title compound (157 mg) was obtained as a colorless amorphous powder from N-(3-methylbutan-2-yl)pyridin-2-amine (112 mg) and 2-(4-(((4-(1-cyclopropyl-3-ethoxy-3-oxopropyl)pyridin-2-yl)oxy)methyl)piperidin-1-yl)-4-methoxybenzoic acid (150 mg).

MS (ESI+): [M+H]$^+$ 601.3.

Example 122

3-cyclopropyl-3-(2-((1-(5-methoxy-2-((2-methylpropyl)(6-methylpyridin-2-yl)carbamoyl)phenyl)piperidin-4-yl)methoxy)pyridin-4-yl)propanoic acid By a method similar to that in Example 32, step 2 and Example 1, step 4, the title compound (82 mg) was obtained as a pale-yellow amorphous powder from 2-(4-(((4-(1-cyclopropyl-3-ethoxy-3-oxopropyl)pyridin-2-yl)oxy)methyl)piperidin-1-yl)-4-methoxybenzoic acid (106.7 mg) and 6-methyl-N-(2-methylpropyl)pyridin-2-amine (72.6 mg).

MS (ESI+): [M+H]$^+$ 601.3.

Example 123

3-cyclopropyl-3-(2-((1-(5-methoxy-2-((2-methylpropyl)(4-methylpyridin-2-yl)carbamoyl)phenyl)piperidin-4-yl)methoxy)pyridin-4-yl)propanoic acid In the same manner as in Example 32, step 2 and Example 1, step 4, the title compound (117 mg) was obtained as a grayish white solid from 2-(4-(((4-(1-cyclopropyl-3-ethoxy-3-oxopropyl)pyridin-2-yl)oxy)methyl)piperidin-1-yl)-4-methoxybenzoic acid (132 mg) and 4-methyl-N-(2-methylpropyl)pyridin-2-amine (90 mg).

MS (ESI+): [M+H]$^+$ 601.3.

Example 124

3-cyclopropyl-3-(2-((1-(2-((cyclopropylmethyl)(6-methylpyridin-2-yl)carbamoyl)-5-methoxyphenyl)piperidin-4-yl)methoxy)pyridin-4-yl)propanoic acid Step 1)
N-(cyclopropylmethyl)-6-methylpyridin-2-amine In the same manner as in Example 36, step 1, the title compound (1.16 g) was obtained as a pale-yellow oil from 6-methylpyridin-2-amine (2.89 g).

MS (ESI+): [M+H]$^+$ 163.1.

Step 2) 3-cyclopropyl-3-(2-((1-(2-((cyclopropylmethyl)(6-methylpyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (110 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (167 mg) and N-(cyclopropylmethyl)-6-methylpyridin-2-amine (112 mg).
MS (ESI+): [M+H]$^+$ 599.3.

Example 125

3-cyclopropyl-3-(2-((1-(2-((cyclopropylmethyl)(4-methylpyridin-2-yl)carbamoyl)-5-methoxyphenyl)piperidin-4-yl)methoxy)pyridin-4-yl)propanoic acid Step 1) N-(cyclopropylmethyl)-4-methylpyridin-2-amine In the same manner as in Example 36, step 1, the title compound (1.11 g) was obtained as a pale-yellow oil from 4-methylpyridin-2-amine (2.89 g).
MS (ESI+): [M+H]$^+$ 163.0.

Step 2) 3-cyclopropyl-3-(2-((1-(2-((cyclopropylmethyl)(4-methylpyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (125 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (168 mg) and N-(cyclopropylmethyl)-4-methylpyridin-2-amine (113 mg).
MS (ESI+): [M+H]$^+$ 599.3.

Example 126

3-cyclopropyl-3-(2-((1-(2-((2,2-difluoropropyl)(pyridin-2-yl)carbamoyl)-5-methoxyphenyl)piperidin-4-yl)methoxy)pyridin-4-yl)propanoic acid Step 1) 2,2-difluoropropyl methanesulfonate 2,2-Difluoropropan-1-ol (297 mg) and methanesulfonyl chloride (0.263 mL) were dissolved in THF (15 mL), and triethylamine (0.646 mL) was added at room temperature. After stirring for 20 min, saturated aqueous ammonium chloride solution was added to the reaction mixture at room temperature, and the mixture was extracted with ethyl acetate. The extract was washed with saturated brine, dried over anhydrous magnesium sulfate, and the solvent was evaporated under reduced pressure to give a crude product (540 mg) of the title compound as a colorless oil. This compound was used for the next step without further purification.
$^1$H NMR (300 MHz, CDCl$_3$) δ 1.72 (3H, t, J=18.6 Hz), 3.10 (3H, s), 4.31 (2H, t, J=11.4 Hz).

Step 2) tert-butyl(2,2-difluoropropyl)pyridin-2-ylcarbamate

To a solution of tert-butyl pyridin-2-ylcarbamate (300 mg) in DMF (4 mL) was added sodium hydride (60% in oil, 124 mg) at 0° C., and the mixture was stirred for 10 min. A solution of 2,2-difluoropropyl methanesulfonate (540 mg) obtained in step 1 in DMF (1.5 mL) was added thereto, and the mixture was stirred at room temperature for 1 hr. The mixture was allowed to warm to 60° C. and further stirred for 16 hr. Then, cesium carbonate (1006 mg) was added at 60° C., and the mixture was stirred at 110° C. for 16 hr. Water was added to the reaction mixture at room temperature, and the mixture was extracted with ethyl acetate. The extract was washed with saturated brine, dried over anhydrous magnesium sulfate, and the solvent was evaporated under reduced pressure. The residue was purified by silica gel column chromatography (ethyl acetate/hexane) to give the title compound (71 mg) as a colorless oil.
$^1$H NMR (300 MHz, CDCl$_3$) δ 1.22 (3H, t, J=7.0 Hz), 1.51 (9H, s), 3.97 (2H, q, J=7.0 Hz), 6.99 (1H, ddd, J=5.8, 4.9, 2.5 Hz), 7.55-7.64 (2H, m), 8.34-8.41 (1H, m).

Step 3) N-(2,2-difluoropropyl)pyridin-2-amine hydrochloride

To a solution of tert-butyl(2,2-difluoropropyl)(pyridin-2-yl)carbamate (71 mg) in ethyl acetate (2 mL) was added 4N hydrogen chloride ethyl acetate solution (2 mL), and the mixture was stirred at room temperature for 6 hr. The solvent was evaporated under reduced pressure to give a crude product of the title compound as a colorless amorphous powder. This compound was used for the next step without further purification.
MS (ESI+): [M+H]$^+$ 173.0.

Step 4) ethyl 3-cyclopropyl-3-(2-((1-(2-((2,2-difluoropropyl)(pyridin-2-yl)carbamoyl)-5-methoxyphenyl)piperidin-4-yl)methoxy)pyridin-4-yl)propanoate In the same manner as in Example 32, step 2, the title compound (8 mg) was obtained as a colorless oil from N-(2,2-difluoropropyl)pyridin-2-amine hydrochloride (0.26 mmol) obtained in step 3 and 2-(4-(((4-(1-cyclopropyl-3-ethoxy-3-oxopropyl)pyridin-2-yl)oxy)methyl)piperidin-1-yl)-4-methoxybenzoic acid (151 mg).
MS (ESI+): [M+H]$^+$ 637.3.

Step 5) 3-cyclopropyl-3-(2-((1-(2-((2,2-difluoropropyl)(pyridin-2-yl)carbamoyl)-5-methoxyphenyl)piperidin-4-yl)methoxy)pyridin-4-yl)propanoic acid In the same manner as in Example 1, step 4, the title compound (35 mg) was obtained as a colorless amorphous powder from ethyl 3-cyclopropyl-3-(2-((1-(2-((2,2-difluoropropyl)(pyridin-2-yl)carbamoyl)-5-methoxyphenyl)piperidin-4-yl)methoxy)pyridin-4-yl)propanoate (90 mg).
MS (ESI+): [M+H]$^+$ 609.2.

Example 127

3-cyclopropyl-3-(2-((1-(5-methoxy-2-((2-methoxypyridin-4-yl)(2-methylpropyl)carbamoyl)phenyl)piperidin-4-yl)methoxy)pyridin-4-yl)propanoic acid Step 1) 2-methoxy-N-(2-methylpropyl)pyridin-4-amine In the same manner as in Example 36, step 1, the title compound (227 mg) was obtained as colorless liquid from 2-methylpropanal (366 μL) and 2-methoxypyridin-4-amine (1.00 g).
$^1$H NMR (400 MHz, CDCl$_3$) δ 0.97 (6H, d, J=6.7 Hz), 1.75-1.97 (1H, m), 2.93 (2H, t, J=6.3 Hz), 3.88 (3H, s), 4.01-4.27 (1H, m), 5.82 (1H, d, J=1.9 Hz), 6.12 (1H, dd, J=5.8, 2.1 Hz), 7.77 (1H, d, J=5.9 Hz).

Step 2) ethyl 3-cyclopropyl-3-(2-((1-(5-methoxy-2-((2-methoxypyridin-4-yl)(2-methylpropyl)carbamoyl)phenyl)piperidin-4-yl)methoxy)pyridin-4-yl)propanoate In the same manner as in Example 32, step 2, the title compound (22.2 mg) was obtained as a colorless oil from 2-(4-(((4-(1-cyclopropyl-3-ethoxy-3-oxopropyl)pyridin-2-yl)oxy)methyl)piperidin-1-yl)-4-methoxybenzoic acid (100 mg) and 2-methoxy-N-(2-methylpropyl)pyridin-4-amine (93.0 mg).

$^1$H NMR (400 MHz, CDCl$_3$) δ 0.12-0.22 (1H, m), 0.25-0.36 (1H, m), 0.41-0.53 (1H, m), 0.55-0.67 (1H, m), 0.89 (6H, d, J=6.7 Hz), 0.92-1.07 (1H, m), 1.19 (3H, t, J=7.1 Hz), 1.43 (2H, brs), 1.77-1.95 (4H, m), 2.24-2.37 (1H, m), 2.39-2.70 (3H, m), 2.65-2.81 (2H, m), 3.23-3.68 (2H, m), 3.76 (3H, s), 3.83 (3H, s), 3.99-4.13 (3H, m), 4.18 (2H, d, J=6.1 Hz), 6.30 (1H, d, J=1.8 Hz), 6.41 (1H, s), 6.45 (1H, d, J=4.4 Hz), 6.51 (1H, dd, J=8.5, 2.2 Hz), 6.64 (1H, s), 6.72-6.83 (1H, m), 7.22-7.26 (1H, m), 7.84 (1H, d, J=5.6 Hz), 8.07 (1H, d, J=5.3 Hz).

Step 3) 3-cyclopropyl-3-(2-((1-(5-methoxy-2-((2-methoxypyridin-4-yl)(2-methylpropyl)carbamoyl)phenyl)piperidin-4-yl)methoxy)pyridin-4-yl)propanoic acid In the same manner as in Example 1, step 4, the title compound (18.0 mg) was obtained as a white amorphous powder from ethyl 3-cyclopropyl-3-(2-((1-(5-methoxy-2-((2-methoxypyridin-4-yl)(2-methylpropyl)carbamoyl)phenyl)piperidin-4-yl)methoxy)pyridin-4-yl)propanoate (22.2 mg).

MS (ESI+): [M+H]$^+$ 617.3.

Example 128

3-cyclopropyl-3-(2-((1-(5-methoxy-2-((6-methoxypyridin-2-yl)(2-methylpropyl)carbamoyl)phenyl)piperidin-4-yl)methoxy)pyridin-4-yl)propanoic acid Step 1) 6-methoxy-N-(2-methylpropyl)pyridin-2-amine In the same manner as in Example 32, step 1, the title compound (1.28 g) was obtained as a colorless oil from 6-methoxypyridin-2-amine (1.00 g) and 2-methylpropionyl chloride (2.16 mL).

$^1$H NMR (400 MHz, CDCl$_3$) δ 0.98 (6H, d, J=6.7 Hz), 1.89 (1H, dt, J=13.4, 6.7 Hz), 3.06 (2H, t, J=6.3 Hz), 3.84 (3H, s), 4.44 (1H, brs), 5.91 (1H, d, J=7.9 Hz), 5.99 (1H, d, J=7.8 Hz), 7.33 (1H, t, J=7.8 Hz).

Step 2) ethyl 3-cyclopropyl-3-(2-((1-(5-methoxy-2-((6-methoxypyridin-2-yl)(2-methylpropyl)carbamoyl)phenyl)piperidin-4-yl)methoxy)pyridin-4-yl)propanoate In the same manner as in Example 32, step 2, the title compound (107 mg) was obtained as a colorless oil from 2-(4-(((4-(1-cyclopropyl-3-ethoxy-3-oxopropyl)pyridin-2-yl)oxy)methyl)piperidin-1-yl)-4-methoxybenzoic acid (100 mg) and 6-methoxy-N-(2-methylpropyl)pyridin-2-amine (93.0 mg).

$^1$H NMR (400 MHz, CDCl$_3$) δ 0.11-0.21 (1H, m), 0.24-0.33 (1H, m), 0.40-0.50 (1H, m), 0.55-0.66 (1H, m), 0.89 (6H, d, J=5.5 Hz), 0.93-1.04 (1H, m), 1.19 (3H, t, J=7.2 Hz), 1.52-1.58 (2H, m), 1.68-1.99 (4H, m), 2.23-2.36 (1H, m), 2.42-2.68 (3H, m), 2.65-2.81 (2H, m), 3.03-3.53 (1H, m), 3.77 (3H, s), 3.81 (3H, s), 3.94-4.20 (6H, m), 6.25 (2H, brs), 6.34 (1H, d, J=8.2 Hz), 6.50 (1H, dd, J=8.5, 2.3 Hz), 6.61 (1H, s), 6.76 (1H, d, J=5.4 Hz), 7.13-7.23 (1H, m), 7.34 (1H, d, J=8.4 Hz), 8.05 (1H, d, J=5.3 Hz).

Step 3) 3-cyclopropyl-3-(2-((1-(5-methoxy-2-((6-methoxypyridin-2-yl)(2-methylpropyl)carbamoyl)phenyl)piperidin-4-yl)methoxy)pyridin-4-yl)propanoic acid In the same manner as in Example 1, step 4, the title compound (97.1 mg) was obtained as a white amorphous powder from ethyl 3-cyclopropyl-3-(2-((1-(5-methoxy-2-((6-methoxypyridin-4-yl)(2-methylpropyl)carbamoyl)phenyl)piperidin-4-yl)methoxy)pyridin-4-yl)propanoate (107 mg).

MS (ESI+): [M+H]$^+$ 617.3.

Example 129

3-cyclopropyl-3-(2-((1-(5-methoxy-2-((2,2,3,3,3-pentafluoropropyl)carbamoyl)phenyl)piperidin-4-yl)methoxy)pyridin-4-yl)propanoic acid Step 1) ethyl 3-cyclopropyl-3-(2-((1-(5-methoxy-2-((2,2,3,3,3-pentafluoropropyl)carbamoyl)phenyl)piperidin-4-yl)methoxy)pyridin-4-yl)propanoate In the same manner as in Example 32, step 2, the title compound (238 mg) was obtained as a colorless oil from 2,2,3,3,3-pentafluoropropan-1-amine (201 mg) and 2-(4-(((4-(1-cyclopropyl-3-ethoxy-3-oxopropyl)pyridin-2-yl)oxy)methyl)piperidin-1-yl)-4-methoxybenzoic acid (260 mg).

$^1$H NMR (300 MHz, CDCl$_3$) δ 0.10-0.22 (1H, m), 0.24-0.36 (1H, m), 0.40-0.52 (1H, m), 0.55-0.67 (1H, m), 0.92-1.06 (1H, m), 1.19 (3H, t, J=6.9 Hz), 1.47-1.66 (2H, m), 1.92-2.10 (3H, m), 2.25-2.37 (1H, m), 2.64-2.88 (4H, m), 3.11-3.21 (2H, m), 3.85 (3H, s), 4.01-4.11 (2H, m), 4.13-4.28 (4H, m), 6.59-6.65 (1H, m), 6.74-6.87 (3H, m), 8.07 (1H, d, J=5.3 Hz), 8.24 (1H, d, J=8.7 Hz), 10.90 (1H, t, J=5.9 Hz).

Step 2) 3-cyclopropyl-3-(2-((1-(5-methoxy-2-((2,2,3,3,3-pentafluoropropyl)carbamoyl)phenyl)piperidin-4-yl)methoxy)pyridin-4-yl)propanoic acid In the same manner as in Example 1, step 4, the title compound (135 mg) was obtained as a colorless amorphous powder from ethyl 3-cyclopropyl-3-(2-((1-(5-methoxy-2-((2,2,3,3,3-pentafluoropropyl)carbamoyl)phenyl)piperidin-4-yl)methoxy)pyridin-4-yl)propanoate (140 mg).

MS (ESI+): [M+H]$^+$ 586.2.

Example 130

3-cyclopropyl-3-(2-((1-(5-methoxy-2-(methyl(2,2,3,3,3-pentafluoropropyl)carbamoyl)phenyl)piperidin-4-yl)methoxy)pyridin-4-yl)propanoic acid Step 1) ethyl 3-cyclopropyl-3-(2-((1-(5-methoxy-2-(methyl(2,2,3,3,3-pentafluoropropyl)carbamoyl)phenyl)piperidin-4-yl)methoxy)pyridin-4-yl)propanoate Ethyl 3-cyclopropyl-3-(2-((1-(5-methoxy-2-((2,2,3,3,3-pentafluoropropyl)carbamoyl)phenyl)piperidin-4-yl)

methoxy)pyridin-4-yl)propanoate (105 mg) obtained in Example 129, step 1, was dissolved in DMF (3 mL), and sodium hydride (60% in oil, 34.2 mg) was added at room temperature. The mixture was stirred at room temperature for 10 min, iodomethane (0.107 mL) was added, and the mixture was stirred at room temperature overnight. Water was added to the reaction mixture at room temperature, and the mixture was extracted with ethyl acetate. The extract was washed with saturated brine, dried over anhydrous magnesium sulfate, and the solvent was evaporated under reduced pressure. The residue was purified by silica gel column chromatography (ethyl acetate/hexane) to give the title compound (125 mg) as a colorless oil.

MS (ESI+): [M+H]$^+$ 628.5.

Step 2) 3-cyclopropyl-3-(2-((1-(5-methoxy-2-(methyl(2,2,3,3,3-pentafluoropropyl)carbamoyl) phenyl)piperidin-4-yl)methoxy)pyridin-4-yl)propanoic acid In the same manner as in Example 1, step 4, the title compound (89 mg) was obtained as a colorless amorphous powder from ethyl 3-cyclopropyl-3-(2-((1-(5-methoxy-2-(methyl(2,2,3,3,3-pentafluoropropyl)carbamoyl)phenyl)piperidin-4-yl)methoxy)pyridin-4-yl)propanoate (125 mg).

MS (ESI+): [M+H]$^+$ 600.2.

Example 131

3-cyclopropyl-3-(2-((1-(5-methoxy-2-((2-methoxy-2-methylpropyl)(pyridin-2-yl)carbamoyl)phenyl) piperidin-4-yl)methoxy)pyridin-4-yl)propanoic acid Step 1) ethyl 3-cyclopropyl-3-(2-((1-(5-methoxy-2-((2-methoxy-2-methylpropyl)(pyridin-2-yl)carbamoyl)phenyl)piperidin-4-yl)methoxy)pyridin-4-yl)propanoate In the same manner as in Example 32, step 2, the title compound (90.0 mg) was obtained as a colorless oil from 2-(4-(((4-(1-cyclopropyl-3-ethoxy-3-oxopropyl)pyridin-2-yl)oxy)methyl)piperidin-1-yl)-4-methoxybenzoic acid (100 mg) and N-(2-methoxy-2-methylpropyl)pyridin-2-amine (93.0 mg) obtained in Example 35, step 3.

$^1$H NMR (400 MHz, CDCl$_3$) δ 0.12-0.22 (1H, m), 0.25-0.35 (1H, m), 0.40-0.53 (1H, m), 0.55-0.66 (1H, m), 0.91-1.06 (1H, m), 1.13-1.22 (3H, m), 1.19 (6H, s), 1.27-1.94 (5H, m), 2.27-2.35 (1H, m), 2.36-2.75 (3H, m), 2.66-2.79 (2H, m), 2.83 (3H, s), 3.28-3.54 (1H, m), 3.75 (3H, s), 4.02-4.12 (2H, m), 4.17 (2H, d, J=6.7 Hz), 4.24-4.59 (2H, m), 6.20 (1H, s), 6.46 (1H, dd, J=8.3, 1.9 Hz), 6.58 (1H, brs), 6.63 (1H, s), 6.76 (1H, d, J=5.3 Hz), 6.82-6.89 (1H, m), 7.20 (1H, t, J=8.2 Hz), 7.24-7.27 (1H, m), 8.07 (1H, d, J=5.1 Hz), 8.34 (1H, d, J=3.9 Hz).

Step 2) 3-cyclopropyl-3-(2-((1-(5-methoxy-2-((2-methoxy-2-methylpropyl)(pyridin-2-yl)carbamoyl) phenyl)piperidin-4-yl)methoxy)pyridin-4-yl)propanoic acid In the same manner as in Example 1, step 4, the title compound (82.6 mg) was obtained as a white amorphous powder from ethyl 3-cyclopropyl-3-(2-((1-(5-methoxy-2-((2-methoxy-2-methylpropyl)(pyridin-2-yl)carbamoyl)phenyl)piperidin-4-yl)methoxy)pyridin-4-yl)propanoate (90.0 mg).

MS (ESI+): [M+H]$^+$ 617.3.

Example 132

3-(2-((1-(2-((3-cyanophenyl)(2-methylpropyl)carbamoyl)-5-methoxyphenyl)piperidin-4-yl)methoxy) pyridin-4-yl)-3-cyclopropylpropanoic acid Step 1) 3-((2-methylpropyl)amino)benzonitrile In the same manner as in Example 36, step 1, the title compound (386 mg) was obtained as a pale-yellow oil from 3-aminobenzonitrile (1.29 g).

MS (ESI+): [M+H]$^+$ 163.0.

Step 2) 3-(2-((1-(2-((3-cyanophenyl)(2-methylpropyl)carbamoyl)-5-methoxyphenyl)piperidin-4-yl) methoxy)pyridin-4-yl)-3-cyclopropylpropanoic acid In the same manner as in Example 32, step 2 and Example 1, step 4, the title compound (108 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (165 mg) and 3-((2-methylpropyl)amino)benzonitrile (119 mg).

MS (ESI+): [M+H]$^+$ 611.2.

Example 133

3-cyclopropyl-3-(2-((1-(5-methoxy-2-((2-methylpropyl)(phenyl)carbamoyl)phenyl)piperidin-4-yl) methoxy)pyridin-4-yl)propanoic acid Step 1) N-(2-methylpropyl)aniline In the same manner as in Example 32, step 1, the title compound (1.51 g) was obtained as a pale-yellow oil from aniline (1 mL).

$^1$H NMR (300 MHz, CDCl$_3$) δ 0.98 (6H, d, J=6.7 Hz), 1.89 (1H, dquin, J=13.4, 6.7 Hz), 2.93 (2H, d, J=6.8 Hz), 3.68 (1H, brs), 6.50-6.63 (2H, m), 6.63-6.71 (1H, m), 7.09-7.22 (2H, m).

Step 2) 3-cyclopropyl-3-(2-((1-(5-methoxy-2-((2-methylpropyl)(phenyl)carbamoyl)phenyl)piperidin-4-yl)methoxy)pyridin-4-yl)propanoic acid In the same manner as in Example 32, step 2 and Example 1, step 4, the title compound (182 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (171 mg) and N-(2-methylpropyl)aniline (106 mg).

MS (ESI+): [M+H]$^+$ 586.3.

Example 134

3-(2-((1-(2-((2-cyano-2-methylpropyl)(pyridin-2-yl) carbamoyl)-5-methoxyphenyl)piperidin-4-yl) methoxy)pyridin-4-yl)-3-cyclopropylpropanoic acid Step 1) ethyl 3-(2-((1-(2-((2-cyano-2-methylpropyl) (pyridin-2-yl)carbamoyl)-5-methoxyphenyl)piperidin-4-yl)methoxy)pyridin-4-yl)-3-cyclopropylpropanoate In the same manner as in Example 32, step 2, the title compound (115 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (100 mg) and 2,2-dimethyl-3-(pyridin-2-ylamino)propanenitrile (91.0 mg) obtained in Example 43, step 5.

$^1$H NMR (400 MHz, CDCl$_3$) δ 0.11-0.21 (1H, m), 0.25-0.34 (1H, m), 0.41-0.52 (1H, m), 0.54-0.65 (1H, m), 0.91-1.05 (1H, m), 1.19 (3H, t, J=7.2 Hz), 1.27-1.43 (2H, m), 1.38 (6H, brs), 1.62-1.92 (4H, m), 2.26-2.36 (1H, m), 2.37-2.66 (3H, m), 2.65-2.79 (2H, m), 3.19-3.40 (1H, m), 3.77 (3H, s), 4.01-4.11 (2H, m), 4.16 (2H, d, J=6.7 Hz), 4.30-4.79 (2H, m), 6.19 (1H, d, J=1.6 Hz), 6.53 (2H, dd, J=8.5, 2.2 Hz), 6.63 (1H, s), 6.76 (1H, d, J=5.3 Hz), 6.94 (1H, dd, J=7.1, 5.0 Hz), 7.36 (1H, d, J=8.5 Hz), 8.07 (1H, d, J=5.3 Hz), 8.39 (1H, d, J=3.5 Hz).

Step 2) 3-(2-((1-(2-((2-cyano-2-methylpropyl)(pyridin-2-yl)carbamoyl)-5-methoxyphenyl)piperidin-4-yl)methoxy)pyridin-4-yl)-3-cyclopropylpropanoic acid In the same manner as in Example 1, step 4, the title compound (100 mg) was obtained as a white amorphous powder from ethyl 3-(2-((1-(2-((2-cyano-2-methylpropyl)(pyridin-2-yl)carbamoyl)-5-methoxyphenyl)piperidin-4-yl)methoxy)pyridin-4-yl)-3-cyclopropylpropanoate (115 mg).
MS (ESI+): [M+H]$^+$ 612.3.

Example 135

3-cyclopropyl-3-(2-((1-(5-methoxy-2-((4-methoxypyridin-2-yl)(2-methylpropyl)carbamoyl)phenyl)piperidin-4-yl)methoxy)pyridin-4-yl)propanoic acid Step 1)
4-methoxy-N-(2-methylpropyl)pyridin-2-amine To a solution of 2-methylpropanamine (207 µl) in THF (6.65 mL) were added N-ethyldiisopropylamine (1.09 mL), 4-methoxypyridine 1-oxide (208.1 mg) and bromotris(pyrrolidino)phosphonium hexafluorophosphate (1.01 g) at room temperature, and the mixture was stirred for 3.5 hr. To the reaction mixture was added saturated aqueous sodium hydrogen carbonate solution at 0° C., and the mixture was extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane) to give the title compound (215 mg) as a pale-brown oil.
MS (ESI+): [M+H]$^+$ 181.1.

Step 2) 3-cyclopropyl-3-(2-((1-(5-methoxy-2-((4-methoxypyridin-2-yl)(2-methylpropyl)carbamoyl)phenyl)piperidin-4-yl)methoxy)pyridin-4-yl)propanoic acid By a method similar to that in Example 32, step 2 and Example 1, step 4, the title compound (132.6 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (133.9 mg) and 4-methoxy-N-(2-methylpropyl)pyridin-2-amine (100 mg).
MS (ESI+): [M+H]$^+$ 617.3.

Example 136

3-cyclopropyl-3-(2-((1-(5-methoxy-2-((2-methoxypyridin-3-yl)(2-methylpropyl)carbamoyl)phenyl)piperidin-4-yl)methoxy)pyridin-4-yl)propanoic acid In the same manner as in Example 32, step 2 and Example 1, step 4, the title compound (94 mg) was obtained as a grayish white solid from 2-(4-(((4-(1-cyclopropyl-3-ethoxy-3-oxopropyl)pyridin-2-yl)oxy)methyl)piperidin-1-yl)-4-methoxybenzoic acid (119 mg) and 2-methoxy-N-(2-methylpropyl)pyridin-3-amine (89 mg).
MS (ESI+): [M+H]$^+$ 617.3.

Example 137

3-cyclopropyl-3-(2-((1-(2-((2,2-difluoroethyl)(pyridin-2-yl)carbamoyl)-5-methoxyphenyl)piperidin-4-yl)methoxy)pyridin-4-yl)propanoic acid Step 1) N-(2,2-difluoroethyl)pyridin-2-amine In the same manner as in Example 135, step 1, the title compound (210 mg) was obtained as a colorless oil from pyridine 1-oxide (200 mg) and 2,2-difluoroethanamine (213 mg).
$^1$H NMR (300 MHz, CDCl$_3$) δ 3.78 (2H, tdd, J=14.6, 6.5, 4.3 Hz), 4.56 (1H, brs), 6.46 (1H, dt, J=8.3, 0.8 Hz), 6.64 (1H, ddd, J=7.1, 5.1, 0.9 Hz), 7.38-7.46 (1H, m), 8.06-8.14 (1H, m).

Step 2) 3-cyclopropyl-3-(2-((1-(2-((2,2-difluoroethyl)(pyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (88 mg) was obtained as a colorless amorphous powder from N-(2,2-difluoroethyl)pyridin-2-amine (105 mg) and 2-(4-(((4-(1-cyclopropyl-3-ethoxy-3-oxopropyl)pyridin-2-yl)oxy)methyl)piperidin-1-yl)-4-methoxybenzoic acid (146 mg).
MS (ESI+): [M+H]$^+$ 595.2.

Example 138

3-cyclopropyl-3-(2-((1-(5-methoxy-2-(pyridin-2-yl(2,2,3,3-tetrafluoropropyl)carbamoyl)phenyl)piperidin-4-yl)methoxy)pyridin-4-yl)propanoic acid Step 1) N-benzyl-2,2,3,3-tetrafluoropropan-1-amine In the same manner as in Example 14, step 1, the title compound (6.3 g) was obtained as a colorless oil from 1-phenylmethanamine (3.0 g) and 2,2,3,3-tetrafluoropropyl trifluoromethanesulfonate (7.39 g).
$^1$H NMR (300 MHz, CDCl$_3$) δ 1.42-1.58 (1H, m), 3.14 (2H, tt, J=14.3, 1.7 Hz), 3.87 (2H, s), 5.79-6.21 (1H, m), 7.24-7.39 (5H, m).

Step 2) 2,2,3,3-tetrafluoropropan-1-amine hydrochloride

Under a hydrogen atmosphere, a solution of N-benzyl-2,2,3,3-tetrafluoropropan-1-amine (6.3 g) and 20% palladium hydroxide (containing water (50%), 800 mg) in ethanol (50 mL) was stirred at room temperature overnight. The reaction mixture was filtered through celite, 4N hydrogen chloride ethyl acetate solution (14.2 mL) was added to the obtained filtrate, and the solvent was evaporated under reduced pressure. The residue was suspended in ethyl acetate and hexane, and the resulting precipitate was collected by filtration, washed with ethyl acetate, and dried under reduced pressure to give the title compound (3.74 g) as a colorless solid.
$^1$H NMR (300 MHz, DMSO-$d_6$) δ 3.62 (2H, t, J=16.8 Hz), 6.47-6.95 (1H, m), 9.02 (3H, s).

Step 3)
N-(2,2,3,3-tetrafluoropropyl)pyridin-2-amine

In the same manner as in Example 135, step 1, the title compound (100 mg) was obtained as a colorless oil from pyridine 1-oxide (200 mg) and 2,2,3,3-tetrafluoropropan-1-amine hydrochloride (458 mg).
$^1$H NMR (300 MHz, CDCl$_3$) δ 3.99-4.14 (2H, m), 4.54 (1H, brs), 5.67-6.09 (1H, m), 6.49 (1H, d, J=8.3 Hz), 6.67 (1H, ddd, J=7.2, 5.1, 0.9 Hz), 7.40-7.49 (1H, m), 8.12 (1H, dd, J=5.1, 1.1 Hz).

Step 4) 3-cyclopropyl-3-(2-((1-(5-methoxy-2-(pyridin-2-yl(2,2,3,3-tetrafluoropropyl)carbamoyl)phenyl)piperidin-4-yl)methoxy)pyridin-4-yl)propanoic acid In the same manner as in Example 32, step 2 and Example 1, step 4, the title compound (69 mg) was obtained as a colorless amorphous powder from N-(2,2,3,3-tetrafluoropropyl)pyridin-2-amine (100 mg) and 2-(4-(((4-(1-cyclopropyl-3-ethoxy-3-oxopropyl)pyridin-2-yl)oxy)methyl)piperidin-1-yl)-4-methoxybenzoic acid (142 mg).
MS (ESI+): [M+H]$^+$ 645.3.

Example 139

3-cyclopropyl-3-(2-((1-(2-(((2,2-difluorocyclopropyl)methyl)(pyridin-2-yl)carbamoyl)-5-methoxyphenyl)piperidin-4-yl)methoxy)pyridin-4-yl)propanoic acid Step 1)
N-((2,2-difluorocyclopropyl)methyl)pyridin-2-amine In the same manner as in Example 32, step 1, the title compound (129 mg) was obtained as a pale-yellow oil from pyridin-2-amine (514 mg).
MS (ESI+): [M+H]$^+$ 185.0.

Step 2) 3-cyclopropyl-3-(2-((1-(2-(((2,2-difluorocyclopropyl)methyl)(pyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (18.5 mg) was obtained as a pale-yellow oil from 2-(4-(((4-(1-cyclopropyl-3-ethoxy-3-oxopropyl)pyridin-2-yl)oxy)methyl)piperidin-1-yl)-4-methoxybenzoic acid (162 mg) and N-((2,2-difluorocyclopropyl)methyl)pyridin-2-amine (129 mg).
MS (ESI+): [M+H]$^+$ 621.4.

Example 140

3-cyclopropyl-3-(2-((1-(5-methoxy-2-((6-methoxypyridin-3-yl)(2-methylpropyl)carbamoyl)phenyl)piperidin-4-yl)methoxy)pyridin-4-yl)propanoic acid In the same manner as in Example 32, step 2 and Example 1, step 4, the title compound (101 mg) was obtained as a grayish white solid from 2-(4-(((4-(1-cyclopropyl-3-ethoxy-3-oxopropyl)pyridin-2-yl)oxy)methyl)piperidin-1-yl)-4-methoxybenzoic acid (115 mg) and 6-methoxy-N-(2-methylpropyl)pyridin-3-amine (86 mg).
MS (ESI+): [M+H]$^+$ 617.3.

Example 141

3-cyclopropyl-3-(2-((1-(2-((cyclopropylmethyl)(pyridin-2-yl)carbamoyl)-5-methoxyphenyl)piperidin-4-yl)methoxy)pyridin-4-yl)propanoic acid Step 1) 2-(4-(((4-(1-cyclopropyl-3-ethoxy-3-oxopropyl)pyridin-2-yl)oxy)methyl)piperidin-1-yl)-4-methoxybenzoic acid Racemate (500 mg) of 2-(4-(((4-(1-cyclopropyl-3-ethoxy-3-oxopropyl)pyridin-2-yl)oxy)methyl)piperidin-1-yl)-4-methoxybenzoic acid was fractionated by SFC (column: CHIRALPAK AS-H, 20 mmID×250 mmL, manufactured by Daicel Corporation, mobile phase: CO$_2$/ethanol=740/260) to give the title compound (176 mg) having a shorter retention time.

Step 2) ethyl 3-cyclopropyl-3-(2-((1-(2-((cyclopropylmethyl)(pyridin-2-yl)carbamoyl)-5-methoxyphenyl)piperidin-4-yl)methoxy)pyridin-4-yl)propanoate In the same manner as in Example 32, step 2, the title compound (12.0 mg) was obtained as a colorless oil from 2-(4-(((4-(1-cyclopropyl-3-ethoxy-3-oxopropyl)pyridin-2-yl)oxy)methyl)piperidin-1-yl)-4-methoxybenzoic acid (176 mg) having a shorter retention time and N-(cyclopropylmethyl)pyridin-2-amine (135 mg).
$^1$H NMR (300 MHz, CDCl$_3$) δ 0.07-0.23 (3H, m), 0.29 (1H, dt, J=9.5, 4.8 Hz), 0.33-0.40 (2H, m), 0.41-0.52 (1H, m), 0.53-0.67 (1H, m), 0.79-0.93 (1H, m), 0.93-1.08 (1H, m), 1.19 (3H, t, J=7.2 Hz), 1.58 (4H, s), 1.66-1.84 (3H, m), 2.23-2.37 (1H, m), 2.55 (2H, brs), 2.64-2.82 (2H, m), 3.78 (3H, s), 3.99-4.11 (4H, m), 4.14 (2H, d, J=6.4 Hz), 6.21 (1H, d, J=2.1 Hz), 6.43-6.58 (1H, m), 6.60-6.68 (2H, m), 6.76 (1H, dd, J=5.3, 1.4 Hz), 6.90 (1H, dd, J=6.6, 4.8 Hz), 7.26 (1H, s), 7.42 (1H, d, J=8.5 Hz), 8.06 (1H, d, J=5.3 Hz), 8.36 (1H, dd, J=4.9, 1.2 Hz).

Step 3) 3-cyclopropyl-3-(2-((1-(2-((cyclopropylmethyl)(pyridin-2-yl)carbamoyl)-5-methoxyphenyl)piperidin-4-yl)methoxy)pyridin-4-yl)propanoic acid In the same manner as in Example 1, step 4, the title compound (6.00 mg) was obtained as a white amorphous powder from ethyl 3-cyclopropyl-3-(2-((1-(2-((cyclopropylmethyl)(pyridin-2-yl)carbamoyl)-5-methoxyphenyl)piperidin-4-yl)methoxy)pyridin-4-yl)propanoate (12.0 mg).
MS (ESI+): [M+H]$^+$ 585.3.

Example 142

3-cyclopropyl-3-(2-((1-(2-((cyclopropylmethyl)(pyridin-2-yl)carbamoyl)-5-methoxyphenyl)piperidin-4-yl)methoxy)pyridin-4-yl)propanoic acid Step 1) 2-(4-(((4-(1-cyclopropyl-3-ethoxy-3-oxopropyl)pyridin-2-yl)oxy)methyl)piperidin-1-yl)-4-methoxybenzoic acid Racemate (500 mg) of 2-(4-(((4-(1-cyclopropyl-3-ethoxy-3-oxopropyl)pyridin-2-yl)oxy)methyl)piperidin-1- yl)-4-methoxybenzoic acid was fractionated by SFC (column: CHIRALPAK AS-H, 20 mmID×250 mmL, manufactured by Daicel Corporation, mobile phase: CO₂/ethanol=740/260) to give the title compound (197 mg) having a longer retention time.

Step 2) ethyl 3-cyclopropyl-3-(2-((1-(2-((cyclopropylmethyl)(pyridin-2-yl)carbamoyl)-5-methoxyphenyl)piperidin-4-yl)methoxy)pyridin-4-yl)propanoate In the same manner as in Example 32, step 2, the title compound (31.3 mg) was obtained as a colorless oil from 2-(4-(((4-(1-cyclopropyl-3-ethoxy-3-oxopropyl)pyridin-2-yl)oxy)methyl)piperidin-1-yl)-4-methoxybenzoic acid (195 mg) having a longer retention time and N-(cyclopropylmethyl)pyridin-2-amine (150 mg).

¹H NMR (400 MHz, CDCl₃) δ 0.07-0.22 (3H, m), 0.25-0.33 (1H, m), 0.37 (2H, brs), 0.42-0.53 (1H, m), 0.55-0.66 (1H, m), 0.88-1.06 (1H, m), 1.12-1.19 (1H, m), 1.19 (3H, t, J=7.2 Hz), 1.42-1.64 (2H, m), 1.67-1.90 (3H, m), 2.25-2.38 (1H, m), 2.56 (2H, brs), 2.58-2.81 (4H, m), 3.78 (3H, s), 3.98-4.11 (4H, m), 4.14 (2H, d, J=6.5 Hz), 6.21 (1H, brs), 6.52 (1H, dd, J=8.5, 2.3 Hz), 6.58-6.74 (2H, m), 6.76 (1H, dd, J=5.3, 1.3 Hz), 6.84-6.97 (1H, m), 7.20-7.33 (1H, m), 7.42 (1H, d, J=8.4 Hz), 8.06 (1H, d, J=5.3 Hz), 8.36 (1H, d, J=3.6 Hz).

Step 3) 3-cyclopropyl-3-(2-((1-(2-((cyclopropylmethyl)(pyridin-2-yl)carbamoyl)-5-methoxyphenyl)piperidin-4-yl)methoxy)pyridin-4-yl)propanoic acid In the same manner as in Example 1, step 4, the title compound (26.7 mg) was obtained as a white amorphous powder from ethyl 3-cyclopropyl-3-(2-((1-(2-((cyclopropylmethyl)(pyridin-2-yl)carbamoyl)-5-methoxyphenyl)piperidin-4-yl)methoxy)pyridin-4-yl)propanoate (31.3 mg).

MS (ESI+): [M+H]⁺ 585.3.

Example 143

3-cyclopropyl-3-(2-((1-(5-methoxy-2-((6-methylpyridin-2-yl)(2,2,2-trifluoroethyl)carbamoyl)phenyl)piperidin-4-yl)methoxy)pyridin-4-yl)propanoic acid Step 1)
6-methyl-N-(2,2,2-trifluoroethyl)pyridin-2-amine In the same manner as in Example 32, step 1, the title compound (1.34 g) was obtained as a white solid from 6-methylpyridin-2-amine (1.00 g) and trifluoroacetic anhydride (1.57 mL).

¹H NMR (400 MHz, CDCl₃) δ 2.38 (3H, s), 4.07 (2H, qd, J=9.2, 6.9 Hz), 4.53 (1H, brs), 6.29 (1H, d, J=8.2 Hz), 6.54 (1H, d, J=7.3 Hz), 7.35 (1H, t, J=7.8 Hz).

Step 2) ethyl 3-cyclopropyl-3-(2-((1-(5-methoxy-2-((6-methylpyridin-2-yl)(2,2,2-trifluoroethyl)carbamoyl)phenyl)piperidin-4-yl)methoxy)pyridin-4-yl)propanoate In the same manner as in Example 32, step 2, the title compound (93.5 mg) was obtained as a colorless oil from 2-(4-(((4-(1-cyclopropyl-3-ethoxy-3-oxopropyl)pyridin-2-yl)oxy)methyl)piperidin-1-yl)-4-methoxybenzoic acid (100 mg) and 6-methyl-N-(2,2,2-trifluoroethyl)pyridin-2-amine (99.0 mg).

¹H NMR (400 MHz, CDCl₃) δ 0.10-0.22 (1H, m), 0.25-0.35 (1H, m), 0.41-0.52 (1H, m), 0.55-0.66 (1H, m), 0.92-1.06 (1H, m), 1.19 (3H, t, J=7.2 Hz), 1.36-1.61 (2H, m), 1.64-1.90 (3H, m), 2.25-2.36 (1H, m), 2.41-2.63 (3H, m), 2.48 (3H, s), 2.65-2.81 (2H, m), 2.95-3.59 (1H, m), 3.78 (3H, s), 4.02-4.11 (2H, m), 4.16 (2H, d, J=6.4 Hz), 5.08 (2H, brs), 6.22 (1H, d, J=1.8 Hz), 6.33 (1H, brs), 6.53 (1H, dd, J=8.5, 2.3 Hz), 6.62 (1H, s), 6.76 (1H, dd, J=5.4, 1.3 Hz), 6.79 (1H, d, J=7.5 Hz), 7.16 (1H, s), 7.38 (1H, d, J=8.4 Hz), 8.06 (1H, d, J=5.3 Hz).

Step 3) 3-cyclopropyl-3-(2-((1-(5-methoxy-2-((6-methylpyridin-2-yl)(2,2,2-trifluoroethyl)carbamoyl)phenyl)piperidin-4-yl)methoxy)pyridin-4-yl)propanoic acid In the same manner as in Example 1, step 4, the title compound (81.6 mg) was obtained as a white amorphous powder from ethyl 3-cyclopropyl-3-(2-((1-(5-methoxy-2-((6-methylpyridin-2-yl)(2,2,2-trifluoroethyl)carbamoyl)phenyl)piperidin-4-yl)methoxy)pyridin-4-yl)propanoate (93.5 mg).

MS (ESI+): [M+H]⁺ 627.2.

Example 144

3-cyclopropyl-3-(2-((1-(2-(((1-fluorocyclopropyl)methyl)(pyridin-2-yl)carbamoyl)-5-methoxyphenyl)piperidin-4-yl)methoxy)pyridin-4-yl)propanoic acid Step 1) 1-((dibenzylamino)methyl)cyclopropanol Under a nitrogen atmosphere, a 3.0 M solution of ethylmagnesium bromide in THF (9.41 mL) was added dropwise to a solution of ethyl 2-(dibenzylamino)acetate (4.0 g) and tetraisopropyl titanate (827 μL) in THF (50 mL) at 0° C., and the mixture was stirred at room temperature for 16 hr. To the reaction mixture was added saturated aqueous ammonium chloride solution, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (2.05 g) as a pale-yellow oil.

¹H NMR (400 MHz, DMSO-d₆) δ 0.26-0.38 (2H, m), 0.49-0.60 (2H, m), 2.53 (2H, s), 3.67 (4H, s), 5.01 (1H, s), 7.17-7.25 (2H, m), 7.31 (4H, t, J=7.5 Hz), 7.35-7.46 (4H, m).

Step 2)
N,N-dibenzyl-1-(1-fluorocyclopropyl)methanamine

In the same manner as in Example 39, step 1, the title compound (1.05 g) was obtained as a colorless oil from 1-((dibenzylamino)methyl)cyclopropanol (2.05 g).

¹H NMR (400 MHz, CDCl₃) δ 0.45-0.59 (4H, m), 3.88 (4H, s), 4.52 (2H, d, J=49.6 Hz), 7.09-7.48 (10H, m).

Step 3) (1-fluorocyclopropyl)methanamine hydrochloride

N,N-dibenzyl-1-(1-fluorocyclopropyl)methanamine (974 mg) and palladium hydroxide (500 mg) were stirred in methanol (30 mL) under a hydrogen atmosphere (1 atm) at room temperature for 2 hr. The reaction mixture was filtered, a 4N solution of hydrogen chloride ethyl acetate (2.71 mL)

was added to the filtrate, and the solvent was evaporated under reduced pressure to give the title compound (409 mg) as a white solid.

$^1$H NMR (400 MHz, DMSO-d$_6$) δ 0.82-1.19 (4H, m), 4.35-4.70 (2H, m), 8.65 (3H, brs).

Step 4)
N-((l-fluorocyclopropyl)methyl)pyridin-2-amine

In the same manner as in Example 135, step 1, the title compound (91 mg) was obtained as a white solid from (1-fluorocyclopropyl)methanamine hydrochloride (204 mg) and pyridine N-oxide (386 mg).

$^1$H NMR (400 MHz, CDCl$_3$) δ 0.88-1.06 (4H, m), 4.33-4.51 (2H, m), 5.16 (1H, brs), 6.62-6.68 (1H, m), 7.32-7.38 (1H, m), 7.43-7.50 (1H, m), 8.09 (1H, d, J=4.9 Hz).

Step 5) ethyl 3-cyclopropyl-3-(2-((1-(2-(((1-fluorocyclopropyl)methyl)(pyridin-2-yl)carbamoyl)-5-methoxyphenyl)piperidin-4-yl)methoxy)pyridin-4-yl)propanoate In the same manner as in Example 32, step 2, the title compound (77 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (125 mg) and N-((1-fluorocyclopropyl)methyl)pyridin-2-amine (91.0 mg).

$^1$H NMR (400 MHz, CDCl$_3$) δ 0.10-0.24 (1H, m), 0.30 (1H, dq, J=9.7, 4.8 Hz), 0.40-0.52 (1H, m), 0.55-0.67 (1H, m), 0.88-1.18 (4H, m), 0.91-1.04 (1H, m), 1.19 (3H, t, J=7.1 Hz), 1.56 (4H, s), 1.73-1.96 (3H, m), 2.26-2.37 (1H, m), 2.56 (2H, brs), 2.65-2.80 (2H, m), 3.73 (3H, s), 3.95-4.12 (2H, m), 4.17 (2H, d, J=6.3 Hz), 4.35-5.37 (2H, m), 6.21 (1H, d, J=2.3 Hz), 6.47 (1H, dd, J=8.5, 2.3 Hz), 6.63 (1H, s), 6.72-6.81 (1H, m), 6.92 (1H, dd, J=7.0, 5.2 Hz), 7.20-7.33 (2H, m), 7.48 (1H, td, J=7.7, 2.0 Hz), 8.07 (2H, d, J=5.1 Hz).

Step 6) 3-cyclopropyl-3-(2-((1-(2-(((1-fluorocyclopropyl)methyl)(pyridin-2-yl)carbamoyl)-5-methoxyphenyl)piperidin-4-yl)methoxy)pyridin-4-yl)propanoic acid In the same manner as in Example 1, step 4, the title compound (73.0 mg) was obtained as a white amorphous powder from ethyl 3-cyclopropyl-3-(2-((1-(2-(((1-fluorocyclopropyl)methyl)(pyridin-2-yl)carbamoyl)-5-methoxyphenyl)piperidin-4-yl)methoxy)pyridin-4-yl)propanoate (77.0 mg).

MS (ESI+): [M+H]$^+$ 603.3.

Example 145

3-cyclopropyl-3-(2-((1-(5-methoxy-2-((2-methylbutan-2-yl)(pyridin-2-yl)carbamoyl)phenyl)piperidin-4-yl)methoxy)pyridin-4-yl)propanoic acid Step 1) N-(tert-pentyl)pyridin-2-amine By a method similar to that in Example 135, step 1, the title compound (79 mg) was obtained as a pale-orange oil from tert-amylamine (344 μl) and pyridine 1-oxide (224.2 mg).

MS (ESI+): [M+H]$^+$ 165.1.

Step 2) 3-cyclopropyl-3-(2-((1-(5-methoxy-2-((2-methylbutan-2-yl)(pyridin-2-yl)carbamoyl)phenyl)piperidin-4-yl)methoxy)pyridin-4-yl)propanoic acid By a method similar to that in Example 32, step 2 and Example 1, step 4, the title compound (90 mg) was obtained as a pale-yellow amorphous powder from 2-(4-(((4-(1-cyclopropyl-3-ethoxy-3-oxopropyl)pyridin-2-yl)oxy)methyl)piperidin-1-yl)-4-methoxybenzoic acid (110.1 mg) and N-(tert-pentyl)pyridin-2-amine (52.2 mg).

MS (ESI+): [M+H]$^+$ 601.3.

Example 146

3-cyclopropyl-3-(2-((1-(5-methoxy-2-(propan-2-yl(pyridin-2-yl)carbamoyl)phenyl)piperidin-4-yl)methoxy)pyridin-4-yl)propanoic acid By a method similar to that in Example 32, step 2 and Example 1, step 4, the title compound (39.0 mg) was obtained as a pale-yellow amorphous powder from 2-(4-(((4-(1-cyclopropyl-3-ethoxy-3-oxopropyl)pyridin-2-yl)oxy)methyl)piperidin-1-yl)-4-methoxybenzoic acid (111.3 mg) and N-(propan-2-yl)pyridin-2-amine (62.8 mg).

MS (ESI+): [M+H]$^+$ 573.4.

Example 147

3-cyclopropyl-3-(2-((1-(2-((2,2-difluoropropyl)(4-methylpyridin-2-yl)carbamoyl)-5-methoxyphenyl)piperidin-4-yl)methoxy)pyridin-4-yl)propanoic acid Step 1)
N-(2,2-difluoropropyl)-4-methylpyridin-2-amine By a method similar to that in Example 135, step 1, the title compound (145 mg) was obtained as a pale-yellow solid from 2,2-difluoropropylamine hydrochloride (306 mg) and 4-methylpyridine 1-oxide (202.8 mg).

MS (ESI+). found: 186.92.

Step 2) 3-cyclopropyl-3-(2-((1-(2-((2,2-difluoropropyl)(4-methylpyridin-2-yl)carbamoyl)-5-methoxyphenyl)piperidin-4-yl)methoxy)pyridin-4-yl)propanoic acid By a method similar to that in Example 32, step 2 and Example 1, step 4, the title compound (90 mg) was obtained as a pale-yellow amorphous powder from 2-(4-(((4-(1-cyclopropyl-3-ethoxy-3-oxopropyl)pyridin-2-yl)oxy)methyl)piperidin-1-yl)-4-methoxybenzoic acid (109.2 mg) and N-(2,2-difluoropropyl)-4-methylpyridin-2-amine (63.2 mg).

MS (ESI+): [M+H]$^+$ 623.3.

Example 148

3-cyclopropyl-3-(2-((1-(5-methoxy-2-((4-methylpyridin-2-yl)(2,2,2-trifluoroethyl)carbamoyl)phenyl)piperidin-4-yl)methoxy)pyridin-4-yl)propanoic acid In the same manner as in Example 32, step 2 and Example 1, step 4, the title compound (128 mg) was obtained as a grayish white amorphous powder from 2-(4-(((4-(1-cyclopropyl-3-ethoxy-3-oxopropyl)pyridin-2-yl)oxy)methyl)piperidin-1-yl)-4-methoxybenzoic acid (145 mg) and 4-methyl-N-(2,2,2-trifluoroethyl)pyridin-2-amine (114 mg).
MS (ESI+): [M+H]$^+$ 627.2.

Example 149

3-cyclopropyl-3-(2-((1-(2-((2,2-dimethylbutyl)(pyridin-2-yl)carbamoyl)-5-methoxyphenyl)piperidin-4-yl)methoxy)pyridin-4-yl)propanoic acid Step 1) N-(2,2-dimethylbutyl)pyridin-2-amine In the same manner as in Example 1, step 1, a pale-yellow oil (540 mg) was obtained from 2,2-dimethylbutanoic acid (1.0 g) and pyridin-2-amine (737 mg) and dissolved in THF (10 mL). Under a nitrogen atmosphere, the solution was added to a suspension of lithium aluminum hydride (208 mg) in THF (5.4 mL) at 0° C., and the mixture was heated under reflux for 1 hr. To the reaction solution were added water and aqueous sodium hydroxide solution, and the resulting white precipitate was removed by filtration. The filtrate was evaporated under reduced pressure, and the residue was purified by silica gel column chromatography (ethyl acetate/hexane) to give the title compound (388 mg) as a pale-yellow oil.
MS (ESI+): [M+H]$^+$ 179.2.

Step 2) 3-cyclopropyl-3-(2-((1-(2-((2,2-dimethylbutyl)(pyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (128 mg) was obtained as a grayish white amorphous powder from 2-(4-(((4-(1-cyclopropyl-3-ethoxy-3-oxopropyl)pyridin-2-yl)oxy)methyl)piperidin-1-yl)-4-methoxybenzoic acid (133 mg) and N-(2,2-dimethylbutyl)pyridin-2-amine (98 mg).
MS (ESI+): [M+H]$^+$ 615.3.

Example 150

3-cyclopropyl-3-(2-((1-(5-methoxy-2-((2-methylpropyl)(3-methylpyridin-2-yl)carbamoyl)phenyl)piperidin-4-yl)methoxy)pyridin-4-yl)propanoic acid In the same manner as in Example 32, step 2 and Example 1, step 4, the title compound (17 mg) was obtained as a grayish white solid from 2-(4-(((4-(1-cyclopropyl-3-ethoxy-3-oxopropyl)pyridin-2-yl)oxy)methyl)piperidin-1-yl)-4-methoxybenzoic acid (131 mg) and 3-methyl-N-(2-methylpropyl)pyridin-2-amine (89 mg).
MS (ESI+): [M+H]$^+$ 601.3.

Example 151

3-(2-((1-(2-(cyclobutyl(pyridin-2-yl)carbamoyl)-5-methoxyphenyl)piperidin-4-yl)methoxy)pyridin-4-yl)-3-cyclopropylpropanoic acid Step 1) N-cyclobutylpyridin-2-amine In the same manner as in Example 135, step 1, the title compound (308 mg) was obtained as a pale-yellow solid from pyridine 1-oxide (250 mg) and cyclobutanamine (234 mg).
MS (ESI+): [M+H]$^+$ 149.1.

Step 2) 3-(2-((1-(2-(cyclobutyl(pyridin-2-yl)carbamoyl)-5-methoxyphenyl)piperidin-4-yl)methoxy)pyridin-4-yl)-3-cyclopropylpropanoic acid In the same manner as in Example 32, step 2 and Example 1, step 4, the title compound (167 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (150 mg) and N-cyclobutylpyridin-2-amine (92 mg).
MS (ESI+): [M+H]$^+$ 585.3.

Example 152

3-cyclopropyl-3-(2-((1-(2-((2-fluoro-2-methylpropyl)(6-methylpyridin-2-yl)carbamoyl)-5-methoxyphenyl)piperidin-4-yl)methoxy)pyridin-4-yl)propanoic acid Step 1) 2-methyl-1-((6-methylpyridin-2-yl)amino)propan-2-ol In the same manner as in Example 135, step 1, the title compound (211 mg) was obtained as a pale-yellow solid from 2-methylpyridine 1-oxide (500 mg) and 1-amino-2-methylpropan-2-ol (531 mg). MS (ESI+): [M+H]$^+$ 181.1.

Step 2) N-(3-fluoro-3-methylbutan-2-yl)-6-methylpyridin-2-amine

In the same manner as in Example 39, step 1, the title compound (81 mg) was obtained as a pale-yellow oil from 2-methyl-1-((6-methylpyridin-2-yl)amino)propan-2-ol (211 mg).
MS (ESI+): [M+H]$^+$ 183.1.

Step 3) 3-cyclopropyl-3-(2-((1-(2-((2-fluoro-2-methylpropyl)(6-methylpyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (85 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (214 mg) and N-(3-fluoro-3-methylbutan-2-yl)-6-methylpyridin-2-amine (81 mg).
MS (ESI+): [M+H]$^+$ 619.4.

Example 153

3-cyclopropyl-3-(2-((1-(2-((2-fluoro-2-methylpropyl)(4-methylpyridin-2-yl)carbamoyl)-5-methoxyphenyl)piperidin-4-yl)methoxy)pyridin-4-yl)propanoic acid Step 1) 2-methyl-1-((4-methylpyridin-2-yl)amino)propan-2-ol In the same manner as in Example 135, step 1, the title compound (850 mg) was obtained as a pale-yellow oil from 4-methylpyridine 1-oxide (600 mg) and 1-amino-2-methylpropan-2-ol (539 mg). $^1$H NMR (300 MHz, CDCl$_3$) δ 1.25

(6H, s), 2.22 (3H, s), 3.34 (2H, d, J=6.0 Hz), 4.75 (1H, brs), 6.24-6.34 (1H, m), 6.42 (1H, dd, J=5.4, 0.8 Hz), 7.87 (1H, d, J=5.4 Hz).

Step 2) N-(2-fluoro-2-methylpropyl)-4-methylpyridin-2-amine

In the same manner as in Example 39, step 1, the title compound (313 mg) was obtained as a pale-yellow solid from 2-methyl-1-((4-methylpyridin-2-yl)amino)propan-2-ol (850 mg). $^1$H NMR (300 MHz, CDCl$_3$) δ 1.41 (6H, d, J=21.4 Hz), 2.22 (3H, s), 3.54 (2H, dd, J=21.2, 6.6 Hz), 4.60 (1H, brs), 6.25 (1H, s), 6.42 (1H, dd, J=5.2, 0.8 Hz), 7.93 (1H, d, J=5.2 Hz).

Step 3) 3-cyclopropyl-3-(2-((1-(2-((2-fluoro-2-methylpropyl)(4-methylpyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (214 mg) was obtained as a colorless amorphous powder from N-(2-fluoro-2-methylpropyl)-4-methylpyridin-2-amine (151 mg) and 2-(4-(((4-(1-cyclopropyl-3-ethoxy-3-oxopropyl)pyridin-2-yl)oxy)methyl)piperidin-1-yl)-4-methoxybenzoic acid (200 mg). MS (ESI+): [M+H]$^+$ 619.3.

Example 154

3-cyclopropyl-3-(2-((1-(2-(((1-fluorocyclobutyl)methyl)(pyridin-2-yl)carbamoyl)-5-methoxyphenyl)piperidin-4-yl)methoxy)pyridin-4-yl)propanoic acid Step 1)
1-((trimethylsilyl)oxy)cyclobutanecarbonitrile Under a nitrogen atmosphere, trimethylsilyl cyanide (6.00 mL) was added to a solution of cyclobutanone (2.10 g) and zinc iodide (479 mg) in THF (30 mL) at room temperature, and the mixture was stirred at room temperature for 4 hr. The reaction solution was filtered through silica gel, and the solvent in the filtrate was evaporated under reduced pressure to give a crude product of the title compound as a red oil. This compound was used for the next step without further purification.

Step 2) 1-(aminomethyl)cyclobutanol

The crude product (entire amount) of 1-((trimethylsilyl)oxy)cyclobutanecarbonitrile was added to a suspension of lithium aluminum hydride (1.14 g) in diethyl ether (30 mL) at 0° C., and the mixture was stirred at room temperature for 3 hr. To the reaction mixture were added water and aqueous sodium hydroxide solution at 0° C., and the resulting white precipitate was removed by filtration. The solvent in the filtrate was evaporated under reduced pressure to give a crude product of the title compound as a white solid.

Step 3) 1-((pyridin-2-ylamino)methyl)cyclobutanol

In the same manner as in Example 135, step 1, the title compound (583 mg) was obtained as a pale-yellow oil from a crude product (entire amount) of 1-(aminomethyl)cyclobutanol and pyridine N-oxide (1.48 g).
$^1$H NMR (300 MHz, DMSO-d$_6$) δ 1.38-1.54 (1H, m), 1.55-1.71 (1H, m), 1.81-2.06 (4H, m), 3.36 (2H, d, J=5.7 Hz), 5.53 (1H, s), 6.35 (1H, t, J=5.5 Hz), 6.45 (1H, ddd, J=7.0, 5.1, 1.0 Hz), 6.57 (1H, dt, J=8.5, 0.9 Hz), 7.34 (1H, ddd, J=8.6, 6.9, 2.0 Hz), 7.78-8.05 (1H, m).

Step 4)
N-((1-fluorocyclobutyl)methyl)pyridin-2-amine

In the same manner as in Example 39, step 1, the title compound (212 mg) was obtained as a white solid from 1-((pyridin-2-ylamino)methyl)cyclobutanol (583 mg).
$^1$H NMR (300 MHz, CDCl$_3$) δ 1.47-1.69 (1H, m), 1.74-1.96 (1H, m), 2.10-2.45 (4H, m), 3.52-3.78 (2H, m), 4.61 (1H, brs), 6.43 (1H, dt, J=8.4, 0.8 Hz), 6.58 (1H, ddd, J=7.1, 5.1, 0.8 Hz), 7.33-7.47 (1H, m), 7.98-8.14 (1H, m).

Step 5) ethyl 3-cyclopropyl-3-(2-((1-(2-(((1-fluorocyclobutyl)methyl)(pyridin-2-yl)carbamoyl)-5-methoxyphenyl)piperidin-4-yl)methoxy)pyridin-4-yl)propanoate In the same manner as in Example 32, step 2, the title compound (125 mg) was obtained as a colorless oil from 2-(4-(((4-(1-cyclopropyl-3-ethoxy-3-oxopropyl)pyridin-2-yl)oxy)methyl)piperidin-1-yl)-4-methoxybenzoic acid (100 mg) and N-((1-fluorocyclobutyl)methyl)pyridin-2-amine (93.0 mg).
$^1$H NMR (400 MHz, CDCl$_3$) δ 0.12-0.22 (1H, m), 0.25-0.35 (1H, m), 0.41-0.51 (1H, m), 0.55-0.66 (1H, m), 0.91-1.07 (1H, m), 1.19 (3H, t, J=7.1 Hz), 1.58-1.91 (6H, m), 2.09-2.77 (6H, m), 2.09-2.26 (2H, m), 2.27-2.36 (1H, m), 2.66-2.80 (2H, m), 3.19-3.54 (1H, m), 3.76 (3H, s), 3.99-4.12 (2H, m), 4.17 (2H, d, J=6.7 Hz), 4.69 (2H, brs), 6.20 (1H, d, J=2.0 Hz), 6.49 (1H, dd, J=8.5, 2.3 Hz), 6.59 (1H, brs), 6.63 (1H, s), 6.76 (1H, dd, J=5.3, 1.3 Hz), 6.88 (1H, dd, J=6.9, 5.1 Hz), 7.19-7.26 (1H, m), 7.32 (1H, d, J=8.4 Hz), 8.07 (1H, d, J=5.3 Hz), 8.34 (1H, dd, J=4.8, 1.3 Hz).

Step 6) 3-cyclopropyl-3-(2-((1-(2-(((1-fluorocyclobutyl)methyl)(pyridin-2-yl)carbamoyl)-5-methoxyphenyl)piperidin-4-yl)methoxy)pyridin-4-yl)propanoic acid In the same manner as in Example 1, step 4, the title compound (102 mg) was obtained as a white amorphous powder from ethyl 3-cyclopropyl-3-(2-((1-(2-(((1-fluorocyclobutyl)methyl)(pyridin-2-yl)carbamoyl)-5-methoxyphenyl)piperidin-4-yl)methoxy)pyridin-4-yl)propanoate (125 mg).
MS (ESI+): [M+H]$^+$ 617.2.

Example 155

3-cyclopropyl-3-(2-((1-(5-methoxy-2-((3-methoxy-2,2-dimethylpropyl)(pyridin-2-yl)carbamoyl)phenyl)piperidin-4-yl)methoxy)pyridin-4-yl)propanoic acid Step 1)
3-methoxy-2,2-dimethyl-N-(pyridin-2-yl)propanamide Under a nitrogen atmosphere, a 1 M solution of triethylaluminum in toluene (22.5 mL) was added to a solution of 2-aminopyridine (1.41 g) and methyl 3-methoxy-2,2-dimethylpropanoate (2.12 mL) in toluene (30 mL) at room temperature, and the mixture was stirred at 100° C. for 2 hr and heated under reflux for 16 hr. To the reaction solution was added methanol and the mixture was diluted with ethyl acetate. The resulting precipitate was removed by filtration.

The solvent in the filtrate was evaporated under reduced pressure, and the residue was purified by silica gel column chromatography (ethyl acetate/hexane) to give the title compound (803 mg) as a pale-yellow oil.

$^1$H NMR (400 MHz, CDCl$_3$) δ 1.27 (6H, s), 3.44 (2H, s), 3.50 (3H, s), 7.00 (1H, ddd, J=7.3, 5.0, 0.9 Hz), 7.62-7.71 (1H, m), 8.22 (1H, d, J=8.4 Hz), 8.26-8.31 (1H, m), 9.25 (1H, brs).

Step 2)
N-(3-methoxy-2,2-dimethylpropyl)pyridin-2-amine

Under a nitrogen atmosphere, 3-methoxy-2,2-dimethyl-N-(pyridin-2-yl)propanamide (803 mg) was added to a suspension of lithium aluminum hydride (439 mg) in THF (15 mL) at room temperature, and the mixture was heated under reflux for 30 min. To the reaction solution were added water and aqueous sodium hydroxide solution at 0° C., and the resulting white precipitate was removed by filtration. The solvent in the filtrate was evaporated under reduced pressure to give the title compound (734 mg) as a colorless oil.

$^1$H NMR (400 MHz, CDCl$_3$) δ 0.98 (6H, s), 3.17-3.21 (2H, m), 3.19 (2H, s), 3.33 (3H, s), 5.02 (1H, brs), 6.40 (1H, d, J=8.5 Hz), 6.46-6.56 (1H, m), 7.38 (1H, ddd, J=8.5, 7.0, 1.9 Hz), 8.05 (1H, dd, J=5.0, 1.1 Hz).

Step 3) ethyl 3-cyclopropyl-3-(2-((1-(5-methoxy-2-((3-methoxy-2,2-dimethylpropyl)(pyridin-2-yl)carbamoyl)phenyl)piperidin-4-yl)methoxy)pyridin-4-yl)propanoate In the same manner as in Example 32, step 2, the title compound (80.6 mg) was obtained as a colorless oil from 2-(4-(((4-(1-cyclopropyl-3-ethoxy-3-oxopropyl)pyridin-2-yl)oxy)methyl)piperidin-1-yl)-4-methoxybenzoic acid (100 mg) and N-(3-methoxy-2,2-dimethylpropyl)pyridin-2-amine (101 mg).

Step 4) 3-cyclopropyl-3-(2-((1-(5-methoxy-2-((3-methoxy-2,2-dimethylpropyl)(pyridin-2-yl)carbamoyl)phenyl)piperidin-4-yl)methoxy)pyridin-4-yl)propanoic acid In the same manner as in Example 1, step 4, the title compound (69.8 mg) was obtained as a white amorphous powder from ethyl 3-cyclopropyl-3-(2-((1-(5-methoxy-2-((3-methoxy-2,2-dimethylpropyl)(pyridin-2-yl)carbamoyl)phenyl)piperidin-4-yl)methoxy)pyridin-4-yl)propanoate (80.6 mg).

MS (ESI+): [M+H]$^+$ 631.3.

Example 156

3-cyclopropyl-3-(2-((1-(2-((2,2-dimethylpropyl)(pyrimidin-2-yl)carbamoyl)-5-methoxyphenyl)piperidin-4-yl)methoxy)pyridin-4-yl)propanoic acid Step 1) ethyl 3-cyclopropyl-3-(2-((1-(2-((2,2-dimethylpropyl)(pyrimidin-2-yl)carbamoyl)-5-methoxyphenyl)piperidin-4-yl)methoxy)pyridin-4-yl)propanoate In the same manner as in Example 32, step 2, the title compound (106 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (100 mg) and N-(2,2-dimethylpropyl)pyrimidin-2-amine (86.0 mg).

$^1$H NMR (400 MHz, CDCl$_3$) δ 0.14-0.21 (1H, m), 0.25-0.34 (1H, m), 0.41-0.52 (1H, m), 0.55-0.66 (1H, m), 0.86 (9H, s), 0.95-1.04 (1H, m), 1.19 (3H, t, J=7.2 Hz), 1.52-1.89 (5H, m), 2.24-2.35 (1H, m), 2.36-2.64 (3H, m), 2.64-2.83 (2H, m), 3.24 (1H, brs), 3.78 (3H, s), 3.99-4.12 (2H, m), 4.15 (2H, d, J=6.5 Hz), 4.27 (2H, d, J=16.3 Hz), 6.14 (1H, d, J=2.4 Hz), 6.55 (1H, dd, J=8.5, 2.2 Hz), 6.63 (1H, s), 6.72-6.86 (2H, m), 7.46 (1H, d, J=8.4 Hz), 8.07 (1H, d, J=5.3 Hz), 8.31 (2H, d, J=4.8 Hz).

Step 2) 3-cyclopropyl-3-(2-((1-(2-((2,2-dimethylpropyl)(pyrimidin-2-yl)carbamoyl)-5-methoxyphenyl)piperidin-4-yl)methoxy)pyridin-4-yl)propanoic acid In the same manner as in Example 1, step 4, the title compound (102 mg) was obtained as a white amorphous powder from ethyl 3-cyclopropyl-3-(2-((1-(2-((2,2-dimethylpropyl)(pyrimidin-2-yl)carbamoyl)-5-methoxyphenyl)piperidin-4-yl)methoxy)pyridin-4-yl)propanoate (106 mg).

MS (ESI+): [M+H]$^+$ 602.3.

Example 157

3-cyclopropyl-3-(2-((1-(2-((2,2-difluoroethyl)(4-methylpyridin-2-yl)carbamoyl)-5-methoxyphenyl)piperidin-4-yl)methoxy)pyridin-4-yl)propanoic acid Step 1)
N-(2,2-difluoroethyl)-4-methylpyridin-2-amine In the same manner as in Example 135, step 1, the title compound (490 mg) was obtained as a colorless oil from 4-methylpyridine 1-oxide (420 mg) and 2,2-difluoroethanamine (343 mg).

$^1$H NMR (300 MHz, CDCl$_3$) δ 2.23 (3H, s), 3.77 (2H, tdd, J=14.5, 6.5, 4.3 Hz), 4.48 (1H, brs), 5.73-6.18 (1H, m), 6.28 (1H, d, J=0.7 Hz), 6.48 (1H, dd, J=5.2, 0.7 Hz), 7.96 (1H, d, J=5.2 Hz).

Step 2) 3-cyclopropyl-3-(2-((1-(2-((2,2-difluoroethyl)(4-methylpyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (145 mg) was obtained as a colorless amorphous powder from N-(2,2-difluoroethyl)-4-methylpyridin-2-amine (128 mg) and 2-(4-(((4-(1-cyclopropyl-3-ethoxy-3-oxopropyl)pyridin-2-yl)oxy)methyl)piperidin-1-yl)-4-methoxybenzoic acid (180 mg).

MS (ESI+): [M+H]$^+$ 609.2.

Example 158

3-(2-((1-(2-((4-cyanopyridin-2-yl)(2-methylpropyl)carbamoyl)-5-methoxyphenyl)piperidin-4-yl)methoxy)pyridin-4-yl)-3-cyclopropylpropanoic acid By a method similar to that in Example 32, step 2 and Example 1, step 4, the title compound (110 mg) was obtained as a yellow solid from 2-(4-(((4-(1-cyclopropyl-3-ethoxy-3-oxopropyl)pyridin-2-yl)oxy)methyl)piperidin-1- yl)-4-methoxybenzoic acid (126.7 mg) and 2-((2-methylpropyl)amino)pyridine-4-carbonitrile (69.0 mg).
MS (ESI+): [M+H]⁺ 612.3.

Example 159

3-cyclopropyl-3-(2-((1-(5-methoxy-2-((3-methylbutyl)(pyridin-2-yl)carbamoyl)phenyl)piperidin-4-yl)methoxy)pyridin-4-yl)propanoic acid By a method similar to that in Example 32, step 2 and Example 1, step 4, the title compound (83 mg) was obtained as a pale-yellow amorphous powder from 2-(4-(((4-(1-cyclopropyl-3-ethoxy-3-oxopropyl)pyridin-2-yl)oxy)methyl)piperidin-1-yl)-4-methoxybenzoic acid (107.2 mg) and N-isopentylpyridin-2-amine (54.7 mg).
MS (ESI+): [M+H]⁺ 601.3.

Example 160

3-cyclopropyl-3-(2-((1-(2-((2-isopropoxy-2-methylpropyl)(pyridin-2-yl)carbamoyl)-5-methoxyphenyl)piperidin-4-yl)methoxy)pyridin-4-yl)propanoic acid Step 1)
N-(1-hydroxy-2-methylpropan-2-yl)benzamide 2-Amino-2-methyl-1-propanol (4.46 g) and benzoyl chloride (8.71 mL) were added to a mixture of potassium carbonate (104 g), water (333 mL) and ethyl acetate (100 mL) at room temperature, and the mixture was stirred at room temperature for 16 hr. The reaction solution was extracted with ethyl acetate. The extract was washed with water and saturated brine, and dried over anhydrous magnesium sulfate. The solvent was evaporated under reduced pressure, and the residue was purified by silica gel column chromatography (NH, ethyl acetate/hexane) to give the title compound (6.08 g) as a white solid.
¹H NMR (400 MHz, DMSO-d₆) δ 1.31 (6H, s), 3.50 (2H, s), 7.38-7.46 (2H, m), 7.47-7.54 (2H, m), 7.78 (2H, d, J=7.0 Hz).

Step 2) 2-(benzylamino)-2-methylpropan-1-ol

Under a nitrogen atmosphere, a solution of N-(1-hydroxy-2-methylpropan-2-yl)benzamide (6.08 g) in THF (50 mL) was added to a suspension of lithium aluminum hydride in THF (50 mL) at room temperature, and the mixture was heated under reflux for 1 hr. To the reaction solution were added water and aqueous sodium hydroxide solution, and the resulting white precipitate was removed by filtration. The solvent in the filtrate was evaporated under reduced pressure to give the title compound (4.5 g) as a white solid.
¹H NMR (400 MHz, DMSO-d₆) δ 1.00 (6H, s), 3.18-3.34 (3H, m), 3.62 (2H, s), 4.55 (1H, brs), 7.10-7.40 (5H, m).

Step 3) 1-benzyl-2,2-dimethylaziridine

Under a nitrogen atmosphere, methanesulfonyl chloride (3.24 mL) was added dropwise to a solution of 2-(benzylamino)-2-methylpropan-1-ol (5.0 g) and triethylamine (11.7 mL) in THF (80 mL) at 0° C., and the mixture was stirred at 0° C. for 30 min. To the reaction solution was added water at 0° C., and the mixture was extracted with ethyl acetate. The extract was washed with water, saturated aqueous sodium hydrogen carbonate solution and saturated brine, and dried over anhydrous magnesium sulfate. The solvent was evaporated under reduced pressure, and the residue was purified by silica gel column chromatography (NH, ethyl acetate/hexane) to give the title compound (3.30 g) as a colorless oil.
¹H NMR (400 MHz, CDCl₃) δ 1.21-1.29 (7H, m), 1.81 (1H, s), 3.65 (2H, s), 7.20-7.25 (1H, m), 7.29-7.40 (4H, m).

Step 4)
N-benzyl-2-isopropoxy-2-methylpropan-1-amine

Under a nitrogen atmosphere, boron trifluoride diethyl ether complex (432 µL) was added to a solution of 1-benzyl-2,2-dimethylaziridine (500 mg) in isopropylalcohol (20 mL) at room temperature, and the mixture was heated under reflux for 30 min. To the reaction solution was added saturated aqueous sodium hydrogen carbonate solution at room temperature, and the mixture was extracted with ethyl acetate. The extract was washed with water, saturated aqueous sodium hydrogen carbonate solution and saturated brine, and dried over anhydrous magnesium sulfate. The solvent was evaporated under reduced pressure, and the obtained residual solid was washed with diisopropyl ether to give the title compound (442 mg) as a white solid.
¹H NMR (400 MHz, CDCl₃) δ 1.09 (6H, d, J=6.0 Hz), 1.20 (6H, s), 2.53 (2H, s), 3.73-3.80 (1H, m), 3.81 (2H, s), 7.19-7.41 (5H, m).

Step 5) 2-isopropoxy-2-methylpropan-1-amine

N-Benzyl-2-isopropoxy-2-methylpropan-1-amine (400 mg) and palladium hydroxide (200 mg) were stirred in methanol (15 mL) at room temperature for 1 hr under a hydrogen atmosphere (1 atm). The reaction mixture was filtered, and the solvent in the filtrate was evaporated under reduced pressure to give a crude product of the title compound as a pale-yellow oil. This compound was used for the next step without further purification.

Step 6)
N-(2-isopropoxy-2-methylpropyl)pyridin-2-amine

In the same manner as in Example 135, step 1, the title compound (95.4 mg) was obtained as a pale-orange oil from a crude product (entire amount) of 2-isopropoxy-2-methylpropan-1-amine and pyridine N-oxide (286 mg).
¹H NMR (400 MHz, CDCl₃) δ 1.14 (6H, d, J=6.1 Hz), 1.25 (6H, s), 3.27 (2H, d, J=5.3 Hz), 3.83 (1H, spt, J=6.1 Hz), 4.79 (1H, brs), 6.39 (1H, d, J=8.3 Hz), 6.49-6.56 (1H, m), 7.34-7.42 (1H, m), 8.07 (1H, d, J=4.5 Hz).

Step 7) ethyl 3-cyclopropyl-3-(2-((1-(2-((2-isopropoxy-2-methylpropyl)(pyridin-2-yl)carbamoyl)-5-methoxyphenyl)piperidin-4-yl)methoxy)pyridin-4-yl)propanoate In the same manner as in Example 32, step 2, the title compound (111 mg) was obtained as a colorless oil from 2-(4-(((4-(1-cyclopropyl-3-ethoxy-3-oxopropyl)pyridin-2-yl)oxy)methyl)piperidin-1-yl)-4-methoxybenzoic acid (100 mg) and N-(2-isopropoxy-2-methylpropyl)pyridin-2-amine (95.4 mg).
¹H NMR (400 MHz, CDCl₃) δ 0.10-0.21 (1H, m), 0.24-0.34 (1H, m), 0.41-0.52 (1H, m), 0.55-0.65 (1H, m), 0.78 (6H, brs), 0.92-1.05 (2H, m), 1.05-1.30 (6H, m), 1.19 (3H, t, J=7.2 Hz), 1.31-1.91 (4H, m), 2.24-2.35 (1H, m), 2.36-2.70 (3H, m), 2.66-2.79 (2H, m), 3.41 (1H, brs), 3.69 (1H, spt, J=6.1 Hz), 3.74 (3H, s), 4.01-4.11 (2H, m), 4.16 (2H, d, J=6.5 Hz), 4.36 (2H, brs), 6.19 (1H, brs), 6.46 (1H, dd, J=8.3, 2.1 Hz), 6.52-6.66 (1H, m), 6.63 (1H, s), 6.76 (1H, d, J=5.4 Hz), 6.81-6.88 (1H, m), 7.20 (1H, brs), 7.24-7.33 (1H, m), 8.07 (1H, d, J=5.3 Hz), 8.31 (1H, d, J=3.3 Hz).

Step 8) 3-cyclopropyl-3-(2-((1-(2-((2-isopropoxy-2-methylpropyl)(pyridin-2-yl)carbamoyl)-5-methoxyphenyl)piperidin-4-yl)methoxy)pyridin-4-yl)propanoic acid In the same manner as in Example 1, step 4, the title compound (99.1 mg) was obtained as a white amorphous powder from ethyl 3-cyclopropyl-3-(2-((1-(2-((2-isopropoxy-2-methylpropyl)(pyridin-2-yl)carbamoyl)-5-methoxyphenyl)piperidin-4-yl)methoxy)pyridin-4-yl)propanoate (111 mg).
MS (ESI+): [M+H]$^+$ 645.4.

Example 161

3-cyclopropyl-3-(2-((1-(5-methoxy-2-((2-methyl-2-(2,2,2-trifluoroethoxy)propyl)(pyridin-2-yl)carbamoyl)phenyl)piperidin-4-yl)methoxy)pyridin-4-yl)propanoic acid Step 1) N-benzyl-2-methyl-2-(2,2,2-trifluoroethoxy)propan-1-amine In the same manner as in Example 160, step 4, the title compound (446 mg) was obtained as a colorless oil from 1-benzyl-2,2-dimethylaziridine (500 mg) obtained in Example 160, step 3 and trifluoroethanol (20 mL).
$^1$H NMR (400 MHz, CDCl$_3$) δ 1.23 (6H, s), 2.59 (2H, s), 3.70 (2H, q, J=8.7 Hz), 3.82 (2H, s), 7.29-7.41 (5H, m).

Step 2) 2-methyl-2-(2,2,2-trifluoroethoxy)propan-1-amine

In the same manner as in Example 160, step 5, a crude product of the title compound was obtained as a pale-yellow oil from N-benzyl-2-methyl-2-(2,2,2-trifluoroethoxy)propan-1-amine (446 mg). This compound was used for the next step without further purification.

Step 3) N-(2-methyl-2-(2,2,2-trifluoroethoxy)propyl)pyridin-2-amine

In the same manner as in Example 135, step 1, the title compound (55.6 mg) was obtained as a pale-orange oil from a crude product (entire amount) of 2-methyl-2-(2,2,2-trifluoroethoxy)propan-1-amine and pyridine N-oxide (231 mg).
$^1$H NMR (400 MHz, CDCl$_3$) δ 1.28 (6H, s), 3.43 (2H, d, J=5.6 Hz), 3.76 (2H, q, J=8.5 Hz), 4.68 (1H, brs), 6.42 (1H, d, J=8.4 Hz), 6.53-6.59 (1H, m), 7.35-7.42 (1H, m), 8.07 (1H, d, J=3.8 Hz).

Step 4) ethyl 3-cyclopropyl-3-(2-((1-(5-methoxy-2-((2-methyl-2-(2,2,2-trifluoroethoxy)propyl)(pyridin-2-yl)carbamoyl)phenyl)piperidin-4-yl)methoxy)pyridin-4-yl)propanoate In the same manner as in Example 32, step 2, the title compound (72.0 mg) was obtained as a colorless oil from 2-(4-(((4-(1-cyclopropyl-3-ethoxy-3-oxopropyl)pyridin-2-yl)oxy)methyl)piperidin-1-yl)-4-methoxybenzoic acid (100 mg) and N-(2-isopropoxy-2-methylpropyl)pyridin-2-amine (55.6 mg).
$^1$H NMR (400 MHz, CDCl$_3$) δ 0.13-0.22 (1H, m), 0.23-0.35 (1H, m), 0.40-0.52 (1H, m), 0.55-0.65 (1H, m), 0.92-1.05 (1H, m), 1.19 (3H, t, J=7.1 Hz), 1.26 (6H, s), 1.58-1.96 (3H, m), 2.24-2.35 (1H, m), 2.36-2.76 (3H, m), 2.66-2.81 (2H, m), 3.18-3.63 (3H, m), 3.75 (3H, s), 4.00-4.17 (4H, m), 4.16 (2H, d, J=6.5 Hz), 4.27-4.57 (2H, m), 6.19 (1H, s), 6.48 (1H, dd, J=8.4, 2.3 Hz), 6.53 (1H, brs), 6.63 (1H, s), 6.74-6.79 (1H, m), 6.83-6.90 (1H, m), 7.19 (1H, t, J=7.2 Hz), 7.25-7.31 (1H, m), 8.07 (1H, d, J=5.3 Hz), 8.32 (1H, d, J=3.4 Hz).

Step 5) 3-cyclopropyl-3-(2-((1-(5-methoxy-2-((2-methyl-2-(2,2,2-trifluoroethoxy)propyl)(pyridin-2-yl)carbamoyl)phenyl)piperidin-4-yl)methoxy)pyridin-4-yl)propanoic acid In the same manner as in Example 1, step 4, the title compound (62.8 mg) was obtained as a white amorphous powder from ethyl 3-cyclopropyl-3-(2-((1-(5-methoxy-2-((2-methyl-2-(2,2,2-trifluoroethoxy)propyl)(pyridin-2-yl)carbamoyl)phenyl)piperidin-4-yl)methoxy)pyridin-4-yl)propanoate (72 mg).
MS (ESI+): [M+H]$^+$ 685.4.

Example 162

3-cyclopropyl-3-(2-((1-(2-(((3,3-difluorocyclobutyl)methyl)(pyridin-2-yl)carbamoyl)-5-methoxyphenyl)piperidin-4-yl)methoxy)pyridin-4-yl)propanoic acid Step 1) N-((3,3-difluorocyclobutyl)methyl)pyridin-2-amine In the same manner as in Example 135, step 1, the title compound (215 mg) was obtained as a pale-yellow oil from pyridine 1-oxide (150 mg) and 1-(3,3-difluorocyclobutyl)methanamine hydrochloride (311 mg).
MS (ESI+): [M+H]$^+$ 199.0.

Step 2) 3-cyclopropyl-3-(2-((1-(2-(((3,3-difluorocyclobutyl)methyl)(pyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (73 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (134 mg) and N-((3,3-difluorocyclobutyl)methyl)pyridin-2-amine (110 mg).
MS (ESI+): [M+H]$^+$ 635.3.

Example 163

3-cyclopropyl-3-(2-((1-(5-methoxy-2-((2-methylpyridin-4-yl)(2,2,2-trifluoroethyl)carbamoyl)phenyl)piperidin-4-yl)methoxy)pyridin-4-yl)propanoic acid Step 1) 2-methyl-N-(2,2,2-trifluoroethyl)pyridin-4-amine In the same manner as in Example 32, step 1, the title compound (1.43 g) was obtained as a grayish white solid from 2-methylpyridin-4-amine (1.00 g) and trifluoroacetic anhydride (1.57 mL).
MS (ESI+): [M+H]+ 191.0.

Step 2) 3-cyclopropyl-3-(2-((1-(5-methoxy-2-((2-methylpyridin-4-yl)(2,2,2-trifluoroethyl)carbamoyl)phenyl)piperidin-4-yl)methoxy)pyridin-4-yl)propanoic acid In the same manner as in Example 32, step 2 and Example 1, step 4, the title compound (69 mg) was obtained as a grayish white amorphous powder from 2-(4-(((4-(1-cyclopropyl-3-ethoxy-3-oxopropyl)pyridin-2-yl)oxy)methyl)piperidin-1-yl)-4-methoxybenzoic acid (100 mg) and 2-methyl-N-(2,2,2-trifluoroethyl)pyridin-4-amine (79 mg).
MS (ESI+): [M+H]+ 627.2.

Example 164

3-cyclopropyl-3-(2-((1-(5-methoxy-2-((2-methoxy-2-methylpropyl)(4-methylpyridin-2-yl)carbamoyl)phenyl)piperidin-4-yl)methoxy)pyridin-4-yl)propanoic acid Step 1) N-(2-methoxy-2-methylpropyl)-4-methylpyridin-2-amine In the same manner as in Example 135, step 1, the title compound (130 mg) was obtained as a pale-yellow oil from 2-methoxy-2-methylpropan-1-amine hydrochloride (130 mg) and 4-methylpyridine 1-oxide (92 mg).
MS (ESI+): [M+H]+ 195.2.

Step 2) 3-cyclopropyl-3-(2-((1-(5-methoxy-2-((2-methoxy-2-methylpropyl)(4-methylpyridin-2-yl)carbamoyl)phenyl)piperidin-4-yl)methoxy)pyridin-4-yl)propanoic acid In the same manner as in Example 32, step 2 and Example 1, step 4, the title compound (117 mg) was obtained as a grayish white amorphous powder from 2-(4-(((4-(1-cyclopropyl-3-ethoxy-3-oxopropyl)pyridin-2-yl)oxy)methyl)piperidin-1-yl)-4-methoxybenzoic acid (140 mg) and N-(2-methoxy-2-methylpropyl)-4-methylpyridin-2-amine (113 mg).
MS (ESI+): [M+H]+ 631.4.

Example 165

3-cyclopropyl-3-(2-((1-(2-((3,3-difluorocyclobutyl)(pyridin-2-yl)carbamoyl)-5-methoxyphenyl)piperidin-4-yl)methoxy)pyridin-4-yl)propanoic acid Step 1) N-(3,3-difluorocyclobutyl)pyridin-2-amine In the same manner as in Example 135, step 1, the title compound (85 mg) was obtained as a pale-yellow solid from pyridine 1-oxide (66.2 mg) and 3,3-difluorocyclobutanamine hydrochloride (100 mg).
MS (ESI+): [M+H]+ 185.0.

Step 2) 3-cyclopropyl-3-(2-((1-(2-((3,3-difluorocyclobutyl)(pyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (124 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (150 mg) and N-(3,3-difluorocyclobutyl)pyridin-2-amine (85 mg).
MS (ESI+): [M+H]+ 621.3.

Example 166

3-cyclopropyl-3-(2-((1-(5-methoxy-2-(pyrimidin-2-yl(2,2,2-trifluoroethyl)carbamoyl)phenyl)piperidin-4-yl)methoxy)pyridin-4-yl)propanoic acid Step 1) N-(2,2,2-trifluoroethyl)pyrimidin-2-amine In the same manner as in Example 45, step 8, the title compound (513 mg) was obtained as a pale-yellow oil from 2,2,2-trifluoroethylamine (834 μL).
$^1$H NMR (400 MHz, CDCl$_3$) δ 4.18 (2H, qd, J=9.0, 6.9 Hz), 5.32 (1H, brs), 6.67 (1H, t, J=4.8 Hz), 8.33 (2H, d, J=4.8 Hz).

Step 2) ethyl 3-cyclopropyl-3-(2-((1-(5-methoxy-2-(pyrimidin-2-yl(2,2,2-trifluoroethyl)carbamoyl)phenyl)piperidin-4-yl)methoxy)pyridin-4-yl)propanoate In the same manner as in Example 32, step 2, the title compound (75.5 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (112 mg) and N-(2,2,2-trifluoroethyl)pyrimidin-2-amine (168 mg).
$^1$H NMR (400 MHz, CDCl$_3$) δ 0.11-0.20 (1H, m), 0.26-0.36 (1H, m), 0.41-0.52 (1H, m), 0.55-0.68 (1H, m), 0.88-1.06 (1H, m), 1.13-1.42 (3H, m), 1.19 (3H, t, J=7.1 Hz), 1.65-1.86 (3H, m), 2.26-2.37 (1H, m), 2.51 (2H, brs), 2.63-2.82 (3H, m), 3.80 (3H, s), 4.07 (2H, qd, J=7.2, 3.9 Hz), 4.13 (2H, d, J=6.5 Hz), 4.90-5.17 (2H, m), 6.21 (1H, d, J=2.4 Hz), 6.58 (1H, dd, J=8.5, 2.3 Hz), 6.63 (1H, s), 6.77 (1H, d, J=5.3 Hz), 6.89 (1H, t, J=4.8 Hz), 7.51 (1H, d, J=8.5 Hz), 8.07 (1H, d, J=5.3 Hz), 8.36 (2H, d, J=4.8 Hz).

Step 3) 3-cyclopropyl-3-(2-((1-(5-methoxy-2-(pyrimidin-2-yl(2,2,2-trifluoroethyl)carbamoyl)phenyl)piperidin-4-yl)methoxy)pyridin-4-yl)propanoic acid In the same manner as in Example 1, step 4, the title compound (71.4 mg) was obtained as a white amorphous powder from ethyl 3-cyclopropyl-3-(2-((1-(5-methoxy-2-(pyrimidin-2-yl(2,2,2-trifluoroethyl)carbamoyl)phenyl)piperidin-4-yl)methoxy)pyridin-4-yl)propanoate (75.5 mg).
MS (ESI+): [M+H]+ 614.2.

Example 167

3-cyclopropyl-3-(2-((1-(2-((2,2-difluoroethyl)(pyrimidin-2-yl)carbamoyl)-5-methoxyphenyl)piperidin-4-yl)methoxy)pyridin-4-yl)propanoic acid Step 1) N-(2,2-difluoroethyl)pyrimidin-2-amine In the same manner as in Example 45, step 8, the title compound (574 mg) was obtained as a yellow solid from 2,2-difluoroethylamine (849 μL).
$^1$H NMR (400 MHz, CDCl$_3$) δ 3.83 (2H, tdd, J=14.4, 6.5, 4.3 Hz), 5.36 (1H, brs), 5.71-6.18 (1H, m), 6.63 (1H, t, J=4.8 Hz), 8.31 (2H, d, J=4.8 Hz).

Step 2) ethyl 3-cyclopropyl-3-(2-((1-(2-((2,2-difluoroethyl)(pyrimidin-2-yl)carbamoyl)-5-methoxyphenyl)piperidin-4-yl)methoxy)pyridin-4-yl)propanoate In the same manner as in Example 32, step 2, the title compound (108 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (112 mg) and N-(2,2-difluoroethyl)pyrimidin-2-amine (135 mg).

$^1$H NMR (400 MHz, CDCl$_3$) δ 0.12-0.21 (1H, m), 0.25-0.34 (1H, m), 0.41-0.51 (1H, m), 0.56-0.65 (1H, m), 0.92-1.06 (1H, m), 1.15-1.44 (2H, m), 1.16-1.22 (3H, m), 1.62-1.84 (3H, m), 2.26-2.36 (1H, m), 2.50 (2H, t, J=11.5 Hz), 2.61-3.18 (2H, m), 2.65-2.80 (2H, m), 3.80 (3H, s), 4.03-4.11 (2H, m), 4.12 (2H, d, J=6.5 Hz), 4.38-4.93 (2H, m), 6.09-6.44 (1H, m), 6.22 (1H, d, J=2.3 Hz), 6.59 (1H, dd, J=8.5, 2.3 Hz), 6.63 (1H, s), 6.77 (1H, d, J=5.3 Hz), 6.87 (1H, t, J=4.8 Hz), 7.54 (1H, d, J=8.5 Hz), 8.07 (1H, d, J=5.3 Hz), 8.35 (2H, d, J=4.8 Hz).

Step 3) 3-cyclopropyl-3-(2-((1-(2-((2,2-difluoroethyl)(pyrimidin-2-yl)carbamoyl)-5-methoxyphenyl)piperidin-4-yl)methoxy)pyridin-4-yl)propanoic acid In the same manner as in Example 1, step 4, the title compound (101 mg) was obtained as a white amorphous powder from ethyl 3-cyclopropyl-3-(2-((1-(2-((2,2-difluoroethyl)(pyrimidin-2-yl)carbamoyl)-5-methoxyphenyl)piperidin-4-yl)methoxy)pyridin-4-yl)propanoate (108 mg).

MS (ESI+): [M+H]$^+$ 596.2.

Example 168

3-cyclopropyl-3-(2-((1-(2-((4,6-dimethylpyrimidin-2-yl)(2,2,2-trifluoroethyl)carbamoyl)-5-methoxyphenyl)piperidin-4-yl)methoxy)pyridin-4-yl)propanoic acid Step 1) 4,6-dimethyl-N-(2,2,2-trifluoroethyl)pyrimidin-2-amine In the same manner as in Example 45, step 8, a crude product of the title compound (1.44 g) was obtained as a pale-yellow oil from 2-chloro-4,6-dimethylpyrimidine (1.00 g). This compound was used for the next step without further purification.

MS (ESI+): [M+H]$^+$ 206.1.

Step 2) 3-cyclopropyl-3-(2-((1-(2-((4,6-dimethylpyrimidin-2-yl)(2,2,2-trifluoroethyl)carbamoyl)-5-methoxyphenyl)piperidin-4-yl)methoxy)pyridin-4-yl)propanoic acid In the same manner as in Example 32, step 2 and Example 1, step 4, the title compound (68 mg) was obtained as a white amorphous powder from 4,6-dimethyl-N-(2,2,2-trifluoroethyl)pyrimidin-2-amine (145 mg) and 2-(4-(((4-(1-cyclopropyl-3-ethoxy-3-oxopropyl)pyridin-2-yl)oxy)methyl)piperidin-1-yl)-4-methoxybenzoic acid (170 mg).

MS (ESI+): [M+H]$^+$ 642.3.

Example 169

3-cyclopropyl-3-(2-((1-(5-methoxy-2-((4-methylpyrimidin-2-yl)(2,2,2-trifluoroethyl)carbamoyl)phenyl)piperidin-4-yl)methoxy)pyridin-4-yl)propanoic acid Step 1) 4-methyl-N-(2,2,2-trifluoroethyl)pyrimidin-2-amine In the same manner as in Example 45, step 8, a crude product of the title compound (494 mg) was obtained as a pale-yellow solid from 2-chloro-4-methylpyrimidine (500 mg). This compound was used for the next step without further purification.

MS (ESI+): [M+H]$^+$ 192.0.

Step 2) 3-cyclopropyl-3-(2-((1-(5-methoxy-2-((4-methylpyrimidin-2-yl)(2,2,2-trifluoroethyl)carbamoyl)phenyl)piperidin-4-yl)methoxy)pyridin-4-yl)propanoic acid In the same manner as in Example 32, step 2 and Example 1, step 4, the title compound (75.4 mg) was obtained as a pale-yellow amorphous powder from 2-(4-(((4-(1-cyclopropyl-3-ethoxy-3-oxopropyl)pyridin-2-yl)oxy)methyl)piperidin-1-yl)-4-methoxybenzoic acid (170 mg) and 4-methyl-N-(2,2,2-trifluoroethyl)pyrimidin-2-amine (135 mg).

MS (ESI+): [M+H]$^+$ 628.3.

Example 170

3-cyclopropyl-3-(2-((1-(5-methoxy-2-((2,2,3,3,3-pentafluoropropyl)(pyrimidin-2-yl)carbamoyl)phenyl)piperidin-4-yl)methoxy)pyridin-4-yl)propanoic acid Step 1) N-(2,2,3,3,3-pentafluoropropyl)pyrimidin-2-amine In a sealed tube, a mixture of 2-chloropyrimidine (120 mg), 2,2,3,3,3-pentafluoropropan-1-amine (234 mg) and diisopropylethylamine (0.2 mL) was stirred at 120° C. for 4 hr. To the reaction mixture was added water at room temperature, and the mixture was extracted with ethyl acetate. The extract was washed with saturated brine, dried over anhydrous magnesium sulfate, and the solvent was evaporated under reduced pressure. The residue was purified by silica gel column chromatography (ethyl acetate/hexane) to give the title compound (100 mg) as a mixture with 2-chloropyrimidine. This compound was used for the next step without further purification.

$^1$H NMR (300 MHz, CDCl$_3$) δ 4.17-4.32 (2H, m), 5.29 (1H, brs), 6.67 (1H, t, J=4.9 Hz), 8.33 (2H, d, J=4.8 Hz).

Step 2) 3-cyclopropyl-3-(2-((1-(5-methoxy-2-((2,2,3,3,3-pentafluoropropyl)(pyrimidin-2-yl)carbamoyl)phenyl)piperidin-4-yl)methoxy)pyridin-4-yl)propanoic acid In the same manner as in Example 32, step 2 and Example 1, step 4, the title compound (10 mg) was obtained as a colorless amorphous powder from a crude purified product (100 mg) of N-(2,2,3,3,3-pentafluoropropyl)pyrimidin-2- amine and 2-(4-(((4-(1-cyclopropyl-3-ethoxy-3-oxopropyl)pyridin-2-yl)oxy)methyl)piperidin-1-yl)-4-methoxybenzoic acid (130 mg).
MS (ESI+): [M+H]$^+$ 664.2.

Example 171

3-cyclopropyl-3-(2-((1-(5-methoxy-2-((4-methylpyrimidin-2-yl)(2,2,3,3,3-pentafluoropropyl)carbamoyl)phenyl)piperidin-4-yl)methoxy)pyridin-4-yl)propanoic acid Step 1) 4-methyl-N-(2,2,3,3,3-pentafluoropropyl)pyrimidin-2-amine In the same manner as in Example 170, step 1, the title compound (80 mg) was obtained as a mixture with 2-chloro-4-methylpyrimidine from 2-chloro-4-methylpyrimidine (750 mg) and 2,2,3,3,3-pentafluoropropan-1-amine (870 mg). This compound was used for the next step without further purification.
$^1$H NMR (300 MHz, CDCl$_3$) δ 2.36 (3H, s), 4.24 (2H, tdd, J=14.9, 6.7, 0.9 Hz), 5.24 (1H, brs), 6.54 (1H, d, J=5.0 Hz), 8.18 (1H, d, J=5.0 Hz).

Step 2) 3-cyclopropyl-3-(2-((1-(5-methoxy-2-((4-methylpyrimidin-2-yl)(2,2,3,3,3-pentafluoropropyl)carbamoyl)phenyl)piperidin-4-yl)methoxy)pyridin-4-yl)propanoic acid In the same manner as in Example 32, step 2 and Example 1, step 4, the title compound (58 mg) was obtained as a colorless amorphous powder from a crude purified product (80 mg) of 4-methyl-N-(2,2,3,3,3-pentafluoropropyl)pyrimidin-2-amine and 2-(4-(((4-(1-cyclopropyl-3-ethoxy-3-oxopropyl)pyridin-2-yl)oxy)methyl)piperidin-1-yl)-4-methoxybenzoic acid (135 mg).
MS (ESI+): [M+H]$^+$ 678.3.

Example 172

3-cyclopropyl-3-(2-((1-(2-((2,2-difluoroethyl)(4-methylpyrimidin-2-yl)carbamoyl)-5-methoxyphenyl)piperidin-4-yl)methoxy)pyridin-4-yl)propanoic acid Step 1)
N-(2,2-difluoroethyl)-4-methylpyrimidin-2-amine In the same manner as in Example 45, step 8, the title compound (227 mg) was obtained as a white solid from 2-chloro-4-methylpyrimidine and 2,2-difluoroethanamine.
MS (ESI+): [M+H]$^+$ 174.0.

Step 2) 3-cyclopropyl-3-(2-((1-(2-((2,2-difluoroethyl)(4-methylpyrimidin-2-yl)carbamoyl)-5-methoxyphenyl)piperidin-4-yl)methoxy)pyridin-4-yl)propanoic acid In the same manner as in Example 32, step 2 and Example 1, step 4, the title compound (73 mg) was obtained as a grayish white amorphous powder from 2-(4-(((4-(1-cyclopropyl-3-ethoxy-3-oxopropyl)pyridin-2-yl)oxy)methyl)piperidin-1-yl)-4-methoxybenzoic acid (115 mg) and N-(2,2-difluoroethyl)-4-methylpyrimidin-2-amine (83 mg).
MS (ESI+): [M+H]$^+$ 610.2.

Example 173

3-cyclopropyl-3-(2-((1-(2-((2,2-dimethylpropyl)(4-methylpyrimidin-2-yl)carbamoyl)-5-methoxyphenyl)piperidin-4-yl)methoxy)pyridin-4-yl)propanoic acid By a method similar to that in Example 32, step 2 and Example 1, step 4, the title compound (15.1 mg) was obtained as a pale-orange amorphous powder from 2-(4-(((4-(1-cyclopropyl-3-ethoxy-3-oxopropyl)pyridin-2-yl)oxy)methyl)piperidin-1-yl)-4-methoxybenzoic acid (100 mg) and N-(2,2-dimethylpropyl)-4-methylpyrimidin-2-amine (74.3 mg).
MS (ESI+): [M+H]$^+$ 616.3.

Example 174

3-cyclopropyl-3-(2-((1-(2-((2,2-dimethylpropyl)(4,6-dimethylpyrimidin-2-yl)carbamoyl)-5-methoxyphenyl)piperidin-4-yl)methoxy)pyridin-4-yl)propanoic acid Step 1) N-(2,2-dimethylpropyl)-4,6-dimethylpyrimidin-2-amine In the same manner as in Example 45, step 1, the title compound (737 mg) was obtained as a yellow solid from 2-chloro-4,6-dimethylpyrimidine (600 mg) and 2,2-dimethylpropan-1-amine (990 μL).

Step 2) 3-cyclopropyl-3-(2-((1-(2-((2,2-dimethylpropyl)(4,6-dimethylpyrimidin-2-yl)carbamoyl)-5-methoxyphenyl)piperidin-4-yl)methoxy)pyridin-4-yl)propanoic acid In the same manner as in Example 32, step 2 and Example 1, step 4, the title compound (274 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (355 mg) and N-(2,2-dimethylpropyl)-4,6-dimethylpyrimidin-2-amine (284 mg).
MS (ESI+): [M+H]$^+$ 630.4.

Example 175

3-cyclopropyl-3-(2-((1-(5-methoxy-2-((5-methylpyridin-3-yl)(2,2,2-trifluoroethyl)carbamoyl)phenyl)piperidin-4-yl)methoxy)pyridin-4-yl)propanoic acid Step 1)
5-methyl-N-(2,2,2-trifluoroethyl)pyridin-3-amine In the same manner as in Example 32, step 1, the title compound (798 mg) was obtained as a white solid from 5-methylpyridin-3-amine (500 mg).
MS (ESI+): [M+H]$^+$ 191.0.

Step 2) 3-cyclopropyl-3-(2-((1-(5-methoxy-2-((5-methylpyridin-3-yl)(2,2,2-trifluoroethyl)carbamoyl)phenyl)piperidin-4-yl)methoxy)pyridin-4-yl)propanoic acid In the same manner as in Example 32, step 2 and Example 1, step 4, the title compound (59.2 mg) was obtained as a pale-yellow amorphous powder from 2-(4-(((4-(1-cyclopropyl-3-ethoxy-3-oxopropyl)pyridin-2-yl)oxy)methyl)piperidin-1-yl)-4-methoxybenzoic acid (350 mg) and 5-methyl-N-(2,2,2-trifluoroethyl)pyridin-3-amine (69 mg).
MS (ESI+): [M+H]$^+$ 625.3.

Example 176

3-cyclopropyl-3-(2-((1-(5-methoxy-2-((2,2,2-trifluoroethyl)(4-(trifluoromethyl)pyridin-2-yl)carbamoyl)phenyl)piperidin-4-yl)methoxy)pyridin-4-yl)propanoic acid By a method similar to that in Example 32, step 2 and Example 1, step 4, the title compound (45 mg) was obtained as a pale-yellow amorphous powder from 2-(4-(((4-(1-cyclopropyl-3-ethoxy-3-oxopropyl)pyridin-2-yl)oxy)methyl)piperidin-1-yl)-4-methoxybenzoic acid (100 mg) and N-(2,2,2-trifluoroethyl)-4-(trifluoromethyl)pyridin-2-amine (101 mg).
MS (ESI+): [M+H]$^+$ 681.2.

Example 177

3-cyclopropyl-3-(2-((1-(5-methoxy-2-((2-methyl-2-((2,2,2-trifluoroethyl)amino)propyl)(pyridin-2-yl)carbamoyl)phenyl)piperidin-4-yl)methoxy)pyridin-4-yl)propanoic acid Step 1)
2-methyl-N1-(pyridin-2-yl)propane-1,2-diamine In the same manner as in Example 135, step 1, the title compound (547 mg) was obtained as a yellow oil from 2-methylpropane-1,2-diamine (300 mg) and pyridine N-oxide (417 mg).
$^1$H NMR (400 MHz, CDCl$_3$) δ 1.18 (6H, s), 3.21 (2H, d, J=6.0 Hz), 4.86 (1H, brs), 6.43 (1H, d, J=8.4 Hz), 6.54 (1H, dd, J=6.6, 5.5 Hz), 7.33-7.44 (1H, m), 8.07 (1H, d, J=4.0 Hz).

Step 2) 2-methyl-N1-(pyridin-2-yl)-N2-(2,2,2-trifluoroethyl)propane-1,2-diamine

Trifluoromethanesulfonic acid 2,2,2-trifluoroethyl ester (196 μL) was added to a mixture of 2-methyl-N1-(pyridin-2-yl)propane-1,2-diamine (500 mg), cesium carbonate (532 mg) and DMF (3 mL) at room temperature, and the mixture was stirred at room temperature for 64 hr. To the reaction solution was added water at room temperature, and the mixture was extracted with ethyl acetate. The extract was washed with water, saturated aqueous sodium hydrogen carbonate solution and saturated brine, and dried over anhydrous magnesium sulfate. The solvent was evaporated under reduced pressure, and the residue was purified by silica gel column chromatography (ethyl acetate/hexane) to give the title compound (225 mg) as a colorless oil.
$^1$H NMR (400 MHz, CDCl$_3$) δ 1.17 (6H, s), 3.12 (2H, q, J=9.3 Hz), 3.24 (2H, d, J=5.4 Hz), 4.87 (1H, brs), 6.42 (1H, d, J=8.4 Hz), 6.55 (1H, dd, J=6.7, 5.5 Hz), 7.33-7.45 (1H, m), 8.08 (1H, d, J=4.0 Hz).

Step 3) ethyl 3-cyclopropyl-3-(2-((1-(5-methoxy-2-((2-methyl-2-((2,2,2-trifluoroethyl)amino)propyl)(pyridin-2-yl)carbamoyl)phenyl)piperidin-4-yl)methoxy)pyridin-4-yl)propanoate In the same manner as in Example 32, step 2, the title compound (108 mg) was obtained as a colorless amorphous powder from 2-(4-(((4-(1-cyclopropyl-3-ethoxy-3-oxopropyl)pyridin-2-yl)oxy)methyl)piperidin-1-yl)-4-methoxybenzoic acid (100 mg) and 2-methyl-N1-(pyridin-2-yl)-N2-(2,2,2-trifluoroethyl)propane-1,2-diamine (77 mg).
$^1$H NMR (400 MHz, CDCl$_3$) δ 0.13-0.22 (1H, m), 0.25-0.35 (1H, m), 0.42-0.52 (1H, m), 0.56-0.66 (1H, m), 0.91-1.15 (7H, m), 1.19 (3H, t, J=7.1 Hz), 1.23-1.46 (2H, m), 1.66-1.91 (3H, m), 2.26-2.35 (1H, m), 2.35-2.69 (3H, m), 2.66-2.80 (2H, m), 2.86-3.21 (2H, m), 3.23-3.46 (1H, m), 3.76 (3H, s), 4.00-4.11 (2H, m), 4.16 (2H, d, J=6.8 Hz), 4.33 (2H, brs), 6.17 (1H, d, J=2.0 Hz), 6.46-6.58 (2H, m), 6.63 (1H, s), 6.77 (1H, d, J=4.4 Hz), 6.87 (1H, dd, J=7.2, 4.9 Hz), 7.20 (1H, t, J=7.3 Hz), 7.32 (1H, d, J=8.4 Hz), 8.07 (1H, d, J=5.4 Hz), 8.33 (1H, d, J=3.3 Hz).

Step 4) 3-cyclopropyl-3-(2-((1-(5-methoxy-2-((2-methyl-2-((2,2,2-trifluoroethyl)amino)propyl)(pyridin-2-yl)carbamoyl)phenyl)piperidin-4-yl)methoxy)pyridin-4-yl)propanoic acid In the same manner as in Example 1, step 4, the title compound (24.7 mg) was obtained as a white amorphous powder from ethyl 3-cyclopropyl-3-(2-((1-(5-methoxy-2-((2-methyl-2-((2,2,2-trifluoroethyl)amino)propyl)(pyridin-2-yl)carbamoyl)phenyl)piperidin-4-yl)methoxy)pyridin-4-yl)propanoate (30 mg).
MS (ESI+): [M+H]$^+$ 684.3.

Example 178

3-cyclopropyl-3-(2-((1-(2-((2,2-dimethylpropyl)(pyrazin-2-yl)carbamoyl)-5-methoxyphenyl)piperidin-4-yl)methoxy)pyridin-4-yl)propanoic acid Step 1)
6-chloro-N-(2,2-dimethylpropyl)pyrazin-2-amine Under a nitrogen atmosphere, 2,2-dimethylpropan-1-amine (869 μL) was added to a mixture of 2,6-dichloropyrazine (1.0 g), potassium carbonate (1.86 g) and DMA (10 mL) at room temperature, and the mixture was stirred at 80° C. for 2 hr. To the reaction solution was added water at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (845 mg) as a white solid.
$^1$H NMR (400 MHz, CDCl$_3$) δ 0.99 (9H, s), 3.16 (2H, d, J=6.1 Hz), 4.74 (1H, brs), 7.77 (2H, s).

Step 2) N-(2,2-dimethylpropyl)pyrazin-2-amine

6-Chloro-N-(2,2-dimethylpropyl)pyrazin-2-amine (250 mg), 10% palladium carbon (100 mg) and triethylamine (837 μL) were stirred in methanol (15 mL) at room temperature for 1 hr under a hydrogen atmosphere (1 atm). The reaction mixture was filtered, and the solvent in the filtrate was evaporated under reduced pressure to give the title compound (138 mg) as a pale-yellow oil.
$^1$H NMR (300 MHz, CDCl$_3$) δ 0.99 (9H, s), 3.18 (2H, d, J=6.2 Hz), 4.58 (1H, brs), 7.77 (1H, d, J=2.7 Hz), 7.90 (1H, d, J=1.4 Hz), 7.95 (1H, dd, J=2.7, 1.5 Hz).

Step 3) ethyl 3-cyclopropyl-3-(2-((1-(2-((2,2-dimethylpropyl)(pyrazin-2-yl)carbamoyl)-5-methoxyphenyl)piperidin-4-yl)methoxy)pyridin-4-yl)propanoate In the same manner as in Example 32, step 2, the title compound (47.0 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (115 mg) and N-(2,2-dimethylpropyl)pyrazin-2-amine (59.1 mg).
$^1$H NMR (400 MHz, CDCl$_3$) δ 0.13-0.21 (1H, m), 0.26-0.34 (1H, m), 0.41-0.51 (1H, m), 0.56-0.65 (1H, m), 0.83 (9H, s), 0.95-1.04 (1H, m), 1.15-1.35 (2H, m), 1.19 (3H, t, J=7.1 Hz), 1.67-1.91 (3H, m), 2.27-2.35 (1H, m), 2.35-2.65 (3H, m), 2.66-2.79 (2H, m), 3.30 (1H, d, J=11.5 Hz), 3.76 (3H, s), 4.08 (2H, dtt, J=10.8, 7.2, 3.5 Hz), 4.14-4.24 (4H, m), 6.15 (1H, d, J=2.0 Hz), 6.56 (1H, dd, J=8.4, 2.3 Hz), 6.63 (1H, s), 6.77 (1H, d, J=5.4 Hz), 7.42 (1H, d, J=8.4 Hz), 7.83 (1H, brs), 8.01-8.11 (2H, m), 8.27 (1H, d, J=1.5 Hz).

Step 4) 3-cyclopropyl-3-(2-((1-(2-((2,2-dimethylpropyl)(pyrazin-2-yl)carbamoyl)-5-methoxyphenyl)piperidin-4-yl)methoxy)pyridin-4-yl)propanoic acid In the same manner as in Example 1, step 4, the title compound (43.9 mg) was obtained as a pale-yellow amorphous powder from ethyl 3-cyclopropyl-3-(2-((1-(2-((2,2-dimethylpropyl)(pyrazin-2-yl)carbamoyl)-5-methoxyphenyl)piperidin-4-yl)methoxy)pyridin-4-yl)propanoate (47 mg).
MS (ESI+): [M+H]$^+$ 602.3.

Example 179

3-cyclopropyl-3-(2-((1-(2-((2,2-dimethylpropyl)(pyridazin-3-yl)carbamoyl)-5-methoxyphenyl)piperidin-4-yl)methoxy)pyridin-4-yl)propanoic acid Step 1) 6-chloro-N-(2,2-dimethylpropyl)pyridazin-3-amine In the same manner as in Example 177, step 1, the title compound (308 mg) was obtained as a pale-yellow solid from 3,6-dichloropyridazine (1.0 g).
$^1$H NMR (400 MHz, CDCl$_3$) δ 0.99 (9H, s), 3.18 (2H, d, J=6.3 Hz), 4.84 (1H, brs), 6.65 (1H, d, J=9.3 Hz), 7.15 (1H, d, J=9.3 Hz).

Step 2) N-(2,2-dimethylpropyl)pyridazin-3-amine

6-Chloro-N-(2,2-dimethylpropyl)pyridazin-3-amine (300 mg) and 10% palladium carbon (30 mg) were stirred in a mixed solvent of methanol (15 mL) and THF (5 mL) at room temperature for 10 hr under a hydrogen atmosphere (1 atm). The reaction mixture was filtered, and the solvent in the filtrate was evaporated under reduced pressure to give the title compound (186 mg) as a white solid.
$^1$H NMR (400 MHz, CDCl$_3$) δ 1.00 (9H, s), 3.19 (2H, d, J=6.3 Hz), 4.81 (1H, brs), 6.64 (1H, dd, J=9.1, 1.2 Hz), 7.14 (1H, dd, J=9.0, 4.4 Hz), 8.52 (1H, dd, J=4.5, 1.2 Hz).

Step 3) ethyl 3-cyclopropyl-3-(2-((1-(2-((2,2-dimethylpropyl)(pyridazin-3-yl)carbamoyl)-5-methoxyphenyl)piperidin-4-yl)methoxy)pyridin-4-yl)propanoate In the same manner as in Example 32, step 2, the title compound (74.8 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (100 mg) and N-(2,2-dimethylpropyl)pyridazin-3-amine (51.4 mg) obtained in Example 179, step 2.
$^1$H NMR (400 MHz, CDCl$_3$) δ 0.12-0.20 (1H, m), 0.25-0.34 (1H, m), 0.40-0.51 (1H, m), 0.55-0.65 (1H, m), 0.83 (9H, s), 0.93-1.05 (1H, m), 1.19 (3H, t, J=7.2 Hz), 1.57-1.89 (5H, m), 2.26-2.35 (1H, m), 2.39-2.52 (2H, m), 2.58-2.79 (3H, m), 3.28 (1H, d, J=12.8 Hz), 3.77 (3H, s), 3.97-4.13 (2H, m), 4.17 (2H, d, J=6.8 Hz), 4.28-4.59 (2H, m), 6.14 (1H, s), 6.53 (1H, dd, J=8.5, 2.3 Hz), 6.61 (1H, s), 6.71 (1H, brs), 6.74 (1H, d, J=5.5 Hz), 6.95 (1H, dd, J=8.8, 4.6 Hz), 7.39 (1H, d, J=8.4 Hz), 8.05 (1H, d, J=5.3 Hz), 8.76 (1H, d, J=4.3 Hz).

Step 4) 3-cyclopropyl-3-(2-((1-(2-((2,2-dimethylpropyl)(pyridazin-3-yl)carbamoyl)-5-methoxyphenyl)piperidin-4-yl)methoxy)pyridin-4-yl)propanoic acid In the same manner as in Example 1, step 4, the title compound (70.0 mg) was obtained as a white amorphous powder from ethyl 3-cyclopropyl-3-(2-((1-(2-((2,2-dimethylpropyl)(pyridazin-3-yl)carbamoyl)-5-methoxyphenyl)piperidin-4-yl)methoxy)pyridin-4-yl)propanoate (74.8 mg).
MS (ESI+): [M+H]$^+$ 602.3.

Example 180

3-(2-((1-(2-((6-chloropyrazin-2-yl)(2,2-dimethylpropyl)carbamoyl)-5-methoxyphenyl)piperidin-4-yl)methoxy)pyridin-4-yl)-3-cyclopropylpropanoic acid Step 1) ethyl 3-(2-((1-(2-((6-chloropyrazin-2-yl)((2,2-dimethylpropyl))carbamoyl)-5-methoxyphenyl)piperidin-4-yl)methoxy)pyridin-4-yl)-3-cyclopropylpropanoate In the same manner as in Example 32, step 2, the title compound (39.0 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (100 mg) and 6-chloro-N-(2,2-dimethylpropyl)pyrazin-2-amine (62.1 mg).
$^1$H NMR (400 MHz, CDCl$_3$) δ 0.13-0.21 (1H, m), 0.25-0.33 (1H, m), 0.42-0.51 (1H, m), 0.56-0.65 (1H, m), 0.85 (9H, s), 0.93-1.04 (1H, m), 1.19 (3H, t, J=7.2 Hz), 1.53-1.66 (2H, m), 1.73-1.86 (3H, m), 2.27-2.35 (1H, m), 2.38-2.50 (2H, m), 2.55-2.65 (1H, m), 2.66-2.79 (2H, m), 3.26 (1H, d, J=12.4 Hz), 3.77 (3H, s), 4.03-4.12 (2H, m), 4.14-4.25 (4H, m), 6.17 (1H, d, J=2.1 Hz), 6.59 (1H, dd, J=8.4, 2.3 Hz), 6.64 (1H, s), 6.73-6.79 (1H, m), 7.46 (1H, d, J=8.5 Hz), 7.63 (1H, s), 8.04-8.10 (2H, m).

Step 2) 3-(2-((1-(2-((6-chloropyrazin-2-yl)(2,2-dimethylpropyl)carbamoyl)-5-methoxyphenyl)piperidin-4-yl)methoxy)pyridin-4-yl)-3-cyclopropylpropanoic acid In the same manner as in Example 1, step 4, the title compound (31.1 mg) was obtained as a pale-yellow amorphous powder from ethyl 3-(2-((1-(2-((6-chloropyrazin-2-

141 yl)((2,2-dimethylpropyl))carbamoyl)-5-methoxyphenyl)piperidin-4-yl)methoxy)pyridin-4-yl)-3-cyclopropylpropanoate (39.0 mg).
MS (ESI+): [M+H]$^+$ 636.4.

Example 181

3-cyclopropyl-3-(2-((1-(2-((2,2-dimethylpropyl)(pyridin-2-ylmethyl)carbamoyl)-5-methoxyphenyl)piperidin-4-yl)methoxy)pyridin-4-yl)propanoic acid By a method similar to that in Example 2, step 5 and Example 1, step 4, the title compound (73.1 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (148 mg) and 2,2-dimethyl-N-(pyridin-2-ylmethyl)propan-1-amine (109 mg).
MS (ESI+): [M+H]$^+$ 615.3.

Example 182

3-cyclopropyl-3-(2-((1-(5-methoxy-2-((pyridin-2-ylmethyl)(2,2,2-trifluoroethyl)carbamoyl)phenyl)piperidin-4-yl)methoxy)pyridin-4-yl)propanoic acid By a method similar to that in Example 2, step 5 and Example 1, step 4, the title compound (115 mg) was obtained as a pale-orange amorphous powder from 2-(4-(((4-(1-cyclopropyl-3-ethoxy-3-oxopropyl)pyridin-2-yl)oxy)methyl)piperidin-1-yl)-4-methoxybenzoic acid (148 mg) and 2,2,2-trifluoro-N-(pyridin-2-ylmethyl)ethanamine (117 mg).
MS (ESI+): [M+H]$^+$ 627.2.

Example 183

3-cyclopropyl-3-(2-((1-(5-methoxy-2-(pyridin-2-yl(3,3,3-trifluoro-2-methoxypropyl)carbamoyl)phenyl)piperidin-4-yl)methoxy)pyridin-4-yl)propanoic acid Step 1)
3-(dibenzylamino)-1,1,1-trifluoropropan-2-ol Under a nitrogen atmosphere, (trifluoromethyl)oxirane (1.29 mL) was added to a mixture of dibenzylamine (1.92 mL), ytterbium trifluoromethanesulfonate hydrate (319 mg) and acetonitrile (4 mL) at room temperature, and the mixture was stirred at 50° C. for 20 min. To the reaction solution was added water at room temperature, and the mixture was extracted with ethyl acetate. The extract was washed with saturated aqueous sodium hydrogen carbonate solution and saturated brine, and dried over anhydrous magnesium sulfate. The solvent was evaporated under reduced pressure, and the residue was purified by silica gel column chromatography (ethyl acetate/hexane) to give the title compound (2.07 g) as a white solid.
$^1$H NMR (400 MHz, DMSO-d$_6$) δ 2.54-2.62 (1H, m), 2.64-2.72 (1H, m), 3.53-3.63 (2H, m), 3.64-3.73 (2H, m), 4.11-4.27 (1H, m), 6.22 (1H, d, J=6.1 Hz), 7.19-7.27 (2H, m), 7.29-7.42 (8H, m).

Step 2) N,N-dibenzyl-3,3,3-trifluoro-2-methoxypropan-1-amine

Under a nitrogen atmosphere, 60% sodium hydride (oily) (259 mg) was added to a solution of 3-(dibenzylamino)-1,

142

1,1-trifluoropropan-2-ol (1.0 g) and iodomethane (1.01 mL) in DMF (5 mL) at room temperature, and the mixture was stirred at room temperature for 10 min. To the reaction solution was added water at room temperature, and the mixture was extracted with ethyl acetate. The extract was washed with water and saturated brine, and dried over anhydrous magnesium sulfate. The solvent was evaporated under reduced pressure to give a crude product of the title compound as a pale-yellow oil. This compound was used for the next step without further purification.

Step 3) 3,3,3-trifluoro-2-methoxypropan-1-amine hydrochloride

In the same manner as in Example 144, step 3, the title compound (532 mg) was obtained as a white solid from a crude product (entire amount) of N,N-dibenzyl-3,3,3-trifluoro-2-methoxypropan-1-amine.
$^1$H NMR (400 MHz, DMSO-d$_6$) δ 2.97 (1H, brs), 3.12-3.25 (1H, m), 3.56 (3H, s), 4.26 (1H, ddd, J=9.6, 6.6, 3.1 Hz), 8.27 (2H, brs).

Step 4)
N-(3,3,3-trifluoro-2-methoxypropyl)pyridin-2-amine

In the same manner as in Example 135, step 1, the title compound (119 mg) was obtained as a yellow oil from 3,3,3-trifluoro-2-methoxypropan-1-amine hydrochloride (300 mg) and pyridine N-oxide (238 mg).
$^1$H NMR (400 MHz, CDCl$_3$) δ 3.32-3.44 (1H, m), 3.57 (3H, s), 3.78-3.96 (2H, m), 4.66 (1H, brs), 6.44 (1H, d, J=8.4 Hz), 6.62 (1H, dd, J=7.0, 5.1 Hz), 7.36-7.52 (1H, m), 8.12 (1H, d, J=3.9 Hz).

Step 5) ethyl 3-cyclopropyl-3-(2-((1-(5-methoxy-2-(pyridin-2-yl(3,3,3-trifluoro-2-methoxypropyl)carbamoyl)phenyl)piperidin-4-yl)methoxy)pyridin-4-yl)propanoate In the same manner as in Example 32, step 2, the title compound (205 mg) was obtained as a pale-yellow oil from 2-(4-(((4-(1-cyclopropyl-3-ethoxy-3-oxopropyl)pyridin-2-yl)oxy)methyl)piperidin-1-yl)-4-methoxybenzoic acid (192 mg) and N-(3,3,3-trifluoro-2-methoxypropyl)pyridin-2-amine (119 mg).
$^1$H NMR (400 MHz, CDCl$_3$) δ 0.11-0.21 (1H, m), 0.24-0.34 (1H, m), 0.40-0.51 (1H, m), 0.55-0.65 (1H, m), 0.91-1.04 (1H, m), 1.19 (3H, t, J=7.2 Hz), 1.64-1.92 (4H, m), 2.25-2.35 (1H, m), 2.39-2.70 (3H, m), 2.66-2.79 (2H, m), 3.41 (3H, brs), 3.78 (3H, s), 4.02-4.75 (5H, m), 4.03-4.12 (2H, m), 4.14 (2H, d, J=7.2 Hz), 6.21 (1H, brs), 6.54 (1H, dd, J=8.4, 2.1 Hz), 6.62 (1H, s), 6.76 (1H, d, J=5.3 Hz), 6.92 (1H, d, J=5.1 Hz), 7.18-7.33 (2H, m), 7.40 (1H, d, J=6.4 Hz), 8.06 (1H, d, J=5.4 Hz), 8.38 (1H, d, J=3.5 Hz).

Step 6) 3-cyclopropyl-3-(2-((1-(5-methoxy-2-(pyridin-2-yl(3,3,3-trifluoro-2-methoxypropyl)carbamoyl)phenyl)piperidin-4-yl)methoxy)pyridin-4-yl)propanoic acid In the same manner as in Example 1, step 4, the title compound (25.0 mg) was obtained as a white amorphous powder from ethyl 3-cyclopropyl-3-(2-((1-(5-methoxy-2-(pyridin-2-yl(3,3,3-trifluoro-2-methoxypropyl)carbamoyl)phenyl)piperidin-4-yl)methoxy)pyridin-4-yl)propanoate (28.0 mg).

MS (ESI+): [M+H]$^+$ 657.4.

Example 184

3-cyclopropyl-3-(2-((1-(2-((2,2-dimethylpropyl)(pyrimidin-2-yl)carbamoyl)-5-methoxyphenyl)piperidin-4-yl)methoxy)pyridin-4-yl)propanoic acid Step 1) ethyl 3-cyclopropyl-3-(2-((1-(2-((2,2-dimethylpropyl)(pyrimidin-2-yl)carbamoyl)-5-methoxyphenyl)piperidin-4-yl)methoxy)pyridin-4-yl)propanoate In the same manner as in Example 32, step 2, the title compound (115 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (236 mg) having a longer retention time and N-(2,2-dimethylpropyl)pyrimidin-2-amine (202 mg).

$^1$H NMR (400 MHz, CDCl$_3$) δ 0.14-0.21 (1H, m), 0.25-0.34 (1H, m), 0.42-0.51 (1H, m), 0.57-0.67 (1H, m), 0.86 (9H, s), 0.94-1.04 (1H, m), 1.08-1.36 (2H, m, J=7.2, 7.2 Hz), 1.19 (3H, t, J=7.2 Hz), 1.61-1.88 (3H, m), 2.26-2.35 (1H, m), 2.34-2.65 (3H, m), 2.65-2.80 (2H, m), 3.13-3.35 (1H, m), 3.78 (3H, s), 4.02-4.12 (2H, m), 4.15 (2H, d, J=6.7 Hz), 4.17-4.38 (2H, m), 6.14 (1H, d, J=2.4 Hz), 6.55 (1H, dd, J=8.5, 2.3 Hz), 6.63 (1H, s), 6.72-6.86 (2H, m), 7.46 (1H, d, J=8.4 Hz), 8.07 (1H, d, J=5.3 Hz), 8.31 (2H, d, J=4.8 Hz).

Step 2) 3-cyclopropyl-3-(2-((1-(2-((2,2-dimethylpropyl)(pyrimidin-2-yl)carbamoyl)-5-methoxyphenyl)piperidin-4-yl)methoxy)pyridin-4-yl)propanoic acid In the same manner as in Example 1, step 4, the title compound (83.2 mg) was obtained as a white amorphous powder from ethyl 3-cyclopropyl-3-(2-((1-(5-methoxy-2-((2,2-dimethylpropyl)(pyrimidin-2-yl)carbamoyl)phenyl)piperidin-4-yl)methoxy)pyridin-4-yl)propanoate (115 mg).

MS (ESI+): [M+H]$^+$ 602.3.

Example 185

3-cyclopropyl-3-(2-((1-(2-((2-fluoro-2-methylpropyl)(4-methylpyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (236 mg) was obtained as a colorless amorphous powder from N-(2-fluoro-2-methylpropyl)-4-methylpyridin-2-amine (199 mg) obtained in Example 153, step 2 and 2-(4-(((4-(1-cyclopropyl-3-ethoxy-3-oxopropyl)pyridin-2-yl)oxy)methyl)piperidin-1-yl)-4-methoxybenzoic acid (264 mg).

MS (ESI+): [M+H]$^+$ 619.3.

Example 186

3-cyclopropyl-3-(2-((1-(2-(((2R)-3-fluoro-3-methylbutan-2-yl)(pyridin-2-yl)carbamoyl)-5-methoxyphenyl)piperidin-4-yl)methoxy)pyridin-4-yl)propanoic acid Step 1) methyl N-pyridin-2-yl-D-alaninate In the same manner as in Example 135, step 1, the title compound (215 mg) was obtained as a pale-yellow oil from pyridine 1-oxide (300 mg) and methyl D-alaninate hydrochloride (528 mg).

$^1$H NMR (300 MHz, CDCl$_3$) δ 1.49 (3H, d, J=7.1 Hz), 3.74 (3H, s), 4.61 (1H, quin, J=7.3 Hz), 4.83 (1H, d, J=6.7 Hz), 6.43 (1H, dt, J=8.4, 0.9 Hz), 6.60 (1H, ddd, J=7.2, 5.1, 0.9 Hz), 7.34-7.44 (1H, m), 8.05-8.12 (1H, m).

Step 2) (3R)-2-methyl-3-(pyridin-2-ylamino)butan-2-ol

To a solution of methyl N-pyridin-2-yl-D-alaninate (415 mg) in THF (15 mL) was added 1M methylmagnesium bromide THF solution (8.06 mL) at room temperature. The mixture was stirred at room temperature for 20 min, 1M methylmagnesium bromide THF solution (4.00 mL) was added, and the mixture was further stirred for 30 min. To the reaction mixture was added saturated aqueous ammonium chloride solution at room temperature, and the mixture was extracted with ethyl acetate. The extract was washed with saturated brine, dried over anhydrous magnesium sulfate, and the solvent was evaporated under reduced pressure. The residue was purified by silica gel column chromatography (ethyl acetate/hexane) to give the title compound (130 mg) as a brown oil.

$^1$H NMR (300 MHz, CDCl$_3$) δ 1.14-1.29 (10H, m), 3.81-3.91 (1H, m), 4.39 (1H, d, J=6.3 Hz), 6.45 (1H, dt, J=8.4, 0.9 Hz), 6.55 (1H, ddd, J=7.1, 5.1, 0.9 Hz), 7.35-7.42 (1H, m), 7.99-8.07 (1H, m).

Step 3) N-((2R)-3-fluoro-3-methylbutan-2-yl)pyridin-2-amine

In the same manner as in Example 39, step 1, the title compound (83 mg) was obtained as a colorless solid from (3R)-2-methyl-3-(pyridin-2-ylamino)butan-2-ol (130 mg).

$^1$H NMR (300 MHz, CDCl$_3$) δ 1.25 (3H, d, J=6.7 Hz), 1.42 (6H, d, J=21.7 Hz), 3.96-4.18 (1H, m), 4.50 (1H, brs), 6.40 (1H, d, J=8.4 Hz), 6.54 (1H, ddd, J=7.1, 5.1, 0.8 Hz), 7.38 (1H, ddd, J=8.6, 7.0, 1.9 Hz), 8.06 (1H, dd, J=5.1, 1.1 Hz).

Step 4) 3-cyclopropyl-3-(2-((1-(2-(((2R)-3-fluoro-3-methylbutan-2-yl)(pyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (123 mg) was obtained as a colorless amorphous powder from N-((2R)-3-fluoro-3-methylbutan-2-yl)pyridin-2-amine (83 mg) and 2-(4-(((4-(1-cyclopropyl-3-ethoxy-3-oxopropyl)pyridin-2-yl)oxy)methyl)piperidin-1-yl)-4-methoxybenzoic acid (153 mg).

MS (ESI+): [M+H]$^+$ 619.3.

Example 187

3-cyclopropyl-3-(2-((1-(2-(((2S)-3-fluoro-3-methylbutan-2-yl)(pyridin-2-yl)carbamoyl)-5-methoxyphenyl)piperidin-4-yl)methoxy)pyridin-4-yl)propanoic acid

Step 1) N-((2S)-3-fluoro-3-methylbutan-2-yl)pyridin-2-amine

In the same manner as in Example 186, steps 1, 2 and 3, the title compound (116 mg) was obtained as a colorless solid from methyl L-alaninate hydrochloride (1409 mg).

$^1$H NMR (300 MHz, CDCl$_3$) δ 1.24 (3H, d, J=6.6 Hz), 1.42 (6H, d, J=21.7 Hz), 3.97-4.17 (1H, m), 4.48 (1H, d, J=8.0 Hz), 6.39 (1H, d, J=8.4 Hz), 6.54 (1H, ddd, J=7.1, 5.1, 0.9 Hz), 7.38 (1H, ddd, J=8.6, 7.0, 1.9 Hz), 8.06 (1H, dt, J=5.1, 0.9 Hz).

Step 2) 3-cyclopropyl-3-(2-((1-(2-(((2S)-3-fluoro-3-methylbutan-2-yl)(pyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (128 mg) was obtained as a colorless amorphous powder from N-((2S)-3-fluoro-3-methylbutan-2-yl)pyridin-2-amine (116 mg) and 2-(4-(((4-(1-cyclopropyl-3-ethoxy-3-oxopropyl)pyridin-2-yl)oxy)methyl)piperidin-1-yl)-4-methoxybenzoic acid (160 mg).

MS (ESI+): [M+H]$^+$ 619.3.

Example 188

3-cyclopropyl-3-(2-((1-(5-methoxy-2-((2-methoxy-2-methylpropyl)(phenyl)carbamoyl)phenyl)piperidin-4-yl)methoxy)pyridin-4-yl)propanoic acid

Step 1) ethyl 2-(phenylamino)acetate

Under a nitrogen atmosphere, ethyl bromoacetate (3.33 mL) was added to a solution of aniline (2.73 mL) and diisopropylethylamine (10.48 mL) in acetonitrile (25 mL) at 60° C., and the mixture was stirred at 60° C. for 3 hr. The solvent was evaporated under reduced pressure, and the residual solid was washed with water to give a yellow solid. The obtained solid was dissolved in toluene, and the solvent was evaporated under reduced pressure to give a crude product of the title compound (5.09 g) as a yellow solid. This compound was used for the next step without further purification.

$^1$H NMR (400 MHz, CDCl$_3$) δ 1.30 (3H, t, J=7.2 Hz), 3.90 (2H, s), 4.25 (2H, q, J=7.1 Hz), 6.62 (2H, d, J=7.7 Hz), 6.75 (1H, t, J=7.3 Hz), 7.20 (2H, dd, J=8.4, 7.5 Hz).

Step 2) ethyl 2-(benzyl(phenyl)amino)acetate

Benzyl bromide (3.26 mL) was added to a mixture of the crude product (4.09 g) of ethyl 2-(phenylamino)acetate, potassium carbonate (6.31 g) and DMF (25 mL) at room temperature, and the mixture was stirred at 80° C. for 3 hr. To the reaction solution was added water at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (5.41 g) as a pale-yellow oil.

$^1$H NMR (400 MHz, CDCl$_3$) δ 1.26 (3H, t, J=7.1 Hz), 4.07 (2H, s), 4.20 (2H, q, J=7.2 Hz), 4.66 (2H, s), 6.69 (2H, d, J=8.2 Hz), 6.75 (1H, t, J=7.3 Hz), 7.20 (2H, dd, J=8.7, 7.4 Hz), 7.27-7.44 (5H, m).

Step 3) 1-(benzyl(phenyl)amino)-2-methylpropan-2-ol

Under a nitrogen atmosphere, a 1 M solution of methylmagnesium bromide in THF (9.28 mL) was added to a solution of ethyl 2-(benzyl(phenyl)amino)acetate (1.0 g) in THF (10 mL) at room temperature, and the mixture was stirred at room temperature for 30 min. To the reaction solution was added saturated aqueous ammonium chloride solution at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (720 mg) as a pale-yellow oil.

$^1$H NMR (400 MHz, DMSO-d$_6$) δ 1.17 (6H, s), 3.41 (2H, s), 4.73 (2H, s), 6.51 (1H, t, J=7.2 Hz), 6.71 (2H, d, J=8.3 Hz), 7.03 (2H, dd, J=8.5, 7.3 Hz), 7.12-7.21 (3H, m), 7.22-7.34 (2H, m).

Step 4) N-benzyl-N-(2-methoxy-2-methylpropyl)aniline

Under a nitrogen atmosphere, 60% sodium hydride (oily) (564 mg) was added to a solution of 1-(benzyl(phenyl)amino)-2-methylpropan-2-ol (720 mg) and iodomethane (1.76 mL) in DMF (10 mL) at 0° C., and the mixture was stirred at room temperature for 1 hr. To the reaction solution was added water at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (631 mg) as a colorless oil.

$^1$H NMR (400 MHz, CDCl$_3$) δ 1.24 (6H, s), 3.20 (3H, s), 3.49 (2H, s), 4.74 (2H, s), 6.64 (1H, t, J=7.2 Hz), 6.76 (2H, d, J=8.3 Hz), 7.06-7.22 (5H, m), 7.24-7.33 (2H, m).

Step 5) N-(2-methoxy-2-methylpropyl)aniline

N-Benzyl-N-(2-methoxy-2-methylpropyl)aniline (631 mg) and 10% palladium hydroxide (300 mg) were stirred in methanol (30 mL) at room temperature for 1 hr under a hydrogen atmosphere (1 atm). The reaction mixture was filtered, and the solvent in the filtrate was evaporated under reduced pressure to give the title compound (410 mg) as a pale-orange oil.

$^1$H NMR (400 MHz, CDCl$_3$) δ 1.26 (6H, s), 3.07 (2H, d, J=3.5 Hz), 3.21 (3H, s), 3.96 (1H, brs), 6.62 (2H, d, J=7.7 Hz), 6.68 (1H, t, J=7.3 Hz), 7.09-7.22 (2H, m).

Step 6) ethyl 3-cyclopropyl-3-(2-((1-(5-methoxy-2-((2-methoxy-2-methylpropyl)(phenyl)carbamoyl)phenyl)piperidin-4-yl)methoxy)pyridin-4-yl)propanoate In the same manner as in Example 32, step 2, the title compound (27.3 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (100 mg) and N-(2-methoxy-2-methylpropyl)aniline (93.0 mg).

$^1$H NMR (400 MHz, CDCl$_3$) δ 0.13-0.21 (1H, m), 0.25-0.34 (1H, m), 0.43-0.52 (1H, m), 0.56-0.66 (1H, m), 0.95-1.05 (1H, m), 1.19 (3H, t, J=7.2 Hz), 1.18-1.40 (2H, m), 1.25 (6H, s), 1.45-1.61 (2H, m), 1.81-1.99 (3H, m), 2.27-2.36 (1H, m), 2.41-2.75 (2H, m), 2.66-2.79 (2H, m), 2.82 (3H, s), 3.70 (3H, s), 3.97-4.20 (2H, m), 4.02-4.13 (2H, m), 4.20 (2H, d, J=6.1 Hz), 6.24 (1H, d, J=1.8 Hz), 6.42 (1H, dd, J=8.3, 2.1 Hz), 6.64 (1H, s), 6.77 (1H, dd, J=5.4, 1.1 Hz), 6.91-7.08 (5H, m), 7.10 (1H, d, J=8.3 Hz), 8.08 (1H, d, J=5.4 Hz).

Step 7) 3-cyclopropyl-3-(2-((1-(5-methoxy-2-((2-methoxy-2-methylpropyl)(phenyl)carbamoyl)phenyl)piperidin-4-yl)methoxy)pyridin-4-yl)propanoic acid In the same manner as in Example 1, step 4, the title compound (21.3 mg) was obtained as a white amorphous powder from ethyl 3-cyclopropyl-3-(2-((1-(5-methoxy-2-((2-methoxy-2-methylpropyl)(phenyl)carbamoyl)phenyl)piperidin-4-yl)methoxy)pyridin-4-yl)propanoate (27.3 mg).

MS (ESI+): [M+H]$^+$ 616.3.

Example 189

3-cyclopropyl-3-(2-((1-(2-(((1-fluorocyclopropyl)methyl)(phenyl)carbamoyl)-5-methoxyphenyl)piperidin-4-yl)methoxy)pyridin-4-yl)propanoic acid Step 1)
1-((benzyl(phenyl)amino)methyl)cyclopropanol Under a nitrogen atmosphere, 3 M ethylmagnesium bromide (7.43 mL) was added to a solution of ethyl 2-(benzyl(phenyl)amino)acetate (2.0 g) obtained in Example 188, step 2, and tetraisopropyl titanate (653 μL) in THF (30 mL) at 0° C., and the mixture was stirred at 0° C. for 1 hr and at room temperature for 30 min. To the reaction solution was added saturated aqueous ammonium chloride solution at 0° C., and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (1.54 g) as a pale-yellow solid.

$^1$H NMR (300 MHz, DMSO-d$_6$) δ 0.46-0.53 (2H, m), 0.54-0.61 (2H, m), 3.62 (2H, s), 4.66 (2H, s), 5.41 (1H, s), 6.53 (1H, t, J=7.2 Hz), 6.72 (2H, dd, J=8.8, 0.9 Hz), 6.97-7.11 (2H, m), 7.14-7.23 (3H, m), 7.24-7.35 (2H, m).

Step 2)
N-benzyl-N-((1-fluorocyclopropyl)methyl)aniline

In the same manner as in Example 39, step 1, the title compound (518 mg) was obtained as a pale-yellow solid from 1-((benzyl(phenyl)amino)methyl)cyclopropanol (1.0 g).

$^1$H NMR (300 MHz, CDCl$_3$) δ 0.99-1.21 (4H, m), 4.41-4.73 (2H, m), 4.77 (2H, s), 6.59-6.83 (3H, m), 7.06-7.38 (7H, m).

Step 3) N-((1-fluorocyclopropyl)methyl)aniline

In the same manner as in Example 188, step 5, the title compound (212 mg) was obtained as a colorless oil from N-benzyl-N-((1-fluorocyclopropyl)methyl)aniline (518 mg).

$^1$H NMR (300 MHz, CDCl$_3$) δ 0.84-0.99 (4H, m), 4.41 (2H, d, J=48.1 Hz), 4.39 (1H, brs), 6.65-6.79 (3H, m), 7.18 (2H, dd, J=8.4, 7.5 Hz).

Step 4) ethyl 3-cyclopropyl-3-(2-((1-(2-(((1-fluorocyclopropyl)methyl)(phenyl)carbamoyl)-5-methoxyphenyl)piperidin-4-yl)methoxy)pyridin-4-yl)propanoate In the same manner as in Example 32, step 2, the title compound (38.1 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (118 mg) and N-((1-fluorocyclopropyl)methyl)aniline (101 mg).

$^1$H NMR (300 MHz, CDCl$_3$) δ 0.08-0.22 (1H, m), 0.24-0.37 (1H, m), 0.40-0.52 (1H, m), 0.55-0.67 (1H, m), 0.72-1.14 (5H, m), 1.19 (3H, t, J=7.1 Hz), 1.33-1.70 (4H, m), 1.76-1.94 (3H, m), 2.24-2.37 (1H, m), 2.43-2.65 (2H, m), 2.64-2.81 (2H, m), 3.70 (3H, s), 3.98-4.14 (2H, m), 4.06-5.73 (2H, m), 4.19 (2H, d, J=6.0 Hz), 6.22 (1H, d, J=2.4 Hz), 6.45 (1H, dd, J=8.4, 2.4 Hz), 6.64 (1H, s), 6.76 (1H, dd, J=5.4, 1.4 Hz), 6.91-7.09 (5H, m), 7.15 (1H, d, J=8.4 Hz), 8.07 (1H, d, J=5.4 Hz).

Step 5) 3-cyclopropyl-3-(2-((1-(2-(((1-fluorocyclopropyl)methyl)(phenyl)carbamoyl)-5-methoxyphenyl)piperidin-4-yl)methoxy)pyridin-4-yl)propanoic acid In the same manner as in Example 1, step 4, the title compound (34.7 mg) was obtained as a white amorphous powder from ethyl 3-cyclopropyl-3-(2-((1-(2-(((1-fluorocyclopropyl)methyl)(phenyl)carbamoyl)-5-methoxyphenyl)piperidin-4-yl)methoxy)pyridin-4-yl)propanoate (38.1 mg).

MS (ESI+): [M+H]$^+$ 602.3.

Example 190

3-(2-((1-(2-((1-benzylpiperidin-4-yl)(pyridin-2-yl)carbamoyl)-5-methoxyphenyl)piperidin-4-yl)methoxy)pyridin-4-yl)-3-cyclopropylpropanoic acid Step 1) N-(1-benzylpiperidin-4-yl)pyridin-2-amine In the same manner as in Example 135, step 1, the title compound (540 mg) was obtained as a brown solid from pyridine 1-oxide (300 mg) and 1-benzylpiperidin-4-amine (720 mg).

$^1$H NMR (300 MHz, CDCl$_3$) δ 1.43-1.62 (2H, m), 1.95-2.10 (2H, m), 2.19 (2H, td, J=11.4, 2.4 Hz), 2.76-2.91 (2H, m), 3.45-3.71 (3H, m), 4.37 (1H, d, J=7.7 Hz), 6.35 (1H, d, J=8.4 Hz), 6.53 (1H, ddd, J=7.1, 5.0, 0.9 Hz), 7.20-7.45 (6H, m), 8.02-8.10 (1H, m).

Step 2) ethyl 3-(2-((1-(2-((1-benzylpiperidin-4-yl)(pyridin-2-yl)carbamoyl)-5-methoxyphenyl)piperidin-4-yl)methoxy)pyridin-4-yl)-3-cyclopropylpropanoate In the same manner as in Example 32, step 2, the title compound (690 mg) was obtained as a pale-yellow amorphous powder from N-(1-benzylpiperidin-4-yl)pyridin-2-amine (396 mg) and 2-(4-(((4-(1-cyclopropyl-3-ethoxy-3-oxopropyl)pyridin-2-yl)oxy)methyl)piperidin-1-yl)-4-methoxybenzoic acid (550 mg).

MS (ESI+): [M+H]$^+$ 732.4.

Step 3) 3-(2-((1-(2-((l-benzylpiperidin-4-yl)(pyridin-2-yl)carbamoyl)-5-methoxyphenyl)piperidin-4-yl)methoxy)pyridin-4-yl)-3-cyclopropylpropanoic acid In the same manner as in Example 1, step 4, the title compound (102 mg) was obtained as a colorless amorphous powder from ethyl 3-(2-((1-(2-((l-benzylpiperidin-4-yl)(pyridin-2-yl)carbamoyl)-5-methoxyphenyl)piperidin-4-yl)methoxy)pyridin-4-yl)-3-cyclopropylpropanoate (120 mg).

MS (ESI+): [M+H]$^+$ 704.4.

Example 191

3-cyclopropyl-3-(2-((1-(5-methoxy-2-(pyridin-2-yl(1-(2,2,2-trifluoroethyl)piperidin-4-yl)carbamoyl)phenyl)piperidin-4-yl)methoxy)pyridin-4-yl)propanoic acid Step 1) ethyl 3-cyclopropyl-3-(2-((1-(5-methoxy-2-(piperidin-4-yl(pyridin-2-yl)carbamoyl)phenyl)piperidin-4-yl)methoxy)pyridin-4-yl)propanoate Under a hydrogen atmosphere, a solution of ethyl 3-(2-((1-(2-((l-benzylpiperidin-4-yl)(pyridin-2-yl)carbamoyl)-5-methoxyphenyl)piperidin-4-yl)methoxy)pyridin-4-yl)-3-cyclopropylpropanoate (570 mg) obtained in Example 190, step 2, and 10% palladium carbon (55% water-containing, 184 mg) in ethanol (15 mL) was stirred at room temperature for 5 hr. The reaction mixture was filtered through celite, and the filtrate was concentrated under reduced pressure to give the title compound (475 mg) as a colorless oil.

MS (ESI+): [M+H]$^+$ 642.4.

Step 2) ethyl 3-cyclopropyl-3-(2-((1-(5-methoxy-2-(pyridin-2-yl(1-(2,2,2-trifluoroethyl)piperidin-4-yl)carbamoyl)phenyl)piperidin-4-yl)methoxy)pyridin-4-yl)propanoate In the same manner as in Example 14, step 1, the title compound (112 mg) was obtained as a colorless amorphous powder from ethyl 3-cyclopropyl-3-(2-((1-(5-methoxy-2-(piperidin-4-yl(pyridin-2-yl)carbamoyl)phenyl)piperidin-4-yl)methoxy)pyridin-4-yl)propanoate (157 mg) and 2,2,2-trifluoroethyl trifluoromethanesulfonate (114 mg).

MS (ESI+): [M+H]$^+$ 724.4.

Step 3) 3-cyclopropyl-3-(2-((1-(5-methoxy-2-(pyridin-2-yl(1-(2,2,2-trifluoroethyl)piperidin-4-yl)carbamoyl)phenyl)piperidin-4-yl)methoxy)pyridin-4-yl)propanoic acid In the same manner as in Example 1, step 4, the title compound (78 mg) was obtained as a colorless amorphous powder from ethyl 3-cyclopropyl-3-(2-((1-(5-methoxy-2-(pyridin-2-yl(1-(2,2,2-trifluoroethyl)piperidin-4-yl)carbamoyl)phenyl)piperidin-4-yl)methoxy)pyridin-4-yl)propanoate (110 mg).

MS (ESI+): [M+H]$^+$ 696.3.

Example 192

3-cyclopropyl-3-(2-((1-(2-(cyclopropyl(2,2-dimethylpropyl)carbamoyl)-5-methoxyphenyl)piperidin-4-yl)methoxy)pyridin-4-yl)propanoic acid Step 1) N-(2,2-dimethylpropyl)cyclopropanamine hydrochloride To a solution of pivalaldehyde (1.0 g), cyclopropanamine (1.21 mL) and acetic acid (0.665 mL) in THF (10 mL) was added sodium triacetoxyborohydride (3.69 g) at room temperature, and the mixture was stirred overnight. The reaction mixture was diluted with water, and washed with ethyl acetate. The aqueous layer was adjusted to about pH 10 with 2N aqueous sodium hydroxide solution, and extracted with ethyl acetate. The extract was dried over anhydrous magnesium sulfate, 4N hydrogen chloride ethyl acetate solution (5 mL) was added, and the solvent was evaporated under reduced pressure. The residue was suspended in ethyl acetate and hexane, and the resulting precipitate was collected by filtration. The obtained solid was dried under reduced pressure to give the title compound (1.14 g) as a colorless solid.

$^1$H NMR (300 MHz, DMSO-d$_6$) δ 0.65-0.83 (2H, m), 0.91-1.02 (11H, m), 2.60-2.78 (1H, m), 2.80-2.92 (2H, m), 8.56 (2H, brs).

Step 2) 3-cyclopropyl-3-(2-((1-(2-(cyclopropyl(2,2-dimethylpropyl)carbamoyl)-5-methoxyphenyl)piperidin-4-yl)methoxy)pyridin-4-yl)propanoic acid In the same manner as in Example 32, step 2 and Example 1, step 4, the title compound (204 mg) was obtained as a colorless amorphous powder from N-(2,2-dimethylpropyl)cyclopropanamine hydrochloride (136 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).

MS (ESI+): [M+H]$^+$ 564.3.

Example 193

3-cyclopropyl-3-(2-((1-(5-methoxy-2-((1-(2,2,2-trifluoroethyl)piperidin-4-yl)carbamoyl)phenyl)piperidin-4-yl)methoxy)pyridin-4-yl)propanoic acid Step 1) 1-(2,2,2-trifluoroethyl)piperidin-4-amine dihydrochloride A solution of tert-butyl piperidin-4-ylcarbamate (1.0 g), 2,2,2-trifluoroethyl trifluoromethanesulfonate (1.51 g) and triethylamine (1.39 mL) in THF (10 mL) was stirred at 70° C. for 11 hr. To the reaction mixture was added water at room temperature, and the mixture was extracted with ethyl acetate. The extract was washed with saturated brine, dried over anhydrous magnesium sulfate, and the solvent was evaporated under reduced pressure. The obtained pale-yellow solid was dissolved in ethanol (35 mL) and methanol (15 mL), 4N hydrogen chloride ethyl acetate solution (15 mL) was added, and the mixture was stirred at room temperature overnight. To the reaction mixture was added hexane, and the resulting precipitate was collected by filtration. The obtained solid was washed with hexane, and dried under reduced pressure to give the title compound (964 mg) as a colorless solid.

$^1$H NMR (300 MHz, DMSO-d$_6$) δ 1.63-1.85 (2H, m), 1.89-2.06 (2H, m), 2.59-2.82 (2H, m), 2.97-3.28 (3H, m), 3.40-3.72 (1H, m), 8.13-8.52 (3H, m).

Step 2) ethyl 3-cyclopropyl-3-(2-((1-(5-methoxy-2-((1-(2,2,2-trifluoroethyl)piperidin-4-yl)carbamoyl)phenyl)piperidin-4-yl)methoxy)pyridin-4-yl)propanoate In the same manner as in Example 32, step 2, the title compound (348 mg) was obtained as a colorless amorphous powder from 1-(2,2,2-trifluoroethyl)piperidin-4-amine dihydrochloride (238 mg) and 2-(4-(((4-(1-cyclopropyl-3-ethoxy-3-oxopropyl)pyridin-2-yl)oxy)methyl)piperidin-1-yl)-4-methoxybenzoic acid (300 mg).

MS (ESI+): [M+H]$^+$ 647.3.

Step 3) 3-cyclopropyl-3-(2-((1-(5-methoxy-2-((1-(2,2,2-trifluoroethyl)piperidin-4-yl)carbamoyl)phenyl)piperidin-4-yl)methoxy)pyridin-4-yl)propanoic acid In the same manner as in Example 1, step 4, the title compound (67 mg) was obtained as a colorless amorphous powder from ethyl 3-cyclopropyl-3-(2-((1-(5-methoxy-2-((1-(2,2,2-trifluoroethyl)piperidin-4-yl)carbamoyl)phenyl)piperidin-4-yl)methoxy)pyridin-4-yl)propanoate (99 mg).

MS (ESI+): [M+H]$^+$ 619.3.

Example 194

3-cyclopropyl-3-(2-((1-(5-methoxy-2-(methyl(1-(2,2,2-trifluoroethyl)piperidin-4-yl)carbamoyl)phenyl)piperidin-4-yl)methoxy)pyridin-4-yl)propanoic acid Step 1) ethyl 3-cyclopropyl-3-(2-((1-(5-methoxy-2-(methyl(1-(2,2,2-trifluoroethyl)piperidin-4-yl)carbamoyl)phenyl)piperidin-4-yl)methoxy)pyridin-4-yl)propanoate In the same manner as in Example 130, step 1, the title compound (116 mg) was obtained as a brown oil from ethyl 3-cyclopropyl-3-(2-((1-(5-methoxy-2-((1-(2,2,2-trifluoroethyl)piperidin-4-yl)carbamoyl)phenyl)piperidin-4-yl)methoxy)pyridin-4-yl)propanoate (130 mg) obtained in Example 193, step 2.

$^1$H NMR (300 MHz, CDCl$_3$) δ 0.09-0.21 (1H, m), 0.23-0.35 (1H, m), 0.39-0.53 (1H, m), 0.54-0.67 (1H, m), 0.91-1.04 (1H, m), 1.13-1.48 (4H, m), 1.65-2.23 (7H, m), 2.24-2.36 (1H, m), 2.44-3.32 (15H, m), 3.62 (2H, s), 3.78-3.85 (3H, m), 4.01-4.70 (4H, m), 6.50-6.64 (3H, m), 6.72-6.80 (1H, m), 7.07-7.20 (1H, m), 7.98-8.09 (1H, m).

Step 2) 3-cyclopropyl-3-(2-((1-(5-methoxy-2-(methyl(1-(2,2,2-trifluoroethyl)piperidin-4-yl)carbamoyl)phenyl)piperidin-4-yl)methoxy)pyridin-4-yl)propanoic acid In the same manner as in Example 1, step 4, the title compound (70 mg) was obtained as a colorless amorphous powder from ethyl 3-cyclopropyl-3-(2-((1-(5-methoxy-2-(methyl(1-(2,2,2-trifluoroethyl)piperidin-4-yl)carbamoyl)phenyl)piperidin-4-yl)methoxy)pyridin-4-yl)propanoate (116 mg).

MS (ESI+): [M+H]$^+$ 633.3.

Example 195

3-(2-((1-(2-((cyclohexylmethyl)(pyridin-2-yl)carbamoyl)-5-methoxyphenyl)piperidin-4-yl)methoxy)pyridin-4-yl)-3-cyclopropylpropanoic acid By a method similar to that in Example 32, step 2 and Example 1, step 4, the title compound (155 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (148.7 mg) and N-(cyclohexylmethyl)pyridin-2-amine (117 mg).

MS (ESI+): [M+H]$^+$ 627.2.

Example 196

3-cyclopropyl-3-(2-((1-(5-methoxy-2-(pyridin-2-yl(tetrahydro-2H-pyran-4-ylmethyl)carbamoyl)phenyl)piperidin-4-yl)methoxy)pyridin-4-yl)propanoic acid By a method similar to that in Example 32, step 2 and Example 1, step 4, the title compound (91 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (148.7 mg) and N-((tetrahydro-2H-pyran-4-yl)methyl)pyridin-2-amine (118 mg).

MS (ESI+): [M+H]$^+$ 629.4.

Example 197

3-(2-((1-(2-(benzyl(pyridin-2-yl)carbamoyl)-5-methoxyphenyl)piperidin-4-yl)methoxy)pyridin-4-yl)-3-cyclopropylpropanoic acid By a method similar to that in Example 32, step 2 and Example 1, step 4, the title compound (158 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (148.7 mg) and N-benzylpyridin-2-amine (114 mg).

MS (ESI+): [M+H]$^+$ 621.4.

Example 198

3-(2-((1-(2-(cyclopentyl(2,2-dimethylpropyl)carbamoyl)-5-methoxyphenyl)piperidin-4-yl)methoxy)pyridin-4-yl)-3-cyclopropylpropanoic acid By a method similar to that in Example 32, step 2 and Example 1, step 4, the title compound (12.9 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (118 mg) and N-(2,2-dimethylpropyl)cyclopentanamine (379 mg).

MS (ESI+): [M+H]$^+$ 592.3.

Example 199

3-cyclopropyl-3-(2-((1-(2-(2,3-dihydro-4H-1,4-benzoxazin-4-ylcarbonyl)-5-methoxyphenyl)piperidin-4-yl)methoxy)pyridin-4-yl)propanoic acid By a method similar to that in Example 32, step 2 and Example 1, step 4, the title compound (146 mg) was obtained as a white amorphous powder from 2-(4-(((4-(1- cyclopropyl-3-ethoxy-3-oxopropyl)pyridin-2-yl)oxy)methyl)piperidin-1-yl)-4-methoxybenzoic acid (148.7 mg) and 3,4-dihydro-2H-benzo[b][1,4]oxazine (83 mg).
MS (ESI+): [M+H]$^+$ 572.2.

Example 200

3-cyclopropyl-3-(2-((1-(5-methoxy-2-((3-phenyl-morpholin-4-yl)carbonyl)phenyl)piperidin-4-yl)methoxy)pyridin-4-yl)propanoic acid By a method similar to that in Example 32, step 2 and Example 1, step 4, the title compound (95 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (116.6 mg) and 3-phenylmorpholine hydrochloride (96 mg).
MS (ESI+): [M+H]$^+$ 600.2.

Example 201

3-(2-((1-(2-((3-benzylmorpholin-4-yl)carbonyl)-5-methoxyphenyl)piperidin-4-yl)methoxy)pyridin-4-yl)-3-cyclopropylpropanoic acid By a method similar to that in Example 32, step 2 and Example 1, step 4, the title compound (108 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (116.6 mg) and 3-benzylmorpholine hydrochloride (103 mg).
MS (ESI+): [M+H]$^+$ 614.3.

Example 202

3-cyclopropyl-3-(2-((1-(5-methoxy-2-((2,2,6,6-tetrafluoromorpholin-4-yl)carbonyl)phenyl)piperidin-4-yl)methoxy)pyridin-4-yl)propanoic acid By a method similar to that in Example 32, step 2 and Example 1, step 4, the title compound (114 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (116.6 mg) and 2,2,6,6-tetrafluoromorpholine (77 mg).
MS (ESI+): [M+H]$^+$ 596.1.

Example 203

3-cyclopropyl-3-(2-((1-(5-methoxy-2-(((3S)-3-(2-methylpropyl)morpholin-4-yl)carbonyl)phenyl)piperidin-4-yl)methoxy)pyridin-4-yl)propanoic acid By a method similar to that in Example 32, step 2 and Example 1, step 4, the title compound (71.4 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (116.6 mg) and (S)-3-(2-methylpropyl)morpholine hydrochloride (261 mg).
MS (ESI+): [M+H]$^+$ 580.3.

Example 204

3-cyclopropyl-3-(2-((1-(5-methoxy-2-((2-phenyl-morpholin-4-yl)carbonyl)phenyl)piperidin-4-yl)methoxy)pyridin-4-yl)propanoic acid By a method similar to that in Example 32, step 2 and Example 1, step 4, the title compound (105 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (114.7 mg) and 2-phenylmorpholine hydrochloride (95 mg).
MS (ESI+): [M+H]$^+$ 600.2.

Example 205

3-cyclopropyl-3-(2-((1-(5-methoxy-2-((2-(2-methylpropyl)morpholin-4-yl)carbonyl)phenyl)piperidin-4-yl)methoxy)pyridin-4-yl)propanoic acid By a method similar to that in Example 32, step 2 and Example 1, step 4, the title compound (110 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (114.7 mg) and 2-(2-methylpropyl)morpholine (68.1 mg).
MS (ESI+): [M+H]$^+$ 580.3.

Example 206

3-cyclopropyl-3-(2-((1-(2-(cyclopropyl(2,2,3,3-tetrafluoropropyl)carbamoyl)-5-methoxyphenyl)piperidin-4-yl)methoxy)pyridin-4-yl)propanoic acid In the same manner as in Example 14, step 1, Example 32, step 2 and Example 1, step 4, the title compound (126 mg) was obtained as a white amorphous powder from cyclopropylamine (81 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).
MS (ESI+): [M+H]$^+$ 608.2.

Example 207

3-(2-((1-(2-(cyclobutyl(2,2,3,3-tetrafluoropropyl)carbamoyl)-5-methoxyphenyl)piperidin-4-yl)methoxy)pyridin-4-yl)-3-cyclopropylpropanoic acid In the same manner as in Example 14, step 1, Example 32, step 2 and Example 1, step 4, the title compound (186 mg) was obtained as a white amorphous powder from cyclobutylamine (101 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).
MS (ESI+): [M+H]$^+$ 622.3.

Example 208

3-(2-((1-(2-(cyclopentyl(2,2,3,3-tetrafluoropropyl)carbamoyl)-5-methoxyphenyl)piperidin-4-yl)methoxy)pyridin-4-yl)-3-cyclopropylpropanoic acid In the same manner as in Example 14, step 1, Example 32, step 2 and Example 1, step 4, the title compound (89 mg) was obtained as a white amorphous powder from cyclopentylamine (121 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).
MS (ESI+): [M+H]$^+$ 636.3.

Example 209

3-cyclopropyl-3-(2-((1-(2-(ethyl(2,2,3,3,3-pentafluoropropyl)carbamoyl)-5-methoxyphenyl)piperidin-4-yl)methoxy)pyridin-4-yl)propanoic acid Step 1)
N-ethyl-2,2,3,3,3-pentafluoropropan-1-amine In a sealed tube, a mixture of 2M ethanamine THF solution (0.71 mL), 2,2,3,3,3-pentafluoropropyl trifluoromethane sulfonate (400 mg), triethylamine (0.20 mL) and THF (0.3 mL) was stirred at 60° C. for 2.5 hr. This compound in the form of a reaction mixture was used for the next step without purification.

Step 2) 3-cyclopropyl-3-(2-((1-(2-(ethyl(2,2,3,3,3-pentafluoropropyl)carbamoyl)-5-methoxyphenyl)piperidin-4-yl)methoxy)pyridin-4-yl)propanoic acid In the same manner as in Example 32, step 2 and Example 1, step 4, the title compound (183 mg) was obtained as a colorless amorphous powder from the reaction mixture obtained in step 1 and 2-(4-(((4-(1-cyclopropyl-3-ethoxy-3-oxopropyl)pyridin-2-yl)oxy)methyl)piperidin-1-yl)-4-methoxybenzoic acid (200 mg).
MS (ESI+): [M+H]$^+$ 614.3.

Example 210

3-cyclopropyl-3-(2-((1-(5-methoxy-2-((2,2,3,3,3-pentafluoropropyl)(propan-2-yl)carbamoyl)phenyl)piperidin-4-yl)methoxy)pyridin-4-yl)propanoic acid In the same manner as in Example 32, step 2 and Example 1, step 4, the title compound (172 mg) was obtained as a colorless amorphous powder from 2,2,3,3,3-pentafluoro-N-(propan-2-yl)propan-1-amine hydrochloride (189 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).
MS (ESI+): [M+H]$^+$ 628.2.

Example 211

3-cyclopropyl-3-(2-((1-(2-(cyclopropyl(2,2,3,3,3-pentafluoropropyl)carbamoyl)-5-methoxyphenyl)piperidin-4-yl)methoxy)pyridin-4-yl)propanoic acid In the same manner as in Example 209, step 1 and step 2, the title compound (113 mg) was obtained as a colorless amorphous powder from cyclopropanamine (81 mg), 2,2,3,3,3-pentafluoropropyl trifluoromethanesulfonate (400 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).
MS (ESI+): [M+H]$^+$ 626.2.

Example 212

3-(2-((1-(2-(cyclobutyl(2,2,3,3,3-pentafluoropropyl)carbamoyl)-5-methoxyphenyl)piperidin-4-yl)methoxy)pyridin-4-yl)-3-cyclopropylpropanoic acid In the same manner as in Example 209, step 1 and step 2, the title compound (138 mg) was obtained as a colorless amorphous powder from cyclobutanamine (101 mg), 2,2,3,3,3-pentafluoropropyl trifluoromethanesulfonate (400 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).
MS (ESI+): [M+H]$^+$ 640.3.

Example 213

3-cyclopropyl-3-(2-((1-(2-(ethyl(2,2,3,3-tetrafluoropropyl)carbamoyl)-5-methoxyphenyl)piperidin-4-yl)methoxy)pyridin-4-yl)propanoic acid In the same manner as in Example 209, step 1 and step 2, the title compound (193 mg) was obtained as a colorless amorphous powder from 2M ethanamine THF solution (0.75 mL), 2,2,3,3-tetrafluoropropyl trifluoromethanesulfonate (400 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).
MS (ESI+): [M+H]$^+$ 596.2.

Example 214

3-cyclopropyl-3-(2-((1-(5-methoxy-2-(propan-2-yl(2,2,3,3-tetrafluoropropyl)carbamoyl)phenyl)piperidin-4-yl)methoxy)pyridin-4-yl)propanoic acid In the same manner as in Example 209, step 1 and step 2, the title compound (59 mg) was obtained as a colorless amorphous powder from propan-2-amine (89 mg), 2,2,3,3-tetrafluoropropyl trifluoromethanesulfonate (400 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).
MS (ESI+): [M+H]$^+$ 610.2.

Example 215

3-cyclopropyl-3-(2-((1-(5-methoxy-2-(propan-2-yl(2,2,2-trifluoroethyl)carbamoyl)phenyl)piperidin-4-yl)methoxy)pyridin-4-yl)propanoic acid In the same manner as in Example 209, step 1 and step 2, the title compound (114 mg) was obtained as a colorless amorphous powder from propan-2-amine (89 mg), 2,2,2-trifluoroethyl trifluoromethanesulfonate (350 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).
MS (ESI+): [M+H]$^+$ 578.2.

Example 216

3-cyclopropyl-3-(2-((1-(2-(ethyl(2,2,2-trifluoroethyl)carbamoyl)-5-methoxyphenyl)piperidin-4-yl)methoxy)pyridin-4-yl)propanoic acid By a method similar to that in Example 32, step 2 and Example 1, step 4, the title compound (149 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (159.6 mg) and N-ethyl-2,2,2-trifluoroethanamine hydrochloride (108 mg).
MS (ESI+): [M+H]$^+$ 564.3.

Example 217

3-(2-((1-(2-(bis(2,2,2-trifluoroethyl)carbamoyl)-5-methoxyphenyl)piperidin-4-yl)methoxy)pyridin-4-yl)-3-cyclopropylpropanoic acid By a method similar to that in Example 32, step 2 and Example 1, step 4, the title compound (77 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (159.6 mg) and bis(2,2,2-trifluoroethyl)amine (109 μl).
MS (ESI+): [M+H]$^+$ 618.2.

Example 218

3-cyclopropyl-3-(2-((1-(2-(cyclopropyl(2,2,2-trifluoroethyl)carbamoyl)-5-methoxyphenyl)piperidin-4-yl)methoxy)pyridin-4-yl)propanoic acid In the same manner as in Example 209, step 1 and step 2, the title compound (161 mg) was obtained as a grayish white amorphous powder from cyclopropanamine (100 mg), 2,2,2-trifluoroethyl trifluoromethanesulfonate (407 mg) and 2-(4-(((4-(1-cyclopropyl-3-ethoxy-3-oxopropyl)pyridin-2-yl)oxy)methyl)piperidin-1-yl)-4-methoxybenzoic acid (211 mg).
MS (ESI+): [M+H]$^+$ 576.2.

Example 219

3-(2-((1-(2-(cyclobutyl(2,2,2-trifluoroethyl)carbamoyl)-5-methoxyphenyl)piperidin-4-yl)methoxy)pyridin-4-yl)-3-cyclopropylpropanoic acid In the same manner as in Example 209, step 1 and step 2, the title compound (101 mg) was obtained as a grayish white amorphous powder from cyclobutanamine (100 mg), 2,2,2-trifluoroethyl trifluoromethanesulfonate (326 mg) and 2-(4-(((4-(1-cyclopropyl-3-ethoxy-3-oxopropyl)pyridin-2-yl)oxy)methyl)piperidin-1-yl)-4-methoxybenzoic acid (204 mg).
MS (ESI+): [M+H]$^+$ 590.3.

Example 220

3-(2-((1-(2-(cyclopentyl(2,2,2-trifluoroethyl)carbamoyl)-5-methoxyphenyl)piperidin-4-yl)methoxy)pyridin-4-yl)-3-cyclopropylpropanoic acid In the same manner as in Example 209, step 1 and step 2, the title compound (30 mg) was obtained as a pale-yellow amorphous powder from cyclopentanamine (100 mg), 2,2,2-trifluoroethyl trifluoromethanesulfonate (273 mg) and 2-(4-(((4-(1-cyclopropyl-3-ethoxy-3-oxopropyl)pyridin-2-yl)oxy)methyl)piperidin-1-yl)-4-methoxybenzoic acid (198 mg).
MS (ESI+): [M+H]$^+$ 604.4.

Example 221

3-cyclopropyl-3-(2-((1-(2-(2,3-dihydro-1-benzofuran-3-yl(2,2,3,3-tetrafluoropropyl)carbamoyl)-5-methoxyphenyl)piperidin-4-yl)methoxy)pyridin-4-yl)propanoic acid In the same manner as in Example 14, step 1, Example 32, step 2 and Example 1, step 4, the title compound (120 mg) was obtained as a white amorphous powder from 2,3-dihydro-1-benzofuran-3-amine (266 mg) and 2-(4-(((4-(1-cyclopropyl-3-ethoxy-3-oxopropyl)pyridin-2-yl)oxy)methyl)piperidin-1-yl)-4-methoxybenzoic acid (449 mg).
MS (ESI+): [M+H]$^+$ 686.3.

Example 222

3-cyclopropyl-3-(2-((1-(2-((2,2-dimethylpropyl)(6-(trifluoromethyl)pyridin-2-yl)carbamoyl)-5-methoxyphenyl)piperidin-4-yl)methoxy)pyridin-4-yl)propanoic acid Step 1) N-(2,2-dimethylpropyl)-6-(trifluoromethyl)pyridin-2-amine In a sealed tube, a mixture of 2-chloro-6-(trifluoromethyl)pyridine (310 mg) and 2,2-dimethylpropan-1-amine (744 mg) was stirred at 100° C. for 18 hr. After allowing to cool to room temperature, the reaction mixture was purified by silica gel column chromatography (ethyl acetate/hexane) to give the title compound (200 mg) as a mixture with 2-chloro-6-(trifluoromethyl)pyridine. This compound in the form of a reaction mixture was used for the next step without further purification.
$^1$H NMR (300 MHz, CDCl$_3$) δ 0.99 (9H, s), 3.10 (2H, d, J=6.2 Hz), 4.82 (1H, brs), 6.54 (1H, d, J=8.5 Hz), 6.89 (1H, d, J=7.3 Hz), 7.51 (1H, t, J=8.0 Hz).

Step 2) 3-cyclopropyl-3-(2-((1-(2-((2,2-dimethylpropyl)(6-(trifluoromethyl)pyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (87 mg) was obtained as a colorless amorphous powder from a crude purified product (193 mg) of N-(2,2-dimethylpropyl)-6-(trifluoromethyl)pyridin-2-amine and 2-(4-(((4-(1-cyclopropyl-3-ethoxy-3-oxopropyl)pyridin-2-yl)oxy)methyl)piperidin-1-yl)-4-methoxybenzoic acid (200 mg).
MS (ESI+): [M+H]$^+$ 669.3.

Example 223

3-cyclopropyl-3-(2-((1-(2-((2,2-dimethylpropyl)(4-(trifluoromethyl)pyrimidin-2-yl)carbamoyl)-5-methoxyphenyl)piperidin-4-yl)methoxy)pyridin-4-yl)propanoic acid Step 1) N-(2,2-dimethylpropyl)-4-(trifluoromethyl)pyrimidin-2-amine In a sealed tube, a mixture of 2-chloro-4-(trifluoromethyl)pyrimidine (300 mg) and 2,2-dimethylpropan-1-amine (358 mg) was stirred at 100° C. for 18 hr. After allowing to cool to room temperature, the reaction mixture was purified by silica gel column chromatography (ethyl acetate/hexane) to give the title compound (364 mg) as a colorless solid.
$^1$H NMR (300 MHz, CDCl$_3$) δ 0.97 (9H, s), 3.31 (2H, d, J=6.4 Hz), 5.43 (1H, brs), 6.78 (1H, d, J=4.9 Hz), 8.45 (1H, brs).

Step 2) 3-cyclopropyl-3-(2-((1-(2-((2,2-dimethylpropyl)(4-(trifluoromethyl)pyrimidin-2-yl)carbamoyl)-5-methoxyphenyl)piperidin-4-yl)methoxy)pyridin-4-yl)propanoic acid In the same manner as in Example 32, step 2 and Example 1, step 4, the title compound (161 mg) was obtained as a colorless amorphous powder from N-(2,2-dimethylpropyl)-4-(trifluoromethyl)pyrimidin-2-amine (193 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).
MS (ESI+): [M+H]+ 670.3.

Example 224

3-cyclopropyl-3-(2-((1-(2-((4-cyclopropylpyrimidin-2-yl)(2,2-dimethylpropyl)carbamoyl)-5-methoxyphenyl)piperidin-4-yl)methoxy)pyridin-4-yl)propanoic acid Step 1) 2-chloro-4-cyclopropylpyrimidine To a solution of 2,4-dichloropyrimidine (5.0 g) and acetylacetone iron (III) in THF (30 mL) and N-methyl-2-pyrrolidone (NMP) (5 mL) was added dropwise 1 M cyclopropylmagnesium bromide (67 mL) under ice-cooling. The reaction mixture was stirred at room temperature for 1 hr. To the reaction mixture was added water at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (3.1 g) as an orange oil.
$^1$H NMR (300 MHz, CDCl$_3$) δ 1.08-1.32 (4H, m), 1.92-2.07 (1H, m), 7.08 (1H, d, J=5.1 Hz), 8.35 (1H, d, J=5.1 Hz).

Step 2) 4-cyclopropyl-N-(2,2-dimethylpropyl)pyrimidin-2-amine

In the same manner as in Example 45, step 8, the title compound (1.79 g) was obtained as pale-yellow crystals from 2-chloro-4-cyclopropylpyrimidine (1.5 g).
MS (ESI+): [M+H]+ 206.2.

Step 3) 3-cyclopropyl-3-(2-((1-(2-((4-cyclopropylpyrimidin-2-yl)(2,2-dimethylpropyl)carbamoyl)-5-methoxyphenyl)piperidin-4-yl)methoxy)pyridin-4-yl)propanoic acid In the same manner as in Example 32, step 2 and Example 1, step 4, the title compound (58 mg) was obtained as a pale-yellow amorphous powder from 4-cyclopropyl-N-(2,2-dimethylpropyl)pyrimidin-2-amine (145 mg) and 2-(4-(((4-(1-cyclopropyl-3-ethoxy-3-oxopropyl)pyridin-2-yl)oxy)methyl)piperidin-1-yl)-4-methoxybenzoic acid (170 mg).
MS (ESI+): [M+H]+ 642.3.

Example 225

3-cyclopropyl-3-(2-((1-(2-((2,2-dimethylpropyl)(4-((2,2-dimethylpropyl)carbamoyl)-6-methylpyridin-2-yl)carbamoyl)-5-methoxyphenyl)piperidin-4-yl)methoxy)pyridin-4-yl)propanoic acid Step 1) N-(2,2-dimethylpropyl)-2-((2,2-dimethylpropyl)amino)-6-methylisonicotinamide In a sealed tube, a mixture of methyl 2-chloro-6-methylisonicotinate (300 mg), 2,2-dimethylpropan-1-amine (423 mg), palladium acetate (36 mg), (9,9-dimethyl-9H-xanthene-4,5-diyl)bis(diphenylphosphine) (94 mg), sodium tert-butoxide (233 mg) and toluene (1.5 mL) was stirred at 100° C. for 20 min. The reaction mixture was purified by silica gel column chromatography (ethyl acetate/hexane) to give the title compound (110 mg) as a colorless amorphous powder.
$^1$H NMR (300 MHz, CDCl$_3$) δ 0.91-1.07 (18H, m, J=2.5 Hz), 2.41 (3H, s), 3.07 (2H, d, J=6.0 Hz), 3.25 (2H, d, J=6.4 Hz), 4.72 (1H, t, J=5.7 Hz), 5.98-6.18 (1H, m), 6.58 (2H, s).

Step 2) 3-cyclopropyl-3-(2-((1-(2-((2,2-dimethylpropyl)(4-((2,2-dimethylpropyl)carbamoyl)-6-methylpyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (27 mg) was obtained as a colorless amorphous powder from N-(2,2-dimethylpropyl)-2-((2,2-dimethylpropyl)amino)-6-methylisonicotinamide (110 mg) and 2-(4-(((4-(1-cyclopropyl-3-ethoxy-3-oxopropyl)pyridin-2-yl)oxy)methyl)piperidin-1-yl)-4-methoxybenzoic acid (100 mg).
MS (ESI+): [M+H]+ 728.5.

Example 226

3-cyclopropyl-3-(2-((1-(2-((2,2-dimethylpropyl)(6-methyl-4-(pyrrolidin-1-ylcarbonyl)pyridin-2-yl)carbamoyl)-5-methoxyphenyl)piperidin-4-yl)methoxy)pyridin-4-yl)propanoic acid Step 1) (2-chloro-6-methylpyridin-4-yl)(pyrrolidin-1-yl)methanone In the same manner as in Example 32, step 2, the title compound (580 mg) was obtained as a colorless solid from pyrrolidine (228 mg) and 2-chloro-6-methylisonicotinic acid (500 mg).
$^1$H NMR (300 MHz, CDCl$_3$) δ 1.85-2.05 (4H, m), 2.57 (3H, s), 3.37 (2H, t, J=6.4 Hz), 3.63 (2H, t, J=6.8 Hz), 7.16 (1H, d, J=0.6 Hz), 7.19-7.24 (1H, m).

Step 2) (2-((2,2-dimethylpropyl)amino)-6-methylpyridin-4-yl)(pyrrolidin-1-yl)methanone In the same manner as in Example 225, step 1, the title compound (105 mg) was obtained as brown solid from (2-chloro-6-methylpyridin-4-yl)(pyrrolidin-1-yl)methanone (100 mg).
$^1$H NMR (300 MHz, CDCl$_3$) δ 0.98 (9H, s), 1.80-2.02 (4H, m), 2.37 (3H, s), 3.01 (2H, d, J=6.1 Hz), 3.38 (2H, t, J=6.5 Hz), 3.61 (2H, t, J=6.8 Hz), 4.68 (1H, t, J=5.9 Hz), 6.25 (1H, s), 6.45 (1H, s).

Step 3) 3-cyclopropyl-3-(2-((1-(2-((2,2-dimethylpropyl)(6-methyl-4-(pyrrolidin-1-ylcarbonyl)pyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (28 mg) was obtained as a colorless amorphous powder from (2-((2,2-dimethylpropyl)amino)-6-methylpyridin-4-yl)(pyrrolidin-1-yl)methanone (105 mg) and 2-(4-(((4-(1-cyclopropyl-3-ethoxy-3-oxopropyl)pyridin-2-yl)oxy)methyl)piperidin-1-yl)-4-methoxybenzoic acid (100 mg).
MS (ESI+): [M+H]+ 712.4.

Example 227

3-cyclopropyl-3-(2-((1-(2-((2,2-dimethylpropyl)(1-methyl-2-oxo-1,2-dihydropyridin-3-yl)carbamoyl)-5-methoxyphenyl)piperidin-4-yl)methoxy)pyridin-4-yl)propanoic acid

Step 1) 3-((2,2-dimethylpropyl)amino)pyridin-2 (1H)-one

Under a nitrogen atmosphere, 2,2-dimethylpropanoyl chloride (1.29 mL) was added to a solution of 2-methoxy-pyridin-3-amine (1.0 g) in DMA (10 mL) at room temperature, and the mixture was stirred at room temperature for 30 min. To the reaction solution was added water at room temperature, and the mixture was extracted with ethyl acetate. The extract was washed with water and saturated brine, dried over anhydrous magnesium sulfate, and the solvent was evaporated under reduced pressure. Under a nitrogen atmosphere, the obtained residue was dissolved in THF. The solution was added to a suspension of lithium aluminum hydride in THF (20 mL) at room temperature, and the mixture was heated under reflux for 2 hr. To the reaction solution were added water and aqueous sodium hydroxide solution, and the resulting precipitate was removed by filtration. The solvent in the filtrate was evaporated under reduced pressure, and the residue was purified by silica gel column chromatography (ethyl acetate/hexane) to give the title compound (882 mg) as a pale-green solid.

$^1$H NMR (400 MHz, DMSO-$d_6$) δ 0.93 (9H, s), 2.82 (2H, d, J=6.1 Hz), 5.03 (1H, t, J=5.8 Hz), 6.06 (1H, t, J=6.8 Hz), 6.25 (1H, d, J=7.0 Hz), 6.57 (1H, d, J=6.5 Hz), 11.39 (1H, brs).

Step 2) 3-((2,2-dimethylpropyl)amino)-1-methyl-pyridin-2(1H)-one

Under a nitrogen atmosphere, 1,1'-(azodicarbonyl)dipiperidine (336 mg) and tributylphosphine (329 μL) were added to a solution of 3-((2,2-dimethylpropyl)amino)pyridin-2 (1H)-one (150 mg) and methanol (51 μL) in toluene (10 mL) at room temperature, and the mixture was stirred for 16 hr. The reaction solution was diluted with ethyl acetate/hexane (1:1), and the resulting white precipitate was removed by filtration. The solvent in the filtrate was evaporated under reduced pressure, and the residue was purified by silica gel column chromatography (ethyl acetate/hexane) to give the title compound (144 mg) as a green oil.

$^1$H NMR (400 MHz, CDCl$_3$) δ 1.00 (9H, s), 2.84 (2H, d, J=5.9 Hz), 3.56 (3H, s), 5.13 (1H, brs), 6.07-6.14 (1H, m), 6.14-6.19 (1H, m), 6.57 (1H, d, J=5.6 Hz).

Step 3) ethyl 3-cyclopropyl-3-(2-((1-(5-methoxy-2-((1-methyl-2-oxo-1,2-dihydropyridin-3-yl)((2,2-dimethylpropyl))carbamoyl)phenyl)piperidin-4-yl)methoxy)pyridin-4-yl)propanoate In the same manner as in Example 32, step 2, the title compound (111 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (100 mg) and 3-((2,2-dimethylpropyl)amino)-1-methylpyridin-2(1H)-one (55.4 mg).

MS (ESI+): [M+H]$^+$ 659.6.

Step 4) 3-cyclopropyl-3-(2-((1-(2-((2,2-dimethylpropyl)(1-methyl-2-oxo-1,2-dihydropyridin-3-yl)carbamoyl)-5-methoxyphenyl)piperidin-4-yl)methoxy)pyridin-4-yl)propanoic acid In the same manner as in Example 1, step 4, the title compound (97.4 mg) was obtained as a white amorphous powder from ethyl 3-cyclopropyl-3-(2-((1-(5-methoxy-2-((1-methyl-2-oxo-1,2-dihydropyridin-3-yl)((2,2-dimethylpropyl))carbamoyl)phenyl)piperidin-4-yl)methoxy)pyridin-4-yl)propanoate (111 mg).

MS (ESI+): [M+H]$^+$ 631.3.

Example 228

3-cyclopropyl-3-(2-((1-(2-((2,2-dimethylpropyl)(2,6-dimethylpyrimidin-4-yl)carbamoyl)-5-methoxyphenyl)piperidin-4-yl)methoxy)pyridin-4-yl)propanoic acid

Step 1) N-(2,2-dimethylpropyl)-2,6-dimethylpyrimidin-4-amine

In a sealed tube, a mixture of 4-chloro-2,6-dimethylpyrimidine (360 mg), 2,2-dimethylpropan-1-amine (440 mg), triethylamine (511 mg) and NMP (0.3 mL) was stirred at 70° C. for 12 hr. To the reaction mixture was added water at room temperature, and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (405 mg) as a colorless oil.

$^1$H NMR (300 MHz, CDCl$_3$) δ 0.98 (9H, s), 2.32 (3H, s), 2.46 (3H, s), 3.04 (2H, d, J=6.1 Hz), 4.89 (1H, brs), 6.02 (1H, s).

Step 2) 3-cyclopropyl-3-(2-((1-(2-((2,2-dimethylpropyl)(2,6-dimethylpyrimidin-4-yl)carbamoyl)-5-methoxyphenyl)piperidin-4-yl)methoxy)pyridin-4-yl)propanoic acid In the same manner as in Example 32, step 2 and Example 1, step 4, the title compound (10 mg) was obtained as a colorless amorphous powder from N-(2,2-dimethylpropyl)-2,6-dimethylpyrimidin-4-amine (190 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).

MS (ESI+): [M+H]$^+$ 630.3.

Example 229

3-cyclopropyl-3-(2-((1-(2-((2,2-dimethylpropyl)(2-methylpyrimidin-4-yl)carbamoyl)-5-methoxyphenyl)piperidin-4-yl)methoxy)pyridin-4-yl)propanoic acid In the same manner as in Example 228, step 1 and step 2, the title compound (8 mg) was obtained as a colorless amorphous powder from 4-chloro-2-methylpyrimidine (200 mg), 2,2-dimethylpropan-1-amine (271 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).

MS (ESI+): [M+H]$^+$ 616.3.

Example 230

3-cyclopropyl-3-(2-((1-(2-((2,2-dimethylpropyl)(6-methylpyrimidin-4-yl)carbamoyl)-5-methoxyphenyl)piperidin-4-yl)methoxy)pyridin-4-yl)propanoic acid In the same manner as in Example 228, step 1 and step 2, the title compound (102 mg) was obtained as a colorless amorphous powder from 4-chloro-6-methylpyrimidine (200 mg), 2,2-dimethylpropan-1-amine (271 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).
MS (ESI+): [M+H]$^+$ 616.3.

Example 231

3-cyclopropyl-3-(2-((1-(2-((2,2-dimethylpropyl)(5-methylpyridin-3-yl)carbamoyl)-5-methoxyphenyl)piperidin-4-yl)methoxy)pyridin-4-yl)propanoic acid Step 1) N-(2,2-dimethylpropyl)-5-methylpyridin-3-amine In the same manner as in Example 32, step 1, the title compound (529 mg) was obtained as a pale-yellow solid from 5-methylpyridin-3-amine (500 mg).
MS (ESI+): [M+H]$^+$ 179.1.

Step 2) 3-cyclopropyl-3-(2-((1-(2-((2,2-dimethylpropyl)(5-methylpyridin-3-yl)carbamoyl)-5-methoxyphenyl)piperidin-4-yl)methoxy)pyridin-4-yl)propanoic acid In the same manner as in Example 32, step 2 and Example 1, step 4, the title compound (72.3 mg) was obtained as a pale-yellow oil from 2-(4-(((4-(1-cyclopropyl-3-ethoxy-3-oxopropyl)pyridin-2-yl)oxy)methyl)piperidin-1-yl)-4-methoxybenzoic acid (379 mg) and N-(2,2-dimethylpropyl)-5-methylpyridin-3-amine (70 mg).
MS (ESI+): [M+H]$^+$ 615.3.

Example 232

3-cyclopropyl-3-(2-((1-(2-((2,2-dimethylpropyl)(5-methylpyridazin-3-yl)carbamoyl)-5-methoxyphenyl)piperidin-4-yl)methoxy)pyridin-4-yl)propanoic acid Step 1) N-(2,2-dimethylpropyl)-5-methylpyridazin-3-amine In the same manner as in Example 225, step 1, the title compound (110 mg) was obtained as a pale-yellow solid from 3-chloro-5-methylpyridazine (200 mg) and 2,2-dimethylpropan-1-amine (271 mg).
$^1$H NMR (300 MHz, CDCl$_3$) δ 1.00 (9H, s), 2.23 (3H, d, J=0.4 Hz), 3.16 (2H, d, J=6.2 Hz), 4.74 (1H, brs), 6.44 (1H, d, J=0.8 Hz), 8.38 (1H, d, J=1.6 Hz).

Step 2) 3-cyclopropyl-3-(2-((1-(2-((2,2-dimethylpropyl)(5-methylpyridazin-3-yl)carbamoyl)-5-methoxyphenyl)piperidin-4-yl)methoxy)pyridin-4-yl)propanoic acid In the same manner as in Example 32, step 2 and Example 1, step 4, the title compound (64 mg) was obtained as a colorless amorphous powder from N-(2,2-dimethylpropyl)-5-methylpyridazin-3-amine (80 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).
MS (ESI+): [M+H]$^+$ 616.3.

Example 233

3-cyclopropyl-3-(2-((1-(2-((2,2-dimethylpropyl)(1-(2,2,2-trifluoroethyl)piperidin-3-yl)carbamoyl)-5-methoxyphenyl)piperidin-4-yl)methoxy)pyridin-4-yl)propanoic acid Step 1) benzyl 3-oxopiperidine-1-carboxylate A mixture of piperidin-3-one hydrochloride (500 mg), benzyl carbonochloridate (1.58 mL), triethylamine (2.57 mL), THF (15 mL) and pyridine (5 mL) was stirred at 60° C. for 30 min. The solvent was evaporated under reduced pressure, and the residue was purified by silica gel column chromatography (ethyl acetate/hexane) to give the title compound (770 mg) as a mixture with benzyl alcohol.
$^1$H NMR (300 MHz, CDCl$_3$) δ 1.90-2.07 (2H, m), 2.48 (2H, t, J=6.7 Hz), 3.58-3.72 (2H, m), 4.08 (2H, s), 5.15 (2H, s), 7.27-7.44 (5H, m).

Step 2) benzyl 3-((tert-butoxycarbonyl)(2,2-dimethylpropyl)amino)piperidine-1-carboxylate A crude purified product (770 mg) of benzyl 3-oxopiperidine-1-carboxylate, 2,2-dimethylpropan-1-amine (643 mg) and acetic acid (0.5 mL) were dissolved in THF (10 mL), and sodium triacetoxyborohydride (1563 mg) was added at room temperature. The mixture was stirred at room temperature for 1 hr, to the reaction mixture was added water at room temperature, and the mixture was extracted with ethyl acetate. The extract was washed with saturated brine, dried over anhydrous magnesium sulfate, and the solvent was evaporated under reduced pressure. The obtained residue was dissolved in THF (10 mL), di-tert-butyl dicarbonate (1610 mg) and triethylamine (2.57 mL) were added at room temperature, and the mixture was stirred at 60° C. for 6 hr. The solvent was evaporated under reduced pressure, and the residue was purified by silica gel column chromatography (ethyl acetate/hexane) to give the title compound (690 mg) as a colorless oil.
$^1$H NMR (300 MHz, CDCl$_3$) δ 0.89 (9H, brs), 1.31-1.53 (10H, m), 1.66-1.95 (2H, m), 2.10-3.82 (6H, m), 3.99-4.27 (2H, m), 4.99-5.22 (2H, m), 7.28-7.41 (5H, m).

Step 3) N-(2,2-dimethylpropyl)-1-(2,2,2-trifluoroethyl)piperidin-3-amine dihydrochloride Under a hydrogen atmosphere, a solution of benzyl 3-((tert-butoxycarbonyl)(2,2-dimethylpropyl)amino)piperidine-1-carboxylate (690 mg) and 10% palladium carbon (55% water-containing, 403 mg) in methanol (10 mL) was stirred at room temperature for 2 hr. The reaction mixture was filtered through celite, and the filtrate was concentrated under reduced pressure. The obtained residue was dissolved in THF (5 mL), 2,2,2-trifluoroethyl trifluoromethanesulfonate (594 mg) and triethylamine (0.475 mL) were added, and the mixture was stirred at 60° C. for 3 hr. To the reaction mixture was added saturated aqueous sodium hydrogen carbonate solution at room temperature, and the mixture was extracted with ethyl acetate. The extract was washed with saturated brine, dried over anhydrous magnesium sulfate, and the solvent was evaporated under reduced pressure. The obtained residue was dissolved in methanol (5 mL), 4N hydrogen chloride ethyl acetate solution (2.56 mL) was added, and the mixture was stirred at room temperature overnight. The solvent was evaporated under reduced pressure, the residue was suspended in methanol, ethyl acetate and hexane, and the resulting precipitate was collected by filtration. The obtained solid was dried under reduced pressure to give the title compound (474 mg) as a colorless solid.

$^1$H NMR (300 MHz, DMSO-$d_6$) δ 1.01 (9H, s), 1.38-1.62 (2H, m), 1.66-1.84 (1H, m), 2.01-2.19 (1H, m), 2.31-2.47 (1H, m), 2.59-2.96 (4H, m), 3.05-3.25 (1H, m), 3.27-3.46 (3H, m), 8.28-9.90 (3H, m).

Step 4) 3-cyclopropyl-3-(2-((1-(2-((2,2-dimethylpropyl)(1-(2,2,2-trifluoroethyl)piperidin-3-yl)carbamoyl)-5-methoxyphenyl)piperidin-4-yl)methoxy)pyridin-4-yl)propanoic acid In the same manner as in Example 32, step 2 and Example 1, step 4, the title compound (120 mg) was obtained as a colorless amorphous powder from N-(2,2-dimethylpropyl)-1-(2,2,2-trifluoroethyl)piperidin-3-amine dihydrochloride (150 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).

MS (ESI+): [M+H]$^+$ 689.3.

Example 234

3-cyclopropyl-3-(2-((1-(2-((2,2-dimethylpropyl)(3-fluoro-6-methylpyridin-2-yl)carbamoyl)-5-methoxyphenyl)piperidin-4-yl)methoxy)pyridin-4-yl)propanoic acid Step 1) N-(2,2-dimethylpropyl)-3-fluoro-6-methylpyridin-2-amine In a sealed tube, a mixture of 2-chloro-3-fluoro-6-methylpyridine (225 mg) and 2,2-dimethylpropan-1-amine (0.5 mL) was stirred at 130° C. for 40 hr. The reaction mixture was allowed to cool to room temperature, and purified by silica gel column chromatography (ethyl acetate/hexane) to give the title compound (90 mg) as a pale-yellow oil.

$^1$H NMR (300 MHz, CDCl$_3$) δ 0.97 (9H, s), 2.34 (3H, s), 3.32 (2H, d, J=6.1 Hz), 4.51 (1H, brs), 6.27 (1H, dd, J=7.8, 3.0 Hz), 6.97 (1H, dd, J=11.3, 7.8 Hz).

Step 2) 3-cyclopropyl-3-(2-((1-(2-((2,2-dimethylpropyl)(3-fluoro-6-methylpyridin-2-yl)carbamoyl)-5-methoxyphenyl)piperidin-4-yl)methoxy)pyridin-4-yl)propanoic acid In the same manner as in Example 32, step 2 and Example 1, step 4, the title compound (102 mg) was obtained as a colorless amorphous powder from N-(2,2-dimethylpropyl)-3-fluoro-6-methylpyridin-2-amine (90 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).

MS (ESI+): [M+H]$^+$ 633.3.

Example 235

3-cyclopropyl-3-(2-((1-(2-((2,2-dimethylpropyl)(5-(trifluoromethyl)pyridin-3-yl)carbamoyl)-5-methoxyphenyl)piperidin-4-yl)methoxy)pyridin-4-yl)propanoic acid Step 1) N-(2,2-dimethylpropyl)-5-(trifluoromethyl)pyridin-3-amine In the same manner as in Example 45, step 8, the title compound (7 mg) was obtained as a pale-yellow solid from 2,2-dimethylpropan-1-amine (272 μL) and 3-chloro-5-(trifluoromethyl)pyridine (84 mg).

MS (ESI+): [M+H]$^+$ 233.1.

Step 2) 3-cyclopropyl-3-(2-((1-(2-((2,2-dimethylpropyl)(5-(trifluoromethyl)pyridin-3-yl)carbamoyl)-5-methoxyphenyl)piperidin-4-yl)methoxy)pyridin-4-yl)propanoic acid In the same manner as in Example 32, step 2 and Example 1, step 4, the title compound (6 mg) was obtained as a pale-yellow oil from 2-(4-(((4-(1-cyclopropyl-3-ethoxy-3-oxopropyl)pyridin-2-yl)oxy)methyl)piperidin-1-yl)-4-methoxybenzoic acid (22 mg) and N-(2,2-dimethylpropyl)-5-(trifluoromethyl)pyridin-3-amine (7 mg).

MS (ESI+): [M+H]$^+$ 669.3.

Example 236

3-cyclopropyl-3-(2-((1-(5-methoxy-2-((2,2,2-trifluoroethyl)(5-(trifluoromethyl)pyridin-3-yl)carbamoyl)phenyl)piperidin-4-yl)methoxy)pyridin-4-yl)propanoic acid Step 1) N-(2,2,2-trifluoroethyl)-5-(trifluoromethyl)pyridin-3-amine In the same manner as in Example 225, step 1, the title compound (89 mg) was obtained as a pale-yellow solid from 2,2,2-trifluoroethanamine (98 μL) and 3-chloro-5-(trifluoromethyl)pyridine (114 mg).

MS (ESI+): [M+H]$^+$ 245.1.

Step 2) 3-cyclopropyl-3-(2-((1-(5-methoxy-2-((2,2,2-trifluoroethyl)(5-(trifluoromethyl)pyridin-3-yl)carbamoyl)phenyl)piperidin-4-yl)methoxy)pyridin-4-yl)propanoic acid In the same manner as in Example 32, step 2 and Example 1, step 4, the title compound (28 mg) was obtained as a pale-yellow solid from 2-(4-(((4-(1-cyclopropyl-3-ethoxy-3-oxopropyl)pyridin-2-yl)oxy)methyl)piperidin-1-yl)-4-methoxybenzoic acid (103 mg) and N-(2,2-dimethylpropyl)-5-(trifluoromethyl)pyridin-3-amine (52 mg).

MS (ESI+): [M+H]$^+$ 681.2.

Example 237

3-cyclopropyl-3-(2-((1-(2-((cyclopropylmethyl)(4-(trifluoromethyl)pyrimidin-2-yl)carbamoyl)-5-methoxyphenyl)piperidin-4-yl)methoxy)pyridin-4-yl)propanoic acid Step 1) N-(cyclopropylmethyl)-4-(trifluoromethyl)pyrimidin-2-amine To a solution of 2-chloro-4-(trifluoromethyl)pyrimidine (300 mg) in THF (2 mL) was added 1-cyclopropylmethanamine (351 mg) at room temperature. The mixture was stirred at room temperature for 2 days, and the reaction mixture was purified by silica gel column chromatography (ethyl acetate/hexane) to give the title compound (330 mg) as a colorless oil.

$^1$H NMR (300 MHz, CDCl$_3$) δ 0.22-0.32 (2H, m), 0.49-0.60 (2H, m), 1.00-1.17 (1H, m), 3.31 (2H, dd, J=7.1, 5.5 Hz), 5.51 (1H, brs), 6.80 (1H, d, J=4.9 Hz), 8.47 (1H, d, J=4.6 Hz).

Step 2) 3-cyclopropyl-3-(2-((1-(2-((cyclopropylmethyl)(4-(trifluoromethyl)pyrimidin-2-yl)carbamoyl)-5-methoxyphenyl)piperidin-4-yl)methoxy)pyridin-4-yl)propanoic acid In the same manner as in Example 32, step 2 and Example 1, step 4, the title compound (25 mg) was obtained as a colorless amorphous powder from N-(cyclopropylmethyl)-4-(trifluoromethyl)pyrimidin-2-amine (180 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).

MS (ESI+): [M+H]$^+$ 654.3.

Example 238

3-cyclopropyl-3-(2-((1-(2-((2,6-dimethylpyrimidin-4-yl)(2,2,2-trifluoroethyl)carbamoyl)-5-methoxyphenyl)piperidin-4-yl)methoxy)pyridin-4-yl)propanoic acid Step 1) 2,6-dimethyl-N-(2,2,2-trifluoroethyl)pyrimidin-4-amine In the same manner as in Example 225, step 1, the title compound (75 mg) was obtained as a pale-orange solid from 4-chloro-2,6-dimethylpyrimidine (200 mg) and 2,2,2-trifluoroethanamine (417 mg).

$^1$H NMR (300 MHz, CDCl$_3$) δ 2.34 (3H, s), 2.51 (3H, s), 4.11 (2H, qd, J=9.0, 6.9 Hz), 4.84 (1H, brs), 6.13 (1H, s).

Step 2) 3-cyclopropyl-3-(2-((1-(2-((2,6-dimethylpyrimidin-4-yl)(2,2,2-trifluoroethyl)carbamoyl)-5-methoxyphenyl)piperidin-4-yl)methoxy)pyridin-4-yl)propanoic acid In the same manner as in Example 32, step 2 and Example 1, step 4, the title compound (47 mg) was obtained as a colorless amorphous powder from 2,6-dimethyl-N-(2,2,2-trifluoroethyl)pyrimidin-4-amine (75 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).

MS (ESI+): [M+H]$^+$ 640.3.

Example 239

3-cyclopropyl-3-(2-((1-(5-methoxy-2-((2-methylpyrimidin-4-yl)(2,2,2-trifluoroethyl)carbamoyl)phenyl)piperidin-4-yl)methoxy)pyridin-4-yl)propanoic acid Step 1) 2-methyl-N-(2,2,2-trifluoroethyl)pyrimidin-4-amine In the same manner as in Example 225, step 1, the title compound (40 mg) was obtained as a pale-orange solid from 4-chloro-2-methylpyrimidine (200 mg) and 2,2,2-trifluoroethanamine (462 mg).

$^1$H NMR (300 MHz, CDCl$_3$) δ 2.53 (3H, s), 4.14 (2H, qd, J=8.9, 6.8 Hz), 4.89 (1H, brs), 6.27 (1H, d, J=5.9 Hz), 8.18 (1H, d, J=5.9 Hz).

Step 2) 3-cyclopropyl-3-(2-((1-(5-methoxy-2-((2-methylpyrimidin-4-yl)(2,2,2-trifluoroethyl)carbamoyl)phenyl)piperidin-4-yl)methoxy)pyridin-4-yl)propanoic acid In the same manner as in Example 32, step 2 and Example 1, step 4, the title compound (16 mg) was obtained as a colorless amorphous powder from 2-methyl-N-(2,2,2-trifluoroethyl)pyrimidin-4-amine (40 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).

MS (ESI+): [M+H]$^+$ 626.1.

Example 240

3-cyclopropyl-3-(2-((1-(5-methoxy-2-((6-methylpyrimidin-4-yl)(2,2,2-trifluoroethyl)carbamoyl)phenyl)piperidin-4-yl)methoxy)pyridin-4-yl)propanoic acid Step 1) 6-methyl-N-(2,2,2-trifluoroethyl)pyrimidin-4-amine In the same manner as in Example 225, step 1, the title compound (145 mg) was obtained as a pale-orange solid from 4-chloro-6-methylpyrimidine (200 mg) and 2,2,2-trifluoroethanamine (462 mg).

$^1$H NMR (300 MHz, CDCl$_3$) δ 2.53 (3H, s), 4.14 (2H, qd, J=8.9, 6.8 Hz), 4.89 (1H, brs), 6.27 (1H, d, J=5.9 Hz), 8.18 (1H, d, J=5.9 Hz).

Step 2) 3-cyclopropyl-3-(2-((1-(5-methoxy-2-((6-methylpyrimidin-4-yl)(2,2,2-trifluoroethyl)carbamoyl)phenyl)piperidin-4-yl)methoxy)pyridin-4-yl)propanoic acid In the same manner as in Example 32, step 2 and Example 1, step 4, the title compound (70 mg) was obtained as a colorless amorphous powder from 6-methyl-N-(2,2,2-trifluoroethyl)pyrimidin-4-amine (75 mg) and 2-(4-(((4-(1-cyclopropyl-3-ethoxy-3-oxopropyl)pyridin-2-yl)oxy)methyl)piperidin-1-yl)-4-methoxybenzoic acid (200 mg).

MS (ESI+): [M+H]$^+$ 626.1.

Example 241

3-cyclopropyl-3-(2-((1-(5-methoxy-2-((6-methylpyridin-2-yl)carbamoyl)phenyl)piperidin-4-yl)methoxy)pyridin-4-yl)propanoic acid In the same manner as in Example 32, step 2 and Example 1, step 4, the title compound (132 mg) was obtained as white crystals from 2-amino-6-methylpyridine (76 mg) and 2-(4-(((4-(1-cyclopropyl-3-ethoxy-3-oxopropyl)pyridin-2-yl)oxy)methyl)piperidin-1-yl)-4-methoxybenzoic acid (170 mg).

MS (ESI+): [M+H]$^+$ 545.2.

Example 242

3-cyclopropyl-3-(2-((1-(5-methoxy-2-(pyridin-2-ylcarbamoyl)phenyl)piperidin-4-yl)methoxy)pyridin-4-yl)propanoic acid In the same manner as in Example 32, step 2 and Example 1, step 4, the title compound (106 mg) was obtained as white crystals from 2-aminopyridine (66 mg) and 2-(4-(((4-(1-cyclopropyl-3-ethoxy-3-oxopropyl)pyridin-2-yl)oxy)methyl)piperidin-1-yl)-4-methoxybenzoic acid (170 mg).
MS (ESI+): [M+H]+ 531.2.

Example 243

3-cyclopropyl-3-(2-((1-(2-((2,2-dimethylpropyl)(4,6-dimethylpyridin-2-yl)carbamoyl)-5-methoxyphenyl)piperidin-4-yl)methoxy)pyridin-4-yl)propanoic acid Step 1)
N-(2,2-dimethylpropyl)-4,6-dimethylpyridin-2-amine By a method similar to that in Example 135, step 1, the title compound (160 mg) was obtained as a pale-yellow oil from 2,2-dimethylpropan-1-amine (313 μl) and 2,4-dimethylpyridine 1-oxide (262.4 mg).
MS (ESI+): [M+H]+ 193.1.

Step 2) ethyl 3-cyclopropyl-3-(2-((1-(2-((2,2-dimethylpropyl)(4,6-dimethylpyridin-2-yl)carbamoyl)-5-methoxyphenyl)piperidin-4-yl)methoxy)pyridin-4-yl)propanoate Under a nitrogen atmosphere, to a solution of 2-(4-(((4-(1-cyclopropyl-3-ethoxy-3-oxopropyl)pyridin-2-yl)oxy)methyl)piperidin-1-yl)-4-methoxybenzoic acid (158.6 mg) in toluene (657 μl) was added 1-chloro-N,N-2-trimethylpropylamine (47.8 μl) at 0° C. The mixture was stirred at room temperature for 3 hr, a solution of 4,6-dimethyl-N-(2,2-dimethylpropyl)pyridin-2-amine (76 mg) in toluene (657 μl) and triethylamine (55.0 μl) were added at room temperature, and the mixture was stirred at 100° C. for 2 hr. The reaction mixture was cooled to room temperature, the solvent was evaporated under reduced pressure, and the residue was purified by silica gel column chromatography (NH, ethyl acetate/hexane) to give the title compound (184 mg) as a colorless oil.
MS (ESI+): [M+H]+ 657.6.

Step 3) 3-cyclopropyl-3-(2-((1-(2-((2,2-dimethylpropyl)(4,6-dimethylpyridin-2-yl)carbamoyl)-5-methoxyphenyl)piperidin-4-yl)methoxy)pyridin-4-yl)propanoic acid By a method similar to that in Example 1, step 4, the title compound (167 mg) was obtained as a white amorphous powder from ethyl 3-cyclopropyl-3-(2-((1-(2-((2,2-dimethylpropyl)(4,6-dimethylpyridin-2-yl)carbamoyl)-5-methoxyphenyl)piperidin-4-yl)methoxy)pyridin-4-yl)propanoate (183.8 mg).
MS (ESI+): [M+H]+ 629.4.

Example 244

3-cyclopropyl-3-(2-((1-(2-((cyclopropylmethyl)(4,6-dimethylpyridin-2-yl)carbamoyl)-5-methoxyphenyl)piperidin-4-yl)methoxy)pyridin-4-yl)propanoic acid Step 1)
N-(cyclopropylmethyl)-4,6-dimethylpyridin-2-amine By a method similar to that in Example 135, step 1, the title compound (150 mg) was obtained as a yellow oil from aminomethylcyclopropane (241 μl) and 2,4-dimethylpyridine 1-oxide (273.7 mg).
MS (ESI+): [M+H]+ 177.1.

Step 2) 3-cyclopropyl-3-(2-((1-(2-((cyclopropylmethyl)(4,6-dimethylpyridin-2-yl)carbamoyl)-5-methoxyphenyl)piperidin-4-yl)methoxy)pyridin-4-yl)propanoic acid By a method similar to that in Example 243, step 2 and Example 1, step 4, the title compound (153 mg) was obtained as a white amorphous powder from 2-(4-(((4-(1-cyclopropyl-3-ethoxy-3-oxopropyl)pyridin-2-yl)oxy)methyl)piperidin-1-yl)-4-methoxybenzoic acid (159.7 mg) and N-(cyclopropylmethyl)-4,6-dimethylpyridin-2-amine (70.0 mg).
MS (ESI+): [M+H]+ 613.3.

Example 245

(3S)-3-cyclopropyl-3-(2-((1-(2-((2,2-dimethylpropyl)(6-methylpyridin-2-yl)carbamoyl)-5-methoxyphenyl)piperidin-4-yl)methoxy)pyridin-4-yl)propanoic acid Step 1) tert-butyl 4-(((4-cyanopyridin-2-yl)oxy)methyl)piperidine-1-carboxylate To a solution of tert-butyl 4-(hydroxymethyl)piperidine-1-carboxylate (4.27 kg) in DMF (14 L) was added 60% sodium hydride (oily) (936 g) at 0° C., and the mixture was stirred at 0° C. for 40 min. To the reaction solution was added a solution of 2-chloroisonicotinonitrile (2.50 kg) in DMF (6.0 L), and the mixture was stirred at 0° C. for 2 hr. The reaction mixture was diluted with ethyl acetate, water was added, and the mixture was extracted with ethyl acetate. The extract was washed with saturated brine, and dried over anhydrous sodium sulfate. The solvent was evaporated under reduced pressure, and the obtained white solid was washed with petroleum ether, and dried to give the title compound (4.20 kg) as a white solid.
$^1$H NMR (300 MHz, CDCl$_3$): δ 1.26 (2H, qd, J=12.3, 4.5 Hz), 1.46 (9H, s), 1.79 (2H, d, J=12.6 Hz), 1.85-2.09 (1H, m), 2.74 (2H, t, J=12.1 Hz), 4.13 (2H, brs.), 4.19 (2H, d, J=6.3 Hz), 6.98 (1H, t, J=1.2 Hz), 7.06 (1H, dd, J=5.1, 1.2 Hz), 8.28 (1H, dd, J=5.1, 0.8 Hz).

Step 2) tert-butyl 4-(((4-(cyclopropylcarbonyl)pyridin-2-yl)oxy)methyl)piperidine-1-carboxylate A solution of tert-butyl 4-(((4-cyanopyridin-2-yl)oxy)methyl)piperidine-1-carboxylate (4.00 kg) in THF (15 L) was added dropwise to a 1 M solution of cyclopropylmagnesium bromide in THF (22.7 L) at room temperature, and the mixture was stirred at room temperature for 2 hr. To the reaction mixture was carefully added 1N hydrochloric acid at 10° C. or lower, and the mixture was extracted with ethyl acetate. The extract was washed with water and saturated brine, and dried over anhydrous sodium sulfate. The solvent was evaporated under reduced pressure to give a crude product (4.50 kg) of the title compound as a brown oil. This compound was used for the next step without further purification.

Step 3) tert-butyl 4-(((4-((1E)-1-cyclopropyl-3-ethoxy-3-oxoprop-1-en-1-yl)pyridin-2-yl)oxy)methyl)piperidine-1-carboxylate Ethyl diethylphosphonoacetate (4.95 kg) was added to a suspension of 60% sodium hydride (oily) (888 g) in THF (15

L) at 0° C., and the mixture was stirred for 30 min. To the reaction solution was added a solution of a crude product (4.00 kg) of tert-butyl 4-(((4-(cyclopropylcarbonyl)pyridin-2-yl)oxy)methyl)piperidine-1-carboxylate in THF (15 L), and the mixture was stirred at 80° C. for 3 hr. The reaction solution was poured into saturated aqueous ammonium chloride solution (15 L), and the mixture was extracted with ethyl acetate. The extract was washed with saturated brine, and dried over anhydrous sodium sulfate. The solvent was evaporated under reduced pressure to give a crude product (4.50 kg) of the title compound as a brown oil. This compound was used for the next step without further purification.

Step 4) tert-butyl 4-(((4-(1-cyclopropyl-3-ethoxy-3-oxopropyl)pyridin-2-yl)oxy)methyl)piperidine-1-carboxylate Zinc powder (3.97 kg) was added in several portions to a solution of tert-butyl 4-(((4-((1E)-1-cyclopropyl-3-ethoxy-3-oxoprop-1-en-1-yl)pyridin-2-yl)oxy)methyl)piperidine-1-carboxylate (4.40 kg) in acetic acid (20 L) at room temperature, and the mixture was stirred at room temperature for 2 hr. The reaction mixture was filtered, and the solvent was evaporated under reduced pressure. The residue was basified with saturated aqueous sodium hydrogen carbonate solution, and the mixture was extracted with ethyl acetate. The extract was washed with saturated aqueous sodium hydrogen carbonate solution and saturated brine, and dried over anhydrous sodium sulfate. The solvent was evaporated under reduced pressure, and the residue was purified by silica gel column chromatography (ethyl acetate/hexane) to give the title compound (2.60 kg) as a pale-yellow oil.

$^1$H NMR (300 MHz, CDCl$_3$): δ 0.17 (1H, dt, J=9.6, 4.8 Hz), 0.28 (1H, dt, J=9.6, 4.8 Hz), 0.39-0.52 (1H, m), 0.54-0.66 (1H, m), 0.94-1.08 (1H, m), 1.15-1.22 (3H, m), 1.27-1.35 (2H, m), 1.46 (9H, s), 1.81 (2H, d, J=12.0 Hz), 1.88-2.01 (1H, m), 2.30 (1H, dt, J=9.6, 7.5 Hz), 2.58-2.84 (4H, m), 4.02-4.10 (2H, m), 4.10-4.23 (4H, m), 6.58-6.62 (1H, m), 6.76 (1H, dd, J=5.4, 1.5 Hz), 7.86-8.16 (1H, m).

Step 5) 3-(2-((1-(tert-butoxycarbonyl)piperidin-4-yl)methoxy)pyridin-4-yl)-3-cyclopropylpropanoic acid To a solution of tert-butyl 4-(((4-(1-cyclopropyl-3-ethoxy-3-oxopropyl)pyridin-2-yl)oxy)methyl)piperidine-1-carboxylate (2.50 kg) in methanol (12 L) was added 4N aqueous sodium hydroxide solution (5.8 L) at room temperature, and the mixture was stirred at room temperature for 2 hr. The solvent was evaporated under reduced pressure, and the residue was dissolved in water and extracted with diethyl ether. The aqueous layer was acidified (pH=4-5) with 1N hydrochloric acid, and the resulting solid was collected by filtration, washed with petroleum ether and dried to give the title compound (2.10 kg) as a white solid.

$^1$H NMR (300 MHz, CDCl$_3$): δ 0.12-0.20 (1H, m), 0.30-0.34 (1H, m), 0.41-0.51 (1H, m), 0.56-0.65 (1H, m), 0.95-1.01 (1H, m), 1.18-1.32 (2H, m), 1.46 (9H, s), 1.77-1.82 (2H, m), 1.91-1.98 (1H, m), 2.28 (1H, dd, J=17.1, 7.5 Hz), 2.69-2.84 (4H, m), 4.10-4.13 (4H, m), 6.61 (1H, 2), 6.75 (1H, dd, J=5.4, 1.2 Hz), 8.04 (1H, d, J=5.4 Hz).

Step 6) (1R)-1-(4-methylphenyl)ethanaminium (3S)-3-(2-((1-(tert-butoxycarbonyl)piperidin-4-yl)methoxy)pyridin-4-yl)-3-cyclopropylpropanoate To a solution of 3-(2-((1-(tert-butoxycarbonyl)piperidin-4-yl)methoxy)pyridin-4-yl)-3-cyclopropylpropanoic acid (870 g) in ethanol (5.4 L) was added dropwise a solution of (S)-1-(p-tolyl)ethanamine (291 g) in ethyl acetate (11 L) at room temperature, and the mixture was stirred in dry air at room temperature for 17 hr. The resulting white precipitate was collected by filtration, washed with ethyl acetate/ethanol (2:1, 2.4 L), and dried to give crude crystals (477 g) of the title compound. The obtained crude crystals (237 g) were dissolved in ethanol (3.1 L) at 70° C., and heptane (4.7 L) was added dropwise at 60-65° C. Seed crystals were added, and the mixture was stirred at 50° C. for 1.5 hr and at room temperature for 12 hr. The resulting white solid was collected by filtration, washed with ethanol/heptane (1:2), and dried to give the title compound as crude crystals (182 g). Crude crystals (372 g) of the title compound were obtained in the same manner and dissolved in ethanol (4.8 L) at 70° C. Heptane (7.4 L) was added dropwise at 60-65° C., seed crystals were added, and the mixture was stirred at 50° C. for 1.5 hr, at room temperature for 12 hr, and under ice-cooling for 1 hr. The resulting white solid was collected by filtration, washed with ethanol/heptane (1:2), and dried to give the title compound (340 g).

Step 7) (3S)-3-(2-((1-(tert-butoxycarbonyl)piperidin-4-yl)methoxy)pyridin-4-yl)-3-cyclopropylpropanoic acid To a suspension of (1R)-1-(4-methylphenyl)ethanaminium (3S)-3-(2-((1-(tert-butoxycarbonyl)piperidin-4-yl)methoxy)pyridin-4-yl)-3-cyclopropylpropanoate (190 g) in ethyl acetate (1.9 L) was added dropwise 1N hydrochloric acid (1.9 L) at 0° C., and the mixture was stirred at room temperature for 1 hr. Ethyl acetate/THF (1:1, 1.0 L), ethyl acetate/THF (1:1, 1.0 L) and sodium chloride (500 g) were added and the mixture was extracted. The extract was added to saturated brine (1.0 L) and sodium chloride (30 g) and the mixture was washed with 1N hydrochloric acid, and dried over anhydrous magnesium sulfate. The solvent was evaporated under reduced pressure to give a crude product (162 g) of the title compound as a white solid. This compound was used for the next step without further purification.

Step 8) ethyl(3S)-3-cyclopropyl-3-(2-(piperidin-4-ylmethoxy)pyridin-4-yl)propanoate To a solution of the crude product (162 g) of (3S)-3-(2-((1-(tert-butoxycarbonyl)piperidin-4-yl)methoxy)pyridin-4-yl)-3-cyclopropylpropanoic acid in ethanol (1.6 L) was added conc. sulfuric acid (39.0 mL) at room temperature, and the mixture was stirred at 80° C. for 1 hr. The reaction solution was neutralized with 2N aqueous sodium hydroxide solution (293 mL) under ice-cooling and the solvent was evaporated under reduced pressure. The residue was dissolved in ethyl acetate/THF (1:1, 1.0 L) and water (250 mL), and basified with 2N aqueous sodium hydroxide solution (147 mL). Sodium chloride (300 g) was added, the mixture was extracted twice with ethyl acetate/THF (1:1, 1.0 L), and the extract was dried over anhydrous magnesium sulfate. The solvent was evaporated under reduced pressure to give a crude product (145 g) of the title compound as a pale-yellow oil. This compound was used for the next step without further purification.

Step 9) 2,2-dimethyl-N-(6-methylpyridin-2-yl)propanamide

Under a nitrogen atmosphere, to a solution of 6-methylpyridin-2-amine (50.0 g) in DMA (240 mL) was added dropwise 2,2-dimethylpropanoyl chloride (83.6 g) at 20° C. and the mixture was stirred at room temperature for 5 hr. To the reaction solution was added saturated aqueous sodium hydrogen carbonate solution at 20° C., and the mixture was extracted with ethyl acetate. The extract was washed with saturated aqueous potassium carbonate solution and saturated brine, and dried over anhydrous sodium sulfate. The solvent was evaporated under reduced pressure, and the obtained solid was washed with petroleum ether to give the title compound (47.0 g) as a white solid.

$^1$H NMR (400 MHz, DMSO): δ 1.21 (9H, s), 2.39 (3H, s), 6.92-6.94 (1H, d, J=7.6 Hz), 7.60-7.64 (1H, m), 7.82-7.84 (1H, d, J=8.4 Hz), 9.59 (1H, s).

Step 10)
N-(2,2-dimethylpropyl)-6-methylpyridin-2-amine

Under a nitrogen atmosphere, to a suspension of lithium aluminum hydride (65.0 g) in THF (1.5 L) was added a solution of 2,2-dimethyl-N-(6-methylpyridin-2-yl)propanamide (110 g) in THF (1.5 L) at 0° C., and the mixture was stirred at 60° C. for 2 hr. To the reaction solution were successively added water (65 mL), 4N aqueous sodium hydroxide solution (65 mL) and water (195 mL) at 0° C., and the resulting white precipitate was removed by filtration. The solvent in the filtrate was evaporated under reduced pressure to give the title compound (107 g) as a colorless oil.

$^1$H NMR (400 MHz, DMSO): δ 0.89 (9H, s), 2.20 (3H, s), 3.05-3.07 (2H, d, J=6.4 Hz), 6.14 (1H, s), 6.24-6.26 (1H, d, J=6.8 Hz), 6.29-6.31 (1H, d, J=8.4 Hz), 7.16-7.20 (1H, m).

Step 11) N-(2,2-dimethylpropyl)-2-fluoro-4-methoxy-N-(6-methylpyridin-2-yl)benzamide Under a nitrogen atmosphere, to a solution of 2-fluoro-4-methoxybenzoic acid (76.0 g) in DMF (2.0 mL) and THF (300 mL) was added dropwise oxalyl chloride (62.4 g) at 20° C. over 1 hr. The solvent in the reaction solution was evaporated under reduced pressure to give an acid chloride intermediate as a yellow oil. Under a nitrogen atmosphere, to a solution of N-(2,2-dimethylpropyl)-6-methylpyridin-2-amine (72.4 g) and triethylamine (123 g) in THF (500 mL) was added a solution of the obtained acid chloride intermediate in THF (500 mL) at 0° C., and the mixture was stirred at 20° C. for 10 hr. To the reaction solution was added water (500 mL) at 20° C., and the mixture was extracted 3 times with ethyl acetate (500 mL). The extract was washed with water (500 mL), 1N aqueous sodium hydroxide solution (200 mL) and saturated brine (300 mL), and dried over anhydrous sodium sulfate. The solvent was evaporated under reduced pressure, and the residue was purified by silica gel column chromatography (NH, ethyl acetate/petroleum ether) to give the title compound (67.5 g) as a white solid.

$^1$H NMR (400 MHz, CDCl$_3$): δ 0.87 (9H, s), 2.48 (3H, s), 3.74 (3H, s), 4.14 (2H, s), 6.39-6.41 (1H, d, J=11.2 Hz), 6.53-6.56 (1H, m), 6.59-6.61 (1H, d, J=8.0 Hz), 6.84-6.86 (1H, d, J=7.6 Hz), 7.13-7.15 (1H, m), 7.28-7.30 (1H, m).

Step 12) ethyl(3S)-3-cyclopropyl-3-(2-((1-(2-((2,2-dimethylpropyl)(6-methylpyridin-2-yl)carbamoyl)-5-methoxyphenyl)piperidin-4-yl)methoxy)pyridin-4-yl)propanoate Under a nitrogen atmosphere, a mixture of a crude product (12.1 g) of ethyl(3S)-3-cyclopropyl-3-(2-(piperidin-4-ylmethoxy)pyridin-4-yl)propanoate, N-(2,2-dimethylpropyl)-2-fluoro-4-methoxy-N-(6-methylpyridin-2-yl)benzamide (12.0 g) and cesium carbonate (17.8 g) was stirred at 130° C. for 19 hr. The reaction mixture was diluted with toluene (330 mL) and filtered through NH silica gel. The filtrate was dissolved in ethyl acetate, and extracted with 2N hydrochloric acid. The extract was basified with 2N aqueous sodium hydroxide solution and saturated aqueous sodium hydrogen carbonate solution. The mixture was extracted with ethyl acetate, and the extract was washed with saturated brine, and dried over anhydrous magnesium sulfate. The solvent was evaporated under reduced pressure to give the title compound (16.7 g) as a pale-orange amorphous powder.

$^1$H NMR (300 MHz, CDCl$_3$) δ 0.11-0.22 (1H, m), 0.24-0.36 (1H, m), 0.39-0.53 (1H, m), 0.53-0.67 (1H, m), 0.82 (9H, s), 0.91-1.07 (1H, m), 1.15-1.37 (1H, m), 1.19 (3H, t, J=7.2 Hz), 1.44-1.89 (4H, m), 2.19-2.84 (5H, m), 2.21-2.37 (1H, m), 2.44 (3H, s), 3.31-3.45 (1H, m), 3.75 (3H, s), 3.97-4.39 (6H, m), 6.19 (1H, d, J=1.9 Hz), 6.33 (1H, brs), 6.48 (1H, dd, J=8.5, 2.5 Hz), 6.63 (1H, s), 6.70 (1H, d, J=7.6 Hz), 6.76 (1H, dd, J=5.5, 1.3 Hz), 7.08 (1H, t, J=7.7 Hz), 7.29 (1H, d, J=8.3 Hz), 8.07 (1H, d, J=5.3 Hz).

Step 13) (3S)-3-cyclopropyl-3-(2-((1-(2-((2,2-dimethylpropyl)(6-methylpyridin-2-yl)carbamoyl)-5-methoxyphenyl)piperidin-4-yl)methoxy)pyridin-4-yl)propanoic acid To a solution of ethyl(3S)-3-cyclopropyl-3-(2-((1-(2-((2,2-dimethylpropyl)(6-methylpyridin-2-yl)carbamoyl)-5-methoxyphenyl)piperidin-4-yl)methoxy)pyridin-4-yl)propanoate (16.7 g) in THF (170 mL) and methanol (85 mL) was added 1N aqueous sodium hydroxide solution (170 mL) at room temperature, and the mixture was stirred at 60° C. for 30 min. To the reaction solution was added 1N hydrochloric acid (170 mL), and the mixture was extracted twice with ethyl acetate (150 mL). The extract was washed with saturated brine (150 mL), dried over anhydrous magnesium sulfate, and the solvent was evaporated under reduced pressure. The residue was dissolved in isopropyl acetate (107 mL) at 60° C., heptane (123 mL) was added dropwise at 60° C., and the mixture was stirred for 30 min. Heptane (65 mL) was further added dropwise at 60° C., and the mixture was stirred for 30 min. The mixture was cooled to room temperature and stirred for 1 hr. The resulting crystals were collected by filtration, and washed with isopropyl acetate/heptane (1:3) to give the title compound as a white solid (13.4 g).

$^1$H NMR (400 MHz, DMSO-d$_6$) δ 0.10-0.22 (1H, m), 0.23-0.39 (2H, m), 0.45-0.56 (1H, m), 0.77 (9H, s), 0.93-1.05 (1H, m), 1.10-1.30 (1H, m), 1.45-1.60 (1H, m), 1.61-1.86 (3H, m), 2.18-2.28 (1H, m), 2.30-2.66 (4H, m), 2.36 (3H, s), 2.68 (2H, d, J=7.4 Hz), 3.69 (3H, s), 3.93-4.27 (4H, m), 6.21 (1H, brs), 6.45 (1H, brs), 6.52 (1H, d, J=8.4 Hz), 6.71 (1H, s), 6.85 (1H, d, J=7.5 Hz), 6.91 (1H, d, J=5.1 Hz), 7.14 (1H, d, J=8.4 Hz), 7.28 (1H, t, J=7.7 Hz), 8.04 (1H, d, J=5.3 Hz), 12.09 (1H, brs).

MS (ESI+): [M+H]$^+$ 615.3.

Example 246

(3S)-3-cyclopropyl-3-(2-((1-(2-((2,2-dimethylpropyl)(4,6-dimethylpyrimidin-2-yl)carbamoyl)-5-methoxyphenyl)piperidin-4-yl)methoxy)pyridin-4-yl)propanoic acid Step 1) allyl 2-fluoro-4-methoxybenzoate To a suspension of 2-fluoro-4-methoxybenzoic acid (176 g) and potassium carbonate (186 g) in DMF (900 mL) was added 3-bromoprop-1-ene (107 mL) at room temperature, and the mixture was stirred at 50° C. for 2 hr. To the reaction mixture was added water at room temperature, and the mixture was extracted with ethyl acetate. The extract was washed with water and saturated brine, and dried over anhydrous magnesium sulfate. The solvent was evaporated under reduced pressure to give a crude product (220.7 g) of the title compound as a pale-yellow oil. This compound was used for the next step without further purification.

MS (ESI+): [M+H]$^+$ 211.2.

Step 2) allyl 2-(4-(((4-((1S)-1-cyclopropyl-3-ethoxy-3-oxopropyl)pyridin-2-yl)oxy)methyl)piperidin-1-yl)-4-methoxybenzoate To a mixture of allyl 2-fluoro-4-methoxybenzoate (77 g) and ethyl(3S)-3-cyclopropyl-3-(2-(piperidin-4-ylmethoxy) pyridin-4-yl)propanoate (130 g) was added cesium carbonate (179 g) at room temperature, and the mixture was stirred at 100° C. for 2 hr. To the reaction mixture was added DMSO (50 ml), and the mixture was stirred at 100° C. overnight. The reaction mixture was diluted with ethyl acetate (1250 mL), and the insoluble material was removed by filtration. The filtrate was washed with a mixture of saturated brine and water, dried over anhydrous sodium sulfate, and treated with NH-silica gel pad. The solvent was evaporated under reduced pressure, and the residue was treated with NH-silica gel pad. The solvent was evaporated under reduced pressure to give the title compound (141 g) as a colorless oil.

MS (ESI+): [M+H]$^+$ 523.4.

Step 3) 2-(4-(((4-((1S)-1-cyclopropyl-3-ethoxy-3-oxopropyl)pyridin-2-yl)oxy)methyl)piperidin-1-yl)-4-methoxybenzoic acid To a solution of allyl 2-(4-(((4-((1S)-1-cyclopropyl-3-ethoxy-3-oxopropyl)pyridin-2-yl)oxy)methyl)piperidin-1-yl)-4-methoxybenzoate (146 g) and morpholine (47.3 mL) in THF (1500 mL) was added tetrakis(triphenylphosphine) palladium(0) (6.26 g) at room temperature, and the mixture was stirred at room temperature overnight under a nitrogen atmosphere. The reaction mixture was diluted with ethyl acetate (750 mL), washed twice with a mixture of saturated brine and water, and dried over anhydrous sodium sulfate. The solvent was evaporated under reduced pressure, and the obtained solid was washed with hexane to give the title compound (116 g) as a pale-yellow solid.

MS (ESI+): [M+H]$^+$ 483.3.

Step 4) ethyl(3S)-3-cyclopropyl-3-(2-((1-(2-((2,2-dimethylpropyl)(4,6-dimethylpyrimidin-2-yl)carbamoyl)-5-methoxyphenyl)piperidin-4-yl)methoxy)pyridin-4-yl)propanoate To a solution of 2-(4-(((4-((1S)-1-cyclopropyl-3-ethoxy-3-oxopropyl)pyridin-2-yl)oxy)methyl)piperidin-1-yl)-4-methoxybenzoic acid (110.5 g) in diethylene glycol dimethyl ether (442 mL) was added 1-chloro-N,N,2-trimethylprop-1-en-1-amine (34.9 mL) at room temperature, and the mixture was stirred at 60° C. for 1 hr. The reaction mixture was cooled to room temperature, N-(2,2-dimethylpropyl)-4,6-dimethylpyrimidin-2-amine (51.0 g) and triethylamine (36.8 mL) were added at room temperature, and the mixture was stirred at 100° C. for 3 hr. The reaction mixture was diluted with ethyl acetate (1100 mL), and washed with water (750 mL). The aqueous layer was extracted with ethyl acetate (500 mL), and the combined organic layer was washed successively with water and saturated brine, and dried over anhydrous sodium sulfate. The solvent was evaporated under reduced pressure, and the obtained residue was purified by NH-silica gel column chromatography (ethyl acetate/hexane) to give the title compound (33 g) as an orange oil, and a mixture of the title compound and N-(2,2-dimethylpropyl)-4,6-dimethylpyrimidin-2-amine. This mixture was dissolved in ethyl acetate, and washed successively with 5% aqueous citric acid solution (750 mL), 10% aqueous citric acid solution (750 mL) and saturated brine (750 mL), and dried over anhydrous sodium sulfate. The solvent was evaporated under reduced pressure to give the title compound (114 g) as an orange oil.

MS (ESI+): [M+H]$^+$ 658.6.

Step 5) (3S)-3-cyclopropyl-3-(2-((1-(2-((2,2-dimethylpropyl)(4,6-dimethylpyrimidin-2-yl)carbamoyl)-5-methoxyphenyl)piperidin-4-yl)methoxy)pyridin-4-yl)propanoic acid To a mixture of ethyl(3S)-3-cyclopropyl-3-(2-((1-(2-((2,2-dimethylpropyl)(4,6-dimethylpyrimidin-2-yl)carbamoyl)-5-methoxyphenyl)piperidin-4-yl)methoxy)pyridin-4-yl)propanoate (140 g) in THF (966 mL) and MeOH (483 mL) was added 1 M aqueous sodium hydroxide solution (966 mL) at 30° C. or lower. The mixture was stirred at 60° C. for 1 hr, 2 M hydrochloric acid (483 mL) was added at 20° C. or lower, and the mixture was concentrated under reduced pressure. The residue was diluted with ethyl acetate (1000 mL), and the aqueous layer was extracted with ethyl acetate (500 mL). The combined organic layer was washed with saturated brine (500 mL), dried over anhydrous sodium sulfate, and treated with a silica gel pad. The solvent was evaporated under reduced pressure and the residue was crystallized from IPE to give a crude product. A suspension of the crude product in isopropyl acetate (900 mL) was stirred at 70° C. for 1 hr, and the insoluble material was removed by filtration. To the filtrate was added heptane (500 mL) at 70° C., and the mixture was stirred for 1 hr. The mixture was cooled to room temperature, and the resulting solid was collected by filtration, and washed with isopropyl acetate/heptane (100 mL/200 mL) to give the title compound (108.3 g).

$^1$H NMR (300 MHz, DMSO-d$_6$) δ 0.17 (1H, dt, J=8.9, 4.2 Hz), 0.22-0.42 (2H, m), 0.43-0.58 (1H, m), 0.72-0.84 (9H, m), 0.87-1.10 (2H, m), 1.32-1.82 (4H, m), 2.02-2.13 (6H, m), 2.16-2.30 (1H, m), 2.31 (2H, brs), 2.54 (1H, brs), 2.60-2.76 (2H, m), 3.09 (1H, brs), 3.64-3.74 (3H, m), 3.94-4.41 (4H, m), 6.15 (1H, d, J=2.3 Hz), 6.52 (1H, dd, J=8.3, 2.3 Hz), 6.71 (1H, s), 6.79 (1H, s), 6.91 (1H, dd, J=5.5, 1.3 Hz), 7.17 (1H, d, J=8.3 Hz), 8.04 (1H, d, J=5.3 Hz), 12.08 (1H, brs).

MS (ESI+): [M+H]$^+$ 630.3.

Example 247

(3S)-3-cyclopropyl-3-(2-((1-(2-((2,2-dimethylpropyl)(pyridin-2-yl)carbamoyl)-5-methoxyphenyl) piperidin-4-yl)methoxy)pyridin-4-yl)propanoic acid Step 1) ethyl(3S)-3-cyclopropyl-3-(2-((1-(2-((2,2-dimethylpropyl)(pyridin-2-yl)carbamoyl)-5-methoxyphenyl)piperidin-4-yl)methoxy)pyridin-4-yl)propanoate To a solution of 2-(4-(((4-((1S)-1-cyclopropyl-3-ethoxy-3-oxopropyl)pyridin-2-yl)oxy)methyl)piperidin-1-yl)-4- methoxybenzoic acid (119 g) in THF (480 mL) was added 1-chloro-N,N,2-trimethylprop-1-en-1-amine (37.6 g) at room temperature, and the mixture was stirred at 50° C. for 1 hr. The reaction mixture was cooled to room temperature, N-(2,2-dimethylpropyl)pyridin-2-amine (46.7 g) and triethylamine (39.6 mL) were added at room temperature, and the mixture was stirred at 60° C. for 3 hr. The reaction mixture was diluted with ethyl acetate (1200 mL), and water (800 mL) was added. The aqueous layer was extracted with ethyl acetate (600 mL), and the combined organic layer was washed successively with a mixture of water and saturated brine, and saturated brine, and dried over anhydrous sodium sulfate. The solvent was evaporated under reduced pressure, and the obtained residue was purified by NH-silica gel column chromatography (ethyl acetate/hexane) to give the title compound (63.8 g) as a yellow oil, and a mixture of the title compound and N-(2,2-dimethylpropyl)pyridin-2-amine. This mixture was dissolved in ethyl acetate, washed successively with 10% aqueous citric acid solution (250 mL) and saturated brine (250 mL), and dried over anhydrous sodium sulfate. The solvent was evaporated under reduced pressure to give the title compound (84.2 g) as a yellow oil.

MS (ESI+): [M+H]$^+$ 629.6.

Step 2) (3S)-3-cyclopropyl-3-(2-((1-(2-((2,2-dimethylpropyl)(pyridin-2-yl)carbamoyl)-5-methoxyphenyl)piperidin-4-yl)methoxy)pyridin-4-yl)propanoic acid To a mixture of ethyl(3S)-3-cyclopropyl-3-(2-((1-(2-((2,2-dimethylpropyl)(pyridin-2-yl)carbamoyl)-5-methoxyphenyl)piperidin-4-yl)methoxy)pyridin-4-yl)propanoate (142 g) in THF (1028 mL) and MeOH (514 mL) was added 1 M aqueous sodium hydroxide solution (1028 mL) at 30° C. or lower. The mixture was stirred at 60° C. for 1 hr, neutralized with 2 M hydrochloric acid at 20° C. or lower, and concentrated under reduced pressure. The residue was diluted with ethyl acetate (1000 mL), and the aqueous layer was extracted with ethyl acetate (500 mL). The combined organic layer was washed successively with 10% aqueous sodium hydrogen carbonate solution (500 mL) and saturated brine (500 mL), dried over anhydrous sodium sulfate, and treated with a silica gel pad. The solvent was evaporated under reduced pressure and the residue was crystallized from IPE and TBME to give a crude product. A suspension of the crude product in isopropyl acetate (900 mL) was stirred at 70° C. for 1 hr, and the insoluble material was removed by filtration. To the filtrate were added heptane (900 mL) and seed crystals at 70° C., and the mixture was stirred for 1 hr. The mixture was cooled to room temperature, and the resulting solid was collected by filtration, and washed with isopropyl acetate/heptane (100 mL/200 mL) to give the title compound (93.5 g).

$^1$H NMR (300 MHz, DMSO-d$_6$) δ 0.11-0.22 (1H, m), 0.22-0.40 (2H, m), 0.45-0.59 (1H, m), 0.77 (9H, s), 0.92-1.08 (1H, m), 1.15-1.39 (1H, m), 1.53 (1H, brs), 1.60-1.87 (3H, m), 2.15-2.31 (1H, m), 2.38 (1H, brs), 2.55-2.75 (3H, m), 3.33 (2H, s), 3.69 (3H, s), 3.94-4.25 (4H, m), 6.21 (1H, d, J=1.9 Hz), 6.52 (1H, dd, J=8.5, 2.5 Hz), 6.63-6.77 (2H, m), 6.92 (1H, dd, J=5.5, 1.3 Hz), 6.99 (1H, dd, J=7.0, 5.1 Hz), 7.14 (1H, d, J=8.3 Hz), 7.34-7.46 (1H, m), 8.04 (1H, d, J=5.3 Hz), 8.33 (1H, dd, J=4.7, 1.3 Hz), 12.08 (1H, brs).

MS (ESI+): [M+H]$^+$ 601.3.

Example 248

(3S)-3-cyclopropyl-3-(2-((1-(5-methoxy-2-((6-methylpyridin-2-yl)carbamoyl)phenyl)piperidin-4-yl)methoxy)pyridin-4-yl)propanoic acid In the same manner as in Example 32, step 2 and Example 1, step 4, the title compound (106 mg) was obtained as white crystals from 2-amino-6-methylpyridine (76 mg) and 2-(4-(((4-((1S)-1-cyclopropyl-3-ethoxy-3-oxopropyl)pyridin-2-yl)oxy)methyl)piperidin-1-yl)-4-methoxybenzoic acid (170 mg).

MS (ESI+): [M+H]$^+$ 545.2.

Example 249

(3S)-3-cyclopropyl-3-(2-((1-(5-methoxy-2-(pyridin-2-ylcarbamoyl)phenyl)piperidin-4-yl)methoxy)pyridin-4-yl)propanoic acid In the same manner as in Example 32, step 2 and Example 1, step 4, the title compound (106 mg) was obtained as white crystals from 2-aminopyridine (66 mg) and 2-(4-(((4-((1S)-1-cyclopropyl-3-ethoxy-3-oxopropyl)pyridin-2-yl)oxy)methyl)piperidin-1-yl)-4-methoxybenzoic acid (170 mg).

MS (ESI+): [M+H]$^+$ 531.1.

Example 250

3-cyclopropyl-3-(2-((1-(2-((2,2-dimethylpropyl)(6-methylpyridin-2-yl)carbamoyl)-4-fluoro-5-methoxyphenyl)piperidin-4-yl)methoxy)pyridin-4-yl)propanoic acid Step 1) ethyl 3-cyclopropyl-3-(2-(piperidin-4-ylmethoxy)pyridin-4-yl)propanoate To a solution of 3-(2-((1-(tert-butoxycarbonyl)piperidin-4-yl)methoxy)pyridin-4-yl)-3-cyclopropylpropanoic acid (20.0 g) in ethanol (200 mL) was added sulfuric acid (6.59 mL) at room temperature, and the mixture was stirred at 80° C. for 30 min. The solvent was evaporated under reduced pressure, and the residue was diluted with ethyl acetate (100 mL) and THF (100 mL), and neutralized with 2N aqueous sodium hydroxide solution (99 mL). Sodium chloride was added, and the mixture was extracted with ethyl acetate (50 mL) and THF (50 mL). The extract was washed with saturated brine (50 mL), and dried over anhydrous magnesium sulfate. The solvent was evaporated under reduced pressure to give a crude product (17.1 g) of the title compound as an orange oil. This compound was used for the next step without further purification.

Step 2) 2,5-difluoro-4-hydroxybenzoic acid 2,4,5-Trifluorobenzoic acid (5.00 g), sodium hydroxide (4.54 g) and water (25 mL) were heated at 160° C. for 10 min under microwave irradiation. To the reaction solution was added 1N hydrochloric acid at room temperature, and the mixture was extracted with ethyl acetate. The extract was washed with water and saturated brine, and dried over anhydrous magnesium sulfate. The solvent was evaporated under reduced pressure, and the obtained solid was washed with hexane to give the title compound (4.50 g) as a white solid.

$^1$H NMR (400 MHz, DMSO-d$_6$) δ 6.80 (1H, dd, J=11.8, 7.0 Hz), 7.58 (1H, dd, J=11.4, 7.0 Hz), 11.25 (1H, brs), 12.99 (1H, brs).

Step 3) methyl 2,5-difluoro-4-methoxybenzoate

Under a nitrogen atmosphere, iodomethane (4.04 mL) was added to a mixture of 2,5-difluoro-4-hydroxybenzoic acid (4.50 g), potassium carbonate (10.7 g) and DMF (25 mL) at room temperature, and the mixture was stirred at 60° C. for 20 min. To the reaction solution was added water at room temperature, and the resulting precipitates were collected by filtration, washed with water and dried to give the title compound (5.27 g) as a white solid.
$^1$H NMR (400 MHz, CDCl$_3$) δ 3.91 (3H, s), 3.93 (3H, s), 6.71 (1H, dd, J=11.6, 6.7 Hz), 7.66 (1H, dd, J=11.3, 6.8 Hz).

Step 4) 2,5-difluoro-4-methoxybenzoic acid

1N Aqueous sodium hydroxide solution (50 mL) was added to a solution of methyl 2,5-difluoro-4-methoxybenzoate (5.27 g) in THF (50 mL) and methanol (25 mL) at room temperature, and the mixture was stirred at 60° C. for 20 min. The reaction solution was neutralized with 1N hydrochloric acid at room temperature, and extracted with ethyl acetate. The extract was washed with water and saturated brine, and dried over anhydrous magnesium sulfate. The solvent was evaporated under reduced pressure to give the title compound (3.53 g) as a white solid.
$^1$H NMR (400 MHz, DMSO-d$_6$) δ 3.92 (3H, s), 7.21 (1H, dd, J=12.1, 7.0 Hz), 7.62 (1H, dd, J=11.6, 7.0 Hz), 13.16 (1H, brs).

Step 5) N-(2,2-dimethylpropyl)-2,5-difluoro-4-methoxy-N-(6-methylpyridin-2-yl)benzamide In the same manner as in Example 1, step 1, the title compound (354 mg) was obtained as a white solid from 2,5-difluoro-4-methoxybenzoic acid (300 mg) and N-(2,2-dimethylpropyl)-6-methylpyridin-2-amine (292 mg).
$^1$H NMR (400 MHz, CDCl$_3$) δ 0.86 (9H, s), 2.46 (3H, s), 3.80 (3H, s), 4.09 (2H, s), 6.45 (1H, dd, J=10.3, 6.9 Hz), 6.64 (1H, d, J=7.9 Hz), 6.87 (1H, d, J=7.5 Hz), 6.98 (1H, dd, J=10.8, 6.1 Hz), 7.32 (1H, t, J=7.8 Hz).

Step 6) ethyl 3-cyclopropyl-3-(2-((1-(2-((2,2-dimethylpropyl)(6-methylpyridin-2-yl)carbamoyl)-4-fluoro-5-methoxyphenyl)piperidin-4-yl)methoxy)pyridin-4-yl)propanoate In the same manner as in Example 1, step 2, the title compound (37.0 mg) was obtained as a white amorphous powder from N-(2,2-dimethylpropyl)-2,5-difluoro-4-methoxy-N-(6-methylpyridin-2-yl)benzamide (69.7 mg) and ethyl 3-cyclopropyl-3-(2-(piperidin-4-ylmethoxy)pyridin-4-yl)propanoate (73.1 mg).
$^1$H NMR (400 MHz, CDCl$_3$) δ 0.12-0.22 (1H, m), 0.25-0.36 (1H, m), 0.43-0.52 (1H, m), 0.55-0.67 (1H, m), 0.83 (9H, s), 0.93-1.06 (1H, m), 1.19 (3H, t, J=7.2 Hz), 1.28-1.44 (1H, m), 1.49-1.70 (1H, m), 1.71-1.90 (3H, m), 2.26-2.35 (1H, m), 2.33-2.82 (5H, m), 2.43 (3H, s), 3.37 (1H, brs), 3.81 (3H, s), 3.99-4.12 (2H, m), 4.00-4.39 (2H, m), 4.17 (2H, d, J=6.1 Hz), 6.32 (1H, d, J=6.7 Hz), 6.42 (1H, brs), 6.63 (1H, s), 6.73 (1H, d, J=7.5 Hz), 6.77 (1H, d, J=5.1 Hz), 7.03-7.20 (1H, m), 7.07 (1H, d, J=11.2 Hz), 8.07 (1H, d, J=5.3 Hz).

Step 7) 3-cyclopropyl-3-(2-((1-(2-((2,2-dimethylpropyl)(6-methylpyridin-2-yl)carbamoyl)-4-fluoro-5-methoxyphenyl)piperidin-4-yl)methoxy)pyridin-4-yl)propanoic acid In the same manner as in Example 1, step 4, the title compound (28.3 mg) was obtained as a white solid from ethyl 3-cyclopropyl-3-(2-((1-(2-((2,2-dimethylpropyl)(6-methylpyridin-2-yl)carbamoyl)-4-fluoro-5-methoxyphenyl)piperidin-4-yl)methoxy)pyridin-4-yl)propanoate (37.0 mg).
MS (ESI+): [M+H]$^+$ 633.3.

Example 251

3-cyclopropyl-3-(2-((1-(2-((2,2-dimethylpropyl)(6-methylpyridin-2-yl)carbamoyl)-3-fluoro-5-methoxyphenyl)piperidin-4-yl)methoxy)pyridin-4-yl)propanoic acid Step 1) 2,6-difluoro-4-methoxybenzoic acid Under a nitrogen atmosphere, a 1.6 M solution of n-butyllithium in hexane (31.2 mL) was added to a solution of 1,3-difluoro-5-methoxybenzene (5.54 g) in THF (120 mL) at −78° C., and the mixture was stirred at −78° C. for 30 min. Sublimated dry ice (8.46 g) was added to the reaction solution through a silica gel tube at −78° C., and the mixture was stirred at room temperature for 5 min. To the reaction solution was added 1N hydrochloric acid at 0° C., and the mixture was extracted with ethyl acetate/THF. The extract was washed with saturated brine, and dried over anhydrous magnesium sulfate. The solvent was evaporated under reduced pressure and the obtained solid was washed with hexane and diisopropyl ether to give the title compound (5.00 g) as a white solid.
$^1$H NMR (400 MHz, DMSO-d$_6$) δ 3.83 (3H, s), 6.82 (2H, d, J=11.0 Hz), 13.43 (1H, brs).

Step 2) N-(2,2-dimethylpropyl)-2,6-difluoro-4-methoxy-N-(5-methylpyridin-2-yl)benzamide In the same manner as in Example 1, step 1, the title compound (682 mg) was obtained as a white solid from 2,6-difluoro-4-methoxybenzoic acid (500 mg) and N-(2,2-dimethylpropyl)-6-methylpyridin-2-amine (711 mg).
$^1$H NMR (400 MHz, CDCl$_3$) δ 0.87 (9H, brs), 2.44 (3H, s), 3.72 (3H, s), 4.09 (2H, s), 6.26 (2H, d, J=9.4 Hz), 6.76 (1H, brs), 6.87 (1H, d, J=7.5 Hz), 7.30-7.42 (1H, m).

Step 3) ethyl 3-cyclopropyl-3-(2-((1-(2-((2,2-dimethylpropyl)(6-methylpyridin-2-yl)carbamoyl)-3-fluoro-5-methoxyphenyl)piperidin-4-yl)methoxy)pyridin-4-yl)propanoate In the same manner as in Example 1, step 2, the title compound (191 mg) was obtained as a white amorphous powder from N-(2,2-dimethylpropyl)-2,6-difluoro-4-methoxy-N-(5-methylpyridin-2-yl)benzamide (150 mg) and ethyl 3-cyclopropyl-3-(2-(piperidin-4-ylmethoxy)pyridin-4-yl)propanoate (143 mg).
$^1$H NMR (400 MHz, CDCl$_3$) δ 0.10-0.21 (1H, m), 0.26-0.34 (1H, m), 0.42-0.53 (1H, m), 0.56-0.66 (1H, m), 0.86 (9H, s), 0.93-1.06 (1H, m), 1.19 (3H, t, J=7.1 Hz), 1.30-1.47 (1H, m), 1.49-1.66 (1H, m), 1.73-1.91 (3H, m), 2.26-2.34 (1H, m), 2.36-2.55 (2H, m), 2.41 (3H, s), 2.57-2.82 (3H, m), 3.54 (1H, d, J=11.5 Hz), 3.71 (3H, s), 4.01-4.29 (6H, m), 5.98 (1H, s), 6.21 (1H, d, J=10.9 Hz), 6.53 (1H, d, J=7.9 Hz), 6.63 (1H, s), 6.71-6.81 (2H, m), 7.15 (1H, t, J=7.7 Hz), 8.07 (1H, d, J=5.3 Hz).

Step 4) 3-cyclopropyl-3-(2-((1-(2-((2,2-dimethylpropyl)(6-methylpyridin-2-yl)carbamoyl)-3-fluoro-5-methoxyphenyl)piperidin-4-yl)methoxy)pyridin-4-yl)propanoic acid In the same manner as in Example 1, step 4, the title compound (173 mg) was obtained as a white amorphous powder from ethyl 3-cyclopropyl-3-(2-((1-(2-((2,2-dimethylpropyl)(6-methylpyridin-2-yl)carbamoyl)-3-fluoro-5-methoxyphenyl)piperidin-4-yl)methoxy)pyridin-4-yl)propanoate (191 mg).
MS (ESI+): [M+H]$^+$ 633.3.

Example 252

3-cyclopropyl-3-(2-((1-(6-((2,2-dimethylpropyl)(6-methylpyridin-2-yl)carbamoyl)-2-fluoro-3-methoxyphenyl)piperidin-4-yl)methoxy)pyridin-4-yl)propanoic acid Step 1) 2,3-difluoro-4-hydroxybenzoic acid In the same manner as in Example 250, step 1, a crude product of the title compound was obtained as a white solid from 2,3,4-trifluorobenzoic acid (1.00 g). This compound was used for the next step without further purification.

Step 2) methyl 2,3-difluoro-4-methoxybenzoate

In the same manner as in Example 250, step 2, the title compound (422 mg) was obtained as a white solid from a crude product (entire amount) of 2,3-difluoro-4-hydroxybenzoic acid.
$^1$H NMR (400 MHz, CDCl$_3$) δ 3.89-3.94 (3H, m), 3.96 (3H, s), 6.78 (1H, t, J=7.5 Hz), 7.62-7.86 (1H, m).

Step 3) 2,3-difluoro-4-methoxybenzoic acid

In the same manner as in Example 250, step 3, the title compound (387 mg) was obtained as a white solid from methyl 2,3-difluoro-4-methoxybenzoate (422 mg).
$^1$H NMR (400 MHz, DMSO-d$_6$) δ 3.94 (3H, s), 7.12 (1H, t, J=8.0 Hz), 7.69 (1H, t, J=7.8 Hz), 13.22 (1H, brs).

Step 4) N-(2,2-dimethylpropyl)-2,3-difluoro-4-methoxy-N-(6-methylpyridin-2-yl)benzamide In the same manner as in Example 1, step 1, the title compound (455 mg) was obtained as a white solid from 2,3-difluoro-4-methoxybenzoic acid (387 mg) and N-(2,2-dimethylpropyl)-6-methylpyridin-2-amine (376 mg).
$^1$H NMR (400 MHz, CDCl$_3$) δ 0.86 (9H, s), 2.45 (3H, s), 3.84 (3H, s), 4.10 (2H, s), 6.57 (1H, t, J=7.7 Hz), 6.63 (1H, d, J=8.0 Hz), 6.86 (1H, d, J=7.5 Hz), 6.91 (1H, t, J=7.8 Hz), 7.31 (1H, t, J=7.8 Hz).

Step 5) ethyl 3-cyclopropyl-3-(2-((1-(6-((2,2-dimethylpropyl)(6-methylpyridin-2-yl)carbamoyl)-2-fluoro-3-methoxyphenyl)piperidin-4-yl)methoxy)pyridin-4-yl)propanoate In the same manner as in Example 1, step 2, the title compound (188 mg) was obtained as a white amorphous powder from N-(2,2-dimethylpropyl)-2,3-difluoro-4-methoxy-N-(6-methylpyridin-2-yl)benzamide (150 mg) and ethyl 3-cyclopropyl-3-(2-(piperidin-4-ylmethoxy)pyridin-4-yl)propanoate (157 mg).
$^1$H NMR (400 MHz, CDCl$_3$) δ 0.11-0.21 (1H, m), 0.23-0.35 (1H, m), 0.40-0.51 (1H, m), 0.53-0.66 (1H, m), 0.85 (9H, brs), 0.94-1.05 (1H, m), 1.19 (3H, t, J=7.1 Hz), 1.38-1.55 (2H, m), 1.70-1.98 (3H, m), 2.24-2.36 (1H, m), 2.44 (3H, s), 2.59-2.85 (4H, m), 3.06-3.41 (2H, m), 3.81 (3H, s), 3.99-4.38 (4H, m), 4.15 (2H, d, J=6.4 Hz), 6.48 (1H, brs), 6.52-6.59 (1H, m), 6.62 (1H, s), 6.71-6.81 (2H, m), 6.85 (1H, d, J=7.3 Hz), 7.18 (1H, brs), 8.06 (1H, d, J=5.4 Hz).

Step 6) 3-cyclopropyl-3-(2-((1-(6-((2,2-dimethylpropyl)(6-methylpyridin-2-yl)carbamoyl)-2-fluoro-3-methoxyphenyl)piperidin-4-yl)methoxy)pyridin-4-yl)propanoic acid In the same manner as in Example 1, step 4, the title compound (141 mg) was obtained as a white amorphous powder from ethyl 3-cyclopropyl-3-(2-((1-(6-((2,2-dimethylpropyl)(6-methylpyridin-2-yl)carbamoyl)-2-fluoro-3-methoxyphenyl)piperidin-4-yl)methoxy)pyridin-4-yl)propanoate (188 mg).
MS (ESI+): [M+H]$^+$ 633.3.

Example 253

3-cyclopropyl-3-(2-((1-(6-((2,2-dimethylpropyl)(6-methylpyridin-2-yl)carbamoyl)-2,4-difluoro-3-methoxyphenyl)piperidin-4-yl)methoxy)pyridin-4-yl)propanoic acid Step 1) 2,3,5-trifluoro-4-hydroxybenzoic acid In the same manner as in Example 250, step 1, the title compound (4.67 g) was obtained as a white solid from 2,3,4,5-tetrafluorobenzoic acid (5.00 g).
$^1$H NMR (400 MHz, DMSO-d$_6$) δ 7.47 (1H, dd, J=10.9, 6.6 Hz), 11.79 (1H, brs), 13.35 (1H, brs).

Step 2) methyl 2,3,5-trifluoro-4-methoxybenzoate

In the same manner as in Example 250, step 2, a crude product of the title compound was obtained as a pale-yellow solid from 2,3,5-trifluoro-4-hydroxybenzoic acid (4.67 g). This compound was used for the next step without further purification.

Step 3) 2,3,5-trifluoro-4-methoxybenzoic acid

In the same manner as in Example 250, step 3, the title compound (3.66 g) was obtained as a white solid from a crude product (entire amount) of methyl 2,3,5-trifluoro-4-methoxybenzoate.
$^1$H NMR (400 MHz, DMSO-d$_6$) δ 4.09 (3H, s), 7.56 (1H, dd, J=11.0, 5.8 Hz), 13.65 (1H, brs).

Step 4) N-(2,2-dimethylpropyl)-2,3,5-trifluoro-4-methoxy-N-(6-methylpyridin-2-yl)benzamide In the same manner as in Example 1, step 1, the title compound (317 mg) was obtained as a white solid from 2,3,5-trifluoro-4-methoxybenzoic acid (300 mg) and N-(2,2-dimethylpropyl)-6-methylpyridin-2-amine (266 mg).

¹H NMR (400 MHz, CDCl₃) δ 0.86 (9H, s), 2.44 (3H, s), 3.98 (3H, s), 4.07 (2H, s), 6.70 (1H, d, J=7.8 Hz), 6.77 (1H, dd, J=9.1, 5.7 Hz), 6.90 (1H, d, J=7.4 Hz), 7.37 (1H, t, J=7.8 Hz).

Step 5) ethyl 3-cyclopropyl-3-(2-((1-(6-((2,2-dimethylpropyl)(6-methylpyridin-2-yl)carbamoyl)-2,4-difluoro-3-methoxyphenyl)piperidin-4-yl)methoxy)pyridin-4-yl)propanoate In the same manner as in Example 1, step 2, the title compound (24.0 mg) was obtained as a colorless oil from N-(2,2-dimethylpropyl)-2,3,5-trifluoro-4-methoxy-N-(6-methylpyridin-2-yl)benzamide (150 mg) and ethyl 3-cyclopropyl-3-(2-(piperidin-4-ylmethoxy)pyridin-4-yl)propanoate (136 mg).
¹H NMR (400 MHz, CDCl₃) δ 0.11-0.21 (1H, m), 0.24-0.35 (1H, m), 0.40-0.51 (1H, m), 0.54-0.66 (1H, m), 0.86 (9H, br. s), 0.94-1.05 (1H, m), 1.19 (3H, t, J=7.1 Hz), 1.48 (2H, d, J=10.7 Hz), 1.79 (2H, d, J=11.5 Hz), 1.88 (1H, brs), 2.25-2.35 (1H, m), 2.43 (3H, s), 2.56 (1H, brs), 2.64-2.87 (3H, m), 3.04-3.35 (2H, m), 3.92 (3H, s), 4.01-4.30 (6H, m), 6.58 (1H, d, J=7.3 Hz), 6.62 (1H, s), 6.67 (1H, d, J=9.5 Hz), 6.76 (1H, d, J=5.1 Hz), 6.81 (1H, d, J=7.3 Hz), 7.20-7.32 (1H, m), 8.07 (1H, d, J=5.3 Hz).

Step 6) 3-cyclopropyl-3-(2-((1-(6-((2,2-dimethylpropyl)(6-methylpyridin-2-yl)carbamoyl)-2,4-difluoro-3-methoxyphenyl)piperidin-4-yl)methoxy)pyridin-4-yl)propanoic acid In the same manner as in Example 1, step 4, the title compound (12.6 mg) was obtained as a white solid from ethyl 3-cyclopropyl-3-(2-((1-(6-((2,2-dimethylpropyl)(6-methylpyridin-2-yl)carbamoyl)-2,4-difluoro-3-methoxyphenyl)piperidin-4-yl)methoxy)pyridin-4-yl)propanoate (24.0 mg).
MS (ESI+): [M+H]⁺ 651.4.

Example 254

3-cyclopropyl-3-(3-((1-(3-((2,2-dimethylpropyl)(pyridin-2-yl)carbamoyl)-6-methoxypyridin-2-yl)piperidin-4-yl)methoxy)phenyl)propanoic acid Step 1) 2-chloro-6-methoxynicotinic acid To a solution (250 mL) of 2,6-dichloronicotinic acid (5.00 g) in methanol was added potassium tert-butoxide (8.77 g), and the mixture was heated under reflux for 10 hr. The solvent in the reaction mixture was evaporated under reduced pressure, and the residue was suspended in water and neutralized with 1N HCl. The precipitate was collected by filtration to give the title compound (3.15 g) as a white solid.
MS (ESI+): [M+H]⁺ 188.0.

Step 2) benzyl 2-chloro-6-methoxynicotinate

In the same manner as in Example 59, step 2, the title compound (2.05 g) was obtained as a colorless oil from 2-chloro-6-methoxynicotinic acid (1.5 g).
MS (ESI+): [M+H]⁺ 278.0.

Step 3) benzyl 2-(4-((3-(1-cyclopropyl-3-ethoxy-3-oxopropyl)phenoxy)methyl)piperidin-1-yl)-6-methoxynicotinate To a solution (8 mL) of benzyl 2-chloro-6-methoxynicotinate (500 mg) in DMF were added ethyl 3-cyclopropyl-3-(3-(piperidin-4-ylmethoxy)phenyl)propanoate (656 mg) and potassium carbonate (747 mg) and the mixture was stirred at 100° C. for 2.5 hr. To the reaction mixture was added water and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (920 mg) as a colorless oil.
MS (ESI+): [M+H]⁺ 573.3.

Step 4) 2-(4-((3-(1-cyclopropyl-3-ethoxy-3-oxopropyl)phenoxy)methyl)piperidin-1-yl)-6-methoxynicotinic acid In the same manner as in Example 59, step 4, the title compound (781 mg) was obtained as a pale-yellow oil from benzyl 2-(4-((3-(1-cyclopropyl-3-ethoxy-3-oxopropyl)phenoxy)methyl)piperidin-1-yl)-6-methoxynicotinate (920 mg).
MS (ESI+): [M+H]⁺ 483.2.

Step 5) 3-cyclopropyl-3-(3-((1-(3-((2,2-dimethylpropyl)(pyridin-2-yl)carbamoyl)-6-methoxypyridin-2-yl)piperidin-4-yl)methoxy)phenyl)propanoic acid In the same manner as in Example 32, step 2 and Example 1, step 4, the title compound (140 mg) was obtained as a pale-yellow oil from 2-(4-((3-(1-cyclopropyl-3-ethoxy-3-oxopropyl)phenoxy)methyl)piperidin-1-yl)-6-methoxynicotinic acid (150 mg) and N-(2,2-dimethylpropyl)pyridin-2-amine (102 mg).
MS (ESI+): [M+H]⁺ 601.3.

Example 255

3-cyclopropyl-3-(2-((1-(5-((2,2-dimethylpropyl)(6-methylpyridin-2-yl)carbamoyl)-2-methoxypyridin-4-yl)piperidin-4-yl)methoxy)pyridin-4-yl)propanoic acid Step 1) 4,6-dichloronicotinic acid Lithium hydroxide monohydrate (665 mg) was added to a solution of methyl 4,6-dichloronicotinate (2.97 g) in THF (60 mL) and water (15 mL) at room temperature, and the mixture was stirred at room temperature for 1 hr. To the reaction solution was added 6N hydrochloric acid at room temperature, and the solvent was evaporated under reduced pressure. The residual solid was washed with water to give a white solid. The filtrate was extracted with ethyl acetate. The extract was washed with water and saturated brine, combined with an ethyl acetate solution of the solid obtained earlier, and dried over anhydrous magnesium sulfate. The solvent was evaporated under reduced pressure to give the title compound (2.60 g) as a pale-yellow solid.
¹H NMR (400 MHz, DMSO-d₆) δ 7.94 (1H, s), 8.81 (1H, s), 13.63-14.30 (1H, m).

Step 2) benzyl 4,6-dichloronicotinate

Under a nitrogen atmosphere, benzyl bromide (1.36 mL) was added to a mixture of 4,6-dichloronicotinic acid (2.0 g), potassium carbonate (2.88 g) and DMF (20 mL) at room temperature, and the mixture was stirred at 60° C. for 10 min. To the reaction solution was added water at room temperature, and the mixture was extracted with ethyl acetate. The extract was washed with water and saturated brine, and dried over anhydrous magnesium sulfate. The solvent was evaporated under reduced pressure to give a crude product (3.06 g) of the title compound as a pale-yellow oil. This compound was used for the next step without further purification.

$^1$H NMR (400 MHz, CDCl$_3$) δ 5.40 (2H, s), 7.32-7.50 (6H, m), 8.87 (1H, s).

Step 3) benzyl 6-chloro-4-(4-(hydroxymethyl)piperidin-1-yl)nicotinate

A mixture of the crude product of benzyl 4,6-dichloronicotinate (3.06 g), piperidin-4-ylmethanol (1.29 g), potassium carbonate (2.11 g) and DMF (30 mL) was stirred at 60° C. for 1 hr. To the reaction solution was added water at room temperature, and the mixture was extracted with ethyl acetate. The extract was washed with water and saturated brine, and dried over anhydrous magnesium sulfate. The solvent was evaporated under reduced pressure to give a crude product (3.94 g) of the title compound as a pale-yellow oil. This compound was used for the next step without further purification.

Step 4) benzyl 6-chloro-4-(4-(((tetrahydro-2H-pyran-2-yl)oxy)methyl)piperidin-1-yl)nicotinate p-Toluenesulfonic acid monohydrate (208 mg) was added to a solution of the crude product (3.94 g) of benzyl 6-chloro-4-(4-(hydroxymethyl)piperidin-1-yl)nicotinate and 3,4-dihydro-2H-pyran (2.00 mL) in THF (20 mL) at room temperature, and the mixture was stirred at room temperature for 16 hr. To the reaction solution was added saturated aqueous sodium hydrogen carbonate solution at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (3.50 g) as a colorless oil.

$^1$H NMR (400 MHz, CDCl$_3$) δ 1.29-1.46 (2H, m), 1.47-1.65 (4H, m), 1.66-1.90 (5H, m), 2.89 (2H, t, J=12.0 Hz), 3.22 (1H, dd, J=9.3, 6.1 Hz), 3.44 (2H, d, J=12.5 Hz), 3.48-3.55 (1H, m), 3.56-3.65 (1H, m), 3.77-3.90 (1H, m), 4.56 (1H, brs), 5.34 (2H, s), 6.75 (1H, s), 7.31-7.47 (5H, m), 8.50 (1H, s).

Step 5) benzyl 6-methoxy-4-(4-(((tetrahydro-2H-pyran-2-yl)oxy)methyl)piperidin-1-yl)nicotinate Under a nitrogen atmosphere, a solution of benzyl 6-chloro-4-(4-(((tetrahydro-2H-pyran-2-yl)oxy)methyl)piperidin-1-yl)nicotinate (3.37 g) in DMF (10 mL) was added to a 28% solution of sodium methoxide in methanol (14.4 mL) at room temperature, and the mixture was stirred at room temperature for 1 hr and at 50° C. for 1 hr. The mixture was diluted with ethyl acetate, 1N hydrochloric acid was added to the reaction solution at 0° C., and the mixture was extracted with ethyl acetate. The extract was washed with water and saturated brine, and dried over anhydrous magnesium sulfate. The solvent was evaporated under reduced pressure. The residue was dissolved in THF (30 mL) and methanol (15 mL), 1N aqueous sodium hydroxide solution (30 mL) was added, and the mixture was stirred at 60° C. for 24 hr. The mixture was diluted with ethyl acetate, and extracted with 1N aqueous sodium hydroxide solution (25 mL). The extract was neutralized with 1N hydrochloric acid (55 mL) and extracted with ethyl acetate. The extract was washed with water and saturated brine, and dried over anhydrous magnesium sulfate. The solvent was evaporated under reduced pressure. Benzyl bromide (1.02 mL) was added to a mixture of the obtained residue, potassium carbonate (2.46 g) and DMF (30 mL) at room temperature, and the mixture was stirred at room temperature for 16 hr. To the reaction solution was added water at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (2.70 g) as a colorless oil.

$^1$H NMR (400 MHz, CDCl$_3$) δ 1.29-1.48 (2H, m), 1.48-1.66 (4H, m), 1.66-1.92 (5H, m), 2.77 (2H, t, J=11.7 Hz), 3.22 (1H, dd, J=9.2, 6.5 Hz), 3.43 (2H, d, J=11.9 Hz), 3.47-3.56 (1H, m), 3.56-3.65 (1H, m), 3.84 (1H, t, J=9.6 Hz), 3.92 (3H, s), 4.57 (1H, brs), 5.32 (2H, s), 6.14 (1H, s), 7.29-7.40 (3H, m), 7.40-7.49 (2H, m), 8.54 (1H, s).

Step 6) benzyl 4-(4-(hydroxymethyl)piperidin-1-yl)-6-methoxynicotinate

2N Hydrochloric acid (12.3 mL) was added to a solution of benzyl 6-methoxy-4-(4-(((tetrahydro-2H-pyran-2-yl)oxy)methyl)piperidin-1-yl)nicotinate (2.70 g) in THF (30 mL) at room temperature, and the mixture was stirred at 40° C. for 4 hr and at 50° C. for 1 hr. To the reaction solution was added saturated aqueous sodium hydrogen carbonate solution at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (1.67 g) as a colorless oil.

$^1$H NMR (400 MHz, DMSO-d$_6$) δ 1.05-1.19 (2H, m), 1.42-1.57 (1H, m), 1.62 (2H, d, J=12.0 Hz), 2.73 (2H, t, J=11.8 Hz), 3.22 (2H, t, J=5.6 Hz), 3.35 (2H, d, J=12.5 Hz), 3.83 (3H, s), 4.45 (1H, t, J=5.2 Hz), 5.28 (2H, s), 6.20 (1H, s), 7.26-7.52 (5H, m), 8.32 (1H, s).

Step 7) benzyl 4-(4-(((4-(1-cyclopropyl-3-ethoxy-3-oxopropyl)pyridin-2-yl)oxy)methyl)piperidin-1-yl)-6-methoxynicotinatoyl)oxy)methyl)piperidin-1-yl)-6-methoxynicotinate In the same manner as in Example 45, step 6, the title compound (522 mg) was obtained as a pale-orange oil from benzyl 4-(4-(hydroxymethyl)piperidin-1-yl)-6-methoxynicotinate (576 mg) and methyl 3-cyclopropyl-3-(2-hydroxypyridin-4-yl)propanoate (329 mg).

$^1$H NMR (400 MHz, CDCl$_3$) δ 0.08-0.22 (1H, m), 0.24-0.36 (1H, m), 0.39-0.53 (1H, m), 0.55-0.67 (1H, m), 0.91-1.07 (1H, m), 1.19 (3H, t, J=7.1 Hz), 1.40-1.55 (2H, m), 1.83 (2H, d, J=11.8 Hz), 1.96 (1H, brs), 2.25-2.36 (1H, m), 2.62-2.87 (4H, m), 3.46 (2H, d, J=12.0 Hz), 3.93 (3H, s), 4.01-4.19 (4H, m), 5.33 (2H, s), 6.16 (1H, s), 6.61 (1H, s), 6.76 (1H, d, J=5.3 Hz), 7.29-7.49 (5H, m), 8.05 (1H, d, J=5.1 Hz), 8.55 (1H, s).

Step 8) 4-(4-(((4-(1-cyclopropyl-3-ethoxy-3-oxopropyl)pyridin-2-yl)oxy)methyl)piperidin-1-yl)-6-methoxynicotinic acid Benzyl 4-(4-(((4-(1-cyclopropyl-3-ethoxy-3-oxopropyl)pyridin-2-yl)oxy)methyl)piperidin-1-yl)-6-methoxynicotinatoyl)oxy)methyl)piperidin-1-yl)-6-methoxypyridine-3-carboxylate (522 mg) and 10% palladium carbon (300 mg) were stirred in THF (15 mL) under a hydrogen atmosphere (1 atm) at room temperature for 20 min. The reaction mixture was filtered, and the solvent in the filtrate was evaporated under reduced pressure to give the title compound (407 mg) as a colorless amorphous powder.

$^1$H NMR (400 MHz, DMSO-d$_6$) δ 0.08-0.20 (1H, m), 0.22-0.29 (1H, m), 0.31-0.40 (1H, m), 0.44-0.56 (1H, m), 0.95-1.05 (1H, m), 1.08 (3H, t, J=7.1 Hz), 1.37-1.49 (2H, m), 1.80 (2H, d, J=11.8 Hz), 1.88-2.04 (1H, m), 2.16-2.30 (1H, m), 2.75 (2H, d, J=7.4 Hz), 2.83 (2H, t, J=12.1 Hz), 3.45 (2H, d, J=12.2 Hz), 3.84 (3H, s), 3.92-4.02 (2H, m), 4.13 (2H, d, J=6.1 Hz), 6.26 (1H, s), 6.72 (1H, s), 6.91 (1H, d, J=5.3 Hz), 8.03 (1H, d, J=5.1 Hz), 8.33 (1H, s), 12.87 (1H, brs).

Step 9) ethyl 3-cyclopropyl-3-(2-((1-(5-((2,2-dimethylpropyl)(6-methylpyridin-2-yl)carbamoyl)-2-methoxypyridin-4-yl)piperidin-4-yl)methoxy)pyridin-4-yl)propanoate In the same manner as in Example 32, step 2, the title compound (14.5 mg) was obtained as a colorless oil from 4-(4-(((4-(1-cyclopropyl-3-ethoxy-3-oxopropyl)pyridin-2-yl)oxy)methyl)piperidin-1-yl)-6-methoxynicotinic acid (73 mg) and N-(2,2-dimethylpropyl)-6-methylpyridin-2-amine (67.3 mg).

$^1$H NMR (400 MHz, CDCl$_3$) δ 0.09-0.21 (1H, m), 0.24-0.35 (1H, m), 0.42-0.53 (1H, m), 0.55-0.67 (1H, m), 0.82 (9H, s), 0.90-1.05 (1H, m), 1.19 (3H, t, J=7.2 Hz), 1.25-2.01 (6H, m), 2.30 (1H, q, J=8.4 Hz), 2.45 (3H, s), 2.47-2.91 (4H, m), 3.43 (1H, brs), 3.88 (3H, s), 4.00-4.29 (6H, m), 5.79 (1H, s), 6.43 (1H, brs), 6.62 (1H, s), 6.76 (2H, d, J=6.1 Hz), 7.19 (1H, t, J=7.6 Hz), 7.99 (1H, s), 8.05 (1H, d, J=5.1 Hz).

Step 10) 3-cyclopropyl-3-(2-((1-(5-((2,2-dimethylpropyl)(6-methylpyridin-2-yl)carbamoyl)-2-methoxypyridin-4-yl)piperidin-4-yl)methoxy)pyridin-4-yl)propanoic acid In the same manner as in Example 1, step 4, the title compound (13.5 mg) was obtained as a white amorphous powder from ethyl 3-cyclopropyl-3-(2-((1-(5-((2,2-dimethylpropyl)(6-methylpyridin-2-yl)carbamoyl)-2-methoxypyridin-4-yl)piperidin-4-yl)methoxy)pyridin-4-yl)propanoate (14.5 mg).

MS (ESI+): [M+H]$^+$ 616.3.

Example 256

3-cyclopropyl-3-(2-((1-(2-methoxy-5-(pyridin-2-yl(2,2,2-trifluoroethyl)carbamoyl)pyridin-4-yl)piperidin-4-yl)methoxy)pyridin-4-yl)propanoic acid Step 1) ethyl 3-cyclopropyl-3-(2-((1-(2-methoxy-5-(pyridin-2-yl(2,2,2-trifluoroethyl)carbamoyl)pyridin-4-yl)piperidin-4-yl)methoxy)pyridin-4-yl)propanoate In the same manner as in Example 32, step 2, the title compound (30.8 mg) was obtained as a colorless oil from 4-(4-(((4-(1-cyclopropyl-3-ethoxy-3-oxopropyl)pyridin-2-yl)oxy)methyl)piperidin-1-yl)-6-methoxynicotinic acid (58.7 mg) and N-(2,2,2-trifluoroethyl)pyridin-2-amine (53.5 mg).

$^1$H NMR (400 MHz, CDCl$_3$) δ 0.12-0.22 (1H, m), 0.26-0.33 (1H, m), 0.41-0.52 (1H, m), 0.56-0.66 (1H, m), 0.92-1.05 (1H, m), 1.19 (3H, t, J=7.2 Hz), 1.26-1.52 (2H, m), 1.75 (2H, d, J=11.7 Hz), 1.83-1.98 (1H, m), 2.27-2.35 (1H, m), 2.58-2.81 (4H, m), 3.17 (2H, brs), 3.90 (3H, s), 4.02-4.11 (2H, m), 4.14 (2H, d, J=6.7 Hz), 4.83-5.05 (2H, m), 5.84 (1H, s), 6.62 (1H, s), 6.67 (1H, d, J=7.9 Hz), 6.77 (1H, d, J=5.3 Hz), 7.02 (1H, dd, J=7.2, 5.0 Hz), 7.38 (1H, t, J=7.8 Hz), 8.03-8.08 (2H, m), 8.42 (1H, d, J=4.4 Hz).

Step 2) 3-cyclopropyl-3-(2-((1-(2-methoxy-5-(pyridin-2-yl(2,2,2-trifluoroethyl)carbamoyl)pyridin-4-yl)piperidin-4-yl)methoxy)pyridin-4-yl)propanoic acid In the same manner as in Example 1, step 4, the title compound (18.6 mg) was obtained as a white amorphous powder from ethyl 3-cyclopropyl-3-(2-((1-(2-methoxy-5-(pyridin-2-yl(2,2,2-trifluoroethyl)carbamoyl)pyridin-4-yl)piperidin-4-yl)methoxy)pyridin-4-yl)propanoate (30.8 mg).

MS (ESI+): [M+H]$^+$ 614.2.

Example 257

3-cyclopropyl-3-(2-((1-(5-((2,2-dimethylpropyl)(6-methylpyrimidin-4-yl)carbamoyl)-2-methoxypyridin-4-yl)piperidin-4-yl)methoxy)pyridin-4-yl)propanoic acid In the same manner as in Example 32, step 2 and Example 1, step 4, the title compound (21 mg) was obtained as a colorless amorphous powder from N-(2,2-dimethylpropyl)-6-methylpyrimidin-4-amine (68 mg) and 4-(4-(((4-(1-cyclopropyl-3-ethoxy-3-oxopropyl)pyridin-2-yl)oxy)methyl)piperidin-1-yl)-6-methoxynicotinic acid (115 mg) obtained in Example 255, step 8. MS (ESI+): [M+H]$^+$ 617.2.

Example 258

3-cyclopropyl-3-(2-((1-(2-((2,2-dimethylpropyl)(6-methylpyridin-2-yl)carbamoyl)-5-methylphenyl)piperidin-4-yl)methoxy)pyridin-4-yl)propanoic acid Step 1) N-(2,2-dimethylpropyl)-2-fluoro-4-methyl-N-(6-methylpyridin-2-yl)benzamide In the same manner as in Example 1, step 1, the title compound (718 mg) was obtained as a white solid from 2-fluoro-4-methylbenzoic acid (865 mg) and N-(2,2-dimethylpropyl)-6-methylpyridin-2-amine (500 mg).

MS (ESI+): [M+H]$^+$ 315.2.

Step 2) 3-cyclopropyl-3-(2-((1-(2-((2,2-dimethylpropyl)(6-methylpyridin-2-yl)carbamoyl)-5-methylphenyl)piperidin-4-yl)methoxy)pyridin-4-yl)propanoic acid In the same manner as in Example 245, step 12 and Example 1, step 4, the title compound (70 mg) was obtained as grayish white solid from ethyl 3-cyclopropyl-3-(2-(piperidin-4-ylmethoxy)pyridin-4-yl)propanoate (155 mg) and N-(2,2-dimethylpropyl)-2-fluoro-4-methyl-N-(6-methylpyridin-2-yl)benzamide (113 mg).

MS (ESI+): [M+H]$^+$ 599.3.

Example 259

3-cyclopropyl-3-(2-((1-(2-((2,2-dimethylpropyl)(6-methylpyridin-2-yl)carbamoyl)-5-hydroxyphenyl)piperidin-4-yl)methoxy)pyridin-4-yl)propanoic acid

Step 1) 4-(benzyloxy)-N-(2,2-dimethylpropyl)-2-fluoro-N-(6-methylpyridin-2-yl)benzamide In the same manner as in Example 1, step 1, the title compound (478 mg) was obtained as grayish white solid from 4-(benzyloxy)-2-fluorobenzoic acid (2.0 g) and N-(2,2-dimethylpropyl)-6-methylpyridin-2-amine (724 mg).
MS (ESI+): [M+H]$^+$ 407.2.

Step 2) ethyl 3-(2-((1-(5-(benzyloxy)-2-((2,2-dimethylpropyl)(6-methylpyridin-2-yl)carbamoyl)phenyl)piperidin-4-yl)methoxy)pyridin-4-yl)-3-cyclopropylpropanoate In the same manner as in Example 245, step 12, the title compound (200 mg) was obtained as a pale-yellow oil from ethyl 3-cyclopropyl-3-(2-(piperidin-4-ylmethoxy)pyridin-4-yl)propanoate (176 mg) and 4-(benzyloxy)-N-(2,2-dimethylpropyl)-2-fluoro-N-(6-methylpyridin-2-yl)benzamide (215 mg).
MS (ESI+): [M+H]$^+$ 719.5.

Step 3) ethyl 3-cyclopropyl-3-(2-((1-(2-((2,2-dimethylpropyl)(6-methylpyridin-2-yl)carbamoyl)-5-hydroxyphenyl)piperidin-4-yl)methoxy)pyridin-4-yl)propanoate In the same manner as in Example 199, step 1, the title compound (155 mg) was obtained as a colorless oil from ethyl 3-(2-((1-(5-(benzyloxy)-2-((2,2-dimethylpropyl)(6-methylpyridin-2-yl)carbamoyl)phenyl)piperidin-4-yl)methoxy)pyridin-4-yl)-3-cyclopropylpropanoate (180 mg).
MS (ESI+): [M+H]$^+$ 629.4.

Step 4) 3-cyclopropyl-3-(2-((1-(2-((2,2-dimethylpropyl)(6-methylpyridin-2-yl)carbamoyl)-5-hydroxyphenyl)piperidin-4-yl)methoxy)pyridin-4-yl)propanoic acid In the same manner as in Example 1, step 4, the title compound (6.3 mg) was obtained as a grayish white amorphous powder from ethyl 3-cyclopropyl-3-(2-((1-(2-((2,2-dimethylpropyl)(6-methylpyridin-2-yl)carbamoyl)-5-hydroxyphenyl)piperidin-4-yl)methoxy)pyridin-4-yl)propanoate (15 mg).
MS (ESI+): [M+H]$^+$ 601.3.

Example 260

3-(2-((1-(5-cyano-2-((2,2-dimethylpropyl)(6-methylpyridin-2-yl)carbamoyl)phenyl)piperidin-4-yl)methoxy)pyridin-4-yl)-3-cyclopropylpropanoic acid

Step 1) 4-cyano-N-(2,2-dimethylpropyl)-2-fluoro-N-(6-methylpyridin-2-yl)benzamide In the same manner as in Example 1, step 1, the title compound (503 mg) was obtained as a pale-orange solid from 4-cyano-2-fluorobenzoic acid (500 mg) and N-(2,2-dimethylpropyl)-6-methylpyridin-2-amine (360 mg).
$^1$H NMR (400 MHz, CDCl$_3$) δ 0.88 (9H, s), 2.36 (3H, s), 4.06 (2H, s), 6.75 (1H, d, J=7.4 Hz), 6.88 (1H, d, J=7.5 Hz), 7.18 (1H, d, J=8.7 Hz), 7.27-7.34 (2H, m), 7.37 (1H, t, J=7.7 Hz).

Step 2) ethyl 3-(2-((1-(5-cyano-2-((2,2-dimethylpropyl)(6-methylpyridin-2-yl)carbamoyl)phenyl)piperidin-4-yl)methoxy)pyridin-4-yl)-3-cyclopropylpropanoate In the same manner as in Example 1, step 2, the title compound (235 mg) was obtained as a colorless oil from 4-cyano-N-(2,2-dimethylpropyl)-2-fluoro-N-(6-methylpyridin-2-yl)benzamide (150 mg) and ethyl 3-cyclopropyl-3-(2-(piperidin-4-ylmethoxy)pyridin-4-yl)propanoate (153 mg).
$^1$H NMR (400 MHz, CDCl$_3$) δ 0.11-0.22 (1H, m), 0.25-0.34 (1H, m), 0.41-0.51 (1H, m), 0.55-0.67 (1H, m), 0.85 (9H, s), 0.93-1.06 (1H, m), 1.19 (3H, t, J=7.2 Hz), 1.25-1.39 (1H, m), 1.53-1.68 (1H, m), 1.74-1.94 (3H, m), 2.04 (1H, s), 2.26-2.35 (1H, m), 2.38 (3H, s), 2.41-2.65 (2H, m), 2.66-2.81 (3H, m), 3.46 (1H, d, J=10.9 Hz), 4.02-4.12 (2H, m), 4.12-4.27 (4H, m), 6.41 (1H, d, J=7.8 Hz), 6.63 (1H, s), 6.72-6.81 (2H, m), 6.91 (1H, s), 7.14 (1H, t, J=7.8 Hz), 7.20 (1H, d, J=7.5 Hz), 7.41 (1H, d, J=7.9 Hz), 8.07 (1H, d, J=5.1 Hz).

Step 3) 3-(2-((1-(5-cyano-2-((2,2-dimethylpropyl)(6-methylpyridin-2-yl)carbamoyl)phenyl)piperidin-4-yl)methoxy)pyridin-4-yl)-3-cyclopropylpropanoic acid In the same manner as in Example 1, step 4, the title compound (44.8 mg) was obtained as a white solid from ethyl 3-(2-((1-(5-cyano-2-((2,2-dimethylpropyl)(6-methylpyridin-2-yl)carbamoyl)phenyl)piperidin-4-yl)methoxy)pyridin-4-yl)-3-cyclopropylpropanoate (50.0 mg).
MS (ESI+): [M+H]$^+$ 610.3.

Example 261

3-(2-((1-(5-carbamoyl-2-((2,2-dimethylpropyl)(6-methylpyridin-2-yl)carbamoyl)phenyl)piperidin-4-yl)methoxy)pyridin-4-yl)-3-cyclopropylpropanoic acid

Step 1) N1-(2,2-dimethylpropyl)-2-fluoro-N1-(6-methylpyridin-2-yl)benzene-1,4-dicarboxamide 30% Hydrogen peroxide aqueous solution (235 μL) was added to a mixture of 4-cyano-N-(2,2-dimethylpropyl)-2-fluoro-N-(6-methylpyridin-2-yl)benzamide (150 mg), potassium carbonate (96 mg) and DMSO (2 mL) at room temperature, and the mixture was stirred at room temperature for 5 min. To the reaction solution was added water at room temperature, and the mixture was extracted with ethyl acetate. The extract was washed with saturated brine, and dried over anhydrous magnesium sulfate. The solvent was evaporated under reduced pressure and the obtained solid was washed with diisopropyl ether to give the title compound (134 mg) as a white solid.
$^1$H NMR (400 MHz, DMSO-d$_6$) δ 0.81 (9H, s), 2.27 (3H, s), 3.98 (2H, s), 6.90-7.02 (2H, m), 7.26 (1H, t, J=7.2 Hz), 7.44-7.60 (4H, m), 8.00 (1H, brs).

Step 2) ethyl 3-(2-((1-(5-carbamoyl-2-((2,2-dimethylpropyl)(6-methylpyridin-2-yl)carbamoyl)phenyl)piperidin-4-yl)methoxy)pyridin-4-yl)-3-cyclopropylpropanoate In the same manner as in Example 1, step 2, the title compound (50.4 mg) was obtained as a pale-yellow amorphous powder from N1-(2,2-dimethylpropyl)-2-fluoro-N1-(6-methylpyridin-2-yl)benzene-1,4-dicarboxamide (134 mg) and ethyl 3-cyclopropyl-3-(2-(piperidin-4-ylmethoxy)pyridin-4-yl)propanoate (130 mg).

$^1$H NMR (400 MHz, CDCl$_3$) δ 0.11-0.23 (1H, m), 0.25-0.34 (1H, m), 0.41-0.52 (1H, m), 0.56-0.67 (1H, m), 0.85 (9H, brs), 0.95-1.04 (1H, m), 1.19 (3H, t, J=7.2 Hz), 1.24-1.41 (1H, m), 1.52-1.70 (1H, m), 1.74-1.93 (3H, m), 2.31 (1H, q, J=8.0 Hz), 2.40 (3H, s), 2.43-2.87 (5H, m), 3.47 (1H, brs), 3.97-4.31 (6H, m), 5.50 (1H, brs), 6.00 (1H, brs), 6.40 (1H, d, J=7.9 Hz), 6.64 (1H, s), 6.71 (1H, d, J=7.3 Hz), 6.77 (1H, d, J=5.4 Hz), 7.08 (1H, t, J=7.6 Hz), 7.21-7.27 (2H, m), 7.38 (1H, d, J=7.7 Hz), 8.07 (1H, d, J=5.3 Hz).

Step 3) 3-(2-((1-(5-carbamoyl-2-((2,2-dimethylpropyl)(6-methylpyridin-2-yl)carbamoyl)phenyl)piperidin-4-yl)methoxy)pyridin-4-yl)-3-cyclopropylpropanoic acid In the same manner as in Example 1, step 4, the title compound (20.9 mg) was obtained as a white amorphous powder from ethyl 3-(2-((1-(5-carbamoyl-2-((2,2-dimethylpropyl)(6-methylpyridin-2-yl)carbamoyl)phenyl)piperidin-4-yl)methoxy)pyridin-4-yl)-3-cyclopropylpropanoate (50.4 mg).

MS (ESI+): [M+H]$^+$ 628.3.

Example 262

3-cyclopropyl-3-(2-((1-(2-((2,2-dimethylpropyl)(6-methylpyridin-2-yl)carbamoyl)-5-(methylsulfanyl)phenyl)piperidin-4-yl)methoxy)pyridin-4-yl)propanoic acid

Step 1) ethyl 3-(2-((1-(5-bromo-2-formylphenyl)piperidin-4-yl)methoxy)pyridin-4-yl)-3-cyclopropylpropanoate In the same manner as in Example 1, step 2, the title compound (960 mg) was obtained as a brown oil from ethyl 3-cyclopropyl-3-(2-(piperidin-4-ylmethoxy)pyridin-4-yl)propanoate (730 mg) obtained in Example 250, step 1, and 4-bromo-2-fluorobenzaldehyde (580 mg).

$^1$H NMR (300 MHz, CDCl$_3$) δ 0.11-0.22 (1H, m), 0.25-0.35 (1H, m), 0.41-0.53 (1H, m), 0.54-0.67 (1H, m), 0.93-1.05 (1H, m), 1.19 (3H, t, J=7.2 Hz), 1.56-1.72 (2H, m), 1.89-2.03 (3H, m), 2.26-2.37 (1H, m), 2.63-2.82 (2H, m), 2.93 (2H, td, J=12.0, 1.9 Hz), 3.28-3.39 (2H, m), 4.02-4.13 (2H, m), 4.22 (2H, d, J=6.0 Hz), 6.62-6.65 (1H, m), 6.77 (1H, dd, J=5.3, 1.4 Hz), 7.19-7.26 (2H, m), 7.65 (1H, d, J=8.2 Hz), 8.06 (1H, d, J=5.4 Hz), 10.21 (1H, d, J=0.6 Hz).

Step 2) 4-bromo-2-(4-(((4-(1-cyclopropyl-3-ethoxy-3-oxopropyl)pyridin-2-yl)oxy)methyl)piperidin-1-yl)benzoic acid To a solution of ethyl 3-(2-((1-(5-bromo-2-formylphenyl)piperidin-4-yl)methoxy)pyridin-4-yl)-3-cyclopropylpropanoate (750 mg), sodium dihydrogen phosphate (873 mg) and 2-methylbut-2-ene (1.55 mL) in tert-butanol (12 mL), acetone (4 mL) and water (4 mL) was added sodium chlorite (395 mg) at room temperature, and the mixture was stirred overnight. Sodium thiosulfate was added, and the mixture was diluted with saturated brine and extracted with ethyl acetate. The extract was dried over anhydrous magnesium sulfate. The solvent was evaporated under reduced pressure, and the residue was purified by silica gel column chromatography (ethyl acetate/hexane) to give the title compound (715 mg) as a colorless oil.

MS (ESI+): [M+H]$^+$ 531.2.

Step 3) 2-(4-(((4-(1-cyclopropyl-3-ethoxy-3-oxopropyl)pyridin-2-yl)oxy)methyl)piperidin-1-yl)-4-(methylsulfanyl)benzoic acid Under a nitrogen atmosphere, to a solution of 4-bromo-2-(4-(((4-(1-cyclopropyl-3-ethoxy-3-oxopropyl)pyridin-2-yl)oxy)methyl)piperidin-1-yl)benzoic acid (230 mg) in DMSO (2 mL) were added copper (I) iodide (82 mg) and zinc (II) fluoride (36 mg), and the mixture was stirred at 140° C. for 18 hr. The reaction mixture was allowed to cool to room temperature, and purified by silica gel column chromatography (ethyl acetate/hexane) to give the title compound (48 mg) as a brown oil.

MS (ESI+): [M+H]$^+$ 499.3.

Step 4) 3-cyclopropyl-3-(2-((1-(2-((2,2-dimethylpropyl)(6-methylpyridin-2-yl)carbamoyl)-5-(methylsulfanyl)phenyl)piperidin-4-yl)methoxy)pyridin-4-yl)propanoic acid In the same manner as in Example 32, step 2 and Example 1, step 4, the title compound (32 mg) was obtained as a colorless amorphous powder from N-(2,2-dimethylpropyl)-6-methylpyridin-2-amine (69 mg) and 2-(4-(((4-(1-cyclopropyl-3-ethoxy-3-oxopropyl)pyridin-2-yl)oxy)methyl)piperidin-1-yl)-4-(methylsulfanyl)benzoic acid (48 mg).

MS (ESI+): [M+H]$^+$ 631.3.

Example 263

3-(2-((1-(5-bromo-2-((2,2-dimethylpropyl)(6-methylpyridin-2-yl)carbamoyl)phenyl)piperidin-4-yl)methoxy)pyridin-4-yl)-3-cyclopropylpropanoic acid In the same manner as in Example 32, step 2 and Example 1, step 4, the title compound (85 mg) was obtained as a colorless amorphous powder from N-(2,2-dimethylpropyl)-6-methylpyridin-2-amine (242 mg) and 4-bromo-2-(4-(((4-(1-cyclopropyl-3-ethoxy-3-oxopropyl)pyridin-2-yl)oxy)methyl)piperidin-1-yl)benzoic acid (360 mg) obtained in Example 262, step 2.

MS (ESI+): [M+H]$^+$ 663.2.

Example 264

3-cyclopropyl-3-(2-((1-(2-((2,2-dimethylpropyl)(6-methylpyridin-2-yl)carbamoyl)-5-(methylsulfonyl)phenyl)piperidin-4-yl)methoxy)pyridin-4-yl)propanoic acid

Step 1) ethyl 3-cyclopropyl-3-(2-((1-(2-formyl-5-(methylsulfonyl)phenyl)piperidin-4-yl)methoxy)pyridin-4-yl)propanoate Under a nitrogen atmosphere, to a solution of ethyl 3-(2-((1-(5-bromo-2-formylphenyl)piperidin-4-yl)methoxy)

pyridin-4-yl)-3-cyclopropylpropanoate (210 mg) obtained in Example 262, step 1, in DMSO (3 mL) were added sodium methanesulfinate (208 mg) and copper (I) iodide (82 mg), and the mixture was stirred at 100° C. for 15 hr. The reaction mixture was allowed to cool to room temperature, and purified by silica gel column chromatography (ethyl acetate/hexane) to give the title compound (165 mg) as a pale-yellow oil.

MS (ESI+): [M+H]$^+$ 515.2.

Step 2) 2-(4-(((4-(1-cyclopropyl-3-ethoxy-3-oxopropyl)pyridin-2-yl)oxy)methyl)piperidin-1-yl)-4-(methylsulfonyl)benzoic acid In the same manner as in Example 262, step 2, the title compound (135 mg) was obtained as a colorless oil from ethyl 3-cyclopropyl-3-(2-((1-(2-formyl-5-(methylsulfonyl)phenyl)piperidin-4-yl)methoxy)pyridin-4-yl)propanoate (165 mg).

MS (ESI+): [M+H]$^+$ 531.2.

Step 3) 3-cyclopropyl-3-(2-((1-(2-((2,2-dimethylpropyl)(6-methylpyridin-2-yl)carbamoyl)-5-(methylsulfonyl)phenyl)piperidin-4-yl)methoxy)pyridin-4-yl)propanoic acid In the same manner as in Example 32, step 2 and Example 1, step 4, the title compound (71 mg) was obtained as a colorless amorphous powder from N-(2,2-dimethylpropyl)-6-methylpyridin-2-amine (91 mg) and 2-(4-(((4-(1-cyclopropyl-3-ethoxy-3-oxopropyl)pyridin-2-yl)oxy)methyl)piperidin-1-yl)-4-(methylsulfonyl)benzoic acid (153 mg).

MS (ESI+): [M+H]$^+$ 663.2.

Example 265

3-(2-((1-(5-chloro-2-((2,2-dimethylpropyl)(6-methylpyridin-2-yl)carbamoyl)-3-fluorophenyl)piperidin-4-yl)methoxy)pyridin-4-yl)-3-cyclopropylpropanoic acid Step 1) 4-chloro-N-(2,2-dimethylpropyl)-2,6-difluoro-N-(6-methylpyridin-2-yl)benzamide In the same manner as in Example 32, step 2, the title compound (200 mg) was obtained as a pale-yellow amorphous powder from N-(2,2-dimethylpropyl)-6-methylpyridin-2-amine (370 mg) and 4-chloro-2,6-difluorobenzoic acid (200 mg).

$^1$H NMR (300 MHz, CDCl$_3$) δ 0.88 (9H, s), 2.39 (3H, s), 4.06 (2H, s), 6.69-6.86 (3H, m), 6.90 (1H, d, J=7.6 Hz), 7.39 (1H, t, J=7.7 Hz).

Step 2) ethyl 3-(2-((1-(5-chloro-2-((2,2-dimethylpropyl)(6-methylpyridin-2-yl)carbamoyl)-3-fluorophenyl)piperidin-4-yl)methoxy)pyridin-4-yl)-3-cyclopropylpropanoate Under a nitrogen atmosphere, a mixture of 4-chloro-N-(2,2-dimethylpropyl)-2,6-difluoro-N-(6-methylpyridin-2-yl)benzamide (200 mg), ethyl 3-cyclopropyl-3-(2-(piperidin-4-ylmethoxy)pyridin-4-yl)propanoate (188 mg) obtained in Example 250, step 1, and cesium carbonate (185 mg) was stirred at 120° C. for 1 hr. The reaction mixture was allowed to cool to 80° C., diluted with ethyl acetate, and purified by silica gel column chromatography (ethyl acetate/hexane) to give the title compound (285 mg) as a colorless amorphous powder.

MS (ESI+): [M+H]$^+$ 665.3.

Step 3) 3-(2-((1-(5-chloro-2-((2,2-dimethylpropyl)(6-methylpyridin-2-yl)carbamoyl)-3-fluorophenyl)piperidin-4-yl)methoxy)pyridin-4-yl)-3-cyclopropylpropanoic acid In the same manner as in Example 1, step 4, the title compound (143 mg) was obtained as a colorless amorphous powder from ethyl 3-(2-((1-(5-chloro-2-((2,2-dimethylpropyl)(6-methylpyridin-2-yl)carbamoyl)-3-fluorophenyl)piperidin-4-yl)methoxy)pyridin-4-yl)-3-cyclopropylpropanoate (150 mg).

MS (ESI+): [M+H]$^+$ 637.3.

Example 266

3-(2-((1-(5-chloro-2-((2,2-dimethylpropyl)(6-methylpyridin-2-yl)carbamoyl)phenyl)piperidin-4-yl)methoxy)pyridin-4-yl)-3-cyclopropylpropanoic acid Step 1) 4-chloro-N-(2,2-dimethylpropyl)-2-fluoro-N-(6-methylpyridin-2-yl)benzamide In the same manner as in Example 1, step 1, the title compound (258 mg) was obtained as a pale-yellow solid from 4-chloro-2-fluorobenzoic acid (587 mg) and N-(2,2-dimethylpropyl)-6-methylpyridin-2-amine (300 mg).

MS (ESI+): [M+H]$^+$ 335.1.

Step 2) 3-(2-((1-(5-chloro-2-((2,2-dimethylpropyl)(6-methylpyridin-2-yl)carbamoyl)phenyl)piperidin-4-yl)methoxy)pyridin-4-yl)-3-cyclopropylpropanoic acid In the same manner as in Example 245, step 12 and Example 1, step 4, the title compound (113 mg) was obtained as a grayish white amorphous powder from ethyl 3-cyclopropyl-3-(2-(piperidin-4-ylmethoxy)pyridin-4-yl)propanoate (99 mg) and 4-chloro-N-(2,2-dimethylpropyl)-2-fluoro-N-(6-methylpyridin-2-yl)benzamide (100 mg).

MS (ESI+): [M+H]$^+$ 619.3.

Example 267

3-cyclopropyl-3-(2-((1-(5-(difluoromethoxy)-2-((2,2-dimethylpropyl)(6-methylpyridin-2-yl)carbamoyl)phenyl)piperidin-4-yl)methoxy)pyridin-4-yl)propanoic acid To a solution (2 mL) of ethyl 3-cyclopropyl-3-(2-((1-(2-((2,2-dimethylpropyl)(6-methylpyridin-2-yl)carbamoyl)-5-hydroxyphenyl)piperidin-4-yl)methoxy)pyridin-4-yl)propanoate (100 mg) obtained in Example 259, step 3, and methyl chloro(difluoro)acetate (101 mL) in DMA was added cesium carbonate (155 mg), and the mixture was stirred at 100° C. for 3 hr. To the reaction mixture was added water, and the mixture was extracted with ethyl acetate. The extract was washed with water and saturated brine, and dried over anhydrous sodium sulfate. The solvent was evaporated under reduced pressure, and the residue was purified by silica gel column chromatography (ethyl acetate/hexane). The obtained residue was fractionated by HPLC (C18, mobile phase: water/acetonitrile (0.1% TFA-containing system)). To the obtained fraction was added saturated aqueous sodium hydrogen carbonate solution, and the mixture was extracted with ethyl acetate. The extract was dried over anhydrous magnesium sulfate, and concentrated under reduced pressure. In the same manner as in Example 1, step 4, the title compound (55 mg) was obtained as a grayish white amorphous powder from the obtained pale-yellow oil (57 mg).

MS (ESI+): [M+H]$^+$ 651.3.

Example 268

3-cyclopropyl-3-(2-(1-(1-(2-((2,2-dimethylpropyl) (6-methylpyridin-2-yl)carbamoyl)-5-methoxyphenyl)piperidin-4-yl)ethoxy)pyridin-4-yl)propanoic acid Step 1) N-(2,2-dimethylpropyl)-2-(4-formylpiperidin-1-yl)-4-methoxy-N-(6-methylpyridin-2-yl)benzamide To a solution of N-(2,2-dimethylpropyl)-2-(4-(hydroxymethyl)piperidin-1-yl)-4-methoxy-N-(6-methylpyridin-2-yl) benzamide (210 mg) obtained in Example 110, step 2, and triethylamine (0.69 mL) in DMSO (3 mL) was added sulfur trioxide pyridine complex (314 mg) at room temperature, and the mixture was stirred for 1 hr. The reaction mixture was diluted with ethyl acetate and water, sodium thiosulfate was added, and the mixture was stirred for 30 min and extracted with ethyl acetate. The extract was washed with saturated brine, and dried over anhydrous magnesium sulfate. The solvent was evaporated under reduced pressure to give the title compound (230 mg) as a brown oil. This compound was used for the next step without further purification.

$^1$H NMR (300 MHz, CDCl$_3$) δ 0.81 (9H, s), 1.42-1.96 (4H, m), 2.18-2.31 (1H, m), 2.32-2.80 (6H, m), 3.20-3.49 (1H, m), 3.75 (3H, s), 4.04-4.38 (2H, m), 6.18 (1H, d, J=2.1 Hz), 6.32 (1H, brs), 6.51 (1H, dd, J=8.5, 2.4 Hz), 6.72 (1H, d, J=7.5 Hz), 7.09 (1H, t, J=7.9 Hz), 7.28-7.33 (1H, m), 9.69 (1H, d, J=1.0 Hz).

Step 2) N-(2,2-dimethylpropyl)-2-(4-(1-hydroxyethyl)piperidin-1-yl)-4-methoxy-N-(6-methylpyridin-2-yl)benzamide To a solution of N-(2,2-dimethylpropyl)-2-(4-formylpiperidin-1-yl)-4-methoxy-N-(6-methylpyridin-2-yl)benzamide (230 mg) in THF (10 mL) was added 1 M methylmagnesium bromide THF solution (1.97 mL) at 0° C., and the mixture was stirred at 0° C. for 1 hr. To the reaction mixture was added saturated aqueous ammonium chloride solution at 0° C., and the mixture was extracted with ethyl acetate. The extract was dried over anhydrous magnesium sulfate and the solvent was evaporated under reduced pressure. The residue was purified by silica gel column chromatography (ethyl acetate/hexane) to give the title compound (164 mg) as a colorless solid.

$^1$H NMR (300 MHz, CDCl$_3$) δ 0.81 (9H, s), 1.04-1.65 (8H, m), 1.66-1.81 (1H, m), 2.29-2.73 (6H, m), 3.26-3.70 (2H, m), 3.75 (3H, s), 4.05-4.41 (2H, m), 6.18 (1H, d, J=2.0 Hz), 6.34 (1H, brs), 6.48 (1H, dd, J=8.4, 2.4 Hz), 6.71 (1H, d, J=7.6 Hz), 7.09 (1H, t, J=7.5 Hz), 7.28 (1H, d, J=9.4 Hz).

Step 3) ethyl 3-cyclopropyl-3-(2-(1-(1-(2-((2,2-dimethylpropyl)(6-methylpyridin-2-yl)carbamoyl)-5-methoxyphenyl)piperidin-4-yl)ethoxy)pyridin-4-yl) propanoate In the same manner as in Example 45, step 6, the title compound (95 mg) was obtained as a brown amorphous powder from N-(2,2-dimethylpropyl)-2-(4-(1-hydroxyethyl) piperidin-1-yl)-4-methoxy-N-(6-methylpyridin-2-yl)benzamide (164 mg) and ethyl 3-cyclopropyl-3-(2-hydroxypyridin-4-yl)propanoate (176 mg).

MS (ESI+): [M+H]$^+$ 657.4.

Step 4) 3-cyclopropyl-3-(2-(1-(1-(2-((2,2-dimethylpropyl)(6-methylpyridin-2-yl)carbamoyl)-5-methoxyphenyl)piperidin-4-yl)ethoxy)pyridin-4-yl) propanoic acid In the same manner as in Example 1, step 4, the title compound (86 mg) was obtained as a colorless amorphous powder from ethyl 3-cyclopropyl-3-(2-(1-(1-(2-((2,2-dimethylpropyl)(6-methylpyridin-2-yl)carbamoyl)-5-methoxyphenyl)piperidin-4-yl)ethoxy)pyridin-4-yl)propanoate (95 mg).

MS (ESI+): [M+H]$^+$ 629.3.

Example 269

3-(3-((1-(2-((2,2-dimethylpropyl)(6-methylpyridin-2-yl)carbamoyl)-5-methoxyphenyl)piperidin-4-yl) methoxy)phenyl)-3-methoxypropanoic acid Step 1) ethyl 3-(3-(benzyloxy)phenyl)-3-methoxypropanoate A mixture of ethyl 3-(3-(benzyloxy)phenyl)-3-hydroxypropanoate (2.5 g), iodomethane (4.73 g), silver (1) oxide (3.86 g) and toluene (50 mL) was stirred under a nitrogen atmosphere at 100° C. for 15 hr. Insoluble material was removed, and the filtrate was concentrated. The residue was purified by silica gel column chromatography (ethyl acetate/hexane) to give the title compound (1.81 g) as a colorless oil.

$^1$H NMR (300 MHz, CDCl$_3$) δ1.18-1.27 (3H, m), 2.56 (1H, dd, J=15.3, 4.6 Hz), 2.77 (1H, dd, J=15.3, 9.2 Hz), 3.22 (3H, s), 4.09-4.25 (2H, m), 4.61 (1H, dd, J=9.2, 4.6 Hz), 5.07 (2H, s), 6.86-6.95 (2H, m), 6.95-7.01 (1H, m), 7.18-7.49 (6H, m).

Step 2) ethyl 3-(3-hydroxyphenyl)-3-methoxypropanoate

In the same manner as in Example 2, step 4, the title compound (900 mg) was obtained as a colorless oil from ethyl 3-(3-(benzyloxy)phenyl)-3-methoxypropanoate (1.8 g).

$^1$H NMR (300 MHz, DMSO-d$_6$) δ1.10-1.17 (3H, m), 2.53-2.71 (2H, m), 3.09 (3H, s), 3.98-4.09 (2H, m), 4.46 (1H, dd, J=8.7, 5.2 Hz), 6.63-6.77 (3H, m), 7.14 (1H, td, J=7.5, 0.8 Hz), 9.40 (1H, s).

Step 3) 3-(3-((1-(2-((2,2-dimethylpropyl)(6-methylpyridin-2-yl)carbamoyl)-5-methoxyphenyl)piperidin-4-yl)methoxy)phenyl)-3-methoxypropanoic acid By a method similar to that in Example 135, step 1 and Example 1, step 4, the title compound (98 mg) was obtained as a white amorphous powder from N-(2,2-dimethylpropyl)-2-(4-(hydroxymethyl)piperidin-1-yl)-4-methoxy-N-(6-methylpyridin-2-yl)benzamide (110.1 mg) and ethyl 3-(3-hydroxyphenyl)-3-methoxypropanoate (63.8 mg).

MS (ESI+): [M+H]$^+$ 604.4.

Example 270

3-(3-((1-(2-((2,2-dimethylpropyl)(6-methylpyridin-2-yl)carbamoyl)-5-methoxyphenyl)piperidin-4-yl)methoxy)phenyl)-3-ethoxypropanoic acid Step 1) ethyl 3-(3-hydroxyphenyl)-3-ethoxypropanoate In the same manner as in Example 269, step 1 and Example 2, step 4, the title compound (660 mg) was obtained as a colorless oil from ethyl 3-(3-(benzyloxy)phenyl)-3-hydroxypropanoate (2.5 g).

$^1$H NMR (300 MHz, DMSO-d$_6$) δ1.05 (3H, t, J=7.0 Hz), 1.10-1.19 (3H, m), 2.53-2.68 (2H, m), 3.19-3.34 (2H, m), 3.95-4.13 (2H, m), 4.57 (1H, dd, J=8.5, 5.5 Hz), 6.62-6.76 (3H, m), 7.08-7.17 (1H, m), 9.38 (1H, s).

Step 2) 3-(3-((1-(2-((2,2-dimethylpropyl)(6-methylpyridin-2-yl)carbamoyl)-5-methoxyphenyl)piperidin-4-yl)methoxy)phenyl)-3-ethoxypropanoic acid By a method similar to that in Example 135, step 1 and Example 1, step 4, the title compound (99.8 mg) was obtained as a white amorphous powder from N-(2,2-dimethylpropyl)-2-(4-(hydroxymethyl)piperidin-1-yl)-4-methoxy-N-(6-methylpyridin-2-yl)benzamide (103.6 mg) and ethyl 3-ethoxy-3-(3-hydroxyphenyl)propanoate (63.8 mg).

MS (ESI+): [M+H]$^+$ 618.3.

Example 271

3-methoxy-3-(2-((1-(5-methoxy-2-((4-methylpyridin-2-yl)(2,2,2-trifluoroethyl)carbamoyl)phenyl)piperidin-4-yl)methoxy)pyridin-4-yl)propanoic acid Step 1) tert-butyl 4-(((4-formylpyridin-2-yl)oxy)methyl)piperidine-1-carboxylate To a solution of tert-butyl 4-(((4-cyanopyridin-2-yl)oxy)methyl)piperidine-1-carboxylate (6.30 g) obtained in Example 245, step 1, in toluene (25 mL) was added a 1.5 M solution (14.6 mL) of diisobutylaluminum hydride in toluene at −78° C. The mixture was stirred at room temperature for 1 hr, a 1.5 M solution (6.6 mL) of diisobutylaluminum hydride in toluene was added at 0° C., and the mixture was stirred at room temperature for 1 hr. To the reaction mixture were added saturated aqueous ammonium chloride solution and potassium sodium tartrate at room temperature and the mixture was stirred for 1 hr and extracted with ethyl acetate. The extract was washed with saturated brine, and dried over anhydrous magnesium sulfate. The solvent was evaporated under reduced pressure. The residue was purified by silica gel column chromatography (ethyl acetate/hexane) to give the title compound (1.00 g) as a pale-yellow oil.

$^1$H NMR (300 MHz, CDCl$_3$) δ 1.20-1.37 (2H, m), 1.47 (9H, s), 1.74-1.88 (2H, m), 1.89-2.07 (1H, m), 2.65-2.85 (2H, m), 4.04-4.27 (4H, m), 7.13 (1H, t, J=1.0 Hz), 7.28 (1H, dd, J=5.2, 1.3 Hz), 8.34 (1H, d, J=5.2 Hz), 10.01 (1H, s).

Step 2) tert-butyl 4-(((4-(3-ethoxy-1-hydroxy-3-oxopropyl)pyridin-2-yl)oxy)methyl)piperidine-1-carboxylate Under a nitrogen atmosphere, to a solution of diisopropylamine (0.96 mL) in THF (10 mL) was added 1.6 M n-butyllithium hexane solution (2.93 mL) at −78° C., and the mixture was stirred for 10 min. Ethyl acetate (6.11 mL) was added at −78° C., and the mixture was stirred for 30 min. Thereto was added a solution of tert-butyl 4-(((4-formylpyridin-2-yl)oxy)methyl)piperidine-1-carboxylate (1.00 g) in THF (8 mL) at −78° C., and the mixture was stirred at −78° C. for 1 hr. The mixture was gradually warmed to room temperature over 1 hr. To the reaction mixture was added saturated aqueous ammonium chloride solution at room temperature, and the mixture was extracted with ethyl acetate. The extract was washed with saturated brine, and dried over anhydrous magnesium sulfate. The solvent was evaporated under reduced pressure. The residue was purified by silica gel column chromatography (ethyl acetate/hexane) to give the title compound (307 mg) as a colorless oil.

MS (ESI+): [M+H]$^+$ 409.2.

Step 3) tert-butyl 4-(((4-(3-ethoxy-1-methoxy-3-oxopropyl)pyridin-2-yl)oxy)methyl)piperidine-1-carboxylate To a solution of tert-butyl 4-(((4-(3-ethoxy-1-hydroxy-3-oxopropyl)pyridin-2-yl)oxy)methyl)piperidine-1-carboxylate (307 mg) in toluene (5 mL) were added iodomethane (0.231 mL) and silver (I) oxide (343 mg), and the mixture was stirred at 100° C. for 15 hr. Iodomethane (0.462 mL) and silver (I) oxide (172 mg) were further added, and the mixture was stirred at 100° C. for 5 hr. The reaction mixture was filtered through celite, and the filtrate was concentrated under reduced pressure. The residue was purified by silica gel column chromatography (ethyl acetate/hexane) to give the title compound (128 mg) as a pale-yellow oil.

MS (ESI+): [M+H]$^+$ 423.2.

Step 4) ethyl 3-(2-((1-(2-formyl-5-methoxyphenyl)piperidin-4-yl)methoxy)pyridin-4-yl)-3-methoxypropanoate To a solution of tert-butyl 4-(((4-(3-ethoxy-1-methoxy-3-oxopropyl)pyridin-2-yl)oxy)methyl)piperidine-1-carboxylate (128 mg) in acetonitrile (2 mL) was added trifluoroacetic acid (1 mL) at 0° C. and the mixture was stirred at room temperature for 2.5 hr, and concentrated under reduced pressure. Toluene azeotropic distillation was performed twice. To the obtained residue were added DMSO (3 mL), 2-fluoro-4-methoxybenzaldehyde (92 mg) and potassium carbonate (166 mg), and the mixture was stirred at 100° C. for 3.5 hr. To the reaction mixture was added water at room temperature, and the mixture was extracted with ethyl acetate. The extract was washed with saturated brine, and dried over anhydrous magnesium sulfate. The solvent was evaporated under reduced pressure. The residue was purified by silica gel column chromatography (ethyl acetate/hexane) to give the title compound (89 mg) as a colorless oil.

MS (ESI+): [M+H]$^+$ 457.2.

Step 5) 2-(4-(((4-(3-ethoxy-1-methoxy-3-oxopropyl)pyridin-2-yl)oxy)methyl)piperidin-1-yl)-4-methoxybenzoic acid In the same manner as in Example 262, step 2, the title compound (86 mg) was obtained as a colorless amorphous powder from ethyl 3-(2-((1-(2-formyl-5-methoxyphenyl)piperidin-4-yl)methoxy)pyridin-4-yl)-3-methoxypropanoate (89 mg).
MS (ESI+): [M+H]+ 473.2.

Step 6) 3-methoxy-3-(2-((1-(5-methoxy-2-((4-methylpyridin-2-yl)(2,2,2-trifluoroethyl)carbamoyl)phenyl)piperidin-4-yl)methoxy)pyridin-4-yl)propanoic acid In the same manner as in Example 32, step 2 and Example 1, step 4, the title compound (31 mg) was obtained as a colorless amorphous powder from 4-methyl-N-(2,2,2-trifluoroethyl)pyridin-2-amine (104 mg) and 2-(4-(((4-(3-ethoxy-1-methoxy-3-oxopropyl)pyridin-2-yl)oxy)methyl)piperidin-1-yl)-4-methoxybenzoic acid (86 mg).
MS (ESI+): [M+H]+ 617.2.

Example 272

3-(2-((1-(2-((2,2-dimethylpropyl)(6-methylpyridin-2-yl)carbamoyl)-5-methoxyphenyl)piperidin-4-yl)methoxy)pyridin-4-yl)-3-ethoxypropanoic acid Step 1) tert-butyl 4-(((4-(1,3-diethoxy-3-oxopropyl)pyridin-2-yl)oxy)methyl)piperidine-1-carboxylate In the same manner as in Example 271, step 3, the title compound (720 mg) was obtained as pale-yellow gummy substance-like mixture from tert-butyl 4-(((4-(3-ethoxy-1-hydroxy-3-oxopropyl)pyridin-2-yl)oxy)methyl)piperidine-1-carboxylate (1.31 g) obtained in Example 271, step 2, and iodoethane (3.6 mL).
MS (ESI+): [M+H]+ 437.3.

Step 2) ethyl 3-ethoxy-3-(2-((1-(2-formyl-5-methoxyphenyl)piperidin-4-yl)methoxy)pyridin-4-yl)propanoate In the same manner as in Example 271, step 4, the title compound (136 mg) was obtained as a colorless gummy substance from tert-butyl 4-(((4-(1,3-diethoxy-3-oxopropyl)pyridin-2-yl)oxy)methyl)piperidine-1-carboxylate (720 mg).
MS (ESI+): [M+H]+ 471.3.

Step 3) 2-(4-(((4-(1,3-diethoxy-3-oxopropyl)pyridin-2-yl)oxy)methyl)piperidin-1-yl)-4-methoxybenzoic acid In the same manner as in Example 271, step 5, the title compound (129 mg) was obtained as a colorless gummy substance from ethyl 3-ethoxy-3-(2-((1-(2-formyl-5-methoxyphenyl)piperidin-4-yl)methoxy)pyridin-4-yl)propanoate (135 mg).
MS (ESI+): [M+H]+ 487.3.

Step 4) 3-(2-((1-(2-((2,2-dimethylpropyl)(6-methylpyridin-2-yl)carbamoyl)-5-methoxyphenyl)piperidin-4-yl)methoxy)pyridin-4-yl)-3-ethoxypropanoic acid In the same manner as in Example 32, step 2 and Example 1, step 4, the title compound (28 mg) was obtained as a grayish white amorphous powder from 2-(4-(((4-(1,3-diethoxy-3-oxopropyl)pyridin-2-yl)oxy)methyl)piperidin-1-yl)-4-methoxybenzoic acid (128 mg) and N-(2,2-dimethylpropyl)-6-methylpyridin-2-amine (70.3 mg).
MS (ESI+): [M+H]+ 619.3.

Example 273

3-cyclopropyl-3-(2-((1-(2-((2,2-dimethylpropyl)(pyrimidin-2-yl)carbamoyl)-5-methoxyphenyl)piperidin-4-yl)methoxy)-5-fluoropyridin-4-yl)propanoic acid Step 1) cyclopropyl(5-fluoro-2-methoxypyridin-4-yl)methanol Under a nitrogen atmosphere, a solution (1.6 M, 29.5 mL) of n-butyllithium in hexane was added to a solution of diisopropylamine (6.60 mL) in THF (80 mL) at −15° C. and the mixture was stirred at −15° C. for 5 min. A solution of 5-fluoro-2-methoxypyridine (5.00 g) in THF (30 mL) was added dropwise to the reaction mixture at −78° C. over 15 min, and the mixture was stirred at −78° C. for 1.5 hr. A solution of cyclopropanecarbaldehyde (3.53 mL) in THF (15 mL) was added dropwise to the reaction mixture at −78° C. over 20 min and the mixture was stirred at −78° C. for 30 min. To the reaction mixture was added saturated aqueous ammonium chloride solution at 0° C., and the mixture was extracted with ethyl acetate. The extract was washed with water and saturated brine, and dried over anhydrous magnesium sulfate. The solvent was evaporated under reduced pressure to give a crude product (8.87 g) of the title compound as a pale-yellow oil. This compound was used for the next step without further purification.
$^1$H NMR (300 MHz, DMSO-$d_6$) δ 0.25-0.52 (4H, m), 0.94-1.14 (1H, m), 3.82 (3H, s), 4.30 (1H, dd, J=6.9, 5.0 Hz), 5.52 (1H, d, J=4.9 Hz), 6.88 (1H, d, J=4.8 Hz), 8.05 (1H, d, J=1.8 Hz).

Step 2) cyclopropyl(5-fluoro-2-methoxypyridin-4-yl)methanone

To a solution of cyclopropyl(5-fluoro-2-methoxypyridin-4-yl)methanol (entire amount) obtained in Example 273, step 1, and triethylamine (55.2 mL) in DMSO (200 mL) was added sulfur trioxide pyridine complex (31.5 g), and the mixture was stirred at room temperature for 30 min. To the reaction mixture was added water at room temperature, and the mixture was extracted with ethyl acetate. The extract was washed with water and saturated brine, and dried over anhydrous magnesium sulfate. The solvent was evaporated under reduced pressure to give a crude product (7.49 g) of the title compound as a brown oil. This compound was used for the next step without further purification.
$^1$H NMR (300 MHz, DMSO-$d_6$) δ 1.07-1.22 (4H, m), 2.56-2.67 (1H, m), 3.88 (3H, s), 7.06 (1H, d, J=4.7 Hz), 8.34 (1H, d, J=1.9 Hz).

Step 3) ethyl 3-cyclopropyl-3-(5-fluoro-2-methoxypyridin-4-yl)acrylate

Under a nitrogen atmosphere, to a suspension of 60% sodium hydride (oily) (2.76 g) in THF (100 mL) was added ethyl diethylphosphonoacetate (15.2 mL) at 0° C. and the mixture was stirred at 0° C. for 5 min. To the obtained colorless solution was added cyclopropyl(5-fluoro-2-methoxypyridin-4-yl)methanone (entire amount) obtained in Example 273, step 2, at 0° C., and the mixture was stirred at room temperature for 30 min. To the reaction mixture was added water at room temperature, and the mixture was extracted with ethyl acetate. The extract was washed with water and saturated brine, and dried over anhydrous magnesium sulfate. The solvent was evaporated under reduced pressure to give a crude product of the title compound as a brown oil. This compound was used for the next step without further purification.

Step 4) ethyl 3-cyclopropyl-3-(5-fluoro-2-methoxypyridin-4-yl)propanoate

To a solution of ethyl 3-cyclopropyl-3-(5-fluoro-2-methoxypyridin-4-yl)acrylate (entire amount) obtained in Example 273, step 3, in acetic acid (100 mL) was added zinc powder (50.2 g), and the mixture was stirred at room temperature for 30 min. The reaction mixture was filtered, and the solvent in the filtrate was evaporated under reduced pressure. The residue was purified by silica gel column chromatography (ethyl acetate/hexane) to give the title compound (5.72 g) as a colorless oil.

$^1$H NMR (400 MHz, DMSO-$d_6$) δ 0.05-0.16 (1H, m), 0.23-0.41 (2H, m), 0.47-0.58 (1H, m), 0.99-1.08 (1H, m), 1.08 (3H, t, J=7.1 Hz), 2.51-2.59 (1H, m), 2.73-2.90 (2H, m), 3.81 (3H, s), 3.90-4.07 (2H, m), 6.91 (1H, d, J=4.9 Hz), 8.05 (1H, s).

Step 5) ethyl 3-cyclopropyl-3-(5-fluoro-2-hydroxypyridin-4-yl)propanoate

Under a nitrogen atmosphere, to a solution of ethyl 3-cyclopropyl-3-(5-fluoro-2-methoxypyridin-4-yl)propanoate (5.72 g) in DMF (10 mL) was added pyridinium chloride (24.7 g), and the mixture was stirred at 130° C. for 1 hr. To the reaction mixture was added ethyl acetate at 0° C. and the resulting precipitate was filtered off. The solvent in the filtrate was evaporated under reduced pressure, and the residue was purified by silica gel column chromatography (methanol/ethyl acetate) to give the title compound (4.29 g) as a colorless oil.

$^1$H NMR (400 MHz, DMSO-$d_6$) δ 0.07-0.18 (1H, m), 0.21-0.31 (1H, m), 0.35-0.44 (1H, m), 0.47-0.60 (1H, m), 0.93-1.05 (1H, m), 1.10 (3H, t, J=7.0 Hz), 2.35-2.46 (1H, m), 2.66-2.86 (2H, m), 3.90-4.09 (2H, m), 6.43 (1H, d, J=5.9 Hz), 7.60 (1H, d, J=4.0 Hz), 11.14 (1H, brs).

Step 6) ethyl 3-cyclopropyl-3-(5-fluoro-2-methoxypyridin-4-yl)propanoate

Racemate (3.09 g) of ethyl 3-cyclopropyl-3-(5-fluoro-2-methoxypyridin-4-yl)propanoate was fractionated by HPLC (column: CHIRALPAK AS (CC001), 50 mmID×500 mmL, manufactured by Daicel Corporation, mobile phase: hexane/2-propanol=950/50) to give the title compound (tR1: 1.36 g) having a shorter retention time and the title compound (tR2: 1.38 g) having a longer retention time.

Step 7) tert-butyl 4-(((4-(1-cyclopropyl-3-ethoxy-3-oxopropyl)-5-fluoropyridin-2-yl)oxy)methyl)piperidine-1-carboxylate In the same manner as in Example 45, step 6, the title compound (1.09 g) was obtained as a colorless oil from ethyl 3-cyclopropyl-3-(5-fluoro-2-methoxypyridin-4-yl)propanoate (1.08 g) having a longer retention time and tert-butyl 4-(hydroxymethyl)piperidine-1-carboxylate (895 mg).

$^1$H NMR (400 MHz, CDCl$_3$) δ 0.14-0.24 (1H, m), 0.26-0.37 (1H, m), 0.39-0.52 (1H, m), 0.54-0.68 (1H, m), 0.97-1.12 (1H, m), 1.13-1.35 (2H, m), 1.18 (3H, t, J=7.2 Hz), 1.46 (9H, s), 1.79 (2H, d, J=13.1 Hz), 1.86-2.01 (1H, m), 2.50-2.60 (1H, m), 2.64-2.82 (4H, m), 4.00-4.16 (6H, m), 6.62 (1H, d, J=4.9 Hz), 7.89 (1H, d, J=1.5 Hz).

Step 8) ethyl 3-cyclopropyl-3-(5-fluoro-2-(piperidin-4-ylmethoxy)pyridin-4-yl)propanoate hydrochloride Under a nitrogen atmosphere, to a solution of tert-butyl 4-(((4-(1-cyclopropyl-3-ethoxy-3-oxopropyl)-5-fluoropyridin-2-yl)oxy)methyl)piperidine-1-carboxylate (1.09 g) in ethyl acetate (3.0 mL) was added 4N hydrogen chloride ethyl acetate (3.02 mL) solution at room temperature, and the mixture was stirred at room temperature for 1 hr. The solvent in the reaction solution was evaporated under reduced pressure to give a crude product of the title compound as a colorless amorphous powder. This compound was used for the next step without further purification.

Step 9) ethyl 3-cyclopropyl-3-(5-fluoro-2-((1-(2-formyl-5-methoxyphenyl)piperidin-4-yl)methoxy)pyridin-4-yl)propanoate In the same manner as in Example 1, step 2, the title compound (724 mg) was obtained as a pale-yellow oil from a crude product (entire amount) of ethyl 3-cyclopropyl-3-(5-fluoro-2-(piperidin-4-ylmethoxy)pyridin-4-yl)propanoate hydrochloride and 2-fluoro-4-methoxybenzaldehyde (448 mg).

$^1$H NMR (400 MHz, CDCl$_3$) δ 0.15-0.24 (1H, m), 0.28-0.37 (1H, m), 0.42-0.50 (1H, m), 0.58-0.68 (1H, m), 1.01-1.14 (1H, m), 1.19 (3H, t, J=7.1 Hz), 1.57-1.72 (2H, m), 1.87-2.02 (3H, m), 2.50-2.62 (1H, m), 2.79 (2H, d, J=7.4 Hz), 2.88 (2H, t, J=11.3 Hz), 3.37 (2H, d, J=11.9 Hz), 3.86 (3H, s), 4.02-4.12 (2H, m), 4.17 (2H, d, J=6.0 Hz), 6.56 (1H, d, J=2.3 Hz), 6.61 (1H, dd, J=8.6, 2.1 Hz), 6.65 (1H, d, J=4.9 Hz), 7.80 (1H, d, J=8.7 Hz), 7.91 (1H, d, J=1.6 Hz), 10.14 (1H, s).

Step 10) 2-(4-(((4-(1-cyclopropyl-3-ethoxy-3-oxopropyl)-5-fluoropyridin-2-yl)oxy)methyl)piperidin-1-yl)-4-methoxybenzoic acid In the same manner as in Example 262, step 2, the title compound (552 mg) was obtained as a colorless amorphous powder from ethyl 3-cyclopropyl-3-(5-fluoro-2-((1-(2-formyl-5-methoxyphenyl)piperidin-4-yl)methoxy)pyridin-4-yl)propanoate (724 mg).

$^1$H NMR (400 MHz, DMSO-$d_6$) δ 0.07-0.18 (1H, m), 0.25-0.33 (1H, m), 0.34-0.43 (1H, m), 0.48-0.59 (1H, m), 1.00-1.26 (1H, m), 1.08 (4H, t, J=7.1 Hz), 1.40-1.61 (2H, m), 1.90-2.16 (3H, m), 2.51-2.61 (2H, m), 2.76-2.90 (2H, m), 3.02-3.20 (2H, m), 3.85 (3H, s), 3.97 (2H, ddquin, J=10.6, 7.1, 3.7 Hz), 4.18 (2H, d, J=6.4 Hz), 6.94 (1H, d, J=4.8 Hz), 6.99 (1H, dd, J=8.7, 2.3 Hz), 7.27 (1H, d, J=2.1 Hz), 7.98 (1H, d, J=8.8 Hz), 8.06 (1H, d, J=1.4 Hz).

Step 11) ethyl 3-cyclopropyl-3-(5-fluoro-2-((1-(2-((2,2-dimethylpropyl)(pyrimidin-2-yl)carbamoyl)-5-methoxyphenyl)piperidin-4-yl)methoxy)pyridin-4-yl)propanoate In the same manner as in Example 32, step 2, the title compound (93.1 mg) was obtained as a white amorphous powder from 2-(4-(((4-(1-cyclopropyl-3-ethoxy-3-oxopropyl)-5-fluoropyridin-2-yl)oxy)methyl)piperidin-1-yl)-4- methoxybenzoic acid (100 mg) and N-(2,2-dimethylpropyl) pyrimidin-2-amine (83.0 mg).

$^1$H NMR (400 MHz, CDCl$_3$) δ 0.14-0.25 (1H, m), 0.26-0.37 (1H, m), 0.41-0.51 (1H, m), 0.57-0.67 (1H, m), 0.86 (9H, s), 1.00-1.11 (1H, m), 1.19 (3H, t, J=7.1 Hz), 1.52-1.86 (5H, m), 2.29-2.68 (3H, m), 2.53-2.61 (1H, m), 2.78 (2H, d, J=7.4 Hz), 3.10-3.34 (1H, m), 3.78 (3H, s), 4.01-4.15 (4H, m), 4.27 (2H, d, J=15.8 Hz), 6.14 (1H, d, J=2.4 Hz), 6.55 (1H, dd, J=8.5, 2.3 Hz), 6.64 (1H, d, J=4.9 Hz), 6.80 (1H, t, J=4.8 Hz), 7.45 (1H, d, J=8.5 Hz), 7.91 (1H, d, J=1.6 Hz), 8.32 (2H, d, J=4.8 Hz).

Step 12) 3-cyclopropyl-3-(2-((1-(2-((2,2-dimethylpropyl)(pyrimidin-2-yl)carbamoyl)-5-methoxyphenyl)piperidin-4-yl)methoxy)-5-fluoropyridin-4-yl) propanoic acid In the same manner as in Example 1, step 4, the title compound (89.4 mg) was obtained as a white amorphous powder from ethyl 3-cyclopropyl-3-(5-fluoro-2-((1-(2-((2,2-dimethylpropyl)(pyrimidin-2-yl)carbamoyl)-5-methoxyphenyl)piperidin-4-yl)methoxy)pyridin-4-yl)propanoate (93.1 mg).

MS (ESI+): [M+H]$^+$ 620.3.

Example 274

3-cyclopropyl-3-(2-((1-(2-((2,2-dimethylpropyl)(6-methylpyridin-2-yl)carbamoyl)-5-methoxyphenyl) piperidin-4-yl)methoxy)-5-fluoropyridin-4-yl)propanoic acid By a method similar to that in Example 135, step 1 and Example 1, step 4, the title compound (83 mg) was obtained as a pale-white amorphous powder from N-(2,2-dimethylpropyl)-2-(4-(hydroxymethyl)piperidin-1-yl)-4-methoxy-N-(6-methylpyridin-2-yl)benzamide (106.6 mg) and ethyl 3-cyclopropyl-3-(5-fluoro-2-hydroxypyridin-4-yl)propanoate (69.8 mg).

MS (ESI+): [M+H]$^+$ 633.3.

Example 275

3-cyclopropyl-3-(3-((1-(2-((2,2-dimethylpropyl)(6-methylpyridin-2-yl)carbamoyl)-5-methoxyphenyl) piperidin-4-yl)methoxy)-2-fluorophenyl)propanoic acid In the same manner as in Example 45, step 6 and Example 1, step 4, the title compound (180 mg) was obtained as a white amorphous powder from methyl 3-cyclopropyl-3-(2-fluoro-3-hydroxyphenyl)propanoate (103 mg).

MS (ESI+): [M+H]$^+$ 632.3.

Example 276

3-(3-((1-(2-((2,2-dimethylpropyl)(6-methylpyridin-2-yl)carbamoyl)-5-methoxyphenyl)piperidin-4-yl) methoxy)phenyl)-4-methoxybutanoic acid Step 1) 2-methoxy-1-(3-(tetrahydro-2H-pyran-2-yloxy)phenyl)ethanone To a solution of methyl methoxyacetate (3.79 g) in THF (50 mL) was added dropwise 0.5 M (3-(tetrahydro-2H-pyran-2-yloxy)phenyl)magnesium bromide (80 mL) at −78° C. The reaction mixture was stirred at −78° C. for 1 hr and at room temperature for 3 hr. To the reaction mixture was added water at room temperature, insoluble material was removed, and the mixture was extracted with ethyl acetate. The extract was washed with water and saturated brine, and dried over anhydrous magnesium sulfate. The solvent was evaporated under reduced pressure to give the title compound (9.0 g) as a brown oil. This compound was used for the next step without further purification.

Step 2) ethyl(2Z)-4-methoxy-3-(3-(tetrahydro-2H-pyran-2-yloxy)phenyl)but-2-enoate To a suspension of sodium hydride (oily)(2.88 g) in THF (100 mL) was added 2-methoxy-1-(3-(tetrahydro-2H-pyran-2-yloxy)phenyl)ethanone (9.0 g) under ice-cooling, and the mixture was stirred for 30 min. To the reaction mixture was added ethyl(diethoxyphosphoryl)acetate (16.1 g), and the mixture was stirred at 50° C. for 15 hr. To the reaction mixture was added saturated aqueous ammonium chloride solution at room temperature, and the mixture was extracted with ethyl acetate. The extract was washed with water and saturated brine, and dried over anhydrous magnesium sulfate. The solvent was evaporated under reduced pressure to give the title compound (11.0 g) as a brown oil. This compound was used for the next step without further purification.

Step 3) ethyl(2Z)-3-(3-hydroxyphenyl)-4-methoxybut-2-enoate

To a solution of ethyl(2Z)-4-methoxy-3-(3-(tetrahydro-2H-pyran-2-yloxy)phenyl)but-2-enoate (11.0 g) in acetic acid (50 mL) was slowly added zinc powder (22.5 g) at room temperature, and the mixture was stirred at 50° C. for 3 hr. Insoluble material was filtered off, and the filtrate was evaporated under reduced pressure. To the residue was added 1N hydrochloric acid (20 mL), and the mixture was washed with ethyl acetate. The aqueous layer was neutralized with saturated aqueous sodium hydrogen carbonate solution, and extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (390 mg) as a pale-yellow oil.

$^1$H NMR (400 MHz, CDCl$_3$) δ 1.20 (3H, t, J=7.2 Hz), 3.49 (2H, s), 3.72 (3H, s), 4.12 (2H, q, J=7.1 Hz), 5.02 (1H, br. s.), 6.52 (1H, s), 6.66 (1H, dd, J=8.0, 2.0 Hz), 6.75 (1H, t, J=1.9 Hz), 6.84 (1H, d, J=7.7 Hz), 7.14 (1H, t, J=7.9 Hz).

Step 4) ethyl 3-(3-hydroxyphenyl)-4-methoxybutanoate

In the same manner as in Example 2, step 4, the title compound (380 mg) was obtained as a colorless oil from ethyl(2Z)-3-(3-hydroxyphenyl)-4-methoxybut-2-enoate (390 mg).

MS (ESI−): [M−H]$^-$ 237.1.

Step 5) 3-(3-((1-(2-((2,2-dimethylpropyl)(6-methylpyridin-2-yl)carbamoyl)-5-methoxyphenyl)piperidin-4-yl)methoxy)phenyl)-4-methoxybutanoic acid In the same manner as in Example 45, step 6 and Example 1, step 4, the title compound (235 mg) was obtained as a white amorphous powder from ethyl 3-(3-hydroxyphenyl)-4-methoxybutanoate (109 mg).
MS (ESI+): [M+H]⁺ 618.3.

Example 277

3-(3-((1-(2-((2,2-dimethylpropyl)(6-methylpyridin-2-yl)carbamoyl)-5-methoxyphenyl)piperidin-4-yl)methoxy)phenyl)-3-methylbutanoic acid Step 1) ethyl 3-(3-methoxyphenyl)-3-methylbutanoate A solution of 5-(2-(3-methoxyphenyl)propan-2-yl)-2,2-dimethyl-1,3-dioxane-4,6-dione (5.4 g) in DMF (20 mL) and ethanol (10 mL) was stirred at 100° C. for 15 hr. The reaction mixture was concentrated under reduced pressure, and ethyl acetate was added to the residue and the mixture was washed with water. The extract was washed with saturated brine, and dried over anhydrous magnesium sulfate. The residue was purified by silica gel column chromatography (ethyl acetate/hexane) to give the title compound (3.2 g) as a colorless oil.
$^1$H NMR (300 MHz, CDCl$_3$) δ 1.11 (3H, t, J=7.1 Hz), 1.44 (6H, s), 2.59 (2H, s), 3.80 (3H, s), 4.00 (2H, q, J=7.1 Hz), 6.74 (1H, ddd, J=8.2, 2.5, 0.8 Hz), 6.92 (1H, t, J=2.1 Hz), 6.96 (1H, ddd, J=7.8, 1.8, 0.8 Hz), 7.18-7.28 (1H, m).

Step 2) ethyl 3-(3-hydroxyphenyl)-3-methylbutanoate

To a solution of ethyl 3-(3-methoxyphenyl)-3-methylbutanoate (3.2 g) and dodecane-1-thiol (13.7 g) in toluene (100 mL) was added aluminum chloride (5.42 g) under ice-cooling, and the mixture was stirred at room temperature for 1 hr. To the reaction mixture was added 1N hydrochloric acid at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (1.6 g) as a colorless oil.
$^1$H NMR (300 MHz, CDCl$_3$) δ 1.11 (3H, t, J=7.1 Hz), 1.43 (6H, s), 2.59 (2H, s), 4.00 (2H, q, J=7.1 Hz), 4.98 (1H, s), 6.66 (1H, ddd, J=8.0, 2.5, 0.8 Hz), 6.85 (1H, t, J=2.1 Hz), 6.90-6.96 (1H, m), 7.11-7.22 (1H, m).

Step 3) 3-(3-((1-(2-((2,2-dimethylpropyl)(6-methyl-pyridin-2-yl)carbamoyl)-5-methoxyphenyl)piperidin-4-yl)methoxy)phenyl)-3-methylbutanoic acid In the same manner as in Example 45, step 6 and Example 1, step 4, the title compound (241 mg) was obtained as a white amorphous powder from ethyl 3-(3-hydroxyphenyl)-3-methylbutanoate (100 mg).
MS (ESI+): [M+H]⁺ 602.4.

Example 278

(3-(3-((1-(2-((2,2-dimethylpropyl)(6-methylpyridin-2-yl)carbamoyl)-5-methoxyphenyl)piperidin-4-yl)methoxy)phenyl)oxetan-3-yl)acetic acid Step 1) ethyl(3-(3-(benzyloxy)phenyl)oxetan-3-yl)acetate To a solution of di-μ-chloro-bis[η²,η²-(cycloocta-1,5-diene)rhodium] (73.5 mg) in 1,4-dioxane (5 mL) was added 1.5 M aqueous potassium hydroxide solution (3.73 mL) and the mixture was stirred at room temperature for 15 min. To the reaction mixture was added dropwise a solution of ethyl oxetan-3-ylideneacetate (530 mg) and 3-benzyloxyphenylboronic acid (1.7 g) in 1,4-dioxane (5 mL), and the mixture was stirred for 30 min. To the reaction mixture was added saturated brine at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (1.32 g) as a pale-yellow oil.
$^1$H NMR (400 MHz, CDCl$_3$) δ 1.13 (3H, t, J=7.2 Hz), 3.09 (2H, s), 3.97-4.05 (2H, m), 4.81-4.87 (2H, m), 4.99 (2H, d, J=6.3 Hz), 5.05 (2H, s), 6.72-6.77 (1H, m), 6.78-6.81 (1H, m), 6.86 (1H, ddd, J=8.3, 2.5, 0.7 Hz), 7.22-7.28 (1H, m), 7.29-7.47 (5H, m).

Step 2) ethyl(3-(3-hydroxyphenyl)oxetan-3-yl)acetate

In the same manner as in Example 2, step 4, the title compound (818 mg) was obtained as a colorless oil from ethyl(3-(3-(benzyloxy)phenyl)oxetan-3-yl)acetate (1.32 g).
$^1$H NMR (300 MHz, CDCl$_3$) δ 1.13 (3H, t, J=7.1 Hz), 3.10 (2H, s), 4.02 (2H, q, J=7.2 Hz), 4.86 (2H, d, J=6.3 Hz), 5.00 (2H, d, J=6.2 Hz), 5.42 (1H, s), 6.63-6.70 (2H, m), 6.72 (1H, d, J=2.1 Hz), 7.20 (1H, t, J=7.9 Hz).

Step 3) (3-(3-((1-(2-((2,2-dimethylpropyl)(6-methyl-pyridin-2-yl)carbamoyl)-5-methoxyphenyl)piperidin-4-yl)methoxy)phenyl)oxetan-3-yl)acetic acid In the same manner as in Example 45, step 6 and Example 1, step 4, the title compound (114 mg) was obtained as a white amorphous powder from ethyl(3-(3-hydroxyphenyl)oxetan-3-yl)acetate (80 mg).
MS (ESI+): [M+H]⁺ 616.3.

Example 279

(3S)-cyclopropyl-3-(3-(((3RS,4SR)-1-(2-((2,2-dimethylpropyl)(pyridin-2-yl)carbamoyl)-5-methoxy-phenyl)-3-methylpiperidin-4-yl)methoxy)phenyl)propanoic acid Step 1) methyl-1-(2-formyl-5-methoxyphenyl)-3-methylpiperidine-4-carboxylate In the same manner as in Example 1, step 1, the title compound (7.2 g) was obtained as a colorless oil from methyl-3-methylpiperidine-4-carboxylate (8.42 g).
MS (ESI+): [M+H]⁺ 292.2.

Step 2) trans-4-methoxy-2-((3SR,4RS)-4-(methoxy-carbonyl)-3-methylpiperidin-1-yl)benzoic acid To a solution of methyl-1-(2-formyl-5-methoxyphenyl)-3-methylpiperidine-4-carboxylate (4.3 g) obtained in step 1 in acetonitrile (120 mL) were added periodic acid (7.4 g) and pyridinium chloroformate (64 mg) at room temperature. The reaction mixture was stirred for 48 hr, and diluted with ethyl acetate. The organic layer was washed with water and saturated brine, and dried over anhydrous sodium sulfate. The residue was purified by silica gel column chromatography (ethyl acetate/hexane) to give the title compound (1.1 g) as a pale-yellow solid, and 4-methoxy-2-((3RS,4RS)-4-(methoxycarbonyl)-3-methylpiperidin-1-yl)benzoic acid (1.2 g) as a pale-yellow solid.
MS (ESI+): [M+H]$^+$ 308.2.

Step 3) trans-methyl(3RS,4SR)-1-(2-((2,2-dimethylpropyl)(pyridin-2-yl)carbamoyl)-5-methoxyphenyl)-3-methylpiperidine-4-carboxylate In the same manner as in Example 32, step 2, the title compound was obtained as a crude product from 4-methoxy-2-((3SR,4RS)-4-(methoxycarbonyl)-3-methylpiperidin-1-yl)benzoic acid (150 mg) obtained in step 2.
MS (ESI+): [M+H]$^+$ 454.3.

Step 4) N-(2,2-dimethylpropyl)-2-((3RS,4SR)-4-(hydroxymethyl)-3-methylpiperidin-1-yl)-4-methoxy-N-(pyridin-2-yl)benzamide A solution of methyl(3RS,4SR)-1-(2-((2,2-dimethylpropyl)(pyridin-2-yl)carbamoyl)-5-methoxyphenyl)-3-methylpiperidine-4-carboxylate obtained in step 3 and lithium borohydride (32.0 mg) in THF (4 mL) was stirred at 60° C. for 4 hr, lithium borohydride (10.7 mg) was added, and the reaction mixture was stirred at 60° C. for 4 hr. To the reaction mixture was added 1 M hydrochloric acid at room temperature, and the mixture was extracted with ethyl acetate. The extract was washed with water and saturated brine, and dried over anhydrous magnesium sulfate. The residue was purified by silica gel column chromatography (ethyl acetate/hexane) to give the title compound (205.2 mg) as a white solid.
MS (ESI+): [M+H]$^+$ 426.3.

Step 5) ethyl(3S)-cyclopropyl-3-(3-(((3RS,4SR)-1-(2-((2,2-dimethylpropyl)(pyridin-2-yl)carbamoyl)-5-methoxyphenyl)-3-methylpiperidin-4-yl)methoxy)phenyl)propanoate In the same manner as in Example 45, step 6, the title compound (199.2 mg) was obtained as a colorless oil from N-(2,2-dimethylpropyl)-2-((3RS,4SR)-4-(hydroxymethyl)-3-methylpiperidin-1-yl)-4-methoxy-N-(pyridin-2-yl)benzamide (205.2 mg) obtained in step 4.
MS (ESI+): [M+H]$^+$ 628.4.

Step 6) (3S)-cyclopropyl-3-(3-(((3RS,4SR)-1-(2-((2,2-dimethylpropyl)(pyridin-2-yl)carbamoyl)-5-methoxyphenyl)-3-methylpiperidin-4-yl)methoxy)phenyl)propanoic acid In the same manner as in Example 1, step 4, the title compound (38.5 mg) was obtained as a white amorphous powder from ethyl(3S)-cyclopropyl-3-(3-(((3RS,4SR)-1-(2-((2,2-dimethylpropyl)(pyridin-2-yl)carbamoyl)-5-methoxyphenyl)-3-methylpiperidin-4-yl)methoxy)phenyl)propanoate (49.0 mg) obtained in step 5.
MS (ESI+): [M+H]$^+$ 614.3.

Example 280

(3S)-cyclopropyl-3-(3-(((3RS,4RS)-1-(2-((2,2-dimethylpropyl)(pyridin-2-yl)carbamoyl)-5-methoxyphenyl)-3-methylpiperidin-4-yl)methoxy)phenyl)propanoic acid Step 1) methyl(3RS,4RS)-1-(2-((2,2-dimethylpropyl)(pyridin-2-yl)carbamoyl)-5-methoxyphenyl)-3-methylpiperidine-4-carboxylate In the same manner as in Example 32, step 2, the title compound (538.3 mg) was obtained as a colorless oil from 4-methoxy-2-((3RS,4RS)-4-(methoxycarbonyl)-3-methylpiperidin-1-yl)benzoic acid (400 mg) obtained in Example 279, step 2.
MS (ESI+): [M+H]$^+$ 454.7.

Step 2) N-(2,2-dimethylpropyl)-2-((3RS,4RS)-4-(hydroxymethyl)-3-methylpiperidin-1-yl)-4-methoxy-N-(pyridin-2-yl)benzamide In the same manner as in Example 279, step 4, the title compound (472.9 mg) was obtained as a white solid from methyl(3RS,4RS)-1-(2-((2,2-dimethylpropyl)(pyridin-2-yl)carbamoyl)-5-methoxyphenyl)-3-methylpiperidine-4-carboxylate (538.3 mg) obtained in step 1.
MS (ESI+): [M+H]$^+$ 426.3.

Step 3) ethyl(3S)-cyclopropyl-3-(3-(((3RS,4RS)-1-(2-((2,2-dimethylpropyl)(pyridin-2-yl)carbamoyl)-5-methoxyphenyl)-3-methylpiperidin-4-yl)methoxy)phenyl)propanoate In the same manner as in Example 45, step 6, the title compound (51.2 mg) was obtained as a colorless oil from N-(2,2-dimethylpropyl)-2-((3RS,4RS)-4-(hydroxymethyl)-3-methylpiperidin-1-yl)-4-methoxy-N-(pyridin-2-yl)benzamide (150 mg) obtained in step 2.
MS (ESI+): [M+H]$^+$ 628.6.

Step 4) (3S)-cyclopropyl-3-(3-(((3RS,4RS)-1-(2-((2,2-dimethylpropyl)(pyridin-2-yl)carbamoyl)-5-methoxyphenyl)-3-methylpiperidin-4-yl)methoxy)phenyl)propanoic acid In the same manner as in Example 1, step 4, the title compound (34.5 mg) was obtained as a white amorphous powder from ethyl(3S)-cyclopropyl-3-(3-(((3RS,4RS)-1-(2-((2,2-dimethylpropyl)(pyridin-2-yl)carbamoyl)-5-methoxyphenyl)-3-methylpiperidin-4-yl)methoxy)phenyl)propanoate (51.2 mg) obtained in step 3.
MS (ESI+): [M+H]$^+$ 614.3.

Example 281

(3S)-cyclopropyl-3-(3-((1-(2-((2,2-dimethylpropyl)(pyridin-2-yl)carbamoyl)-5-methoxyphenyl)-3,3-difluoropiperidin-4-yl)methoxy)phenyl)propanoic acid Step 1) 2-(4-((benzyloxy)methyl)-3,3-difluoropiperidin-1-yl)-4-methoxybenzaldehyde In the same manner as in Example 1, step 1, the title compound (50.5 mg) was obtained as a yellow oil from 4-((benzyloxy)methyl)-3,3-difluoropiperidine (0.376 g).
MS (ESI+): [M+H]$^+$ 376.1.

Step 2) 2-(4-((benzyloxy)methyl)-3,3-difluoropiperidin-1-yl)-4-methoxybenzoic acid In the same manner as in Example 262, step 2, the title compound was obtained as a crude product from 2-(4-

((benzyloxy)methyl)-3,3-difluoropiperidin-1-yl)-4-methoxybenzaldehyde (50.5 mg) obtained in step 1.
MS (ESI+): [M+H]$^+$ 392.2.

Step 3) 2-(3,3-difluoro-4-(phenoxymethyl)piperidin-1-yl)-N-(2,2-dimethylpropyl)-4-methoxy-N-(pyridin-2-yl)benzamide In the same manner as in Example 32, step 2, the title compound (44.7 mg) was obtained as a colorless oil from 2-(4-((benzyloxy)methyl)-3,3-difluoropiperidin-1-yl)-4-methoxybenzoic acid obtained in step 2.
MS (ESI+): [M+H]$^+$ 538.3.

Step 4) 2-(3,3-difluoro-4-(hydroxymethyl)piperidin-1-yl)-N-(2,2-dimethylpropyl)-4-methoxy-N-(pyridin-2-yl)benzamide A solution of 2-(3,3-difluoro-4-(phenoxymethyl)piperidin-1-yl)-N-(2,2-dimethylpropyl)-4-methoxy-N-(pyridin-2-yl)benzamide (44.7 mg) obtained in step 3 and palladium-carbon (20 mg) in methanol (2 mL) was stirred under a hydrogen atmosphere at 60° C. for 2 hr. The reaction mixture was filtered through celite, and the solvent was evaporated under reduced pressure to give the title compound as a crude product.
MS (ESI+): [M+H]$^+$ 448.2.

Step 5) (3S)-cyclopropyl-3-(3-((1-(2-((2,2-dimethylpropyl)(pyridin-2-yl)carbamoyl)-5-methoxyphenyl)-3,3-difluoropiperidin-4-yl)methoxy)phenyl)propanoic acid In the same manner as in Example 279, step 5 to step 6, the title compound (8.9 mg) was obtained as a white amorphous powder from 2-(3,3-difluoro-4-(hydroxymethyl)piperidin-1-yl)-N-(2,2-dimethylpropyl)-4-methoxy-N-(pyridin-2-yl)benzamide obtained in step 4.
MS (ESI+): [M+H]$^+$ 636.4.

Example 282

3-cyclopropyl-3-(3-((1-(2-((2,2-dimethylpropyl)(pyridin-2-yl)carbamoyl)-5-methoxyphenyl)azetidin-3-yl)methoxy)phenyl)propanoic acid Step 1) methyl 1-(2-formyl-5-methoxyphenyl)azetidine-3-carboxylate A mixture of methyl azetidine-3-carboxylate hydrochloride (1.48 g), 2-fluoro-4-methoxybenzaldehyde (1.65 g), cesium carbonate (7.95 g), tetrabutylammonium iodide (360 mg) and DMSO (30 mL) was stirred at 120° C. overnight. To the reaction mixture was added water at room temperature, and the mixture was extracted with ethyl acetate. The extract was washed with water and saturated brine, and dried over anhydrous magnesium sulfate. The solvent was evaporated under reduced pressure. A mixture of the obtained residue, potassium carbonate (2.70 g), iodomethane (1.22 mL) and DMF (30 mL) was stirred at room temperature for 1 hr. To the reaction mixture was added water at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (1.00 g) as a yellow oil.
MS (ESI+): [M+H]$^+$ 250.1.

Step 2) 4-methoxy-2-(3-(methoxycarbonyl)azetidin-1-yl)benzoic acid

In the same manner as in Example 262, step 2, a crude product of the title compound was obtained as a brown solid from methyl 1-(2-formyl-5-methoxyphenyl)azetidine-3-carboxylate (1.00 g). This compound was used for the next step without further purification.

Step 3) methyl 1-(2-((2,2-dimethylpropyl)(pyridin-2-yl)carbamoyl)-5-methoxyphenyl)azetidine-3-carboxylate In the same manner as in Example 32, step 2, a crude product of the title compound was obtained as a pale-yellow oil from N-(2,2-dimethylpropyl)pyridin-2-amine (302 mg) and a crude product (entire amount) of 4-methoxy-2-(3-(methoxycarbonyl)azetidin-1-yl)benzoic acid. This compound was used for the next step without further purification.
MS (ESI+): [M+H]$^+$ 412.3.

Step 4) N-(2,2-dimethylpropyl)-2-(3-(hydroxymethyl)azetidin-1-yl)-4-methoxy-N-(pyridin-2-yl)benzamide To a solution of a crude product (entire amount) of methyl 1-(2-((2,2-dimethylpropyl)(pyridin-2-yl)carbamoyl)-5-methoxyphenyl)azetidine-3-carboxylate in THF (5 mL) was added lithium tetrahydroborate (36.0 mg) at 0° C., and the mixture was stirred at room temperature for 3 hr. To the reaction mixture was added saturated aqueous ammonium chloride solution at 0° C., and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (146 mg) as a white amorphous powder.
MS (ESI+): [M+H]$^+$ 384.3.

Step 5) ethyl-3-cyclopropyl-3-(3-((1-(2-((2,2-dimethylpropyl)(pyridin-2-yl)carbamoyl)-5-methoxyphenyl)azetidin-3-yl)methoxy)phenyl)propanoate In the same manner as in Example 45, step 6, the title compound (71.2 mg) was obtained as a yellow oil from N-(2,2-dimethylpropyl)-2-(3-(hydroxymethyl)azetidin-1-yl)-4-methoxy-N-(pyridin-2-yl)benzamide (73.2 mg) and ethyl(3RS)-3-cyclopropyl-3-(3-hydroxyphenyl)propanoate (45.0 mg).
MS (ESI+): [M+H]$^+$ 600.6.

Step 6) 3-cyclopropyl-3-(3-((1-(2-((2,2-dimethylpropyl)(pyridin-2-yl)carbamoyl)-5-methoxyphenyl)azetidin-3-yl)methoxy)phenyl)propanoic acid In the same manner as in Example 1, step 4, the title compound (55.9 mg) was obtained as a white amorphous powder from ethyl 3-cyclopropyl-3-(3-((1-(2-((2,2-dimethylpropyl)(pyridin-2-yl)carbamoyl)-5-methoxyphenyl)azetidin-3-yl)methoxy)phenyl)propanoate (71.2 mg).
MS (ESI+): [M+H]$^+$ 572.3.

Example 283

3-cyclopropyl-3-(3-((1-(2-((2,2-dimethylpropyl)(pyridin-2-yl)carbamoyl)-5-methoxyphenyl)pyrrolidin-3-yl)methoxy)phenyl)propanoic acid Step 1) 2-(3-(hydroxymethyl)pyrrolidin-1-yl)-4-methoxybenzaldehyde In the same manner as in Example 1, step 2, the title compound (1.86 g) was obtained as a yellow oil from 2-fluoro-4-methoxybenzaldehyde (1.78 g) and pyrrolidin-3-ylmethanol (1.06 g)
MS (ESI+): [M+H]$^+$ 236.2.

Step 2) 2-(3-(((tert-butyl(dimethyl)silyl)oxy)methyl)pyrrolidin-1-yl)-4-methoxybenzaldehyde To a solution of 2-(3-(hydroxymethyl)pyrrolidin-1-yl)-4-methoxybenzaldehyde (1.86 g) and imidazole (1.08 g) in DMF (20 mL) was added tert-butyl(chloro)dimethylsilane (1.79 g), and the mixture was stirred at room temperature for 1 hr. To the reaction mixture was added saturated aqueous ammonium chloride solution at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (2.53 g) as a pale-yellow oil.
MS (ESI+): [M+H]$^+$ 350.2.

Step 3) 2-(3-(((tert-butyl(dimethyl)silyl)oxy)methyl)pyrrolidin-1-yl)-4-methoxybenzoic acid In the same manner as in Example 262, step 2, the title compound (619 mg) was obtained as a brown oil from 2-(3-(((tert-butyl(dimethyl)silyl)oxy)methyl)pyrrolidin-1-yl)-4-methoxybenzaldehyde (2.41 g).
$^1$H NMR (300 MHz, CDCl$_3$) δ 0.08 (6H, s), 0.91 (9H, s), 1.79-1.92 (1H, m), 2.12-2.25 (1H, m), 2.60-2.71 (1H, m), 3.08 (1H, dd, J=10.1, 6.5 Hz), 3.20 (2H, dd, J=7.0 Hz), 3.25-3.33 (1H, m), 3.60-3.72 (2H, m), 3.86 (3H, s), 6.87-6.92 (2H, m), 8.21-8.25 (1H, m).

Step 4) 2-(3-(((tert-butyl(dimethyl)silyl)oxy)methyl)pyrrolidin-1-yl)-N-(2,2-dimethylpropyl)-4-methoxy-N-(pyridin-2-yl)benzamide In the same manner as in Example 32, step 2, a crude product of the title compound was obtained as a pale-yellow oil from N-(2,2-dimethylpropyl)pyridin-2-amine (557 mg) and 2-(3-(((tert-butyl(dimethyl)silyl)oxy)methyl)pyrrolidin-1-yl)-4-methoxybenzoic acid (619 mg). This compound was used for the next step without further purification.
MS (ESI+): [M+H]$^+$ 512.3.

Step 5) N-(2,2-dimethylpropyl)-2-(3-(hydroxymethyl)pyrrolidin-1-yl)-4-methoxy-N-(pyridin-2-yl)benzamide To a solution of a crude product (entire amount) of 2-(3-(((tert-butyl(dimethyl)silyl)oxy)methyl)pyrrolidin-1-yl)-N-(2,2-dimethylpropyl)-4-methoxy-N-(pyridin-2-yl)benzamide in THF (8 mL) was added 1 M tetrabutylammonium fluoride THF solution (3.39 mL), and the mixture was stirred at room temperature for 2 hr. To the reaction mixture was added saturated aqueous ammonium chloride solution at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (337 mg) as a white amorphous powder.
MS (ESI+): [M+H]$^+$ 398.4.

Step 6) methyl 3-cyclopropyl-3-(3-((1-(2-((2,2-dimethylpropyl)(pyridin-2-yl)carbamoyl)-5-methoxyphenyl)pyrrolidin-3-yl)methoxy)phenyl)propanoate In the same manner as in Example 45, step 6, the title compound (110 mg) was obtained as yellow amorphous powder from N-(2,2-dimethylpropyl)-2-(3-(hydroxymethyl)pyrrolidin-1-yl)-4-methoxy-N-(pyridin-2-yl)benzamide (81.2 mg) and methyl 3-cyclopropyl-3-(3-hydroxyphenyl)propanoate (45.0 mg).
MS (ESI+): [M+H]$^+$ 600.6.

Step 7) 3-cyclopropyl-3-(3-((1-(2-((2,2-dimethylpropyl)(pyridin-2-yl)carbamoyl)-5-methoxyphenyl)pyrrolidin-3-yl)methoxy)phenyl)propanoic acid In the same manner as in Example 1, step 4, the title compound (78.9 mg) was obtained as a colorless oil from methyl 3-cyclopropyl-3-(3-((1-(2-((2,2-dimethylpropyl)(pyridin-2-yl)carbamoyl)-5-methoxyphenyl)pyrrolidin-3-yl)methoxy)phenyl)propanoate (110 mg).
MS (ESI+): [M+H]$^+$ 586.3.

Example 284

3-cyclopropyl-3-(2-((1-(5-((2,2-dimethylpropyl)(4,6-dimethylpyridin-2-yl)carbamoyl)-2-methoxypyridin-4-yl)piperidin-4-yl)methoxy)pyridin-4-yl)propanoic acid Step 1) ethyl 3-cyclopropyl-3-(2-((1-(5-((2,2-dimethylpropyl)(4,6-dimethylpyridin-2-yl)carbamoyl)-2-methoxypyridin-4-yl)piperidin-4-yl)methoxy)pyridin-4-yl)propanoate To 4-(4-(((4-(1-cyclopropyl-3-ethoxy-3-oxopropyl)pyridin-2-yl)oxy)methyl)piperidin-1-yl)-6-methoxynicotinic acid (105.4 mg) in THF (872 μl) was added 1-chloro-N,N-2-trimethylpropylamine (33.4 μl) at 0° C. The reaction mixture was stirred at room temperature for 5 hr, and the solvent was evaporated under reduced pressure. The residue was dissolved in toluene (2.18 mL), N-(2,2-dimethylpropyl)-4,6-dimethylpyridin-2-amine (50.3 mg) and triethylamine (36.5 μl) were added at room temperature, and the mixture was stirred at 100° C. for 17 hr. The reaction mixture was cooled to room temperature. The solvent was evaporated under reduced pressure, and the residue was purified by silica gel column chromatography (NH, ethyl acetate/hexane) to give the title compound (90 mg) as a colorless oil.
MS (ESI+): [M+H]$^+$ 658.6.

Step 2) 3-cyclopropyl-3-(2-((1-(5-((2,2-dimethyl-propyl)(4,6-dimethylpyridin-2-yl)carbamoyl)-2-methoxypyridin-4-yl)piperidin-4-yl)methoxy)pyridin-4-yl)propanoic acid By a method similar to that in Example 1, step 4, the title compound (63.7 mg) was obtained as a white amorphous powder from ethyl 3-cyclopropyl-3-(2-((1-(5-((2,2-dimethylpropyl)(4,6-dimethylpyridin-2-yl)carbamoyl)-2-methoxypyridin-4-yl)piperidin-4-yl)methoxy)pyridin-4-yl)propanoate (72.5 mg).

MS (ESI+): [M+H]$^+$ 630.3.

Example 285

3-cyclopropyl-3-(2-((1-(5-((cyclopropylmethyl)(4,6-dimethylpyridin-2-yl)carbamoyl)-2-methoxypyridin-4-yl)piperidin-4-yl)methoxy)pyridin-4-yl)propanoic acid By a method similar to that in Example 284, step 1 and Example 1, step 4, the title compound (61.5 mg) was obtained as a white amorphous powder from 4-(4-(((4-(1-cyclopropyl-3-ethoxy-3-oxopropyl)pyridin-2-yl)oxy)methyl)piperidin-1-yl)-6-methoxynicotinic acid (102.7 mg) and N-(cyclopropylmethyl)-4,6-dimethylpyridin-2-amine (44.9 mg).

MS (ESI+): [M+H]$^+$ 614.3.

Example 286

3-cyclopropyl-3-(2-((1-(5-((2,2-dimethylpropyl)(2,6-dimethylpyrimidin-4-yl)carbamoyl)-2-methoxypyridin-4-yl)piperidin-4-yl)methoxy)pyridin-4-yl)propanoic acid Step 1) ethyl 3-cyclopropyl-3-(2-((1-(5-((2,2-dimethylpropyl)(2,6-dimethylpyrimidin-4-yl)carbamoyl)-2-methoxypyridin-4-yl)piperidin-4-yl)methoxy)pyridin-4-yl)propanoate Under a nitrogen atmosphere, 4-(4-(((4-(1-cyclopropyl-3-ethoxy-3-oxopropyl)pyridin-2-yl)oxy)methyl)piperidin-1-yl)-6-methoxynicotinic acid (200 mg) obtained in Example 255, step 8, was dissolved in toluene (5 mL), and 1-chloro-N,N,2-trimethylprop-1-en-1-amine (83 mg) was added at room temperature. The mixture was stirred at 60° C. for 1 hr, N-(2,2-dimethylpropyl)-2,6-dimethylpyrimidin-4-amine (120 mg) obtained in Example 228, step 1, and triethylamine (0.2 mL) were added, and the mixture was stirred at 100° C. for 10 hr. The reaction mixture was concentrated under reduced pressure, and the residue was purified by silica gel column chromatography (ethyl acetate/hexane) to give the title compound (165 mg) as a colorless oil.

MS (ESI+): [M+H]$^+$ 659.4.

Step 2) 3-cyclopropyl-3-(2-((1-(5-((2,2-dimethyl-propyl)(2,6-dimethylpyrimidin-4-yl)carbamoyl)-2-methoxypyridin-4-yl)piperidin-4-yl)methoxy)pyridin-4-yl)propanoic acid In the same manner as in Example 1, step 4, the title compound (90 mg) was obtained as a colorless amorphous powder from ethyl 3-cyclopropyl-3-(2-((1-(5-((2,2-dimethylpropyl)(2,6-dimethylpyrimidin-4-yl)carbamoyl)-2-methoxypyridin-4-yl)piperidin-4-yl)methoxy)pyridin-4-yl)propanoate (165 mg).

MS (ESI+): [M+H]$^+$ 631.3.

Example 287

3-cyclopropyl-3-(2-((1-(5-((2,2-dimethylpropyl)(6-methylpyridin-2-yl)carbamoyl)-2-methoxypyrimidin-4-yl)piperidin-4-yl)methoxy)pyridin-4-yl)propanoic acid Step 1) (1-(5-bromo-2-chloropyrimidin-4-yl)piperidin-4-yl)methanol To a solution of 5-bromo-2,4-dichloropyrimidine (5.00 g) and triethylamine (4.59 mL) in THF (50 mL) was added a solution of piperidin-4-ylmethanol (2.53 g) in THF (20 mL) at 0° C. Under a nitrogen atmosphere, the mixture was stirred at 0° C. for 1 hr, to the reaction mixture was added water at room temperature, and the mixture was extracted with ethyl acetate. The extract was washed with water and saturated brine, and dried over anhydrous magnesium sulfate. The solvent was evaporated under reduced pressure to give a crude product of the title compound as a pale-yellow oil. This compound was used for the next step without further purification.

$^1$H NMR (400 MHz, CDCl$_3$) δ 1.31-1.46 (3H, m), 1.75-1.93 (2H, m), 2.97 (2H, t, J=12.8 Hz), 3.56 (2H, brs), 4.54 (2H, d, J=13.3 Hz), 4.71 (1H, d, J=11.8 Hz), 8.22 (1H, s).

Step 2) (1-(5-bromo-2-methoxypyrimidin-4-yl)piperidin-4-yl)methanol

A 28% solution of sodium methoxide in methanol (44.5 mL) was added to a solution of a crude product (entire amount) of (1-(5-bromo-2-chloropyrimidin-4-yl)piperidin-4-yl)methanol obtained in Example 287, step 1, in THF (50 mL) at 0° C. Under a nitrogen atmosphere, the mixture was stirred at 0° C. for 1 hr, water was added to the reaction mixture at room temperature, and the mixture was extracted with ethyl acetate. The extract was washed with water and saturated brine, and dried over anhydrous magnesium sulfate. The solvent was evaporated under reduced pressure. The residue was purified by silica gel column chromatography (ethyl acetate/hexane) to give the title compound (5.43 g) as a colorless oil.

$^1$H NMR (400 MHz, CDCl$_3$) δ 1.29-1.46 (3H, m), 1.72-1.91 (2H, m), 2.92 (2H, t, J=12.8 Hz), 3.48-3.61 (2H, m), 3.92 (3H, s), 4.46 (2H, d, J=13.3 Hz), 8.17 (1H, s).

Step 3) 5-bromo-2-methoxy-4-(4-((tetrahydro-2H-pyran-2-yloxy)methyl)piperidin-1-yl)pyrimidine To a solution of (1-(5-bromo-2-methoxypyrimidin-4-yl)piperidin-4-yl)methanol (3.00 g) and 3,4-dihydro-2H-pyran (1.82 mL) in THF (30 mL) was added p-toluenesulfonic acid.monohydrate (378 mg) at room temperature, and the mixture was stirred at 60° C. for 1 hr. To the reaction mixture was added saturated aqueous sodium hydrogen carbonate solution at room temperature, and the mixture was extracted with ethyl acetate. The extract was washed with water and saturated brine, and dried over anhydrous magnesium sulfate. The solvent was evaporated under reduced pressure.

The residue was purified by silica gel column chromatography (ethyl acetate/hexane) to give the title compound (3.70 g) as a colorless oil.

$^1$H NMR (400 MHz, CDCl$_3$) δ 1.39 (2H, q, J=12.0 Hz), 1.49-1.99 (8H, m), 2.92 (2H, t, J=12.8 Hz), 3.27 (1H, t, J=7.6 Hz), 3.51 (1H, d, J=10.5 Hz), 3.64 (1H, t, J=8.0 Hz), 3.74 (1H, brs), 3.85 (1H, t, J=9.3 Hz), 3.91 (3H, s), 4.44 (2H, d, J=12.8 Hz), 4.58 (1H, brs), 8.17 (1H, s).

Step 4) methyl 2-methoxy-4-(4-((tetrahydro-2H-pyran-2-yloxy)methyl)piperidin-1-yl)pyrimidine-5-carboxylate (1-(5-Bromo-2-methoxypyrimidin-4-yl)piperidin-4-yl) methanol (530 mg), [1,1'-bis(diphenylphosphino)ferrocene] dichloropalladium(II) (112 mg), triethylamine (956 µL), methanol (2.00 mL) and DMF (8 mL) were stirred under a carbon monoxide (0.5 MPa) atmosphere at 120° C. for 7 hr. The solvent was evaporated under reduced pressure to give a crude product of the title compound as a brown oil. This compound was used for the next step without further purification.

$^1$H NMR (400 MHz, CDCl$_3$) δ 1.29-1.45 (2H, m), 1.47-1.60 (4H, m), 1.65-2.00 (5H, m), 3.02 (2H, t, J=12.8 Hz), 3.26 (1H, t, J=7.5 Hz), 3.51 (1H, d, J=11.4 Hz), 3.63 (1H, t, J=7.8 Hz), 3.80-3.86 (1H, m), 3.85 (3H, s), 3.95 (3H, s), 4.06-4.20 (2H, m), 4.57 (1H, brs), 8.60 (1H, s).

Step 5) benzyl 4-(4-(hydroxymethyl)piperidin-1-yl)-2-methoxypyrimidine-5-carboxylate To a solution of a crude product (entire amount) of methyl 2-methoxy-4-(4-((tetrahydro-2H-pyran-2-yloxy)methyl)piperidin-1-yl)pyrimidine-5-carboxylate in THF (10 mL) and methanol (5.0 mL) was added 1N aqueous sodium hydroxide solution (10 mL) at room temperature, and the mixture was heated under reflux for 16 hr. The solvent was evaporated under reduced pressure, and to the residue were added DMF (15 mL), potassium carbonate (379 mg) and benzyl bromide (244 µL) at room temperature, and the mixture was stirred at 80° C. for 30 min. To the reaction mixture was added water at room temperature, and the mixture was extracted with ethyl acetate. The extract was washed with water and saturated brine, and dried over anhydrous magnesium sulfate. The solvent was evaporated under reduced pressure, and to the residue were added methanol (5 mL) and p-toluenesulfonic acid.monohydrate (26.1 mg), and the mixture was stirred at 60° C. for 30 min. To the reaction mixture was added saturated aqueous sodium hydrogen carbonate solution at room temperature, and the mixture was extracted with ethyl acetate. The extract was washed with water and saturated brine, and dried over anhydrous magnesium sulfate. The solvent was evaporated under reduced pressure. The residue was purified by silica gel column chromatography (ethyl acetate/hexane) to give the title compound (200 mg) as a colorless oil.

$^1$H NMR (400 MHz, DMSO-d$_6$) δ 0.98-1.24 (2H, m), 1.55-1.77 (3H, m), 2.94 (2H, t, J=12.5 Hz), 3.17-3.27 (2H, m), 3.85 (3H, s), 3.92-4.10 (2H, m), 4.37-4.52 (1H, m), 5.28 (2H, s), 7.31-7.49 (5H, m), 8.48 (1H, s).

Step 6) benzyl 4-(4-(((4-(1-cyclopropyl-3-ethoxy-3-oxopropyl)pyridin-2-yl)oxy)methyl)piperidin-1-yl)-2-methoxypyrimidine-5-carboxylate In the same manner as in Example 45, step 6, the title compound (198 mg) was obtained as a pale-orange oil from benzyl 4-(4-(hydroxymethyl)piperidin-1-yl)-2-methoxypyrimidine-5-carboxylate (200 mg) and ethyl 3-cyclopropyl-3-(2-hydroxypyridin-4-yl)propanoate (158 mg).

$^1$H NMR (400 MHz, CDCl$_3$) δ 0.06-0.22 (1H, m), 0.24-0.37 (1H, m), 0.41-0.52 (1H, m), 0.54-0.66 (1H, m), 0.91-1.05 (1H, m), 1.18 (3H, t, J=7.1 Hz), 1.42 (2H, q, J=12.0 Hz), 1.86 (2H, d, J=13.9 Hz), 2.01-2.15 (1H, m), 2.23-2.37 (1H, m), 2.61-2.81 (2H, m), 3.01 (2H, t, J=12.9 Hz), 3.95 (3H, s), 4.02-4.20 (6H, m), 5.30 (2H, s), 6.61 (1H, s), 6.76 (1H, brs), 7.30-7.47 (5H, m), 8.04 (1H, brs), 8.65 (1H, s).

Step 7) 4-(4-(((4-(1-cyclopropyl-3-ethoxy-3-oxopropyl)pyridin-2-yl)oxy)methyl)piperidin-1-yl)-2-methoxypyrimidine-5-carboxylic acid Benzyl 4-(4-(((4-(1-cyclopropyl-3-ethoxy-3-oxopropyl) pyridin-2-yl)oxy)methyl)piperidin-1-yl)-2-methoxypyrimidine-5-carboxylate (198 mg) and 10% palladium carbon (100 mg) were stirred in ethyl acetate (5.0 mL) under a hydrogen atmosphere (1 atm) at room temperature for 20 min. The reaction mixture was filtered, and the solvent in the filtrate was evaporated under reduced pressure to give the title compound (149 mg) as a white amorphous powder.

$^1$H NMR (400 MHz, DMSO-d$_6$) δ 0.11-0.20 (1H, m), 0.21-0.29 (1H, m), 0.30-0.40 (1H, m), 0.45-0.57 (1H, m), 0.94-1.04 (1H, m), 1.08 (3H, t, J=7.3 Hz), 1.27-1.45 (2H, m), 1.69-1.89 (2H, m), 1.96-2.15 (1H, m), 2.18-2.30 (1H, m), 2.75 (2H, d, J=7.2 Hz), 3.03 (2H, t, J=12.6 Hz), 3.86 (3H, s), 3.90-4.03 (2H, m), 4.05-4.18 (4H, m), 6.71 (1H, s), 6.91 (1H, d, J=4.0 Hz), 8.03 (1H, d, J=3.6 Hz), 8.45 (1H, s), 12.81 (1H, brs).

Step 8) ethyl 3-cyclopropyl-3-(2-((1-(5-((2,2-dimethylpropyl)(6-methylpyridin-2-yl)carbamoyl)-2-methoxypyrimidin-4-yl)piperidin-4-yl)methoxy) pyridin-4-yl)propanoate In the same manner as in Example 32, step 2, the title compound (32.9 mg) was obtained as a pale-yellow amorphous powder from 4-(4-(((4-(1-cyclopropyl-3-ethoxy-3-oxopropyl)pyridin-2-yl)oxy)methyl)piperidin-1-yl)-2-methoxypyrimidine-5-carboxylic acid (50.0 mg) and N-(2,2-dimethylpropyl)-6-methylpyridin-2-amine (27.6 mg).

$^1$H NMR (400 MHz, CDCl$_3$) δ 0.12-0.20 (1H, m), 0.24-0.33 (1H, m), 0.41-0.52 (1H, m), 0.56-0.67 (1H, m), 0.83 (9H, s), 0.94-1.05 (1H, m), 1.18 (3H, t, J=6.9 Hz), 1.31-1.49 (2H, m), 1.84 (2H, d, J=13.4 Hz), 1.97-2.13 (1H, m), 2.30 (1H, d, J=8.9 Hz), 2.45 (3H, s), 2.63-2.82 (2H, m), 2.72-3.14 (2H, m), 3.85 (3H, s), 4.00-4.11 (4H, m), 4.15 (2H, d, J=6.3 Hz), 4.17-4.31 (2H, m), 6.61 (2H, brs), 6.77 (1H, brs), 6.86 (1H, d, J=7.7 Hz), 7.34 (1H, t, J=8.1 Hz), 7.89 (1H, s), 8.04 (1H, brs).

Step 9) 3-cyclopropyl-3-(2-((1-(5-((2,2-dimethylpropyl)(6-methylpyridin-2-yl)carbamoyl)-2-methoxypyrimidin-4-yl)piperidin-4-yl)methoxy) pyridin-4-yl)propanoic acid In the same manner as in Example 1, step 4, the title compound (31.3 mg) was obtained as a white amorphous powder from ethyl 3-cyclopropyl-3-(2-((1-(5-((2,2-dimethylpropyl)(6-methylpyridin-2-yl)carbamoyl)-2-methoxypyrimidin-4-yl)piperidin-4-yl)methoxy)pyridin-4-yl)propanoate (32.9 mg).

MS (ESI+): [M+H]$^+$ 617.3.

The IUPAC names, structural formulas and MS (Found) of the compounds of Examples 1-287 are shown below.

TABLE 2-1
| Ex. No. | structural formula | IUPAC name | MS |
|---|---|---|---|
| 1 | 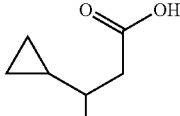 | 3-cyclopropyl-3-(3-((1-(5-methoxy-2-(methyl(2-methyl-propyl)carbamoyl)phenyl)-piperidin-4-yl)methoxy)-phenyl)propanoic acid | 523.3 |
| 2 | 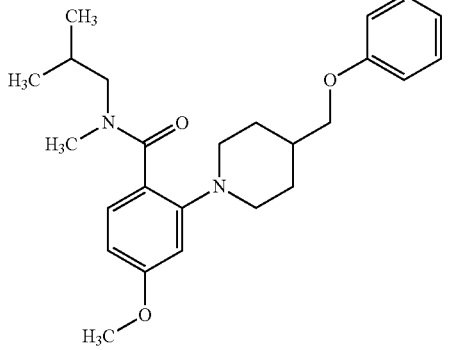 | 3-cyclopropyl-3-(3-((1-(2-((2,2-dimethylpropyl)-carbamoyl)-5-methoxyphenyl)piperidin-4-yl)methoxy)phenyl)propanoic acid | 523.4 |
| 3 | 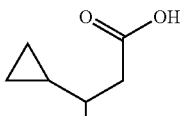 | 3-cyclopropyl-3-(3-((1-(5-methoxy-2-(morpholin-4-ylcarbonyl)phenyl)-piperidin-4-yl)-methoxy)phenyl)propanoic acid | 523.3 |

TABLE 2-1-continued

| Ex. No. | structural formula | IUPAC name | MS |
|---|---|---|---|
| 4 | | 3-cyclopropyl-3-(3-((1-(2-(2,3-dihydro-1H-indol-1-ylcarbonyl)-5-methoxyphenyl)piperidin-4-yl)methoxy)phenyl)propanoic acid | 555.3 |
| 5 | | 3-cyclopropyl-3-(3-((1-(2-(((2R,6S)-2,6-dimethylmorpholin-4-yl)-carbonyl)-5-methoxyphenyl)piperidin-4-yl)methoxy)phenyl)propanoic acid | 551.3 |
| 6 | | 3-(3-((1-(2-((2-cyanoethyl)(phenyl)-carbamoyl)-5-methoxyphenyl)piperidin-4-yl)methoxy)phenyl)-3-cyclopropylpropanoic acid | 582.3 |

TABLE 2-2

| Ex. No. | structural formula | IUPAC name | MS |
|---|---|---|---|
| 7 | | 3-cyclopropyl-3-(3-((1-(2-((4-fluorophenyl)-(methyl)carbamoyl)-5-methoxyphenyl)piperidin-4-yl)methoxy)-phenyl)propanoic acid | 561.3 |

TABLE 2-2-continued

| Ex. No. | structural formula | IUPAC name | MS |
|---|---|---|---|
| 8 | | 3-cyclopropyl-3-(3-((1-(2-((3-fluorophenyl)-(methyl)carbamoyl)-5-methoxyphenyl)piperidin-4-yl)methoxy)-phenyl)propanoic acid | 561.3 |
| 9 | | 3-cyclopropyl-3-(3-((1-(2-((2-fluorophenyl)(methyl)carbamoyl)-5-methoxyphenyl)piperidin-4-yl)methoxy)-phenyl)propanoic acid | 561.3 |
| 10 | | 3-(3-((1-(2-((4-chlorophenyl)(methyl)-carbamoyl)-5-methoxyphenyl)piperidin-4-yl)methoxy)phenyl)-3-cyclopropylpropanoic acid | 577.2 |
| 11 | | 3-cyclopropyl-3-(3-((1-(2-(ethyl(pyridin-2-yl)carbamoyl)-5-methoxyphenyl)piperidin-4-yl)methoxy)phenyl)-propanoic acid | 558.3 |
| 12 | | 3-(3-((1-(2-((2-chlorophenyl)(methyl)-carbamoyl)-5-methoxyphenyl)piperidin-4-yl)methoxy)phenyl)-3-cyclopropylpropanoic acid | 577.2 |

TABLE 2-3

| Ex. No. | structural formula | IUPAC name | MS |
|---|---|---|---|
| 13 | | 3-cyclopropyl-3-(3-((1-(5-methoxy-2-(methyl(pyridin-4-yl)carbamoyl)phenyl)-piperidin-4-yl)methoxy)phenyl)-propanoic acid | 544.2 |
| 14 | | 3-cyclopropyl-3-(3-((1-(5-methoxy-2-((4-(2,2,3,3,3-pentafluoropropyl)-piperazin-1-yl)carbonyl)phenyl)piperidin-4-yl)methoxy)phenyl)-propanoic acid | 654.3 |
| 15 | | 3-(3-((1-(2-((4-tert-butylpiperazin-1-yl)carbonyl)-5-methoxyphenyl)piperidin-4-yl)methoxy)phenyl)-3-cyclopropylpropanoic acid | 578.3 |
| 16 | | 3-cyclopropyl-3-(3-((1-(5-methoxy-2-((4-methylpiperazin-1-yl)carbonyl)phenyl)piperidin-4-yl)methoxy)phenyl)-propanoic acid | 536.3 |

TABLE 2-3-continued

| Ex. No. | structural formula | IUPAC name | MS |
|---|---|---|---|
| 17 | | 3-cyclopropyl-3-(3-((1-(5-methoxy-2-(methyl(pyridin-3-yl)carbamoyl)phenyl)-piperidin-4-yl)methoxy)phenyl)-propanoic acid | 544.2 |
| 18 | | 3-(3-((1-(2-((3-chlorophenyl)(methyl)-carbamoyl)-5-methoxyphenyl)piperidin-4-yl)methoxy)phenyl)-3-cyclopropylpropanoic acid | 577.2 |

TABLE 2-4

| Ex. No. | structural formula | IUPAC name | MS |
|---|---|---|---|
| 19 | | 3-cyclopropyl-3-(3-((1-(2-((2-fluorobenzyl)-(methyl)carbamoyl)-5-methoxyphenyl)piperidin-4-yl)methoxy)phenyl)-propanoic acid | 575.3 |
| 20 | | 3-cyclopropyl-3-(3-((1-(2-((3-fluorobenzyl)-(methyl)carbamoyl)-5-methoxyphenyl)piperidin-4-yl)methoxy)phenyl)-propanoic acid | 575.3 |

TABLE 2-4-continued

| Ex. No. | structural formula | IUPAC name | MS |
|---|---|---|---|
| 21 | | 3-cyclopropyl-3-(3-((1-(2-((4-fluorobenzyl)-(methyl)carbamoyl)-5-methoxyphenyl)piperidin-4-yl)methoxy)phenyl)-propanoic acid | 575.3 |
| 22 | | 3-cyclopropyl-3-(3-((1-(5-methoxy-2-(methyl(pyridin-2-ylmethyl)carbamoyl)-phenyl)piperidin-4-yl)methoxy)-phenyl)propanoic acid | 558.3 |
| 23 | | 3-cyclopropyl-3-(3-((1-(5-methoxy-2-(methyl(pyridin-3-ylmethyl)carbamoyl)-phenyl)piperidin-4-yl)methoxy)-phenyl)propanoic acid | 558.3 |
| 24 | | 3-(3-((1-(2-((3-chlorobenzyl)(methyl)-carbamoyl)-5-methoxyphenyl)piperidin-4-yl)methoxy)phenyl)-3-cyclopropylpropanoic acid | 591.2 |

TABLE 2-5

| Ex. No. | structural formula | IUPAC name | MS |
|---|---|---|---|
| 25 | | 3-cyclopropyl-3-(3-((1-(5-methoxy-2-(methyl(6-methylpyridin-2-yl)carbamoyl)phenyl)-piperidin-4-yl)-methoxy)phenyl)propanoic acid | 558.3 |
| 26 | | 3-cyclopropyl-3-(3-((1-(5-methoxy-2-(methyl(4-methylpyridin-2-yl)carbamoyl)phenyl)-piperidin-4-yl)-methoxy)phenyl)propanoic acid | 558.3 |
| 27 | | 3-(3-((1-(2-((3-cyanophenyl)(methyl)-carbamoyl)-5-methoxyphenyl)piperidin-4-yl)methoxy)phenyl)-3-cyclopropylpropanoic acid | 568.3 |
| 28 | | 3-cyclopropyl-3-(3-((1-(2-((2,2-dimethylpropyl)(2-methylpropyl)carbamoyl)-5-methoxyphenyl)-piperidin-4-yl)methoxy)-phenyl)propanoic acid | 579.3 |

TABLE 2-5-continued

| Ex. No. | structural formula | IUPAC name | MS |
|---|---|---|---|
| 29 | | 3-cyclopropyl-3-(3-((1-(2-((2,2-dimethylmorpholin-4-yl)carbonyl)-5-methoxyphenyl)piperidin-4-yl)methoxy)phenyl)propanoic acid | 551.3 |
| 30 | | 3-(3-((1-(2-((2-tert-butylpyrrolidin-1-yl)carbonyl)-5-methoxyphenyl)piperidin-4-yl)methoxy)phenyl)-3-cyclopropylpropanoic acid | 563.3 |

TABLE 2-6

| Ex. No. | structural formula | IUPAC name | MS |
|---|---|---|---|
| 31 | | 3-cyclopropyl-3-(3-((1-(5-methoxy-2-(((3R)-3-(2-methylpropyl)morpholin-4-yl)carbonyl)phenyl)piperidin-4-yl)methoxy)phenyl)propanoic acid | 579.3 |
| 32 | | 3-cyclopropyl-3-(3-((1-(2-((2,2-dimethylpropyl)(6-methylpyridin-2-yl)carbamoyl)-5-methoxyphenyl)piperidin-4-yl)methoxy)phenyl)propanoic acid | 614.4 |

TABLE 2-6-continued

| Ex. No. | structural formula | IUPAC name | MS |
|---|---|---|---|
| 33 | | 3-cyclopropyl-3-(3-((1-(2-((2,2-dimethylpropyl)(4-methylpyridin-2-yl)carbamoyl)-5-methoxyphenyl)piperidin-4-yl)methoxy)phenyl)-propanoic acid | 614.4 |
| 34 | | 3-cyclopropyl-3-(3-((1-(2-((2,2-dimethylpropyl)(pyridin-2-yl)carbamoyl)-5-methoxyphenyl)piperidin-4-yl)methoxy)phenyl)-propanoic acid | 600.3 |
| 35 | | 3-cyclopropyl-3-(3-((1-(5-methoxy-2-((2-methoxy-2-methylpropyl)(pyridin-2-yl)carbamoyl)phenyl)-piperidin-4-yl)-methoxy)phenyl)propanoic acid | 616.3 |
| 36 | | 3-cyclopropyl-3-(3-((1-(2-((cyclopropylmethyl)(4-methylpyridin-2-yl)carbamoyl)-5-methoxyphenyl)piperidin-4-yl)methoxy)phenyl)-propanoic acid | 598.3 |

TABLE 2-7

| Ex. No. | structural formula | IUPAC name | MS |
|---|---|---|---|
| 37 | | 3-(3-((1-(2-((4-cyano-4-methylpiperidin-1-yl)carbonyl)-5-methoxyphenyl)piperidin-4-yl)methoxy)phenyl)-3-cyclopropylpropanoic acid | 560.3 |
| 38 | | 3-(3-((1-(2-((4-cyano-4-(2-methylpropyl)piperidin-1-yl)carbonyl)-5-methoxyphenyl)piperidin-4-yl)methoxy)phenyl)-3-cyclopropylpropanoic acid | 602.3 |
| 39 | | 3-cyclopropyl-3-(3-((1-(2-((2-fluoro-2-methylpropyl)(pyridin-2-yl)carbamoyl)-5-methoxyphenyl)piperidin-4-yl)methoxy)phenyl)propanoic acid | 604.4 |
| 40 | | 3-cyclopropyl-3-(3-((1-(2-((cyclopropylmethyl)-(pyridin-2-yl)carbamoyl)-5-methoxyphenyl)-piperidin-4-yl)-methoxy)phenyl)propanoic acid | 584.3 |

TABLE 2-7-continued

| Ex. No. | structural formula | IUPAC name | MS |
|---|---|---|---|
| 41 | 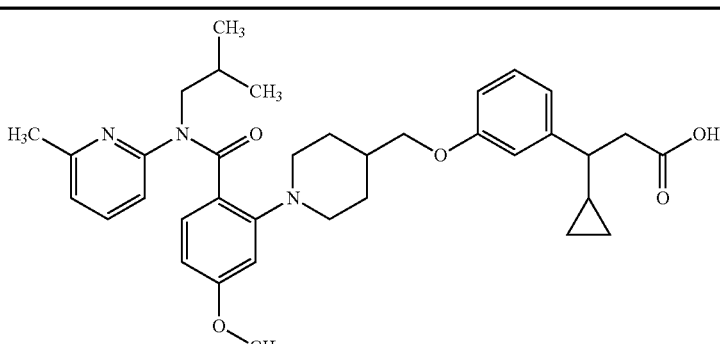 | 3-cyclopropyl-3-(3-((1-(5-methoxy-2-((2-methylpropyl)(6-methylpyridin-2-yl)carbamoyl)phenyl)-piperidin-4-yl)methoxy)-phenyl)propanoic acid | 600.3 |
| 42 | 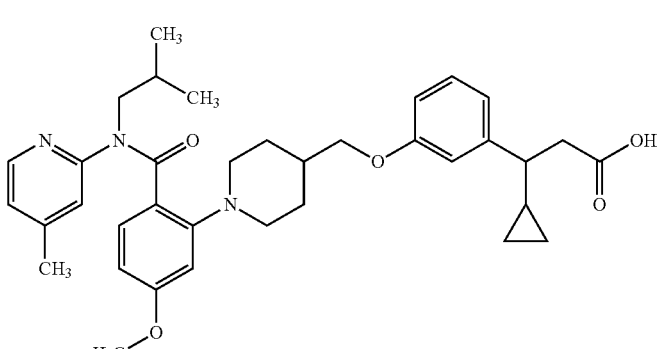 | 3-cyclopropyl-3-(3-((1-(5-methoxy-2-((2-methylpropyl)(4-methylpyridin-2-yl)carbamoyl)phenyl)-piperidin-4-yl)methoxy)-phenyl)propanoic acid | 600.3 |

TABLE 2-8

| Ex. No. | structural formula | IUPAC name | MS |
|---|---|---|---|
| 43 | 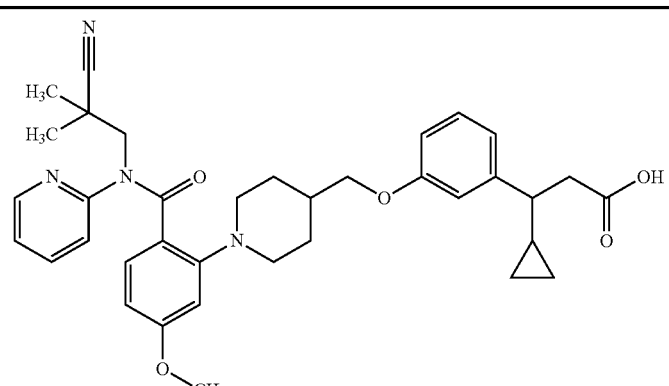 | 3-(3-((1-(2-((2-cyano-2-methylpropyl)(pyridin-2-yl)carbamoyl)-5-methoxyphenyl)piperidin-4-yl)methoxy)phenyl)-3-cyclopropylpropanoic acid | 611.2 |
| 44 | 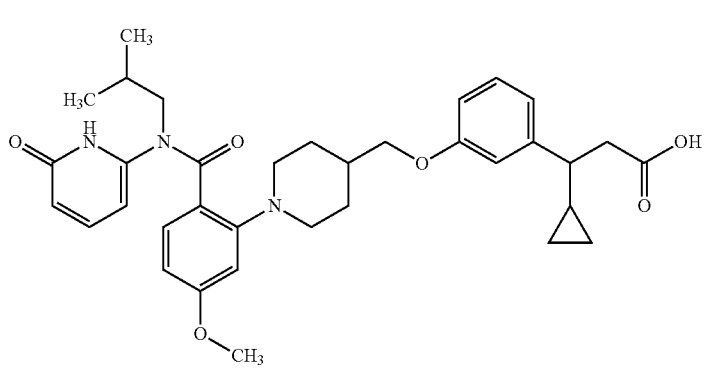 [SMILES: COc1ccc(C(=O)N(CC(C)C)c2cccc(=O)[nH]2)c(N2CCC(COc3cccc(C(CC(=O)O)C4CC4)c3)CC2)c1] | 3-cyclopropyl-3-(3-((1-(5-methoxy-2-((2-methylpropyl)(6-oxo-1,6-dihydropyridin-2-yl)carbamoyl)phenyl)-piperidin-4-yl)methoxy)-phenyl)propanoic acid | 602.2 |

TABLE 2-8-continued

| Ex. No. | structural formula | IUPAC name | MS |
|---|---|---|---|
| 45 | 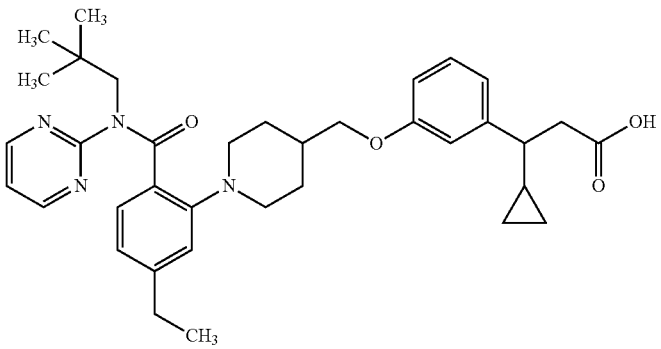 [SMILES: CCc1ccc(C(=O)N(CC(C)(C)C)c2ncccn2)c(N2CCC(COc3cccc(C(CC(=O)O)C4CC4)c3)CC2)c1] | 3-cyclopropyl-3-(3-((1-(2-((2,2-dimethylpropyl)-(pyrimidin-2-yl)carbamoyl)-5-ethylphenyl)piperidin-4-yl)methoxy)phenyl)-propanoic acid | 599.4 |
| 46 | 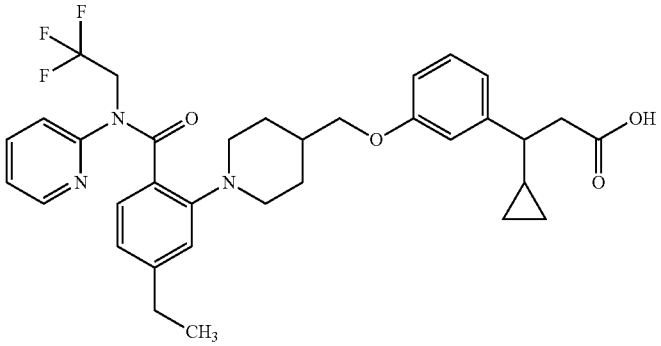 | 3-cyclopropyl-3-(3-((1-(5-ethyl-2-(pyridin-2-yl(2,2,2-trifluoroethyl)-carbamoyl)phenyl)-piperidin-4-yl)methoxy)-phenyl)propanoic acid | 610.3 |
| 47 | 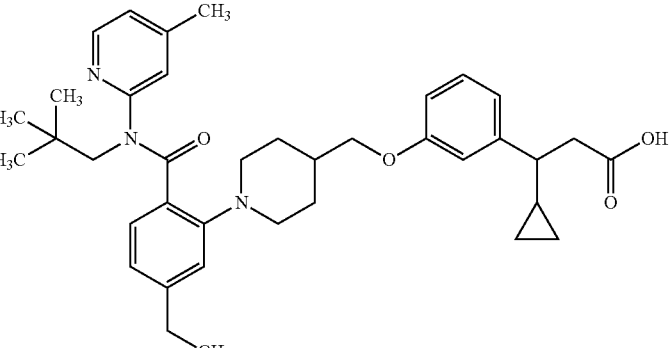 | 3-cyclopropyl-3-(3-((1-(2-((2,2-dimethylpropyl)(4-methylpyridin-2-yl)carbamoyl)-5-ethylphenyl)piperidin-4-yl)methoxy)phenyl)-propanoic acid | 612.4 |
| 48 | 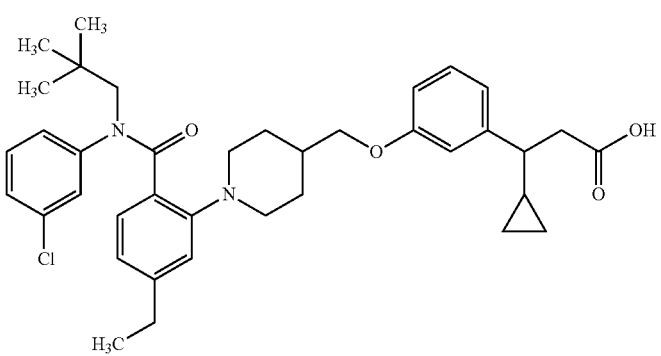 | 3-(3-((1-(2-((3-chlorophenyl)(2,2-dimethylpropyl)-carbamoyl)-5-ethylphenyl)piperidin-4-yl)methoxy)phenyl)-3-cyclopropylpropanoic acid | 631.3 |

TABLE 2-9

| Ex. No. | structural formula | IUPAC name | MS |
|---|---|---|---|
| 49 | 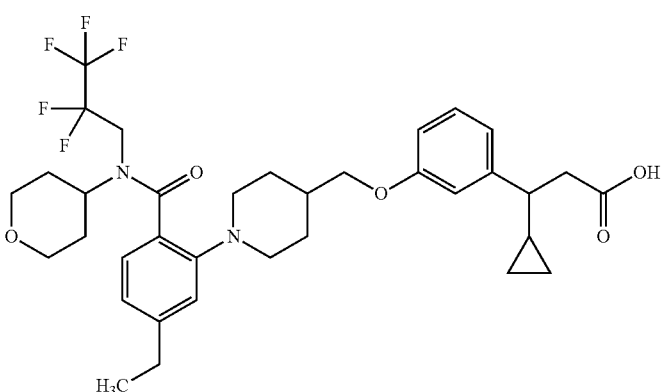 | 3-cyclopropyl-3-(3-((1-(5-ethyl-2-((2,2,3,3,3-pentafluoropropyl)-(tetrahydro-2H-pyran-4-yl)carbamoyl)phenyl)-piperidin-4-yl)methoxy)phenyl)-propanoic acid | 667.4 |
| 50 | 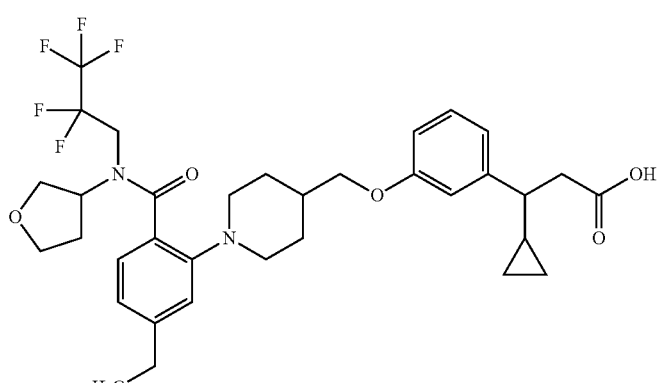 | 3-cyclopropyl-3-(3-((1-(5-ethyl-2-((2,2,3,3,3-pentafluoropropyl)-(tetrahydrofuran-3-yl)carbamoyl)phenyl)-piperidin-4-yl)methoxy)phenyl)-propanoic acid | 653.4 |
| 51 | 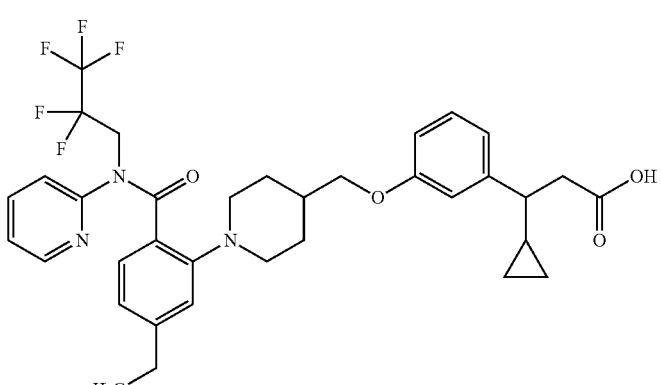 | 3-cyclopropyl-3-(3-((1-(5-ethyl-2-((2,2,3,3,3-pentafluoropropyl)-(pyridin-2-yl)carbamoyl)phenyl)-piperidin-4-yl)methoxy)phenyl)-propanoic acid | 660.3 |
| 52 | 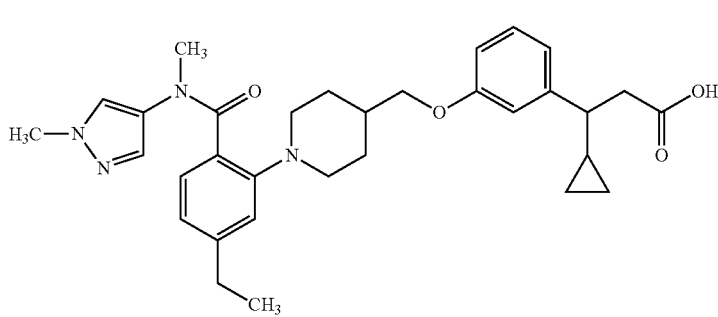 [SMILES: CCc1ccc(C(=O)N(C)c2cnn(C)c2)c(N2CCC(COc3cccc(C(CC(=O)O)C4CC4)c3)CC2)c1] | 3-cyclopropyl-3-(3-((1-(5-ethyl-2-(methyl(1-methyl-1H-pyrazol-4-yl)carbamoyl)phenyl)-piperidin-4-yl)methoxy)phenyl)-propanoic acid | 545.3 |

TABLE 2-9-continued

| Ex. No. | structural formula | IUPAC name | MS |
|---|---|---|---|
| 53 | 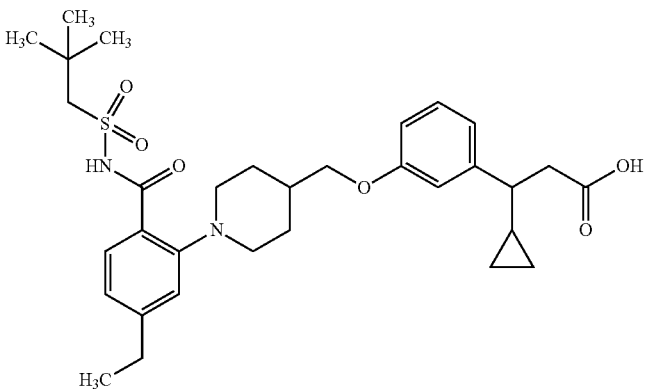 [SMILES: CCc1ccc(C(=O)NS(=O)(=O)CC(C)(C)C)c(N2CCC(COc3cccc(C(CC(=O)O)C4CC4)c3)CC2)c1] | 3-cyclopropyl-3-(3-((1-(2-(((2,2-dimethylpropyl)sulfonyl)-carbamoyl)-5-ethylphenyl)piperidin-4-yl)methoxy)phenyl)-propanoic acid | 585.3 |
| 54 | 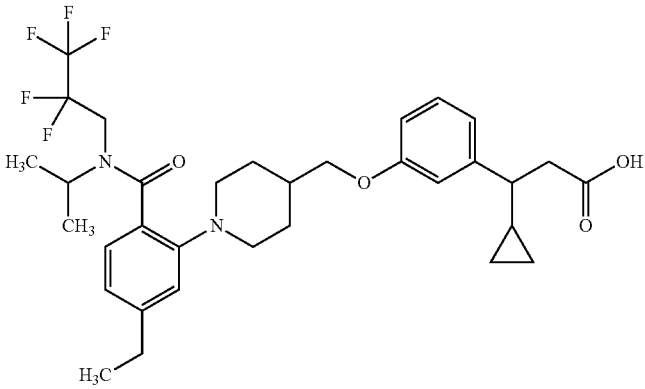 [SMILES: CCc1ccc(C(=O)N(CC(F)(F)C(F)(F)F)C(C)C)c(N2CCC(COc3cccc(C(CC(=O)O)C4CC4)c3)CC2)c1] | 3-cyclopropyl-3-(3-((1-(5-ethyl-2-((2,2,3,3,3-pentafluoropropyl)-(propan-2-yl)carbamoyl)-phenyl)piperidin-4-yl)methoxy)phenyl)-propanoic acid | 625.3 |

TABLE 2-10

| Ex. No. | structural formula | IUPAC name | MS |
|---|---|---|---|
| 55 | 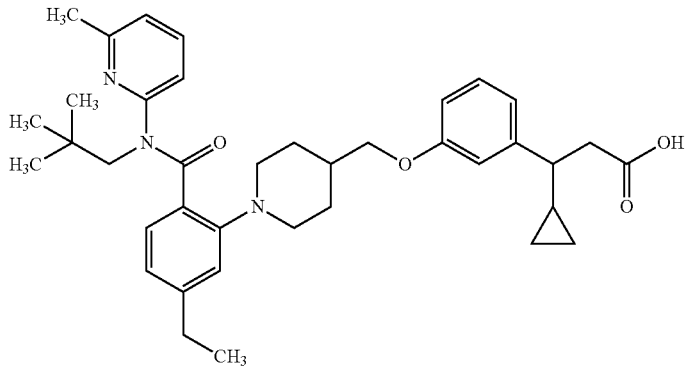 | 3-cyclopropyl-3-(3-((1-(2-((2,2-dimethylpropyl)(6-methylpyridin-2-yl)carbamoyl)-5-ethylphenyl)piperidin-4-yl)methoxy)phenyl)-propanoic acid | 612.3 |

TABLE 2-10-continued

| Ex. No. | IUPAC name | MS |
|---|---|---|
| 56 | 3-cyclopropyl-3-(3-((1-(2-((2,2-dimethylpropyl)(pyridin-2-yl)carbamoyl)-5-ethylphenyl)piperidin-4-yl)methoxy)phenyl)-propanoic acid | 598.4 |
| 57 | 3-cyclopropyl-3-(3-((1-(5-ethyl-2-(methyl(1,3-oxazol-2-yl)carbamoyl)phenyl)-piperidin-4-yl)methoxy)phenyl)-propanoic acid | 532.3 |
| 58 | 3-cyclopropyl-3-(3-((1-(2-(((2,2-dimethylpropyl)sulfonyl)-(methyl)carbamoyl)-5-ethylphenyl)piperidin-4-yl)methoxy)phenyl)-propanoic acid | 599.3 |
| 59 | 3-(3-((1-(6-chloro-3-((2,2-dimethylpropyl)(pyridin-2-yl)carbamoyl)pyridin-2-yl)piperidin-4-yl)methoxy)phenyl)-3-cyclopropylpropanoic acid | 605.3 |

TABLE 2-10-continued

| Ex. No. | structural formula | IUPAC name | MS |
|---|---|---|---|
| 60 | | 3-cyclopropyl-3-(3-((1-(3-((2,2-dimethylpropyl)(pyridin-2-yl)carbamoyl)-6-ethylpyridin-2-yl)piperidin-4-yl)methoxy)phenyl)-propanoic acid | 599.4 |

TABLE 2-11

| Ex. No. | structural formula | IUPAC name | MS |
|---|---|---|---|
| 61 | | 3-cyclopropyl-3-(3-((1-(2-((2-(2,2-dimethylpropanoyl)-hydrazino)carbonyl)-5-methoxyphenyl)piperidin-4-yl)methoxy)-phenyl)propanoic acid | 552.3 |
| 62 | | 3-cyclopropyl-3-(3-((1-(5-methoxy-2-((2-methylpropyl)(pyridin-2-yl)carbamoyl)phenyl)-piperidin-4-yl)methoxy)-phenyl)propanoic acid | 586.4 |

TABLE 2-11-continued

| Ex. No. | structural formula | IUPAC name | MS |
|---|---|---|---|
| 63 | 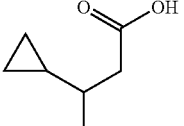 | 3-(3-((1-(2-((cycloheptylmethyl)-carbamoyl)-5-methoxyphenyl)piperidin-4-yl)methoxy)phenyl)-3-cyclopropylpropanoic acid | 563.3 |
| 64 | 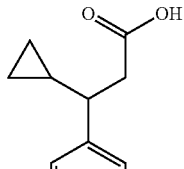 | 3-(3-((1-(2-((2-cyclohexylethyl)-carbamoyl)-5-methoxyphenyl)piperidin-4-yl)methoxy)phenyl)-3-cyclopropylpropanoic acid | 563.3 |
| 65 | 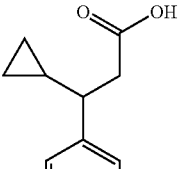 | 3-(3-((1-(2-(((1R)-1-cyclohexylethyl)-carbamoyl)-5-methoxyphenyl)piperidin-4-yl)methoxy)phenyl)-3-cyclopropylpropanoic acid | 563.3 |

TABLE 2-11-continued

| Ex. No. | structural formula | IUPAC name | MS |
|---|---|---|---|
| 66 | 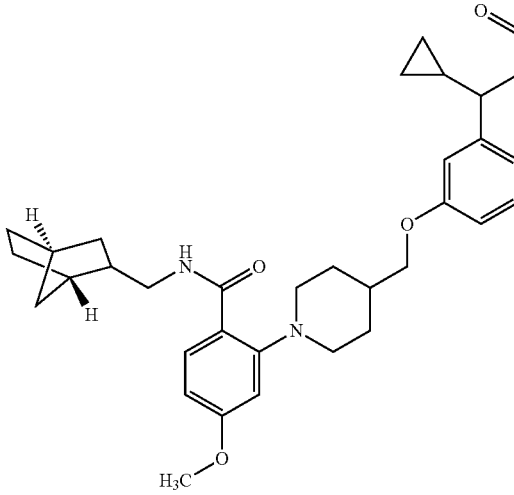 | 3-(3-((1-(2-(((1S,4R)-bicyclo[2.2.1]hept-2-ylmethyl)carbamoyl)-5-methoxyphenyl)piperidin-4-yl)methoxy)phenyl)-3-cyclopropylpropanoic acid | 561.3 |

TABLE 2-12

| Ex. No. | structural formula | IUPAC name | MS |
|---|---|---|---|
| 67 | 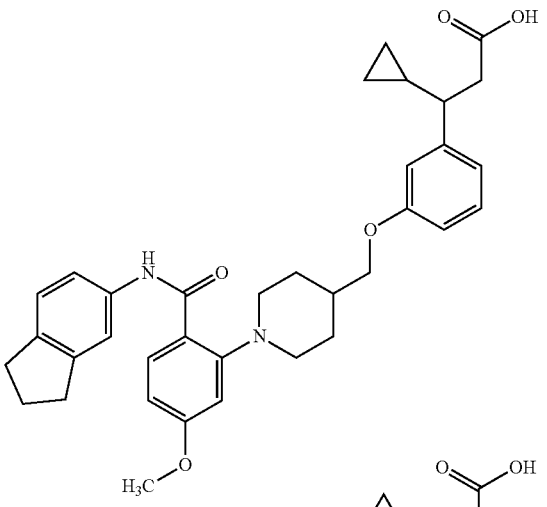 | 3-cyclopropyl-3-(3-((1-(2-(2,3-dihydro-1H-inden-5-ylcarbamoyl)-5-methoxyphenyl)piperidin-4-yl)methoxy)-phenyl)propanoic acid | 569.3 |
| 68 | 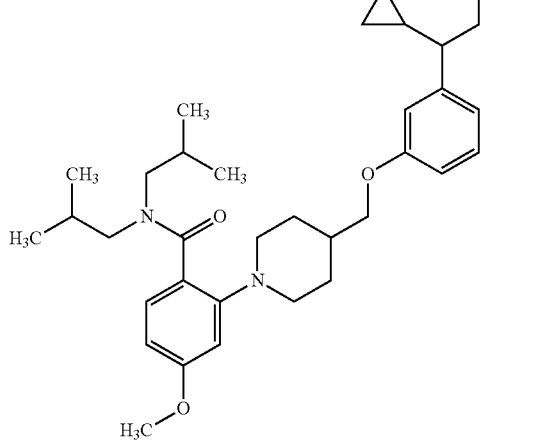 | 3-(3-((1-(2-(bis(2-methylpropyl)carbamoyl)-5-methoxyphenyl)-piperidin-4-yl)methoxy)-phenyl)-3-cyclopropylpropanoic acid | 565.4 |

TABLE 2-12-continued

| Ex. No. | structural formula | IUPAC name | MS |
|---|---|---|---|
| 69 | 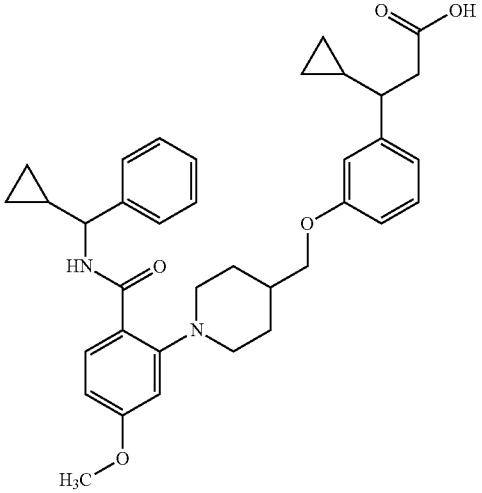 [SMILES: COc1ccc(C(=O)NC(c2ccccc2)C2CC2)c(N2CCC(COc3cccc(C(CC(=O)O)C4CC4)c3)CC2)c1] | 3-cyclopropyl-3-(3-((1-(2-((cyclopropyl(phenyl)-methyl)carbamoyl)-5-methoxyphenyl)piperidin-4-yl)methoxy)phenyl)-propanoic acid | 583.4 |
| 70 | 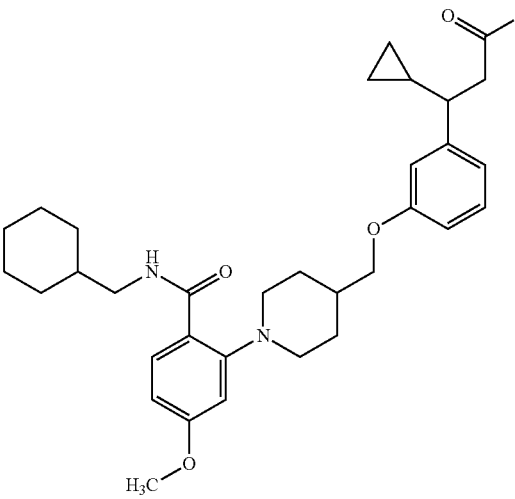 | 3-(3-((1-(2-((cyclohexylmethyl)carba-moyl)-5-methoxyphenyl)piperidin-4-yl)methoxy)phenyl)-3-cyclopropylpropanoic acid | 549.3 |
| 71 | 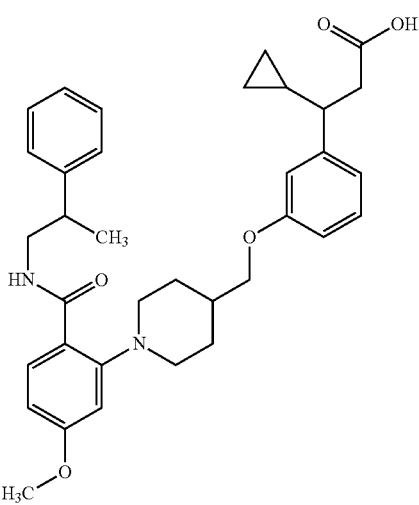 [SMILES: COc1ccc(C(=O)NCC(C)c2ccccc2)c(N2CCC(COc3cccc(C(CC(=O)O)C4CC4)c3)CC2)c1] | 3-cyclopropyl-3-(3-((1-(5-methoxy-2-((2-phenylpropyl)carbamoyl)-phenyl)piperidin-4-yl)methoxy)phenyl)-propanoic acid | 571.4 |

TABLE 2-12-continued

| Ex. No. | structural formula | IUPAC name | MS |
|---|---|---|---|
| 72 | | 3-cyclopropyl-3-(3-((1-(2-(hexyl(methyl)carbamoyl)-5-methoxyphenyl)piperidin-4-yl)methoxy)-phenyl)propanoic acid | 551.4 |

TABLE 2-13

| Ex. No. | structural formula | IUPAC name | MS |
|---|---|---|---|
| 73 | | 3-cyclopropyl-3-(3-((1-(2-((3,3-dimethylbutyl)carbamoyl)-5-methoxyphenyl)piperidin-4-yl)methoxy)-phenyl)propanoic acid | 537.3 |
| 74 | | 3-cyclopropyl-3-(3-((1-(2-(2,3-dihydro-1H-inden-1-ylcarbamoyl)-5-methoxyphenyl)piperidin-4-yl)methoxy)-phenyl)propanoic acid | 569.3 |

TABLE 2-13-continued
| Ex. No. | structural formula | IUPAC name | MS |
|---|---|---|---|
| 75 | 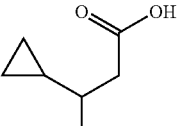 | 3-cyclopropyl-3-(3-((1-(5-methoxy-2-(methyl(3-phenylpropyl)carbamoyl)-phenyl)piperidin-4-yl)-methoxy)phenyl)propanoic acid | 585.3 |
| 76 | 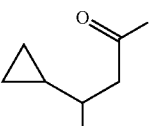 | 3-cyclopropyl-3-(3-((1-(5-methoxy-2-(((1R)-1-phenylethyl)carbamoyl)-phenyl)piperidin-4-yl)methoxy)phenyl)-propanoic acid | 557.3 |
| 77 | 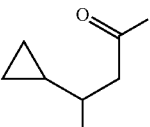 | 3-(3-((1-(2-(benzyl(methyl)-carbamoyl)-5-methoxyphenyl)piperidin-4-yl)methoxy)phenyl)-3-cyclopropylpropanoic acid | 557.3 |

TABLE 2-13-continued

| Ex. No. | structural formula | IUPAC name | MS |
|---|---|---|---|
| 78 | 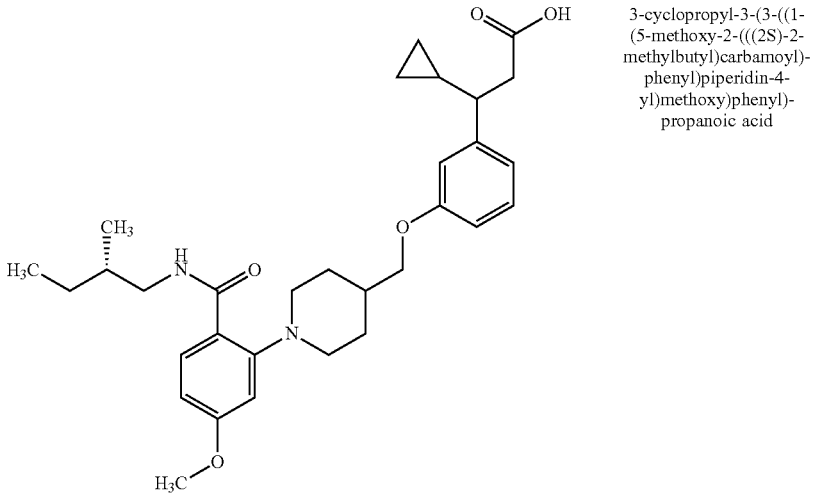 | 3-cyclopropyl-3-(3-((1-(5-methoxy-2-(((2S)-2-methylbutyl)carbamoyl)-phenyl)piperidin-4-yl)methoxy)phenyl)-propanoic acid | 523.3 |

TABLE 2-14

| Ex. No. | structural formula | IUPAC name | MS |
|---|---|---|---|
| 79 | 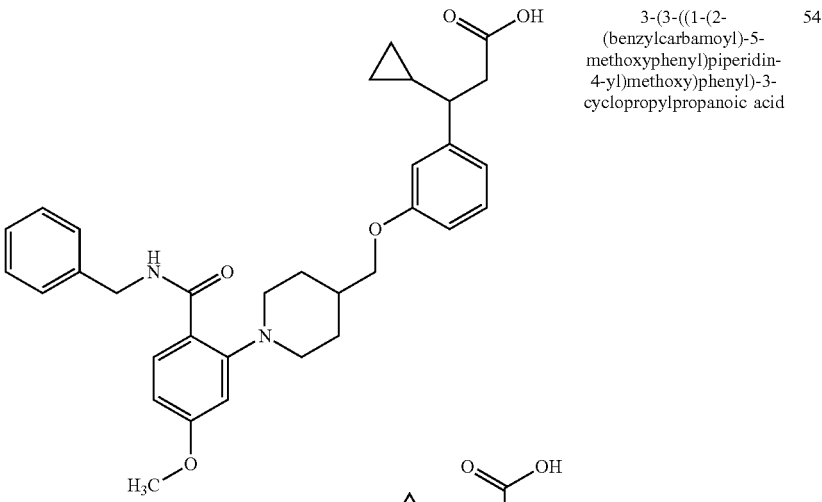 | 3-(3-((1-(2-(benzylcarbamoyl)-5-methoxyphenyl)piperidin-4-yl)methoxy)phenyl)-3-cyclopropylpropanoic acid | 543.3 |
| 80 | 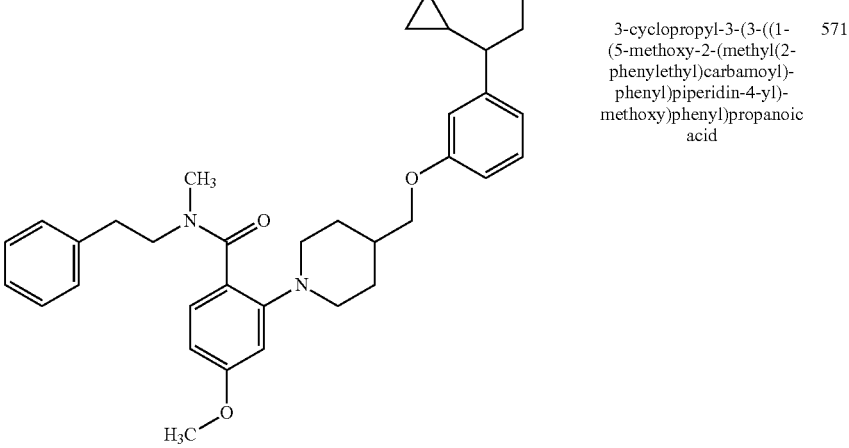 | 3-cyclopropyl-3-(3-((1-(5-methoxy-2-(methyl(2-phenylethyl)carbamoyl)-phenyl)piperidin-4-yl)-methoxy)phenyl)propanoic acid | 571.4 |

TABLE 2-14-continued
| Ex. No. | structural formula | IUPAC name | MS |
|---|---|---|---|
| 81 | 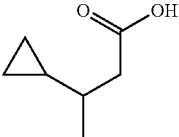 | 3-cyclopropyl-3-(3-((1-(5-methoxy-2-(pentan-3-ylcarbamoyl)phenyl)-piperidin-4-yl)methoxy)phenyl)-propanoic acid | 523.3 |
| 82 | 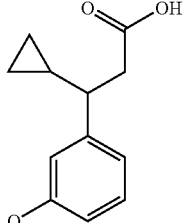 | 3-(3-((1-(2-(cyclohexyl(methyl)-carbamoyl)-5-methoxyphenyl)piperidin-4-yl)methoxy)phenyl)-3-cyclopropylpropanoic acid | 549.3 |
| 83 | 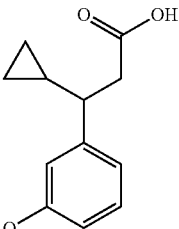 | 3-(3-((1-(2-(cyclopentyl(ethyl)-carbamoyl)-5-methoxyphenyl)piperidin-4-yl)methoxy)phenyl)-3-cyclopropylpropanoic acid | 549.3 |

TABLE 2-14-continued

| Ex. No. | structural formula | IUPAC name | MS |
|---|---|---|---|
| 84 | 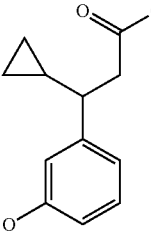 | 3-cyclopropyl-3-(3-((1-(5-methoxy-2-(phenylcarbamoyl)phenyl)-piperidin-4-yl)methoxy)phenyl)-propanoic acid | 529.2 |

TABLE 2-15

| Ex. No. | structural formula | IUPAC name | MS |
|---|---|---|---|
| 85 | 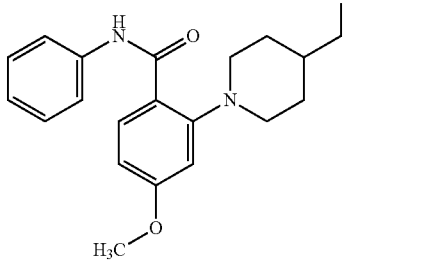 | 3-cyclopropyl-3-(3-((1-(5-methoxy-2-((3-methylbutan-2-yl)carbamoyl)phenyl)-piperidin-4-yl)-methoxy)phenyl)propanoic acid | 523.3 |
| 86 | 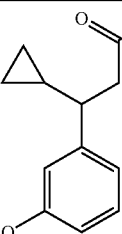 | 3-cyclopropyl-3-(3-((1-(5-methoxy-2-((2-methylphenyl)carbamoyl)-phenyl)piperidin-4-yl)methoxy)phenyl)-propanoic acid | 543.3 |

TABLE 2-15-continued
| Ex. No. | structural formula | IUPAC name | MS |
|---|---|---|---|
| 87 | 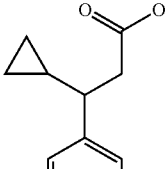 | 3-cyclopropyl-3-(3-((1-(5-methoxy-2-(methyl(phenyl)-carbamoyl)phenyl)-piperidin-4-yl)methoxy)phenyl)-propanoic acid | 543.3 |
| 88 | 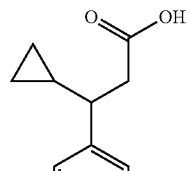 | 3-(3-((1-(2-((cyclobutylmethyl)-carbamoyl)-5-methoxyphenyl)piperidin-4-yl)methoxy)phenyl)-3-cyclopropylpropanoic acid | 521.3 |
| 89 | 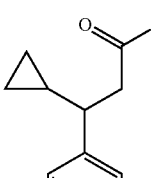 | 3-cyclopropyl-3-(3-((1-(2-((2-fluorophenyl)carbamoyl)-5-methoxyphenyl)-piperidin-4-yl)-methoxy)phenyl)propanoic acid | 547.2 |

TABLE 2-15-continued

| Ex. No. | structural formula | IUPAC name | MS |
|---|---|---|---|
| 90 | 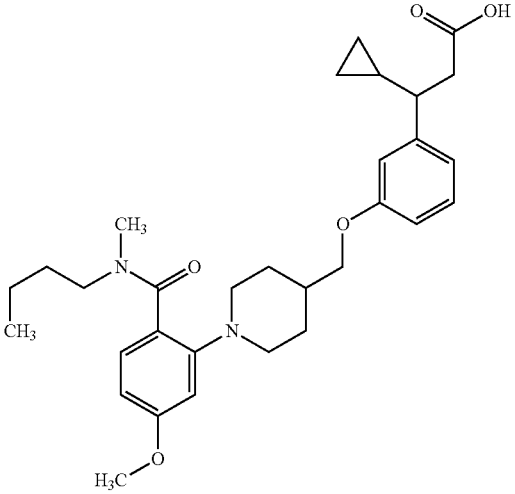 [SMILES: CCCCN(C)C(=O)c1ccc(OC)cc1N1CCC(COc2cccc(C(CC(=O)O)C3CC3)c2)CC1] | 3-(3-((1-(2-(butyl(methyl)carbamoyl)-5-methoxyphenyl)piperidin-4-yl)methoxy)phenyl)-3-cyclopropylpropanoic acid | 523.3 |

TABLE 2-16

| Ex. No. | structural formula | IUPAC name | MS |
|---|---|---|---|
| 91 | 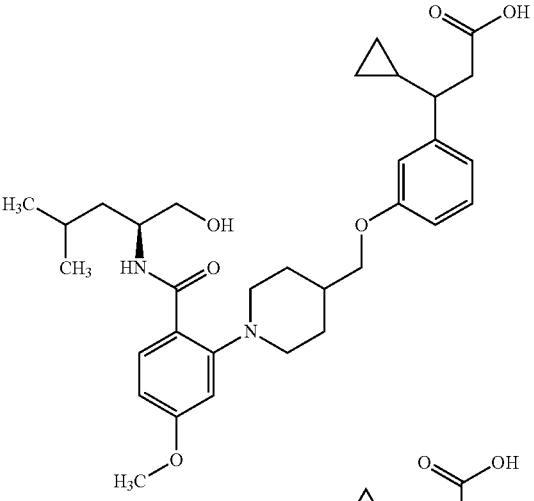 | 3-cyclopropyl-3-(3-((1-(2-(((2S)-1-hydroxy-4-methylpentan-2-yl)carbamoyl)-5-methoxyphenyl)piperidin-4-yl)methoxy)-phenyl)propanoic acid | 553.3 |
| 92 | 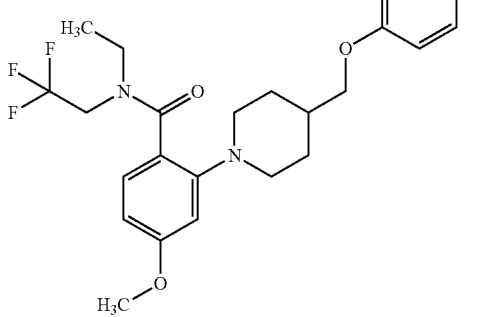 | 3-cyclopropyl-3-(3-((1-(2-(ethyl(2,2,2-trifluoroethyl)-carbamoyl)-5-methoxyphenyl)piperidin-4-yl)methoxy)phenyl)-propanoic acid | 563.3 |

TABLE 2-16-continued

| Ex. No. | structural formula | IUPAC name | MS |
|---|---|---|---|
| 93 | 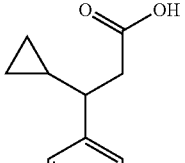 | 3-cyclopropyl-3-(3-((1-(5-methoxy-2-((1-methoxybutan-2-yl)carbamoyl)phenyl)-piperidin-4-yl)methoxy)phenyl)-propanoic acid | 539.3 |
| 94 | 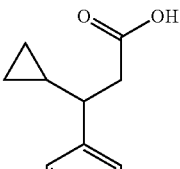 | 3-cyclopropyl-3-(3-((1-(2-(ethyl(pyridin-4-ylmethyl)carbamoyl)-5-methoxyphenyl)piperidin-4-yl)methoxy)phenyl)-propanoic acid | 572.4 |
| 95 | 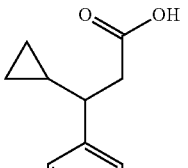 | 3-cyclopropyl-3-(3-((1-(5-methoxy-2-(piperidin-1-ylcarbonyl)phenyl)-piperidin-4-yl)methoxy)phenyl)-propanoic acid | 521.3 |

TABLE 2-16-continued

| Ex. No. | structural formula | IUPAC name | MS |
|---|---|---|---|
| 96 | 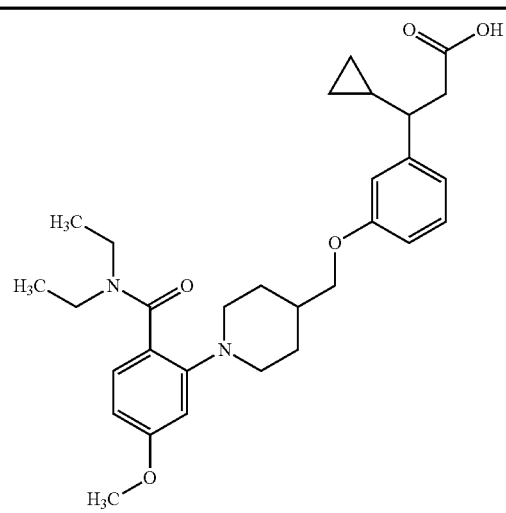 | 3-cyclopropyl-3-(3-((1-(2-(diethylcarbamoyl)-5-methoxyphenyl)piperidin-4-yl)methoxy)phenyl)-propanoic acid | 509.3 |

TABLE 2-17

| Ex. No. | structural formula | IUPAC name | MS |
|---|---|---|---|
| 97 | | 3-cyclopropyl-3-(3-((1-(5-methoxy-2-(tetrahydro-2H-thiopyran-4-ylcarbamoyl)phenyl)-piperidin-4-yl)methoxy)phenyl)-propanoic acid | 553.3 |
| 98 | | 3-cyclopropyl-3-(3-((1-(2-(((2S)-1-hydroxy-3-methylbutan-2-yl)carbamoyl)-5-methoxyphenyl)piperidin-4-yl)methoxy)phenyl)-propanoic acid | 539.3 |

TABLE 2-17-continued

| Ex. No. | structural formula | IUPAC name | MS |
|---|---|---|---|
| 99 | | 3-cyclopropyl-3-(3-((1-(2-((3-hydroxy-2,2-dimethylpropyl)-carbamoyl)-5-methoxyphenyl)piperidin-4-yl)methoxy)-phenyl)propanoic acid | 539.3 |
| 100 | | 3-cyclopropyl-3-(3-((1-(5-methoxy-2-((pyridin-4-ylmethyl)carbamoyl)-phenyl)piperidin-4-yl)methoxy)phenyl)-propanoic acid | 544.2 |
| 101 | | 3-cyclopropyl-3-(3-((1-(5-methoxy-2-(pyrimidin-5-ylcarbamoyl)phenyl)-piperidin-4-yl)methoxy)phenyl)-propanoic acid | 531.2 |

TABLE 2-17-continued

| Ex. No. | structural formula | IUPAC name | MS |
|---|---|---|---|
| 102 | 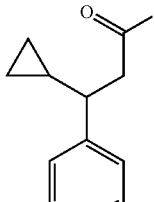 | 3-cyclopropyl-3-(3-((1-(5-methoxy-2-(methyl(pyridin-2-yl)carbamoyl)phenyl)-piperidin-4-yl)methoxy)phenyl)-propanoic acid | 544.2 |

TABLE 2-18

| Ex. No. | structural formula | IUPAC name | MS |
|---|---|---|---|
| 103 | 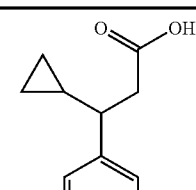 | 3-(3-((1-(2-((2-cyanoethyl)(methyl)-carbamoyl)-5-methoxyphenyl)piperidin-4-yl)methoxy)phenyl)-3-cyclopropylpropanoic acid | 520.3 |
| 104 | 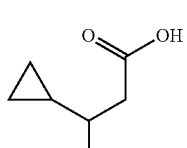 | 3-cyclopropyl-3-(3-((1-(2-((2,2-dimethylpropyl)(methyl)-carbamoyl)-5-methoxyphenyl)piperidin-4-yl)methoxy)phenyl)-propanoic acid | 537.3 |

TABLE 2-18-continued

| Ex. No. | structural formula | IUPAC name | MS |
|---|---|---|---|
| 105 | | 3-cyclopropyl-3-(3-((1-(5-methoxy-2-((4-methoxypiperidin-1-yl)carbonyl)phenyl)-piperidin-4-yl)methoxy)phenyl)-propanoic acid | 551.3 |
| 106 | | 3-cyclopropyl-3-(3-((1-(5-methoxy-2-((pyrimidin-2-ylmethyl)carbamoyl)-phenyl)piperidin-4-yl)-methoxy)phenyl)propanoic acid | 545.2 |
| 107 | | 3-cyclopropyl-3-(3-((1-(5-methoxy-2-((2-(piperidin-1-yl)ethyl)-carbamoyl)phenyl)-piperidin-4-yl)-methoxy)phenyl)propanoic acid | 564.3 |

TABLE 2-18-continued

| Ex. No. | structural formula | IUPAC name | MS |
|---|---|---|---|
| 108 | 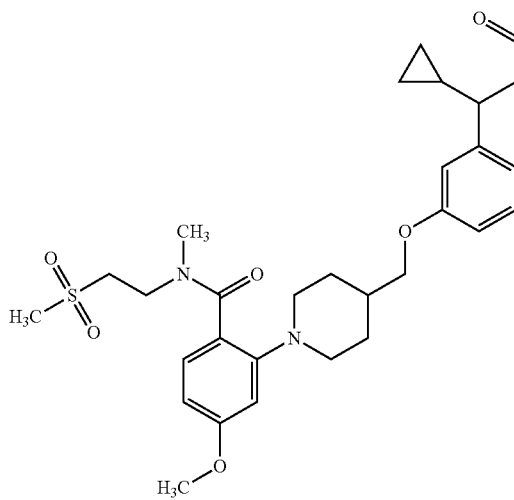 | 3-cyclopropyl-3-(3-((1-(5-methoxy-2-(methyl(2-(methylsulfonyl)ethyl)-carbamoyl)phenyl)-piperidin-4-yl)-methoxy)phenyl)propanoic acid | 573.3 |

TABLE 2-19

| Ex. No. | structural formula | IUPAC name | MS |
|---|---|---|---|
| 109 | 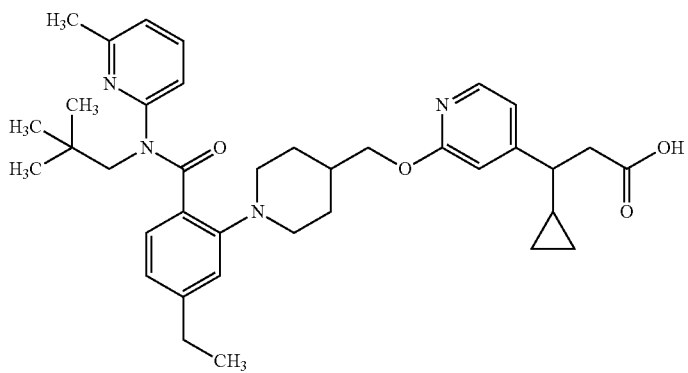 [SMILES: CCc1ccc(C(=O)N(CC(C)(C)C)c2cccc(C)n2)c(N2CCC(COc3cc(C(CC(=O)O)C4CC4)ccn3)CC2)c1] | 3-cyclopropyl-3-(2-((1-(2-((2,2-dimethylpropyl)(6-methylpyridin-2-yl)carbamoyl)-5-ethylphenyl)piperidin-4-yl)methoxy)pyridin-4-yl)propanoic acid | 613.4 |
| 110 | 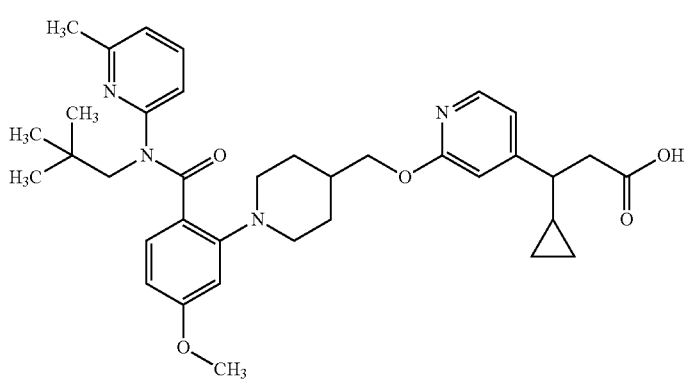 | 3-cyclopropyl-3-(2-((1-(2-((2,2-dimethylpropyl)(6-methylpyridin-2-yl)carbamoyl)-5-methoxyphenyl)piperidin-4-yl)methoxy)pyridin-4-yl)propanoic acid | 615.3 |

TABLE 2-19-continued

| Ex. No. | structural formula | IUPAC name | MS |
|---|---|---|---|
| 111 | 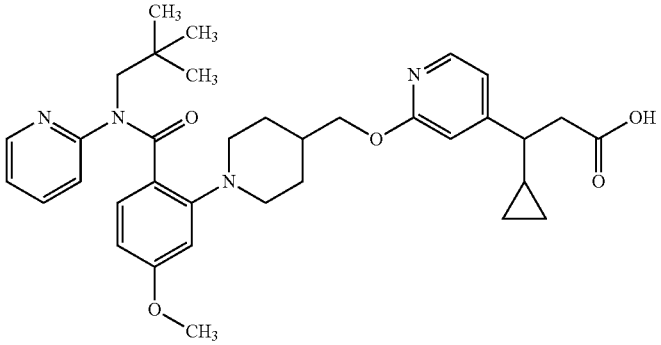 [SMILES: COc1ccc(C(=O)N(CC(C)(C)C)c2ccccn2)c(N2CCC(COc3cc(C(CC(=O)O)C4CC4)ccn3)CC2)c1] | 3-cyclopropyl-3-(2-((1-(2-((2,2-dimethylpropyl)(pyridin-2-yl)carbamoyl)-5-methoxyphenyl)piperidin-4-yl)methoxy)pyridin-4-yl)propanoic acid | 601.3 |
| 112 | 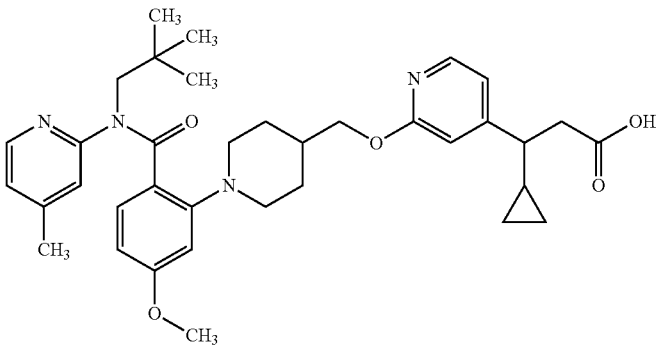 [SMILES: COc1ccc(C(=O)N(CC(C)(C)C)c2cc(C)ccn2)c(N2CCC(COc3cc(C(CC(=O)O)C4CC4)ccn3)CC2)c1] | 3-cyclopropyl-3-(2-((1-(2-((2,2-dimethylpropyl)(4-methylpyridin-2-yl)carbamoyl)-5-methoxyphenyl)piperidin-4-yl)methoxy)pyridin-4-yl)propanoic acid | 615.3 |
| 113 | 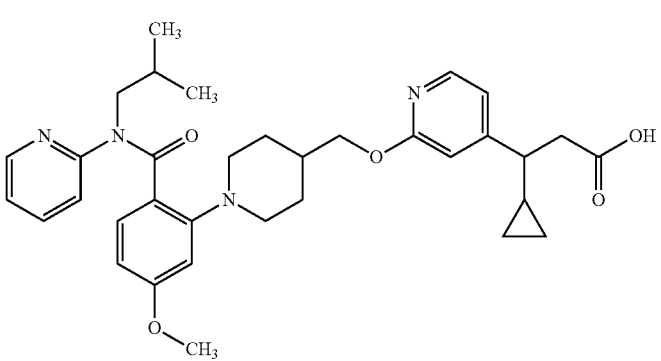 [SMILES: COc1ccc(C(=O)N(CC(C)C)c2ccccn2)c(N2CCC(COc3cc(C(CC(=O)O)C4CC4)ccn3)CC2)c1] | 3-cyclopropyl-3-(2-((1-(5-methoxy-2-((2-methylpropyl)(pyridin-2-yl)carbamoyl)phenyl)-piperidin-4-yl)methoxy)pyridin-4-yl)propanoic acid | 587.3 |
| 114 | 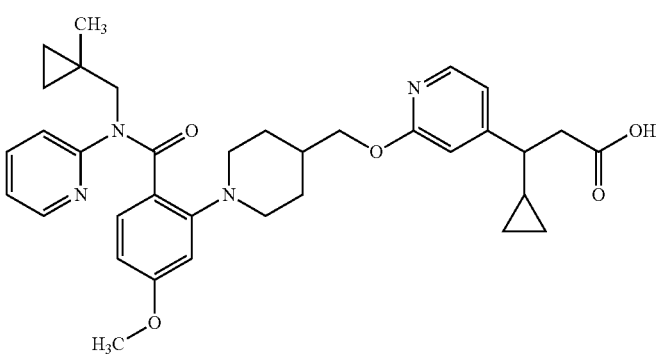 [SMILES: COc1ccc(C(=O)N(CC2(C)CC2)c2ccccn2)c(N2CCC(COc3cc(C(CC(=O)O)C4CC4)ccn3)CC2)c1] | 3-cyclopropyl-3-(2-((1-(5-methoxy-2-(((1-methylcyclopropyl)methyl)-(pyridin-2-yl)-carbamoyl)phenyl)-piperidin-4-yl)methoxy)pyridin-4-yl)propanoic acid | 599.3 |

TABLE 2-20

| Ex. No. | structural formula | IUPAC name | MS |
|---|---|---|---|
| 115 | 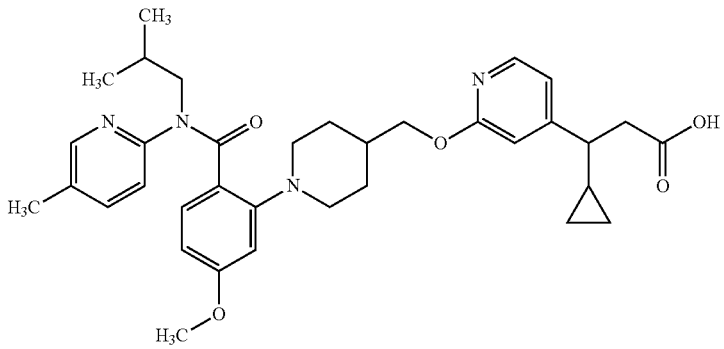 [SMILES: COc1ccc(C(=O)N(CC(C)C)c2ccc(C)cn2)c(N2CCC(COc3cc(C(CC(=O)O)C4CC4)ccn3)CC2)c1] | 3-cyclopropyl-3-(2-((1-(5-methoxy-2-((2-methylpropyl)(5-methylpyridin-2-yl)carbamoyl)phenyl)-piperidin-4-yl)methoxy)pyridin-4-yl)propanoic acid | 601.3 |
| 116 | 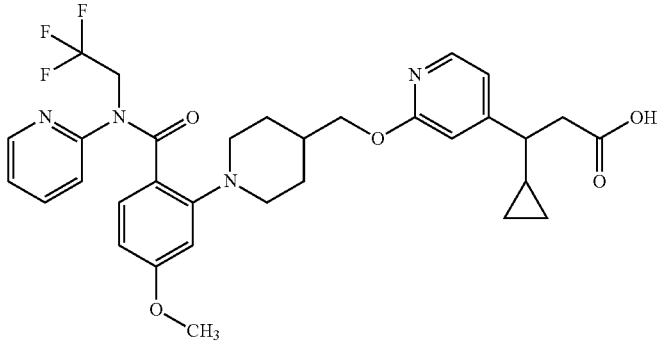 | 3-cyclopropyl-3-(2-((1-(5-methoxy-2-(pyridin-2-yl(2,2,2-trifluoroethyl)-carbamoyl)phenyl)-piperidin-4-yl)methoxy)pyridin-4-yl)propanoic acid | 613.2 |
| 117 | 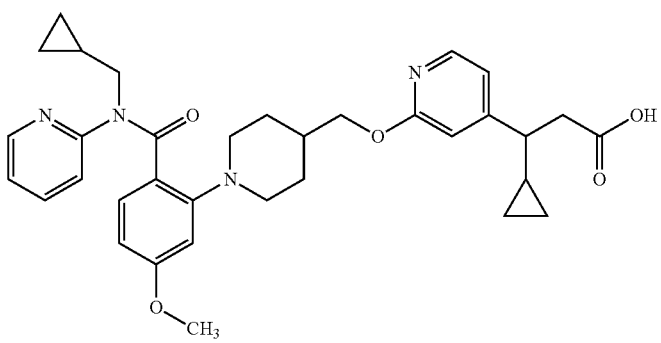 | 3-cyclopropyl-3-(2-((1-(2-((cyclopropylmethyl)-(pyridin-2-yl)carbamoyl)-5-methoxyphenyl)-piperidin-4-yl)methoxy)pyridin-4-yl)propanoic acid | 585.3 |
| 118 | 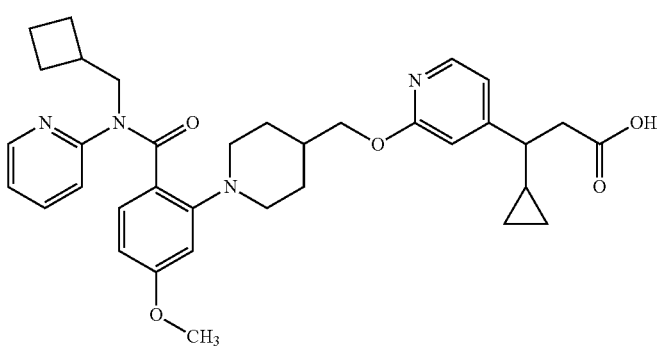 [SMILES: COc1ccc(C(=O)N(CC2CCC2)c2ccccn2)c(N2CCC(COc3cc(C(CC(=O)O)C4CC4)ccn3)CC2)c1] | 3-(2-((1-(2-((cyclobutylmethyl)-(pyridin-2-yl)carbamoyl)-5-methoxyphenyl)-piperidin-4-yl)methoxy)-pyridin-4-yl)-3-cyclopropylpropanoic acid | 599.3 |

TABLE 2-20-continued

| Ex. No. | structural formula | IUPAC name | MS |
|---|---|---|---|
| 119 | 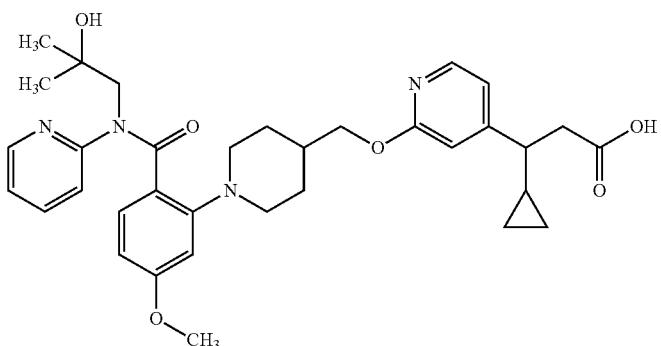 | 3-cyclopropyl-3-(2-((1-(2-((2-hydroxy-2-methylpropyl)(pyridin-2-yl)carbamoyl)-5-methoxyphenyl)piperidin-4-yl)methoxy)pyridin-4-yl)propanoic acid | 603.3 |
| 120 | 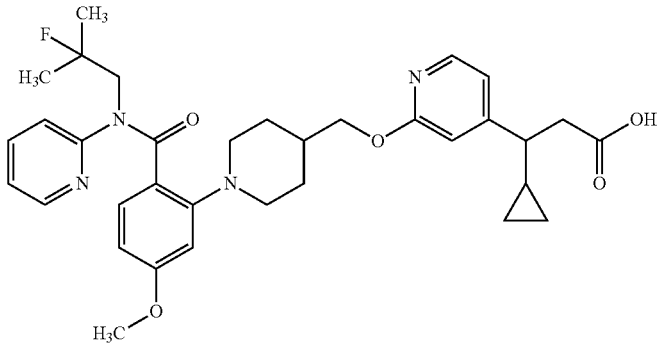 [SMILES: COc1ccc(C(=O)N(CC(C)(C)F)c2ccccn2)c(N2CCC(COc3cc(C(CC(=O)O)C4CC4)ccn3)CC2)c1] | 3-cyclopropyl-3-(2-((1-(2-((2-fluoro-2-methylpropyl)(pyridin-2-yl)carbamoyl)-5-methoxyphenyl)piperidin-4-yl)methoxy)pyridin-4-yl)propanoic acid | 605.3 |

TABLE 2-21

| Ex. No. | structural formula | IUPAC name | MS |
|---|---|---|---|
| 121 | 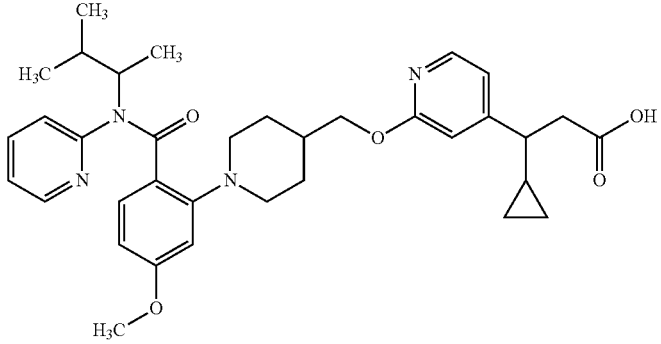 [SMILES: COc1ccc(C(=O)N(c2ccccn2)C(C)C(C)C)c(N2CCC(COc3cc(C(CC(=O)O)C4CC4)ccn3)CC2)c1] | 3-cyclopropyl-3-(2-((1-(5-methoxy-2-((3-methylbutan-2-yl)(pyridin-2-yl)carbamoyl)phenyl)-piperidin-4-yl)methoxy)pyridin-4-yl)propanoic acid | 601.3 |
| 122 | 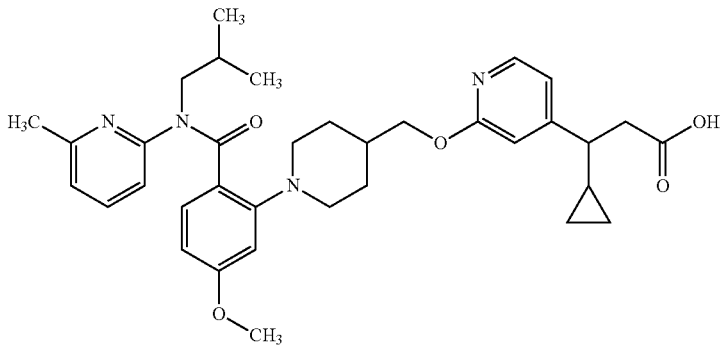 | 3-cyclopropyl-3-(2-((1-(5-methoxy-2-((2-methylpropyl)(6-methylpyridin-2-yl)carbamoyl)phenyl)-piperidin-4-yl)methoxy)pyridin-4-yl)propanoic acid | 601.3 |

TABLE 2-21-continued

| Ex. No. | structural formula | IUPAC name | MS |
|---|---|---|---|
| 123 | 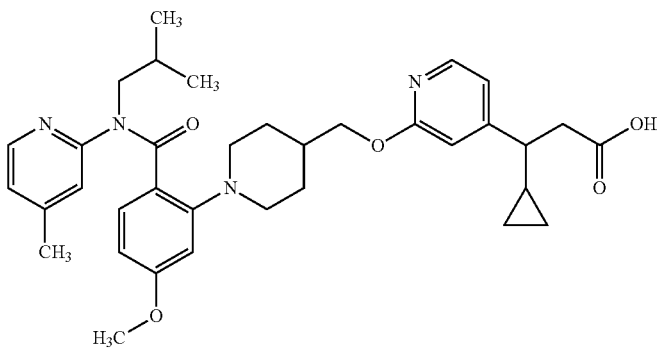 [SMILES: COc1ccc(C(=O)N(CC(C)C)c2cc(C)ccn2)c(N2CCC(COc3cc(C(CC(=O)O)C4CC4)ccn3)CC2)c1] | 3-cyclopropyl-3-(2-((1-(5-methoxy-2-((2-methylpropyl)(4-methylpyridin-2-yl)carbamoyl)phenyl)-piperidin-4-yl)methoxy)pyridin-4-yl)propanoic acid | 601.3 |
| 124 | 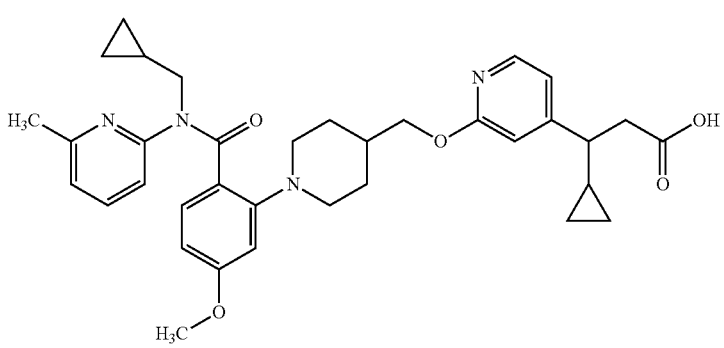 [SMILES: COc1ccc(C(=O)N(CC2CC2)c2cccc(C)n2)c(N2CCC(COc3cc(C(CC(=O)O)C4CC4)ccn3)CC2)c1] | 3-cyclopropyl-3-(2-((1-(2-((cyclopropylmethyl)-(6-methylpyridin-2-yl)carbamoyl)-5-methoxyphenyl)piperidin-4-yl)methoxy)pyridin-4-yl)propanoic acid | 599.3 |
| 125 | 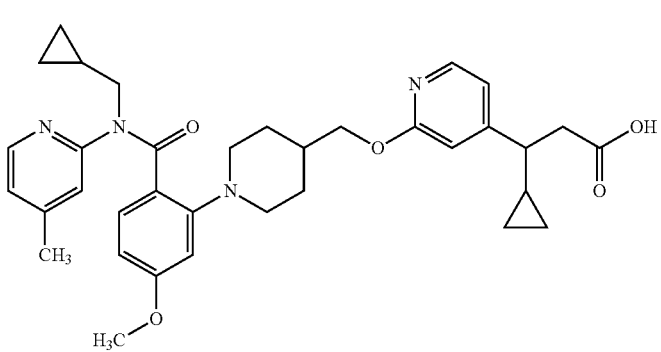 [SMILES: COc1ccc(C(=O)N(CC2CC2)c2cc(C)ccn2)c(N2CCC(COc3cc(C(CC(=O)O)C4CC4)ccn3)CC2)c1] | 3-cyclopropyl-3-(2-((1-(2-((cyclopropylmethyl)-(4-methylpyridin-2-yl)carbamoyl)-5-methoxyphenyl)piperidin-4-yl)methoxy)pyridin-4-yl)propanoic acid | 599.3 |
| 126 | 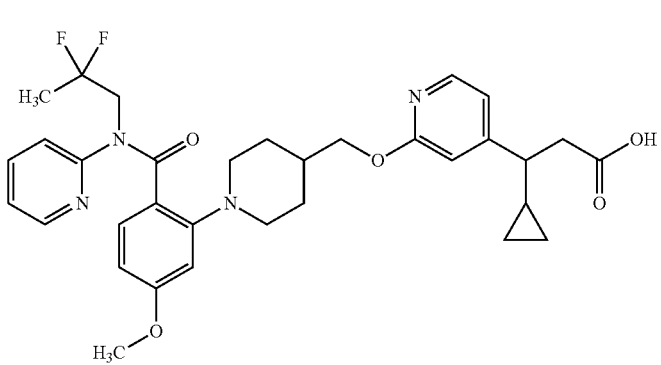 [SMILES: COc1ccc(C(=O)N(CC(C)(F)F)c2ccccn2)c(N2CCC(COc3cc(C(CC(=O)O)C4CC4)ccn3)CC2)c1] | 3-cyclopropyl-3-(2-((1-(2-((2,2-difluoropropyl)(pyridin-2-yl)carbamoyl)-5-methoxyphenyl)piperidin-4-yl)methoxy)pyridin-4-yl)propanoic acid | 609.2 |

TABLE 2-22

| Ex. No. | structural formula | IUPAC name | MS |
|---|---|---|---|
| 127 | | 3-cyclopropyl-3-(2-((1-(5-methoxy-2-((2-methylpyridin-4-yl)(2-methylpropyl)carbamoyl)-phenyl)piperidin-4-yl)methoxy)pyridin-4-yl)propanoic acid | 617.3 |
| 128 | | 3-cyclopropyl-3-(2-((1-(5-methoxy-2-((6-methoxypyridin-2-yl)(2-methylpropyl)carbamoyl)-phenyl)piperidin-4-yl)methoxy)pyridin-4-yl)propanoic acid | 617.3 |
| 129 | | 3-cyclopropyl-3-(2-((1-(5-methoxy-2-((2,2,3,3,3-pentafluoropropyl)-carbamoyl)phenyl)-piperidin-4-yl)methoxy)pyridin-4-yl)propanoic acid | 586.2 |
| 130 | | 3-cyclopropyl-3-(2-((1-(5-methoxy-2-(methyl(2,2,3,3,3-pentafluoropropyl)-carbamoyl)phenyl)-piperidin-4-yl)methoxy)pyridin-4-yl)propanoic acid | 600.2 |

TABLE 2-22-continued

| Ex. No. | structural formula | IUPAC name | MS |
|---|---|---|---|
| 131 | | 3-cyclopropyl-3-(2-((1-(5-methoxy-2-((2-methoxy-2-methylpropyl)(pyridin-2-yl)carbamoyl)-phenyl)piperidin-4-yl)methoxy)pyridin-4-yl)propanoic acid | 617.3 |
| 132 | | 3-(2-((1-(2-((3-cyanophenyl)(2-methylpropyl)carbamoyl)-5-methoxyphenyl)piperidin-4-yl)methoxy)pyridin-4-yl)-3-cyclopropylpropanoic acid | 611.2 |

TABLE 2-23

| Ex. No. | structural formula | IUPAC name | MS |
|---|---|---|---|
| 133 | | 3-cyclopropyl-3-(2-((1-(5-methoxy-2-((2-methylpropyl)(phenyl)-carbamoyl)phenyl)-piperidin-4-yl)methoxy)pyridin-4-yl)propanoic acid | 586.3 |

TABLE 2-23-continued

| Ex. No. | structural formula | IUPAC name | MS |
|---|---|---|---|
| 134 | | 3-(2-((1-(2-((2-cyano-2-methylpropyl)(pyridin-2-yl)carbamoyl)-5-methoxyphenyl)piperidin-4-yl)methoxy)pyridin-4-yl)-3-cyclopropylpropanoic acid | 612.3 |
| 135 | | 3-cyclopropyl-3-(2-((1-(5-methoxy-2-((4-methoxypyridin-2-yl)(2-methylpropyl)carbamoyl)-phenyl)piperidin-4-yl)methoxy)pyridin-4-yl)propanoic acid | 617.3 |
| 136 | | 3-cyclopropyl-3-(2-((1-(5-methoxy-2-((2-methoxypyridin-3-yl)(2-methylpropyl)carbamoyl)-phenyl)piperidin-4-yl)methoxy)pyridin-4-yl)propanoic acid | 617.3 |
| 137 | | 3-cyclopropyl-3-(2-((1-(2-((2,2-difluoroethyl)(pyridin-2-yl)carbamoyl)-5-methoxyphenyl)piperidin-4-yl)methoxy)pyridin-4-yl)propanoic acid | 595.2 |

TABLE 2-23-continued

| Ex. No. | structural formula | IUPAC name | MS |
|---|---|---|---|
| 138 | | 3-cyclopropyl-3-(2-((1-(5-methoxy-2-(pyridin-2-yl(2,2,3,3-tetrafluoropropyl)-carbamoyl)phenyl)-piperidin-4-yl)methoxy)pyridin-4-yl)propanoic acid | 645.3 |

TABLE 2-24

| Ex. No. | structural formula | IUPAC name | MS |
|---|---|---|---|
| 139 | | 3-cyclopropyl-3-(2-((1-(2-(((2,2-sifluorocyclopropyl)-methyl)(pyridin-2-yl)carbamoyl)-5-methoxyphenyl)piperidin-4-yl)methoxy)pyridin-4-yl)propanoic acid | 621.4 |
| 140 | | 3-cyclopropyl-3-(2-((1-(5-methoxy-2-((6-methoxypyridin-3-yl)(2-methylpropyl)carbamoyl)-phenyl)piperidin-4-yl)methoxy)pyridin-4-yl)propanoic acid | 617.3 |
| 141 | | 3-cyclopropyl-3-(2-((1-(2-((cyclopropylmethyl)-(pyridin-2-yl)carbamoyl)-5-methoxyphenyl)piperidin-4-yl)methoxy)pyridin-4-yl)propanoic acid | 585.3 |

TABLE 2-24-continued

| Ex. No. | structural formula | IUPAC name | MS |
|---|---|---|---|
| 142 | | 3-cyclopropyl-3-(2-((1-(2-((cyclopropylmethyl)-(pyridin-2-yl)carbamoyl)-5-methoxyphenyl)piperidin-4-yl)methoxy)pyridin-4-yl)propanoic acid | 585.3 |
| 143 | | 3-cyclopropyl-3-(2-((1-(5-methoxy-2-((6-methylpyridin-2-yl)(2,2,2-trifluoroethyl)-carbamoyl)phenyl)-piperidin-4-yl)methoxy)pyridin-4-yl)propanoic acid | 627.2 |
| 144 | | 3-cyclopropyl-3-(2-((1-(2-(((1-fluorocyclo-propyl)methyl)(pyridin-2-yl)carbamoyl)-5-methoxyphenyl)piperidin-4-yl)methoxy)pyridin-4-yl)propanoic acid | 603.3 |

TABLE 2-25

| Ex. No. | structural formula | IUPAC name | MS |
|---|---|---|---|
| 145 | | 3-cyclopropyl-3-(2-((1-(5-methoxy-2-((2-methylbutan-2-yl)(pyridin-2-yl)carbamoyl)phenyl)-piperidin-4-yl)methoxy)pyridin-4-yl)propanoic acid | 601.3 |

TABLE 2-25-continued

| Ex. No. | structural formula | IUPAC name | MS |
|---|---|---|---|
| 146 | 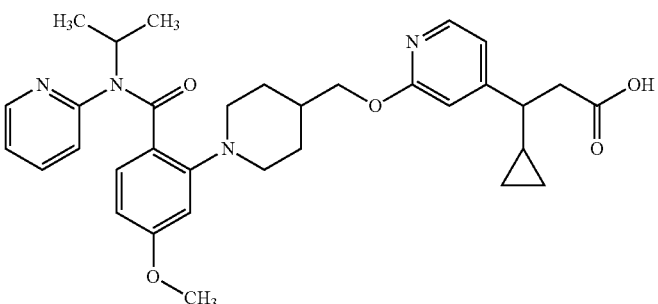 | 3-cyclopropyl-3-(2-((1-(5-methoxy-2-(propan-2-yl(pyridin-2-yl)carbamoyl)phenyl)-piperidin-4-yl)methoxy)pyridin-4-yl)propanoic acid | 573.4 |
| 147 | 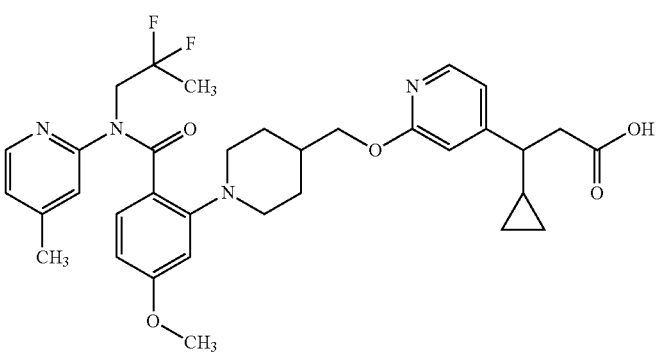 [SMILES: COc1ccc(C(=O)N(CC(C)(F)F)c2cc(C)ccn2)c(N2CCC(COc3cc(C(CC(=O)O)C4CC4)ccn3)CC2)c1] | 3-cyclopropyl-3-(2-((1-(2-((2,2-difluoropropyl)-(4-methylpyridin-2-yl)carbamoyl)-5-methoxyphenyl)piperidin-4-yl)methoxy)pyridin-4-yl)propanoic acid | 623.3 |
| 148 | 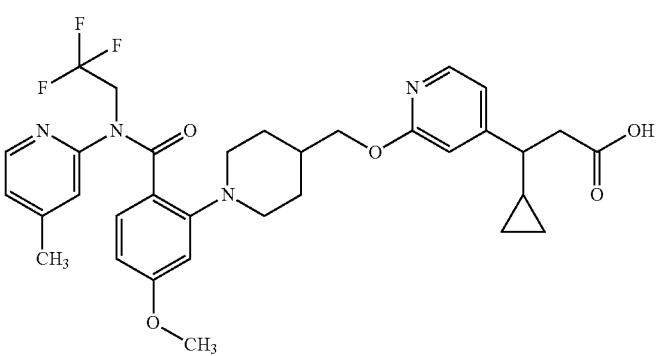 [SMILES: COc1ccc(C(=O)N(CC(F)(F)F)c2cc(C)ccn2)c(N2CCC(COc3cc(C(CC(=O)O)C4CC4)ccn3)CC2)c1] | 3-cyclopropyl-3-(2-((1-(5-methoxy-2-((4-methylpyridin-2-yl)-(2,2,2-trifluoroethyl)-carbamoyl)phenyl)-piperidin-4-yl)methoxy)pyridin-4-yl)propanoic acid | 627.2 |
| 149 | 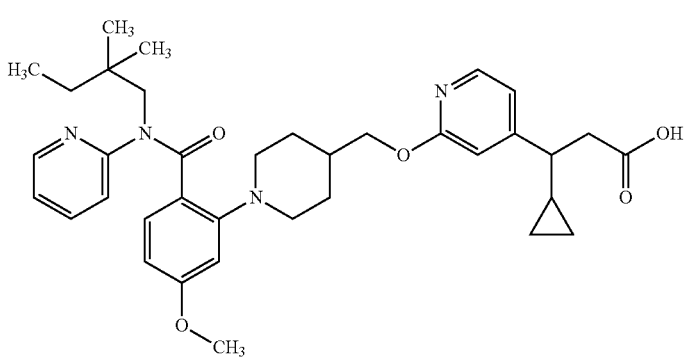 [SMILES: CCC(C)(C)CN(C(=O)c1ccc(OC)cc1N1CCC(COc2cc(C(CC(=O)O)C3CC3)ccn2)CC1)c1ccccn1] | 3-cyclopropyl-3-(2-((1-(2-((2,2-dimethylbutyl)(pyridin-2-yl)carbamoyl)-5-methoxyphenyl)piperidin-4-yl)methoxy)pyridin-4-yl)propanoic acid | 615.3 |

TABLE 2-25-continued

| Ex. No. | structural formula | IUPAC name | MS |
|---|---|---|---|
| 150 | 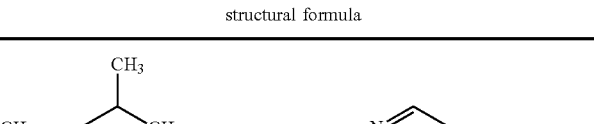 | 3-cyclopropyl-3-(2-((1-(5-methoxy-2-((2-methylpropyl)(3-methylpyridin-2-yl)carbamoyl)phenyl)-piperidin-4-yl)methoxy)pyridin-4-yl)propanoic acid | 601.3 |

TABLE 2-26

| Ex. No. | structural formula | IUPAC name | MS |
|---|---|---|---|
| 151 | | 3-(2-((1-(2-(cyclobutyl(pyridin-2-yl)carbamoyl)-5-methoxyphenyl)piperidin-4-yl)methoxy)pyridin-4-yl)-3-cyclopropylpropanoic acid | 585.3 |
| 152 | | 3-cyclopropyl-3-(2-((1-(2-((2-fluoro-2-methylpropyl)(6-methylpyridin-2-yl)carbamoyl)-5-methoxyphenyl)piperidin-4-yl)methoxy)pyridin-4-yl)propanoic acid | 619.4 |
| 153 | | 3-cyclopropyl-3-(2-((1-(2-((2-fluoro-2-methylpropyl)(4-methylpyridin-2-yl)carbamoyl)-5-methoxyphenyl)piperidin-4-yl)methoxy)pyridin-4-yl)propanoic acid | 619.3 |

TABLE 2-26-continued

| Ex. No. | structural formula | IUPAC name | MS |
|---|---|---|---|
| 154 | | 3-cyclopropyl-3-(2-((1-(2-(((1-fluorocyclobutyl)-methyl)(pyridin-2-yl)carbamoyl)-5-methoxyphenyl)piperidin-4-yl)methoxy)pyridin-4-yl)propanoic acid | 617.2 |
| 155 | | 3-cyclopropyl-3-(2-((1-(5-methoxy-2-((3-methoxy-2,2-dimethylpropyl)(pyridin-2-yl)carbamoyl)phenyl)-piperidin-4-yl)methoxy)pyridin-4-yl)propanoic acid | 631.3 |
| 156 | | 3-cyclopropyl-3-(2-((1-(2-((2,2-dimethylpropyl)(pyrimidin-2-yl)carbamoyl)-5-methoxyphenyl)piperidin-4-yl)methoxy)pyridin-4-yl)propanoic acid | 602.3 |

TABLE 2-27

| Ex. No. | structural formula | IUPAC name | MS |
|---|---|---|---|
| 157 | | 3-cyclopropyl-3-(2-((1-(2-((2,2-difluoroethyl)(4-methylpyridin-2-yl)carbamoyl)-5-methoxyphenyl)piperidin-4-yl)methoxy)pyridin-4-yl)propanoic acid | 609.2 |

TABLE 2-27-continued

| Ex. No. | structural formula | IUPAC name | MS |
|---|---|---|---|
| 158 | | 3-(2-((1-(2-((4-cyanopyridin-2-yl)(2-methylpropyl)carbamoyl)-5-methoxyphenyl)piperidin-4-yl)methoxy)pyridin-4-yl)-3-cyclopropylpropanoic acid | 612.3 |
| 159 | | 3-cyclopropyl-3-(2-((1-(5-methoxy-2-((3-methylbutyl)(pyridin-2-yl)carbamoyl)phenyl)-piperidin-4-yl)methoxy)pyridin-4-yl)propanoic acid | 601.3 |
| 160 | | 3-cyclopropyl-3-(2-((1-(2-((2-isopropoxy-2-methylpropyl)(pyridin-2-yl)carbamoyl)-5-methoxyphenyl)piperidin-4-yl)methoxy)pyridin-4-yl)propanoic acid | 645.4 |
| 161 | | 3-cyclopropyl-3-(2-((1-(5-methoxy-2-((2-methyl-2-(2,2,2-trifluoroethoxy)propyl)-(pyridin-2-yl)-carbamoyl)phenyl)-piperidin-4-yl)methoxy)pyridin-4-yl)propanoic acid | 685.4 |

TABLE 2-27-continued

| Ex. No. | structural formula | IUPAC name | MS |
|---|---|---|---|
| 162 | | 3-cyclopropyl-3-(2-((1-(2-(((3,3-difluorocyclobutyl)-methyl)(pyridin-2-yl)carbamoyl)-5-methoxyphenyl)piperidin-4-yl)methoxy)pyridin-4-yl)propanoic acid | 635.3 |

TABLE 2-28

| Ex. No. | structural formula | IUPAC name | MS |
|---|---|---|---|
| 163 | | 3-cyclopropyl-3-(2-((1-(5-methoxy-2-((2-methylpyridin-4-yl)(2,2,2-trifluoroethyl)carbamoyl)-phenyl)piperidin-4-yl)methoxy)pyridin-4-yl)propanoic acid | 627.2 |
| 164 | | 3-cyclopropyl-3-(2-((1-(5-methoxy-2-((2-methoxy-2-methylpropyl)(4-methylpyridin-2-yl)carbamoyl)phenyl)-piperidin-4-yl)methoxy)pyridin-4-yl)propanoic acid | 631.4 |

TABLE 2-28-continued

| Ex. No. | structural formula | IUPAC name | MS |
|---|---|---|---|
| 165 | | 3-cyclopropyl-3-(2-((1-(2-((3,3-difluorocyclobutyl)-(pyridin-2-yl)carbamoyl)-5-methoxyphenyl)piperidin-4-yl)methoxy)pyridin-4-yl)propanoic acid | 621.3 |
| 166 | | 3-cyclopropyl-3-(2-((1-(5-methoxy-2-(pyrimidin-2-yl(2,2,2-trifluoroethyl)carbamoyl)-phenyl)piperidin-4-yl)methoxy)pyridin-4-yl)propanoic acid | 614.2 |
| 167 | | 3-cyclopropyl-3-(2-((1-(2-((2,2-difluoroethyl)(pyrimidin-2-yl)carbamoyl)-5-methoxyphenyl)piperidin-4-yl)methoxy)pyridin-4-yl)propanoic acid | 596.2 |
| 168 | | 3-cyclopropyl-3-(2-((1-(2-((4,6-dimethylpyrimidin-2-yl)(2,2,2-trifluoroethyl)carbamoyl)-5-methoxyphenyl)piperidin-4-yl)methoxy)pyridin-4-yl)propanoic acid | 642.3 |

TABLE 2-29

| Ex. No. | structural formula | IUPAC name | MS |
|---|---|---|---|
| 169 | 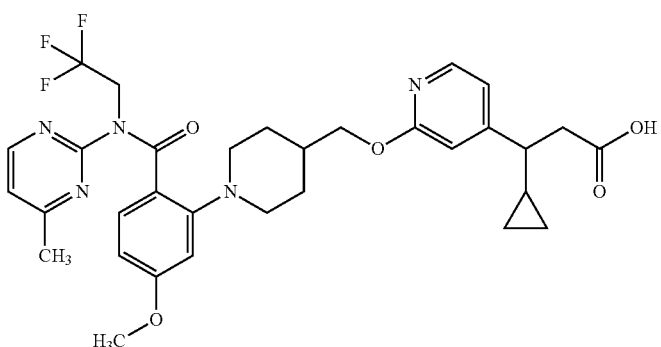 | 3-cyclopropyl-3-(2-((1-(5-methoxy-2-((4-methyl-pyrimidin-2-yl)(2,2,2-trifluoroethyl)carbamoyl)-phenyl)piperidin-4-yl)-methoxy)pyridin-4-yl)propanoic acid | 628.3 |
| 170 | 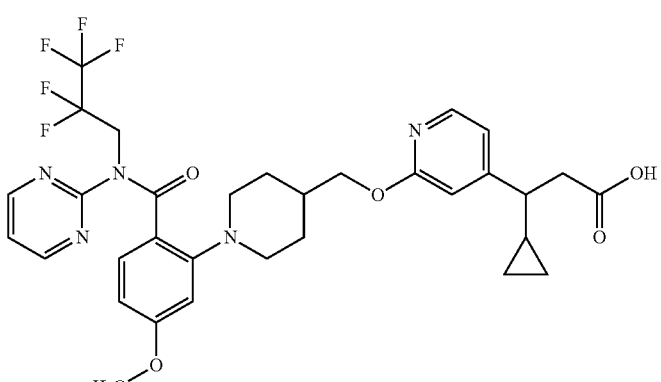 | 3-cyclopropyl-3-(2-((1-(5-methoxy-2-((2,2,3,3,3-pentafluoropropyl)-(pyrimidin-2-yl)-carbamoyl)phenyl)-piperidin-4-yl)methoxy)pyridin-4-yl)propanoic acid | 664.2 |
| 171 | 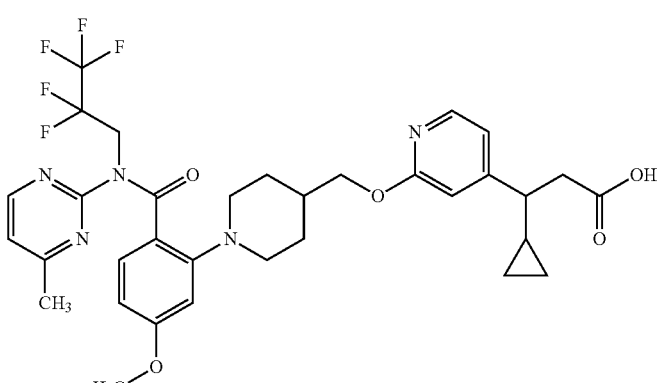 | 3-cyclopropyl-3-(2-((1-(5-methoxy-2-((4-methyl-pyrimidin-2-yl)(2,2,3,3,3-pentafluoropropyl)-carbamoyl)phenyl)-piperidin-4-yl)methoxy)pyridin-4-yl)propanoic acid | 678.3 |
| 172 | 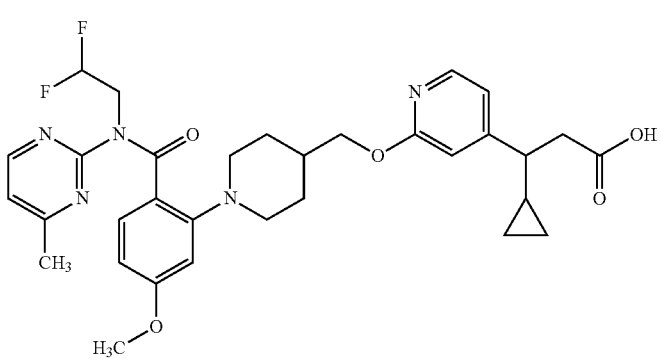 [SMILES: COc1ccc(C(=O)N(CC(F)F)c2nccc(C)n2)c(N2CCC(COc3cc(C(CC(=O)O)C4CC4)ccn3)CC2)c1] | 3-cyclopropyl-3-(2-((1-(2-((2,2-difluoroethyl)(4-methylpyrimidin-2-yl)carbamoyl)-5-methoxyphenyl)piperidin-4-yl)methoxy)pyridin-4-yl)propanoic acid | 610.2 |

TABLE 2-29-continued

| Ex. No. | structural formula | IUPAC name | MS |
|---|---|---|---|
| 173 | | 3-cyclopropyl-3-(2-((1-(2-((2,2-dimethylpropyl)(4-methylpyrimidin-2-yl)carbamoyl)-5-methoxyphenyl)piperidin-4-yl)methoxy)pyridin-4-yl)propanoic acid | 616.3 |
| 174 | | 3-cyclopropyl-3-(2-((1-(2-((2,2-dimethylpropyl)(4,6-dimethylpyrimidin-2-yl)carbamoyl)-5-methoxyphenyl)piperidin-4-yl)methoxy)pyridin-4-yl)propanoic acid | 630.4 |

TABLE 2-30

| Ex. No. | structural formula | IUPAC name | MS |
|---|---|---|---|
| 175 | | 3-cyclopropyl-3-(2-((1-(5-methoxy-2-((5-methylpyridin-3-yl)(2,2,2-trifluoroethyl)carbamoyl)-phenyl)piperidin-4-yl)methoxy)pyridin-4-yl)propanoic acid | 625.3 |
| 176 | | 3-cyclopropyl-3-(2-((1-(5-methoxy-2-((2,2,2-trifluoroethyl)(4-(trifluoromethyl)pyridin-2-yl)carbamoyl)-phenyl)piperidin-4-yl)methoxy)pyridin-4-yl)propanoic acid | 681.2 |

TABLE 2-30-continued

| Ex. No. | structural formula | IUPAC name | MS |
|---|---|---|---|
| 177 | | 3-cyclopropyl-3-(2-((1-(5-methoxy-2-((2-methyl-2-((2,2,2-trifluoroethyl)-amino)propyl)(pyridin-2-yl)carbamoyl)phenyl)-piperidin-4-yl)methoxy)pyridin-4-yl)propanoic acid | 684.3 |
| 178 | | 3-cyclopropyl-3-(2-((1-(2-((2,2-dimethylpropyl)-(pyrazin-2-yl)carbamoyl)-5-methoxyphenyl)piperidin-4-yl)methoxy)pyridin-4-yl)propanoic acid | 602.3 |
| 179 | | 3-cyclopropyl-3-(2-((1-(2-((2,2-dimethylpropyl)-(pyridazin-3-yl)-carbamoyl)-5-methoxyphenyl)piperidin-4-yl)methoxy)pyridin-4-yl)propanoic acid | 602.3 |
| 180 | | 3-(2-((1-(2-((6-chloropyrazin-2-yl)(2,2-dimethylpropyl)carbamoyl)-5-methoxyphenyl)piperidin-4-yl)methoxy)pyridin-4-yl)-3-cyclopropylpropanoic acid | 636.4 |

TABLE 2-31

| Ex. No. | structural formula | IUPAC name | MS |
|---|---|---|---|
| 181 | | 3-cyclopropyl-3-(2-((1-(2-((2,2-dimethylpropyl)(pyridin-2-ylmethyl)carbamoyl)-5-methoxyphenyl)piperidin-4-yl)methoxy)pyridin-4-yl)propanoic acid | 615.3 |
| 182 | | 3-cyclopropyl-3-(2-((1-(5-methoxy-2-((pyridin-2-ylmethyl)(2,2,2-trifluoroethyl)-carbamoyl)phenyl)-piperidin-4-yl)methoxy)pyridin-4-yl)propanoic acid | 627.2 |
| 183 | | 3-cyclopropyl-3-(2-((1-(5-methoxy-2-(pyridin-2-yl(3,3,3-trifluoro-2-methoxypropyl)carbamoyl)-phenyl)piperidin-4-yl)methoxy)pyridin-4-yl)propanoic acid | 657.4 |
| 184 | | 3-cyclopropyl-3-(2-((1-(2-((2,2-dimethylpropyl)-(pyrimidin-2-yl)carbamoyl)-5-methoxyphenyl)piperidin-4-yl)methoxy)pyridin-4-yl)propanoic acid | 602.3 |

TABLE 2-31-continued

| Ex. No. | structural formula | IUPAC name | MS |
|---|---|---|---|
| 185 | | 3-cyclopropyl-3-(2-((1-(2-((2-fluoro-2-methyl-propyl)(4-methylpyridin-2-yl)carbamoyl)-5-methoxyphenyl)piperidin-4-yl)methoxy)pyridin-4-yl)propanoic acid | 619.3 |
| 186 | | 3-cyclopropyl-3-(2-((1-(2-(((2R)-3-fluoro-3-methylbutan-2-yl)(pyridin-2-yl)carbamoyl)-5-methoxyphenyl)piperidin-4-yl)methoxy)pyridin-4-yl)propanoic acid | 619.3 |

TABLE 2-32

| Ex. No. | structural formula | IUPAC name | MS |
|---|---|---|---|
| 187 | | 3-cyclopropyl-3-(2-((1-(2-(((2S)-3-fluoro-3-methylbutan-2-yl)(pyridin-2-yl)carbamoyl)-5-methoxyphenyl)piperidin-4-yl)methoxy)pyridin-4-yl)propanoic acid | 619.3 |
| 188 | | 3-cyclopropyl-3-(2-((1-(5-methoxy-2-((2-methoxy-2-methylpropyl)(phenyl)carbamoyl)phenyl)-piperidin-4-yl)methoxy)pyridin-4-yl)propanoic acid | 616.3 |

TABLE 2-32-continued

| Ex. No. | structural formula | IUPAC name | MS |
|---|---|---|---|
| 189 | 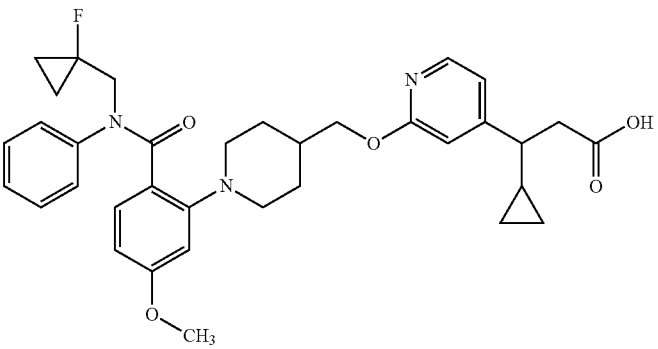 [SMILES: COc1ccc(C(=O)N(CC2(F)CC2)c2ccccc2)c(N2CCC(COc3cc(C(CC(=O)O)C4CC4)ccn3)CC2)c1] | 3-cyclopropyl-3-(2-((1-(2-(((1-fluorocyclopropyl)methyl)-(phenyl)carbamoyl)-5-methoxyphenyl)piperidin-4-yl)methoxy)pyridin-4-yl)propanoic acid | 602.3 |
| 190 | 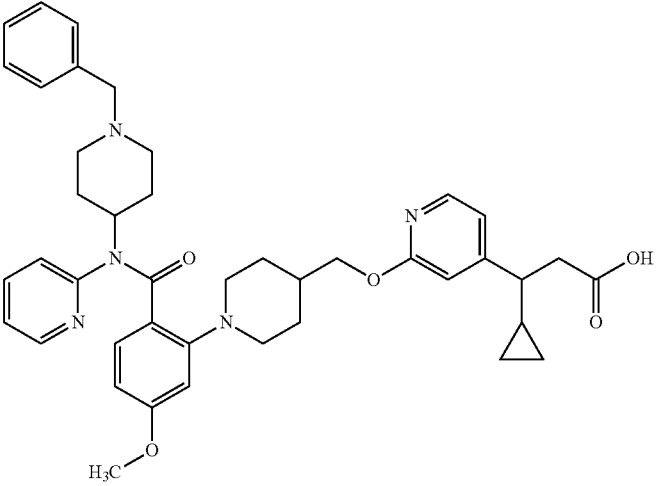 [SMILES: COc1ccc(C(=O)N(c2ccccn2)C2CCN(Cc3ccccc3)CC2)c(N2CCC(COc3cc(C(CC(=O)O)C4CC4)ccn3)CC2)c1] | 3-(2-((1-(2-((1-benzylpiperidin-4-yl)(pyridin-2-yl)carbamoyl)-5-methoxyphenyl)piperidin-4-yl)methoxy)pyridin-4-yl)-3-cyclopropylpropanoic acid | 704.4 |
| 191 | 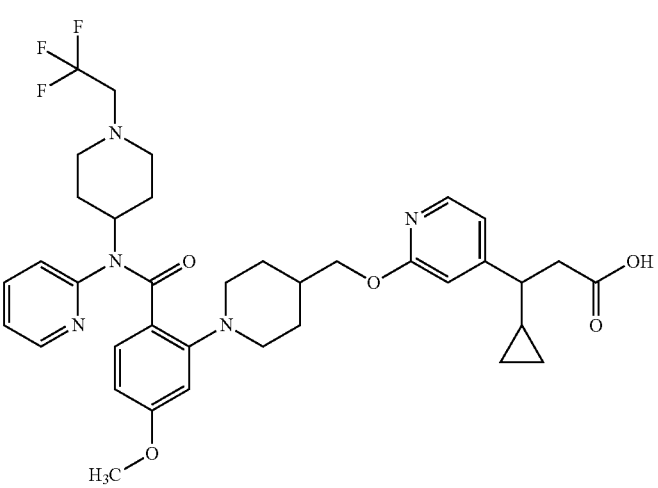 [SMILES: COc1ccc(C(=O)N(c2ccccn2)C2CCN(CC(F)(F)F)CC2)c(N2CCC(COc3cc(C(CC(=O)O)C4CC4)ccn3)CC2)c1] | 3-cyclopropyl-3-(2-((1-(5-methoxy-2-(pyridin-2-yl(1-(2,2,2-trifluoroethyl)piperidin-4-yl)carbamoyl)phenyl)-piperidin-4-yl)methoxy)pyridin-4-yl)propanoic acid | 696.3 |

TABLE 2-32-continued

| Ex. No. | structural formula | IUPAC name | MS |
|---|---|---|---|
| 192 | 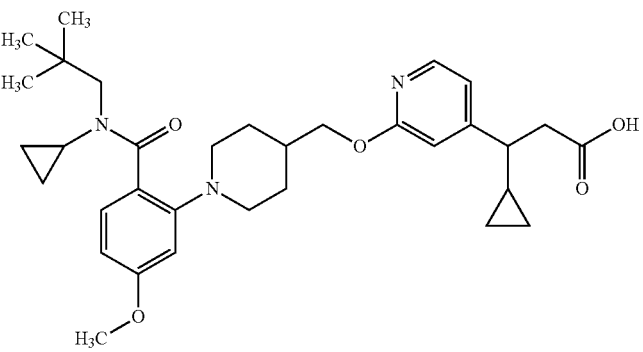 [SMILES: COc1ccc(C(=O)N(CC(C)(C)C)C2CC2)c(N2CCC(COc3cc(C(CC(=O)O)C4CC4)ccn3)CC2)c1] | 3-cyclopropyl-3-(2-((1-(2-(cyclopropyl(2,2-dimethylpropyl)carbamoyl)-5-methoxyphenyl)piperidin-4-yl)methoxy)pyridin-4-yl)propanoic acid | 564.3 |

TABLE 2-33

| Ex. No. | structural formula | IUPAC name | MS |
|---|---|---|---|
| 193 | 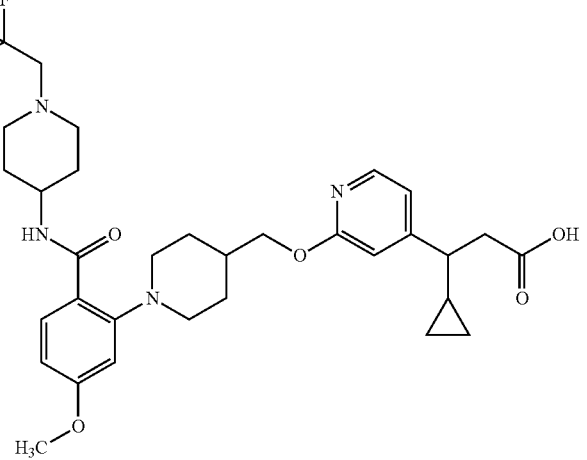 | 3-cyclopropyl-3-(2-((1-(5-methoxy-2-((1-(2,2,2-trifluoroethyl)piperidin-4-yl)carbamoyl)phenyl)-piperidin-4-yl)methoxy)pyridin-4-yl)propanoic acid | 619.3 |
| 194 | 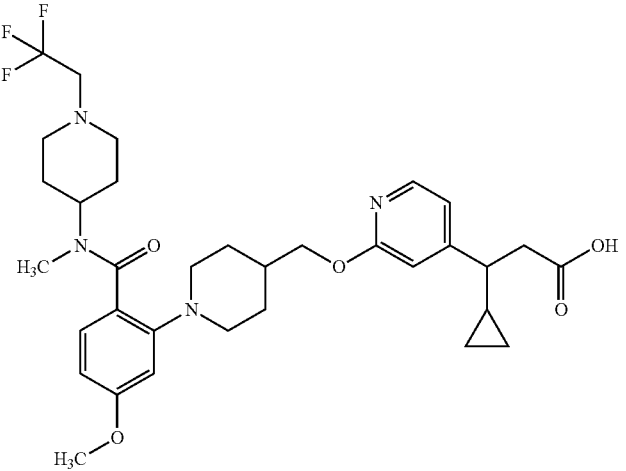 [SMILES: COc1ccc(C(=O)N(C)C2CCN(CC(F)(F)F)CC2)c(N2CCC(COc3cc(C(CC(=O)O)C4CC4)ccn3)CC2)c1] | 3-cyclopropyl-3-(2-((1-(5-methoxy-2-(methyl(1-(2,2,2-trifluoroethyl)piperidin-4-yl)carbamoyl)phenyl)-piperidin-4-yl)methoxy)pyridin-4-yl)propanoic acid | 633.3 |

TABLE 2-33-continued

| Ex. No. | structural formula | IUPAC name | MS |
|---|---|---|---|
| 195 | | 3-(2-((1-(2-((cyclohexylmethyl)-(pyridin-2-yl)carbamoyl)-5-methoxyphenyl)piperidin-4-yl)methoxy)pyridin-4-yl)-3-cyclopropylpropanoic acid | 627.2 |
| 196 | | 3-cyclopropyl-3-(2-((1-(5-methoxy-2-(pyridin-2-yl(tetrahydro-2H-pyran-4-ylmethyl)carbamoyl)-phenyl)piperidin-4-yl)methoxy)pyridin-4-yl)propanoic acid | 629.4 |
| 197 | | 3-(2-((1-(2-(benzyl(pyridin-2-yl)carbamoyl)-5-methoxyphenyl)piperidin-4-yl)methoxy)pyridin-4-yl)-3-cyclopropylpropanoic acid | 621.4 |
| 198 | | 3-(2-((1-(2-(cyclopentyl(2,2-dimethylpropyl)carbamoyl)-5-methoxyphenyl)piperidin-4-yl)methoxy)pyridin-4-yl)-3-cyclopropylpropanoic acid | 592.3 |

TABLE 2-34

| Ex. No. | structural formula | IUPAC name | MS |
|---|---|---|---|
| 199 | 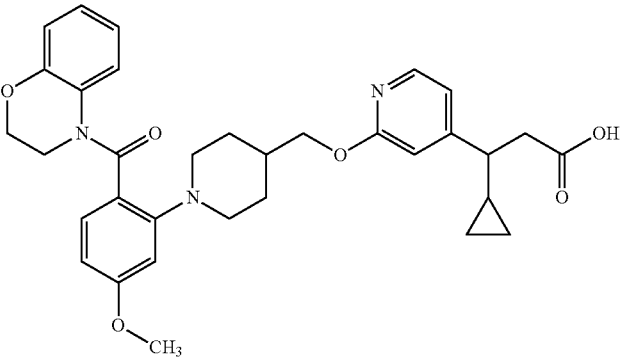 [SMILES: COc1ccc(C(=O)N2CCOc3ccccc32)c(N2CCC(COc3cc(C(CC(=O)O)C4CC4)ccn3)CC2)c1] | 3-cyclopropyl-3-(2-((1-(2-(2,3-dihydro-4H-1,4-benzooxazin-4-ylcarbonyl)-5-methoxyphenyl)piperidin-4-yl)methoxy)pyridin-4-yl)propanoic acid | 572.2 |
| 200 | 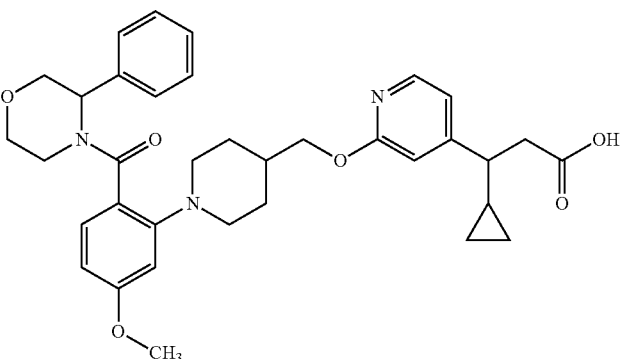 | 3-cyclopropyl-3-(2-((1-(5-methoxy-2-((3-phenylmorpholin-4-yl)carbonyl)phenyl)-piperidin-4-yl)methoxy)pyridin-4-yl)propanoic acid | 600.2 |
| 201 | 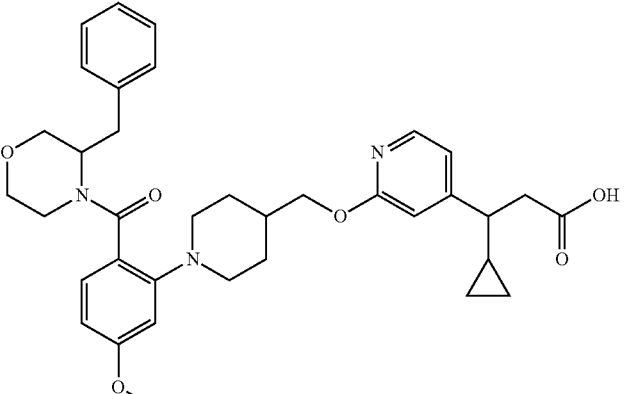 | 3-(2-((1-(2-((3-benzylmorpholin-4-yl)carbonyl)-5-methoxyphenyl)piperidin-4-yl)methoxy)pyridin-4-yl)-3-cyclopropylpropanoic acid | 614.3 |
| 202 | 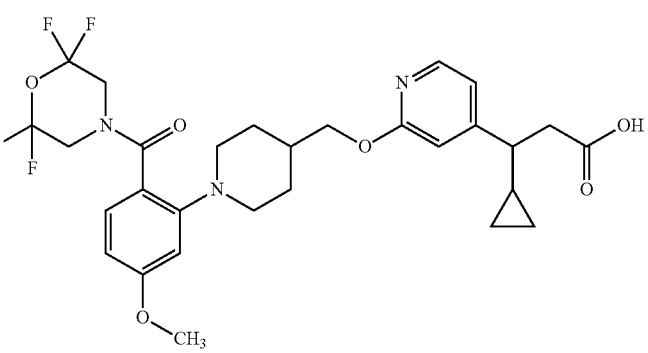 | 3-cyclopropyl-3-(2-((1-(5-methoxy-2-((2,2,6,6-tetrafluoromorpholin-4-yl)carbonyl)phenyl)-piperidin-4-yl)methoxy)pyridin-4-yl)propanoic acid | 596.1 |

TABLE 2-34-continued

| Ex. No. | structural formula | IUPAC name | MS |
|---|---|---|---|
| 203 | | 3-cyclopropyl-3-(2-((1-(5-methoxy-2-(((3S)-3-(2-methylpropyl)morpholin-4-yl)carbonyl)phenyl)-piperidin-4-yl)methoxy)pyridin-4-yl)propanoic acid | 580.3 |
| 204 | | 3-cyclopropyl-3-(2-((1-(5-methoxy-2-((2-phenylmorpholin-4-yl)carbonyl)phenyl)-piperidin-4-yl)methoxy)pyridin-4-yl)propanoic acid | 600.2 |

TABLE 2-35

| Ex. No. | structural formula | IUPAC name | MS |
|---|---|---|---|
| 205 | | 3-cyclopropyl-3-(2-((1-(5-methoxy-2-((2-(2-methylpropyl)morpholin-4-yl)carbonyl)phenyl)-piperidin-4-yl)methoxy)pyridin-4-yl)propanoic acid | 580.3 |

TABLE 2-35-continued

| Ex. No. | structural formula | IUPAC name | MS |
|---|---|---|---|
| 206 | | 3-cyclopropyl-3-(2-((1-(2-(cyclopropyl(2,2,3,3-tetrafluoropropyl)-carbamoyl)-5-methoxyphenyl)piperidin-4-yl)methoxy)pyridin-4-yl)propanoic acid | 608.2 |
| 207 | | 3-(2-((1-(2-(cyclobutyl(2,2,3,3-tetrafluoropropyl)-carbamoyl)-5-methoxyphenyl)piperidin-4-yl)methoxy)pyridin-4-yl)-3-cyclopropylpropanoic acid | 622.3 |
| 208 | | 3-(2-((1-(2-(cyclopentyl(2,2,3,3-tetrafluoropropyl)-carbamoyl)-5-methoxyphenyl)piperidin-4-yl)methoxy)pyridin-4-yl)-3-cyclopropylpropanoic acid | 636.3 |
| 209 | | 3-cyclopropyl-3-(2-((1-(2-(ethyl(2,2,3,3,3-pentafluoropropyl)-carbamoyl)-5-methoxyphenyl)piperidin-4-yl)methoxy)pyridin-4-yl)propanoic acid | 614.3 |

TABLE 2-35-continued

| Ex. No. | structural formula | IUPAC name | MS |
|---|---|---|---|
| 210 | | 3-cyclopropyl-3-(2-((1-(5-methoxy-2-((2,2,3,3,3-pentafluoropropyl)-(propan-2-yl)carbamoyl)-phenyl)piperidin-4-yl)methoxy)pyridin-4-yl)propanoic acid | 628.2 |

TABLE 2-36

| Ex. No. | structural formula | IUPAC name | MS |
|---|---|---|---|
| 211 | | 3-cyclopropyl-3-(2-((1-(2-(cyclopropyl(2,2,3,3,3-pentafluoropropyl)-carbamoyl)-5-methoxyphenyl)piperidin-4-yl)methoxy)pyridin-4-yl)propanoic acid | 626.2 |
| 212 | | 3-(2-((1-(2-(cyclobutyl-(2,2,3,3,3-pentafluoropropyl)carbamoyl)-5-methoxyphenyl)piperidin-4-yl)methoxy)pyridin-4-yl)-3-cyclopropylpropanoic acid | 640.3 |

TABLE 2-36-continued

| Ex. No. | structural formula | IUPAC name | MS |
|---|---|---|---|
| 213 | | 3-cyclopropyl-3-(2-((1-(2-(ethyl(2,2,3,3-tetrafluoropropyl)-carbamoyl)-5-methoxyphenyl)piperidin-4-yl)methoxy)pyridin-4-yl)propanoic acid | 596.2 |
| 214 | | 3-cyclopropyl-3-(2-((1-(5-methoxy-2-(propan-2-yl(2,2,3,3-tetrafluoropropyl)-carbamoyl)phenyl)-piperidin-4-yl)methoxy)pyridin-4-yl)propanoic acid | 610.2 |
| 215 | | 3-cyclopropyl-3-(2-((1-(5-methoxy-2-(propan-2-yl(2,2,3,3-trifluoroethyl)-carbamoyl)phenyl)-piperidin-4-yl)methoxy)pyridin-4-yl)propanoic acid | 578.2 |
| 216 | | 3-cyclopropyl-3-(2-((1-(2-(ethyl(2,2,2-trifluoroethyl)-carbamoyl)-5-methoxyphenyl)piperidin-4-yl)methoxy)pyridin-4-yl)propanoic acid | 564.3 |

TABLE 2-37

| Ex. No. | structural formula | IUPAC name | MS |
|---|---|---|---|
| 217 | | 3-(2-((1-(2-(bis(2,2,2-trifluoroethyl)carbamoyl)-5-methoxyphenyl)piperidin-4-yl)methoxy)pyridin-4-yl)-3-cyclopropylpropanoic acid | 618.2 |
| 218 | | 3-cyclopropyl-3-(2-((1-(2-(cyclopropyl(2,2,2-trifluoroethyl)carbamoyl)-5-methoxyphenyl)piperidin-4-yl)methoxy)pyridin-4-yl)propanoic acid | 576.2 |
| 219 | | 3-(2-((1-(2-(cyclobutyl(2,2,2-trifluoroethyl)carbamoyl)-5-methoxyphenyl)piperidin-4-yl)methoxy)pyridin-4-yl)-3-cyclopropylpropanoic acid | 590.3 |
| 220 | | 3-(2-((1-(2-(cyclopentyl(2,2,2-trifluoroethyl)carbamoyl)-5-methoxyphenyl)piperidin-4-yl)methoxy)pyridin-4-yl)-3-cyclopropylpropanoic acid | 604.4 |

TABLE 2-37-continued

| Ex. No. | structural formula | IUPAC name | MS |
|---|---|---|---|
| 221 | | 3-cyclopropyl-3-(2-((1-(2-(2,3-dihydro-1-benzofuran-3-yl(2,2,3,3-tetrafluoropropyl)-carbamoyl)-5-methoxyphenyl)piperidin-4-yl)methoxy)pyridin-4-yl)propanoic acid | 686.3 |
| 222 | | 3-cyclopropyl-3-(2-((1-(2-((2,2-dimethylpropyl)(6-(trifluoromethyl)pyridin-2-yl)carbamoyl)-5-methoxyphenyl)piperidin-4-yl)methoxy)pyridin-4-yl)propanoic acid | 669.3 |

TABLE 2-38

| Ex. No. | structural formula | IUPAC name | MS |
|---|---|---|---|
| 223 | | 3-cyclopropyl-3-(2-((1-(2-((2,2-dimethylpropyl) (4-(trifluoromethyl)-pyrimidin-2-yl)carbamoyl)-5-methoxyphenyl)piperidin-4-yl)methoxy)pyridin-4-yl)propanoic acid | 670.3 |
| 224 | | 3-cyclopropyl-3-(2-((1-(2-((4-cyclopropylpyrimidin-2-yl) (2,2-dimethylpropyl)carbamoyl)-5-methoxyphenyl)piperidin-4-yl)methoxy)pyridin-4-yl)propanoic acid | 642.3 |

TABLE 2-38-continued

| Ex. No. | structural formula | IUPAC name | MS |
|---|---|---|---|
| 225 | | 3-cyclopropyl-3-(2-((1-(2-((2,2-dimethylpropyl) (4-((2,2-dimethylpropyl)-carbamoyl)-6-methyl-pyridin-2-yl)carbamoyl)-5-methoxyphenyl)piperidin-4-yl)methoxy)pyridin-4-yl)propanoic acid | 728.5 |
| 226 | | 3-cyclopropyl-3-(2-((1-(2-((2,2-dimethylpropyl) (6-methyl-4-(pyrrolidin-1-ylcarbonyl)pyridin-2-yl)carbamoyl)-5-methoxyphenyl)piperidin-4-yl)methoxy)pyridin-4-yl)propanoic acid | 712.4 |
| 227 | | 3-cyclopropyl-3-(2-((1-(2-((2,2-dimethylpropyl) (1-methyl-2-oxo-1,2-dihydropyridin-3-yl)carbamoyl)-5-methoxyphenyl)piperidin-4-yl)methoxy)pyridin-4-yl)propanoic acid | 631.3 |
| 228 | | 3-cyclopropyl-3-(2-((1-(2-((2,2-dimethylpropyl) (2,6-dimethylpyrimidin-4-yl)carbamoyl)-5-methoxyphenyl)piperidin-4-yl)methoxy)pyridin-4-yl)propanoic acid | 630.3 |

TABLE 2-39

| Ex. No. | structural formula | IUPAC name | MS |
|---|---|---|---|
| 229 | | 3-cyclopropyl-3-(2-((1-(2-((2,2-dimethylpropyl) (2-methylpyrimidin-4-yl)carbamoyl)-5-methoxyphenyl) piperidin-4-yl) methoxy)pyridin-4-yl)propanoic acid | 616.3 |
| 230 | | 3-cyclopropyl-3-(2-((1-(2-((2,2-dimethylpropyl) (6-methylpyrimidin-4-yl)carbamoyl)-5-methoxyphenyl) piperidin-4-yl) methoxy)pyridin-4-yl)propanoic acid | 616.3 |
| 231 | | 3-cyclopropyl-3-(2-((1-(2-((2,2-dimethylpropyl) (5-methylpyridin-3-yl)carbamoyl)-5-methoxyphenyl) piperidin-4-yl)methoxy)pyridin-4-yl)propanoic acid | 615.3 |
| 232 | | 3-cyclopropyl-3-(2-((1-(2-((2,2-dimethylpropyl) (5-methylpyridazin-3-yl)carbamoyl)-5-methoxyphenyl) piperidin-4-yl)methoxy)pyridin-4-yl)propanoic acid | 616.3 |

TABLE 2-39-continued

| Ex. No. | structural formula | IUPAC name | MS |
|---|---|---|---|
| 233 | | 3-cyclopropyl-3-(2-((1-(2-((2,2-dimethylpropyl) (1-(2,2,2-trifluoroethyl)piperidin-3-yl)carbamoyl)-5-methoxyphenyl) piperidin-4-yl)methoxy)pyridin-4-yl)propanoic acid | 689.3 |
| 234 | | 3-cyclopropyl-3-(2-((1-(2-((2,2-dimethylpropyl) (3-fluoro-6-methylpyridin-2-yl)carbamoyl)-5-methoxyphenyl) piperidin-4-yl)methoxy)pyridin-4-yl)propanoic acid | 633.3 |

TABLE 2-40

| Ex. No. | structural formula | IUPAC name | MS |
|---|---|---|---|
| 235 | | 3-cyclopropyl-3-(2-((1-(2-((2,2-dimethylpropyl) (5-(trifluoromethyl)pyridin-3-yl)carbamoyl)-5-methoxyphenyl)piperidin-4-yl)methoxy)pyridin-4-yl)propanoic acid | 669.3 |
| 236 | | 3-cyclopropyl-3-(2-((1-(5-methoxy-2-((2,2,2-trifluoroethyl) (5-(trifluoromethyl)pyridin-3-yl)carbamoyl)-phenyl)piperidin-4-yl)methoxy)pyridin-4-yl)propanoic acid | 681.2 |

TABLE 2-40-continued

| Ex. No. | structural formula | IUPAC name | MS |
|---|---|---|---|
| 237 | | 3-cyclopropyl-3-(2-((1-(2-((cyclopropylmethyl) (4-(trifluoromethyl)-pyrimidin-2-yl)carbamoyl)-5-methoxyphenyl)piperidin-4-yl)methoxy)pyridin-4-yl)propanoic acid | 654.3 |
| 238 | | 3-cyclopropyl-3-(2-((1-(2-((2,6-dimethylpyrimidin-4-yl) (2,2,2-trifluoroethyl)-carbamoyl)-5-methoxyphenyl)piperidin-4-yl)methoxy)pyridin-4-yl)propanoic acid | 640.3 |
| 239 | | 3-cyclopropyl-3-(2-((1-(5-methoxy-2-((2-methyl-pyrimidin-4-yl) (2,2,2-trifluoroethyl)carbamoyl)-phenyl)piperidin-4-yl)methoxy)pyridin-4-yl)propanoic acid | 626.1 |
| 240 | | 3-cyclopropyl-3-(2-((1-(5-methoxy-2-((6-methylpyrimidin-4-yl)-(2,2,2-trifluoroethyl)-carbamoyl)phenyl)-piperidin-4-yl)methoxy)-pyridin-4-yl)propanoic acid | 626.1 |

TABLE 2-41

| Ex. No. | structural formula | IUPAC name | MS |
|---|---|---|---|
| 241 | | 3-cyclopropyl-3-(2-((1-(5-methoxy-2-((6-methylpyridin-2-yl)-carbamoyl)phenyl)-piperidin-4-yl)methoxy)pyridin-4-yl)propanoic acid | 545.2 |
| 242 | | 3-cyclopropyl-3-(2-((1-(5-methoxy-2-(pyridin-2-ylcarbamoyl)phenyl)-piperidin-4-yl)methoxy)pyridin-4-yl)propanoic acid | 531.2 |
| 243 | | 3-cyclopropyl-3-(2-((1-(2-((2-dimethylpropyl)-(4,6-dimethylpyridin-2-yl)carbamoyl)-5-methoxyphenyl)piperidin-4-yl)methoxy)pyridin-4-yl)propanoic acid | 629.4 |
| 244 | | 3-cyclopropyl-3-(2-((1-(2-((cyclopropylmethyl)-(4,6-dimethylpyridin-2-yl)carbamoyl)-5-methoxyphenyl)piperidin-4-yl)methoxy)pyridin-4-yl)propanoic acid | 613.3 |

TABLE 2-41-continued

| Ex. No. | structural formula | IUPAC name | MS |
|---|---|---|---|
| 245 | | (3S)-3-cyclopropyl-3-(2-((1-(2-((2,2-dimethylpropyl) (6-methylpyridin-2-yl)carbamoyl)-5-methoxyphenyl)piperidin-4-yl)methoxy)pyridin-4-yl)propanoic acid | 615.3 |
| 246 | | (3S)-3-cyclopropyl-3-(2-((1-(2-((2,2-dimethylpropyl) (4,6-dimethylpyrimidin-2-yl)carbamoyl)-5-methoxyphenyl)piperidin-4-yl)methoxy)pyridin-4-yl)propanoic acid | 630.3 |

TABLE 2-42

| Ex. No. | structural formula | IUPAC name | MS |
|---|---|---|---|
| 247 | | (3S)-3-cyclopropyl-3-(2-((1-(2-((2,2-dimethylpropyl) (pyridin-2-yl)carbamoyl)-5-methoxyphenyl)piperidin-4-yl)methoxy)pyridin-4-yl)propanoic acid | 601.3 |
| 248 | | (3S)-3-cyclopropyl-3-(2-((1-(5-methoxy-2-((6-methylpyridin-2-yl)-carbamoyl)phenyl)-piperidin-4-yl)methoxy)pyridin-4-yl)propanoic acid | 545.2 |

TABLE 2-42-continued

| Ex. No. | structural formula | IUPAC name | MS |
|---|---|---|---|
| 249 | | (3S)-3-cyclopropyl-3-(2-((1-(5-methoxy-2-(pyridin-2-ylcarbamoyl)phenyl)-piperidin-4-yl)methoxy)pyridin-4-yl)propanoic acid | 531.2 |
| 250 | | 3-cyclopropyl-3-(2-((1-(2-((2,2-dimethylpropyl) (6-methylpyridin-2-yl)carbamoyl)-4-fluoro-5-methoxyphenyl)piperidin-4-yl)methoxy)pyridin-4-yl)propanoic acid | 633.3 |
| 251 | | 3-cyclopropyl-3-(2-((1-(2-((2,2-dimethylpropyl) (6-methylpyridin-2-yl)carbamoyl)-3-fluoro-5-methoxyphenyl)piperidin-4-yl)methoxy)pyridin-4-yl)propanoic acid | 633.3 |
| 252 | | 3-cyclopropyl-3-(2-((1-(6-((2,2-dimethylpropyl)-(6-methylpyridin-2-yl)carbamoyl)-2-fluoro-3-methoxyphenyl)piperidin-4-yl)methoxy)pyridin-4-yl)propanoic acid | 633.3 |

TABLE 2-43

| Ex. No. | structural formula | IUPAC name | MS |
|---|---|---|---|
| 253 | | 3-cyclopropyl-3-(2-((1-(6-((2,2-dimethylpropyl) (6-methylpyridin-2-yl)carbamoyl)-2,4-difluoro-3-methoxyphenyl)piperidin-4-yl)methoxy)pyridin-4-yl)propanoic acid | 651.4 |
| 254 | | 3-cyclopropyl-3-(3-((1-(3-((2,2-dimethylpropyl)-(pyridin-2-yl)carbamoyl)-6-methoxypyridin-2-yl)piperidin-4-yl)methoxy)phenyl)-propanoic acid | 601.3 |
| 255 | | 3-cyclopropyl-3-(2-((1-(5-((2,2-dimethylpropyl) (6-methylpyridin-2-yl)-carbamoyl)-2-methoxy-pyridin-4-yl)piperidin-4-yl)methoxy)pyridin-4-yl)propanoic acid | 616.3 |
| 256 | | 3-cyclopropyl-3-(2-((1-(2-methoxy-5-(pyridin-2-yl(2,2,2-trifluoroethyl)-carbamoyl)pyridin-4-yl)piperidin-4-yl)-methoxy)pyridin-4-yl)propanoic acid | 614.2 |

TABLE 2-43-continued

| Ex. No. | structural formula | IUPAC name | MS |
|---|---|---|---|
| 257 | | 3-cyclopropyl-3-(2-((1-(5-((2,2-dimethylpropyl) (6-methylpyrimidin-4-yl)carbamoyl)-2-methoxypyridin-4-yl)piperidin-4-yl)methoxy)pyridin-4-yl)propanoic acid | 617.2 |
| 258 | | 3-cyclopropyl-3-(2-((1-(2-((2,2-dimethylpropyl) (6-methylpyridin-2-yl)-carbamoyl)-5-methylphenyl)piperidin-4-yl)methoxy)pyridin-4-yl)propanoic acid | 599.3 |

TABLE 2-44

| Ex. No. | structural formula | IUPAC name | MS |
|---|---|---|---|
| 259 | | 3-cyclopropyl-3-(2-((1-(2-((2,2-dimethylpropyl) (6-methylpyridin-2-yl)carbamoyl)-5-hydroxyphenyl)piperidin-4-yl)methoxy)pyridin-4-yl)propanoic acid | 601.3 |
| 260 | | 3-(2-((1-(5-cyano-2-((2,2-dimethylpropyl) (6-methylpyridin-2-yl)-carbamoyl)phenyl)-piperidin-4-yl)methoxy)-pyridin-4-yl)-3-cyclopropylpropanoic acid | 610.3 |

TABLE 2-44-continued

| Ex. No. | structural formula | IUPAC name | MS |
|---|---|---|---|
| 261 | 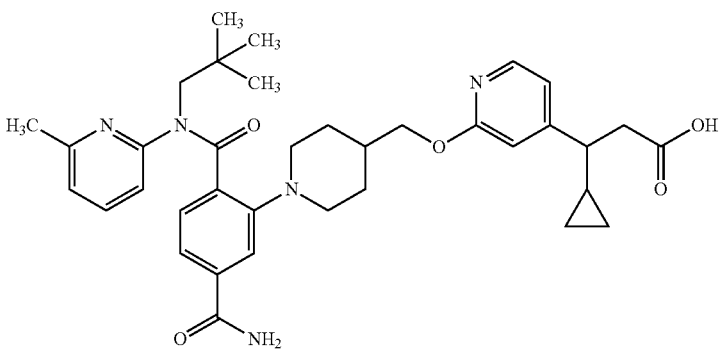 [SMILES: Cc1cccc(N(CC(C)(C)C)C(=O)c2ccc(C(N)=O)cc2N2CCC(COc3cc(C(CC(=O)O)C4CC4)ccn3)CC2)n1] | 3-(2-((1-(5-carbamoyl-2-((2,2-dimethylpropyl) (6-methylpyridin-2-yl)carbamoyl)phenyl)-piperidin-4-yl)methoxy)pyridin-4-yl)-3-cyclopropylpropanoic acid | 628.3 |
| 262 | 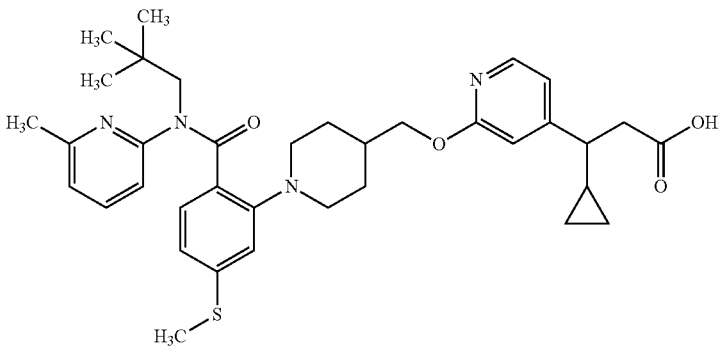 [SMILES: CSc1ccc(C(=O)N(CC(C)(C)C)c2cccc(C)n2)c(N2CCC(COc3cc(C(CC(=O)O)C4CC4)ccn3)CC2)c1] | 3-cyclopropyl-3-(2-((1-(2-((2,2-dimethylpropyl) (6-methylpyridin-2-yl)carbamoyl)-5-(methylsulfanyl)phenyl)-piperidin-4-yl)methoxy)pyridin-4-yl)propanoic acid | 631.3 |
| 263 | 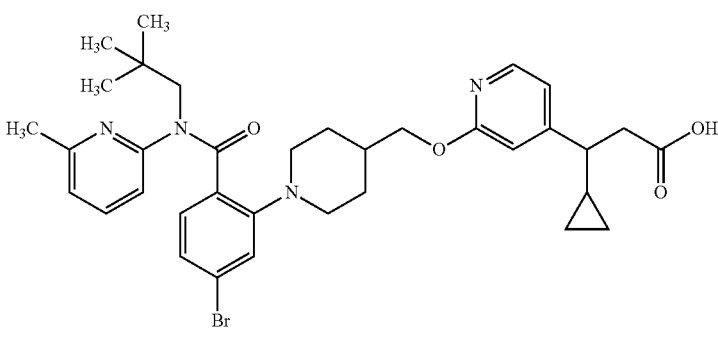 [SMILES: Cc1cccc(N(CC(C)(C)C)C(=O)c2ccc(Br)cc2N2CCC(COc3cc(C(CC(=O)O)C4CC4)ccn3)CC2)n1] | 3-(2-((1-(5-bromo-2-((2,2-dimethylpropyl) (6-methylpyridin-2-yl)carbamoyl)phenyl)-piperidin-4-yl)methoxy)pyridin-4-yl)-3-cyclopropylpropanoic acid | 663.2 |
| 264 | 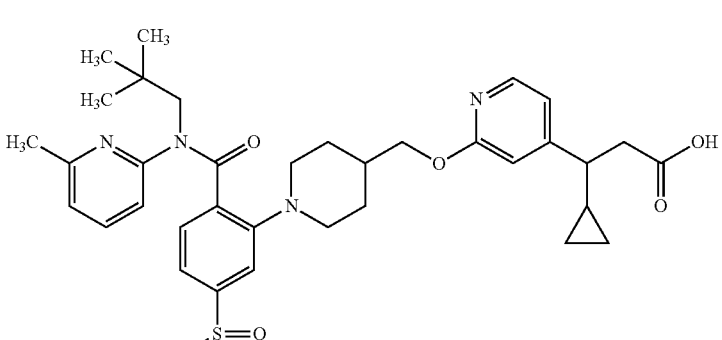 | 3-cyclopropyl-3-(2-((1-(2-((2,2-dimethylpropyl) (6-methylpyridin-2-yl)-carbamoyl)-5-(methyl-sulfonyl)phenyl)piperidin-4-yl)methoxy)pyridin-4-yl)propanoic acid | 663.2 |

TABLE 2-45

| Ex. No. | structural formula | IUPAC name | MS |
|---|---|---|---|
| 265 | | 3-(2-((1-(5-chloro-2-((2,2-dimethylpropyl)(6-methylpyridin-2-yl)carbamoyl)-3-fluorophenyl)piperidin-4-yl)methoxy)pyridin-4-yl)-3-cyclopropylpropanoic acid | 637.3 |
| 266 | | 3-(2-((1-(5-chloro-2-((2,2-dimethylpropyl)(6-methylpyridin-2-yl)carbamoyl)phenyl)-piperidin-4-yl)methoxy)-pyridin-4-yl)-3-cyclopropylpropanoic acid | 619.3 |
| 267 | | 3-cyclopropyl-3-(2-((1-(5-(difluoromethoxy)-2-((2,2-dimethylpropyl)(6-methylpyridin-2-yl)-carbamoyl)phenyl)-piperidin-4-yl)methoxy)-pyridin-4-yl)propanoic acid | 651.3 |
| 268 | | 3-cyclopropyl-3-(2-(1-(1-(2-((2,2-dimethylpropyl)-(6-methylpyridin-2-yl)carbamoyl)-5-methoxyphenyl)piperidin-4-yl)ethoxy)pyridin-4-yl)propanoic acid | 629.3 |

TABLE 2-45-continued

| Ex. No. | structural formula | IUPAC name | MS |
|---|---|---|---|
| 269 | | 3-(3-((1-(2-((2,2-dimethylpropyl) (6-methylpyridin-2-yl)carbamoyl)-5-methoxyphenyl)piperidin-4-yl)methoxy)phenyl)-3-methoxypropanoic acid | 604.4 |
| 270 | | 3-(3-((1-(2-((2,2-dimethylpropyl) (6-methylpyridin-2-yl)carbamoyl)-5-methoxyphenyl)piperidin-4-yl)methoxy)phenyl)-3-ethoxypropanoic acid | 618.3 |

TABLE 2-46

| Ex. No. | structural formula | IUPAC name | MS |
|---|---|---|---|
| 271 | | 3-methoxy-3-(2-((1-(5-methoxy-2-((4-methylpyridin-2-yl)-(2,2,2-trifluoroethyl)-carbamoyl)phenyl)-piperidin-4-yl)methoxy)pyridin-4-yl)propanoic acid | 617.2 |
| 272 | | 3-(2-((1-(2-((2,2-dimethylpropyl) (6-methylpyridin-2-yl)-carbamoyl)-5-methoxy-phenyl)piperidin-4-yl)methoxy)pyridin-4-yl)-3-ethoxypropanoic acid | 619.3 |

TABLE 2-46-continued

| Ex. No. | structural formula | IUPAC name | MS |
|---|---|---|---|
| 273 | | 3-cyclopropyl-3-(2-((1-(2-((2-dimethylpropyl)-(pyrimidin-2-yl)-carbamoyl)-5-methoxy-phenyl)piperidin-4-yl)-methoxy)-5-fluoropyridin-4-yl)propanoic acid | 620.3 |
| 274 | | 3-cyclopropyl-3-(2-((1-(2-((2,2-dimethylpropyl)-(6-methylpyridin-2-yl)carbamoyl)-5-methoxyphenyl)piperidin-4-yl)methoxy)-5-fluoropyridin-4-yl)propanoic acid | 633.3 |
| 275 | | 3-cyclopropyl-3-(3-((1-(2-((2-dimethylpropyl)-(6-methylpyridin-2-yl)-carbamoyl)-5-methoxy-phenyl)piperidin-4-yl)methoxy)-2-fluoro-phenyl)propanoic acid | 632.3 |
| 276 | | 3-(3-((1-(2-((2,2-dimethylpropyl) (6-methylpyridin-2-yl)carbamoyl)-5-methoxyphenyl)piperidin-4-yl)methoxy)phenyl)-4-methoxybutanoic acid | 618.3 |

TABLE 2-47

| Ex. No. | structural formula | IUPAC name | MS |
|---|---|---|---|
| 277 | | 3-(3-((1-(2-((2,2-dimethylpropyl) (6-methylpyridin-2-yl)carbamoyl)-5-methoxyphenyl)piperidin-4-yl)methoxy)phenyl)-3-methylbutanoic acid | 602.4 |
| 278 | | (3-(3-((1-(2-((2,2-dimethylpropyl) (6-methylpyridin-2-yl)carbamoyl)-5-methoxyphenyl)piperidin-4-yl)methoxy)phenyl)oxetan-3-yl)acetic acid | 616.3 |
| 279 | | (3S)-cyclopropyl-3-(3-(((3R,4S)-1-(2-((2,2-dimethylpropyl) (pyridin-2-yl)carbamoyl)-5-methoxyphenyl)-3-methylpiperidin-4-yl)methoxy)phenyl)-propanoic acid | 614.3 |
| 280 | | (3S)-cyclopropyl-3-(3-(((3R,4R)-1-(2-((2,2-dimethylpropyl) (pyridin-2-yl)carbamoyl)-5-methoxyphenyl)-3-methylpiperidin-4-yl)methoxy)phenyl)-propanoic acid | 614.3 |

TABLE 2-47-continued

| Ex. No. | structural formula | IUPAC name | MS |
|---|---|---|---|
| 281 | | (3S)-cyclopropyl-3-(3-((1-(2-((2,2-dimethylpropyl)-(pyridin-2-yl)carbamoyl)-5-methoxyphenyl)-3,3-difluoropiperidin-4-yl)methoxy)phenyl)-propanoic acid | 636.4 |
| 282 | | 3-cyclopropyl-3-(3-((1-(2-((2,2-dimethylpropyl)-(pyridin-2-yl)carbamoyl)-5-methoxyphenyl)azetidin-3-yl)methoxy)-phenyl)propanoic acid | 572.3 |

TABLE 2-48

| Ex. No. | structural formula | IUPAC name | MS |
|---|---|---|---|
| 283 | | 3-cyclopropyl-3-(3-((1-(2-((2-dimethylpropyl)-(pyridin-2-yl)carbamoyl)-5-methoxyphenyl)-pyrrolidin-3-yl)methoxy)-phenyl)propanoic acid | 586.3 |

TABLE 2-48-continued

| Ex. No. | structural formula | IUPAC name | MS |
|---|---|---|---|
| 284 | | 3-cyclopropyl-3-(2-((1-(5-((2,2-dimethylpropyl) (4,6-dimethylpyridin-2-yl)-carbamoyl)-2-methoxypyridin-4-yl)-piperidin-4-yl)-methoxy)pyridin-4-yl)propanoic acid | 630.3 |
| 285 | | 3-cyclopropyl-3-(2-((1-(5-((cyclopropylmethyl) (4,6-dimethylpyridin-2-yl)carbamoyl)-2-methoxypyridin-4-yl)piperidin-4-yl)methoxy)pyridin-4-yl)propanoic acid | 614.3 |
| 286 | | 3-cyclopropyl-3-(2-((1-(5-((2,2-dimethylpropyl) (2,6-dimethylpyrimidin-4-yl)carbamoyl)-2-methoxypyridin-4-yl)piperidin-4-yl)methoxy)pyridin-4-yl)propanoic acid | 631.3 |
| 287 | | 3-cyclopropyl-3-(2-((1-(5-((2,2-dimethylpropyl) (6-methylpyridin-2-yl)carbamoyl)-2-methoxypyrimidin-4-yl)piperidin-4-yl)methoxy)pyridin-4-yl)propanoic acid | 617.3 |

Experimental Example 1

Construction of Human GPR40 Expressing CHO Cells

Plasmid hGPR40/pAKKO-1.11H for mammalian cells expression, wherein cDNA fragment (SEQ ID NO: 1) encoding the full-length human GPR40 was incorporated into an expression vector pAKKO-1.11H (Biochimica et Biophysica Acta vol. 1219 pp. 251-259 (1994)), was transfected into CHO-dhfr(−) cells (ATCC, CRL-9096) by using Lipofectamine 2000 (Invitrogen:11668-019). After transfection, the limiting dilution-culture method was performed to select clone in selection medium (nucleic acid-free α-MEM (Invitrogen:12561-056)) containing 10% dialyzed bovine serum (Invitrogen:26400-044)). The expression level of human GPR40 mRNA was confirmed by TaqMan PCR (Life Technologies), and the intracellular calcium mobilization activity of GPR40 ligand (γ-linolenic acid) was confirmed by FLIPR (Molecular Devices), and a clone of human GPR40 expressing CHO cells was selected.

Experimental Example 2

Evaluation of Human GPR40 Agonist Activity with Increase in Intracellular $Ca^{2+}$ Concentration as an Index CHO(dhfr−) cells that stably expressed human GPR40 were suspended in MEMα (Nikken Bio Medical Laboratory) containing 10% dialyzed bovine serum (JR Scientific), 10 mM HEPES (Life Technologies), 100 U/mL penicillin, 100 μg/mL streptomycin (Life Technologies), and plated on a 384 well black/clear cell culture plate at 10,000 cells/well. After culture overnight in a $CO_2$ incubator at 37° C., the culture supernatant was removed, and loading buffer [$Ca^{2+}$ probe attached to Calcium Kit II-iCellux (DOJINDO) was dissolved in assay buffer (20 mM HEPES, 0.1% fatty acid-free BSA (Sigma-Aldrich), 2.5 mM probenecid (DOJINDO)-containing HESS (Life Technologies))] was added at 30 μL/well. After leaving for 1 hr at room temperature under light shielding, assay buffer containing the test compound at a final concentration of 1 μM was added at 10 μL/well in FLIPR Tetra (Molecular Devices), and the fluorescence amount was successively measured. Human GPR40 agonist activity calculated using an increase in the intracellular $Ca^{2+}$ concentration as an index, wherein the activity of 10 μM of the compound of Example 153 was 100%, and the activity when DMSO was added instead of the test compound was 0%.

TABLE 3

| Example No. | Activity |
|---|---|
| 1 | 97% |
| 4 | 97% |
| 5 | 85% |
| 6 | 73% |
| 54 | 89% |
| 55 | 84% |
| 56 | 83% |
| 57 | 58% |
| 59 | 73% |
| 60 | 52% |
| 62 | 101% |
| 109 | 90% |
| 110 | 104% |
| 111 | 100% |
| 112 | 98% |
| 113 | 102% |
| 114 | 98% |
| 115 | 96% |
| 116 | 101% |
| 117 | 95% |
| 118 | 103% |
| 119 | 52% |
| 120 | 100% |
| 121 | 95% |
| 122 | 101% |
| 123 | 99% |
| 124 | 96% |
| 125 | 95% |
| 126 | 99% |
| 127 | 94% |
| 128 | 103% |
| 129 | 81% |
| 130 | 100% |
| 131 | 85% |
| 132 | 99% |
| 133 | 98% |
| 134 | 84% |
| 135 | 94% |
| 136 | 95% |
| 137 | 96% |
| 138 | 102% |
| 139 | 96% |
| 140 | 93% |
| 141 | 81% |
| 142 | 97% |
| 143 | 102% |
| 144 | 79% |
| 145 | 96% |
| 146 | 82% |
| 147 | 97% |
| 148 | 104% |
| 149 | 101% |
| 150 | 84% |
| 151 | 87% |
| 152 | 100% |
| 154 | 100% |
| 155 | 96% |
| 156 | 98% |
| 157 | 96% |
| 158 | 96% |
| 159 | 103% |
| 160 | 97% |
| 161 | 97% |
| 162 | 99% |
| 163 | 89% |
| 164 | 88% |
| 165 | 97% |
| 166 | 97% |
| 167 | 90% |
| 168 | 100% |
| 169 | 106% |
| 170 | 104% |
| 171 | 106% |
| 172 | 97% |
| 173 | 103% |
| 174 | 104% |
| 175 | 90% |
| 178 | 103% |
| 179 | 84% |
| 180 | 105% |
| 181 | 91% |
| 188 | 95% |
| 189 | 89% |
| 190 | 66% |
| 191 | 86% |
| 192 | 90% |
| 193 | 39% |
| 194 | 77% |
| 195 | 98% |
| 196 | 81% |
| 197 | 103% |
| 198 | 94% |

TABLE 3-continued

| Example No. | Activity |
|---|---|
| 199 | 93% |
| 200 | 89% |
| 201 | 92% |
| 202 | 102% |
| 228 | 99% |
| 229 | 101% |
| 230 | 98% |
| 231 | 92% |
| 232 | 85% |
| 233 | 85% |
| 234 | 97% |
| 235 | 91% |
| 236 | 91% |
| 237 | 98% |
| 238 | 101% |
| 239 | 100% |
| 240 | 99% |
| 241 | 95% |
| 242 | 93% |
| 243 | 101% |
| 244 | 99% |
| 245 | 102% |
| 246 | 103% |
| 247 | 102% |
| 250 | 91% |
| 251 | 91% |
| 252 | 87% |
| 253 | 74% |
| 254 | 74% |
| 255 | 103% |
| 256 | 96% |
| 257 | 98% |
| 258 | 94% |
| 259 | 77% |
| 260 | 89% |
| 261 | 11% |
| 262 | 90% |
| 263 | 94% |
| 264 | 52% |
| 265 | 85% |
| 266 | 94% |
| 267 | 96% |
| 268 | 92% |
| 269 | 103% |
| 270 | 95% |
| 271 | 98% |
| 272 | 95% |
| 273 | 101% |
| 274 | 104% |
| 275 | 99% |
| 276 | 96% |
| 277 | 110% |
| 278 | 78% |
| 279 | 92% |
| 280 | 6% |
| 281 | 92% |
| 284 | 103% |
| 285 | 99% |
| 286 | 107% |
| 287 | 82% |

As is clear from Table 3, the compound of the present invention showed superior GPR40 agonist activity.

Experimental Example 3

The glucose-lowering effects and insulinotropic action of the compound of the present invention were evaluated by an oral glucose tolerance test using N-STZ-1.5 rats.
(1) Animal Used
Streptozotocin (120 mg/kg) was subcutaneously administered to 1 or 2 days-old male Wistar Kyoto rats to prepare type 2 diabetic model N-STZ-1.5 rats. The rats were allowed free access to standard laboratory chow diet (CE-2, CLEA Japan, Inc.).

(2) Experiment Method and Results

Male N-STZ-1.5 rats (25-week-old) were fasted for 15-17 hr, and the body weight was measured. Heparin (Ajinomoto Co., Inc.) as an anticoagulant and aprotinin (SIGMA) as a protease inhibitor were added, blood samples were collected from tail vein. The blood was centrifuged, the concentrations of glucose and triglyceride in plasma were measured, and the rats were divided into each group (n=6) based on these parameters. A 0.5% methylcellulose (control group) or a 0.5% methylcellulose suspension containing a test compound (3 mg/kg body weight) was orally administered to the rats at 5 ml/kg and, 1 hr after the administration, glucose solution (Otsuka Pharmaceutical Co., Ltd.) was orally administered at 1.5 g/7.5 ml/kg. Immediately before (0 min value) and 10, 30 and 60 min after the glucose loading, blood was drawn from the tail vein, centrifuged, and the concentrations of glucose and insulin in plasma were measured. The glucose and triglyceride concentrations were measured by automatic analysis apparatus 7180 (Hitachi, Ltd.), and the insulin concentration was measured by rat insulin radioimmunoassay kit (MIllipore). The area under glucose curve (AUC) and insulin AUC were calculated using the following formulas, and the blood glucose decrease rate (%) and insulin increase rate (fold) were calculated by the following formulas from the obtained AUCs. A statistical significant difference from the control group was analyzed by the Dunnett's test or Steel's test. The results are shown in Table 4.

Glucose AUC (0-60 Min):

$$\{(0 \text{ min glucose in plasma})+(10 \text{ min glucose in plasma})\}\times 10/2+\{(10 \text{ min glucose in plasma})+(30 \text{ min glucose in plasma})\}\times 20/2+\{(30 \text{ min glucose in plasma})+(60 \text{ min glucose in plasma})\}\times 30/2$$

insulin AUC (0-60 Min):

$$\{(0 \text{ min insulin in plasma})+(10 \text{ min insulin in plasma})\}\times 10/2+\{(10 \text{ min insulin in plasma})+(30 \text{ min insulin in plasma})\}\times 20/2+\{(30 \text{ min insulin in plasma})+(60 \text{ min insulin in plasma})\}\times 30/2$$

Blood Glucose Decrease Rate (%):

$$[(\text{test compound administration group glucose AUC}/\text{control group glucose AUC})-1]\times 100$$

insulin Increase Rate (Fold):

test compound administration group insulin AUC/control group insulin AUC

TABLE 4

| compound | blood glucose decrease rate (%) | insulin increase rate (fold) |
|---|---|---|
| Example 184 | 27.9$ | 1.4 |
| Example 185 | 30.8$ | 1.6 |
| Example 245 | 44.5$ | 2.1** |
| Example 246 | 42.7$ | 2.1** |
| Example 247 | 41.5$ | 2.0** |

**$p \leq 0.01$, (Dunnett's test)
$$p \leq 0.05$ (Steel's test)

As is clear from Table 4, the compound of the present invention showed superior glucose-lowering effects and insulinotropic action.

| Formulation Example 1 (production of capsule) | |
|---|---|
| 1) compound of Example 1 | 30 mg |
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

| Formulation Example 2 (production of tablets) | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The entire amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Ex. 1 per tablet are obtained.

INDUSTRIAL APPLICABILITY

The compound of the present invention has superior GPR40 agonist activity and GLP-1 secretagogue action, and is useful as an agent for the prophylaxis or treatment of diabetes and the like.

This application is based on a patent application No. 2013-167065 filed in Japan, the contents of which are incorporated in full herein.

The invention claimed is:

1. A compound represented by the formula (I):

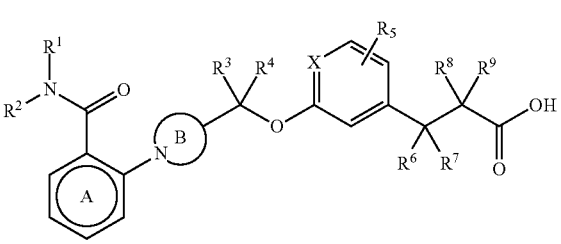

wherein
- ring A is a further optionally substituted aromatic ring;
- ring B is a further optionally substituted 4-6-membered nitrogen-containing saturated ring;
- X is N or CH;
- $R^1$ and $R^2$ are each independently
  - (i) a $C_{1-8}$ alkyl group optionally substituted by 1 or 2 substituents selected from (1) cyano, (2) hydroxy, (3) a $C_{3-10}$ cycloalkyl group optionally substituted by 1 to 3 substituents selected from a halogen atom and a $C_{1-6}$ alkyl group, (4) a $C_{1-6}$ alkoxy group optionally substituted by 1 to 3 halogen atoms, (5) a $C_{6-14}$ aryl group optionally substituted by 1 to 3 halogen atoms, (6) an aromatic heterocyclic group, (7) a nonaromatic heterocyclic group, (8) a $C_{1-6}$ alkylsulfonyl group, (9) a mono- or di-$C_{1-6}$ alkyl-amino group optionally substituted by 1 to 3 halogen atoms and (10) a halogen atom, or
  - (ii) an aromatic heterocyclic group optionally substituted by 1 or 2 substituents selected from (1) cyano, (2) a halogen atom, (3) a $C_{1-6}$ alkyl group optionally substituted by 1 to 3 halogen atoms, (4) a $C_{3-10}$ cycloalkyl group, (5) a $C_{1-6}$ alkoxy group, (6) a nitrogen-containing heterocyclyl-carbonyl group and (7) a mono- or di-$C_{1-6}$ alkyl-carbamoyl group, or a salt thereof;
- $R^3$ and $R^4$ are each independently a hydrogen atom, a halogen atom or a $C_{1-6}$ alkyl group;
- $R^5$, $R^7$, $R^8$ and $R^9$ are each independently a hydrogen atom, a halogen atom, a $C_{1-6}$ alkyl group or a $C_{1-6}$ alkoxy group;
- $R^6$ is a halogen atom, an optionally substituted $C_{1-6}$ alkyl group, an optionally substituted $C_{1-6}$ alkoxy group or an optionally substituted $C_{3-10}$ cycloalkyl group; and
- $R^6$ and $R^7$ are optionally bonded to each other to form, together with the adjacent carbon atom, an optionally substituted 3- to 10-membered ring, or a salt thereof.

2. The compound according to claim 1, wherein ring A is a benzene ring optionally further substituted by 1 or 2 substituents selected from
(1) a $C_{1-6}$ alkylsulfonyl group;
(2) a carbamoyl group;
(3) a hydroxy group;
(4) a $C_{1-6}$ alkoxy group optionally substituted by 1 to 3 halogen atoms;
(5) a $C_{1-6}$ alkylthio group;
(6) a cyano group;
(7) a halogen atom; and
(8) a $C_{1-6}$ alkyl group,
or a salt thereof.

3. The compound according to claim 1, wherein ring B is (1) an azetidine ring, (2) a pyrrolidine ring or (3) a piperidine ring optionally further substituted by 1 or 2 substituents selected from a halogen atom and a $C_{1-6}$ alkyl group, or a salt thereof.

4. The compound according to claim 1, wherein X is N, or a salt thereof.

5. The compound according to claim 1, wherein $R^3$, $R^4$, $R^5$, $R^7$, R and $R^9$ are hydrogen atoms, or a salt thereof.

6. The compound according to claim 1, wherein $R^6$ is a $C_{3-10}$ cycloalkyl group, or a salt thereof.

7. A compound represented by the formula (I):

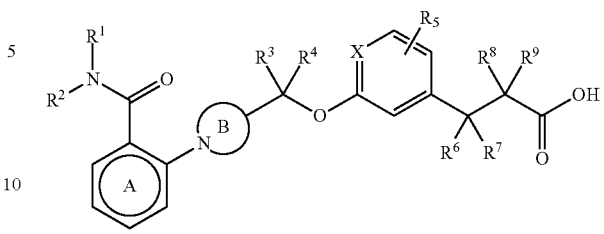

wherein
- ring A is a benzene ring optionally further substituted by 1 or 2 substituents selected from
(1) a $C_{1-6}$ alkylsulfonyl group;
(2) a carbamoyl group;
(3) a hydroxy group;
(4) an $C_{1-6}$ alkoxy group optionally substituted by 1 to 3 halogen atoms;
(5) a $C_{1-6}$ alkylthio group;
(6) a cyano group;
(7) a halogen atom; and
(8) a $C_{1-6}$ alkyl group,
- ring B is (1) an azetidine ring, (2) a pyrrolidine ring or (3) a piperidine ring optionally further substituted by 1 or 2 substituents selected from a halogen atom and a $C_{1-6}$ alkyl group, X is N,
- $R^1$ and $R^2$ are each independently
  - (i) a $C_{1-8}$ alkyl group optionally substituted by 1 or 2 substituents selected from (1) cyano, (2) hydroxy, (3) a $C_{3-10}$ cycloalkyl group optionally substituted by 1 to 3 substituents selected from a halogen atom and a $C_{1-6}$ alkyl group, (4) a $C_{1-6}$ alkoxy group optionally substituted by 1 to 3 halogen atoms, (5) a $C_{6-14}$ aryl group optionally substituted by 1 to 3 halogen atoms, (6) an aromatic heterocyclic group, (7) a nonaromatic heterocyclic group, (8) a $C_{1-6}$ alkylsulfonyl group, (9) a mono- or di-$C_{1-6}$ alkyl-amino group optionally substituted by 1 to 3 halogen atoms and (10) a halogen atom, or
  - (ii) an aromatic heterocyclic group optionally substituted by 1 or 2 substituents selected from (1) cyano, (2) a halogen atom, (3) a $C_{1-6}$ alkyl group optionally substituted by 1 to 3 halogen atoms, (4) a $C_{3-10}$ cycloalkyl group, (5) a $C_{1-6}$ alkoxy group, (6) a nitrogen-containing heterocyclyl-carbonyl group and (7) a mono- or di-$C_{1-6}$ alkyl-carbamoyl group,
- $R^3$, $R^4$, $R^5$, $R^7$, $R^8$ and $R^9$ are hydrogen atoms, and
- $R^6$ is a $C_{3-10}$ cycloalkyl group, or a salt thereof.

8. (3S)-3-cyclopropyl-3-(2-((1-(2-((2,2-dimethylpropyl)(6-methylpyridin-2-yl)carbamoyl)-5-methoxyphenyl)piperidin-4-yl)methoxy)pyridin-4-yl)propanoic acid or a salt thereof.

9. (3S)-3-cyclopropyl-3-(2-((1-(2-((2,2-dimethylpropyl)(4,6-dimethylpyrimidin-2-yl)carbamoyl)-5-methoxyphenyl)piperidin-4-yl)methoxy)pyridin-4-yl)propanoic acid or a salt thereof.

10. (3S)-3-cyclopropyl-3-(2-((1-(2-((2,2-dimethylpropyl)(pyridin-2-yl)carbamoyl)-5-methoxyphenyl)piperidin-4-yl)methoxy)pyridin-4-yl)propanoic acid or a salt thereof.

11. A medicament comprising the compound according to claim 1 or a salt thereof.

12. The medicament according to claim 11, which is a GPR40 receptor function regulator.

13. The medicament according to claim 11, which is a therapeutic agent for diabetes.

14. A method of treating diabetes in a mammal, comprising administering an effective amount of the compound according to claim 1 or a salt thereof to the mammal.

15. A method of regulating GPR40 receptor function in a mammal, comprising administering an effective amount of the compound according to claim 1 or a salt thereof to the mammal.

16. The compound according to claim 1 or a salt thereof for use for the treatment of diabetes.

* * * * *

SEQUENCE LISTING

<160> NUMBER OF SEQ ID NOS: 1

<210> SEQ ID NO 1
<211> LENGTH: 900
<212> TYPE: DNA
<213> ORGANISM: Human
<220> FEATURE:
<223> OTHER INFORMATION: cDNA encoding human GPR40

<400> SEQUENCE: 1

```
atggacctgc ccccgcagct ctccttcggc ctctatgtgg ccgcctttgc gctgggcttc      60
ccgctcaacg tcctggccat ccgaggcgcg acggcccacg cccggctccg tctcacccct     120
agcctggtct acgccctgaa cctgggctgc tccgacctgc tgctgacagt ctctctgccc     180
ctgaaggcgg tggaggcgct agcctccggg gcctggcctc tgccggcctc gctgtgcccc     240
gtcttcgcgg tgcccactt cttcccactc tatgccggcg ggggcttcct ggccgccctg     300
agtgcaggcc gctacctggg agcagccttc ccttgggct accaagcctt ccggaggccg     360
tgctattcct gggggtgtg cgcggccatc tgggccctcg tcctgtgtca cctgggtctg     420
gtctttgggt tggaggctcc aggaggctgg ctggaccaca gcaacacctc cctgggcatc     480
aacacaccgg tcaacggctc tccggtctgc ctggaggcct gggacccggc ctctgccggc     540
ccggcccgct tcagcctctc tctcctgctc tttttttctgc ccttggccat cacagccttc     600
tgctacgtgg gctgcctccg ggcactggcc cgctccggcc tgacgcacag gcggaagctg     660
cgggccgcct gggtggccgg cggggccctc ctcacgctgc tgctctgcgt aggaccctac     720
aacgcctcca cgtggccag cttcctgtac cccaatctag gaggctcctg gcggaagctg     780
gggctcatca cgggtgcctg gagtgtggtg cttaatccgc tggtgaccgg ttacttggga     840
aggggtcctg gcctgaagac agtgtgtgcg gcaagaacgc aaggggggaa gtcccagaag     900
```